US007501488B2

(12) United States Patent
Jensen et al.

(10) Patent No.: US 7,501,488 B2
(45) Date of Patent: Mar. 10, 2009

(54) PROTEORHODOPSIN MUTANTS WITH IMPROVED OPTICAL CHARACTERISTICS

(75) Inventors: Rasmus B. Jensen, Mountain View, CA (US); Bradley Kelemen, Menlo Park, CA (US)

(73) Assignee: Genencor International, Inc., Palo Alto, CA (US)

( * ) Notice: Subject to any disclaimer, the term of this patent is extended or adjusted under 35 U.S.C. 154(b) by 829 days.

(21) Appl. No.: 10/724,264

(22) Filed: Nov. 26, 2003

(65) Prior Publication Data

US 2005/0095605 A1 May 5, 2005

Related U.S. Application Data

(60) Provisional application No. 60/429,518, filed on Nov. 26, 2002.

(51) Int. Cl.
*C07K 1/00* (2006.01)
*C12P 21/06* (2006.01)

(52) U.S. Cl. ...................................... 530/350; 435/69.1

(58) Field of Classification Search ................ 435/69.1; 530/350

See application file for complete search history.

(56) References Cited

U.S. PATENT DOCUMENTS

2007/0192889 A1 * 8/2007 La Rosa et al. ............. 800/278

FOREIGN PATENT DOCUMENTS

WO WO01/83701 A2 11/2001
WO WO02/10207 A2 2/2002
WO PCT/US03/38194 12/2005

OTHER PUBLICATIONS

Oesterhelt, Dieter et al., "Bacteriorhodopsin : a biological material for information processing", *Quarterly Reviews of Biophysics* 24, 4 (1991), pp. 425-478.

Parthasarathy, et al., "Site-directed mutagenesis of proteorhodopsin; Study of light activated proton transfer," *Biophysical Journal*, 82(1), Part 2: 226A-227A (2002).

Oded Bejà, et al., "Proteorhodopsin Phototrophy in Ocean", 2001, *in Nature*, 411, pp. 786-789.

Oded Bejà, et al., "Bacterial Rhodopsin: Evidence for a New Type of Phototrophy in Sea", 2000 in *Science*, 289, pp. 1902-1906.

Andrei K. Dioumaev, et al., "Proton Transfers in the Photochemical Reaction Cycle of Proteorhodopsin," 2002, *Biochem.* 41, pp. 5348-5358.

Andrei K. Dioumaev, et al., "Proton Transport by Proteorhodopsin Requires that Renital Schiff Base Cunterion Asp-97 Be Anionic," 2003, *Am. Chem. Society.* 42, pp. 6582-6587.

Thomas Friedrick, et al., "Proteorhodopsin is a Light-driven Proton Pump with Variable Vectoriality," 2002, *J. Mol. Biol.*, 321, pp. 821-838.

N.A. Hampp, "Bacteriorhodopsin: mutating a biomaterial into an optoelectronic material," 2000, *Appl. Microbiol Biotechnol.*, 53, pp. 633-639.

Bradley R. Kelemen, et al., "Proteorhodopsini in living color: diversith of spectral properties within living bacterial cells," 2003, *Biochimica et Biophysica Acta*, 1618, pp. 25-32.

Richard A. Krebs, et al., "Resonance Raman Characterization of Proteorhodopsin's Chromophore Environment," 2003, *J. Phys. Chem. B G*, 107, pp. 7877-7883.

Richard A. Krebs, et al., "Detection of fast light-activated H+ release and M intermediate formation from Proteorphodopsin," 2002, *BMC Physiol.* 2, pp. 5-12, published Apr. 9, 2002.

Melinda Lakatos, et al., "Photochemical Reaction Cycle of Proteorhodopsin at Low pH," 2003, *Biophysical*, 84, pp. 3252-3256.

Dikla Man, et al., "Diversification and spectral tuning in marine proteorhodopsins," 2003, *J. EMBO*, 22, pp. 1725-1731.

Gazalah Sabehi, et al., "Novel Proterorhodopsin variants from Mediterranean and Red Seas," 2003, *Environmental Microbiol.*, 5(10), pp. 842-849.

José R. dela Torre, et al., "Proteorhodopsin genes are distributed among divergent marine bacterial taxa," 2003, *PNAS*, 100(22), pp. 12830-12850.

György Varó, et al., "Characterization of Photochemical Reaction Cycle of Proteorhodopsin," *J. Biophysical*, 2003, 84, pp. 1202-1207.

Wei-Wu Wang et al., "Spectroscopic and Photochemical Characterization of a Deep Ocean Proteorhodopsin," 2003, *J. Biol. Chem.*, 278(36), pp. 33985-33991.

* cited by examiner

*Primary Examiner*—Maryam Monshipouri
(74) *Attorney, Agent, or Firm*—Howrey LLP; Viola T. Kung

(57) ABSTRACT

The present invention is directed to a proteorhodopsin mutant having improved optical characteristics. One improved optical characteristic is having a lower pH ($pK_{rh}$) at which equal concentrations of the acidic and basic spectral form of the proteorhodopsin molecules are present. Another improved optical characteristic is having a smaller difference in maximum absorption wavelength between the basic and the acidic form. The mutant comprises a mutation in a conserved amino acid residue of a proteorhodopsin variant, which causes spectral shifts. A preferred mutation site is a conserved histidine residue at amino acid position 75 of Bac31A8, or position 77 of Hot75m1, or its equivalent position of a proteorhodopsin variant. Another preferred mutation site is a conserved arginine residue at amino acid position 94 of Bac31A8, or position 96 of Hot75m1, or its equivalent position of a proteorhodopsin variant.

13 Claims, 106 Drawing Sheets

```
     ThrMetGlyLys LeuLeuLeu IleLeuGly SerAlaIleAla LeuProSer·
  1  ACCATGGGTA AATTATTACT GATATTAGGT AGTGCTATTG CACTTCCATC
     ·PheAlaAla AlaGlyGlyAsp LeuAspIle SerAspThr ValGlyValSer·
 51  ATTTGCTGCT GCTGGTGGCG ATCTAGATAT AAGTGATACT GTTGGTGTTT
     · PheTrpLeu ValThrAla GlyMetLeuAla AlaThrVal PhePhePhe
101  CATTCTGGCT GGTTACAGCT GGTATGTTAG CGGCAACTGT GTTCTTTTTT
     ValGluArgAsp GlnValSer AlaLysTrp LysThrSerLeu AlaValSer·
151  GTAGAAAGAG ACCAAGTCAG CGCTAAGTGG AAAACTTCAC TTGCTGTATC
     ·GlyLeuIle ThrGlyIleAla PheTrpHis TyrLeuTyr MetArgGlyVal·
201  TGGTTTAATT ACTGGTATAG CTTTTTGGCA TTATCTCTAT ATGAGAGGTG
     · TrpIleAsp ThrGlyAsp ThrProThrVal PheArgTyr IleAspTrp
251  TTTGGATAGA CACTGGTGAT ACCCCAACAG TATTCAGATA TATTGATTGG
     LeuLeuThrVal ProLeuGln MetValGlu PheTyrLeuIle LeuAlaAla·
301  TTATTAACTG TTCCATTACA AATGGTTGAG TTCTATCTAA TTCTTGCTGC
     ·CysThrSer ValAlaAlaSer LeuPheLys LysLeuLeu AlaGlySerLeu·
351  TTGTACAAGT GTTGCTGCTT CATTATTTAA GAAGCTTCTA GCTGGTTCAT
     · ValMetLeu GlyAlaGly PheAlaGlyGlu AlaGlyLeu AlaProVal
401  TAGTAATGTT AGGTGCTGGA TTTGCAGGCG AAGCTGGATT AGCTCCTGTA
     LeuProAlaPhe IleIleGly MetAlaGly TrpLeuTyrMet IleTyrGlu·
451  TTACCTGCTT TCATTATTGG TATGGCTGGA TGGTTATACA TGATTTATGA
     ·LeuTyrMet GlyGluGlyLys AlaAlaVal SerThrAla SerProAlaVal·
501  GCTATATATG GGTGAAGGTA AGGCTGCTGT AAGTACTGCA AGTCCTGCTG
     · AsnSerAla TyrAsnAla MetMetMetIle IleValVal GlyTrpAla
551  TTAACTCTGC ATACAACGCA ATGATGATGA TTATTGTTGT TGGATGGGCA
     IleTyrProAla GlyTyrAla AlaGlyTyr LeuMetGlyGly GluGlyVal·
601  ATTTATCCTG CTGGATATGC TGCTGGTTAC CTAATGGGTG GCGAAGGTGT
     ·TyrAlaSer AsnLeuAsnLeu IleTyrAsn LeuAlaAsp LeuValAsnLys·
651  ATACGCTTCA AACTTAAACC TTATATATAA CCTTGCCGAC CTTGTTAACA
     · IleLeuPhe GlyLeuIle IleTrpAsnVal AlaValLys GluSerSer
701  AGATTCTATT TGGTTTGATC ATTTGGAATG TTGCTGTTAA AGAATCTTCT
     AsnAla
751  AATGCT
```

Figure 1-1

```
    MetLysLeuLeu LeuIleLeu GlySerVal IleAlaLeuPro ThrPheAla·
  1 ATGAAATTAT TACTGATATT AGGTAGTGTT ATTGCACTTC CTACATTTGC
    ·AlaGlyGly GlyAspLeuAsp AlaSerAsp TyrThrGly ValSerPheTrp·
 51 TGCAGGTGGT GGTGACCTTG ATGCTAGTGA TTACACTGGT GTTTCTTTTT
    · LeuValThr AlaAlaLeu LeuAlaSerThr ValPhePhe PheValGlu
101 GGTTAGTTAC TGCTGCTTTA TTAGCATCTA CTGTATTTTT CTTTGTTGAA
    ArgAspArgVal SerAlaLys TrpLysThr SerLeuThrVal SerGlyLeu·
151 AGAGATAGAG TTTCTGCAAA ATGGAAAACA TCATTAACTG TATCTGGTCT
    ·ValThrGly IleAlaPheTrp HisTyrMet TyrMetArg GlyValTrpIle·
201 TGTTACTGGT ATTGCTTTCT GGCATTACAT GTACATGAGA GGGGTATGGA
    · GluThrGly AspSerPro ThrValPheArg TyrIleAsp TrpLeuLeu
251 TTGAAACTGG TGATTCGCCA ACTGTATTTA GATACATTGA TTGGTTACTA
    ThrValProLeu LeuIleCys GluPheTyr LeuIleLeuAla AlaAlaThr·
301 ACAGTTCCTC TATTAATATG TGAATTCTAC TTAATTCTTG CTGCTGCAAC
    ·AsnValAla GlySerLeuPhe LysLysLeu LeuValGly SerLeuValMet·
351 TAATGTTGCT GGATCATTAT TTAAGAAATT ACTAGTTGGT TCTCTTGTTA
    · LeuValPhe GlyTyrMet GlyGluAlaGly IleMetAla AlaTrpPro
401 TGCTTGTGTT TGGTTACATG GGTGAAGCAG GAATCATGGC TGCATGGCCT
    AlaPheIleIle GlyCysLeu AlaTrpVal TyrMetIleTyr GluLeuTrp·
451 GCATTCATTA TTGGGTGTTT AGCTTGGGTA TACATGATTT ATGAATTATG
    ·AlaGlyGlu GlyLysSerAla CysAsnThr AlaSerPro AlaValGlnSer·
501 GGCTGGAGAA GGAAAATCTG CATGTAATAC TGCAAGTCCT GCTGTGCAAT
    · AlaTyrAsn ThrMetMet TyrIleIleIle PheGlyTrp AlaIleTyr
551 CAGCTTACAA CACAATGATG TATATTATCA TCTTTGGTTG GGCGATTTAT
    ProValGlyTyr PheThrGly TyrLeuMet GlyAspGlyGly SerAlaLeu·
601 CCTGTAGGTT ATTTCACAGG TTACCTGATG GGTGACGGTG GATCAGCTCT
    ·AsnLeuAsn LeuIleTyrAsn LeuAlaAsp PheValAsn LysIleLeuPhe·
651 TAACTTAAAC CTTATCTATA ACCTTGCTGA CTTTGTTAAC AAGATTCTAT
    · GlyLeuIle IleTrpAsn ValAlaValLys GluSerSer AsnAla***
701 TTGGTTTAAT TATATGGAAT GTTGCTGTTA AAGAATCTTC TAATGCTTAA
```

Figure 1-2

```
    ThrMetGlyLys LeuLeuLeu IleLeuGly SerValIleAla LeuProThr·
  1 ACCATGGGTA AATTATTACT GATATTAGGT AGTGTTATTG CACTTCCTAC
    ·PheAlaAla GlyGlyGlyAsp LeuAspAla SerAspTyr ThrGlyValSer·
 51 ATTTGCTGCA GGTGGTGGTG ACCTTGATGC TAGTGATTAC ACTGGTGTTT
    · PheTrpLeu ValThrAla AlaLeuLeuAla SerThrVal PhePhePhe
101 CTTTTTGGTT AGTTACTGCT GCTCTATTAG CATCTACTGT ATTTTTCTTT
    ValGluArgAsp ArgValSer AlaLysTrp LysThrSerLeu ThrValSer·
151 GTTGAAAGAG ATAGAGTTTC TGCAAAATGG AAAACATCAT TAACTGTATC
    ·GlyLeuVal ThrGlyIleAla PheTrpHis TyrMetTyr MetArgGlyVal·
201 GGGTCTTGTT ACTGGTATTG CTTTCTGGCA TTACATGTAC ATGAGAGGGG
    · TrpIleGlu ThrGlyAsp SerProThrVal PheArgTyr IleAspTrp
251 TATGGATTGA GACTGGTGAT TCGCCAACTG TATTTAGATA CATTGATTGG
    LeuLeuThrVal ProLeuLeu IleCysGlu PheTyrLeuIle LeuAlaAla·
301 TTACTAACAG TTCCTCTATT GATATGTGAA TTCTACTTAA TTCTTGCTGC
    ·AlaThrAsn ValAlaAlaGly LeuPheLys LysLeuLeu ValGlySerLeu·
351 TGCAACAAAT GTTGCTGCTG GCCTGTTTAA GAAATTATTG GTTGGTTCTC
    · ValMetLeu ValPheGly TyrMetGlyGlu AlaGlyIle MetAsnAla
401 TTGTTATGCT TGTGTTTGGT TACATGGGTG AGGCAGGAAT TATGAACGCT
    TrpGlyAlaPhe ValIleGly CysLeuAla TrpValTyrMet IleTyrGlu·
451 TGGGGTGCAT TCGTTATTGG GTGTTTAGCT TGGGTATACA TGATTTATGA
    ·LeuTrpAla GlyGluGlyLys AlaAlaCys AsnThrAla SerProAlaVal·
501 ACTATGGGCT GGAGAAGGCA AGGCTGCATG TAATACTGCA AGTCCTGCTG
    · GlnSerAla TyrAsnThr MetMetTyrIle IleIlePhe GlyTrpAla
551 TGCAATCAGC TTACAACACA ATGATGTATA TAATCATCTT TGGTTGGGCA
    IleTyrProVal GlyTyrPhe ThrGlyTyr LeuMetGlyAsp GlyGlySer·
601 ATTTATCCTG TAGGTTATTT CACAGGTTAC CTAATGGGTG ACGGTGGATC
    ·AlaLeuAsn LeuAsnLeuIle TyrAspLeu AlaAspPhe ValAsnLysIle·
651 AGCTCTTAAC TTAAACCTTA TCTATGACCT TGCTGACTTT GTTAACAAGA
    · LeuPheGly LeuIleIle TrpAsnValAla ValLysGlu SerSerAsn
701 TTCTATTTGG TTTAATTATA TGGAATGTTG CTGTTAAAGA ATCTTCTAAT
    AlaLys
751 GCTAAGG
```

Figure 1-3

```
    ThrMetGlyLys LeuLeuLeu IleLeuGly SerValIleAla LeuProThr·
  1 ACCATGGGTA AATTATTACT GATATTAGGT AGTGTTATTG CACTTCCTAC
    ·PheAlaAla GlyGlyGlyAsp LeuAspAla SerAspTyr ThrGlyValSer·
 51 ATTTGCTGCA GGTGGCGGTG ACCTTGATGC TAGTGATTAC ACTGGTGTTT
    · PheTrpLeu ValThrAla AlaLeuLeuAla SerThrVal PhePhePhe
101 CTTTTTGGTT AGTTACAGCT GCTCTATTAG CATCTACTGT ATTTTTCTTT
    ValGluArgAsp ArgValSer AlaLysTrp LysThrSerLeu ThrValSer·
151 GTTGAAAGAG ATAGAGTTTC TGCAAAATGG AAAACATCAT TAACTGTATC
    ·GlyLeuVal ThrGlyIleAla PheTrpHis TyrMetTyr MetArgGlyVal·
201 TGGTCTTGTT ACTGGTATTG CTTTCTGGCA TTACATGTAC ATGAGAGGAG
    · TrpIleGlu ThrGlyAsp SerProThrVal PheArgTyr IleAspTrp
251 TATGGATTGA AACTGGTGAT TCGCCTACTG TATTTAGATA CATTGATTGG
    LeuLeuThrVal ProLeuLeu IleCysGlu PheTyrLeuIle LeuAlaAla·
301 TTACTAACAG TTCCTTTATT AATATGTGAA TTCTACTTAA TTCTTGCTGC
    ·AlaThrAsn ValAlaGlySer LeuPheLys LysLeuLeu ValGlySerLeu·
351 TGCAACTAAT GTTGCCGGCT CATTATTTAA GAAACTTCTA GTTGGTTCTC
    · ValMetLeu ValPheGly TyrMetGlyGlu AlaGlyIle MetAlaAla
401 TTGTTATGCT TGTGTTTGGT TACATGGGTG AAGCAGGAAT TATGGCAGCT
    TrpProAlaPhe IleIleGly CysLeuAla TrpValTyrMet IleTyrGlu·
451 TGGCCTGCAT TCATTATTGG GTGTTTAGCT TGGGTATACA TGATTTATGA
    ·LeuTyrAla GlyGluGlyLys SerAlaCys AsnThrAla SerProSerVal·
501 ACTATATGCT GGAGAAGGAA AATCTGCATG TAATACTGCA AGTCCTTCGG
    · GlnSerAla TyrAsnThr MetMetAlaIle IleValPhe GlyTrpAla
551 TTCAATCAGC TTACAACACA ATGATGGCTA TCATAGTCTT CGGTTGGGCA
    IleTyrProIle GlyTyrPhe ThrGlyTyr LeuMetGlyAsp GlyGlySer·
601 ATTTATCCTA TAGGTTATTT CACAGGTTAC CTAATGGGTG ACGGTGGATC
    ·AlaLeuAsn LeuAsnLeuIle TyrAsnLeu AlaAspPhe ValAsnLysIle·
651 AGCTCTTAAC TTAAACCTTA TTTATAACCT TGCTGACTTT GTTAACAAGA
    · LeuPheGly LeuIleIle TrpAsnValAla ValLysGlu SerSerAsn
701 TTCTATTTGG TTTAATTATA TGGAATGTTG CTGTTAAAGA ATCTTCTAAT
    AlaLys
751 GCTAAGG
```

Figure 1-4

```
    ThrMetGlyLys LeuLeuLeu IleLeuGly SerValIleAla LeuProThr·
  1 ACCATGGGTA AATTATTACT GATATTAGGT AGTGTTATTG CACTTCCTAC
    ·PheAlaAla GlyGlyGlyAsp LeuAspAla SerAspTyr ThrGlyValSer·
 51 ATTTGCTGCA GGTGGTGGTG ACCTTGATGC TAGTGATTAC ACTGGTGTTT
    · PheTrpLeu ValThrAla AlaLeuLeuAla SerThrVal PhePhePhe
101 CTTTTTGGTT AGTTACTGCT GCTCTATTAG CATCTACTGT ATTTTTCTTT
    ValGluArgAsp ArgValSer AlaLysTrp LysThrSerLeu ThrValSer·
151 GTTGAAAGAG ATAGAGTTTC TGCAAAATGG AAAACATCAT TAACTGTATC
    ·GlyLeuVal ThrGlyIleAla PheTrpHis TyrMetTyr MetArgGlyVal·
201 GGGTCTTGTT ACTGGTATTG CTTTCTGGCA TTACATGTAC ATGAGAGGGG
    · TrpIleGlu ThrGlyAsp SerProThrVal PheArgTyr IleAspTrp
251 TATGGATTGA GACCGGTGAT TCGCCAACTG TATTTAGATA CATTGATTGG
    LeuLeuThrVal ProLeuLeu IleCysGlu PheTyrLeuIle LeuAlaAla·
301 TTACTAACAG TTCCTCTATT GATATGTGAA TTCTACTTAA TTCTTGCTGC
    ·AlaThrAsn ValAlaAlaGly LeuPheLys LysLeuLeu ValGlySerLeu·
351 TGCAACAAAT GTTGCTGCTG GCCTGTTTAA GAAATTATTG GTTGGTTCTC
    · ValMetLeu ValPheGly TyrMetGlyGlu AlaGlyIle MetAsnAla
401 TTGTTATGCT TGTGTTTGGT TACATGGGTG AGGCAGGAAT TATGAACGCT
    TrpGlyAlaPhe ValIleGly CysLeuAla TrpValTyrMet IleTyrGlu·
451 TGGGGTGCAT TCGTTATTGG GTGTTTAGCT TGGGTATACA TGATTTATGA
    ·LeuTrpAla GlyGluGlyLys AlaAlaCys AsnThrAla SerProAlaVal·
501 ACTATGGGCT GGAGAAGGCA AGGCTGCATG TAATACTGCA AGTCCTGCTG
    · GlnSerAla TyrAsnThr MetMetTyrIle IleIlePhe GlyTrpAla
551 TGCAATCAGC TTACAACACA ATGATGTATA TAATCATCTT TGGTTGGGCA
    IleTyrProVal GlyTyrPhe ThrGlyTyr LeuMetGlyAsp GlyGlySer·
601 ATTTATCCTG TAGGTTATTT CACAGGTTAC CTAATGGGTG ACGGTGGATC
    ·AlaLeuAsn LeuAsnLeuIle TyrAsnLeu AlaAspPhe ValAsnLysIle·
651 AGCTCTTAAC TTAAACCTTA TCTATAACCT TGCTGACTTT GTTAACAAGA
    · LeuPheGly LeuIleIle TrpAsnValAla ValLysGlu SerSerAsn
701 TTCTATTTGG TTTAATTATA TGGAATGTTG CTGTTAAAGA ATCTTCTAAT
    Ala
751 GCT
```

Figure 1-5

```
    ThrMetGlyLys LeuLeuLeu IleLeuGly SerAlaIleAla LeuProSer·
  1 ACCATGGGTA AATTATTACT GATATTAGGT AGTGCTATTG CACTTCCATC
    ·PheAlaAla AlaGlyGlyAsp LeuAspIle SerAspThr ValGlyValSer·
 51 ATTTGCTGCT GCTGGTGGCG ATCTAGATAT AAGTGATACT GTTGGTGTTT
    · PheTrpLeu ValThrAla GlyMetLeuAla AlaThrVal PhePhePhe
101 CATTCTGGCT GGTTACAGCT GGTATGTTAG CGGCAACTGT ATTCTTTTTT
    ValGluArgAsp GlnValSer AlaLysTrp LysThrSerLeu ThrValSer·
151 GTAGAAAGAG ACCAAGTCAG CGCTAAGTGG AAAACTTCAC TTACTGTATC
    ·GlyLeuIle ThrGlyIleAla PheTrpHis TyrLeuTyr MetArgGlyVal·
201 TGGTTTAATT ACTGGTATAG CTTTTTGGCA TTATCTCTAC ATGAGAGGTG
    · TrpIleAsp ThrGlyAsp ThrProThrVal PheArgTyr IleAspTrp
251 TTTGGATAGA TACTGGTGAT ACACCAACAG TATTTAGATA TATTGATTGG
    LeuLeuThrVal ProLeuGln MetValGlu PheTyrLeuIle LeuAlaAla·
301 TTATTAACTG TTCCATTACA AATGGTTGAG TTCTATCTAA TTCTTGCTGC
    ·CysThrSer ValAlaAlaSer LeuPheLys LysLeuLeu AlaGlySerLeu·
351 TTGTACAAGT GTTGCTGCTT CATTATTTAA GAAGCTTCTA GCTGGTTCAT
    · ValMetLeu GlyAlaGly PheAlaGlyGlu AlaGlyLeu AlaProVal
401 TAGTAATGTT AGGTGCTGGA TTTGCAGGCG AAGCTGGTTT AGCTCCTGTA
    LeuProAlaPhe IleIleGly MetAlaGly TrpLeuTyrMet IleTyrGlu·
451 TTACCTGCTT TCATTATTGG TATGGCTGGA TGGTTATACA TGATTTATGA
    ·LeuHisMet GlyGluGlyLys AlaAlaVal SerThrAla SerProAlaVal·
501 GCTACATATG GGTGAAGGTA AGGCTGCTGT AAGTACTGCA AGTCCTGCTG
    · AsnSerAla TyrAsnAla MetMetLysIle IleValIle GlyTrpAla
551 TTAACTCTGC ATACAACGCA ATGATGAAGA TTATTGTTAT TGGATGGGCA
    IleTyrProAla GlyTyrAla AlaGlyTyr LeuMetSerGly AspGlyVal·
601 ATTTATCCTG CTGGATATGC TGCTGGTTAC CTAATGAGTG GTGACGGTGT
    ·TyrAlaSer AsnLeuAsnLeu IleTyrAsn LeuAlaAsp PheValAsnLys·
651 ATACGCTTCA AACTTAAACC TTATATATAA CCTTGCTGAC TTTGTTAACA
    · IleLeuPhe GlyLeuIle IleTrpAsnVal AlaValLys GluSerSer
701 AGATTCTATT TGGTTTGATC ATTTGGAATG TTGCTGTTAA AGAATCTTCT
    AsnAla
751 AATGCTA
```

Figure 1-6

```
     ThrMetGlyLys LeuLeuLeu IleLeuGly SerAlaIleAla LeuProSer·
  1  ACCATGGGTA AATTATTACT GATATTAGGT AGTGCTATTG CACTTCCATC
     ·PheAlaAla AlaGlyGlyAsp LeuAspIle SerAspThr ValGlyValSer·
 51  ATTTGCTGCT GCTGGTGGCG ATCTAGATAT AAGTGATACT GTTGGTGTTT
     · PheTrpLeu ValThrAla GlyMetLeuAla AlaThrVal PhePhePhe
101  CATTCTGGCT GGTTACAGCT GGTATGTTAG CGGCAACTGT GTTCTTTTTT
     ValGluArgAsp GlnValSer AlaLysTrp LysThrSerLeu ThrValSer·
151  GTAGAAAGAG ACCAAGTCAG CGCTAAGTGG AAAACTTCAC TTACTGTATC
     ·GlyLeuIle ThrGlyIleAla PheTrpHis TyrLeuTyr MetArgGlyVal·
201  TGGTTTAATT ACTGGTATAG CTTTTTGGCA TTATCTCTAT ATGAGAGGTG
     · TrpIleAsp ThrGlyAsp ThrProThrVal PheArgTyr IleAspTrp
251  TTTGGATAGA CACTGGTGAT ACCCCAACAG TATTCAGATA TATTGATTGG
     LeuLeuThrVal ProLeuGln ValValGlu PheTyrLeuIle LeuAlaAla·
301  TTATTAACTG TTCCATTACA AGTGGTTGAG TTCTATCTAA TTCTTGCTGC
     ·CysThrSer ValAlaAlaSer LeuPheLys LysLeuLeu AlaGlySerLeu·
351  TTGTACAAGT GTTGCTGCTT CATTATTTAA GAAGCTTCTA GCTGGTTCAT
     · ValMetLeu GlyAlaGly PheAlaGlyGlu AlaGlyLeu AlaProVal
401  TAGTAATGTT AGGTGCTGGA TTTGCAGGCG AAGCTGGATT AGCTCCTGTA
     LeuProAlaPhe IleIleGly MetAlaGly TrpLeuTyrMet IleTyrGlu·
451  TTACCTGCTT TCATTATTGG TATGGCTGGA TGGTTATACA TGATTTATGA
     ·LeuTyrMet GlyGluGlyLys AlaAlaVal SerThrAla SerProAlaVal·
501  GCTATATATG GGTGAAGGTA AGGCTGCTGT AAGTACTGCA AGTCCTGCTG
     · AsnSerAla TyrAsnAla MetMetMetIle IleValVal GlyTrpAla
551  TTAACTCTGC ATACAACGCA ATGATGATGA TTATTGTTGT TGGATGGGCA
     IleTyrProAla GlyTyrAla AlaGlyTyr LeuMetGlyGly GluGlyVal·
601  ATTTATCCTG CTGGATATGC TGCTGGTTAC CTAATGGGTG GCGAAGGTGT
     ·TyrAlaSer AsnLeuAsnLeu IleTyrAsn LeuAlaAsp PheValAsnLys·
651  ATACGCTTCA AACTTAAACC TTATATATAA CCTTGCTGAC TTTGTTAACA
     · IleLeuPhe GlyLeuIle IleTrpAsnVal AlaValLys GluSerSer
701  AGATTCTATT TGGTTTGATC ATTTGGAATG TTGCTGTTAA AGAATCTTCT
     AsnAla
751  AATGCT
```

Figure 1-7

```
     ThrMetGlyLys LeuLeuLeu IleLeuGly SerAlaIleAla LeuProSer·
  1  ACCATGGGTA AATTATTACT GATATTAGGT AGTGCTATTG CACTTCCATC
     ·PheAlaAla AlaGlyGlyAsp LeuAspIle SerAspThr ValGlyValSer·
 51  ATTTGCTGCT GCTGGTGGCG ATCTAGATAT AAGTGATACT GTTGGTGTTT
     · PheTrpLeu ValThrAla GlyMetLeuAla AlaThrVal PhePhePhe
101  CATTCTGGCT GGTTACAGCT GGTATGTTAG CGGCAACTGT GTTCTTTTTT
     ValGluArgAsp GlnValSer AlaLysTrp LysThrSerLeu ThrValSer·
151  GTAGAAAGAG ACCAAGTCAG CGCTAAGTGG AAAACTTCAC TTACTGTATC
     ·GlyLeuIle ThrGlyIleAla PheTrpHis TyrLeuTyr MetArgGlyVal·
201  TGGTTTAATT ACTGGTATAG CTTTTTGGCA TTATCTCTAT ATGAGAGGTG
     · TrpIleAsp ThrGlyAsp ThrProThrVal PheArgTyr IleAspTrp
251  TTTGGATAGA CACTGGTGAT ACCCCAACAG TATTCAGATA TATTGATTGG
     LeuLeuThrVal ProLeuGln MetValGlu PheTyrLeuIle LeuAlaAla·
301  TTATTAACTG TTCCATTACA AATGGTTGAG TTCTATCTAA TTCTTGCTGC
     ·CysThrAsn ValAlaAlaSer LeuPheLys LysLeuLeu AlaGlySerLeu·
351  TTGTACAAAT GTTGCTGCTT CATTATTTAA GAAGCTTCTA GCTGGTTCAT
     · ValMetLeu GlyAlaGly PheAlaGlyGlu AlaGlyLeu AlaProVal
401  TAGTAATGTT AGGTGCTGGA TTTGCAGGCG AAGCTGGATT GGCTCCTGTA
     TrpProAlaPhe IleIleGly MetAlaGly TrpLeuTyrMet IleTyrGlu·
451  TGGCCTGCTT TCATTATTGG TATGGCTGGA TGGTTATACA TGATTTATGA
     ·LeuTyrMet GlyGluGlyLys AlaAlaVal SerThrAla SerProAlaVal·
501  GCTATATATG GGTGAAGGTA AGGCTGCTGT AAGTACTGCA AGTCCTGCTG
     · AsnSerAla TyrAsnAla MetMetValIle IleValVal GlyTrpAla
551  TTAACTCTGC ATACAACGCA ATGATGGTGA TTATTGTTGT TGGATGGGCA
     IleTyrProAla GlyTyrAla AlaGlyTyr LeuMetGlyGly GluGlyVal·
601  ATTTATCCTG CTGGATATGC TGCTGGTTAC CTAATGGGTG GCGAAGGTGT
     ·TyrAlaSer AsnLeuAsnLeu IleTyrAsn LeuAlaAsp LeuValAsnLys·
651  ATACGCTTCA AACTTAAACC TTATATATAA CCTTGCCGAC CTTGTTAACA
     · IleLeuPhe GlyLeuIle IleTrpAsnVal AlaValLys GluSerSer
701  AGATTCTATT TGGTTTGATC ATTTGGAATG TTGCTGTTAA AGAATCTTCT
     AsnAla
751  AATGCT
```

Figure 1-8

```
    ThrMetGlyLys LeuLeuLeu IleLeuGly SerValIleAla LeuProThr·
  1 ACCATGGGTA AATTATTACT GATATTAGGT AGTGTTATTG CACTTCCTAC
    ·PheAlaAla GlyGlyGlyAsp LeuAspAla SerAspTyr ThrGlyValSer·
 51 ATTTGCTGCA GGTGGTGGTG ACCTTGATGC TAGTGATTAC ACTGGTGTTT
    · PheTrpLeu ValThrAla AlaLeuLeuAla SerThrVal PhePhePhe
101 CTTTTTGGTT AGTTACTGCT GCTCTATTAG CATCTACTGT ATTTTTCTTT
    ValGluArgAsp ArgValSer AlaLysTrp LysThrSerLeu ThrValSer·
151 GTTGAAAGAG ATAGAGTTTC TGCAAAATGG AAAACATCAT TAACTGTATC
    ·GlyLeuVal ThrGlyIleAla PheTrpHis TyrMetTyr MetArgGlyVal·
201 TGGTCTTGTT ACTGGTATTG CTTTCTGGCA TTACATGTAC ATGAGAGGGG
    · TrpIleGlu ThrGlyAsp SerProThrVal PheArgTyr IleAspTrp
251 TATGGATTGA GACTGGTGAT TCGCCAACTG TATTTAGATA CATTGATTGG
    LeuLeuThrVal ProLeuLeu IleCysGlu PheTyrLeuIle LeuAlaAla·
301 TTACTAACAG TTCCTCTATT GATATGTGAA TTCTACTTAA TTCTTGCTGC
    ·AlaThrAsn ValAlaAlaGly LeuPheLys LysLeuLeu ValGlySerLeu·
351 TGCAACAAAT GTTGCTGCTG GCCTGTTTAA GAAATTATTG GTTGGTTCTC
    · ValMetLeu ValPheGly TyrMetGlyGlu AlaGlyIle MetAsnAla
401 TTGTTATGCT TGTGTTTGGT TACATGGGTG AGGCAGGAAT TATGAACGCT
    TrpProAlaPhe IleIleGly CysLeuAla TrpValTyrMet IleTyrGlu·
451 TGGCCTGCAT TCATTATTGG GTGTTTAGCT TGGGTATACA TGATTTATGA
    ·LeuTyrAla GlyGluGlyLys SerAlaCys AsnThrAla SerProSerVal·
501 ACTATATGCT GGAGAAGGAA AATCTGCATG TAATACTGCA AGTCCTTCGG
    · GlnSerAla TyrAsnThr MetMetAlaIle IleValPhe GlyTrpAla
551 TTCAATCAGC TTACAACACA ATGATGGCTA TCATAGTCTT CGGTTGGGCA
    IleTyrProVal GlyTyrPhe ThrGlyTyr LeuMetGlyAsp GlyGlySer·
601 ATTTATCCTG TAGGTTATTT CACAGGTTAC CTAATGGGTG ACGGTGGATC
    ·AlaLeuAsn LeuAsnLeuIle TyrAsnLeu AlaAspPhe ValAsnLysIle·
651 AGCTCTTAAC TTAAACCTTA TTTATAACCT TGCTGACTTT GTTAACAAGA
    · LeuPheGly LeuIleIle TrpAsnValAla ValLysGlu SerSerAsn
701 TTCTATTTGG TTTAATTATA TGGAATGTTG CTGTTAAAGA ATCTTCTAAT
    Ala
751 GCT
```

Figure 1-9

```
    ThrMetGlyLys LeuLeuLeu IleLeuGly SerValIleAla LeuProThr·
  1 ACCATGGGTA AATTATTACT GATATTAGGT AGTGTTATTG CACTTCCTAC
    ·PheAlaAla GlyGlyGlyAsp LeuAspAla SerAspTyr ThrGlyValSer·
 51 ATTTGCTGCA GGTGGTGGTG ACCTTGATGC TAGTGATTAC ACTGGTGTTT
    · PheTrpLeu ValThrAla AlaLeuLeuAla SerThrVal PhePhePhe
101 CTTTTTGGTT AGTTACTGCT GCTTTATTAG CATCTACTGT ATTTTTCTTT
    ValGluArgAsp ArgValSer AlaLysTrp LysThrSerLeu ThrValSer·
151 GTTGAAAGAG ATAGAGTTTC TGCAAAATGG AAAACATCAT TAACTGTATC
    ·GlyLeuVal ThrGlyIleAla PheTrpHis TyrMetTyr MetArgGlyVal·
201 TGGTCTTGTT ACTGGTATTG CTTTCTGGCA TTACATGTAC ATGAGAGGGG
    · TrpIleGlu ThrGlyAsp SerProThrVal PheArgTyr IleAspTrp
251 TATGGATTGA AACTGGTGAT TCGCCAACTG TATTTAGATA CATTGATTGG
    LeuLeuThrVal ProLeuLeu IleCysGlu PheTyrLeuIle LeuAlaAla·
301 TTACTAACAG TTCCTCTATT AATATGTGAA TTCTACTTAA TTCTTGCTGC
    ·AlaThrAsn ValAlaAlaGly LeuPheLys LysLeuLeu ValGlySerLeu·
351 TGCTACTAAT GTTGCTGCTG GCCTGTTTAA GAAATTATTG GTTGGTTCTC
    · ValMetLeu ValPheGly TyrMetGlyGlu AlaGlyIle MetAsnAla
401 TTGTTATGCT TGTGTTTGGT TACATGGGTG AAGCAGGAAT TATGAACGCT
    TrpGlyAlaPhe ValIleGly CysLeuAla TrpValTyrMet IleTyrGlu·
451 TGGGGTGCAT TCGTTATTGG GTGTTTAGCT TGGGTATACA TGATTTATGA
    ·LeuTrpLeu GlyGluGlyLys AlaAlaCys AsnThrAla SerProAlaVal·
501 GCTTTGGCTT GGAGAAGGAA AAGCTGCGTG TAATACAGCA AGTCCTGCTG
    · GlnSerAla TyrAsnThr MetMetMetIle IleIlePhe GlyTrpAla
551 TTCAGTCAGC TTACAACACA ATGATGATGA TCATCATCTT TGGTTGGGCA
    IleTyrProVal GlyTyrPhe ThrGlyTyr LeuMetGlyAsp GlyGlySer·
601 ATTTATCCTG TAGGTTATTT CACAGGTTAC CTAATGGGTG ACGGTGGATC
    ·AlaLeuAsn LeuAsnLeuIle TyrAsnLeu AlaAspPhe ValAsnLysIle·
651 AGCACTTAAC TTAAACCTTA TCTATAACCT TGCTGACTTT GTTAACAAGA
    · LeuPheGly LeuIleIle TrpAsnValAla ValLysGlu SerSerAsn
701 TTCTATTTGG TTTAATTATA TGGAATGTTG CTGTTAAAGA ATCTTCTAAT
    Ala
751 GCT
```

Figure 1-10

```
     ThrMetGlyLys LeuLeuLeu IleLeuGly SerValIleAla LeuProThr·
  1  ACCATGGGTA AATTATTACT GATATTAGGT AGTGTTATTG CACTTCCTAC
     ·PheAlaAla GlyGlyGlyAsp LeuAspAla SerAspTyr ThrGlyValSer·
 51  ATTTGCTGCA GGTGGTGGTG ACCTTGATGC TAGTGATTAC ACTGGTGTTT
     · PheTrpLeu ValThrAla AlaLeuLeuAla SerThrVal PhePhePhe
101  CTTTTTGGTT AGTTACTGCT GCTTTATTAG CATCTACTGT ATTTTTCTTT
     ValGluArgAsp ArgValSer AlaLysTrp LysThrSerLeu ThrValSer·
151  GTTGAAAGAG ATAGAGTTTC TGCAAAATGG AAAACATCAT TAACTGTATC
     ·GlyLeuVal ThrGlyIleAla PheTrpHis TyrMetTyr MetArgGlyVal·
201  TGGTCTTGTT ACTGGTATTG CTTTCTGGCA TTACATGTAC ATGAGAGGGG
     · TrpIleGlu ThrGlyAsp SerProThrVal PheArgTyr IleAspTrp
251  TATGGATTGA AACTGGTGAT TCGCCAACTG TATTTAGATA CATTGATTGG
     LeuLeuThrVal ProLeuLeu IleCysGlu PheTyrLeuIle LeuAlaAla·
301  TTACTAACAG TTCCTCTATT AATATGTGAA TTCTACTTAA TTCTTGCTGC
     ·AlaThrAsn ValAlaAlaGly LeuPheLys LysLeuLeu ValGlySerLeu·
351  TGCAACTAAT GTTGCTGCTG GCCTGTTTAA GAAATTATTG GTTGGTTCTC
     · ValMetLeu ValPheGly TyrMetGlyGlu AlaGlyIle MetAsnAla
401  TTGTTATGCT TGTGTTTGGT TACATGGGTG AGGCAGGAAT TATGAACGCT
     TrpGlyAlaPhe ValIleGly CysLeuAla TrpValTyrMet IleTyrGlu·
451  TGGGGTGCAT TCGTTATTGG GTGTTTAGCT TGGGTATACA TGATTTATGA
     ·LeuTrpAla GlyGluGlyLys AlaAlaCys AsnThrAla SerProAlaVal·
501  ACTATGGGCT GGAGAAGGCA AGGCTGCATG TAATACTGCA AGTCCTGCTG
     · GlnSerAla TyrAsnThr MetMetTyrIle IleIlePhe GlyTrpAla
551  TGCAATCAGC TTACAACACA ATGATGTATA TAATCATCTT TGGTTGGGCA
     IleTyrProVal GlyTyrPhe ThrGlyTyr LeuMetGlyAsp GlyGlySer·
601  ATTTATCCTG TAGGTTATTT CACAGGTTAC CTAATGGGTG ACGGTGGATC
     ·AlaLeuAsn LeuAsnLeuIle TyrAsnLeu AlaAspPhe ValAsnLysIle·
651  AGCTCTTAAC TTAAACCTTA TCTATAACCT TGCTGACTTT GTTAACAAGA
     · LeuPheGly LeuIleIle TrpAsnValAla ValLysGlu SerSerAsn
701  TTCTATTTGG TTTAATTATA TGGAATGTTG CTGTTAAAGA ATCTTCTAAT
     Ala
751  GCT
```

Figure 1-11

```
     ThrMetGlyLys LeuLeuLeu IleLeuGly SerValIleAla LeuProThr·
  1  ACCATGGGTA AATTATTACT GATATTAGGT AGTGTTATTG CACTTCCTAC
     ·PheAlaAla GlyGlyGlyAsp LeuAspAla SerAspTyr ThrGlyValSer·
 51  ATTTGCTGCA GGTGGCGGTG ACCTTGATGC TAGTGATTAC ACTGGTGTTT
     · PheTrpLeu ValThrAla AlaLeuLeuAla SerThrVal PhePhePhe
101  CTTTTTGGTT AGTTACAGCT GCTCTATTAG CATCTACTGT ATTTTTCTTT
     ValGluArgAsp ArgValSer AlaLysTrp LysThrSerLeu ThrValSer·
151  GTTGAAAGAG ATAGAGTTTC TGCAAAATGG AAAACATCAT TAACTGTATC
     ·GlyLeuVal ThrGlyIleAla PheTrpHis TyrMetTyr MetArgGlyVal·
201  TGGTCTTGTT ACTGGTATTG CTTTCTGGCA TTACATGTAC ATGAGAGGGG
     · TrpIleGlu ThrGlyAsp SerProThrVal PheArgTyr IleAspTrp
251  TATGGATTGA AACTGGTGAT TCGCCAACTG TATTTAGATA CATTGATTGG
     LeuLeuThrVal ProLeuLeu IleCysGlu PheTyrLeuIle LeuAlaAla·
301  TTACTAACAG TTCCTCTATT AATATGTGAA TTCTACTTAA TTCTTGCTGC
     ·AlaThrAsn ValAlaGlySer LeuPheLys LysLeuLeu ValGlySerLeu·
351  TGCTACTAAT GTTGCTGGAT CATTATTTAA GAAATTACTA GTTGGTTCTC
     · ValMetLeu ValPheGly TyrMetGlyGlu AlaGlnIle MetAlaAla
401  TTGTTATGCT TGTGTTTGGT TACATGGGTG AAGCACAAAT TATGGCTGCA
     TrpProAlaPhe IleIleGly CysLeuAla TrpValTyrMet IleTyrGlu·
451  TGGCCTGCAT TCATTATTGG GTGTTTAGCT TGGGTATACA TGATTTATGA
     ·LeuTyrAla GlyGluGlyLys SerAlaCys AsnThrAla SerProSerVal·
501  ACTATATGCT GGAGAAGGAA AATCTGCATG TAATACTGCA AGTCCTTCGG
     · GlnSerAla TyrAsnThr MetMetAlaIle IleValPhe GlyTrpAla
551  TTCAATCAGC TTACAACACA ATGATGGCTA TCATAGTCTT CGGTTGGGCA
     IleTyrProVal GlyTyrPhe ThrGlyTyr LeuMetGlyAsp GlyGlySer·
601  ATTTATCCTG TAGGTTATTT CACAGGTTAC CTAATGGGTG ACGGTGGGTC
     ·AlaLeuAsn LeuAsnLeuIle TyrAsnLeu AlaAspPhe ValAsnLysIle·
651  AGCTCTTAAC TTAAACCTTA TTTATAACCT TGCTGACTTT GTTAACAAGA
     · LeuLeuGly LeuIleIle TrpAsnValAla ValLysGlu SerSerAsn
701  TTCTACTTGG TTTAATTATA TGGAATGTTG CTGTTAAAGA ATCTTCTAAT
     Ala
751  GCT
```

Figure 1-12

```
    ThrMetGlyLys LeuLeuLeu IleLeuGly SerValIleAla LeuProThr·
  1 ACCATGGGTA AATTATTACT GATATTAGGT AGTGTTATTG CACTTCCTAC
    ·PheAlaAla GlyGlyGlyAsp LeuAspAla SerAspTyr ThrGlyValSer·
 51 ATTTGCTGCA GGTGGTGGTG ACCTTGATGC TAGTGATTAC ACTGGTGTTT
    · PheTrpLeu ValThrAla AlaLeuLeuAla SerThrVal PhePhePhe
101 CTTTTTGGTT AGTTACTGCT GCTTTATTAG CATCTACTGT ATTTTTCTTT
    ValGluArgAsp ArgValSer AlaLysTrp LysThrSerLeu ThrValSer·
151 GTTGAAAGAG ATAGAGTTTC TGCAAAATGG AAAACATCAT TAACTGTATC
    ·GlyLeuVal ThrGlyIleAla PheTrpHis TyrMetTyr MetArgGlyVal·
201 TGGTCTTGTT ACTGGTATTG CTTTCTGGCA TTACATGTAC ATGAGAGGGG
    · TrpIleGlu ThrGlyAsp SerProThrVal PheArgTyr IleAspTrp
251 TATGGATTGA AACTGGTGAT TCGCCAACTG TATTTAGATA CATTGATTGG
    LeuLeuThrVal ProLeuLeu IleCysGlu PheTyrLeuIle LeuAlaAla·
301 TTACTAACAG TTCCTCTATT AATATGTGAA TTCTACTTAA TTCTTGCTGC
    ·AlaAlaAsn ValAlaGlySer LeuPheLys LysLeuLeu ValGlySerLeu·
351 TGCAGCTAAT GTTGCTGGAT CATTATTTAA GAAATTACTA GTTGGTTCTC
    · ValMetLeu ValPheGly TyrMetGlyGlu AlaGlyIle MetAlaAla
401 TTGTTATGCT TGTGTTTGGT TACATGGGTG AAGCAGGAAT CATGGCTGCA
    TrpProAlaPhe IleIleGly CysLeuAla TrpValTyrMet IleTyrGlu·
451 TGGCCTGCAT TCATTATTGG GTGTTTAGCT TGGGTATACA TGATTTATGA
    ·LeuTrpAla GlyGluGlyLys SerAlaCys AsnThrAla SerProAlaVal·
501 ATTATGGGCT GGAGAAGGAA AATCTGCATG TAATACTGCA AGTCCTGCTG
    · GlnSerAla TyrAsnThr MetMetTyrIle IleIlePhe GlyTrpAla
551 TGCAATCAGC CTACAACACA ATGATGTATA TTATCATCTT TGGTTGGGCG
    IleTyrProVal GlyTyrPhe ThrGlyTyr LeuMetGlyAsp GlyGlySer·
601 ATTTATCCTG TAGGTTATTT CACAGGTTAC TTGATGGGTG ACGGTGGATC
    ·AlaLeuAsn LeuAsnLeuIle TyrAsnLeu AlaAspPhe ValAsnLysIle·
651 AGCTCTTAAC TTAAACCTTA TCTATAACCT TGCTGACTTT GTTAACAAGA
    · LeuPheGly LeuIleIle TrpAsnValAla ValLysGlu SerSer
701 TTCTATTTGG TTTAATTATA TGGAATGTTG CTGTTAAAGA ATCTTCTA
```

Figure 1-13

```
    ThrMetGlyLys LeuLeuLeu IleIleGly SerValIleAla LeuProThr·
  1 ACCATGGGTA AATTATTACT GATAATAGGT AGTGTTATTG CACTTCCTAC
    ·PheAlaAla GlyGlyGlyAsp LeuAspAla SerAspTyr ThrGlyValSer·
 51 ATTTGCTGCA GGTGGCGGTG ACCTTGATGC TAGTGATTAC ACTGGTGTTT
    · PheTrpLeu ValThrAla AlaLeuLeuAla SerThrVal PhePhePhe
101 CTTTTTGGTT AGTTACAGCT GCTCTATTAG CATCTACTGT ATTTTTCTTT
    ValGluArgAsp ArgValSer AlaLysTrp LysThrSerLeu ThrValSer·
151 GTTGAAAGAG ATAGAGTTTC TGCAAAATGG AAAACATCAT TAACTGTATC
    ·GlyLeuVal ThrGlyIleAla PheTrpHis TyrMetTyr MetArgGlyVal·
201 TGGTCTTGTT ACTGGTATTG CTTTCTGGCA TTACATGTAC ATGAGAGGAG
    · TrpIleGlu ThrGlyAsp SerProThrVal PheArgTyr IleAspTrp
251 TATGGATTGA AACTGGTGAT TCGCCAACTG TATTTAGATA CATTGATTGG
    LeuLeuThrVal ProLeuLeu IleCysGlu PheTyrLeuIle LeuAlaAla·
301 TTACTAACAG TTCCTTTATT AATATGTGAA TTCTACTTAA TTCTTGCTGC
    ·AlaThrAsn ValAlaGlySer LeuPheLys LysLeuLeu ValGlySerLeu·
351 TGCAACTAAT GTTGCCGGCT CATTATTTAA GAAACTTCTA GTTGGTTCTC
    · ValMetLeu ValPheGly TyrMetGlyGlu AlaGlyIle MetAlaAla
401 TTGTTATGCT TGTGTTTGGT TACATGGGTG AAGCAGGAAT TATGGCAGCT
    TrpProAlaPhe IleIleGly CysLeuAla TrpValTyrMet IleTyrGlu·
451 TGGCCTGCAT TCATTATTGG GTGTTTAGCT TGGGTATATA TGATTTATGA
    ·LeuTyrAla GlyGluGlyLys SerAlaCys AsnThrAla SerProAlaVal·
501 ACTATATGCT GGAGAAGGAA AATCTGCATG TAATACAGCA AGTCCTGCTG
    · GlnSerAla TyrAsnThr MetMetTyrIle IleValPhe GlyTrpAla
551 TGCAATCAGC TTACAACACA ATGATGTATA TTATCGTCTT TGGTTGGGCG
    IleTyrProVal GlyTyrPhe ThrGlyTyr LeuMetGlyAsp GlyGlySer·
601 ATTTATCCTG TAGGTTATTT CACAGGTTAC CTGATGGGTG ACGGTGGATC
    ·AlaLeuAsn LeuAsnLeuIle TyrAsnLeu AlaAspPhe ValAsnLysIle·
651 AGCTCTTAAC TTAAACCTTA TCTATAACCT TGCTGACTTT GTTAACAAGA
    · LeuPheGly LeuIleIle TrpAsnValAla ValLysGlu SerSerAsn
701 TTCTATTTGG TTTAATTATA TGGAATGTTG CTGTTAAAGA ATCTTCTAAT
    Ala
751 GCT
```

Figure 1-14

```
    ThrMetGlyLys LeuLeuLeu IleLeuGly SerValIleAla LeuProThr·
  1 ACCATGGGTA AATTATTACT GATATTAGGT AGTGTTATTG CACTTCCTAC
    ·PheAlaAla GlyGlyGlyAsp LeuAspAla SerAspTyr ThrGlyValSer·
 51 ATTTGCTGCA GGTGGTGGTG ACCTTGATGC TAGTGATTAC ACTGGTGTTT
    · PheTrpLeu ValThrAla AlaLeuLeuAla SerThrVal PhePhePhe
101 CTTTTTGGTT AGTTACTGCT GCTCTATTAG CATCTACTGT ATTTTTCTTT
    ValGluArgAsp ArgValSer AlaLysTrp LysThrSerLeu ThrValSer·
151 GTTGAAAGAG ATAGAGTTTC TGCAAAATGG AAAACATCAT TAACTGTATC
    ·GlyLeuVal ThrGlyIleAla PheTrpHis TyrMetTyr MetArgGlyVal·
201 GGGTCTTGTT ACTGGTATTG CTTTCTGGCA TTACATGTAC ATGAGAGGGG
    · TrpIleGlu ThrGlyAsp SerProThrVal PheArgTyr IleAspTrp
251 TATGGATTGA GACTGGTGAT TCGCCAACTG TATTTAGATA CATTGATTGG
    LeuLeuThrVal ProLeuLeu IleCysGlu PheTyrLeuIle LeuAlaAla·
301 TTACTAACAG TTCCTCTATT GATATGTGAA TTCTACTTAA TTCTTGCTGC
    ·AlaThrAsn ValAlaAlaGly LeuPheLys LysLeuLeu ValGlySerLeu·
351 TGCAACAAAT GTTGCTGCTG GCCTGTTTAA GAAATTATTG GTTGGTTCTC
    · ValMetLeu ValPheGly TyrMetGlyGlu AlaGlyIle MetAsnAla
401 TTGTTATGCT TGTGTTTGGT TACATGGGTG AGGCAGGAAT TATGAACGCT
    TrpGlyAlaPhe ValIleGly CysLeuAla TrpValTyrMet IleTyrGlu·
451 TGGGGTGCAT TCGTTATTGG GTGTTTAGCT TGGGTATACA TGATTTATGA
    ·LeuTrpAla GlyGluGlyLys AlaAlaCys AsnThrAla SerProAlaVal·
501 ACTATGGGCT GGAGAAGGCA AGGCTGCATG TAATACTGCA AGTCCTGCTG
    · GlnSerAla TyrAsnThr MetMetTyrIle IleIlePhe GlyTrpAla
551 TGCAATCAGC TTACAACACA ATGATGTATA TAATCATCTT TGGTTGGGCA
    IleTyrProVal GlyTyrPhe ThrGlyTyr LeuMetGlyAsp GlyGlySer·
601 ATTTATCCTG TAGGTTATTT CACAGGTTAC CTAATGGGTG ACGGTGGATC
    ·AlaLeuAsn LeuAsnLeuIle TyrAsnLeu AlaAspPhe ValAsnLysAsn·
651 AGCTCTTAAC TTAAACCTTA TCTATAACCT TGCTGACTTT GTTAACAAGA
    · LeuPheGly LeuIleIle TrpAsnValAla ValLysGlu SerSer
701 ATCTATTTGG TTTAATTATA TGGAATGTTG CTGTTAAAGA ATCTTCTA
```

Figure 1-15

```
    ThrMetGlyLys LeuLeuArg IleLeuGly SerValIleAla LeuProThr·
  1 ACCATGGGTA AATTATTACG GATATTAGGT AGTGTTATTG CACTTCCTAC
    ·PheAlaAla GlyGlyGlyAsp LeuAspAla SerAspTyr ThrGlyValSer·
 51 ATTTGCTGCA GGTGGCGGTG ACCTTGATGC TAGTGATTAC ACTGGTGTTT
    · PheTrpLeu ValThrAla AlaLeuLeuAla SerThrVal PhePhePhe
101 CTTTTTGGTT AGTTACAGCT GCTCTATTAG CATCTACTGT ATTTTTCTTT
    ValGluArgAsp ArgValSer AlaLysTrp LysThrSerLeu ThrValSer·
151 GTTGAAAGAG ATAGAGTTTC TGCAAAATGG AAAACATCAT TAACTGTATC
    ·GlyLeuVal ThrGlyIleAla PheTrpHis TyrMetTyr MetArgGlyVal·
201 TGGTCTTGTT ACTGGTATTG CTTTCTGGCA TTACATGTAT ATGAGAGGAG
    · TrpIleGlu ThrGlyAsp SerProThrVal PheArgTyr IleAspTrp
251 TATGGATTGA AACTGGTGAT TCGCCAACTG TATTTAGATA CATTGATTGG
    LeuLeuThrVal ProLeuLeu IleCysGlu PheTyrLeuIle LeuAlaAla·
301 TTACTAACAG TTCCTTTATT AATATGTGAA TTCTACTTAA TTCTTGCTGC
    ·AlaThrAsn ValAlaGlySer LeuPheLys LysLeuLeu ValGlySerLeu·
351 TGCAACTAAT GTTGCTGGAT CATTATTTAA GAAATTACTA GTTGGTTCTC
    · ValMetLeu ValPheGly TyrMetGlyGlu AlaGlyIle MetAlaAla
401 TTGTTATGCT TGTGTTTGGT TACATGGGTG AAGCAGGAAT CATGGCTGCA
    TrpProAlaPhe IleIleGly CysLeuAla TrpValTyrMet IleTyrGlu·
451 TGGCCTGCAT TCATTATTGG GTGTTTAGCT TGGGTATACA TGATTTATGA
    ·LeuTrpAla GlyGluGlyLys SerAlaCys AsnThrAla SerProAlaVal·
501 ACTATGGGCT GGAGAAGGAA AATCTGCATG TAATACTGCA AGTCCTGCTG
    · GlnSerAla TyrAsnThr MetMetTyrIle IleIleVal GlyTrpAla
551 TGCAATCAGC TTACAACACA ATGATGTATA TCATCATCGT TGGTTGGGCG
    IleTyrProVal GlyTyrPhe ThrGlyTyr LeuMetGlyAsp GlyGlySer·
601 ATTTATCCTG TAGGTTATTT CACAGGTTAC CTGATGGGTG ACGGTGGATC
    ·AlaLeuAsn LeuAsnLeuIle TyrAsnLeu AlaAspPhe ValAsnLysIle·
651 AGCTCTTAAC TTAAACCTTA TCTATAACCT TGCTGACTTT GTTAACAAGA
    · LeuPheGly LeuIleIle TrpAsnValAla ValLysGlu SerSerAsn
701 TTCTATTTGG TTTAATTATA TGGAATGTTG CTGTTAAAGA ATCTTCTAAT
    Ala
751 GCT
```

Figure 1-16

```
    ThrMetGlyLys LeuLeuLeu IleLeuGly SerValIleAla LeuProThr·
  1 ACCATGGGTA AATTATTACT GATATTAGGT AGTGTTATTG CACTTCCTAC
    ·PheAlaAla GlyGlyGlyAsp LeuAspAla SerAspTyr ThrGlyValSer·
 51 ATTTGCTGCA GGTGGCGGTG ACCTTGATGC TAGTGATTAC ACTGGTGTTT
    · PheTrpLeu ValThrAla AlaLeuLeuAla SerThrVal PhePhePhe
101 CTTTTTGGTT AGTTACAGCT GCTCTATTAG CATCTACTGT ATTTTTCTTT
    ValGluArgAsp ArgValSer AlaLysTrp LysThrSerLeu ThrValSer·
151 GTTGAAAGAG ATAGAGTTTC TGCAAAATGG AAAACATCAT TAACTGTATC
    ·GlyLeuVal ThrGlyIleAla PheTrpHis TyrMetTyr MetArgGlyVal·
201 TGGTCTTGTT ACTGGTATTG CTTTCTGGCA TTACATGTAC ATGAGAGGAG
    · TrpIleGlu ThrGlyAsp SerProThrVal PheArgTyr IleAspTrp
251 TATGGATTGA AACTGGTGAT TCGCCAACTG TATTTAGATA CATTGATTGG
    LeuLeuThrVal ProLeuLeu IleCysGlu PheTyrLeuIle LeuAlaAla·
301 TTACTAACAG TTCCTTTATT AATATGTGAA TTCTACTTAA TTCTTGCTGC
    ·AlaThrAsn ValAlaGlySer LeuPheLys LysLeuLeu ValGlySerLeu·
351 TGCAACTAAT GTTGCCGGCT CATTATTTAA GAAACTTCTA GTTGGTTCTC
    · ValMetLeu ValPheGly TyrMetGlyGlu AlaGlyIle MetAlaAla
401 TTGTTATGCT TGTGTTTGGT TACATGGGTG AAGCAGGAAT TATGGCAGCT
    TrpProAlaPhe IleIleGly CysLeuAla TrpValTyrMet IleTyrGlu·
451 TGGCCTGCAT TCATTATTGG GTGTTTAGCT TGGGTATACA TGATTTATGA
    ·LeuTyrAla GlyGluGlyLys SerAlaCys AsnThrAla SerProSerVal·
501 ACTATATGCT GGAGAAGGAA AATCTGCATG TAATACTGCA AGTCCTTCGG
    · GlnSerAla TyrAsnThr MetMetAlaIle IleValPhe GlyTrpAla
551 TTCAATCAGC TTACAACACA ATGATGGCTA TCATAGTCTT CGGTTGGGCA
    IleTyrProVal GlyTyrPhe ThrGlyTyr LeuMetGlyAsp GlyGlySer·
601 ATTTATCCTG TAGGTTATTT CACAGGTTAC CTAATGGGTG ACGGTGGATC
    ·AlaLeuAsn LeuAsnLeuIle TyrAsnLeu AlaAspPhe ValAsnLysIle·
651 AGCTCTTAAC TTAAACCTTA TTTATAACCT TGCTGACTTT GTTAACAAGA
    · LeuPheGly LeuIleIle TrpAsnValAla ValLysGlu SerSerAsn
701 TTCTATTTGG TTTAATTATA TGGAATGTTG CTGTTAAAGA ATCTTCTAAT
    Ala
751 GCT
```

Figure 1-17

```
    ThrMetGlyLys LeuLeuLeu IleLeuGly SerValIleAla LeuProThr·
  1 ACCATGGGTA AATTATTACT GATATTAGGT AGTGTTATTG CACTTCCTAC
    ·PheAlaAla GlyGlyGlyAsp LeuAspAla SerAspTyr ThrGlyValSer·
 51 ATTTGCTGCA GGTGGTGGTG ACCTTGATGC TAGTGATTAC ACTGGTGTTT
    · PheTrpLeu ValThrAla AlaLeuLeuAla SerThrVal PhePhePhe
101 CTTTTTGGTT AGTTACTGCT GCTTTATTAG CATCTACTGT ATTTTTCTTT
    ValGluArgAsp ArgValSer AlaLysTrp LysThrSerLeu ThrValSer·
151 GTTGAAAGAG ATAGAGTTTC TGCAAAATGG AAAACATCAT TAACTGTATC
    ·GlyLeuVal ThrGlyIleAla PheTrpHis TyrMetTyr MetArgGlyVal·
201 TGGTCTTGTT ACTGGTATTG CTTTCTGGCA TTACATGTAC ATGAGAGGGG
    · TrpIleGlu ThrGlyAsp SerProThrVal PheArgTyr IleAspTrp
251 TATGGATTGA AACTGGTGAT TCGCCAACTG TATTTAGATA CATTGATTGG
    LeuLeuThrVal ProLeuLeu IleCysGlu PheTyrLeuIle LeuAlaAla·
301 TTACTAACAG TTCCTCTATT AATATGTGAA TTCTACTTAA TTCTTGCTGC
    ·AlaThrAsn ValAlaGlySer LeuPheLys LysLeuLeu ValGlySerLeu·
351 TGCTACTAAT GTTGCCGGCT CATTATTTAA GAAACTTCTA GTTGGTTCTC
    · ValMetLeu ValPheGly TyrMetGlyGlu AlaGlyIle MetAlaAla
401 TTGTTATGCT TGTGTTTGGT TACATGGGTG AAGCAGGAAT TATGGCAGCT
    TrpProAlaPhe IleIleGly CysLeuAla TrpValTyrMet IleTyrGlu·
451 TGGCCTGCAT TCATTATTGG GTGTTTAGCT TGGGTATACA TGATTTATGA
    ·LeuTyrAla GlyGluGlyLys SerAlaCys AsnThrAla SerProSerVal·
501 ACTATATGCT GGAGAAGGAA AATCTGCATG TAATACTGCA AGTCCTTCGG
    · GlnSerAla TyrAsnThr MetMetAlaIle IleValPhe GlyTrpAla
551 TTCAATCAGC TTACAACACA ATGATGGCTA TCATAGTCTT CGGTTGGGCA
    IleTyrProVal GlyTyrPhe ThrGlyTyr LeuMetGlyAsp GlyGlySer·
601 ATTTATCCTG TAGGTTATTT CACAGGTTAC CTAATGGGTG ACGGTGGATC
    ·AlaLeuAsn LeuAsnLeuIle TyrAsnLeu AlaAspPhe ValAsnLysIle·
651 AGCTCTTAAC TTAAACCTTA TTTATAACCT TGCTGACTTT GTTAACAAGA
    · LeuPheGly LeuIleIle TrpAsnAlaAla ValLysGlu SerSerAsn
701 TTCTATTTGG TTTAATTATA TGGAATGCTG CTGTTAAAGA ATCTTCTAAT
    Ala
751 GCT
```

Figure 1-18

```
     ThrMetGlyLys LeuLeuLeu IleLeuGly SerValIleAla LeuProThr·
  1  ACCATGGGTA AATTATTACT GATATTAGGT AGTGTTATTG CACTTCCTAC
     ·PheAlaAla GlyGlyGlyAsp LeuAspAla SerAspTyr ThrGlyValSer·
 51  ATTTGCTGCA GGTGGTGGTG ACCTTGATGC TAGTGATTAC ACTGGTGTTT
     · PheTrpLeu ValThrAla AlaLeuLeuAla SerThrVal PhePhePhe
101  CTTTTTGGTT AGTTACTGCT GCTTTATTAG CATCTACTGT ATTTTTCTTT
     ValGluArgAsp ArgValSer AlaLysTrp LysThrSerLeu ThrValSer·
151  GTTGAAAGAG ATAGAGTTTC TGCAAAATGG AAAACATCAT TAACTGTATC
     ·GlyLeuVal ThrGlyIleAla PheTrpHis TyrMetTyr MetArgGlyVal·
201  TGGTCTTGTT ACTGGTATTG CTTTCTGGCA TTACATGTAT ATGAGAGGGG
     · TrpIleGlu ThrGlyAsp SerProThrVal PheArgTyr IleAspTrp
251  TATGGATTGA AACTGGTGAT TCGCCAACTG TATTTAGATA CATAGATTGG
     LeuLeuThrVal ProLeuLeu IleCysGlu PheTyrLeuIle LeuAlaAla·
301  TTACTAACAG TTCCTTTATT AATATGTGAA TTCTACTTAA TTCTTGCCGC
     ·AlaThrAsn ValAlaGlySer LeuPheLys LysLeuLeu ValGlySerLeu·
351  TGCAACTAAT GTTGCTGGAT CATTATTTAA GAAATTACTT GTTGGTTCTC
     · ValMetLeu ValPheGly TyrMetGlyGlu AlaGlyIle MetAlaAla
401  TTGTTATGCT TGTGTTTGGT TACATGGGTG AAGCAGGAAT CATGGCTGCA
     TrpProAlaPhe IleIleGly CysLeuAla TrpValTyrMet IleTyrGlu·
451  TGGCCTGCAT TCATTATTGG GTGTTTAGCT TGGGTATACA TGATTTATGA
     ·LeuTrpAla GlyGluGlyLys SērAlaCys AsnThrAla SerProAlaVal·
501  ACTATGGGCT GGAGAAGGAA AATCTGCATG TAATACTGCA AGTCCTGCTG
     · GlnSerAla TyrAsnThr MetMetTyrIle IleIlePhe GlyTrpAla
551  TGCAATCAGC TTACAACACA ATGATGTATA TCATCATCTT TGGTTGGGCG
     IleTyrProVal GlyTyrPhe ThrGlyTyr LeuMetGlyAsp GlyGlySer·
601  ATTTATCCTG TAGGTTATTT CACAGGTTAC CTTATGGGTG ACGGTGGATC
     ·AlaLeuAsn LeuAsnLeuIle TyrAsnLeu AlaAspPhe ValAsnLysIle·
651  AGCACTTAAC TTAAACCTTA TTTATAACCT TGCTGACTTT GTTAACAAGA
     · LeuPheGly LeuIleIle TrpAsnValAla ValLysGlu SerSerAsn
701  TTCTATTTGG TTTAATTATA TGGAATGTTG CTGTTAAAGA ATCTTCTAAT
     Ala
751  GCT
```

Figure 1-19

```
    ThrMetGlyLys LeuLeuLeu IleLeuGly SerValIleAla LeuProThr·
  1 ACCATGGGTA AATTATTACT GATATTAGGT AGTGTTATTG CACTTCCTAC
    ·PheAlaAla GlyGlyGlyAsp LeuAspAla SerAspTyr ThrGlyValSer·
 51 ATTTGCTGCA GGTGGCGGTG ACCTTGATGC TAGTGATTAC ACTGGTGTTT
    · PheTrpLeu ValThrAla AlaLeuLeuAla SerThrVal PhePhePhe
101 CTTTTTGGTT AGTTACAGCT GCTCTATTAG CGTCTACTGT ATTTTTCTTT
    ValGluArgAsp ArgValSer AlaLysTrp LysThrSerLeu ThrValSer·
151 GTTGAAAGAG ATAGAGTTTC TGCAAAATGG AAAACATCAT TAACTGTATC
    ·GlyLeuVal ThrGlyIleAla PheTrpHis TyrMetTyr MetArgGlyVal·
201 TGGTCTTGTT ACTGGTATTG CTTTCTGGCA TTACATGTAT ATGAGAGGAG
    · TrpIleGlu ThrGlyAsp SerProThrVal PheArgTyr IleAspTrp
251 TATGGATTGA AACTGGTGAT TCGCCAACTG TATTTAGATA CATTGATTGG
    LeuLeuThrVal ProLeuLeu IleCysGlu PheTyrLeuIle LeuAlaAla·
301 TTACTAACAG TTCCTTTATT AATATGTGAA TTCTACTTAA TTCTTGCTGC
    ·AlaThrAsn ValAlaGlySer LeuPheLys LysLeuLeu ValGlySerLeu·
351 TGCAACTAAT GTTGCCGGCT CATTATTTAA GAAACTTCTA GTTGGTTCTC
    · ValMetLeu ValPheGly TyrMetGlyGlu AlaGlyIle MetAlaAla
401 TTGTTATGCT TGTGTTTGGT TACATGGGTG AAGCAGGAAT AATGGCGGCT
    TrpProAlaPhe IleValGly CysLeuAla TrpValTyrMet IleTyrGlu·
451 TGGCCTGCAT TCATCGTTGG ATGTTTAGCA TGGGTATATA TGATTTATGA
    ·LeuTrpAla GlyGluGlyLys SerAlaCys AsnThrAla SerProAlaVal·
501 ACTATGGGCT GGTGAAGGAA AATCTGCATG TAATACTGCA AGTCCTGCTG
    · GlnSerAla TyrAsnThr MetMetTyrIle IleIleVal GlyTrpAla
551 TACAGTCAGC TTACAACACA ATGATGTATA TCATCATCGT TGGTTGGGCA
    IleTyrProVal GlyTyrPhe ThrGlyTyr LeuMetGlyAsp GlyGlySer·
601 ATTTATCCTG TAGGTTATTT CACAGGTTAC CTAATGGGTG ACGGTGGATC
    ·AlaLeuAsn LeuAsnLeuIle TyrAsnLeu AlaAspPhe ValAsnLysIle·
651 AGCTCTTAAT CTAAACCTTA TTTATAACCT TGCTGACTTT GTTAACAAGA
    · LeuPheGly LeuIleIle TrpAsnValAla ValLysGlu SerSerAsn
701 TTCTATTTGG TTTAATTATA TGGAATGTTG CTGTTAAAGA ATCTTCTAAT
    Ala
751 GCT
```

Figure 1-20

```
    ThrMetGlyLys LeuLeuLeu IleLeuGly SerAlaIleAla LeuProSer·
  1 ACCATGGGTA AATTATTACT GATATTAGGT AGTGCTATTG CACTTCCATC
    ·PheAlaAla AlaGlyGlyAsp LeuAspIle SerAspThr ValGlyValSer·
 51 ATTTGCTGCT GCTGGTGGCG ATCTAGATAT AAGTGATACT GTTGGTGTTT
    · PheTrpLeu ValThrAla GlyMetLeuAla AlaThrVal PhePhePhe
101 CATTCTGGCT GGTTACAGCT GGTATGTTAG CGGCAACTGT ATTCTTTTTT
    ValGluArgAsp GlnValSer AlaLysTrp LysThrSerLeu ThrValSer·
151 GTAGAAAGAG ACCAAGTCAG CGCTAAGTGG AAAACTTCAC TTACTGTATC
    ·GlyLeuIle ThrGlyIleAla PheTrpHis TyrLeuTyr MetArgGlyVal·
201 TGGTTTAATT ACTGGTATAG CTTTTTGGCA TTATCTCTAC ATGAGAGGTG
    · TrpIleAsp ThrGlyAsp ThrProThrVal PheArgTyr IleAspTrp
251 TTTGGATAGA TACTGGTGAT ACACCAACAG TATTTAGATA TATTGATTGG
    LeuLeuThrVal ProLeuGln MetValGlu PheTyrLeuIle LeuAlaAla·
301 CTATTAACTG TTCCATTACA AATGGTTGAG TTCTATCTAA TTCTTGCTGC
    ·CysThrSer ValAlaAlaSer LeuPheLys LysLeuLeu AlaGlySerLeu·
351 TTGTACAAGT GTTGCTGCTT CATTATTTAA GAAGCTTCTA GCTGGTTCAT
    · ValMetLeu GlyAlaGly PheAlaGlyGlu AlaGlyLeu AlaProVal
401 TAGTAATGTT AGGTGCTGGA TTTGCAGGCG AAGCTGGTTT AGCTCCTGTA
    LeuProAlaPhe IleLeuGly MetAlaGly TrpLeuTyrMet IleTyrGlu·
451 TTACCTGCTT TCATTCTTGG TATGGCTGGT TGGTTATACA TGATTTATGA
    ·LeuHisMet GlyGluGlyLys AlaAlaVal SerThrAla SerProAlaVal·
501 GCTACATATG GGTGAAGGTA AGGCTGCTGT AAGTACTGCA AGTCCTGCTG
    · AsnSerAla TyrAsnAla MetMetLysIle IleValIle GlyTrpAla
551 TTAACTCTGC TTACAATGCA ATGATGAAGA TTATTGTTAT TGGATGGGCA
    IleTyrProAla GlyTyrAla AlaGlyTyr LeuMetSerGly AspGlyVal·
601 ATTTATCCTG CTGGATATGC TGCTGGTTAC CTAATGAGTG GTGACGGTGT
    ·TyrAlaSer AsnLeuAsnLeu IleTyrAsn LeuAlaAsp PheValAsnLys·
651 ATACGCTTCA AACTTAAACC TTATATATAA CCTTGCTGAC TTTGTTAACA
    · IleLeuPhe GlyLeuIle IleTrpAsnVal AlaValLys GluSerSer
701 AGATTCTATT TGGTTTGATC ATTTGGAATG TTGCTGTTAA AGAATCTTCT
    AsnAla
751 AATGCT
```

Figure 1-21

```
    ThrMetGlyLys LeuLeuLeu IleLeuGly SerAlaIleAla LeuProSer·
  1 ACCATGGGTA AATTATTACT GATATTAGGT AGTGCTATTG CACTTCCATC
    ·PheAlaAla AlaGlyGlyAsp LeuAspIle SerAspThr ValGlyValSer·
 51 ATTTGCTGCT GCTGGTGGCG ATCTAGATAT AAGTGATACT GTTGGTGTTT
    · PheTrpLeu ValThrAla GlyMetLeuAla AlaThrVal PhePhePhe
101 CATTCTGGCT GGTTACAGCT GGTATGTTAG CGGCAACTGT GTTCTTTTTT
    ValGluArgAsp GlnValSer AlaGluTrp LysThrSerLeu ThrValSer·
151 GTAGAAAGAG ACCAAGTCAG CGCTGAGTGG AAAACTTCAC TTACTGTATC
    ·GlyLeuIle ThrGlyIleAla PheTrpHis TyrLeuTyr MetArgGlyVal·
201 TGGTTTAATT ACTGGTATAG CTTTTTGGCA TTATCTCTAT ATGAGAGGTG
    · TrpIleAsp ThrGlyAsp ThrProThrVal PheArgTyr IleAspTrp
251 TTTGGATAGA TACTGGTGAT ACCCCAACAG TATTCAGATA TATTGATTGG
    LeuLeuThrVal ProLeuGln MetValGlu PheTyrLeuIle LeuAlaAla·
301 TTATTAACTG TTCCATTACA AATGGTTGAG TTCTATCTAA TTCTTGCTGC
    ·CysThrSer ValAlaAlaSer LeuPheLys LysLeuLeu AlaGlySerLeu·
351 TTGTACAAGT GTTGCTGCTT CATTATTTAA GAAGCTTCTA GCTGGTTCAT
    · ValMetLeu GlyAlaGly PheAlaGlyGlu AlaGlyLeu AlaProVal
401 TAGTAATGTT AGGTGCTGGA TTTGCAGGCG AAGCTGGATT AGCTCCTGTA
    LeuProAlaPhe IleIleGly MetAlaGly TrpLeuTyrMet IleTyrGlu·
451 TTACCTGCTT TCATTATTGG TATGGCTGGA TGGTTATACA TGATTTATGA
    ·LeuTyrMet GlyGluGlyLys AlaAlaVal SerThrAla SerProAlaVal·
501 GCTATATATG GGTGAAGGTA AGGCTGCTGT AAGTACTGCA AGTCCTGCTG
    · AsnSerAla TyrAsnAla MetMetMetIle IleValVal GlyTrpAla
551 TTAACTCTGC ATACAACGCA ATGATGATGA TTATTGTTGT TGGATGGGCA
    IleTyrProAla GlyTyrAla AlaGlyTyr LeuMetGlyGly GluGlyVal·
601 ATTTATCCTG CTGGATATGC TGCTGGTTAC CTAATGGGTG GCGAAGGTGT
    ·TyrAlaSer AsnLeuAsnLeu IleTyrAsn LeuAlaAsp PheValAsnLys·
651 ATACGCTTCA AACTTAAACC TTATATATAA CCTTGCTGAC TTTGTTAACA
    · IleLeuPhe GlyLeuIle IleTrpAsnVal AlaValLys GluSerSer
701 AGATTCTATT TGGTTTGATC ATTTGGAATG TTGCTGTTAA AGAATCTTCT
    AsnAla
751 AATGCT
```

Figure 1-22

```
    ThrMetGlyLys LeuLeuLeu IleLeuGly SerAlaIleAla LeuProSer·
  1 ACCATGGGTA AATTATTACT GATATTAGGT AGTGCTATTG CACTTCCATC
    ·PheAlaAla AlaGlyGlyAsp LeuAspIle SerAspThr ValGlyValSer·
 51 ATTTGCTGCT GCTGGTGGCG ATCTAGATAT AAGTGATACT GTTGGTGTTT
    · PheTrpLeu ValThrAla GlyMetLeuAla AlaThrVal PhePhePhe
101 CATTCTGGCT GGTTACAGCT GGTATGTTAG CGGCAACTGT GTTCTTTTTT
    ValGluArgAsp GlnValSer AlaLysTrp LysThrSerLeu ThrValSer·
151 GTAGAAAGAG ACCAAGTCAG CGCTAAGTGG AAAACTTCAC TTACTGTATC
    ·GlyLeuIle ThrGlyIleAla PheTrpHis TyrLeuTyr MetArgGlyVal·
201 TGGTTTAATT ACTGGTATAG CCTTTTGGCA TTATCTCTAT ATGAGAGGTG
    · TrpIleAsp ThrGlyAsp ThrProThrVal PheArgTyr IleAspTrp
251 TTTGGATAGA CACTGGTGAT ACCCCAACAG TATTCAGATA TATTGATTGG
    LeuLeuThrVal ProLeuGln MetValGlu PheTyrLeuIle LeuAlaAla·
301 TTATTAACTG TTCCATTACA AATGGTTGAG TTCTATCTAA TTCTTGCTGC
    ·CysThrAsn ValAlaAlaSer LeuPheLys LysLeuLeu AlaGlySerLeu·
351 TTGTACAAAT GTTGCTGCTT CATTATTTAA GAAGCTTCTA GCTGGTTCAT
    · ValMetLeu GlyAlaGly PheAlaGlyGlu AlaGlyLeu AlaProVal
401 TAGTAATGTT AGGTGCTGGA TTTGCAGGCG AAGCTGGATT AGCTCCTGTA
    TrpProAlaPhe IleIleGly MetAlaGly TrpLeuTyrMet IleTyrGlu·
451 TGGCCTGCTT TCATTATTGG TATGGCTGGA TGGTTATACA TGATTTATGA
    ·LeuTyrMet GlyGluGlyLys AlaAlaVal SerThrAla SerProAlaVal·
501 GCTATATATG GGTGAAGGTA AGGCTGCTGT AAGTACTGCA AGTCCTGCTG
    · AsnSerAla TyrAsnAla MetMetMetIle IleValVal GlyTrpAla
551 TTAACTCTGC ATACAACGCA ATGATGATGA TTATTGTTGT TGGATGGGCA
    IleTyrProAla GlyTyrAla AlaGlyTyr LeuMetGlyGly GluGlyVal·
601 ATTTATCCTG CTGGATATGC TGCTGGTTAC CTAATGGGTG GCGAAGGTGT
    ·TyrAlaSer AsnLeuAsnLeu IleTyrAsn LeuAlaAsp PheValAsnLys·
651 ATACGCTTCA AACCTAAACC TTATATATAA CCTTGCTGAC TTTGTTAACA
    · IleLeuPhe GlyLeuIle IleTrpAsnVal AlaValLys GluSerSer
701 AGATTCTATT TGGTTTGATC ATTTGGAATG TTGCTGTTAA AGAATCTTCT
    AsnAla
751 AATGCT
```

Figure 1-23

```
     ThrMetGlyLys LeuLeuLeu IleLeuGly SerAlaIleAla LeuProSer·
  1  ACCATGGGTA AATTATTACT GATATTAGGT AGTGCTATTG CGCTTCCATC
     ·PheAlaAla AlaGlyGlyAsp LeuAspIle SerAspThr ValGlyValSer·
 51  ATTTGCTGCT GCTGGTGGCG ATCTAGATAT AAGTGATACT GTTGGTGTTT
     · PheTrpLeu ValThrAla GlyMetLeuAla AlaThrVal PhePhePhe
101  CATTCTGGCT GGTTACGGCT GGTATGTTAG CGGCAACTGT ATTCTTTTTT
     ValGluArgAsp GlnValSer AlaLysTrp LysThrSerLeu ThrValSer·
151  GTAGAAAGAG ACCAAGTCAG CGCTAAGTGG AAAACTTCAC TTACTGTATC
     ·GlyLeuIle ThrGlyIleAla PheTrpHis TyrLeuTyr MetArgGlyVal·
201  TGGTTTAATT ACTGGTATAG CTTTTTGGCA TTATCTCTAC ATGAGAGGTG
     · TrpIleAsp ThrGlyAsp ThrProThrVal PheArgTyr IleAspTrp
251  TTTGGATAGA TACTGGTGAT ACACCAACAG TATTTAGATA TATTGATTGG
     LeuLeuThrVal ProLeuGln MetValGlu PheTyrLeuIle LeuAlaAla·
301  TTATTAACTG TTCCATTACA AATGGTTGAG TTCTATCTAA TTCTTGCCGC
     ·CysThrSer ValAlaAlaSer LeuPheLys LysLeuLeu AlaGlySerLeu·
351  TTGTACAAGT GTTGCTGCTT CATTATTTAA GAAGCTTCTA GCTGGTTCAT
     · ValMetLeu GlyAlaGly SerAlaGlyGlu AlaGlyLeu AlaProVal
401  TGGTAATGTT AGGTGCTGGA TCTGCAGGCG AAGCTGGATT AGCTCCTGTA
     LeuProAlaPhe IleIleGly MetAlaGly TrpLeuTyrMet IleTyrGlu·
451  TTACCTGCTT TCATTATTGG TATGGCTGGA TGGTTATACA TGATTTATGA
     ·LeuTyrMet GlyGluGlyLys AlaAlaVal SerThrAla SerProAlaVal·
501  GCTATATATG GGTGAAGGTA AGGCTGCTGT AAGTACTGCA AGTCCTGCTG
     · AsnSerAla TyrAsnAla MetMetMetIle IleValVal GlyTrpAla
551  TTAACTCTGC ATACAACGCA ATGATGATGA TTATTGTTGT TGGATGGGCA
     IleTyrProAla GlyTyrAla AlaGlyTyr LeuMetGlyGly GluGlyVal·
601  ATTTATCCTG CTGGATATGC TGCTGGTTAC CTAATGGGTG GCGAAGGTGT
     ·TyrAlaSer AsnLeuAsnLeu IleTyrAsn LeuAlaAsp PheValAsnLys·
651  ATACGCTTCA AACTTAAACC TCATATATAA CCTTGCTGAC TTTGTTAACA
     · IleLeuPhe GlyLeuIle IleTrpAsnVal AlaValLys GluSerSer
701  AGATTCTATT TGGTTTGATC ATTTGGAATG TTGCTGTTAA AGAATCTTCT
     AsnAla
751  AATGCT
```

Figure 1-24

```
    ThrMetGlyLys LeuLeuLeu IleLeuGly SerAlaIleAla LeuProSer·
  1 ACCATGGGTA AATTATTACT GATATTAGGT AGTGCTATTG CACTTCCATC
    ·PheAlaAla AlaGlyGlyAsp LeuAspIle SerAspThr ValGlyValSer·
 51 ATTTGCTGCT GCTGGTGGCG ATCTAGATAT AAGTGATACT GTTGGTGTTT
    · PheTrpLeu ValThrAla GlyMetLeuAla AlaThrVal PhePhePhe
101 CATTCTGGCT GGTTACAGCT GGTATGTTAG CGGCAACTGT GTTCTTTTTT
    ValGluArgAsp GlnValSer AlaLysTrp LysThrSerLeu ThrValSer·
151 GTAGAAAGAG ACCAAGTCAG CGCTAAGTGG AAAACTTCAC TTACTGTATC
    ·GlyLeuIle ThrGlyIleAla PheTrpHis TyrLeuTyr MetArgGlyVal·
201 TGGTTTAATT ACTGGTATAG CTTTTTGGCA TTATCTCTAT ATGAGAGGTG
    · TrpIleAsp ThrGlyAsp ThrProThrVal PheArgTyr IleAspTrp
251 TTTGGATAGA CACTGGTGAT ACCCCAACAG TATTCAGATA TATTGATTGG
    LeuLeuThrVal ProLeuGln MetValGlu PheTyrLeuIle LeuAlaAla·
301 TTATTAACTG TTCCATTACA AATGGTTGAG TTCTATCTAA TTCTTGCTGC
    ·CysThrAsn ValAlaAlaSer LeuPheLys LysLeuLeu AlaGlySerLeu·
351 TTGTACAAAT GTTGCTGCTT CATTATTTAA GAAGCTTCTA GCTGGTTCAT
    · ValMetLeu GlyAlaGly PheAlaGlyGlu AlaGlyLeu AlaProVal
401 TAGTAATGTT AGGTGCTGGA TTTGCAGGCG AAGCTGGATT AGCTCCTGTA
    TrpProAlaPhe IleIleGly MetAlaGly TrpLeuTyrMet IleTyrGlu·
451 TGGCCTGCTT TCATTATTGG TATGGCTGGA TGGTTATACA TGATTTATGA
    ·LeuTyrMet GlyGluGlyLys AlaAlaVal SerThrAla SerProAlaVal·
501 GCTATATATG GGTGAAGGTA AGGCTGCTGT AAGTACTGCA AGTCCTGCTG
    · AsnSerAla TyrAsnAla MetMetValIle IleValVal GlyTrpAla
551 TTAACTCTGC ATACAACGCA ATGATGGTGA TTATTGTTGT TGGATGGGCA
    IleTyrProAla GlyTyrAla AlaGlyTyr LeuMetGlyGly GluGlyVal·
601 ATTTATCCTG CTGGATATGC TGCTGGTTAC CTAATGGGTG GCGAAGGTGT
    ·TyrAlaSer AsnLeuAsnLeu IleTyrAsn LeuAlaAsp PheValAsnLys·
651 ATACGCTTCA AACCTAAACC TTATATATAA CCTTGCTGAC TTTGTTAACA
    · IleLeuPhe GlyLeuIle IleTrpAsnVal AlaValLys GluSerSer
701 AGATTCTATT TGGTTTGATC ATTTGGAATG TTGCTGTTAA AGAATCTTCT
    AsnAla
751 AATGCT
```

Figure 1-25

```
    ThrMetGlyLys LeuLeuLeu IleLeuGly SerAlaIleAla LeuProSer·
  1 ACCATGGGTA AATTATTACT GATATTAGGT AGTGCTATTG CACTTCCATC
    ·PheAlaAla AlaGlyGlyAsp LeuAspIle SerAspThr ValGlyValSer·
 51 ATTTGCTGCT GCTGGTGGCG ATCTAGATAT AAGTGATACT GTTGGTGTTT
    · PheTrpLeu ValThrAla GlyMetLeuAla AlaThrVal PhePhePhe
101 CATTCTGGCT GGTTACAGCT GGTATGTTAG CGGCAACTGT GTTCTTTTTT
    ValGluArgAsp GlnValSer AlaLysTrp LysThrSerLeu ThrValSer·
151 GTAGAAAGAG ACCAAGTCAG CGCTAAGTGG AAAACTTCAC TTACTGTATC
    ·GlyLeuIle ThrGlyIleAla PheTrpHis TyrLeuTyr MetArgGlyVal·
201 TGGTTTAATT ACTGGTATAG CTTTTTGGCA TTATCTCTAT ATGAGAGGTG
    · TrpIleAsp ThrGlyAsp ThrProThrVal PheArgTyr IleAspTrp
251 TTTGGATAGA CACTGGTGAT ACCCCAACAG TATTCAGATA TATTGATTGG
    LeuLeuThrVal ProLeuGln MetValGlu PheTyrLeuIle LeuAlaAla·
301 TTATTAACTG TTCCATTACA AATGGTTGAG TTCTATCTAA TTCTTGCTGC
    ·CysThrSer ValAlaAlaSer LeuPheLys LysLeuLeu AlaGlySerLeu·
351 TTGTACAAGT GTTGCTGCTT CATTATTTAA GAAGCTTCTA GCTGGTTCAT
    · ValMetLeu GlyAlaGly PheAlaGlyGlu AlaGlyLeu AlaProVal
401 TAGTAATGTT AGGTGCTGGA TTTGCAGGCG AAGCTGGATT AGCTCCTGTA
    LeuProAlaPhe IleIleGly MetAlaGly TrpLeuTyrMet IleTyrGlu·
451 TTACCTGCTT TCATTATTGG TATGGCTGGA TGGTTATACA TGATTTATGA
    ·LeuTyrMet GlyGluGlyLys AlaAlaVal SerThrAla SerProAlaVal·
501 GCTATATATG GGTGAAGGTA AGGCTGCTGT AAGTACTGCA AGTCCTGCTG
    · AsnSerAla TyrAsnAla MetMetMetIle IleValVal GlyTrpAla
551 TTAACTCTGC ATACAACGCA ATGATGATGA TTATTGTTGT TGGATGGGCA
    IleTyrProAla GlyTyrAla AlaGlyTyr LeuMetGlyGly GluGlyVal·
601 ATTTATCCTG CTGGATATGC TGCTGGTTAC CTAATGGGTG GCGAAGGTGT
    ·TyrAlaSer AsnLeuAsnLeu IleTyrAsn LeuAlaAsp LeuValAsnLys·
651 ATACGCTTCA AACTTAAACC TTATATATAA CCTTGCTGAC CTTGTTAACA
    · IleLeuPhe GlyLeuIle IleTrpAsnVal AlaValLys GluSerSer
701 AGATTCTATT TGGTTTGATC ATTTGGAATG TTGCTGTTAA AGAATCTTCT
    AsnAla
751 AATGCT
```

Figure 1-26

```
    ThrMetGlyLys LeuLeuLeu IleLeuGly SerAlaIleAla LeuProSer·
  1 ACCATGGGTA AATTATTACT GATATTAGGT AGTGCTATTG CACTTCCATC
    ·PheAlaAla AlaGlyGlyAsp LeuAspIle SerAspThr ValGlyValSer·
 51 ATTTGCTGCT GCTGGTGGCG ATCTAGATAT AAGTGATACT GTTGGTGTTT
    · PheTrpLeu ValThrAla GlyMetLeuAla AlaThrVal PhePhePhe
101 CATTCTGGCT GGTTACAGCT GGTATGTTAG CGGCAACTGT GTTCTTTTTT
    ValGluArgAsp GlnValSer AlaLysTrp LysThrSerLeu ThrValSer·
151 GTAGAAAGAG ACCAAGTCAG CGCTAAGTGG AAAACTTCAC TTACTGTATC
    ·GlyLeuIle ThrGlyIleAla PheTrpHis TyrLeuTyr MetArgGlyVal·
201 TGGTTTAATT ACTGGTATAG CTTTTTGGCA TTATCTCTAT ATGAGAGGTG
    · TrpIleAsp ThrGlyAsp ThrProThrVal PheArgTyr IleAspTrp
251 TTTGGATAGA CACTGGTGAT ACCCCAACAG TATTCAGATA TATTGATTGG
    LeuLeuThrVal ProLeuGln ValValGlu PheTyrLeuIle LeuAlaAla·
301 TTATTAACTG TTCCATTACA AGTGGTTGAG TTCTATCTAA TTCTTGCTGC
    ·CysThrSer ValAlaAlaSer LeuPheLys LysLeuLeu AlaGlySerLeu·
351 TTGTACAAGT GTTGCTGCTT CATTATTTAA GAAGCTTCTA GCTGGTTCAT
    · ValMetLeu GlyAlaGly PheAlaGlyGlu AlaGlyLeu AlaProVal
401 TAGTAATGTT AGGTGCTGGA TTTGCAGGCG AAGCTGGATT AGCTCCTGTA
    LeuProAlaPhe IleIleGly MetAlaGly TrpLeuTyrMet IleTyrGlu·
451 TTACCTGCTT TCATTATTGG TATGGCTGGA TGGTTATACA TGATTTATGA
    ·LeuTyrMet GlyGluGlyLys AlaAlaVal SerThrAla SerProAlaVal·
501 GCTATATATG GGTGAAGGCA AGGCTGCTGT AAGTACTGCA AGTCCTGCTG
    · AsnProAla TyrAsnAla MetMetMetIle IleValVal GlyTrpAla
551 TTAACCCTGC ATACAACGCA ATGATGATGA TTATTGTTGT TGGATGGGCA
    IleTyrProAla GlyTyrAla AlaGlyTyr LeuMetGlyGly GluGlyVal·
601 ATTTATCCTG CTGGATATGC TGCTGGTTAC CTAATGGGTG GCGAAGGTGT
    ·TyrAlaSer AsnLeuAsnLeu IleTyrAsn LeuAlaAsp PheValAsnLys·
651 ATACGCTTCA AACTTAAACC TTATATATAA CCTTGCTGAC TTTGTTAACA
    · IleLeuPhe GlyLeuIle IleTrpAsnVal AlaValLys GluSerSer
701 AGATTCTATT TGGTTTGATC ATTTGGAATG TTGCTGTTAA AGAATCTTCT
    AsnAla
751 AATGCT
```

Figure 1-27

```
     ThrMetGlyLys LeuLeuLeu IleLeuGly SerAlaIleAla LeuProSer·
  1  ACCATGGGTA AATTATTACT GATATTAGGT AGTGCTATTG CACTTCCATC
     ·PheAlaAla AlaGlyGlyAsp LeuAspIle SerAspThr ValGlyValSer·
 51  ATTTGCTGCT GCTGGTGGCG ATCTAGATAT AAGTGATACT GTTGGTGTTT
     · PheTrpLeu ValThrAla GlyMetLeuAla AlaThrVal PhePhePhe
101  CATTCTGGCT GGTTACAGCT GGTATGTTAG CGGCAACTGT ATTCTTTTTT
     ValGluArgAsp GlnValSer AlaLysTrp LysThrSerLeu ThrValSer·
151  GTAGAAAGAG ACCAAGTCAG CGCTAAGTGG AAAACTTCAC TTACTGTATC
     ·GlyLeuIle ThrGlyIleAla PheTrpHis TyrLeuTyr MetArgGlyVal·
201  TGGTTTAATT ACTGGTATAG CTTTTTGGCA TTATCTCTAC ATGAGAGGTG
     · TrpIleAsp ThrGlyAsp ThrProThrVal PheArgTyr IleAspTrp
251  TTTGGATAGA TACTGGTGAT ACACCAACAG TATTTAGATA TATTGATTGG
     LeuLeuThrVal ProLeuGln MetValGlu PheTyrLeuIle LeuAlaAla·
301  TTATTAACTG TTCCATTACA AATGGTTGAG TTCTATCTAA TTCTTGCTGC
     ·CysThrSer ValAlaAlaSer LeuPheLys LysLeuLeu AlaGlySerLeu·
351  TTGTACAAGT GTTGCTGCTT CATTATTTAA GAAGCTTCTA GCTGGTTCAT
     · ValMetLeu GlyAlaGly PheAlaGlyGlu AlaGlyLeu AlaProVal
401  TAGTAATGTT AGGTGCTGGA TTTGCAGGCG AAGCTGGTTT AGCTCCTGTA
     LeuProAlaPhe IleIleGly MetAlaGly TrpLeuTyrMet IleTyrGlu·
451  TTACCTGCTT TCATTATTGG TATGGCTGGA TGGTTATACA TGATTTATGA
     ·LeuHisMet GlyGluGlyLys AlaAlaVal SerThrAla SerProAlaVal·
501  GCTACATATG GGTGAAGGTA AGGCTGCTGT AAGTACTGCA AGTCCTGCTG
     · AsnSerAla TyrAsnAla MetMetLysIle IleValIle GlyTrpAla
551  TTAACTCTGC ATACAACGCA ATGATGAAGA TTATTGTTAT TGGATGGGCA
     IleTyrProAla GlyTyrAla AlaGlyTyr LeuMetSerGly AspGlyVal·
601  ATTTATCCTG CTGGATATGC TGCTGGTTAC CTAATGAGTG GTGACGGTGT
     ·TyrAlaSer AsnLeuAsnLeu IleTyrAsn LeuAlaAsp PheValAsnLys·
651  ATACGCTTCA AACTTAAACC TTATATATAA CCTTGCTGAC TTTGTTAACA
     · IleLeuPhe GlyLeuIle IleTrpAsnVal AlaValLys GluSerSer
701  AGATTCTATT TGGTTTGATC ATTTGGAATG TTGCTGTTAA AGAATCTTCT
     AsnAla
751  AATGCT
```

Figure 1-28

```
    ThrMetGlyLys LeuLeuLeu IleLeuGly SerAlaIleAla LeuProSer·
  1 ACCATGGGTA AATTATTACT GATATTAGGT AGTGCTATTG CACTTCCATC
    ·PheAlaAla AlaGlyGlyAsp LeuAspIle SerAspThr ValGlyValSer·
 51 ATTTGCTGCT GCTGGTGGCG ATCTAGATAT AAGTGATACT GTTGGTGTTT
    · PheTrpLeu ValThrAla GlyMetLeuAla AlaThrVal PhePhePhe
101 CATTCTGGCT GGTTACAGCT GGTATGTTAG CGGCAACTGT GTTCTTTTTT
    ValGluArgAsp GlnValSer AlaLysTrp LysThrSerLeu ThrValSer·
151 GTAGAAAGAG ACCAAGTCAG CGCTAAGTGG AAAACTTCAC TTACTGTATC
    ·GlyLeuIle ThrGlyIleAla PheTrpHis TyrLeuTyr MetArgGlyVal·
201 TGGTTTAATT ACTGGTATAG CTTTTTGGCA TTATCTCTAT ATGAGAGGTG
    · TrpIleAsp ThrGlyAsp ThrProThrVal PheArgTyr IleAspTrp
251 TTTGGATAGA TACTGGTGAT ACCCCAACAG TATTCAGATA TATTGATTGG
    LeuLeuThrVal ProLeuGln MetValGlu PheTyrLeuIle LeuAlaAla·
301 TTATTAACTG TTCCATTACA AATGGTTGAG TTCTATCTAA TTCTTGCTGC
    ·CysThrSer ValAlaAlaSer LeuPheLys LysLeuLeu AlaGlySerLeu·
351 TTGTACAAGT GTTGCTGCTT CATTATTTAA GAAGCTTCTA GCTGGTTCAT
    · ValMetLeu GlyAlaGly PheAlaGlyGlu AlaGlyLeu AlaProVal
401 TAGTAATGTT AGGTGCTGGA TTTGCAGGCG AAGCTGGATT AGCTCCTGTA
    LeuProAlaPhe IleIleGly MetAlaGly TrpLeuTyrMet IleTyrGlu·
451 TTACCTGCTT TCATTATTGG TATGGCTGGA TGGCTATACA TGATTTATGA
    ·LeuTyrMet GlyGluGlyLys AlaAlaVal SerThrAla SerProAlaVal·
501 GCTATATATG GGTGAAGGTA AGGCTGCTGT AAGTACTGCA AGTCCTGCTG
    · AsnSerAla TyrAsnAla MetMetMetIle IleValVal GlyTrpAla
551 TTAACTCTGC ATACAACGCA ATGATGATGA TTATTGTTGT TGGATGGGCA
    IleTyrProAla GlyTyrAla AlaGlyTyr LeuMetGlyGly GluGlyVal·
601 ATTTATCCTG CTGGATATGC TGCTGGTTAC CTAATGGGTG GCGAAGGCGT
    ·TyrAlaSer AsnLeuAsnLeu IleTyrAsn LeuAlaAsp PheValAsnLys·
651 ATACGCTTCA AACTTAAACC TTATATATAA CCTTGCTGAC TTTGTTAACA
    · IleLeuPhe GlyLeuIle IleTrpAsnVal AlaValLys GluSerSer
701 AGATTCTATT TGGTTTGATC ATTTGGAATG TTGCTGTTAA AGAATCTTCT
    AsnAla
751 AATGCT
```

Figure 1-29

```
    MetGlyLysLeu LeuLeuIle LeuGlySer ValIleAlaLeu ProThrPhe·
  1 ATGGGTAAAT TATTACTGAT ATTAGGTAGT GTTATCGCGC TTCCAACATT
    ·AlaAlaGly GlyGlyAspLeu AspAlaSer AspTyrThr GlyValSerPhe·
 51 TGCTGCTGGC GGTGGCGATC TTGATGCTAG TGACTACACT GGTGTTTCAT
    · TrpLeuVal ThrAlaAla LeuLeuAlaSer ThrValPhe PhePheVal
101 TCTGGTTAGT TACTGCTGCT CTATTAGCGT CTACTGTATT CTTCTTTGTT
    GluArgAspArg ValSerAla LysTrpLys ThrSerLeuThr ValSerGly·
151 GAAAGAGATA GAGTGTCTGC AAAATGGAAA ACTTCATTAA CAGTATCTGG
    ·LeuValThr GlyIleAlaPhe TrpHisTyr MetTyrMet ArgGlyValTrp·
201 TTTAGTTACT GGTATTGCTT TTTGGCATTA TATGTACATG AGAGGTGTAT
    · IleGluThr GlyAspSer ProThrValPhe ArgTyrIle AspTrpLeu
251 GGATAGAAAC TGGTGATTCG CCTACTGTCT TTAGATACAT CGACTGGTTA
    LeuThrValPro LeuLeuIle CysGluPhe TyrLeuIleLeu AlaAlaAla·
301 TTAACTGTGC CTTTACTAAT ATGTGAGTTC TATCTGATAC TTGCTGCAGC
    ·ThrAsnVal AlaGlySerLeu PheLysLys LeuLeuVal GlySerLeuVal·
351 TACTAATGTT GCTGGTTCAT TATTTAAGAA ATTGCTAGTT GGTTCTCTTG
    · MetLeuVal PheGlyTyr MetGlyGluAla GlyIleMet AlaAlaTrp
401 TGATGCTTGT GTTTGGTTAC ATGGGTGAAG CAGGAATAAT GGCAGCTTGG
    ProAlaPheIle IleGlyCys LeuAlaTrp ValTyrMetIle TyrGluLeu·
451 CCTGCATTCA TCATTGGATG TTTAGCATGG GTATATATGA TTTATGAACT
    ·TrpAlaGly GluGlyLysSer AlaCysAsn ThrAlaSer ProAlaValGln·
501 ATGGGCTGGT GAAGGAAAAT CTGCATGCAA TACTGCAAGT CCTGCTGTAC
    · SerAlaTyr AsnThrMet MetTyrIleIle IleValGly TrpAlaIle
551 AGTCAGCTTA CAACACAATG ATGTATATCA TCATCGTTGG TTGGGCAATT
    TyrProValGly TyrPheThr GlyTyrLeu MetGlyAspGly GlySerAla·
601 TATCCTGTAG GTTATTTCAC AGGTTACCTA ATGGGTGACG GTGGATCAGC
    ·LeuAsnLeu AsnLeuIleTyr AsnLeuAla AspPheVal AsnLysIleLeu·
651 TCTTAATCTA AACCTTATTT ATAACCTTGC TGACTTTGTT AACAAGATTC
    · PheGlyLeu IleIleTrp AsnValAlaVal LysLysSer SerAsnAla
701 TATTTGGTTT AATTATATGG AATGTTGCTG TTAAAAAATC TTCTAATGCT
751 A
```

Figure 1-30

```
    MetGlyLysLeu LeuLeuIle LeuGlyAsn ValIleAlaLeu ProThrPhe·
  1 ATGGGTAAAT TATTACTGAT ATTAGGTAAT GTTATCGCGC TTCCAACATT
    ·AlaAlaGly GlyGlyAspLeu AspAlaSer AspTyrThr GlyValSerPhe·
 51 TGCTGCTGGC GGTGGCGATC TTGATGCTAG TGACTACACT GGTGTTTCAT
    · TrpLeuVal ThrAlaAla LeuLeuAlaSer ThrValPhe PhePheVal
101 TCTGGTTAGT TACTGCTGCT CTATTAGCGT CTACTGTATT CTTCTTTGTT
    GluArgAspArg ValSerAla LysTrpLys ThrSerLeuThr ValSerGly·
151 GAAAGAGATA GAGTGTCTGC AAAATGGAAA ACTTCATTAA CAGTATCTGG
    ·LeuValThr GlyIleAlaPhe TrpHisTyr MetTyrMet ArgGlyValTrp·
201 TTTAGTTACT GGTATTGCTT TTTGGCATTA TATGTACATG AGAGGTGTAT
    · IleGluThr GlyAspSer ProThrValPhe ArgTyrIle AspTrpLeu
251 GGATAGAAAC TGGTGATTCG CCTACTGTCT TTAGATACAT CGACTGGTTA
    LeuThrValPro LeuLeuIle CysGluPhe TyrLeuIleLeu AlaAlaAla·
301 TTAACTGTGC CTTTACTAAT ATGTGAGTTC TATCTGATAC TTGCTGCAGC
    ·ThrAsnVal AlaGlySerLeu PheLysLys LeuLeuVal GlySerLeuVal·
351 TACTAATGTT GCTGGTTCAT TATTTAAGAA ATTGCTAGTT GGTTCTCTTG
    · MetLeuVal PheGlyTyr MetGlyGluAla GlyIleMet AlaAlaTrp
401 TGATGCTTGT GTTCGGTTAC ATGGGTGAAG CAGGAATAAT GGCAGCTTGG
    ProAlaPheIle IleGlyCys LeuAlaTrp ValTyrMetIle TyrGluLeu·
451 CCTGCATTCA TCATTGGGTG TTTAGCATGG GTATATATGA TTTATGAGCT
    ·TrpAlaGly GluGlyLysSer AlaCysAsn ThrAlaSer ProAlaValGln·
501 ATGGGCTGGT GAAGGAAAAT CTGCATGTAA TACTGCAAGT CCTGCTGTAC
    · SerAlaTyr AsnThrMet MetTyrIleIle IleValGly TrpAlaIle
551 AGTCAGCTTA CAACACTATG ATGTATATTA TCATTGTTGG TTGGGCGATT
    TyrProValGly TyrPheThr GlyTyrLeu MetGlyAspGly GlySerAla·
601 TATCCTGTAG GCTATTTCAC TGGTTACCTC ATGGGTGACG GTGGATCAGC
    ·LeuAsnLeu AsnLeuIleTyr AsnLeuAla AspPheVal AsnLysIleLeu·
651 TCTTAATTTA AACCTTATTT ATAACCTTGC TGACTTTGTT AACAAGATTC
    · PheGlyLeu IleIleTrp AsnValAlaVal LysGluSer SerAsnAla
701 TATTTGGTTT AATTATATGG AATGTTGCTG TTAAAGAATC TTCTAATGCT
751 A
```

Figure 1-31

```
    MetGlyLysLeu LeuLeuIle LeuGlySer ValIleAlaLeu ProThrPhe·
  1 ATGGGTAAAT TATTACTGAT ATTAGGTAGT GTTATTGCGC TTCCAACATT
    ·AlaAlaGly GlyGlyAspLeu AspAlaSer AspTyrThr GlyValSerPhe·
 51 TGCCGCTGGC GGTGGCGATC TTGATGCTAG TGACTACACT GGTGTTTCTT
    · TrpLeuVal ThrAlaAla LeuLeuAlaSer ThrValPhe PhePheVal
101 TCTGGTTAGT TACTGCTGCT CTATTAGCAT CTACTGTATT CTTCTTTGTT
    GluArgAspArg ValSerAla LysTrpLys ThrSerLeuThr ValSerGly·
151 GAAAGGGATA GAGTATCTGC AAAATGGAAA ACTTCATTAA CAGTATCTGG
    ·LeuValThr GlyIleAlaPhe TrpHisTyr MetTyrMet ArgGlyValTrp·
201 TTTAGTTACT GGTATTGCTT TTTGGCATTA TATGTACATG AGAGGTGTAT
    · IleGluThr GlySerSer ProThrValPhe ArgTyrIle AspTrpLeu
251 GGATAGAAAC TGGTAGTTCA CCTACTGTCT TTAGATACAT TGACTGGCTA
    LeuThrValPro LeuLeuIle CysGluPhe TyrLeuIleLeu AlaAlaAla·
301 TTAACAGTGC CTTTACTAAT ATGTGAGTTC TATTTAATAC TTGCCGCAGC
    ·ThrAsnVal AlaGlySerLeu PheLysLys LeuLeuVal GlySerLeuVal·
351 TACTAATGTT GCTGGTTCAT TATTTAAGAA ATTGCTAGTT GGTTCTCTTG
    · MetLeuVal PheGlyTyr MetGlyGluAla GlyIleMet AlaAlaTrp
401 TGATGCTTGT GTTTGGTTAC ATGGGTGAAG CAGGAATAAT GGCAGCTTGG
    ProAlaPheIle IleGlyCys LeuAlaTrp ValTyrMetIle TyrGluLeu·
451 CCTGCATTCA TCATTGGATG TTTAGCATGG GTATATATGA TTTATGAGCT
    ·TrpAlaGly GluGlyLysSer AlaCysAsn ThrAlaSer ProAlaValGln·
501 ATGGGCTGGT GAAGGAAAAT CTGCATGTAA TACTGCAAGT CCTGCTGTAC
    · SerAlaTyr AsnThrMet MetTyrIleIle IleAlaGly TrpAlaIle
551 AGTCAGCTTA CAACACAATG ATGTATATCA TCATCGCTGG TTGGGCAATT
    TyrProValGly TyrPheThr GlyTyrLeu MetGlyAspGly GlySerAla·
601 TATCCTGTAG GTTATTTCAC AGGTTACCTA ATGGGTGACG GTGGATCAGC
    ·LeuAsnLeu AsnLeuIleTyr AsnLeuAla AspPheVal AsnLysIleLeu·
651 TCTTAATCTA AACCTTATTT ATAACCTTGC TGACTTTGTT AACAAGATTC
    · PheGlyLeu IleIleTrp AsnValAlaVal LysGluSer SerAsnAla
701 TATTTGGTTT AATTATATGG AATGTTGCTG TTAAAGAATC TTCTAATGCT
751 A
```

Figure 1-32

```
     MetGlyLysLeu LeuLeuIle LeuGlySer ValIleAlaLeu ProThrPhe·
  1  ATGGGTAAAT TATTACTGAT ATTAGGTAGT GTTATCGCGC TTCCAACATT
     ·AlaAlaGly GlyGlyAspLeu AspAlaSer AspTyrThr GlyValSerPhe·
 51  TGCTGCTGGC GGTGGCGATC TTGATGCTAG TGACTACACT GGTGTTTCAT
     · TrpLeuVal ThrAlaAla LeuLeuAlaSer ThrValPhe PhePheVal
101  TCTGGTTAGT TACTGCTGCT CTATTAGCGT CTACTGTATT CTTCTTTGTT
     GluArgAspArg ValSerAla LysTrpLys ThrSerLeuThr ValSerGly·
151  GAAAGAGATA GAGTGTCTGC AAAATGGAAA ACTTCATTAA CAGTATCTGG
     ·LeuValThr GlyIleAlaPhe TrpHisTyr MetTyrMet ArgGlyValTrp·
201  TTTAGTTACT GGTATTGCTT TTTGGCATTA TATGTACATG AGAGGTGTAT
     · IleGluThr GlyAspSer ProThrValPhe ArgTyrIle AspTrpLeu
251  GGATAGAAAC TGGTGATTCG CCTACTGTCT TTAGATACAT CGACTGGTTA
     LeuThrValPro LeuLeuIle CysGluPhe TyrLeuIleLeu AlaAlaAla·
301  TTAACTGTGC CTTTACTAAT ATGTGAGTTC TATCTGATAC TTGCTGCAGC
     ·ThrAsnVal AlaGlySerLeu PheLysLys LeuLeuVal GlySerLeuVal·
351  TACTAATGTT GCTGGTTCAT TATTTAAGAA ATTGCTAGTT GGTTCTCTTG
     · MetLeuVal PheGlyTyr MetGlyGluAla GlyIleMet AlaAlaTrp
401  TGATGCTTGT GTTTGGTTAC ATGGGTGAAG CAGGAATAAT GGCAGCTTGG
     ProAlaPheIle IleGlyCys LeuAlaTrp ValTyrMetIle TyrGluLeu·
451  CCTGCATTCA TCATTGGATG TTTAGCATGG GTATATATGA TTTATGAACT
     ·TrpAlaGly GluGlyLysSer AlaCysAsn ThrAlaSer ProAlaValGln·
501  ATGGGCTGGT GAAGGAAAAT CTGCATGCAA TACTGCAAGT CCTGCTGTAC
     · SerAlaTyr AsnThrMet MetTyrIleIle IleValGly TrpAlaIle
551  AGTCAGCTTA CAACACAATG ATGTATATCA TCATCGTTGG TTGGGCAATT
     TyrProValGly TyrPheThr GlyTyrLeu MetGlyAspGly GlySerAla·
601  TATCCTGTAG GTTATTTCAC AGGTTACCTA ATGGGTGACG GTGGATCAGC
     ·LeuAsnLeu AsnLeuIleTyr AsnLeuAla AspPheVal AsnLysIleLeu·
651  TCTTAATCTA AACCTTATTT ATAACCTTGC TGACTTTGTT AACAAGATTC
     · PheGlyLeu IleIleTrp AsnValAlaVal LysGluSer SerAsnAla
701  TATTTGGTTT AATTATATGG AATGTTGCTG TTAAAGAATC TTCTAATGCT
751  A
```

Figure 1-33

```
     MetGlyLysLeu LeuLeuIle LeuGlySer ValIleAlaLeu ProThrPhe·
  1  ATGGGTAAAT TATTACTGAT ATTAGGTAGT GTTATCGCGC TTCCAACATT
     ·AlaAlaGly GlyGlyAspLeu AspAlaSer AspTyrThr GlyValSerPhe·
 51  TGCTGCTGGC GGTGGCGATC TTGATGCTAG TGACTACACT GGTGTTTCAT
     · TrpLeuVal ThrAlaAla LeuLeuAlaSer ThrValPhe PhePheVal
101  TCTGGTTAGT TACTGCTGCT CTATTAGCGT CTACTGTATT CTTCTTTGTT
     GluArgAspArg ValSerAla LysTrpLys ThrSerLeuThr ValSerGly·
151  GAAAGAGATA GAGTGTCTGC AAAATGGAAA ACTTCATTAA CAGTATCTGG
     ·LeuValThr GlyIleAlaPhe TrpHisTyr MetTyrMet ArgGlyValTrp·
201  TTTAGTTACT GGTATTGCTT TTTGGCATTA TATGTACATG AGAGGTGTAT
     · IleGluThr GlySerSer ProThrValPhe ArgTyrIle AspTrpLeu
251  GGATAGAAAC TGGTAGTTCA CCTACTGTCT TTAGATACAT TGACTGGCTA
     LeuThrValPro LeuLeuIle CysGluPhe TyrLeuIleLeu AlaAlaAla·
301  TTAACAGTGC CTTTACTAAT ATGTGAGTTC TATTTAATAC TTGCCGCAGC
     ·ThrAsnVal AlaGlySerLeu PheLysLys LeuLeuVal GlySerLeuVal·
351  TACTAATGTT GCTGGTTCAT TATTTAAGAA ATTGCTAGTT GGTTCTCTTG
     · MetLeuVal PheGlyTyr MetGlyGluAla GlyIleMet AlaAlaTrp
401  TTATGCTTGT GTTCGGTTAC ATGGGTGAAG CAGGAATAAT GGCAGCTTGG
     ProAlaPheIle IleGlyCys LeuAlaTrp ValTyrMetIle TyrGluLeu·
451  CCTGCATTCA TCATTGGGTG TTTAGCATGG GTATATATGA TTTATGAGCT
     ·TrpAlaGly GluGlyLysSer AlaCysAsn ThrAlaSer ProAlaValGln·
501  ATGGGCTGGT GAAGGAAAAT CTGCATGTAA TACTGCAAGT CCTGCTGTAC
     · SerAlaTyr AsnThrMet MetTyrIleIle IleAlaGly TrpAlaIle
551  AGTCAGCTTA CAACACAATG ATGTATATCA TCATCGCTGG TTGGGCAATT
     TyrProValGly TyrPheThr GlyTyrLeu MetGlyAspGly GlySerAla·
601  TATCCTGTAG GTTATTTCAC AGGTTACCTA ATGGGTGACG GTGGATCAGC
     ·LeuAsnLeu AsnLeuAsnTyr AsnLeuAla AspPheVal AsnLysIleLeu·
651  TCTTAATCTA AACCTTAATT ATAACCTTGC TGACTTTGTT AACAAGATTC
     · PheGlyLeu IleIleTrp AsnValAlaVal LysGluSer SerAsnAla
701  TATTTGGTTT AATTATATGG AATGTTGCTG TTAAAGAATC TTCTAATGCT
751  A
```

Figure 1-34

```
     MetGlyLysLeu LeuLeuIle LeuGlySer ValIleAlaLeu ProThrPhe·
  1  ATGGGTAAAT TATTACTGAT ATTAGGTAGT GTTATCGCGC TTCCAACATT
     ·AlaAlaGly GlyGlyAspLeu AspAlaSer AspTyrThr GlyValSerPhe·
 51  TGCTGCTGGC GGTGGCGATC TTGATGCTAG TGACTATACT GGTGTTTCAT
     · TrpLeuVal ThrAlaAla LeuLeuAlaSer ThrValPhe PhePheVal
101  TCTGGTTAGT TACTGCTGCT CTATTAGCGT CTACTGTATT CTTCTTTGTT
     GluArgAspArg ValSerAla LysTrpLys ThrSerLeuThr ValSerGly·
151  GAAAGAGATA GAGTGTCTGC AAAATGGAAA ACTTCATTAA CAGTATCTGG
     ·LeuValThr GlyIleAlaPhe TrpHisTyr MetTyrMet ArgGlyValTrp·
201  TTTAGTTACT GGTATTGCTT TTTGGCATTA TATGTACATG AGAGGTGTAT
     · IleGluThr GlyAspSer ProThrValPhe ArgTyrIle AspTrpLeu
251  GGATAGAAAC TGGTGATTCG CCTACTGTCT TTAGATACAT AGACTGGTTA
     LeuThrValPro LeuLeuIle CysGluPhe TyrLeuIleLeu AlaAlaAla·
301  TTAACTGTGC CTTTACTAAT ATGTGAGTTC TATCTGATAC TTGCTGCAGC
     ·ThrAsnVal AlaGlySerLeu PheLysLys LeuLeuVal GlySerLeuVal·
351  TACTAATGTT GCTGGTTCAT TATTTAAGAA ATTGCTAGTT GGTTCTCTTG
     · MetLeuVal PheGlyTyr MetGlyGluAla GlyIleMet AlaAlaTrp
401  TGATGCTTGT GTTTGGTTAC ATGGGTGAAG CAGGAATAAT GGCAGCTTGG
     ProAlaPheIle IleGlyCys LeuAlaTrp ValTyrMetIle TyrGluLeu·
451  CCTGCATTCA TCATTGGATG TTTAGCATGG GTATATATGA TTTATGAACT
     ·TrpAlaGly GluGlyLysSer AlaCysAsn ThrAlaSer ProAlaValGln·
501  ATGGGCTGGT GAAGGAAAAT CTGCATGCAA TACTGCAAGT CCTGCTGTAC
     · SerAlaTyr AsnThrMet MetTyrIleIle IleValGly TrpAlaIle
551  AATCAGCTTA CAACACAATG ATGTATATCA TCATCGTTGG TTGGGCAATT
     TyrProValGly TyrPheThr GlyTyrLeu MetGlyAspGly GlySerAla·
601  TATCCTGTAG GTTATTTCAC AGGTTACCTA ATGGGTGACG GTGGATCAGC
     ·LeuAsnLeu AsnLeuIleTyr AsnLeuAla AspPheVal AsnLysIleLeu·
651  TCTTAATCTA AACCTTATTT ATAACCTTGC TGACTTTGTT AACAAGATTC
     · PheGlyLeu IleIleTrp AsnValAlaVal LysGluSer SerAsnAla
701  TATTTGGTTT AATTATATGG AATGTTGCTG TTAAAGAATC TTCTAATGCT
751  A
```

Figure 1-35

```
    MetGlyLysLeu LeuLeuIle LeuGlySer ValIleAlaLeu ProThrPhe·
  1 ATGGGTAAAT TATTACTGAT ATTAGGTAGT GTTATTGCGC TTCCAACATT
    ·AlaAlaGly GlyGlyAspLeu AspAlaSer AspTyrThr GlyValSerPhe·
 51 TGCCGCTGGC GGTGGCGATC TTGATGCTAG TGACTACACT GGTGTTTCTT
    · TrpLeuVal ThrAlaAla LeuLeuAlaSer ThrValPhe PhePheVal
101 TCTGGTTAGT TACTGCTGCT CTATTAGCAT CTACTGTATT CTTCTTTGTT
    GluArgAspArg ValSerAla LysTrpLys ThrSerLeuThr ValSerGly·
151 GAAAGGGATA GAGTATCTGC AAAATGGAAA ACTTCATTAA CAGTATCTGG
    ·LeuValThr GlyIleAlaPhe TrpHisTyr MetTyrMet ArgGlyValTrp·
201 TTTAGTTACT GGTATTGCTT TTTGGCATTA TATGTACATG AGAGGTGTAT
    · IleGluThr GlySerSer ProThrValPhe ArgTyrIle AspTrpLeu
251 GGATAGAAAC TGGTAGTTCA CCTACTGTCT TTAGATACAT TGACTGGCTA
    LeuThrValPro LeuLeuIle CysGluPhe TyrLeuIleLeu AlaAlaAla·
301 TTAACAGTGC CTTTACTAAT ATGTGAGTTC TATTTAATAC TTGCCGCAGC
    ·ThrAsnVal AlaGlySerLeu PheLysLys LeuLeuVal GlySerLeuVal·
351 TACTAATGTT GCTGGTTCAT TATTTAAGAA ATTGCTAGTT GGTTCTCTTG
    · MetLeuVal PheGlyTyr MetGlyGluAla GlyIleMet AlaAlaTrp
401 TTATGCTTGT GTTCGGTTAC ATGGGTGAAG CAGGAATAAT GGCAGCTTGG
    ProAlaPheIle IleGlyCys LeuAlaTrp ValTyrMetIle TyrGluLeu·
451 CCTGCATTCA TCATTGGATG TTTAGCATGG GTATATATGA TTTATGAACT
    ·TrpAlaGly GluGlyLysSer AlaCysAsn ThrAlaSer ProAlaValGln·
501 ATGGGCTGGT GAAGGAAAAT CTGCATGCAA TACTGCAAGT CCTGCTGTAC
    · SerAlaTyr AsnThrMet MetTyrIleIle IleValGly TrpAlaIle
551 AGTCAGCTTA CAACACAATG ATGTATATCA TCATCGTTGG TTGGGCAATT
    TyrProValGly TyrPheThr GlyTyrLeu MetGlyAspGly GlySerAla·
601 TATCCTGTAG GTTATTTCAC AGGTTACCTA ATGGGTGACG GTGGATCAGC
    ·LeuAsnLeu AsnLeuIleTyr AsnLeuAla AspPheVal AsnLysIleLeu·
651 TCTTAATCTA AACCTTATTT ATAACCTTGC TGACTTTGTT AACAAGATTC
    · PheGlyLeu IleIleTrp AsnValAlaVal LysGluSer SerAsnAla
701 TATTTGGTTT AATTATATGG AATGTTGCTG TTAAAGAATC TTCTAATGCT
751 A
```

Figure 1-36

```
    MetGlyLysLeu LeuLeuIle-LeuGlySer ValIleAlaLeu ProThrPhe·
  1 ATGGGTAAAT TATTACTGAT ATTAGGTAGT GTTATTGCGC TTCCAACATT
    ·AlaAlaGly GlyGlyAspLeu AspAlaSer AspTyrThr GlyValSerPhe·
 51 TGCCGCTGGT GGTGGTGACC TGGATGCTAG TGACTACACT GGTGTATCTT
    · TrpLeuVal ThrAlaAla LeuLeuAlaSer ThrValPhe PhePheVal
101 TCTGGTTAGT TACTGCTGCT CTATTAGCAT CTACTGTATT TTTCTTTGTT
    GluArgAspArg ValSerAla LysTrpLys ThrSerLeuThr ValSerGly·
151 GAAAGAGACA GAGTTTCTGC TAAATGGAAA ACATCATTAA CAGTATCTGG
    ·LeuValThr GlyIleAlaPhe TrpHisTyr MetTyrMet ArgGlyValTrp·
201 TTTAGTTACT GGTATTGCTT TTTGGCATTA CATGTACATG AGAGGTGTAT
    · IleGluThr GlyAspSer ProThrValPhe ArgTyrIle AspTrpLeu
251 GGATTGAAAC TGGTGATTCA CCAACTGTTT TTAGATACAT CGACTGGTTG
    LeuThrValPro LeuLeuIle CysGluPhe TyrLeuIleLeu AlaAlaAla·
301 CTAACTGTGC CTTTACTAAT TTGTGAGTTC TACTTAATAC TAGCAGCAGC
    ·ThrAsnVal AlaGlySerLeu PheLysLys LeuLeuVal GlySerLeuVal·
351 TACTAACGTT GCTGGTTCTT TATTCAAGAA ATTACTAGTT GGTTCTCTTG
    · MetLeuVal PheGlyTyr MetGlyGluAla GlyIleMet AlaAlaTrp
401 TTATGCTTGT GTTTGGTTAC ATGGGTGAAG CAGGAATTAT GGCAGCCTGG
    ProAlaPheIle IleGlyCys LeuAlaTrp ValTyrMetIle TyrGluLeu·
451 CCTGCATTCA TTATAGGATG TTTAGCATGG GTATACATGA TTTATGAATT
    ·TrpAlaGly GluGlyLysSer AlaCysAsn ThrAlaSer ProAlaValGln·
501 ATGGGCTGGA GAAGGAAAGT CTGCATGTAA CACTGCAAGT CCTGCAGTTC
    · SerAlaTyr AsnThrMet MetTyrIleIle IlePheGly TrpAlaIle
551 AGTCAGCTTA CAACACAATG ATGTATATCA TCATCTTTGG TTGGGCTATT
    TyrLeuValGly TyrPheThr GlyTyrLeu MetGlyAspGly GlySerAla·
601 TACCTTGTAG GTTATTTCAC TGGTTACCTA ATGGGTGACG GTGGATCAGC
    ·LeuAsnLeu AsnLeuIleTyr AsnLeuAla AspPheVal AsnLysIleLeu·
651 TCTTAACTTA AACCTTATCT ATAACCTTGC TGACTTTGTT AACAAGATTC
    · PheGlyLeu IleIleTrp AsnValAlaVal LysGluSer SerAsnAla
701 TATTTGGTTT AATTATATGG AATGTTGCTG TTAAAGAATC TTCTAATGCT
751 A
```

Figure 1-37

```
    MetGlyLysLeu LeuLeuIle LeuGlySer ValIleAlaLeu ProThrPhe·
  1 ATGGGTAAAT TATTACTGAT ATTAGGTAGT GTTATTGCGC TTCCAACATT
    ·AlaAlaGly GlyGlyAspLeu AspAlaSer AspTyrThr GlyValSerPhe·
 51 TGCCGCTGGC GGTGGCGATC TTGATGCTAG TGACTACACT GGTGTTTCTT
    · TrpLeuVal ThrAlaAla LeuLeuAlaSer ThrValPhe PhePheVal
101 TCTGGTTAGT TACTGCTGCT CTATTAGCAT CTACTGTATT CTTCTTTGTT
    GluArgAspArg ValSerAla LysTrpLys ThrSerLeuThr ValSerGly·
151 GAAAGGGATA GAGTATCTGC AAAATGGAAA ACTTCATTAA CAGTATCTGG
    ·LeuValThr GlyIleAlaPhe TrpHisTyr MetTyrMet ArgGlyValTrp·
201 TTTAGTTACT GGTATTGCTT TTTGGCATTA TATGTACATG AGAGGTGTAT
    · IleGluThr GlySerSer ProThrValPhe ArgTyrIle AspTrpLeu
251 GGATAGAAAC TGGTAGTTCA CCTACTGTCT TTAGATACAT TGACTGGCTA
    LeuThrValPro LeuLeuIle CysGluPhe TyrLeuIleLeu AlaAlaAla·
301 TTAACAGTGC CTTTACTAAT ATGTGAGTTC TATTTAATAC TTGCCGCAGC
    ·ThrAsnVal AlaGlySerLeu PheLysLys LeuLeuVal GlySerLeuVal·
351 TACTAATGTT GCTGGTTCAT TATTTAAGAA ATTGCTAGTT GGTTCTCTTG
    · MetLeuVal PheGlyTyr MetGlyGluAla GlyIleMet AlaAlaTrp
401 TTATGCTTGT GTTCGGTTAC ATGGGTGAAG CAGGAATAAT GGCAGCTTGG
    ProAlaPheIle IleGlyCys LeuAlaTrp ValTyrMetIle TyrGluLeu·
451 CCTGCATTCA TCATTGGGTG TTTAGCATGG GTATATATGA TTTATGAGCT
    ·TrpAlaGly GluGlyLysSer AlaCysAsn ThrAlaSer ProAlaValGln·
501 ATGGGCTGGT GAAGGAAAAT CTGCATGTAA TACTGCAAGT CCTGCTGTAC
    · SerAlaTyr AsnThrMet MetTyrIleIle IleAlaGly TrpAlaIle
551 AGTCAGCTTA CAACACAATG ATGTATATCA TCATCGCTGG TTGGGCAATT
    TyrProValGly TyrPheThr GlyTyrLeu MetGlyAspGly GlySerAla·
601 TATCCTGTAG GTTATTTCAC AGGTTACCTA ATGGGTGACG GTGGATCAGC
    ·LeuAsnLeu AsnLeuIleTyr AsnLeuAla AspPheVal AsnLysIleLeu·
651 TCTTAATCTA AACCTTATTT ATAACCTTGC TGACTTTGTT AACAAGATTC
    · PheGlyLeu IleIleTrp AsnValAlaVal LysGluSer SerAsnAla
701 TATTTGGTTT AATTATATGG AATGTTGCTG TTAAAGAATC TTCTAATGCT
751 A
```

Figure 1-38

```
     MetGlyLysLeu LeuLeuIle LeuGlySer ValIleAlaLeu ProThrPhe·
  1  ATGGGTAAAT TATTACTGAT ATTAGGTAGT GTTATCGCGC TTCCAACATT
     ·AlaAlaGly GlyGlyAspLeu AspAlaSer AspTyrThr GlyValSerPhe·
 51  TGCTGCTGGC GGTGGCGATC TTGATGCTAG TGACTACACT GGTGTTTCAT
     · TrpLeuVal ThrAlaAla LeuLeuAlaSer ThrValPhe PhePheVal
101  TCTGGTTAGT TACTGCTGCT CTATTAGCGT CTACTGTATT CTTCTTTGTT
     GluArgAspArg ValSerAla LysTrpLys ThrSerLeuThr ValSerGly·
151  GAAAGAGATA GAGTGTCTGC AAAATGGAAA ACTTCATTAA CAGTATCTGG
     ·LeuValThr GlyIleAlaPhe TrpHisTyr MetTyrMet ArgGlyValTrp·
201  TTTAGTTACT GGTATTGCTT TTTGGCATTA TATGTACATG AGAGGTGTAT
     · IleGluThr GlyAspSer ProThrValPhe ArgTyrIle AspTrpLeu
251  GGATAGAAAC TGGTGATTCG CCTACTGTCT TTAGATACAT CGACTGGTTA
     LeuThrValPro LeuLeuIle CysGluPhe TyrLeuIleLeu AlaAlaAla·
301  TTAACTGTGC CTTTACTAAT ATGTGAGTTC TATCTGATAC TTGCTGCAGC
     ·ThrAsnVal AlaGlySerLeu PheLysLys LeuLeuVal GlySerLeuVal·
351  TACTAATGTT GCTGGTTCAT TATTTAAGAA ATTGCTAGTT GGTTCTCTTG
     · MetLeuVal PheGlyTyr MetGlyGluAla GlyIleMet AlaAlaTrp
401  TGATGCTTGT GTTTGGTTAC ATGGGTGAAG CAGGAATAAT GGCAGCTTGG
     ProAlaPheIle IleGlyCys LeuAlaTrp ValTyrMetIle TyrGluLeu·
451  CCTGCATTCA TCATTGGATG TTTAGCATGG GTATATATGA TTTATGAACT
     ·TrpAlaGly GluGlyLysSer AlaCysAsn ThrAlaSer ProAlaValGln·
501  ATGGGCTGGT GAAGGAAAAT CTGCATGCAA TACTGCAAGT CCTGCTGTAC
     · SerAlaTyr AsnThrMet MetTyrIleIle IleValGly TrpAlaIle
551  AGTCAGCTTA CAACACAATG ATGTATATCA TCATCGTTGG TTGGGCAATT
     TyrProValGly TyrPheThr GlyTyrLeu MetGlyAspGly GlySerAla·
601  TATCCTGTAG GTTATTTCAC AGGTTACCTA ATGGGTGACG GTGGATCAGC
     ·LeuAsnLeu AsnLeuIleTyr AsnLeuAla AspPheVal AsnLysIleLeu·
651  TCTTAATCTA AACCTTATTT ATAACCTTGC TGACTTTGTT AACAAGATTC
     · PheGlyLeu IleIleTrp AsnValAlaVal LysGluSer SerAsnAla
701  TATTTGGTTT AATTATATGG AATGTTGCTG TTAAAGAATC TTCTAATGCT
751  A
```

Figure 1-39

```
     MetGlyLysLeu LeuLeuIle LeuGlySer ValIleAlaLeu ProThrPhe·
  1  ATGGGTAAAT TATTACTGAT ATTAGGTAGT GTTATTGCAC TTCCTACATT
     ·AlaAlaGly GlyGlyAspLeu AspAlaSer AspTyrThr GlyValSerPhe·
 51  TGCTGCAGGT GGTGGTGACC TTGATGCTAG TGATTACACT GGTGTTTCTT
     · TrpLeuVal ThrAlaAla LeuLeuAlaSer ThrValPhe PhePheVal
101  TTTGGTTAGT TACTGCTGCT TTATTAGCAT CTACTGTATT TTTCTTTGTT
     GluArgAspArg ValSerAla LysTrpLys ThrSerLeuAla ValSerGly·
151  GAAAGAGATA GAGTTTCTGC AAAATGGAAA ACATCATTAG CTGTATCTGG
     ·LeuIleThr GlyIleAlaPhe TrpHisCys MetTyrMet ArgGlyValTrp·
201  TCTTATTACT GGTATTGCGT TCTGGCATTG CATGTACATG AGAGGGGTAT
     · IleGluThr GlyAspSer ProThrValPhe ArgTyrIle AspTrpLeu
251  GGATTGAAAC TGGTGATTCG CCAACTGTAT TTAGATACAT TGATTGGTTA
     LeuThrValPro LeuLeuIle CysGluPhe TyrLeuIleLeu AlaAlaAla·
301  CTAACAGTTC CTCTATTAAT ATGTGAATTC TACTTAATTC TTGCTGCTGC
     ·ThrAsnVal AlaGlySerLeu PheLysLys LeuLeuVal GlySerLeuVal·
351  AACTAATGTT GCTGGATCAT TATTTAAGAA ATTACTAGTT GGTTCTCTTG
     · MetLeuVal PheGlyTyr MetGlyGluAla GlyIleMet AlaAlaTrp
401  TTATGCTTGT GTTTGGTTAC ATGGGTGAAG CAGGAATCAT GGCTGCATGG
     ProAlaPheIle IleGlyCys LeuAlaTrp ValTyrMetIle TyrGluLeu·
451  CCTGCATTCA TTATTGGGTG TTTAGCTTGG GTATACATGA TTTATGAATT
     ·TrpAlaGly GluGlyLysSer AlaCysAsn ThrAlaSer ProAlaValGln·
501  ATGGGCTGGA GAAGGAAAAT CTGCATGTAA TACTGCAAGT CCTGCTGTGC
     · SerAlaTyr AsnThrMet MetTyrIleIle ValPheGly TrpAlaIle
551  AATCAGCTTA CAACACAATG ATGTATATTA TCGTCTTTGG TTGGGCGATT
     TyrProValGly TyrPheThr GlyTyrLeu MetGlyAspGly GlySerAla·
601  TATCCTGTAG GTTATTTCAC AGGTTACCTG ATGGGTGACG GTGGATCAGC
     ·LeuAsnLeu AsnLeuIleTyr AsnLeuAla AspPheVal AsnLysIleLeu·
651  TCTTAACTTA AACCTTATCT ATAACCTTGC TGACTTTGTT AACAAGATTC
     · PheGlyLeu IleIleTrp AsnValAlaVal LysGluSer SerAsnAla
701  TATTTGGTTT AATTATATGG AATGTTGCTG TTAAAGAATC TTCTAATGCT
```

Figure 1-40

```
    MetGlyLysLeu LeuLeuIle LeuGlySer ValIleAlaLeu ProThrPhe·
  1 ATGGGTAAAT TATTACTGAT ATTAGGTAGT GTTATTGCAC TTCCTACATT
    ·AlaAlaGly GlyGlyAspLeu AspAlaSer AspTyrThr GlyValSerPhe·
 51 TGCTGCAGGT GGTGGTGACC TTGATGCTAG TGATTACACT GGTGTTTCTT
    · TrpLeuVal ThrAlaAla LeuLeuAlaSer ThrValPhe SerPheVal
101 TTTGGTTAGT TACTGCTGCT TTATTAGCAT CTACTGTATT TTCCTTTGTT
    GluArgAspArg ValSerAla LysTrpLys ThrSerLeuThr ValSerGly·
151 GAAAGAGATA GAGTTTCTGC AAAATGGAAA ACATCATTAA CTGTATCTGG
    ·LeuIleThr GlyIleAlaPhe TrpHisTyr MetTyrMet ArgGlyValTrp·
201 TCTTATTACT GGTATTGCTT TCTGGCATTA CATGTACATG AGAGGGGTAT
    · IleGluThr GlyAspSer ProThrValPhe ArgTyrIle AspTrpLeu
251 GGATTGAAAC TGGTGATTCG CCAACTGTAT TTAGATACAT TGATTGGTTA
    LeuThrValPro LeuLeuIle CysGluPhe TyrLeuIleLeu AlaAlaAla·
301 CTAACAGTTC CTCTATTAAT ATGTGAATTC TACTTAATTC TTGCTGCTGC
    ·ThrAsnVal AlaGlySerLeu PheLysLys LeuLeuVal GlySerLeuVal·
351 AACTAATGTT GCTGGATCAT TATTTAAGAA ATTACTAGTT GGTTCTCTTG
    · MetLeuVal PheGlyTyr MetGlyGluAla GlyIleMet AlaAlaTrp
401 TTATGCTTGT GTTTGGTTAC ATGGGTGAAG CAGGAATCAT GGCTGCATGG
    ProAlaPheIle IleGlyCys LeuAlaTrp ValTyrMetIle TyrGluLeu·
451 CCTGCATTCA TTATTGGGTG TTTAGCTTGG GTATACATGA TTTATGAATT
    ·TrpAlaGly GluGlyLysSer AlaCysAsn ThrAlaSer ProAlaValGln·
501 ATGGGCTGGA GAAGGAAAAT CTGCATGTAA TACTGCAAGT CCTGCTGTGC
    · SerAlaTyr AsnThrMet MetTyrIleIle IlePheGly TrpAlaIle
551 AATCAGCTTA CAACACAATG ATGTATATTA TCATCTTTGG TTGGGCGATT
    TyrProValGly TyrPheThr GlyTyrLeu MetGlyAspGly GlySerAla·
601 TATCCTGTAG GTTATTTCAC AGGTTACCTG ATGGGTGACG GTGGATCAGC
    ·LeuAsnLeu AsnLeuIleTyr AsnLeuAla AspPheVal AsnLysIleLeu·
651 TCTTAACTTA AACCTTATCT ATAACCTTGC TGACTTTGTT AACAAGATTC
    · PheGlyLeu IleIleTrp AsnValAlaVal LysGluSer SerAsnAla
701 TATTTGGTTT AATTATATGG AATGTTGCTG TTAAAGAATC TTCTAATGCT
```

Figure 1-41

```
    MetGlyLysLeu LeuLeuIle LeuGlySer ValIleAlaLeu ProThrPhe·
  1 ATGGGTAAAT TATTACTGAT ATTAGGTAGT GTTATTGCAC TTCCTACATT
    ·AlaAlaGly GlyGlyAspLeu AspAlaSer AspTyrThr GlyValSerPhe·
 51 TGCTGCAGGT GGTGGTGACC TTGATGCTAG TGATTACACT GGTGTTTCTT
    · TrpLeuVal ThrAlaAla LeuLeuAlaSer ThrValPhe PhePheVal
101 TTTGGTTAGT TACTGCTGCT TTATTAGCAT CTACTGTATT TTTCTTTGTT
    GluArgAspArg ValSerAla LysTrpLys ThrSerLeuThr ValSerGly·
151 GAAAGAGATA GAGTTTCTGC AAAATGGAAA ACATCATTAA CTGTATCTGG
    ·LeuIleThr GlyIleAlaPhe TrpHisTyr MetTyrMet ArgGlyValTrp·
201 TCTTATTACT GGTATTGCTT TCTGGCATTA CATGTACATG AGAGGGGTAT
    · IleGluThr GlyAspSer ProThrValPhe ArgTyrIle AspTrpLeu
251 GGATTGAAAC TGGTGATTCG CCAACCGTAT TTAGATACAT TGATTGGTTA
    LeuThrValPro LeuLeuIle CysGluPhe TyrLeuIleLeu AlaAlaAla·
301 CTAACAGTTC CTCTATTAAT ATGTGAATTC TACTTAATTC TTGCTGCTGC
    ·ThrAsnVal AlaGlySerLeu PheLysLys LeuLeuVal GlySerLeuVal·
351 AACTAATGTT GCTGGATCAT TATTTAAGAA ATTACTAGTT GGTTCTCTTG
    · MetLeuVal PheGlyTyr MetGlyGluAla GlyIleMet AlaAlaTrp
401 TTATGCTTGT GTTTGGTTAC ATGGGTGAAG CAGGAATCAT GGCTGCATGG
    ProAlaPheIle IleGlyCys LeuAlaTrp ValTyrMetIle TyrGluLeu·
451 CCTGCATTCA TTATTGGGTG TTTAGCTTGG GTATACATGA TTTATGAATT
    ·TrpAlaGly GluGlyLysSer AlaCysAsn ThrAlaSer ProAlaValGln·
501 ATGGGCTGGA GAAGGAAAAT CTGCATGTAA TACTGCAAGT CCTGCTGTGC
    · SerAlaTyr AsnThrMet MetTyrIleIle IlePheGly TrpAlaIle
551 AATCAGCTTA CAACACAATG ATGTATATTA TCATCTTTGG TTGGGCGATT
    TyrProValGly TyrPheThr GlyTyrLeu MetGlyAspGly GlySerAla·
601 TATCCTGTAG GTTATTTCAC AGGTTACCTG ATGGGTGACG GTGGATCAGC
    ·LeuAsnLeu AsnLeuIleTyr AsnLeuAla AspPheVal AsnLysIleLeu·
651 ACTTAACTTA AACCTTATCT ATAACCTTGC TGACTTTGTT AACAAGATTC
    · PheGlySer IleIleTrp AsnValAlaVal LysGluSer SerAsnAla
701 TATTTGGTTC AATTATATGG AATGTTGCTG TTAAAGAATC TTCTAATGCT
```

Figure 1-42

```
     MetGlyLysLeu LeuLeuIle LeuGlySer ValIleAlaLeu ProThrPhe·
  1  ATGGGTAAAT TATTACTGAT ATTAGGTAGT GTTATTGCAC TTCCTACATT
     ·AlaAlaGly GlyGlyAspLeu AspAlaSer AspTyrThr GlyValSerPhe·
 51  TGCTGCAGGT GGTGGTGACC TTGATGCTAG TGATTACACT GGTGTTTCTT
     · TrpLeuVal ThrAlaAla LeuLeuAlaSer ThrValPhe PhePheVal
101  TTTGGTTAGT TACTGCTGCT TTATTAGCGT CTACTGTATT CTTCTTTGTT
     GluArgAspArg ValSerAla LysTrpLys ThrSerLeuThr ValSerGly·
151  GAAAGAGATA GAGTGTCTGC AAAATGGAAA ACTTCATTAA CAGTATCTGG
     ·LeuValThr GlyIleAlaPhe TrpHisTyr MetTyrMet ArgGlyValTrp·
201  TTTAGTTACT GGTATTGCTT TTTGGCATTA TATGTACATG AGAGGTGTAT
     · IleGluThr GlyAspSer ProThrValPhe ArgTyrIle AspTrpLeu
251  GGATAGAAAC TGGTGATTCG CCTACTGTCT TTAGATACAT CGACTGGTTA
     LeuThrValPro LeuLeuIle CysGluPhe TyrLeuIleLeu AlaAlaAla·
301  TTAACTGTGC CTTTACTAAT ATGTGAGTTC TATCTGATAC TTGCTGCAGC
     ·ThrAsnVal AlaGlySerLeu PheLysLys LeuLeuVal GlySerLeuVal·
351  TACTAATGTT GCTGGTTCAT TATTTAAGAA ATTGCTAGTT GGTTCTCTTG
     · MetLeuVal PheGlyTyr MetGlyGluAla GlyIleMet AlaAlaTrp
401  TGATGCTTGT GTTTGGTTAC ATGGGTGAAG CAGGAATAAT GGCAGCTTGG
     ProAlaPheIle IleGlyCys LeuAlaTrp ValTyrMetIle TyrGluLeu·
451  CCTGCATTCA TCATTGGGTG TTTAGCATGG GTATATATGA TTTATGAACT
     ·TrpAlaGly GluGlyLysSer AlaCysAsn ThrAlaSer ProAlaValGln·
501  ATGGGCTGGT GAAGGAAAAT CTGCATGCAA TACTGCAAGT CCTGCTGTAC
     · SerAlaTyr AsnThrMet MetTyrIleIle IleValGly TrpAlaIle
551  AGTCAGCTTA CAACACAATG ATGTATATCA TCATCGTTGG TTGGGCAATA
     TyrProValGly TyrPheThr GlyTyrLeu MetGlyAspGly GlySerAla·
601  TATCCTGTAG GTTATTTCAC AGGTTACCTA ATGGGTGACG GTGGATCAGC
     ·LeuAsnLeu AsnLeuIleTyr AsnLeuAla AspPheVal AsnLysIleLeu·
651  TCTTAATCTA AACCTTATCT ATAACCTTGC TGACTTTGTT AACAAGATTC
     · PheGlyLeu IleIleTrp AsnValAlaVal LysGluSer SerAsnAla
701  TATTTGGTTT AATTATATGG AATGTTGCTG TTAAAGAATC TTCTAATGCT
751  A
```

Figure 1-43

```
    MetGlyLysLeu LeuLeuIle LeuGlySer ValIleAlaLeu ProThrPhe·
  1 ATGGGTAAAT TATTACTGAT ATTAGGTAGT GTTATCGCGC TTCCAACATT
    ·AlaAlaGly GlyGlyAspLeu AspAlaSer AspTyrThr GlyValSerPhe·
 51 TGCTGCTGGC GGTGGCGATC TTGATGCTAG TGACTATACT GGTGTTTCAT
    · TrpLeuVal ThrAlaAla LeuLeuAlaSer ThrValPhe PhePheVal
101 TCTGGTTAGT TACTGCTGCT CTATTAGCGT CTACTGTATT CTTCTTTGTT
    GluArgAspArg ValSerAla LysTrpLys ThrSerLeuThr ValSerGly·
151 GAAAGAGATA GAGTGTCTGC AAAATGGAAA ACTTCATTAA CAGTATCTGG
    ·LeuValThr GlyIleAlaPhe TrpHisTyr MetTyrMet ArgGlyValTrp·
201 TTTAGTTACT GGTATTGCTT TTTGGCATTA TATGTACATG AGAGGTGTAT
    · IleGluThr GlyAspSer ProThrValPhe ArgTyrIle AspTrpLeu
251 GGATAGAAAC TGGTGATTCG CCTACTGTCT TTAGATACAT CGACTGGTTA
    LeuThrValPro LeuLeuIle CysGluPhe TyrLeuIleLeu AlaAlaAla·
301 TTAACTGTGC CTTTACTAAT ATGTGAGTTC TATCTGATAC TTGCTGCAGC
    ·ThrAsnVal AlaGlySerLeu PheLysLys LeuLeuVal GlySerLeuVal·
351 TACTAATGTT GCTGGTTCAT TATTTAAGAA ATTGCTAGTT GGTTCTCTTG
    · MetLeuVal PheGlyTyr MetGlyGluAla GlyIleMet AlaAlaTrp
401 TGATGCTTGT GTTTGGTTAC ATGGGTGAAG CAGGAATAAT GGCAGCTTGG
    ProAlaPheIle IleGlyCys LeuAlaTrp ValTyrMetIle TyrGluLeu·
451 CCTGCATTCA TCATTGGATG TTTAGCATGG GTATATATGA TTTATGAACT
    ·TrpAlaGly GluGlyLysSer AlaCysAsn ThrAlaSer ProAlaValGln·
501 ATGGGCTGGT GAAGGAAAAT CTGCATGCAA TACTGCAAGT CCTGCTGTAC
    · SerAlaTyr AsnThrMet MetTyrIleIle IleValGly TrpAlaIle
551 AGTCAGCTTA CAACACAATG ATGTATATCA TCATCGTTGG TTGGGCAATT
    TyrProValGly TyrPheThr GlyTyrLeu MetGlyAspGly GlySerAla·
601 TATCCTGTAG GCTATTTCAC AGGTTACCTA ATGGGTGACG GTGGATCAGC
    ·LeuAsnLeu AsnLeuIleTyr AsnLeuAla AspPheVal AsnLysIleLeu·
651 TCTTAATCTA AACCTTATTT ATAACCTTGC TGACTTTGTT AACAAGATTC
    · PheGlyLeu IleIleTrp AsnValAlaVal LysGluSer SerAsnAla
701 TATTTGGTTT AATTATATGG AATGTTGCTG TTAAAGAATC TTCTAATGCT
751 A
```

Figure 1-44

```
     MetGlyLysLeu LeuLeuIle LeuGlySer ValIleAlaLeu ProThrPhe·
  1  ATGGGTAAAT TATTACTGAT ATTAGGTAGT GTTATTGCAC TTCCTACATT
     ·AlaAlaGly GlyGlyAspLeu AspAlaSer AspTyrThr GlyValSerPhe·
 51  TGCTGCAGGT GGTGGTGACC TTGATGCTAG TGATTACACT GGTGTTTCTT
     · TrpLeuVal ThrAlaAla LeuLeuAlaSer ThrValPhe PhePheVal
101  TTTGGTTAGT TACTGCTGCT TTATTAGCAT CTACTGTATT TTTCTTTGTT
     GluArgAspArg ValSerAla LysTrpLys ThrSerLeuThr ValSerGly·
151  GAAAGAGATA GAGTTTCTGC AAAATGGAAA ACATCATTAA CTGTATCTGG
     ·LeuValThr GlyIleAlaPhe TrpHisTyr MetTyrMet ArgGlyValTrp·
201  TCTTGTTACT GGTATTGCTT TCTGGCATTA CATGTACATG AGAGGGGTAT
     · IleGluThr GlyAspSer ProThrValPhe ArgTyrIle AspTrpLeu
251  GGATTGAAAC TGGTGATTCG CCAACTGTAT TTAGATACAT TGATTGGTTA
     LeuProValPro LeuAlaIle CysGluPhe TyrLeuIleLeu AlaAlaAla·
301  CTACCAGTTC CTCTAGCAAT ATGTGAATTC TACTTAATTC TTGCTGCTGC
     ·ThrAsnVal AlaGlySerLeu PheLysLys LeuLeuVal GlySerLeuVal·
351  AACTAATGTT GCTGGATCAT TATTTAAGAA ATTACTAGTT GGTTCTCTTG
     · MetLeuVal PheGlyTyr MetGlyGluAla GlyIleMet AlaAlaTrp
401  TTATGCTTGT GTTTGGTTAC ATGGGTGAAG CAGGAATCAT GGCTGCATGG
     ProAlaPheIle IleGlyCys LeuAlaTrp ValTyrMetIle TyrGluLeu·
451  CCTGCATTCA TTATTGGGTG TTTAGCTTGG GTATACATGA TTTATGAATT
     ·TrpAlaGly GluGlyLysSer AlaCysAsn ThrAlaSer ProAlaValGln·
501  ATGGGCTGGA GAAGGAAAAT CTGCATGTAA TACTGCAAGT CCTGCTGTGC
     · SerAlaTyr AsnThrMet MetTyrIleIle IlePheGly TrpAlaIle
551  AATCAGCTTA CAACACAATG ATGTATATTA TCATCTTTGG TTGGGCGATT
     TyrProValGly TyrPheThr GlyTyrLeu MetGlyAspGly GlySerAla·
601  TATCCTGTAG GTTATTTCAC AGGTTACCTG ATGGGTGACG GTGGATCAGC
     ·LeuAsnLeu AsnLeuIleTyr AsnLeuAla AspPheVal AsnLysIleLeu·
651  TCTTAACTTA AACCTTATCT ATAACCTTGC TGACTTTGTT AACAAGATTC
     · PheGlyLeu IleIleTrp AsnValAlaVal LysGluSer SerAsnAla
701  TATTTGGTTT AATTATATGG AATGTTGCTG TTAAAGAATC TTCTAATGCT
751  A
```

Figure 1-45

```
     MetGlyLysLeu LeuLeuIle LeuGlySer ValIleAlaLeu ProThrPhe·
  1  ATGGGTAAAT TATTACTGAT ATTAGGTAGT GTTATTGCGC TTCCAACATT
     ·AlaAlaGly GlyGlyAspLeu AspAlaSer AspTyrThr GlyValSerPhe·
 51  TGCCGCTGGT GGTGGTGACC TGGATGCTAG TGACTACACT GGTGTATCTT
     · TrpLeuVal ThrAlaAla LeuLeuAlaSer ThrValPhe PhePheVal
101  TCTGGTTAGT TACTGCTGCT CTATTAGCAT CTACTGTATT TTTCTTTGTT
     GluArgAspArg ValSerAla LysTrpLys ThrSerLeuThr ValSerGly·
151  GAAAGAGACA GAGTTTCTGC TAAATGGAAA ACATCATTAA CAGTATCTGG
     ·LeuValThr GlyIleAlaPhe TrpHisTyr MetTyrMet ArgGlyValTrp·
201  TTTAGTTACT GGTATTGCTT TTTGGCATTA CATGTACATG AGAGGTGTAT
     · IleGluThr GlyAspSer ProThrValPhe ArgTyrIle AspTrpLeu
251  GGATTGAAAC TGGTGATTCA CCAACTGTTT TTAGATACAT CGACTGGTTG
     LeuThrValPro LeuLeuIle CysGluPhe TyrLeuIleLeu AlaAlaAla·
301  CTAACTGTGC CTTTACTAAT TTGTGAGTTC TACTTAATAC TAGCAGCAGC
     ·ThrAsnVal AlaGlySerLeu PheLysLys LeuLeuVal GlySerLeuVal·
351  TACTAACGTT GCTGGTTCTT TATTCAAGAA ATTACTAGTT GGTTCTCTTG
     · MetLeuVal PheGlyTyr MetGlyGluAla GlyIleMet AlaAlaTrp
401  TTATGCTTGT GTTTGGTTAC ATGGGTGAAG CAGGAATTAT GGCAGCCTGG
     ProAlaPheIle IleGlyCys LeuAlaTrp ValTyrMetIle TyrGluLeu·
451  CCTGCATTCA TTATAGGATG TTTAGCATGG GTATACATGA TTTATGAATT
     ·TrpAlaGly GluGlyLysSer AlaCysAsn ThrAlaSer ProAlaValGln·
501  ATGGGCTGGA GAAGGAAAGT CTGCATGTAA CACTGCAAGT CCTGCAGTTC
     · SerAlaTyr AsnThrMet MetTyrIleIle IlePheGly TrpAlaIle
551  AGTCAGCTTA CAACACAATG ATGTATATCA TCATCTTTGG TTGGGCTATT
     TyrLeuValGly TyrPheThr GlyTyrLeu MetGlyAspGly GlySerAla·
601  TACCTTGTAG GTTATTTCAC TGGTTACCTA ATGGGTGACG GTGGATCAGC
     ·LeuAsnLeu AsnLeuIleTyr AsnLeuAla AspPheVal AsnLysIleLeu·
651  TCTTAACTTA AACCTTATCT ATAACCTTGC TGACTTTGTT AACAAGATTC
     · PheGlyLeu IleIleTrp AsnValAlaVal LysGluSer SerAsnAla
701  TATTTGGTTT AATTATATGG AATGTTGCTG TTAAAGAATC TTCTAATGCT
751  A
```

Figure 1-46

```
     MetGlyLysLeu LeuLeuIle LeuGlySer ValIleAlaLeu ProThrPhe·
   1 ATGGGTAAAT TATTACTGAT ATTAGGTAGT GTTATTGCGC TTCCAACATT
     ·AlaAlaGly GlyGlyAspLeu AspAlaSer AspTyrThr GlyValSerPhe·
  51 TGCCGCTGGC GGTGGCGATC TTGATGCTAG TGACTACACT GGTGTTTCTT
     · TrpLeuVal ThrAlaAla LeuLeuAlaSer ThrValPhe PhePheVal
 101 TCTGGTTAGT TACTGCTGCT CTATTAGCAT CTACTGTATT CTTCTTTGTT
     GluArgAspArg ValSerAla LysTrpLys ThrSerLeuThr ValSerGly·
 151 GAAAGGGATA GAGTATCTGC AAAATGGAAA ACTTCATTAA CAGTATCTGG
     ·LeuValThr GlyIleAlaPhe TrpHisTyr MetTyrMet ArgGlyValTrp·
 201 TTTAGTTACT GGTATTGCTT TTTGGCATTA TATGTACATG AGAGGTGTAT
     · IleGluThr GlySerSer ProThrValPhe ArgTyrIle AspTrpLeu
 251 GGATAGAAAC TGGTAGTTCA CCTACTGTCT TTAGATACAT TGACTGGCTA
     LeuThrValPro LeuLeuIle CysGluPhe TyrLeuIleLeu AlaAlaAla·
 301 TTAACAGTGC CTTTACTAAT ATGTGAGTTC TATTTAATAC TTGCCGCAGC
     ·ThrAsnVal AlaGlySerLeu PheLysLys LeuLeuVal GlySerLeuVal·
 351 TACTAATGTT GCTGGTTCAT TATTTAAGAA ATTGCTAGTT GGTTCTCTTG
     · MetLeuVal PheGlyTyr MetGlyGluAla GlyIleMet AlaAlaTrp
 401 TTATGCTTGT GTTTGGTTAC ATGGGTGAAG CAGGAATTAT GGCAGCCTGG
     ProAlaPheIle IleGlyCys LeuAlaTrp ValTyrMetIle TyrGluLeu·
 451 CCTGCATTCA TTATAGGATG TTTAGCATGG GTATACATGA TTTATGAATT
     ·TrpAlaGly GluGlyLysSer AlaCysAsn ThrAlaSer ProAlaValGln·
 501 ATGGGCTGGA GAAGGAAAGT CTGCATGTAA CACTGCAAGT CCTGCAGTTC
     · SerAlaTyr AsnThrMet MetTyrIleIle IlePheGly TrpAlaIle
 551 AGTCAGCTTA CAACACAATG ATGTATATCA TCATCTTTGG TTGGGCTATT
     TyrLeuValGly TyrPheThr GlyTyrLeu MetGlyAspGly GlySerAla·
 601 TACCTTGTAG GTTATTTCAC TGGTTACCTA ATGGGTGACG GTGGATCAGC
     ·LeuAsnLeu AsnLeuIleTyr AsnLeuAla AspPheVal AsnLysIleLeu·
 651 TCTTAACTTA AACCTTATCT ATAACCTTGC TGACTTTGTT AACAAGATTC
     · PheGlyLeu IleIleTrp AsnValAlaVal LysGluSer SerAsnAla
 701 TATTTGGTTT AATTATATGG AATGTTGCTG TTAAAGAATC TTCTAATGCT
 751 A
```

Figure 1-47

```
    MetGlyLysLeu LeuLeuArg LeuGlySer ValIleAlaLeu ProThrPhe·
  1 ATGGGTAAAT TATTACTGAG ATTAGGTAGT GTTATCGCGC TTCCAACATT
    ·AlaAlaGly GlyGlyAspLeu AspAlaSer AspTyrThr GlyValSerPhe·
 51 TGCTGCTGGC GGTGGCGATC TTGATGCTAG TGACTATACT GGTGTTTCAT
    · TrpLeuVal ThrAlaAla LeuLeuAlaSer ThrValPhe PhePheVal
101 TCTGGTTAGT TACTGCTGCT CTATTAGCGT CTACTGTATT CTTCTTTGTT
    GluArgAspArg ValSerAla LysTrpLys ThrSerLeuThr ValSerGly·
151 GAAAGAGATA GAGTGTCTGC AAAATGGAAA ACTTCATTAA CAGTATCTGG
    ·LeuValThr GlyIleAlaPhe TrpHisTyr MetTyrMet ArgGlyValTrp·
201 TTTAGTTACT GGTATTGCTT TTTGGCATTA TATGTACATG AGAGGTGTAT
    · IleGluThr GlyAspSer ProThrValPhe ArgTyrIle AspTrpLeu
251 GGATAGAAAC TGGTGATTCG CCTACTGTCT TTAGATACAT CGACTGGTTA
    LeuThrValPro LeuLeuIle CysGluPhe TyrLeuIleLeu AlaAlaAla·
301 TTAACTGTGC CTTTACTAAT ATGTGAGTTC TATCTGATAC TTGCTGCAGC
    ·ThrAsnVal AlaGlySerLeu PheLysLys LeuLeuVal GlySerLeuVal·
351 TACTAATGTT GCTGGTTCAT TATTTAAGAA ATTGCTAGTT GGTTCTCTTG
    · MetLeuVal PheGlyTyr MetGlyGluAla GlyIleMet AlaAlaTrp
401 TGATGCTTGT GTTTGGTTAC ATGGGTGAAG CAGGAATAAT GGCAGCTTGG
    ProAlaPheIle IleGlyCys LeuAlaTrp ValTyrMetIle TyrGluLeu·
451 CCTGCATTCA TCATTGGATG TTTAGCATGG GTATATATGA TTTATGAACT
    ·TrpAlaGly GluGlyLysSer AlaCysAsn ThrAlaSer ProAlaValGln·
501 ATGGGCTGGT GAAGGAAAAT CTGCATGCAA TACTGCAAGT CCTGCTGTAC
    · SerAlaTyr AsnThrMet MetTyrIleIle IleValGly TrpAlaIle
551 AGTCAGCTTA CAACACAATG ATGTATATCA TCATCGTTGG TTGGGCAATT
    TyrProValGly TyrPheThr GlyTyrLeu MetGlyAspGly GlySerAla·
601 TATCCTGTAG GTTATTTCAC AGGTTACCTA ATGGGTGACG GTGGATCAGC
    ·LeuAsnLeu AsnLeuIleTyr AsnLeuAla AspPheVal AsnLysIleLeu·
651 TCTTAATCTA AACCTTATTT ATAACCTTGC TGACTTTGTT AACAAGATTC
    · PheGlyLeu IleIleTrp AsnValAlaVal LysGluSer SerAsnAla
701 TATTTGGTTT AATTATATGG AATGTTGCTG TTAAAGAATC TTCTAATGCT
751 A
```

Figure 1-48

```
     MetGlyLysLeu LeuLeuIle LeuGlySer ValIleAlaLeu ProThrPhe·
  1  ATGGGTAAAT TATTACTGAT ATTAGGTAGT GTTATTGCAC TTCCTACATT
     ·AlaAlaGly GlyGlyAspLeu AspAlaSer AspTyrThr GlyValSerPhe·
 51  TGCTGCAGGT GGTGGTGACC TTGATGCTAG TGATTACACT GGTGTTTCTT
     · TrpLeuVal ThrAlaAla LeuLeuAlaSer ThrValPhe PhePheVal
101  TTTGGTTAGT TACTGCTGCT TTATTAGCAT CTACTGTATT TTTCTTTGTT
     GluArgAspArg ValSerAla LysTrpLys ThrSerLeuAla ValSerGly·
151  GAAAGAGATA GAGTTTCTGC AAAATGGAAA ACATCATTAG CTGTATCTGG
     ·LeuIleThr GlyIleAlaPhe TrpHisTyr MetTyrMet ArgGlyValTrp·
201  TCTTATTACT GGTATTGCGT TCTGGCATTA CATGTACATG AGAGGGGTAT
     · IleGluThr GlyAspSer ProThrValPhe ArgTyrIle AspTrpLeu
251  GGATTGAAAC TGGTGATTCG CCAACTGTAT TTAGATACAT TGATTGGTTA
     LeuThrValPro LeuLeuIle CysGluPhe TyrLeuIleLeu AlaAlaAla·
301  CTAACAGTTC CTCTATTAAT ATGTGAATTC TACTTAATTC TTGCTGCTGC
     ·ThrAsnVal AlaGlySerLeu PheLysLys LeuLeuVal GlySerLeuVal·
351  AACTAATGTT GCTGGATCAT TATTTAAGAA ATTACTAGTT GGTTCTCTTG
     · MetLeuVal PheGlyTyr MetGlyGluAla GlyIleMet AlaAlaTrp
401  TTATGCTTGT GTTTGGTTAC ATGGGTGAAG CAGGAATCAT GGCTGCATGG
     ProAlaPheIle IleGlyCys LeuAlaTrp ValTyrMetIle TyrGluLeu·
451  CCTGCATTCA TTATTGGGTG TTTAGCTTGG GTATACATGA TTTATGAATT
     ·TrpAlaGly GluGlyLysSer AlaCysAsn ThrAlaSer ProAlaValGln·
501  ATGGGCTGGA GAAGGAAAAT CTGCATGTAA TACTGCAAGT CCTGCTGTGC
     · SerAlaTyr AsnThrMet MetTyrIleIle IleValGly TrpAlaIle
551  AGTCAGCTTA CAACACAATG ATGTATATCA TCATCGTTGG TTGGGCAATA
     TyrProValGly TyrPheThr GlyTyrLeu MetGlyAspGly GlySerAla·
601  TATCCTGTAG GTTATTTCAC AGGTTACCTA ATGGGTGACG GTGGATCAGC
     ·LeuAsnLeu AsnLeuIleTyr AsnLeuAla AspPheVal AsnLysIleLeu·
651  TCTTAATCTA AACCTTATTT ATAACCTTGC TGACTTTGTT AACAAGATTC
     · PheGlyLeu IleIleTrp AsnValAlaVal LysGluSer SerAsnAla
701  TATTTGGTTT AATTATATGG AATGTTGCTG TTAAAGAATC TTCTAATGCT
751  A
```

Figure 1-49

```
    MetGlyLysLeu LeuLeuIle LeuGlySer ValIleAlaLeu ProThrPhe·
  1 ATGGGTAAAT TATTACTGAT CTTAGGTAGT GTTATTGCAC TTCCTACATT
    ·AlaAlaGly GlyGlyAspPro AspAlaSer AspTyrThr GlyValSerPhe·
 51 TGCTGCAGGT GGTGGTGACC CTGATGCTAG TGATTACACT GGTGTTTCTT
    · TrpLeuVal ThrAlaAla LeuLeuAlaSer ThrValPhe PhePheVal
101 TTTGGTTAGT TACTGCTGCT TTATTAGCAT CTACTGTATT TTTCTTTGTT
    GluArgAspArg ValSerAla GluTrpLys ThrSerLeuThr ValSerGly·
151 GAAAGAGATA GAGTTTCTGC AGAATGGAAA ACATCATTAA CTGTATCTGG
    ·LeuValThr GlyIleAlaPhe TrpHisTyr MetTyrMet ArgGlyValTrp·
201 TCTTGTTACT GGTATTGCTT TCTGGCATTA CATGTACATG AGAGGGGTAT
    · IleGluThr GlyAspSer ProThrValPhe ArgTyrIle AspTrpLeu
251 GGATTGAAAC TGGTGATTCG CCAACTGTAT TTAGATACAT TGATTGGTTA
    LeuThrValPro LeuGluIle CysGluPhe TyrLeuIleLeu AlaAlaAla·
301 CTAACAGTTC CTCTAGAAAT ATGTGAATTC TACTTAATTC TTGCTGCTGC
    ·ThrAsnVal AlaGlySerLeu PheLysLys LeuLeuVal GlySerLeuVal·
351 AACTAATGTT GCTGGATCAT TATTTAAGAA ATTACTAGTT GGTTCTCTTG
    · MetLeuVal PheGlyTyr MetGlyGluAla GlyIleMet AlaAlaTrp
401 TTATGCTTGT GTTTGGTTAC ATGGGTGAAG CAGGAATCAT GGCTGCATGG
    ProAlaPheIle IleGlyCys LeuAlaTrp ValTyrMetIle TyrGluLeu·
451 CCTGCATTCA TTATTGGGTG TTTAGCTTGG GTATACATGA TTTATGAATT
    ·TrpAlaGly GluGlyLysSer AlaCysAsn ThrAlaSer ProAlaValGln·
501 ATGGGCTGGA GAAGGAAAAT CTGCATGTAA TACTGCAAGT CCTGCTGTGC
    · SerAlaTyr AsnThrMet MetTyrIleIle IlePheGly TrpAlaIle
551 AATCAGCTTA CAACACAATG ATGTATATTA TCATCTTTGG TTGGGCGATT
    TyrProValGly TyrPheThr GlyTyrLeu MetGlyAspGly GlySerAla·
601 TATCCTGTAG GTTATTTCAC AGGTTACCTG ATGGGTGACG GTGGATCAGC
    ·LeuAsnLeu AsnLeuIleTyr AsnLeuAla AspPheVal AsnLysIleLeu·
651 TCTTAACTTA AACCTTATCT ATAACCTTGC TGACTTTGTT AACAAGATTC
    · IleGlyLeu IleIleTrp AsnValAlaVal LysGluSer SerAsnAla
701 TAATTGGTTT AATTATATGG AATGTTGCTG TTAAAGAATC TTCTAATGCT
751 A
```

Figure 1-50

```
    MetGlyLysLeu LeuLeuIle LeuGlySer ValIleAlaLeu ProThrPhe·
  1 ATGGGTAAAT TATTACTGAT CTTAGGTAGT GTTATTGCAC TTCCTACATT
    ·AlaAlaGly GlyGlyAspLeu AspAlaSer AspTyrThr GlyValSerPhe·
 51 TGCTGCAGGT GGTGGTGACC TTGATGCTAG TGATTACACT GGTGTTTCTT
    · TrpLeuVal ThrAlaAla LeuLeuAlaSer ThrValPhe PhePheVal
101 TTTGGTTAGT TACTGCTGCT TTATTAGCAT CTACTGTATT TTTCTTTGTT
    GluArgAspArg ValSerAla LysTrpLys ThrSerLeuThr ValSerGly·
151 GAAAGAGATA GAGTTTCTGC AAAATGGAAA ACATCATTAA CTGTATCTGG
    ·LeuValThr GlyIleAlaPhe TrpHisTyr MetTyrMet ArgGlyValTrp·
201 TCTTGTTACT GGTATTGCTT TCTGGCATTA CATGTACATG AGAGGGGTAT
    · IleGluThr GlyAspSer ProThrValPhe ArgTyrIle AspTrpLeu
251 GGATTGAAAC TGGTGATTCG CCAACTGTAT TTAGATACAT TGATTGGTTA
    LeuThrValPro LeuValIle CysGluPhe TyrLeuIleLeu AlaAlaAla·
301 CTAACAGTTC CTCTAGTAAT ATGTGAATTC TACTTAATTC TTGCTGCTGC
    ·ThrAsnVal AlaGlySerLeu PheLysLys LeuLeuVal GlySerLeuVal·
351 AACTAATGTT GCTGGATCAT TATTTAAGAA ATTACTAGTT GGTTCTCTTG
    · MetLeuVal PheGlyTyr MetGlyGluAla GlyIleMet AlaAlaTrp
401 TTATGCTTGT GTTTGGTTAC ATGGGTGAAG CAGGAATCAT GGCTGCATGG
    ProAlaPheIle IleGlyCys LeuAlaTrp ValTyrMetIle TyrGluLeu·
451 CCTGCATTCA TTATTGGGTG TTTAGCTTGG GTATACATGA TTTATGAATT
    ·TrpAlaGly GluGlyLysSer AlaCysAsn ThrAlaSer ProAlaValGln·
501 ATGGGCTGGA GAAGGAAAAT CTGCATGTAA TACTGCAAGT CCTGCTGTGC
    · SerAlaTyr AsnThrMet MetTyrIleIle IlePheGly TrpAlaIle
551 AATCAGCTTA CAACACGATG ATGTATATTA TCATCTTTGG TTGGGCGATT
    TyrProValGly TyrPheThr GlyTyrLeu MetGlyAspGly GlySerAla·
601 TATCCTGTAG GTTATTTCAC AGGTTACCTG ATGGGTGACG GTGGATCAGC
    ·LeuAsnLeu AsnLeuIleTyr AsnLeuAla AspPheVal AsnLysIleLeu·
651 TCTTAACTTA AACCTTATCT ATAACCTTGC TGACTTTGTT AACAAGATTC
    · PheGlyLeu IleIleTrp AsnValAlaVal LysGluSer SerAsnAla
701 TATTTGGTTT AATTATATGG AATGTTGCTG TTAAAGAATC TTCTAATGCT
751 A
```

Figure 1-51

```
    MetGlyLysLeu LeuLeuIle LeuGlySer ValIleAlaLeu ProThrPhe·
  1 ATGGGTAAAT TATTACTGAT ATTAGGTAGT GTTATTGCAC TTCCTACATT
    ·AlaAlaGly GlyGlyAspLeu AspAlaSer AspTyrThr GlyValSerPhe·
 51 TGCTGCAGGT GGTGGTGACC TTGATGCTAG TGATTACACT GGTGTTTCTT
    · TrpLeuVal ThrAlaAla LeuLeuAlaSer ThrValPhe PhePheVal
101 TTTGGTTAGT TACTGCTGCT TTATTAGCAT CTACTGTATT TTTCTTTGTT
    GluArgAspArg ValSerAla LysTrpLys ThrSerLeuThr ValProGly·
151 GAAAGAGATA GAGTTTCTGC AAAATGGAAA ACATCATTAA CTGTACCTGG
    ·LeuIleThr AspIleAlaPhe TrpHisTyr MetTyrMet ArgGlyValTrp·
201 TCTTATTACT GATATTGCTT TCTGGCATTA CATGTACATG AGAGGGGTAT
    · IleGluThr GlyAspSer ProThrValPhe ArgTyrIle AspTrpLeu
251 GGATTGAAAC TGGTGATTCG CCAACTGTAT TTAGATACAT TGATTGGTTA
    LeuThrValPro LeuGlnIle CysGluPhe TyrLeuIleLeu AlaAlaAla·
301 CTAACAGTTC CTCTACAAAT ATGTGAATTC TACTTAATTC TTGCTGCTGC
    ·ThrAsnVal AlaGlySerLeu PheLysLys LeuLeuVal GlySerLeuVal·
351 AACTAATGTT GCTGGATCAT TATTTAAGAA ATTACTAGTT GGTTCTCTTG
    · MetLeuVal PheGlyTyr MetGlyGluAla GlyIleMet AlaAlaTrp
401 TTATGCTTGT GTTTGGTTAC ATGGGTGAAG CAGGAATCAT GGCTGCATGG
    ProAlaPheIle IleGlyCys LeuAlaTrp ValTyrMetIle TyrGluLeu·
451 CCTGCATTCA TTATTGGGTG TTTAGCTTGG GTATACATGA TTTATGAATT
    ·TrpAlaGly GluGlyLysSer AlaCysAsn ThrAlaSer ProAlaValGln·
501 ATGGGCTGGA GAAGGAAAAT CTGCATGTAA TACTGCGAGT CCTGCTGTGC
    · SerAlaTyr AsnThrMet MetTyrIleIle IlePheGly TrpAlaIle
551 AATCAGCTTA CAACACAATG ATGTATATTA TCATCTTTGG TTGGGCGATT
    TyrProValGly TyrPheThr GlyTyrLeu MetGlyAspGly GlySerAla·
601 TATCCTGTAG GTTATTTCAC AGGTTACCTG ATGGGTGACG GTGGATCAGC
    ·LeuAsnLeu AsnLeuIleTyr AsnLeuAla AspPheVal AsnLysIleLeu·
651 TCTTAACTTA AACCTTATCT ATAACCTTGC TGACTTTGTT AACAAGATTC
    · PheGlyLeu IleIleTrp AsnValAlaVal LysGluSer SerAsnAla
701 TATTTGGTTT AATTATATGG AATGTTGCTG TTAAAGAATC TTCTAATGCT
751 A
```

Figure 1-52

```
    MetGlyLysLeu LeuLeuIle LeuGlySer ValIleAlaLeu ProThrPhe·
  1 ATGGGTAAAT TATTACTGAT ATTAGGTAGT GTTATTGCAC TTCCTACATT
    ·AlaAlaGly GlyGlyAspLeu AspAlaSer AspTyrThr GlyValSerPhe·
 51 TGCTGCAGGT GGTGGTGACC TTGATGCTAG TGATTACACT GGTGTTTCTT
    · TrpLeuVal ThrAlaAla LeuLeuAlaSer ThrValPhe PhePheVal
101 TTTGGTTAGT TACTGCTGCT TTATTAGCAT CTACTGTATT TTTCTTTGTT
    GluArgAspArg ValSerAla LysTrpLys ThrSerLeuThr ValProGly·
151 GAAAGAGATA GAGTTTCTGC AAAATGGAAA ACATCATTAA CTGTACCTGG
    ·LeuIleThr AspIleAlaPhe TrpHisTyr MetTyrMet ArgGlyValTrp·
201 TCTTATTACT GATATTGCTT TCTGGCATTA CATGTACATG AGAGGGGTAT
    · IleGluThr GlyAspSer ProThrValPhe ArgTyrIle AspTrpLeu
251 GGATTGAAAC TGGTGATTCG CCAACTGTAT TTAGATACAT TGATTGGTTA
    LeuThrValPro LeuGlnIle CysGluPhe TyrLeuIleLeu AlaAlaAla·
301 CTAACAGTTC CTCTACAAAT ATGTGAATTC TACTTAATTC TTGCTGCTGC
    ·ThrAsnVal AlaGlySerLeu PheLysLys LeuLeuVal GlySerLeuVal·
351 AACTAATGTT GCTGGATCAT TATTTAAGAA ATTACTAGTT GGTTCTCTTG
    · MetLeuVal PheGlyTyr MetGlyGluAla GlyIleMet AlaAlaTrp
401 TTATGCTTGT GTTTGGTTAC ATGGGTGAAG CAGGAATCAT GGCTGCATGG
    ProAlaPheIle IleGlyCys LeuAlaTrp ValTyrMetIle TyrGluLeu·
451 CCTGCATTCA TTATTGGGTG TTTAGCTTGG GTATACATGA TTTATGAATT
    ·TrpAlaGly GluGlyLysSer AlaCysAsn ThrAlaSer ProAlaValGln·
501 ATGGGCTGGA GAAGGAAAAT CTGCATGTAA TACTGCGAGT CCTGCTGTGC
    · SerAlaTyr AsnThrMet MetTyrIleIle IlePheGly TrpAlaIle
551 AATCAGCTTA CAACACAATG ATGTATATTA TCATCTTTGG TTGGGCGATT
    TyrProValGly TyrPheThr GlyTyrLeu MetGlyAspGly GlySerAla·
601 TATCCTGTAG GTTATTTCAC AGGTTACCTG ATGGGTGACG GTGGATCAGC
    ·LeuAsnLeu AsnLeuIleTyr AsnLeuAla AspPheVal AsnLysIleLeu·
651 TCTTAACTTA AACCTTATCT ATAACCTTGC TGACTTTGTT AACAAGATTC
    · PheGlyLeu IleIleTrp AsnValAlaVal LysGluSer SerAsn
701 TATTTGGTTT AATTATATGG AATGTTGCTG TTAAAGAATC TTCTAATT
```

Figure 1-53

```
    MetGlyLysLeu LeuLeuIle LeuGlySer ValIleAlaLeu ProThrPhe·
  1 ATGGGTAAAT TATTACTGAT ATTAGGTAGT GTTATTGCAC TTCCTACATT
    ·AlaAlaGly GlyGlyAspLeu AspAlaSer GlyTyrThr GlyValSerPhe·
 51 TGCTGCAGGT GGTGGTGACC TTGATGCTAG TGGTTACACT GGTGTTTCTT
    · TrpLeuVal ThrAlaAla LeuLeuAlaSer ThrValPhe PhePheVal
101 TTTGGTTAGT TACTGCTGCT TTATTAGCAT CTACTGTATT TTTCTTTGTT
    GluArgAspArg ValSerAla LysTrpLys ThrSerLeuThr ValProGly·
151 GAAAGAGATA GAGTTTCTGC AAAATGGAAA ACATCATTAA CTGTACCTGG
    ·LeuIleThr AspIleAlaPhe TrpHisTyr MetTyrMet ArgGlyValTrp·
201 TCTTATTACT GATATTGCTT TCTGGCATTA CATGTACATG AGAGGGGTAT
    · IleGluThr GlyAspSer ProThrValPhe ArgTyrIle AspTrpLeu
251 GGATTGAAAC TGGTGATTCG CCAACTGTAT TTAGATACAT TGATTGGTTA
    LeuThrValSer LeuGlnIle CysGluPhe TyrLeuIleLeu AlaAlaAla·
301 CTAACAGTTT CTCTACAAAT ATGTGAATTC TACTTAATTC TTGCTGCTGC
    ·ThrAsnVal AlaGlySerLeu PheLysLys LeuLeuVal GlySerLeuVal·
351 AACTAATGTT GCTGGATCAT TATTTAAGAA ATTACTAGTT GGTTCTCTTG
    · MetLeuVal PheGlyTyr MetGlyGluAla GlyIleMet AlaAlaTrp
401 TTATGCTTGT GTTTGGTTAC ATGGGTGAAG CAGGAATCAT GGCTGCATGG
    ProAlaPheIle IleGlyCys LeuAlaTrp ValTyrMetIle TyrGluLeu·
451 CCTGCATTCA TTATTGGGTG TTTAGCTTGG GTATACATGA TTTATGAATT
    ·TrpAlaGly GluGlyLysSer AlaCysAsn ThrAlaSer ProAlaValGln·
501 ATGGGCTGGA GAAGGAAAAT CTGCATGTAA TACTGCGAGT CCTGCTGTGC
    · SerAlaTyr AsnThrMet MetTyrIleIle IlePheGly TrpAlaIle
551 AATCAGCTTA CAACACAATG ATGTATATTA TCATCTTTGG TTGGGCGATT
    TyrProValGly TyrPheThr GlyTyrLeu MetGlyAspGly GlySerAla·
601 TATCCTGTAG GTTATTTCAC AGGTTACCTG ATGGGTGACG GTGGATCAGC
    ·LeuAsnLeu AsnLeuIleTyr AsnLeuAla AspPheVal AsnLysIleLeu·
651 TCTTAACTTA AACCTTATCT ATAACCTTGC TGACTTTGTT AACAAGATTC
    · PheGlyLeu IleIleTrp AsnValAlaVal LysGluSer SerAsnAla
701 TATTTGGTTT AATTATATGG AATGTTGCTG TTAAAGAATC TTCTAATGCT
751 A
```

Figure 1-54

```
    MetGlyLysLeu LeuLeuIle LeuGlySer ValIleAlaLeu ProThrPhe·
  1 ATGGGTAAAT TATTACTGAT ATTAGGTAGT GTTATTGCAC TTCCTACATT
    ·AlaAlaGly GlyGlyAspLeu AspAlaSer AspTyrThr GlyValSerPhe·
 51 TGCTGCAGGT GGTGGTGACC TTGATGCTAG TGATTACACT GGTGTTTCTT
    · TrpLeuVal ThrAlaAla LeuLeuAlaSer ThrValPhe PhePheVal
101 TTTGGTTAGT TACTGCTGCT TTATTAGCAT CTACTGTATT TTTCTTTGTT
    GluArgAspArg ValSerAla LysTrpLys ThrSerLeuThr ValProGly·
151 GAAAGAGATA GAGTTTCTGC AAAATGGAAA ACATCATTAA CTGTACCTGG
    ·LeuValThr GlyIleAlaPhe TrpHisTyr MetTyrMet ArgGlyValTrp·
201 TCTTGTTACT GGTATTGCTT TCTGGCATTA CATGTACATG AGAGGGGTAT
    · IleGluThr GlyAspSer ProAlaValPhe ArgTyrIle AspTrpLeu
251 GGATTGAAAC TGGTGATTCG CCAGCTGTAT TTAGATACAT TGATTGGTTA
    LeuThrValPro LeuGluIle CysGluPhe TyrLeuIleLeu AlaAlaAla·
301 CTAACAGTTC CTCTAGAGAT ATGTGAATTC TACTTGATTC TTGCTGCTGC
    ·ThrAsnVal AlaGlySerLeu PheLysLys LeuLeuVal GlySerLeuVal·
351 AACTAATGTT GCTGGATCAT TATTTAAGAA ATTACTAGTT GGTTCTCTTG
    · MetLeuVal PheGlyTyr MetGlyGluAla GlyIleMet AlaAlaTrp
401 TTATGCTTGT GTTTGGTTAC ATGGGTGAAG CAGGAATCAT GGCTGCATGG
    ProAlaPheIle IleGlyCys LeuAlaTrp ValTyrMetIle TyrGluLeu·
451 CCTGCATTCA TTATTGGGTG TTTAGCTTGG GTATACATGA TTTATGAATT
    ·TrpAlaGly GluGlyLysSer AlaCysAsn ThrAlaSer ProAlaValGln·
501 ATGGGCTGGA GAAGGAAAAT CTGCATGTAA TACTGCAAGT CCTGCTGTGC
    · SerAlaTyr AsnThrMet MetTyrIleIle IlePheGly TrpAlaIle
551 AATCAGCTTA CAACACAATG ATGTATATTA TCATCTTTGG TTGGGCGATT
    TyrProValGly TyrPheThr GlyTyrLeu MetGlyAspGly GlySerAla·
601 TATCCTGTAG GTTATTTCAC AGGTTACCTG ATGGGTGACG GTGGATCAGC
    ·LeuAsnLeu AsnLeuIleTyr AsnLeuAla AspPheVal AsnLysIleLeu·
651 TCTTAACTTA AACCTTATCT ATAACCTTGC TGACTTTGTT AACAAGATTC
    · PheGlyLeu IleIleTrp AsnValAlaVal LysGluSer SerAsnAla
701 TATTTGGTTT AATTATATGG AATGTTGCTG TTAAAGAATC TTCTAATGCT
751 A
```

Figure 1-55

```
    MetGlyLysLeu LeuValMet LeuGlySer ValIleAlaLeu ProThrPhe·
  1 ATGGGTAAAT TATTAGTGAT GTTAGGTAGT GTTATTGCGC TTCCAACATT
    ·AlaAlaGly GlyGlyAspLeu AspAlaSer AspTyrThr GlyValSerPhe·
 51 TGCCGCTGGT GGTGGTGACC TGGATGCTAG TGACTACACT GGTGTATCTT
    · TrpLeuVal ThrAlaAla LeuLeuAlaSer ThrValPhe PhePheVal
101 TCTGGTTAGT TACTGCTGCT CTATTAGCAT CTACTGTATT TTTCTTTGTT
    GluArgAspArg ValSerAla LysTrpLys ThrSerLeuThr ValSerGly·
151 GAAAGAGACA GAGTTTCTGC TAAATGGAAA ACATCATTAA CAGTATCTGG
    ·LeuValThr GlyIleAlaPhe TrpHisTyr MetTyrMet ArgGlyValTrp·
201 TTTAGTTACT GGTATTGCTT TTTGGCATTA CATGTACATG AGAGGTGTAT
    · IleGluThr GlyAspSer ProThrValPhe ArgTyrIle AspTrpLeu
251 GGATTGAAAC TGGTGATTCA CCAACTGTTT TTAGATACAT CGACTGGTTG
    LeuThrValPro LeuLeuIle CysGluPhe TyrLeuIleLeu AlaAlaAla·
301 CTAACTGTGC CTTTACTAAT TTGTGAGTTC TACTTAATAC TAGCAGCAGC
    ·ThrAsnVal AlaGlySerLeu PheLysLys LeuLeuVal GlySerLeuVal·
351 TACTAACGTT GCTGGTTCTT TATTCAAGAA ATTACTAGTT GGTTCTCTTG
    · MetLeuVal PheGlyTyr MetGlyGluAla GlyIleMet AlaAlaTrp
401 TTATGCTTGT GTTTGGTTAC ATGGGTGAAG CAGGAATTAT GGCAGCCTGG
    ProAlaPheIle IleGlyCys LeuAlaTrp ValTyrMetIle TyrGluLeu·
451 CCTGCATTCA TTATAGGATG TTTAGCATGG GTATACATGA TTTATGAATT
    ·TrpAlaGly GluGlyLysSer AlaCysAsn ThrAlaSer ProAlaValGln·
501 ATGGGCTGGA GAAGGAAAGT CTGCATGTAA CACTGCAAGT CCTGCAGTTC
    · SerAlaTyr AsnThrMet MetTyrIleIle IlePheGly TrpAlaIle
551 AGTCAGCTTA CAACACAATG ATGTATATCA TCATCTTTGG TTGGGCTATT
    TyrProValGly TyrPheThr GlyTyrLeu MetGlyAspGly GlySerAla·
601 TACCCTGTAG GTTATTTCAC TGGTTACCTA ATGGGTGACG GTGGATCAGC
    ·LeuAsnLeu AsnLeuIleTyr AsnLeuAla AspPheVal AsnLysIleLeu·
651 TCTTAACTTA AACCTTATCT ATAACCTTGC TGACTTTGTT AACAAGATTC
    · PheGlyLeu IleIleTrp AsnValAlaVal LysGluSer SerAsnAla
701 TATTTGGTTT AATTATATGG AATGTTGCTG TTAAAGAATC TTCTAATGCT
751 A
```

Figure 1-56

```
     MetGlyLysArg LeuValIle LeuGlySer ValIleAlaLeu ProThrPhe·
  1  ATGGGTAAAA GATTAGTGAT ATTAGGTAGT GTTATTGCGC TTCCAACATT
     ·AlaAlaGly GlyGlyAspLeu AspAlaSer AspTyrThr GlyValSerPhe·
 51  TGCCGCTGGT GGTGGTGACC TGGATGCTAG TGACTACACT GGTGTATCTT
     · TrpLeuVal ThrAlaAla LeuLeuAlaSer ThrValPhe PhePheVal
101  TCTGGTTAGT TACTGCTGCT CTATTAGCAT CTACTGTATT TTTCTTTGTT
     GluArgAspArg ValSerAla LysTrpLys ThrSerLeuThr ValSerGly·
151  GAAAGAGACA GAGTTTCTGC TAAATGGAAA ACATCATTAA CAGTATCTGG
     ·LeuValThr GlyIleAlaPhe TrpHisTyr MetTyrMet ArgGlyValTrp·
201  TTTAGTTACT GGTATTGCTT TTTGGCATTA CATGTACATG AGAGGTGTAT
     · IleGluThr GlyAspSer ProThrValPhe ArgTyrIle AspTrpLeu
251  GGATTGAAAC TGGTGATTCA CCAACTGTTT TTAGATACAT CGACTGGTTG
     LeuThrValPro LeuLeuIle CysGluPhe TyrLeuIleLeu AlaAlaAla·
301  CTAACTGTGC CTTTACTAAT TTGTGAGTTC TACTTAATAC TAGCAGCAGC
     ·ThrAsnVal AlaGlySerLeu PheLysLys LeuLeuVal GlySerLeuVal·
351  TACTAACGTT GCTGGTTCTT TATTCAAGAA ATTACTAGTT GGTTCTCTTG
     · MetLeuVal PheGlyTyr MetGlyGluAla GlyIleMet AlaAlaTrp
401  TTATGCTTGT GTTTGGTTAC ATGGGTGAAG CAGGAATTAT GGCAGCCTGG
     ProAlaPheIle IleGlyCys LeuAlaTrp ValTyrMetIle TyrGluLeu·
451  CCTGCATTCA TTATAGGATG TTTAGCATGG GTATACATGA TTTATGAATT
     ·TrpAlaGly GluGlyLysSer AlaCysAsn ThrAlaSer ProAlaValGln·
501  ATGGGCTGGA GAAGGAAAGT CTGCATGTAA CACTGCAAGT CCTGCAGTTC
     · SerAlaTyr AsnThrMet MetTyrIleIle IlePheGly TrpAlaIle
551  AGTCAGCTTA CAACACAATG ATGTATATCA TCATCTTTGG TTGGGCTATT
     TyrLeuValGly TyrPheThr GlyTyrLeu MetGlyAspGly GlySerAla·
601  TACCTTGTAG GTTATTTCAC TGGTTACCTA ATGGGTGACG GTGGATCAGC
     ·LeuAsnLeu AsnLeuIleTyr AsnLeuAla AspPheVal AsnLysIleLeu·
651  TCTTAACTTA AACCTTATCT ATAACCTTGC TGACTTTGTT AACAAGATTC
     · PheGlyLeu IleIleTrp AsnValAlaVal LysGluSer SerAsnAla
701  TATTTGGTTT AATTATATGG AATGTTGCTG TTAAAGAATC TTCTAATGCT
751  A
```

Figure 1-57

```
    MetGlyLysAla LeuLeuMet LeuGlySer ValIleAlaLeu ProThrPhe·
  1 ATGGGTAAAG CATTACTGAT GTTAGGTAGT GTTATTGCGC TTCCAACATT
    ·AlaAlaGly GlyGlyAspLeu AspAlaSer AspTyrThr GlyValSerPhe·
 51 TGCCGCTGGT GGTGGTGACC TGGATGCTAG TGACTACACT GGTGTATCTT
    · TrpLeuVal ThrAlaAla ProLeuAlaSer ThrValPhe PhePheVal
101 TCTGGTTAGT TACTGCTGCT CCATTAGCAT CTACTGTATT TTTCTTTGTT
    GluArgAspArg ValSerAla LysTrpLys ThrSerLeuThr ValSerGly·
151 GAAAGAGACA GAGTTTCTGC TAAATGGAAA ACATCATTAA CAGTATCTGG
    ·LeuValThr GlyIleAlaPhe TrpHisTyr MetTyrMet ArgGlyValTrp·
201 TTTAGTTACT GGTATTGCTT TTTGGCATTA CATGTACATG AGAGGTGTAT
    · IleGluThr GlyAspSer ProThrValPhe ArgTyrIle AspTrpLeu
251 GGATTGAAAC TGGTGATTCA CCAACTGTTT TTAGATACAT CGACTGGTTG
    LeuThrValPro LeuLeuIle CysGluPhe TyrLeuIleLeu AlaAlaAla·
301 CTAACTGTGC CTTTACTAAT TTGTGAGTTC TACTTAATAC TAGCAGCAGC
    ·ThrAsnVal AlaGlySerLeu PheLysLys LeuLeuVal GlySerLeuVal·
351 TACTAACGTT GCTGGTTCTT TATTCAAGAA ATTACTAGTT GGTTCTCTTG
    · MetLeuVal PheGlyTyr MetGlyGluAla GlyIleMet AlaAlaTrp
401 TTATGCTTGT GTTTGGTTAC ATGGGTGAAG CAGGAATTAT GGCAGCCTGG
    ProAlaPheIle IleGlyCys LeuAlaTrp ValTyrMetIle TyrGluLeu·
451 CCTGCATTCA TTATAGGATG TTTAGCATGG GTATACATGA TTTATGAATT
    ·TrpAlaGly GluGlyLysSer AlaCysAsn ThrAlaSer ProAlaValGln·
501 ATGGGCTGGA GAAGGAAAGT CTGCATGTAA CACTGCAAGT CCTGCAGTTC
    · SerAlaTyr AsnThrMet MetTyrIleIle IlePheGly TrpAlaIle
551 AGTCAGCTTA CAACACAATG ATGTATATCA TCATCTTTGG TTGGGCTATT
    TyrLeuValGly TyrPheThr GlyTyrLeu MetGlyAspGly GlySerAla·
601 TACCTTGTAG GTTATTTCAC TGGTTACCTA ATGGGTGACG GTGGATCAGC
    ·LeuAsnLeu AsnLeuIleTyr AsnLeuAla AspPheVal AsnLysIleLeu·
651 TCTTAACTTA AACCTTATCT ATAACCTTGC TGACTTTGTT AACAAGATTC
    · PheGlyLeu IleIleArg AsnValAlaVal LysGluSer SerAsnAla
701 TATTTGGTTT AATTATAAGG AATGTTGCTG TTAAAGAATC TTCTAATGCT
751 A
```

Figure 1-58

```
    MetGlyLysGly LeuLeuMet LeuGlySer ValIleAlaLeu ProSerPhe·
  1 ATGGGTAAAG GATTACTGAT GTTAGGTAGT GTTATTGCGC TTCCATCTTT
    ·AlaAlaGly GlyGlyAspLeu AspAlaSer AspTyrThr GlyValSerPhe·
 51 TGCTGCTGGC GGTGGCGATC TTGATGCTAG TGACTATACA GGTGTTTCAT
    · TrpLeuVal ThrAlaAla LeuLeuAlaSer ThrValPhe PhePheVal
101 TCTGGTTGGT TACTGCTGCA TTATTAGCCT CAACTGTTTT CTTCTTTGTT
    GluArgAspArg ValAlaAla LysTrpLys ThrSerLeuThr ValSerGly·
151 GAAAGAGACA GAGTTGCTGC AAAATGGAAA ACATCGTTAA CAGTATCTGG
    ·LeuValThr GlyIleAlaPhe TrpHisTyr MetTyrMet ArgGlyValTrp·
201 TCTTGTTACT GGTATTGCTT TTTGGCATTA CATGTACATG AGAGGGGTTT
    · ValGluThr GlyGluSer ProThrValPhe ArgTyrIle AspTrpLeu
251 GGGTAGAGAC TGGTGAATCA CCAACTGTAT TCAGATATAT TGACTGGCTA
    LeuThrValPro LeuLeuIle CysGluPhe TyrLeuIleLeu AlaAlaAla·
301 CTAACAGTAC CATTATTAAT ATGTGAGTTC TACTTAATAC TTGCAGCTGC
    ·ThrAsnVal AlaGlySerLeu PheLysLys LeuLeuIle GlySerLeuVal·
351 AACTAATGTT GCTGGTTCTT TATTTAAAAA GCTATTAATT GGTTCTCTTG
    · MetLeuVal PheGlyTyr MetGlyGluAla GlyIleMet AlaAlaTrp
401 TTATGCTTGT GTTTGGTTAC ATGGGTGAAG CAGGAATCAT GGCAGCTTGG
    ProAlaPheIle IleGlyCys LeuAlaTrp PheTyrMetIle TyrGluLeu·
451 CCTGCATTCA TTATTGGGTG CTTAGCTTGG TTCTACATGA TTTATGAACT
    ·TrpAlaGly GluGlyLysSer AlaCysAsn ThrAlaSer ProAlaValGln·
501 ATGGGCTGGT GAAGGAAAGT CTGCTTGTAA TACTGCAAGT CCAGCTGTTC
    · SerAlaTyr AsnThrMet MetTyrIleIle IleIleGly TrpAlaIle
551 AATCAGCATA CAACACGATG ATGTATATTA TTATCATTGG TTGGGCTATT
    TyrProValGly TyrPheThr GlyTyrLeu MetGlyAspGly GlySerAla·
601 TACCCTGTAG GTTACTTTAC TGGTTACCTA ATGGGTGACG GCGGATCTGC
    ·LeuAsnLeu AsnLeuIleTyr AsnLeuAla AspPheVal AsnLysIleLeu·
651 CTTAAACTTA AACCTAATTT ATAACCTTGC TGACTTCGTT AACAAGATTC
    · PheGlyLeu IleIleTrp HisValAlaVal LysGluSer SerAsnAla
701 TATTTGGTTT AATTATCTGG CATGTTGCTG TTAAAGAATC TTCTAATGCT
751 A
```

Figure 1-59

```
    MetGlyLysLeu LeuLeuIle LeuGlySer ValIleAlaLeu ProSerPhe·
  1 ATGGGTAAAT TATTATTGAT CTTAGGTAGT GTTATTGCGC TTCCTTCATT
    ·AlaAlaGly GlyGlyAspLeu AspAlaGly AspTyrThr GlyValSerPhe·
 51 TGCAGCTGGT GGCGGCGACC TTGATGCTGG TGATTACACT GGTGTTAGTT
    · TrpLeuVal ThrAlaAla LeuLeuAlaSer ThrValPhe PhePheIle
101 TTTGGTTAGT GACTGCAGCT CTTTTGGCTT CAACTGTATT TTTCTTTATT
    GluArgAspArg ValAlaAla LysTrpLys ThrSerLeuThr ValSerGly·
151 GAAAGAGATA GAGTTGCTGC TAAATGGAAG ACATCTTTAA CAGTATCTGG
    ·LeuValThr GlyIleAlaPhe TrpHisTyr MetTyrMet ArgGlyValTrp·
201 TCTAGTTACT GGTATTGCTT TCTGGCATTA CATGTACATG AGAGGTGTTT
    · ValGluThr GlyGluSer ProThrValPhe ArgTyrIle AspTrpLeu
251 GGGTCGAAAC TGGTGAATCA CCAACTGTAT TCAGATATAT TGACTGGCTA
    LeuThrValPro LeuLeuIle CysGluPhe TyrLeuIleLeu AlaAlaAla·
301 CTTACAGTGC CTTTATTAAT ATGTGAGTTT TATCTGATTC TTGCAGCTGC
    ·ThrAsnVal AlaGlySerLeu PheLysLys LeuLeuVal GlySerLeuVal·
351 AACTAATGTT GCTGGTTCTT TATTTAAGAA GCTTTTAGTT GGTTCTCTTG
    · MetLeuVal PheGlyTyr MetGlyGluAla GlyIleMet AlaAlaTrp
401 TAATGCTTGT ATTTGGTTAT ATGGGCGAAG CAGGAATTAT GGCAGCTTGG
    ProAlaPheIle ValGlyCys LeuAlaTrp PheTyrMetIle TyrGluLeu·
451 CCTGCATTCA TTGTTGGATG TTTAGCTTGG TTCTATATGA TTTATGAGCT
    ·TrpAlaGly GluGlyLysSer AlaCysAsn ThrAlaSer ProAlaValGln·
501 ATGGGCTGGA GAAGGAAAAT CTGCATGCAA TACTGCAAGT CCAGCTGTTC
    · SerAlaTyr AsnThrMet MetTyrIleIle IleIleGly TrpAlaIle
551 AATCAGCATA CAACACAATG ATGTATATTA TTATCATTGG TTGGGCTATT
    TyrProLeuGly TyrPheThr GlyTyrLeu MetGlyAspGly GlySerAla·
601 TATCCTCTTG GGTACTTTAC TGGTTACCTA ATGGGTGACG GCGGATCAGC
    ·LeuAsnLeu AsnLeuIleTyr AsnLeuAla AspPheVal AsnLysIleLeu·
651 CTTAAACTTA AACCTAATTT ATAACCTTGC TGACTTTGTT AACAAGATTC
    · PheGlyLeu IleIleTrp HisValAlaVal LysGluSer SerAsnAla
701 TATTTGGTTT AATCATATGG CATGTCGCTG TTAAAGAATC TTCTAATGCT
751 A
```

Figure 1-60

```
      MetGlyLysGln LeuLeuIle LeuGlySer ValIleAlaLeu ProSerPhe·
  1   ATGGGTAAAC AATTACTGAT CTTAGGTAGT GTTATTGCGC TTCCATCTTT
      ·AlaAlaGly GlyGlyAspLeu AspAlaSer AspTyrThr GlyValSerPhe·
 51   TGCTGCTGGC GGTGGCGATC TTGATGCTAG TGACTATACA GGTGTTTCAT
      · TrpLeuVal ThrAlaAla LeuLeuAlaSer ThrValPhe PhePheIle
101   TCTGGTTAGT TACTGCTGCA TTATTAGCCT CAACTGTTTT CTTTTTTATT
      GluArgAspArg ValAlaAla LysTrpLys ThrSerLeuThr ValSerGly·
151   GAAAGAGACA GAGTTGCTGC AAAATGGAAA ACGTCGTTAA CAGTATCTGG
      ·LeuValThr GlyIleAlaPhe TrpHisTyr LeuTyrMet ArgGlyValTrp·
201   CCTTGTTACT GGTATTGCTT TTTGGCACTA CTTGTATATG AGAGGAGTTT
      · ValGluThr GlyGluSer ProThrValPhe ArgTyrIle AspTrpLeu
251   GGGTAGAGAC TGGTGAATCA CCAACTGTAT TCAGATATAT TGACTGGTTA
      LeuThrValPro LeuLeuIle CysGluPhe TyrLeuIleLeu AlaAlaAla·
301   CTAACAGTAC CATTATTAAT ATGTGAGTTT TACTTAATAC TTGCAGCTGC
      ·ThrAsnVal AlaGlySerLeu PheLysLys LeuLeuIle GlySerLeuVal·
351   AACTAATGTT GCTGGTTCTT TATTTAAAAA GCTATTAATT GGTTCTCTTG
      · MetLeuVal PheGlyTyr MetGlyGluAla GlyIleMet AlaAlaTrp
401   TGATGCTTGT GTTTGGTTAC ATGGGTGAAG CAGGAATCAT GGCGGCTTGG
      ProAlaPheIle IleGlyCys LeuAlaTrp ValTyrMetIle TyrGluLeu·
451   CCTGCATTCA TTATTGGGTG CTTAGCTTGG GTCTATATGA TATATGAGCT
      ·TrpAlaGly GluGlyLysSer AlaCysAsn ThrAlaSer ProAlaValGln·
501   ATGGGCTGGT GAAGGAAAAT CTGCATGTAA TACTGCAAGT CCAGCTGTTC
      · SerAlaTyr AsnThrMet MetTyrIleIle IlePheGly TrpAlaIle
551   AATCAGCATA CAACACAATG ATGTATATTA TTATCTTTGG TTGGGCTATT
      TyrProValGly TyrPheThr GlyTyrLeu MetGlyAspGly GlySerAla·
601   TACCCTGTAG GTTACTTTAC TGGTTACCTA ATGGGTGACG GCGGATCTGC
      ·LeuAsnLeu AsnLeuIleTyr AsnLeuAla AspPheVal AsnLysIleLeu·
651   CTTAAACTTA AACCTTATCT ATAACCTTGC TGACTTCGTT AACAAGATTC
      · PheGlyLeu IleIleTrp HisValAlaVal LysGluSer SerAsnAla
701   TATTTGGTTT AATTATCTGG CATGTTGCTG TTAAAGAATC TTCTAATGCT
751   A
```

Figure 1-61

```
    MetGlyLysLeu LeuMetMet LeuGlySer ValIleAlaLeu ProSerPhe·
  1 ATGGGTAAAT TATTAATGAT GTTAGGTAGT GTTATTGCGC TTCCTTCATT
    ·AlaAlaSer GlyGlyAspLeu AspAlaSer AspTyrThr GlyValSerPhe·
 51 TGCGGCAAGT GGTGGCGATT TGGATGCTAG TGATTACACT GGTGTTTCAT
    · GlyLeuVal ThrAlaAla LeuLeuAlaSer ThrValPhe PhePheVal
101 TTGGGTTGGT GACTGCAGCT TTATTAGCTT CAACTGTATT TTTCTTTGTT
    GluArgAspArg ValSerAla LysTrpLys ThrSerLeuThr ValSerGly·
151 GAAAGAGATA GAGTTTCTGC TAAATGGAAG ACATCTTTGA CAGTATCAGG
    ·LeuValThr GlyIleAlaPhe TrpHisTyr LeuTyrMet ArgGlyValTrp·
201 TTTAGTTACT GGTATTGCTT TTTGGCATTA CTTATATATG AGAGGTGTAT
    · ValGluThr GlyGluThr ProThrValPhe ArgTyrIle AspTrpLeu
251 GGGTTGAAAC TGGTGAAACT CCAACAGTAT TTAGATATAT TGATTGGTTA
    LeuThrValPro LeuLeuIle CysGluPhe TyrLeuIleLeu AlaAlaAla·
301 TTAACTGTTC CATTACTAAT CTGCGAGTTT TATTTAATTC TAGCTGCTGC
    ·ThrAsnVal AlaGlySerLeu PheLysLys LeuLeuVal GlySerLeuVal·
351 AACTAACGTA GCTGGTTCAT TATTTAAGAA ACTACTTGTT GGTTCACTTG
    · MetLeuVal PheGlyTyr MetGlyGluAla GlyIleMet AlaAlaLeu
401 TAATGCTTGT GTTTGGATAC ATGGGTGAAG CAGGAATCAT GGCAGCTTTG
    ProAlaPheIle IleGlyCys LeuAlaTrp IleTyrMetIle TyrGluLeu·
451 CCTGCATTCA TTATTGGGTG TTTGGCATGG ATATATATGA TTTATGAGCT
    ·TrpAlaGly GluGlyLysSer AlaCysAsn ThrAlaSer ProAlaValGln·
501 TTGGGCTGGA GAAGGGAAAT CTGCATGCAA TACTGCAAGT CCTGCCGTTC
    · SerAlaTyr AsnThrMet MetTyrIleIle IlePheGly TrpLeuIle
551 AATCAGCTTA CAACACCATG ATGTACATCA TCATTTTTGG TTGGTTAATC
    TyrProValGly TyrAlaSer GlyTyrLeu MetGlyAspGly GlySerAla·
601 TATCCAGTTG GTTATGCATC AGGCTATCTA ATGGGCGATG GCGGATCAGC
    ·MetAsnLeu AsnLeuIleTyr AsnLeuAla AspPheVal AsnLysIleLeu·
651 TATGAACTTA AACTTAATAT ATAACCTTGC TGACTTTGTT AACAAGATTC
    · PheGlyLeu IleIleTrp AsnValAlaVal LysGluSer SerAsnAla
701 TATTTGGTTT AATTATCTGG AATGTTGCTG TTAAAGAATC TTCTAATGCT
751 A
```

Figure 1-62

```
    MetGlyLysGly LeuLeuMet LeuGlySer ValIleAlaLeu ProSerPhe·
  1 ATGGGTAAAG GATTACTGAT GTTAGGTAGT GTTATTGCAC TTCCATCCTT
    ·AlaAlaGly GlyGlyAsnLeu AsnAlaAla AspValThr GlyValSerPhe·
 51 TGCAGCTGGT GGAGGCAACT TAAATGCAGC TGATGTAACT GGTGTATCTT
    · TrpLeuVal ThrAlaAla LeuLeuAlaSer ThrValPhe PhePheIle
101 TTTGGCTAGT TACTGCCGCT TTACTTGCTT CAACAGTATT CTTTTTTATT
    GluArgAspArg ValSerAla LysTrpLys ThrSerLeuThr ValSerGly·
151 GAAAGAGATA GAGTTTCTGC AAAATGGAAG ACATCACTAA CAGTATCTGG
    ·LeuValThr GlyIleAlaPhe TrpHisTyr LeuTyrMet ArgGlyValTrp·
201 TTTAGTTACT GGTATTGCTT TTTGGCATTA CCTTTACATG AGAGGTGTTT
    · ValAspSer TrpAsnPro GluThrGlyMet GlyGluSer ProThrGlu
251 GGGTTGATTC TTGGAATCCT GAAACAGGAA TGGGAGAATC TCCAACTGAA
    PheArgTyrIle AspTrpLeu LeuThrVal ProLeuLeuIle CysGluPhe·
301 TTTAGATATA TTGATTGGTT ACTAACAGTA CCTTTATTAA TTTGTGAGTT
    ·TyrLeuIle LeuAlaAlaAla ThrAsnVal AlaGlySer LeuPheLysLys·
351 TTATCTAATA TTAGCTGCTG CAACAAATGT TGCTGGTTCA TTATTCAAAA
    · LeuLeuVal GlySerLeu ValMetLeuIle AlaGlyTyr MetGlyGlu
401 AATTATTAGT TGGTTCATTG GTCATGCTTA TTGCAGGATA CATGGGTGAA
    SerGlyAsnAla AsnValMet IleAlaPhe ValValGlyCys LeuAlaTrp·
451 TCTGGTAATG CCAATGTGAT GATTGCATTC GTAGTTGGAT GCTTAGCATG
    ·LeuTyrMet IleTyrGluLeu TrpAlaGly GluGlyLys AlaAlaCysAsn·
501 GTTGTATATG ATATATGAAT TGTGGGCTGG TGAAGGTAAA GCAGCTTGCA
    · ThrAlaSer ProAlaVal GlnSerAlaTyr AsnThrMet MetTrpIle
551 ATACAGCAAG CCCTGCTGTT CAATCAGCAT ACAATACAAT GATGTGGATC
    IleIleValGly TrpAlaIle TyrProAla GlyTyrAlaAla GlyTyrLeu·
601 ATTATTGTAG GTTGGGCTAT ATATCCTGCT GGATATGCTG CTGGCTATTT
    ·MetGlyGly GluSerValTyr AlaSerAsn LeuAsnLeu IleTyrAsnLeu·
651 GATGGGTGGA GAAAGCGTTT ATGCTTCTAA CCTTAACCTG ATATATAACC
    · AlaAspPhe ValAsnLys IleLeuPheGly LeuIleIle TrpHisVal
701 TTGCTGACTT TGTTAACAAG ATTTTATTTG GTTTAATCAT TTGGCATGTT
    AlaValLysGlu SerSerAsn Ala
751 GCTGTTAAAG AATCTTCTAA TGCTA
```

Figure 1-63

```
    MetGlyLysLeu LeuValMet LeuGlySer ValIleAlaLeu ProSerPhe·
  1 ATGGGTAAAT TATTAGTGAT GTTAGGTAGT GTTATTGCAC TTCCATCCTT
    ·AlaAlaGly GlyGlyAsnLeu AspAlaAla AspValThr GlyValSerPhe·
 51 TGCAGCTGGT GGAGGTAACT TAGATGCAGC TGATGTAACT GGTGTATCTT
    · TrpLeuVal ThrAlaAla LeuLeuAlaSer ThrValPhe PhePheIle
101 TTTGGCTAGT TACTGCGGCT TTACTTGCTT CAACAGTATT CTTTTTTATT
    GluArgAspArg ValSerAla LysTrpLys ThrSerLeuThr ValSerGly·
151 GAAAGAGATA GAGTTTCTGC AAAATGGAAG ACATCACTAA CAGTATCTGG
    ·LeuValThr GlyIleAlaPhe TrpHisTyr LeuTyrMet ArgGlyValTrp·
201 TTTAGTTACT GGTATTGCAT TTTGGCATTA CCTTTATATG AGAGGCGTTT
    · ValAspSer TrpThrGly ProGlyThrGly GluSerPro ThrGluPhe
251 GGGTTGATTC TTGGACTGGT CCAGGAACCG GAGAATCTCC AACTGAATTT
    ArgTyrIleAsp TrpLeuLeu ThrValPro LeuLeuIleCys GluPheTyr·
301 AGATATATTG ATTGGTTACT AACAGTACCT TTATTAATTT GTGAGTTTTA
    ·LeuIleLeu AlaAlaAlaThr AsnValAla GlySerLeu PheLysLysLeu·
351 TCTAATATTA GCTGCTGCAA CAAATGTTGC TGGTTCATTA TTCAAAAAAT
    · LeuValGly SerLeuVal MetLeuIleAla GlyTyrMet GlyGluSer
401 TATTAGTTGG TTCATTGGTC ATGCTTATTG CAGGATACAT GGGTGAATCT
    GlyAsnAlaAsn ValMetIle AlaPheVal ValGlyCysLeu AlaTrpLeu·
451 GGTAATGCCA ATGTGATGAT TGCATTCGTA GTTGGATGCT TAGCATGGTT
    ·TyrMetIle TyrGluLeuTrp AlaGlyGlu GlyLysAla AlaCysAsnThr·
501 GTATATGATA TATGAATTGT GGGCTGGTGA AGGTAAAGCA GCTTGCAATA
    · AlaSerPro AlaValGln SerAlaTyrAsn ThrMetMet TrpIleIle
551 CAGCAAGCCC TGCTGTTCAA TCAGCATACA ATACAATGAT GTGGATCATT
    IleValGlyTrp AlaIleTyr ProAlaGly TyrAlaAlaGly TyrLeuMet·
601 ATTGTAGGTT GGGCTATATA TCCTGCTGGA TATGCTGCTG GCTATTTGAT
    ·GlyGlyGlu SerValTyrAla SerAsnLeu AsnLeuIle TyrAsnLeuAla·
651 GGGTGGAGAA AGCGTTTATG CTTCTAACCT TAACCTGATA TATAACCTTG
    · AspPheVal AsnLysIle LeuPheGlyLeu IleIleTrp HisValAla
701 CTGACTTTGT TAACAAGATT TTATTTGGTT TAATCATTTG GCATGTTGCT
    ValLysGluSer SerAsnAla
751 GTTAAAGAAT CTTCTAATGC TA
```

Figure 1-64

```
     MetGlyLysLeu LeuValMet LeuGlyGly ValIleAlaLeu ProSerPhe·
  1  ATGGGTAAAT TATTAGTGAT GTTAGGTGGT GTTATTGCAC TTCCTTCTTT
     ·AlaAlaGly GlyGlyAspLeu AspIleGly AspSerVal GlyValSerPhe·
 51  TGCTGCTGGT GGTGGTGATC TAGATATAGG AGACTCCGTT GGAGTTTCAT
     · TrpLeuVal ThrAlaAla MetLeuAlaAla ThrValPhe PhePheVal
101  TCTGGCTTGT TACTGCTGCT ATGTTAGCTG CTACTGTTTT CTTTTTTGTT
     GluArgAspGln ValSerAla LysTrpLys ThrSerLeuThr ValSerGly·
151  GAAAGAGACC AAGTAAGCGC AAAGTGGAAA ACATCATTAA CAGTATCAGG
     ·LeuIleThr GlyIleAlaPhe TrpHisTyr LeuTyrMet ArgGlyValTrp·
201  TTTAATTACT GGTATTGCTT TTTGGCATTA TCTTTACATG AGAGGTGTAT
     · IleAspThr GlyGlySer ProThrValPhe ArgTyrIle AspTrpLeu
251  GGATAGATAC AGGTGGAAGC CCAACAGTAT TTAGATATAT TGATTGGTTG
     LeuThrValPro LeuGlnMet ValGluPhe TyrLeuIleLeu AlaAlaCys·
301  CTAACTGTTC CATTACAAAT GGTTGAGTTT TATTTAATTC TTGCAGCTTG
     ·ThrAsnVal AlaGlySerLeu PheLysLys LeuLeuVal GlySerLeuVal·
351  TACTAATGTA GCTGGTTCAT TATTTAAGAA ACTGCTTGTT GGTTCATTAG
     · MetLeuGly AlaGlyPhe AlaGlyGluAla GlyLeuAla ProAlaLeu
401  TAATGTTAGG TGCTGGATTT GCTGGTGAAG CTGGACTAGC TCCTGCATTG
     ProAlaPheIle LeuGlyMet AlaGlyTrp ValTyrMetIle TyrGluLeu·
451  CCTGCTTTCA TACTTGGTAT GGCTGGATGG GTATACATGA TATATGAGCT
     ·TyrMetGly GluGlyLysAla AlaValSer ThrAlaSer ProAlaValAsn·
501  GTATATGGGT GAAGGTAAAG CTGCGGTGAG TACTGCTAGT CCTGCCGTAA
     · SerAlaTyr AsnAlaMet MetMetIleIle ValPheGly TrpSerIle
551  ATTCTGCTTA CAATGCAATG ATGATGATTA TAGTTTTTGG TTGGTCTATT
     TyrProLeuGly TyrValAla GlyTyrLeu MetGlyAlaVal AspProSer·
601  TATCCACTGG GATATGTTGC TGGCTATTTA ATGGGTGCAG TAGATCCAAG
     ·ThrLeuAsn LeuIleTyrAsn LeuAlaAsp PheIleAsn LysIleLeuPhe·
651  TACATTAAAT CTAATATACA ACCTTGCTGA TTTTATTAAT AAGATTTTAT
     · GlyLeuIle IleTrpHis ValAlaValLys GluSerSer AsnAla
701  TCGGTTTAAT AATCTGGCAT GTTGCTGTTA AAGAATCTTC TAATGCTA
```

Figure 1-65

```
    MetGlyLysLeu LeuMetIle LeuGlyGly ValIleAlaLeu ProSerPhe·
  1 ATGGGTAAAT TATTAATGAT CTTAGGTGGT GTTATTGCAC TTCCTTCTTT
    ·AlaAlaGly GlyGlyAspLeu AspIleGly AspSerVal GlyValSerPhe·
 51 TGCTGCTGGT GGTGGTGATC TAGATATAGG AGACTCTGTT GGAGTTTCAT
    · TrpLeuVal ThrAlaAla MetLeuAlaAla ThrValPhe PhePheVal
101 TCTGGCTTGT TACTGCTGCT ATGTTAGCTG CTACTGTTTT CTTTTTTGTT
    GluArgAspGln ValSerAla LysTrpLys ThrSerLeuThr ValSerGly·
151 GAAAGAGACC AAGTAAGCGC AAAGTGGAAA ACATCATTAA CAGTATCAGG
    ·LeuIleThr GlyIleAlaPhe TrpHisTyr LeuTyrMet ArgGlyValTrp·
201 TTTAATTACT GGTATTGCTT TTTGGCATTA TCTTTACATG AGAGGTGTAT
    · IleAspThr GlyGlySer ProThrValPhe ArgTyrIle AspTrpLeu
251 GGATAGATAC AGGTGGAAGC CCAACAGTAT TTAGATATAT TGATTGGTTG
    LeuThrValPro LeuGlnMet ValGluPhe TyrLeuIleLeu AlaAlaCys·
301 CTAACTGTTC CATTACAAAT GGTTGAGTTT TATTTAATTC TTGCAGCTTG
    ·ThrAsnVal AlaGlySerLeu PheLysLys LeuLeuVal GlySerLeuVal·
351 TACTAATGTA GCTGGTTCAT TATTTAAGAA ACTGCTTGTT GGTTCATTAG
    · MetLeuGly AlaGlyPhe AlaGlyGluAla GlyLeuAla ProAlaLeu
401 TAATGTTAGG TGCTGGATTT GCTGGTGAAG CTGGATTAGC TCCTGCATTG
    ProAlaPheIle LeuGlyMet AlaGlyTrp ValTyrMetIle TyrGluLeu·
451 CCTGCTTTCA TACTTGGTAT GGCTGGATGG GTATACATGA TATATGAGCT
    ·TyrMetGly GluGlyLysAla AlaValSer ThrAlaSer ProAlaValAsn·
501 GTATATGGGT GAAGGTAAAG CTGCGGTGAG TACTGCTAGT CCTGCCGTAA
    · SerAlaTyr AsnAlaMet MetMetIleIle ValPheGly TrpSerIle
551 ATTCTGCTTA CAATGCAATG ATGATGATTA TAGTTTTTGG TTGGTCTATT
    TyrProLeuGly TyrValAla GlyTyrLeu MetGlyAlaVal AspProSer·
601 TATCCACTGG GATATGTTGC TGGCTATTTA ATGGGTGCAG TAGATCCAAG
    ·ThrLeuAsn LeuIleTyrAsn LeuAlaAsp PheIleAsn LysIleLeuPhe·
651 TACATTAAAT CTAATATACA ACCTTGCTGA TTTTATTAAT AAGATTTTAT
    · GlyLeuIle IleTrpHis ValAlaValLys GluSerSer AsnAla
701 TCGGTTTAAT AATCTGGCAT GTTGCTGTTA AAGAATCTTC TAATGCTA
```

Figure 1-66

```
    MetGlyLysLeu LeuMetIle LeuGlyGly ValIleAlaLeu ProSerPhe·
  1 ATGGGTAAAT TATTAATGAT ATTAGGTGGT GTTATTGCAC TTCCTTCTTT
    ·AlaAlaGly GlyGlyAspLeu AspIleGly AspSerVal GlyValSerPhe·
 51 TGCTGCTGGT GGTGGTGATC TAGATATAGG AGACTCTGTT GGAGTTTCAT
    · TrpLeuVal ThrAlaAla MetLeuAlaAla ThrValPhe PhePheVal
101 TCTGGCTTGT TACTGCTGCT ATGTTAGCTG CTACTGTTTT CTTTTTTGTT
    GluArgAspGln ValSerAla LysTrpLys ThrSerLeuThr ValSerGly·
151 GAAAGAGACC AAGTAAGCGC AAAATGGAAA ACATCATTAA CAGTATCAGG
    ·LeuIleThr GlyIleAlaPhe TrpHisTyr LeuTyrMet ArgGlyValTrp·
201 TTTAATAACA GGTATTGCTT TCTGGCACTA CTTGTATATG AGAGGGGTTT
    · ValGluThr GlyAspSer ProThrValPhe ArgTyrIle AspTrpLeu
251 GGGTAGAAAC AGGCGATTCA CCAACTGTAT TTAGATATAT AGATTGGCTT
    LeuThrValPro LeuGlnMet ValGluPhe TyrLeuIleLeu AlaAlaCys·
301 TTAACTGTAC CACTACAAAT GGTAGAGTTT TATCTGATAT TAGCTGCATG
    ·ThrAsnVal AlaGlySerLeu PheLysLys LeuLeuIle GlySerLeuVal·
351 TACCAATGTT GCTGGATCTT TATTTAAAAA GCTACTAATC GGTTCATTGG
    · MetLeuIle GlyGlyPhe LeuGlyGluAla GlyMetIle AspValThr
401 TGATGTTGAT AGGAGGTTTC CTAGGTGAAG CTGGTATGAT AGATGTAACA
    LeuAlaPheVal IleGlyMet AlaGlyTrp LeuTyrMetIle TyrGluLeu·
451 CTAGCTTTTG TAATTGGAAT GGCTGGATGG CTATATATGA TCTATGAGCT
    ·TyrMetGly GluGlyLysAla AlaValSer ThrAlaSer ProAlaValAsn·
501 ATACATGGGT GAAGGTAAAG CTGCGGTGAG TACTGCTAGT CCTGCCGTAA
    · SerAlaTyr AsnAlaMet MetLeuIleIle ValValGly TrpSerIle
551 ATTCTGCTTA CAATGCAATG ATGCTTATTA TTGTTGTTGG TTGGTCAATC
    TyrProAlaGly TyrValAla GlyTyrLeu MetGlyGlyGlu GlyValTyr·
601 TATCCTGCTG GATATGTTGC TGGCTATCTT ATGGGCGGTG AAGGAGTATA
    ·AlaSerAsn LeuAsnLeuIle TyrAsnLeu AlaAspPhe IleAsnLysIle·
651 TGCCTCAAAT CTAAACTTAA TATATAACCT TGCTGATTTT ATCAACAAGA
    · LeuPheGly LeuIleIle TrpHisValAla ValLysGlu SerSerAsn
701 TTCTATTTGG TTTAATTATA TGGCATGTTG CTGTTAAAGA ATCTTCTAAT
    Ala
751 GCTA
```

Figure 1-67

```
    MetGlyLysGln LeuLeuIle LeuGlyGly ValIleAlaLeu ProSerPhe·
  1 ATGGGTAAAC AATTACTGAT TTTAGGTGGT GTTATTGCAC TTCCTTCGTT
    ·AlaAlaSer GlyGlyAspLeu AspSerSer AspLeuThr GlyValSerPhe·
 51 TGCTGCAAGT GGGGGCGATC TTGATTCTAG TGATCTTACT GGAGTTTCTT
    · TrpLeuVal ThrAlaAla LeuLeuAlaAla ThrValPhe PhePheVal
101 TTTGGCTTGT TACTGCTGCT CTCTTAGCTG CTACTGTTTT CTTTTTTGTT
    GluArgAspGln ValSerAla LysTrpLys ThrSerLeuThr ValSerGly·
151 GAAAGAGATC AAGTAAGTGC TAAATGGAAA ACATCACTTA CAGTTTCTGG
    ·LeuValThr GlyIleAlaPhe TrpHisTyr LeuTyrMet ArgGlyValTrp·
201 TTTAGTTACT GGTATTGCAT TCTGGCATTA TCTTTATATG AGAGGTGTGT
    · IleGluThr GlyGluThr ProThrValPhe ArgTyrIle AspTrpLeu
251 GGATCGAAAC TGGTGAAACG CCAACAGTAT TTAGATATAT TGATTGGTTG
    LeuThrValPro LeuLeuMet ValGluPhe TyrLeuIleLeu AlaAlaCys·
301 CTAACTGTTC CTTTGCTAAT GGTTGAGTTC TACTTAATCC TTGCAGCGTG
    ·ThrAsnVal AlaGlySerLeu PheLysLys LeuLeuGly GlySerLeuVal·
351 CACAAATGTT GCGGGTTCAT TATTTAAGAA ACTACTTGGT GGTTCGCTTG
    · MetLeuIle AlaGlyTyr MetGlyGluSer GlySerLeu ProValLeu
401 TAATGCTTAT TGCAGGATAT ATGGGTGAGT CTGGAAGTCT TCCAGTATTG
    ProAlaPheIle ValGlyCys LeuAlaTrp PheTyrMetIle TyrGluLeu·
451 CCTGCATTCA TTGTTGGGTG CTTAGCATGG TTCTACATGA TTTATGAACT
    ·TyrAlaGly GluGlyLysAla AlaValThr ThrAlaSer ProAlaValMet·
501 ATATGCTGGT GAAGGTAAGG CTGCAGTTAC TACTGCTAGT CCTGCTGTTA
    · SerAlaTyr AsnThrMet MetLeuIleIle ValValGly TrpAlaIle
551 TGTCTGCATA CAATACTATG ATGTTGATTA TCGTAGTAGG TTGGGCAATT
    TyrProAlaGly TyrAlaAla GlyTyrLeu MetGlyGlyAsp GlyValTyr·
601 TACCCAGCTG GATATGCTGC TGGTTACCTA ATGGGTGGTG ATGGCGTATA
    ·AlaGlnAsn LeuAsnValIle TyrAsnLeu AlaAspPhe ValAsnLysIle·
651 TGCTCAGAAT TTAAACGTTA TATATAACCT TGCTGACTTT GTTAACAAGA
    · LeuPheGly LeuValIle TrpHisValAla ValLysGlu SerSerAsn
701 TTTTATTTGG TTTAGTTATC TGGCATGTTG CTGTTAAAGA ATCTTCTAAT
    Ala
751 GCTA
```

Figure 1-68

```
    MetGlyLysLeu LeuMetIle LeuGlyGly ValIleAlaLeu ProSerPhe·
  1 ATGGGTAAAT TATTAATGAT CTTAGGTGGT GTCATTGCGC TTCCTTCGTT
    ·AlaAlaSer GlyGlyAspLeu AspSerSer AspLeuThr GlyValSerPhe·
 51 TGCTGCAAGT GGTGGCGATC TTGATTCTAG TGATCTTACT GGAGTATCTT
    · TrpLeuVal ThrAlaAla LeuLeuAlaAla ThrValPhe PhePheVal
101 TTTGGCTTGT TACTGCTGCT CTCTTAGCTG CTACTGTTTT CTTTTTTGTT
    GluArgAspGln ValSerAla LysTrpLys ThrSerLeuThr ValSerGly·
151 GAAAGAGATC AAGTAAGTGC TAAATGGAAA ACATCACTTA CAGTTTCTGG
    ·LeuValThr GlyIleAlaPhe TrpHisTyr LeuTyrMet ArgGlyValTrp·
201 TTTAGTTACT GGTATTGCAT TCTGGCATTA TCTCTATATG AGAGGTGTGT
    · IleGluThr GlyGluThr ProThrValPhe ArgTyrIle AspTrpLeu
251 GGATCGAAAC TGGTGAAACG CCAACAGTAT TTAGATATAT TGATTGGTTG
    LeuThrValPro LeuLeuMet ValGluPhe TyrLeuIleLeu AlaAlaCys·
301 CTAACTGTTC CGTTACTAAT GGTTGAGTTC TACTTAATTC TTGCGGCTTG
    ·ThrAsnVal AlaGlySerLeu PheLysLys LeuLeuGly GlySerLeuVal·
351 CACAAATGTT GCGGGCTCAT TATTTAAGAA ACTACTAGGT GGTTCGCTTG
    · MetLeuIle AlaGlyTyr MetGlyGluSer GlySerLeu ProValLeu
401 TAATGCTTAT TGCAGGATAT ATGGGTGAGT CTGGAAGTCT TCCAGTATTG
    ProAlaPheIle ValGlyCys LeuAlaTrp PheTyrMetIle TyrGluLeu·
451 CCTGCATTCA TTGTTGGATG CCTAGCATGG TTCTACATGA TTTATGAACT
    ·TyrAlaGly GluGlyLysAla AlaValThr ThrAlaSer ProAlaValMet·
501 ATATGCTGGT GAAGGTAAGG CTGCAGTTAC TACTGCTAGT CCTGCTGTTA
    · SerAlaTyr AsnThrMet MetLeuIleIle ValValGly TrpAlaIle
551 TGTCTGCATA CAATACTATG ATGTTGATTA TCGTAGTAGG TTGGGCAATT
    TyrProAlaGly TyrAlaAla GlyTyrLeu MetGlyGlyAsp GlyValTyr·
601 TACCCGGCTG GATATGCTGC TGGATACCTA ATGGGTGGTG ATGGCGTATA
    ·AlaGlnAsn LeuAsnValIle TyrAsnLeu AlaAspPhe ValAsnLysIle·
651 TGCTCAGAAT TTAAACGTTA TATATAATCT TGCTGACTTT GTTAACAAGA
    · LeuPheGly LeuValIle TrpHisValAla ValLysGlu SerSerAsn
701 TTTTATTTGG TTTAGTTATC TGGCATGTCG CTGTTAAAGA ATCTTCTAAT
    Ala
751 GCTA
```

Figure 1-69

```
    MetGlyLysLeu LeuValIle LeuGlyGly ValIleAlaLeu ProProPhe·
  1 ATGGGTAAAC TATTAGTGAT ATTAGGTGGT GTCATTGCGC TTCCTCCGTT
    ·AlaAlaSer GlyGlyAspLeu AspSerSer AspLeuThr GlyValSerPhe·
 51 TGCTGCAAGT GGTGGCGATC TTGATTCTAG TGATCTTACT GGAGTATCTT
    · TrpLeuVal ThrAlaAla LeuLeuAlaAla ThrValPhe PhePheVal
101 TTTGGCTTGT TACTGCTGCT CTCTTAGCTG CTACTGTTTT CTTTTTTGTT
    GluArgAspGln ValSerAla LysTrpLys ThrSerLeuThr ValSerGly·
151 GAAAGAGATC AAGTAAGTGC TAAATGGAAA ACATCACTTA CAGTTTCTGG
    ·LeuValThr GlyIleAlaPhe TrpHisTyr LeuTyrMet ArgGlyValTrp·
201 TTTAGTTACT GGTATTGCAT TCTGGCATTA TCTCTATATG AGAGGTGTGT
    · IleGluThr GlyGluThr ProThrValPhe ArgTyrIle AspTrpLeu
251 GGATCGAAAC TGGTGAAACG CCAACAGTAT TTAGATATAT TGATTGGTTG
    LeuThrValPro LeuLeuMet ValGluPhe TyrLeuIleLeu AlaAlaCys·
301 CTAACTGTTC CGTTACTAAT GGTTGAGTTC TACTTAATTC TTGCAGCTTG
    ·ThrAsnVal AlaGlySerLeu PheLysLys LeuLeuGly GlySerLeuVal·
351 CACAAATGTT GCGGGCTCAT TATTTAAGAA ACTACTAGGT GGTTCGCTTG
    · MetLeuIle AlaGlyTyr MetGlyGluSer GlySerLeu ProValLeu
401 TAATGCTTAT TGCAGGATAT ATGGGTGAGT CTGGAAGTCT TCCAGTATTG
    ProAlaPheIle ValGlyCys LeuAlaTrp PheTyrMetIle TyrGluLeu·
451 CCTGCATTCA TTGTTGGATG CCTAGCATGG TTCTACATGA TTTATGAACT
    ·TyrAlaGly GluGlyLysAla AlaValThr ThrAlaSer ProAlaValMet·
501 ATATGCTGGT GAAGGTAAGG CTGCAGTTAC TACTGCTAGT CCTGCTGTTA
    · SerAlaTyr AsnThrMet MetLeuIleIle ValValGly TrpAlaIle
551 TGTCTGCATA CAATACTATG ATGTTGATTA TCGTAGTAGG TTGGGCAATT
    TyrProAlaGly TyrAlaAla GlyTyrLeu MetGlyGlyAsp GlyValTyr·
601 TACCCGGCTG GATATGCTGC TGGATACCTA ATGGGTGGTG ATGGCGTATA
    ·AlaGlnAsn LeuAsnValIle TyrAsnLeu AlaAspPhe ValAsnLysIle·
651 TGCTCAGAAT TTAAACGTTA TATATAATCT TGCTGACTTT GTTAACAAGA
    · LeuPheGly LeuValIle TrpHisValAla ValLysGlu SerSerAsn
701 TTTTATTTGG TTTAGTTATC TGGCATGTCG CTGTTAAAGA ATCTTCTAAT
    Ala
751 GCTA
```

Figure 1-70

```
     LeuLeuIleLeu GlyGlyVal IleAlaLeu ProSerPheAla AlaSerGly·
  1  TTATTGATAT TAGGTGGTGT TATTGCACTT CCTTCGTTTG CTGCAAGTGG
     ·GlyAspLeu AspSerSerAsp LeuThrGly ValSerPhe TrpLeuValThr·
 51  GGGCGATCTT GATTCTAGTG ATCTTACTGG AGTTTCTTTT TGGCTTGTTA
     · AlaAlaLeu LeuAlaAla ThrValPhePhe PheValGlu ArgAspGln
101  CTGCTGCTCT CTTAGCTGCT ACTGTTTTCT TTTTTGTTGA AAGAGATCAA
     ValSerAlaLys TrpLysThr SerLeuThr ValSerGlyLeu ValThrGly·
151  GTAAGTGCTA AATGGAAAAC ATCACTTACA GTTTCTGGTT TAGTTACTGG
     ·IleAlaPhe TrpHisTyrLeu TyrMetArg GlyValTrp IleGluThrGly·
201  TATTGCATTC TGGCATTATC TTTATATGAG AGGTGTGTGG ATCGAAACTG
     · GluThrPro ThrValPhe ArgTyrIleAsp TrpLeuLeu ThrValPro
251  GTGAAACGCC AACAGTATTT AGATATATTG ATTGGTTGCT AACTGTTCCT
     LeuLeuMetVal GluPheTyr LeuIleLeu AlaAlaCysThr AsnValAla·
301  TTGCTAATGG TTGAGTTCTA CTTAATCCTT GCAGCGTGCA CAAATGTTGC
     ·GlySerLeu PheLysLysLeu LeuGlyGly SerLeuVal MetLeuIleAla·
351  GGGTTCATTA TTTAAGAAAC TACTTGGTGG TTCGCTTGTA ATGCTTATTG
     · GlyTyrMet GlyGluSer GlySerLeuPro ValLeuPro AlaPheIle
401  CAGGATATAT GGGTGAGTCT GGAAGTCTTC CAGTATTGCC TGCATTCATT
     ValGlyCysLeu AlaTrpPhe TyrMetIle TyrGluLeuTyr AlaGlyGlu·
451  GTTGGGTGCT TAGCATGGTT CTACATGATT TATGAACTAT ATGCTGGTGA
     ·GlyLysAla AlaValThrThr AlaSerPro AlaValMet SerAlaTyrAsn·
501  AGGTAAGGCT GCAGTTACTA CTGCTAGTCC TGCTGTTATG TCTGCATACA
     · ThrMetMet LeuIleIle ValValGlyTrp AlaIleTyr ProAlaGly
551  ATACTATGAT GTTGATTATC GTAGTAGGTT GGGCAATTTA CCCAGCTGGA
     TyrAlaAlaGly TyrLeuMet GlyGlyAsp GlyValTyrAla GlnAsnLeu·
601  TATGCTGCTG GTTACCTAAT GGGTGGTGAT GGCGTATATG CTCAGAATTT
     ·AsnValIle TyrAsnLeuAla AspPheVal AsnLysIle LeuPheGlyLeu·
651  AAACGTTATA TATAACCTTG CTGACTTTGT TAACAAGATT TTATTTGGTT
     · ValIleTrp HisValAla ValLysGluSer SerAsnAla
701  TAGTTATCTG GCATGTTGCT GTTAAAGAAT CTTCTAATGC TA
```

Figure 1-71

```
    MetGlyLysLeu LeuLeuIle LeuGlyGly ValIleAlaLeu ProSerPhe·
  1 ATGGGTAAAT TATTACTGAT TTTAGGCGGT GTTATTGCGC TTCCTTCGTT
    ·AlaAlaSer GlyGlyAspLeu AspSerSer AspLeuThr GlyValSerPhe·
 51 TGCTGCAAGT GGAGGCGATC TTGATTCTAG TGATCTTACT GGAGTATCTT
    · TrpLeuVal ThrAlaAla LeuLeuAlaAla ThrValPhe PhePheVal
101 TTTGGCTTGT TACTGCTGCT CTCTTAGCTG CTACTGTTTT CTTTTTTGTT
    GluArgAspGln ValSerAla LysTrpLys ThrSerLeuThr ValSerGly·
151 GAAAGAGATC AAGTAAGCGC TAAATGGAAA ACATCACTTA CAGTTTCTGG
    ·LeuValThr GlyIleAlaPhe TrpHisTyr LeuTyrMet ArgGlyValTrp·
201 TTTAGTTACT GGTATTGCAT TCTGGCATTA TCTCTATATG AGAGGTGTGT
    · IleGluThr GlyGluThr ProThrValPhe ArgTyrIle AspTrpLeu
251 GGATCGAAAC CGGTGAAACA CCAACAGTAT TTAGATATAT TGATTGGTTG
    LeuThrValPro LeuLeuMet ValGluPhe TyrLeuIleLeu AlaAlaCys·
301 CTAACTGTTC CGTTACTAAT GGTTGAGTTC TACTTAATCC TCGCAGCTTG
    ·ThrAsnVal AlaGlySerLeu PheLysLys LeuLeuIle GlySerLeuVal·
351 CACTAATGTT GCAGGTTCAT TATTTAAGAA ACTACTAATT GGTTCGCTTG
    · MetLeuIle AlaGlyTyr MetGlyGluSer GlySerLeu ProValLeu
401 TAATGCTTAT TGCAGGATAT ATGGGTGAGT CTGGAAGTCT TCCAGTATTG
    ProAlaPheLeu ValGlyCys AlaAlaTrp LeuTyrMetIle TyrGluLeu·
451 CCTGCATTCC TTGTTGGGTG CGCAGCATGG TTATACATGA TTTATGAACT
    ·TyrAlaGly GluGlyLysAla AlaValThr ThrAlaSer ProAlaValMet·
501 ATATGCTGGT GAAGGTAAGG CTGCAGTTAC TACTGCTAGT CCTGCTGTTA
    · SerAlaTyr AsnThrMet MetLeuIleIle ValValGly TrpAlaIle
551 TGTCTGCATA CAATACTATG ATGTTGATTA TCGTAGTAGG TTGGGCAATA
    TyrProAlaGly TyrAlaAla GlyTyrLeu MetGlyGlyAsp GlyValTyr·
601 TACCCAGCTG GATATGCTGC TGGTTACTTA ATGGGTGGAG ATGGCGTATA
    ·AlaGlnAsn LeuAsnValIle TyrAsnLeu AlaAspPhe ValAsnLysIle·
651 TGCTCAGAAT TTAAACGTTA TATATAACCT TGCTGACTTT GTTAACAAGA
    · LeuPheGly LeuValIle TrpHisValAla ValLysGlu SerSerAsn
701 TTTTATTTGG TTTAGTTATC TGGCATGTTG CTGTTAAAGA ATCTTCTAAT
    Ala
751 GCTA
```

Figure 1-72

```
     MetGlyLysLeu LeuLeuIle LeuGlyGly ValIleAlaLeu ProSerPhe·
  1  ATGGGTAAAT TATTATTGAT CTTAGGCGGT GTTATTGCGC TTCCTTCGTT
     ·AlaAlaSer GlyGlyAspLeu AspSerSer AspLeuThr GlyValSerPhe·
 51  TGCTGCAAGT GGAGGCGATC TTGATTCTAG TGATCTTACT GGAGTATCTT
     · TrpLeuVal ThrAlaAla LeuLeuAlaAla ThrValPhe PhePheVal
101  TTTGGCTTGT TACTGCTGCT CTCTTAGCTG CTACTGTTTT CTTTTTTGTT
     GluArgAspGln ValSerAla LysTrpLys ThrSerLeuThr ValSerGly·
151  GAAAGAGATC AAGTAAGCGC TAAATGGAAA ACATCACTTA CAGTTTCTGG
     ·LeuValThr GlyIleAlaPhe TrpHisTyr LeuTyrMet ArgGlyValTrp·
201  TTTAGTTACT GGTATTGCAT TCTGGCATTA TCTCTATATG AGAGGTGTGT
     · IleGluThr GlyGluThr ProThrValPhe ArgTyrIle AspTrpLeu
251  GGATCGAAAC CGGTGAAACA CCAACAGTAT TTAGGTATAT TGATTGGTTG
     LeuThrValPro LeuLeuMet ValGluPhe TyrLeuIleLeu AlaAlaCys·
301  CTAACTGTTC CGTTACTAAT GGTTGAGTTC TACTTAATCC TCGCAGCTTG
     ·ThrAsnVal AlaGlySerLeu PheLysLys LeuLeuIle GlySerLeuVal·
351  CACTAATGTT GCAGGTTCAT TATTTAAGAA ACTACTAATT GGTTCGCTTG
     · MetLeuIle AlaGlyTyr MetGlyGluSer GlySerLeu ProValLeu
401  TAATGCTTAT TGCAGGATAT ATGGGTGAGT CTGGAAGTCT TCCAGTATTG
     ProAlaPheLeu ValGlyCys AlaAlaTrp LeuTyrMetIle TyrGluLeu·
451  CCTGCATTCC TTGTTGGGTG CGCAGCATGG TTATACATGA TTTATGAACT
     ·TyrAlaGly GluGlyLysAla AlaValThr ThrAlaSer ProAlaValMet·
501  ATATGCTGGT GAAGGTAAGG CTGCAGTTAC TACTGCTAGT CCTGCTGTTA
     · SerAlaTyr AsnThrMet MetLeuIleIle ValValGly TrpAlaIle
551  TGTCTGCATA CAATACTATG ATGTTGATTA TCGTAGTAGG TTGGGCAATA
     TyrProAlaGly TyrAlaAla GlyTyrLeu MetGlyGlyAsp GlyValTyr·
601  TACCCAGCTG GATATGCTGC TGGTTACTTA ATGGGTGGAG ATGGCGTATA
     ·AlaGlnAsn LeuAsnValIle TyrAsnLeu AlaAspPhe ValAsnLysIle·
651  TGCTCAGAAT TTAAACGTTA TATATAACCT TGCTGACTTT GTTAACAAGA
     · LeuPheGly LeuValIle TrpHisValAla ValLysGlu SerSerAsn
701  TTTTATTTGG TTTAGTTATC TGGCATGTTG CTGTTAAAGA ATCTTCTAAT
751  C
```

Figure 1-73

```
     MetGlyLysLeu LeuLeuIle LeuGlyGly ValIleAlaLeu ProSerPhe·
  1  ATGGGTAAAT TATTACTGAT CTTAGGCGGT GTTATTGCGC TTCCTTCGTT
     ·AlaAlaSer GlyGlyAspLeu AspSerSer AspLeuThr GlyValSerPhe·
 51  TGCTGCAAGT GGAGGCGATC TTGATTCTAG TGATCTTACT GGAGTATCTT
     · TrpLeuVal ThrAlaAla LeuLeuAlaAla ThrValPhe PhePheVal
101  TTTGGCTTGT TACTGCTGCT CTCTTAGCTG CTACTGTTTT CTTTTTTGTT
     GluArgAspGln ValSerAla LysTrpLys ThrSerLeuThr ValSerGly·
151  GAAAGAGATC AAGTAAGCGC TAAATGGAAA ACATCACTTA CAGTTTCTGG
     ·LeuValThr GlyIleAlaPhe TrpHisTyr LeuTyrMet ArgGlyValTrp·
201  TTTAGTTACT GGTATTGCAT TCTGGCATTA TCTCTATATG AGAGGTGTGT
     · IleGluThr GlyGluThr ProThrValPhe ArgTyrIle AspTrpLeu
251  GGATCGAAAC CGGTGAAACA CCAACAGTAT TTAGATATAT TGATTGGTTG
     LeuThrValPro LeuLeuMet ValGluPhe TyrLeuIleLeu AlaAlaCys·
301  CTAACTGTTC CGTTACTAAT GGTTGAGTTC TACTTAATCC TCGCAGCTTG
     ·ThrAsnVal AlaGlySerLeu PheLysLys LeuLeuIle GlySerLeuVal·
351  CACTAATGTT GCAGGTTCAT TATTTAAGAA ACTACTAATT GGTTCGCTTG
     · MetLeuIle AlaGlyTyr MetGlyGluSer GlySerLeu ProValLeu
401  TAATGCTTAT TGCAGGATAT ATGGGTGAGT CTGGAAGTCT TCCAGTATTG
     ProAlaPheLeu ValGlyCys AlaAlaTrp LeuTyrMetIle TyrGluLeu·
451  CCTGCATTCC TTGTTGGGTG CGCAGCATGG TTATACATGA TTTATGAACT
     ·TyrAlaGly GluGlyLysAla AlaValThr ThrAlaSer ProAlaValMet·
501  ATATGCTGGT GAAGGTAAGG CTGCAGTTAC TACTGCTAGT CCTGCTGTTA
     · SerAlaTyr AsnThrMet MetLeuIleIle ValValGly TrpAlaIle
551  TGTCTGCATA CAATACTATG ATGTTGATTA TCGTAGTAGG TTGGGCAATA
     TyrProAlaGly TyrAlaAla GlyTyrLeu MetGlyGlyAsp GlyValTyr·
601  TACCCAGCTG GATATGCTGC TGGTTACTTA ATGGGTGGAG ATGGCGTATA
     ·AlaGlnAsn LeuAsnValIle TyrAsnLeu AlaAspPhe ValAsnLysIle·
651  TGCTCAGAAT TTAAACGTTA TATATAACCT TGCTGACTTC GTTAACAAGA
     · LeuPheGly LeuValIle TrpHisValAla ValLysGlu SerSerAsn
701  TTTTATTTGG TTTAGTTATC TGGCATGTTG CTGTTAAAGA ATCTTCTAAT
     Ala
751  GCTA
```

Figure 1-74

```
    MetGlyLysArg LeuValIle LeuGlyGly ValIleAlaLeu ProSerPhe·
  1 ATGGGTAAAA GATTAGTGAT CTTAGGCGGT GTTATTGCGC TTCCTTCGTT
    ·AlaAlaSer GlyGlyAspLeu AspSerSer AspLeuThr GlyValSerPhe·
 51 TGCTGCAAGT GGAGGCGATC TTGATTCTAG TGATCTTACT GGAGTATCTT
    · TrpLeuVal ThrAlaAla LeuLeuAlaAla ThrValPhe PhePheVal
101 TTTGGCTTGT TACTGCTGCT CTCTTAGCTG CTACTGTTTT CTTTTTTGTT
    GluArgAspGln ValSerAla LysTrpLys ThrSerLeuThr ValSerGly·
151 GAAAGAGATC AAGTAAGCGC TAAATGGAAA ACATCACTTA CAGTTTCTGG
    ·LeuValThr GlyIleAlaPhe TrpHisTyr LeuTyrMet ArgGlyValTrp·
201 TTTAGTTACT GGTATTGCAT TCTGGCATTA TCTCTATATG AGAGGTGTGT
    · IleGluThr GlyGluThr ProThrValPhe ArgTyrIle AspTrpLeu
251 GGATCGAAAC CGGTGAAACA CCAACAGTAT TTAGATATAT TGATTGGTTG
    LeuThrValPro LeuLeuMet ValGluPhe TyrLeuIleLeu AlaAlaCys·
301 CTAACTGTTC CGTTACTAAT GGTTGAGTTC TACTTAATCC TCGCAGCTTG
    ·ThrAsnVal AlaGlySerLeu PheLysLys LeuLeuIle GlySerLeuVal·
351 CACTAATGTT GCAGGTTCAT TATTTAAGAA ACTACTAATT GGTTCGCTTG
    · MetLeuIle AlaGlyTyr MetGlyGluSer GlyAsnLeu ProValLeu
401 TAATGCTTAT TGCAGGATAT ATGGGTGAGT CTGGAAATCT TCCAGTATTG
    ProAlaPheLeu IleGlyCys AlaAlaTrp LeuTyrMetIle TyrGluLeu·
451 CCTGCATTCC TTATTGGGTG CGCAGCATGG TTATACATGA TTTATGAACT
    ·TyrAlaGly GluGlyLysAla AlaValThr ThrAlaSer ProAlaValMet·
501 ATATGCTGGT GAAGGTAAGG CTGCAGTTAC TACTGCTAGT CCTGCTGTTA
    · SerAlaTyr AsnThrMet MetLeuIleIle ValValGly TrpAlaIle
551 TGTCTGCATA CAATACTATG ATGTTGATTA TCGTAGTAGG TTGGGCAATA
    TyrProAlaGly TyrAlaAla GlyTyrLeu MetGlyGlyAsp GlyValTyr·
601 TACCCAGCTG GATATGCTGC TGGTTACTTA ATGGGTGGAG ATGGCGTATA
    ·AlaGlnAsn LeuAsnValIle TyrAsnLeu AlaAspPhe ValAsnLysIle·
651 TGCTCAGAAT TTAAACGTTA TATATAACCT TGCTGACTTT GTTAACAAGA
    · LeuPheGly LeuValIle TrpHisValAla ValLysGlu SerSerAsn
701 TTTTATTTGG TTTAGTTATC TGGCATGTTG CTGTTAAAGA ATCTTCTAAT
    Ala
751 GCTA
```

Figure 1-75

```
    SerLysLysLeu LeuAlaThr PheLeuVal ValThrSerIle ProAlaIle·
  1 AGCAAGAAAC TTCTTGCGAC ATTTCTAGTA GTAACATCAA TACCAGCAAT
    ·AlaLeuAla GlyGlyHisSer SerGlyGly LeuAlaGly AspAspCysVal·
 51 AGCATTAGCT GGTGGGCATT CATCTGGTGG TTTAGCAGGA GATGACTGCG
    · GlyValThr PheTrpIle IleSerMetAla MetValAla SerThrVal
101 TAGGTGTTAC TTTCTGGATT ATTTCTATGG CTATGGTTGC TTCAACAGTA
    PhePheIleVal GluArgAsp ArgValSer AlaLysTrpLys ThrSerLeu·
151 TTCTTTATTG TTGAGCGTGA CAGAGTTAGT GCGAAATGGA AAACATCATT
    ·ThrValSer AlaLeuMetThr LeuIleAla AlaValHis TyrPheTyrMet·
201 AACAGTATCA GCGCTTATGA CTTTAATCGC AGCTGTTCAC TATTTCTACA
    · ArgAspVal TrpValAla ThrGlyGluSer ProThrVal PheArgTyr
251 TGAGAGATGT TTGGGTAGCA ACTGGCGAAT CACCAACAGT CTTTAGATAT
    IleAspTrpLeu LeuThrVal ProLeuLeu MetIleGluPhe TyrPheIle·
301 ATAGATTGGT TGTTAACAGT TCCACTTCTA ATGATTGAGT TCTACTTTAT
    ·LeuAlaAla ValThrThrVal SerSerGly IlePheTrp ArgLeuLeuVal·
351 CTTAGCAGCG GTTACAACTG TATCTTCAGG AATTTTCTGG AGATTACTAG
    · GlyThrVal IleMetLeu ValGlyGlyTyr LeuGlyGlu AlaGlyMet
401 TAGGTACTGT AATAATGCTA GTAGGTGGAT ACTTAGGTGA AGCTGGAATG
    IleSerValMet ThrGlyPhe IleIleGly MetIleGlyTrp LeuTyrIle·
451 ATTTCGGTAA TGACAGGTTT CATTATAGGG ATGATAGGTT GGCTATACAT
    ·LeuTyrGlu IlePheAlaGly GluAlaSer LysAlaAsn AlaSerSerGly·
501 TCTTTATGAA ATCTTTGCAG GTGAAGCTAG CAAAGCAAAT GCTTCTAGTG
    · SerAlaAla CysGlnThr AlaPheGlyAla LeuArgLeu IleValThr
551 GAAGTGCAGC TTGTCAAACA GCCTTTGGAG CTTTACGTTT AATCGTAACC
    IleGlyTrpAla IleTyrPro LeuGlyTyr PheLeuGlyTyr LeuGlyGly·
601 ATTGGTTGGG CAATTTATCC GCTAGGATAT TTCTTAGGTT ATCTAGGCGG
    ·GlyAlaAsp ProAlaThrLeu AsnIleVal TyrAsnLeu AlaAspPheVal·
651 TGGGGCAGAC CCAGCTACAT TAAACATTGT TTACAACTTA GCTGACTTTG
    · AsnLysIle AlaPheGly LeuIleIleTrp AlaAlaAla ValLysGlu
701 TAAACAAAAT TGCTTTTGGT TTAATTATAT GGGCAGCAGC TGTTAAAGAA
    SerSerAsnAla
751 TCTTCTAATG CTA
```

Figure 1-76

```
    SerLysLysLeu LeuAlaThr PheLeuVal ValThrSerIle ProAlaIle·
  1 AGCAAGAAAC TTCTTGCGAC ATTTCTAGTA GTAACATCAA TACCAGCAAT
    ·AlaLeuAla GlyGlyHisSer SerGlyGly LeuAlaGly AspAspTyrVal·
 51 AGCATTAGCT GGTGGGCATT CATCTGGTGG TTTAGCAGGA GATGACTACG
    · GlyValThr PheTrpIle IleSerMetAla MetValAla SerThrVal
101 TAGGTGTTAC TTTCTGGATT ATTTCTATGG CTATGGTTGC TTCAACAGTA
    PhePheIleVal GluArgAsp ArgValSer AlaLysTrpLys ThrSerLeu·
151 TTCTTTATTG TTGAGCGTGA CAGAGTTAGT GCGAAATGGA AAACATCATT
    ·ThrValSer AlaLeuValThr LeuIleAla AlaValHis TyrPheTyrMet·
201 AACAGTATCA GCGCTTGTGA CTTTAATCGC AGCTGTTCAC TATTTCTACA
    · ArgAspVal TrpValAla ThrGlyGluSer ProThrVal PheArgTyr
251 TGAGAGATGT TTGGGTAGCA ACTGGCGAAT CACCAACAGT CTTTAGATAT
    IleAspTrpLeu LeuThrVal ProLeuLeu MetIleGluPhe TyrPheIle·
301 ATAGATTGGT TGTTAACAGT TCCACTTCTA ATGATTGAGT TCTACTTTAT
    ·LeuAlaAla ValThrThrVal SerSerGly IlePheTrp ArgLeuLeuVal·
351 CTTAGCAGCG GTTACAACTG TATCTTCAGG AATTTTCTGG AGATTACTAG
    · GlyThrVal IleMetLeu ValGlyGlyTyr LeuGlyGlu AlaGlyMet
401 TAGGTACTGT AATAATGCTA GTAGGTGGAT ACTTAGGTGA AGCTGGAATG
    IleSerValMet ThrGlyPhe IleIleGly MetIleGlyTrp LeuTyrIle·
451 ATTTCGGTAA TGACAGGTTT CATTATAGGG ATGATAGGTT GGCTATACAT
    ·LeuTyrGlu IlePheAlaGly GluAlaSer LysAlaAsn AlaSerSerGly·
501 TCTTTATGAA ATCTTTGCAG GTGAAGCTAG CAAAGCAAAT GCTTCTAGTG
    · SerAlaAla CysGlnThr AlaPheGlyAla LeuArgLeu IleValThr
551 GAAGTGCAGC TTGTCAAACA GCCTTTGGAG CTTTACGTTT AATCGTAACC
    IleGlyTrpAla IleTyrPro LeuGlyTyr PheLeuGlyTyr LeuGlyGly·
601 ATTGGTTGGG CAATTTATCC GCTAGGATAT TTCTTAGGTT ATCTAGGCGG
    ·GlyAlaAsp ProAlaThrLeu AsnIleVal TyrAsnLeu AlaAspPheVal·
651 TGGGGCAGAC CCAGCTACAT TAAACATTGT TTACAACTTA GCTGACTTTG
    · AsnLysIle AlaPheGly LeuIleIleTrp AlaAlaAla ValLysGlu
701 TAAACAAAAT TGCTTTTGGT TTAATTATAT GGGCAGCAGC TGTTAAAGAA
    SerSerAsnAla
751 TCTTCTAATG CTA
```

Figure 1-77

```
     SerLysLysPhe PheSerThr LeuLeuLeu ValThrSerLeu ProThrLeu·
  1  AGCAAAAAGT TTTTTTCGAC GCTTCTATTA GTAACATCCT TGCCAACTTT
     ·AlaLeuAla GlyGlyHisSer SerGlyLeu AlaGlyAsp AspTyrValGly·
 51  AGCTTTAGCA GGTGGGCATT CATCTGGTCT TGCTGGAGAT GACTATGTAG
     · ValThrPhe TrpIleIle SerMetAlaMet ValAlaSer ThrValPhe
101  GTGTTACTTT CTGGATTATT TCCATGGCTA TGGTTGCGTC AACAGTATTT
     PheIleValGlu ArgAspArg ValSerSer LysTrpLysThr SerLeuThr·
151  TTCATTGTGG AGCGTGACAG AGTTAGCTCA AAATGGAAAA CATCATTAAC
     ·ValSerAla LeuValThrLeu IleAlaAla ValHisTyr PheTyrMetArg·
201  AGTATCAGCT TTGGTTACAT TAATTGCTGC AGTGCATTAT TTTTATATGA
     · AspValTrp ValAlaThr GlyGluSerPro ThrValPhe ArgTyrIle
251  GAGATGTATG GGTAGCAACT GGTGAATCAC CAACAGTATT TAGATATATA
     AspTrpLeuLeu ThrValPro LeuLeuMet IleGluPheTyr PheIleLeu·
301  GATTGGTTAT TAACAGTGCC ACTATTAATG ATTGAGTTCT ACTTTATTTT
     ·AlaAlaVal ThrThrValSer SerGlyIle PheTrpArg LeuLeuIleGly·
351  AGCAGCGGTA ACTACAGTTT CTTCAGGAAT ATTCTGGAGA CTATTAATTG
     · ThrValVal MetLeuVal GlyGlyTyrMet GlyGluAla GlyMetIle
401  GTACAGTTGT AATGCTAGTA GGTGGGTATA TGGGTGAAGC TGGAATGATC
     SerValMetThr GlyPheIle IleGlyMet IleGlyTrpLeu TyrIleLeu·
451  TCAGTGATGA CAGGTTTCAT TATCGGGATG ATCGGTTGGC TATATATTCT
     ·TyrGluIle PheAlaGlyGlu AlaSerLys AlaAsnAla SerSerGlySer·
501  TTACGAAATC TTTGCTGGTG AAGCTAGTAA AGCAAACGCT TCTAGTGGAA
     · AlaAlaCys GlnThrAla PheGlyAlaLeu ArgLeuIle ValThrVal
551  GCGCAGCATG CCAAACAGCA TTTGGTGCGT TACGTTTAAT CGTTACAGTT
     GlyTrpAlaIle TyrProIle GlyTyrPhe ValGlyTyrLeu ThrGlyGly·
601  GGTTGGGCGA TCTATCCAAT AGGATACTTC GTAGGCTATC TAACTGGTGG
     ·GlyAlaAsp AlaAlaThrLeu AsnIleVal TyrAsnLeu AlaAspPheVal·
651  TGGTGCAGAC GCAGCTACAC TAAACATAGT TTACAACTTA GCTGATTTTG
     · AsnLysIle AlaPheGly LeuIleIleTrp AlaAlaAla ValLysGlu
701  TAAACAAAAT TGCCTTTGGT TTAATCATAT GGGCAGCAGC TGTTAAAGAA
     SerSerAsnAla
751  TCTTCTAATG CTA
```

Figure 1-78

```
    SerLysLysPhe PheSerThr LeuLeuLeu ValThrSerLeu ProThrLeu·
  1 AGCAAAAAGT TTTTTTCGAC GCTTCTATTA GTAACATCCT TGCCAACTTT
    ·AlaLeuAla GlyGlyHisSer SerGlyLeu AlaGlyAsp AspTyrValGly·
 51 AGCTTTAGCA GGTGGGCATT CATCTGGTCT TGCTGGAGAT GACTATGTAG
    · ValThrPhe TrpIleIle SerMetAlaMet ValAlaSer ThrValPhe
101 GTGTTACTTT CTGGATTATT TCCATGGCTA TGGTTGCGTC AACAGTATTT
    PheIleValGlu ArgAspArg ValSerSer LysTrpLysThr SerLeuThr·
151 TTCATTGTGG AGCGTGACAG AGTTAGCTCA AAATGGAAAA CATCATTAAC
    ·ValSerAla LeuValThrLeu IleAlaAla ValHisTyr PheTyrMetArg·
201 AGTATCAGCT TTGGTTACAT TAATTGCTGC AGTGCATTAT TTTTATATGA
    · AspValTrp ValAlaThr GlyGluSerPro ThrValPhe ArgTyrIle
251 GAGATGTATG GGTAGCAACT GGTGAATCAC CAACAGTATT TAGATATATA
    AspTrpLeuLeu ThrValPro LeuLeuMet IleGluPheTyr PheIleLeu·
301 GATTGGTTAT TAACAGTGCC ACTATTAATG ATTGAGTTCT ACTTTATTTT
    ·AlaAlaVal ThrThrValSer SerGlyIle PheTrpArg LeuLeuIleGly·
351 AGCAGCGGTA ACTACAGTTT CTTCAGGAAT ATTCTGGAGA CTATTAATTG
    · ThrValVal MetLeuVal GlyGlyTyrMet GlyGluAla GlyMetIle
401 GTACAGTTGT AATGCTAGTA GGTGGGTATA TGGGTGAAGC TGGAATGATC
    SerValMetThr GlyPheIle IleGlyMet IleGlyTrpLeu TyrIleLeu·
451 TCAGTGATGA CAGGTTTCAT TATCGGGATG ATCGGTTGGC TATATATTCT
    ·TyrGluIle PheAlaGlyGlu AlaSerLys AlaAsnAla SerSerGlySer·
501 TTACGAAATC TTTGCTGGTG AAGCTAGTAA AGCAAACGCT TCTAGTGGAA
    · AlaAlaCys GlnThrAla PheGlyAlaLeu ArgLeuIle ValThrVal
551 GCGCAGCATG CCAAACAGCA TTTGGTGCGT TACGTTTAAT CGTTACAGTT
    GlyTrpAlaIle TyrProIle GlyTyrPhe ValGlyTyrLeu ThrGlyGly·
601 GGTTGGGCGA TCTATCCAAT AGGATACTTC GTAGGCTATC TAACTGGTGG
    ·GlyAlaAsp AlaAlaThrLeu AsnIleVal TyrAsnLeu AlaAspPheVal·
651 TGGTGCAGAC GCAGCTACAC TAAACATAGT TTACAACTTA GCTGATTTTG
    · AsnLysIle AlaPheGly LeuIleIleTrp AlaAlaAla ValLysGlu
701 TAAACAAAAT TGCCTTTGGT TTAATCATAT GGGCAGCAGC TGTTAAAGAA
    SerSerAsnAla
751 TCTTCTAATG CTA
```

Figure 1-79

```
    MetLysLeuLeu LeuIleLeu GlySerAla IleAlaLeuPro SerPheAla·
  1 ATGAAATTAT TATTGATCTT AGGTAGTGCT ATTGCACTTC CATCATTTGC
    ·AlaAlaGly GlyAspLeuAsp IleSerAsp ThrValGly ValSerPheTrp·
 51 TGCTGCTGGT GGCGATCTAG ATATAAGTGA TACTGTTGGT GTTTCATTCT
    · LeuValThr AlaGlyMet LeuAlaAlaThr ValPhePhe PheValGlu
101 GGCTGGTTAC AGCTGGTATG TTAGCGGCAA CTGTGTTCTT TTTTGTAGAA
    ArgAspGlnVal SerAlaLys TrpLysThr SerLeuThrVal SerGlyLeu·
151 AGAGACCAAG TCAGCGCTAA GTGGAAAACT TCACTTACTG TATCTGGTTT
    ·IleThrGly IleAlaPheTrp HisTyrLeu TyrMetArg GlyValTrpIle·
201 AATTACTGGT ATAGCTTTTT GGCATTATCT CTATATGAGA GGTGTTTGGA
    · AspThrGly AspThrPro ThrValPheArg TyrIleAsp TrpLeuLeu
251 TAGACACTGG TGATACCCCA ACAGTATTCA GATATATTGA TTGGTTATTA
    ThrValProLeu GlnMetVal GluPheTyr LeuIleLeuAla AlaCysThr·
301 ACTGTTCCAT TACAAATGGT TGAGTTCTAT CTAATTCTTG CTGCTTGTAC
    ·SerValAla AlaSerLeuPhe LysLysLeu LeuAlaGly SerLeuValMet·
351 AAGTGTTGCT GCTTCATTAT TTAAGAAGCT TCTAGCTGGT TCATTAGTAA
    · LeuGlyAla GlyPheAla GlyGluAlaGly LeuAlaPro ValLeuPro
401 TGTTAGGTGC TGGATTTGCA GGCGAAGCTG GATTAGCTCC TGTATTACCT
    AlaPheIleIle GlyMetAla GlyTrpLeu TyrMetIleTyr GluLeuTyr·
451 GCTTTCATTA TTGGTATGGC TGGATGGTTA TACATGATTT ATGAGCTATA
    ·MetGlyGlu GlyLysAlaAla ValSerThr AlaSerPro AlaValAsnSer·
501 TATGGGTGAA GGTAAGGCTG CTGTAAGTAC TGCAAGTCCT GCTGTTAACT
    · AlaTyrAsn AlaMetMet MetIleIleVal ValGlyTrp AlaIleTyr
551 CTGCATACAA CGCAATGATG ATGATTATTG TTGTTGGATG GGCAATTTAT
    ProAlaGlyTyr AlaAlaGly TyrLeuMet GlyGlyGluGly ValTyrAla·
601 CCTGCTGGAT ATGCTGCTGG TTACCTAATG GGTGGCGAAG GTGTATACGC
    ·SerAsnLeu AsnLeuIleTyr AsnLeuAla AspPheVal AsnLysIleLeu·
651 TTCAAACTTA AACCTTATAT ATAACCTTGC TGACTTTGTT AACAAGATTC
    · PheGlyLeu IleIleTrp AsnValAlaVal LysGluSer SerAsnAla
701 TATTTGGTTT GATCATTTGG AATGTTGCAG TTAAAGAATC TAGTAATGCT
```

Figure 1-80

```
    MetLysValLeu MetLeuAsn ProGlyAsp HisValAlaIle SerPheTrp·
  1 ATGAAAGTAT TAATGCTAAA TCCCGGAGAT CACGTTGCGA TTTCGTTTTG
    ·LeuIleSer MetAlaMetVal AlaAlaThr AlaPhePhe PheLeuGluArg·
 51 GTTGATCTCT ATGGCCATGG TTGCCGCTAC TGCTTTCTTC TTTCTTGAAA
    · AspArgVal AlaAlaLys TrpLysThrSer LeuThrVal AlaGlyLeu
101 GAGATCGTGT AGCAGCTAAA TGGAAAACGT CCCTTACAGT AGCTGGTTTA
    ValThrGlyIle AlaAlaTrp HisTyrPhe TyrMetArgGly ValTrpVal·
151 GTTACTGGTA TTGCGGCGTG GCACTACTTC TACATGAGAG GCGTATGGGT
    ·AlaThrGly AspSerProThr ValLeuArg TyrIleAsp TrpLeuIleThr·
201 TGCTACTGGT GACTCACCAA CTGTCCTTCG TTACATTGAC TGGTTGATTA
    · ValProLeu GlnIleVal GluPheTyrVal IleLeuAla AlaMetThr
251 CTGTGCCTCT ACAAATCGTA GAATTCTACG TAATTCTTGC AGCGATGACT
    AlaValAlaSer SerLeuPhe TrpArgLeu LeuIleAlaSer IleIleMet·
301 GCTGTTGCTT CAAGCCTTTT CTGGAGACTA TTAATTGCAT CAATTATTAT
    ·LeuValPhe GlyTyrMetGly GluThrGly AlaMetAsn ValThrLeuAla·
351 GCTTGTCTTT GGTTACATGG GTGAAACTGG AGCGATGAAT GTAACTCTAG
    · PheValIle GlyMetAla GlyTrpLeuTyr IleIleTyr GluValPhe
401 CCTTCGTAAT AGGTATGGCT GGATGGTTAT ACATCATCTA CGAGGTTTTT
    AlaGlyGluAla SerLysAla SerAlaGly SerGlyAsnAla AlaGlyGln·
451 GCAGGTGAAG CAAGCAAGGC AAGTGCTGGT AGTGGAAACG CTGCTGGTCA
    ·ThrAlaPhe AsnAlaLeuArg LeuIleVal ThrValGly TrpAlaIleTyr·
501 GACTGCATTT AACGCATTGA GATTAATTGT TACAGTAGGA TGGGCAATTT
    · ProIleGly TyrAlaVal GlyTyrPheGly GlyGlyVal AspAlaGly
551 ATCCAATTGG TTATGCTGTA GGTTACTTCG GTGGTGGCGT AGACGCCGGT
    SerLeuAsnLeu IleTyrAsn LeuAlaAsp PheValAsnLys IleAlaPhe·
601 TCATTGAACT TAATCTATAA CCTTGCAGAC TTTGTTAATA AAATTGCATT
    ·GlyMetAla IleTyrValAla AlaValSer AspSerAsn
651 TGGTATGGCT ATTTATGTAG CTGCAGTATC AGACAGCAAC
```

Figure 1-81

```
    MetLysLeuLeu LeuIleLeu GlySerVal IleAlaLeuPro ThrPheAla·
  1 ATGAAATTAT TACTGATATT AGGTAGTGTT ATTGCACTTC CTACATTTGC
    ·AlaGlyGly GlyAspLeuAsp AlaSerAsp TyrThrGly ValSerPheTrp·
 51 TGCAGGTGGT GGTGACCTTG ATGCTAGTGA TTACACTGGT GTTTCTTTTT
    · LeuValThr AlaAlaLeu LeuAlaSerThr ValPhePhe PheValGlu
101 GGTTAGTTAC TGCTGCTTTA TTAGCATCTA CTGTATTTTT CTTTGTTGAA
    ArgAspArgVal SerAlaLys TrpLysThr SerLeuThrVal SerGlyLeu·
151 AGAGATAGAG TTTCTGCAAA ATGGAAAACA TCATTAACTG TATCTGGTCT
    ·ValThrGly IleAlaPheTrp LysTyrMet TyrMetArg GlyValTrpIle·
201 TGTTACTGGT ATTGCTTTCT GGAAATACAT GTACATGAGA GGGGTATGGA
    · GluThrGly AspSerPro ThrValPheArg TyrIleAsp TrpLeuLeu
251 TTGAAACTGG TGATTCGCCA ACTGTATTTA GATACATTGA TTGGTTACTA
    ThrValProLeu LeuIleCys GluPheTyr LeuIleLeuAla AlaAlaThr·
301 ACAGTTCCTC TATTAATATG TGAATTCTAC TTAATTCTTG CTGCTGCAAC
    ·AsnValAla GlySerLeuPhe LysLysLeu LeuValGly SerLeuValMet·
351 TAATGTTGCT GGATCATTAT TTAAGAAATT ACTAGTTGGT TCTCTTGTTA
    · LeuValPhe GlyTyrMet GlyGluAlaGly IleMetAla AlaTrpPro
401 TGCTTGTGTT TGGTTACATG GGTGAAGCAG GAATCATGGC TGCATGGCCT
    AlaPheIleIle GlyCysLeu AlaTrpVal TyrMetIleTyr GluLeuTrp·
451 GCATTCATTA TTGGGTGTTT AGCTTGGGTA TACATGATTT ATGAATTATG
    ·AlaGlyGlu GlyLysSerAla CysAsnThr AlaSerPro AlaValGlnSer·
501 GGCTGGAGAA GGAAAATCTG CATGTAATAC TGCAAGTCCT GCTGTGCAAT
    · AlaTyrAsn ThrMetMet TyrIleIleIle PheGlyTrp AlaIleTyr
551 CAGCTTACAA CACAATGATG TATATTATCA TCTTTGGTTG GGCGATTTAT
    ProValGlyTyr PheThrGly TyrLeuMet GlyAspGlyGly SerAlaLeu·
601 CCTGTAGGTT ATTTCACAGG TTACCTGATG GGTGACGGTG GATCAGCTCT
    ·AsnLeuAsn LeuIleTyrAsn LeuAlaAsp PheValAsn LysIleLeuPhe·
651 TAACTTAAAC CTTATCTATA ACCTTGCTGA CTTTGTTAAC AAGATTCTAT
    · GlyLeuIle IleTrpAsn ValAlaValLys GluSerSer AsnAla***
701 TTGGTTTAAT TATATGGAAT GTTGCTGTTA AAGAATCTTC TAATGCTTAA
```

Figure 2-1

```
     MetLysLeuLeu LeuIleLeu GlySerVal IleAlaLeuPro ThrPheAla·
  1  ATGAAATTAT TACTGATATT AGGTAGTGTT ATTGCACTTC CTACATTTGC
     ·AlaGlyGly GlyAspLeuAsp AlaSerAsp TyrThrGly ValSerPheTrp·
 51  TGCAGGTGGT GGTGACCTTG ATGCTAGTGA TTACACTGGT GTTTCTTTTT
     · LeuValThr AlaAlaLeu LeuAlaSerThr ValPhePhe PheValGlu
101  GGTTAGTTAC TGCTGCTTTA TTAGCATCTA CTGTATTTTT CTTTGTTGAA
     ArgAspArgVal SerAlaLys TrpLysThr SerLeuThrVal SerGlyLeu·
151  AGAGATAGAG TTTCTGCAAA ATGGAAAACA TCATTAACTG TATCTGGTCT
     ·ValThrGly IleAlaPheTrp AsnTyrMet TyrMetArg GlyValTrpIle·
201  TGTTACTGGT ATTGCTTTCT GGAATTACAT GTACATGAGA GGGGTATGGA
     · GluThrGly AspSerPro ThrValPheArg TyrIleAsp TrpLeuLeu
251  TTGAAACTGG TGATTCGCCA ACTGTATTTA GATACATTGA TTGGTTACTA
     ThrValProLeu LeuIleCys GluPheTyr LeuIleLeuAla AlaAlaThr·
301  ACAGTTCCTC TATTAATATG TGAATTCTAC TTAATTCTTG CTGCTGCAAC
     ·AsnValAla GlySerLeuPhe LysLysLeu LeuValGly SerLeuValMet·
351  TAATGTTGCT GGATCATTAT TTAAGAAATT ACTAGTTGGT TCTCTTGTTA
     · LeuValPhe GlyTyrMet GlyGluAlaGly IleMetAla AlaTrpPro
401  TGCTTGTGTT TGGTTACATG GGTGAAGCAG GAATCATGGC TGCATGGCCT
     AlaPheIleIle GlyCysLeu AlaTrpVal TyrMetIleTyr GluLeuTrp·
451  GCATTCATTA TTGGGTGTTT AGCTTGGGTA TACATGATTT ATGAATTATG
     ·AlaGlyGlu GlyLysSerAla CysAsnThr AlaSerPro AlaValGlnSer·
501  GGCTGGAGAA GGAAAATCTG CATGTAATAC TGCAAGTCCT GCTGTGCAAT
     · AlaTyrAsn ThrMetMet TyrIleIleIle PheGlyTrp AlaIleTyr
551  CAGCTTACAA CACAATGATG TATATTATCA TCTTTGGTTG GGCGATTTAT
     ProValGlyTyr PheThrGly TyrLeuMet GlyAspGlyGly SerAlaLeu·
601  CCTGTAGGTT ATTTCACAGG TTACCTGATG GGTGACGGTG GATCAGCTCT
     ·AsnLeuAsn LeuIleTyrAsn LeuAlaAsp PheValAsn LysIleLeuPhe·
651  TAACTTAAAC CTTATCTATA ACCTTGCTGA CTTTGTTAAC AAGATTCTAT
     · GlyLeuIle IleTrpAsn ValAlaValLys GluSerSer AsnAla***
701  TTGGTTTAAT TATATGGAAT GTTGCTGTTA AAGAATCTTC TAATGCTTAA
```

Figure 2-2

```
    MetLysLeuLeu LeuIleLeu GlySerVal IleAlaLeuPro ThrPheAla·
  1 ATGAAATTAT TACTGATATT AGGTAGTGTT ATTGCACTTC CTACATTTGC
    ·AlaGlyGly GlyAspLeuAsp AlaSerAsp TyrThrGly ValSerPheTrp·
 51 TGCAGGTGGT GGTGACCTTG ATGCTAGTGA TTACACTGGT GTTTCTTTTT
    · LeuValThr AlaAlaLeu LeuAlaSerThr ValPhePhe PheValGlu
101 GGTTAGTTAC TGCTGCTTTA TTAGCATCTA CTGTATTTTT CTTTGTTGAA
    ArgAspArgVal SerAlaLys TrpLysThr SerLeuThrVal SerGlyLeu·
151 AGAGATAGAG TTTCTGCAAA ATGGAAAACA TCATTAACTG TATCTGGTCT
    ·ValThrGly IleAlaPheTrp GlnTyrMet TyrMetArg GlyValTrpIle·
201 TGTTACTGGT ATTGCTTTCT GGCAGTACAT GTACATGAGA GGGGTATGGA
    · GluThrGly AspSerPro ThrValPheArg TyrIleAsp TrpLeuLeu
251 TTGAAACTGG TGATTCGCCA ACTGTATTTA GATACATTGA TTGGTTACTA
    ThrValProLeu LeuIleCys GluPheTyr LeuIleLeuAla AlaAlaThr·
301 ACAGTTCCTC TATTAATATG TGAATTCTAC TTAATTCTTG CTGCTGCAAC
    ·AsnValAla GlySerLeuPhe LysLysLeu LeuValGly SerLeuValMet·
351 TAATGTTGCT GGATCATTAT TTAAGAAATT ACTAGTTGGT TCTCTTGTTA
    · LeuValPhe GlyTyrMet GlyGluAlaGly IleMetAla AlaTrpPro
401 TGCTTGTGTT TGGTTACATG GGTGAAGCAG GAATCATGGC TGCATGGCCT
    AlaPheIleIle GlyCysLeu AlaTrpVal TyrMetIleTyr GluLeuTrp·
451 GCATTCATTA TTGGGTGTTT AGCTTGGGTA TACATGATTT ATGAATTATG
    ·AlaGlyGlu GlyLysSerAla CysAsnThr AlaSerPro AlaValGlnSer·
501 GGCTGGAGAA GGAAAATCTG CATGTAATAC TGCAAGTCCT GCTGTGCAAT
    · AlaTyrAsn ThrMetMet TyrIleIleIle PheGlyTrp AlaIleTyr
551 CAGCTTACAA CACAATGATG TATATTATCA TCTTTGGTTG GGCGATTTAT
    ProValGlyTyr PheThrGly TyrLeuMet GlyAspGlyGly SerAlaLeu·
601 CCTGTAGGTT ATTTCACAGG TTACCTGATG GGTGACGGTG GATCAGCTCT
    ·AsnLeuAsn LeuIleTyrAsn LeuAlaAsp PheValAsn LysIleLeuPhe·
651 TAACTTAAAC CTTATCTATA ACCTTGCTGA CTTTGTTAAC AAGATTCTAT
    · GlyLeuIle IleTrpAsn ValAlaValLys GluSerSer AsnAla***
701 TTGGTTTAAT TATATGGAAT GTTGCTGTTA AAGAATCTTC TAATGCTTAA
```

Figure 2-3

```
    ThrMetGlyLys LeuLeuLeu IleLeuGly SerAlaIleAla LeuProSer·
  1 ACCATGGGTA AATTATTACT GATATTAGGT AGTGCTATTG CACTTCCATC
    ·PheAlaAla AlaGlyGlyAsp LeuAspIle SerAspThr ValGlyValSer·
 51 ATTTGCTGCT GCTGGTGGCG ATCTAGATAT AAGTGATACT GTTGGTGTTT
    · PheTrpLeu ValThrAla GlyMetLeuAla AlaThrVal PhePhePhe
101 CATTCTGGCT GGTTACAGCT GGTATGTTAG CGGCAACTGT GTTCTTTTTT
    ValGluArgAsp GlnValSer AlaLysTrp LysThrSerLeu AlaValSer·
151 GTAGAAAGAG ACCAAGTCAG CGCTAAGTGG AAAACTTCAC TTGCTGTATC
    ·GlyLeuIle ThrGlyIleAla PheTrpLys TyrLeuTyr MetArgGlyVal·
201 TGGTTTAATT ACTGGTATAG CTTTTTGGAA ATATCTCTAT ATGAGAGGTG
    · TrpIleAsp ThrGlyAsp ThrProThrVal PheArgTyr IleAspTrp
251 TTTGGATAGA CACTGGTGAT ACCCCAACAG TATTCAGATA TATTGATTGG
    LeuLeuThrVal ProLeuGln MetValGlu PheTyrLeuIle LeuAlaAla·
301 TTATTAACTG TTCCATTACA AATGGTTGAG TTCTATCTAA TTCTTGCTGC
    ·CysThrSer ValAlaAlaSer LeuPheLys LysLeuLeu AlaGlySerLeu·
351 TTGTACAAGT GTTGCTGCTT CATTATTTAA GAAGCTTCTA GCTGGTTCAT
    · ValMetLeu GlyAlaGly PheAlaGlyGlu AlaGlyLeu AlaProVal
401 TAGTAATGTT AGGTGCTGGA TTTGCAGGCG AAGCTGGATT AGCTCCTGTA
    LeuProAlaPhe IleIleGly MetAlaGly TrpLeuTyrMet IleTyrGlu·
451 TTACCTGCTT TCATTATTGG TATGGCTGGA TGGTTATACA TGATTTATGA
    ·LeuTyrMet GlyGluGlyLys AlaAlaVal SerThrAla SerProAlaVal·
501 GCTATATATG GGTGAAGGTA AGGCTGCTGT AAGTACTGCA AGTCCTGCTG
    · AsnSerAla TyrAsnAla MetMetMetIle IleValVal GlyTrpAla
551 TTAACTCTGC ATACAACGCA ATGATGATGA TTATTGTTGT TGGATGGGCA
    IleTyrProAla GlyTyrAla AlaGlyTyr LeuMetGlyGly GluGlyVal·
601 ATTTATCCTG CTGGATATGC TGCTGGTTAC CTAATGGGTG GCGAAGGTGT
    ·TyrAlaSer AsnLeuAsnLeu IleTyrAsn LeuAlaAsp LeuValAsnLys·
651 ATACGCTTCA AACTTAAACC TTATATATAA CCTTGCCGAC CTTGTTAACA
    · IleLeuPhe GlyLeuIle IleTrpAsnVal AlaValLys GluSerSer
701 AGATTCTATT TGGTTTGATC ATTTGGAATG TTGCTGTTAA AGAATCTTCT
    AsnAla
751 AATGCT
```

Figure 2-4

```
    ThrMetGlyLys LeuLeuLeu IleLeuGly SerAlaIleAla LeuProSer·
  1 ACCATGGGTA AATTATTACT GATATTAGGT AGTGCTATTG CACTTCCATC
    ·PheAlaAla AlaGlyGlyAsp LeuAspIle SerAspThr ValGlyValSer·
 51 ATTTGCTGCT GCTGGTGGCG ATCTAGATAT AAGTGATACT GTTGGTGTTT
    · PheTrpLeu ValThrAla GlyMetLeuAla AlaThrVal PhePhePhe
101 CATTCTGGCT GGTTACAGCT GGTATGTTAG CGGCAACTGT GTTCTTTTTT
    ValGluArgAsp GlnValSer AlaLysTrp LysThrSerLeu AlaValSer·
151 GTAGAAAGAG ACCAAGTCAG CGCTAAGTGG AAAACTTCAC TTGCTGTATC
    ·GlyLeuIle ThrGlyIleAla PheTrpAsn TyrLeuTyr MetArgGlyVal·
201 TGGTTTAATT ACTGGTATAG CTTTTTGGAA TTATCTCTAT ATGAGAGGTG
    · TrpIleAsp ThrGlyAsp ThrProThrVal PheArgTyr IleAspTrp
251 TTTGGATAGA CACTGGTGAT ACCCCAACAG TATTCAGATA TATTGATTGG
    LeuLeuThrVal ProLeuGln MetValGlu PheTyrLeuIle LeuAlaAla·
301 TTATTAACTG TTCCATTACA AATGGTTGAG TTCTATCTAA TTCTTGCTGC
    ·CysThrSer ValAlaAlaSer LeuPheLys LysLeuLeu AlaGlySerLeu·
351 TTGTACAAGT GTTGCTGCTT CATTATTTAA GAAGCTTCTA GCTGGTTCAT
    · ValMetLeu GlyAlaGly PheAlaGlyGlu AlaGlyLeu AlaProVal
401 TAGTAATGTT AGGTGCTGGA TTTGCAGGCG AAGCTGGATT AGCTCCTGTA
    LeuProAlaPhe IleIleGly MetAlaGly TrpLeuTyrMet IleTyrGlu·
451 TTACCTGCTT TCATTATTGG TATGGCTGGA TGGTTATACA TGATTTATGA
    ·LeuTyrMet GlyGluGlyLys AlaAlaVal SerThrAla SerProAlaVal·
501 GCTATATATG GGTGAAGGTA AGGCTGCTGT AAGTACTGCA AGTCCTGCTG
    · AsnSerAla TyrAsnAla MetMetMetIle IleValVal GlyTrpAla
551 TTAACTCTGC ATACAACGCA ATGATGATGA TTATTGTTGT TGGATGGGCA
    IleTyrProAla GlyTyrAla AlaGlyTyr LeuMetGlyGly GluGlyVal·
601 ATTTATCCTG CTGGATATGC TGCTGGTTAC CTAATGGGTG GCGAAGGTGT
    ·TyrAlaSer AsnLeuAsnLeu IleTyrAsn LeuAlaAsp LeuValAsnLys·
651 ATACGCTTCA AACTTAAACC TTATATATAA CCTTGCCGAC CTTGTTAACA
    · IleLeuPhe GlyLeuIle IleTrpAsnVal AlaValLys GluSerSer
701 AGATTCTATT TGGTTTGATC ATTTGGAATG TTGCTGTTAA AGAATCTTCT
    AsnAla
751 AATGCT
```

Figure 2-5

```
    ThrMetGlyLys LeuLeuLeu IleLeuGly SerAlaIleAla LeuProSer·
  1 ACCATGGGTA AATTATTACT GATATTAGGT AGTGCTATTG CACTTCCATC
    ·PheAlaAla AlaGlyGlyAsp LeuAspIle SerAspThr ValGlyValSer·
 51 ATTTGCTGCT GCTGGTGGCG ATCTAGATAT AAGTGATACT GTTGGTGTTT
    · PheTrpLeu ValThrAla GlyMetLeuAla AlaThrVal PhePhePhe
101 CATTCTGGCT GGTTACAGCT GGTATGTTAG CGGCAACTGT GTTCTTTTTT
    ValGluArgAsp GlnValSer AlaLysTrp LysThrSerLeu AlaValSer·
151 GTAGAAAGAG ACCAAGTCAG CGCTAAGTGG AAAACTTCAC TTGCTGTATC
    ·GlyLeuIle ThrGlyIleAla PheTrpGln TyrLeuTyr MetArgGlyVal·
201 TGGTTTAATT ACTGGTATAG CTTTTTGGCA GTATCTCTAT ATGAGAGGTG
    · TrpIleAsp ThrGlyAsp ThrProThrVal PheArgTyr IleAspTrp
251 TTTGGATAGA CACTGGTGAT ACCCCAACAG TATTCAGATA TATTGATTGG
    LeuLeuThrVal ProLeuGln MetValGlu PheTyrLeuIle LeuAlaAla·
301 TTATTAACTG TTCCATTACA AATGGTTGAG TTCTATCTAA TTCTTGCTGC
    ·CysThrSer ValAlaAlaSer LeuPheLys LysLeuLeu AlaGlySerLeu·
351 TTGTACAAGT GTTGCTGCTT CATTATTTAA GAAGCTTCTA GCTGGTTCAT
    · ValMetLeu GlyAlaGly PheAlaGlyGlu AlaGlyLeu AlaProVal
401 TAGTAATGTT AGGTGCTGGA TTTGCAGGCG AAGCTGGATT AGCTCCTGTA
    LeuProAlaPhe IleIleGly MetAlaGly TrpLeuTyrMet IleTyrGlu·
451 TTACCTGCTT TCATTATTGG TATGGCTGGA TGGTTATACA TGATTTATGA
    ·LeuTyrMet GlyGluGlyLys AlaAlaVal SerThrAla SerProAlaVal·
501 GCTATATATG GGTGAAGGTA AGGCTGCTGT AAGTACTGCA AGTCCTGCTG
    · AsnSerAla TyrAsnAla MetMetMetIle IleValVal GlyTrpAla
551 TTAACTCTGC ATACAACGCA ATGATGATGA TTATTGTTGT TGGATGGGCA
    IleTyrProAla GlyTyrAla AlaGlyTyr LeuMetGlyGly GluGlyVal·
601 ATTTATCCTG CTGGATATGC TGCTGGTTAC CTAATGGGTG GCGAAGGTGT
    ·TyrAlaSer AsnLeuAsnLeu IleTyrAsn LeuAlaAsp LeuValAsnLys·
651 ATACGCTTCA AACTTAAACC TTATATATAA CCTTGCCGAC CTTGTTAACA
    · IleLeuPhe GlyLeuIle IleTrpAsnVal AlaValLys GluSerSer
701 AGATTCTATT TGGTTTGATC ATTTGGAATG TTGCTGTTAA AGAATCTTCT
    AsnAla
751 AATGCT
```

Figure 2-6

```
    ThrMetGlyLys LeuLeuLeu IleLeuGly SerAlaIleAla LeuProSer·
  1 ACCATGGGTA AATTATTACT GATATTAGGT AGTGCTATTG CACTTCCATC
    ·PheAlaAla AlaGlyGlyAsp LeuAspIle SerAspThr ValGlyValSer·
 51 ATTTGCTGCT GCTGGTGGCG ATCTAGATAT AAGTGATACT GTTGGTGTTT
    · PheTrpLeu ValThrAla GlyMetLeuAla AlaThrVal PhePhePhe
101 CATTCTGGCT GGTTACAGCT GGTATGTTAG CGGCAACTGT GTTCTTTTTT
    ValGluArgAsp GlnValSer AlaLysTrp LysThrSerLeu AlaValSer·
151 GTAGAAAGAG ACCAAGTCAG CGCTAAGTGG AAAACTTCAC TTGCTGTATC
    ·GlyLeuIle ThrGlyIleAla PheTrpGlu TyrLeuTyr MetArgGlyVal·
201 TGGTTTAATT ACTGGTATAG CTTTTTGGGA ATATCTCTAT ATGAGAGGTG
    · TrpIleAsp ThrGlyAsp ThrProThrVal PheArgTyr IleAspTrp
251 TTTGGATAGA CACTGGTGAT ACCCCAACAG TATTCAGATA TATTGATTGG
    LeuLeuThrVal ProLeuGln MetValGlu PheTyrLeuIle LeuAlaAla·
301 TTATTAACTG TTCCATTACA AATGGTTGAG TTCTATCTAA TTCTTGCTGC
    ·CysThrSer ValAlaAlaSer LeuPheLys LysLeuLeu AlaGlySerLeu·
351 TTGTACAAGT GTTGCTGCTT CATTATTTAA GAAGCTTCTA GCTGGTTCAT
    · ValMetLeu GlyAlaGly PheAlaGlyGlu AlaGlyLeu AlaProVal
401 TAGTAATGTT AGGTGCTGGA TTTGCAGGCG AAGCTGGATT AGCTCCTGTA
    LeuProAlaPhe IleIleGly MetAlaGly TrpLeuTyrMet IleTyrGlu·
451 TTACCTGCTT TCATTATTGG TATGGCTGGA TGGTTATACA TGATTTATGA
    ·LeuTyrMet GlyGluGlyLys AlaAlaVal SerThrAla SerProAlaVal·
501 GCTATATATG GGTGAAGGTA AGGCTGCTGT AAGTACTGCA AGTCCTGCTG
    · AsnSerAla TyrAsnAla MetMetMetIle IleValVal GlyTrpAla
551 TTAACTCTGC ATACAACGCA ATGATGATGA TTATTGTTGT TGGATGGGCA
    IleTyrProAla GlyTyrAla AlaGlyTyr LeuMetGlyGly GluGlyVal·
601 ATTTATCCTG CTGGATATGC TGCTGGTTAC CTAATGGGTG GCGAAGGTGT
    ·TyrAlaSer AsnLeuAsnLeu IleTyrAsn LeuAlaAsp LeuValAsnLys·
651 ATACGCTTCA AACTTAAACC TTATATATAA CCTTGCCGAC CTTGTTAACA
    · IleLeuPhe GlyLeuIle IleTrpAsnVal AlaValLys GluSerSer
701 AGATTCTATT TGGTTTGATC ATTTGGAATG TTGCTGTTAA AGAATCTTCT
    AsnAla
751 AATGCT
```

Figure 2-7

```
    ThrMetGlyLys LeuLeuLeu IleLeuGly SerAlaIleAla LeuProSer·
  1 ACCATGGGTA AATTATTACT GATATTAGGT AGTGCTATTG CACTTCCATC
    ·PheAlaAla AlaGlyGlyAsp LeuAspIle SerAspThr ValGlyValSer·
 51 ATTTGCTGCT GCTGGTGGCG ATCTAGATAT AAGTGATACT GTTGGTGTTT
    · PheTrpLeu ValThrAla GlyMetLeuAla AlaThrVal PhePhePhe
101 CATTCTGGCT GGTTACAGCT GGTATGTTAG CGGCAACTGT GTTCTTTTTT
    ValGluArgAsp GlnValSer AlaLysTrp LysThrSerLeu AlaValSer·
151 GTAGAAAGAG ACCAAGTCAG CGCTAAGTGG AAAACTTCAC TTGCTGTATC
    ·GlyLeuIle ThrGlyIleAla PheTrpTrp TyrLeuTyr MetArgGlyVal·
201 TGGTTTAATT ACTGGTATAG CTTTTTGGTG GTATCTCTAT ATGAGAGGTG
    · TrpIleAsp ThrGlyAsp ThrProThrVal PheArgTyr IleAspTrp
251 TTTGGATAGA CACTGGTGAT ACCCCAACAG TATTCAGATA TATTGATTGG
    LeuLeuThrVal ProLeuGln MetValGlu PheTyrLeuIle LeuAlaAla·
301 TTATTAACTG TTCCATTACA AATGGTTGAG TTCTATCTAA TTCTTGCTGC
    ·CysThrSer ValAlaAlaSer LeuPheLys LysLeuLeu AlaGlySerLeu·
351 TTGTACAAGT GTTGCTGCTT CATTATTTAA GAAGCTTCTA GCTGGTTCAT
    · ValMetLeu GlyAlaGly PheAlaGlyGlu AlaGlyLeu AlaProVal
401 TAGTAATGTT AGGTGCTGGA TTTGCAGGCG AAGCTGGATT AGCTCCTGTA
    LeuProAlaPhe IleIleGly MetAlaGly TrpLeuTyrMet IleTyrGlu·
451 TTACCTGCTT TCATTATTGG TATGGCTGGA TGGTTATACA TGATTTATGA
    ·LeuTyrMet GlyGluGlyLys AlaAlaVal SerThrAla SerProAlaVal·
501 GCTATATATG GGTGAAGGTA AGGCTGCTGT AAGTACTGCA AGTCCTGCTG
    · AsnSerAla TyrAsnAla MetMetMetIle IleValVal GlyTrpAla
551 TTAACTCTGC ATACAACGCA ATGATGATGA TTATTGTTGT TGGATGGGCA
    IleTyrProAla GlyTyrAla AlaGlyTyr LeuMetGlyGly GluGlyVal·
601 ATTTATCCTG CTGGATATGC TGCTGGTTAC CTAATGGGTG GCGAAGGTGT
    ·TyrAlaSer AsnLeuAsnLeu IleTyrAsn LeuAlaAsp LeuValAsnLys·
651 ATACGCTTCA AACTTAAACC TTATATATAA CCTTGCCGAC CTTGTTAACA
    · IleLeuPhe GlyLeuIle IleTrpAsnVal AlaValLys GluSerSer
701 AGATTCTATT TGGTTTGATC ATTTGGAATG TTGCTGTTAA AGAATCTTCT
    AsnAla
751 AATGCT
```

Figure 2-8

```
    ThrMetGlyLys LeuLeuLeu IleLeuGly SerAlaIleAla LeuProSer·
  1 ACCATGGGTA AATTATTACT GATATTAGGT AGTGCTATTG CACTTCCATC
    ·PheAlaAla AlaGlyGlyAsp LeuAspIle SerAspThr ValGlyValSer·
 51 ATTTGCTGCT GCTGGTGGCG ATCTAGATAT AAGTGATACT GTTGGTGTTT
    · PheTrpLeu ValThrAla GlyMetLeuAla AlaThrVal PhePhePhe
101 CATTCTGGCT GGTTACAGCT GGTATGTTAG CGGCAACTGT GTTCTTTTTT
    ValGluArgAsp GlnValSer AlaLysTrp LysThrSerLeu AlaValSer·
151 GTAGAAAGAG ACCAAGTCAG CGCTAAGTGG AAAACTTCAC TTGCTGTATC
    ·GlyLeuIle ThrGlyIleAla PheTrpHis TyrLeuTyr MetArgGlyVal·
201 TGGTTTAATT ACTGGTATAG CTTTTTGGCA TTATCTCTAT ATGAGAGGTG
    · TrpIleAsp ThrGlyAsp ThrProThrVal PheAlaTyr IleAspTrp
251 TTTGGATAGA CACTGGTGAT ACCCCAACAG TATTCGCATA TATTGATTGG
    LeuLeuThrVal ProLeuGln MetValGlu PheTyrLeuIle LeuAlaAla·
301 TTATTAACTG TTCCATTACA AATGGTTGAG TTCTATCTAA TTCTTGCTGC
    ·CysThrSer ValAlaAlaSer LeuPheLys LysLeuLeu AlaGlySerLeu·
351 TTGTACAAGT GTTGCTGCTT CATTATTTAA GAAGCTTCTA GCTGGTTCAT
    · ValMetLeu GlyAlaGly PheAlaGlyGlu AlaGlyLeu AlaProVal
401 TAGTAATGTT AGGTGCTGGA TTTGCAGGCG AAGCTGGATT AGCTCCTGTA
    LeuProAlaPhe IleIleGly MetAlaGly TrpLeuTyrMet IleTyrGlu·
451 TTACCTGCTT TCATTATTGG TATGGCTGGA TGGTTATACA TGATTTATGA
    ·LeuTyrMet GlyGluGlyLys AlaAlaVal SerThrAla SerProAlaVal·
501 GCTATATATG GGTGAAGGTA AGGCTGCTGT AAGTACTGCA AGTCCTGCTG
    · AsnSerAla TyrAsnAla MetMetMetIle IleValVal GlyTrpAla
551 TTAACTCTGC ATACAACGCA ATGATGATGA TTATTGTTGT TGGATGGGCA
    IleTyrProAla GlyTyrAla AlaGlyTyr LeuMetGlyGly GluGlyVal·
601 ATTTATCCTG CTGGATATGC TGCTGGTTAC CTAATGGGTG GCGAAGGTGT
    ·TyrAlaSer AsnLeuAsnLeu IleTyrAsn LeuAlaAsp LeuValAsnLys·
651 ATACGCTTCA AACTTAAACC TTATATATAA CCTTGCCGAC CTTGTTAACA
    · IleLeuPhe GlyLeuIle IleTrpAsnVal AlaValLys GluSerSer
701 AGATTCTATT TGGTTTGATC ATTTGGAATG TTGCTGTTAA AGAATCTTCT
    AsnAla
751 AATGCT
```

Figure 2-9

```
    ThrMetGlyLys LeuLeuLeu IleLeuGly SerAlaIleAla LeuProSer·
  1 ACCATGGGTA AATTATTACT GATATTAGGT AGTGCTATTG CACTTCCATC
    ·PheAlaAla AlaGlyGlyAsp LeuAspIle SerAspThr ValGlyValSer·
 51 ATTTGCTGCT GCTGGTGGCG ATCTAGATAT AAGTGATACT GTTGGTGTTT
    · PheTrpLeu ValThrAla GlyMetLeuAla AlaThrVal PhePhePhe
101 CATTCTGGCT GGTTACAGCT GGTATGTTAG CGGCAACTGT GTTCTTTTTT
    ValGluArgAsp GlnValSer AlaLysTrp LysThrSerLeu AlaValSer·
151 GTAGAAAGAG ACCAAGTCAG CGCTAAGTGG AAAACTTCAC TTGCTGTATC
    ·GlyLeuIle ThrGlyIleAla PheTrpHis TyrLeuTyr MetArgGlyVal·
201 TGGTTTAATT ACTGGTATAG CTTTTTGGCA TTATCTCTAT ATGAGAGGTG
    · TrpIleAsp ThrGlyAsp ThrProThrVal PheGluTyr IleAspTrp
251 TTTGGATAGA CACTGGTGAT ACCCCAACAG TATTCGAATA TATTGATTGG
    LeuLeuThrVal ProLeuGln MetValGlu PheTyrLeuIle LeuAlaAla·
301 TTATTAACTG TTCCATTACA AATGGTTGAG TTCTATCTAA TTCTTGCTGC
    ·CysThrSer ValAlaAlaSer LeuPheLys LysLeuLeu AlaGlySerLeu·
351 TTGTACAAGT GTTGCTGCTT CATTATTTAA GAAGCTTCTA GCTGGTTCAT
    · ValMetLeu GlyAlaGly PheAlaGlyGlu AlaGlyLeu AlaProVal
401 TAGTAATGTT AGGTGCTGGA TTTGCAGGCG AAGCTGGATT AGCTCCTGTA
    LeuProAlaPhe IleIleGly MetAlaGly TrpLeuTyrMet IleTyrGlu·
451 TTACCTGCTT TCATTATTGG TATGGCTGGA TGGTTATACA TGATTTATGA
    ·LeuTyrMet GlyGluGlyLys AlaAlaVal SerThrAla SerProAlaVal·
501 GCTATATATG GGTGAAGGTA AGGCTGCTGT AAGTACTGCA AGTCCTGCTG
    · AsnSerAla TyrAsnAla MetMetMetIle IleValVal GlyTrpAla
551 TTAACTCTGC ATACAACGCA ATGATGATGA TTATTGTTGT TGGATGGGCA
    IleTyrProAla GlyTyrAla AlaGlyTyr LeuMetGlyGly GluGlyVal·
601 ATTTATCCTG CTGGATATGC TGCTGGTTAC CTAATGGGTG GCGAAGGTGT
    ·TyrAlaSer AsnLeuAsnLeu IleTyrAsn LeuAlaAsp LeuValAsnLys·
651 ATACGCTTCA AACTTAAACC TTATATATAA CCTTGCCGAC CTTGTTAACA
    · IleLeuPhe GlyLeuIle IleTrpAsnVal AlaValLys GluSerSer
701 AGATTCTATT TGGTTTGATC ATTTGGAATG TTGCTGTTAA AGAATCTTCT
    AsnAla
751 AATGCT
```

Figure 2-10

```
     ThrMetGlyLys LeuLeuLeu IleLeuGly SerAlaIleAla LeuProSer·
  1  ACCATGGGTA AATTATTACT GATATTAGGT AGTGCTATTG CACTTCCATC
     ·PheAlaAla AlaGlyGlyAsp LeuAspIle SerAspThr ValGlyValSer·
 51  ATTTGCTGCT GCTGGTGGCG ATCTAGATAT AAGTGATACT GTTGGTGTTT
     · PheTrpLeu ValThrAla GlyMetLeuAla AlaThrVal PhePhePhe
101  CATTCTGGCT GGTTACAGCT GGTATGTTAG CGGCAACTGT GTTCTTTTTT
     ValGluArgAsp GlnValSer AlaLysTrp LysThrSerLeu AlaValSer·
151  GTAGAAAGAG ACCAAGTCAG CGCTAAGTGG AAAACTTCAC TTGCTGTATC
     ·GlyLeuIle ThrGlyIleAla PheTrpHis TyrLeuTyr MetArgGlyVal·
201  TGGTTTAATT ACTGGTATAG CTTTTTGGCA TTATCTCTAT ATGAGAGGTG
     · TrpIleAsp ThrGlyAsp ThrProThrVal PheGlnTyr IleAspTrp
251  TTTGGATAGA CACTGGTGAT ACCCCAACAG TATTCCAATA TATTGATTGG
     LeuLeuThrVal ProLeuGln MetValGlu PheTyrLeuIle LeuAlaAla·
301  TTATTAACTG TTCCATTACA AATGGTTGAG TTCTATCTAA TTCTTGCTGC
     ·CysThrSer ValAlaAlaSer LeuPheLys LysLeuLeu AlaGlySerLeu·
351  TTGTACAAGT GTTGCTGCTT CATTATTTAA GAAGCTTCTA GCTGGTTCAT
     · ValMetLeu GlyAlaGly PheAlaGlyGlu AlaGlyLeu AlaProVal
401  TAGTAATGTT AGGTGCTGGA TTTGCAGGCG AAGCTGGATT AGCTCCTGTA
     LeuProAlaPhe IleIleGly MetAlaGly TrpLeuTyrMet IleTyrGlu·
451  TTACCTGCTT TCATTATTGG TATGGCTGGA TGGTTATACA TGATTTATGA
     ·LeuTyrMet GlyGluGlyLys AlaAlaVal SerThrAla SerProAlaVal·
501  GCTATATATG GGTGAAGGTA AGGCTGCTGT AAGTACTGCA AGTCCTGCTG
     · AsnSerAla TyrAsnAla MetMetMetIle IleValVal GlyTrpAla
551  TTAACTCTGC ATACAACGCA ATGATGATGA TTATTGTTGT TGGATGGGCA
     IleTyrProAla GlyTyrAla AlaGlyTyr LeuMetGlyGly GluGlyVal·
601  ATTTATCCTG CTGGATATGC TGCTGGTTAC CTAATGGGTG GCGAAGGTGT
     ·TyrAlaSer AsnLeuAsnLeu IleTyrAsn LeuAlaAsp LeuValAsnLys·
651  ATACGCTTCA AACTTAAACC TTATATATAA CCTTGCCGAC CTTGTTAACA
     · IleLeuPhe GlyLeuIle IleTrpAsnVal AlaValLys GluSerSer
701  AGATTCTATT TGGTTTGATC ATTTGGAATG TTGCTGTTAA AGAATCTTCT
     AsnAla
751  AATGCT
```

Figure 2-11

```
               1                                                   50
     BAC31A8   ..MKLLLILG SVIALPTFAA GGGD....LD ASDYTGVSFW LVTAALLAST
     BAC40E8   TMGKLLLILG SVIALPTFAA GGGD....LD ASDYTGVSFW LVTAALLAST
     BAC64A5   TMGKLLLILG SVIALPTFAA GGGD....LD ASDYTGVSFW LVTAALLAST
      HOT0m1   TMGKLLLILG SVIALPTFAA GGGD....LD ASDYTGVSFW LVTAALLAST
     HOT75m1   TMGKLLLILG SAIALPSFAA AGGD....LD ISDTVGVSFW LVTAGMLAAT
     HOT75m3   TMGKLLLILG SAIALPSFAA AGGD....LD ISDTVGVSFW LVTAGMLAAT
     HOT75m4   TMGKLLLILG SAIALPSFAA AGGD....LD ISDTVGVSFW LVTAGMLAAT
     HOT75m8   TMGKLLLILG SAIALPSFAA AGGD....LD ISDTVGVSFW LVTAGMLAAT
       MB0m1   TMGKLLLILG SVIALPTFAA GGGD....LD ASDYTGVSFW LVTAALLAST
       MB0m2   TMGKLLLILG SVIALPTFAA GGGD....LD ASDYTGVSFW LVTAALLAST
    MB100m10   TMGKLLLILG SVIALPTFAA GGGD....LD ASDYTGVSFW LVTAALLAST
     MB100m5   TMGKLLLILG SVIALPTFAA GGGD....LD ASDYTGVSFW LVTAALLAST
     MB100m7   TMGKLLLILG SVIALPTFAA GGGD....LD ASDYTGVSFW LVTAALLAST
     MB100m9   TMGKLLLILG SVIALPTFAA GGGD....LD ASDYTGVSFW LVTAALLAST
     MB20m12   TMGKLLLILG SVIALPTFAA GGGD....LD ASDYTGVSFW LVTAALLAST
      MB20m2   TMGKLLLILG SVIALPTFAA GGGD....LD ASDYTGVSFW LVTAALLAST
      MB20m5   TMGKLLLILG SVIALPTFAA GGGD....LD ASDYTGVSFW LVTAALLAST
      MB40m1   TMGKLLLIIG SVIALPTFAA GGGD....LD ASDYTGVSFW LVTAALLAST
     MB40m12   TMGKLLRILG SVIALPTFAA GGGD....LD ASDYTGVSFW LVTAALLAST
      MB40m5   TMGKLLLILG SVIALPTFAA GGGD....LD ASDYTGVSFW LVTAALLAST
      MED101   .MGKLLLILG SVIALPTFAA GGGD....LD ASDYTGVSFW LVTAALLAST
      MED102   .MGKLLLILG SVIALPTFAA GGGD....LD ASDYTGVSFW LVTAALLAST
      MED106   .MGKLLLILG SVIALPTFAA GGGD....LD ASDYTGVSFW LVTAALLAST
      MED202   .MGKLLLILG SVIALPTFAA GGGD....LD ASDYTGVSFW LVTAALLAST
      MED204   .MGKLLLILG SVIALPTFAA GGGD....LD ASDYTGVSFW LVTAALLAST
      MED208   .MGKLLLILG SVIALPTFAA GGGD....LD ASDYTGVSFW LVTAALLAST
       MED25   .MGKLLLILG SVIALPTFAA GGGD....LD ASDYTGVSFW LVTAALLAST
       MED26   .MGKLLLILG SVIALPTFAA GGGD....LD ASDYTGVSFW LVTAALLAST
       MED27   .MGKLLLILG NVIALPTFAA GGGD....LD ASDYTGVSFW LVTAALLAST
       MED36   .MGKLLLILG SVIALPTFAA GGGD....LD ASDYTGVSFW LVTAALLAST
  medA15_r8_1  .MGKLLMMLG SVIALPSFAA SGGD....LD ASDYTGVSFG LVTAALLAST
  medA15_R8_3  .MGKLLMILG GVIALPSFAA SGGD....LD SSDLTGVSFW LVTAALLAAT
 medA15_r8ex7  .MGKLLLILG GVIALPSFAA SGGD....LD SSDLTGVSFW LVTAALLAAT
 medA15_R8ex9  .MGKLLLILG GVIALPSFAA SGGD....LD SSDLTGVSFW LVTAALLAAT
  medA15_r9_3  .MGKRLVILG GVIALPSFAA SGGD....LD SSDLTGVSFW LVTAALLAAT
  medA15r10b5  .MGKLLVILG GVIALPPFAA SGGD....LD SSDLTGVSFW LVTAALLAAT
  medA15r11b3  .MGKQLLILG SVIALPSFAA GGGD....LD ASDYTGVSFW LVTAALLAST
  medA15r11b9  .MGKALLMLG SVIALPTFAA GGGD....LD ASDYTGVSFW LVTAAPLAST
   medA15r8b3  .MGKLLLILG SVIALPSFAA GGGD....LD AGDYTGVSFW LVTAALLAST
   medA15r8b8  .SKKFFSTLL LVTSLPTLAL AGGHSSG.LA GDDYVGVTFW IISMAMVAST
   medA15r8b9  .MGKLLVMLG SVIALPSFAA GGGN....LD AADVTGVSFW LVTAALLAST
  medA15r8ex4  .SKKFFSTLL LVTSLPTLAL AGGHSSG.LA GDDYVGVTFW IISMAMVAST
  medA15r8ex6  .MGKLLVMLG SVIALPTFAA GGGD....LD ASDYTGVSFW LVTAALLAST
   medA15r9b5  .MGKGLLMLG SVIALPSFAA GGGD....LD ASDYTGVSFW LVTAALLAST
   medA15r9b7  .MGKQLLILG GVIALPSFAA SGGD....LD SSDLTGVSFW LVTAALLAAT
 medA17_r8_11  .SKKLLATFL VVTSIPAIAL AGGHSSGGLA GDDYVGVTFW IISMAMVAST
 medA17_r8_15  .SKKLLATFL VVTSIPAIAL AGGHSSGGLA GDDCVGVTFW IISMAMVAST
  medA17_R8_6  .MGKLLMILG GVIALPSFAA GGGD....LD IGDSVGVSFW LVTAAMLAAT
   medA17R9_1  .MGKGLLMLG SVIALPSFAA GGGN....LN AADVTGVSFW LVTAALLAST
 medA19_R8_16  .MGKLLVMLG GVIALPSFAA GGGD....LD IGDSVGVSFW LVTAAMLAAT
 medA19_R8_19  .MGKLLMILG GVIALPSFAA GGGD....LD IGDSVGVSFW LVTAAMLAAT
 medA19_R8_20  .MGKLLLILG GVIALPSFAA SGGD....LD SSDLTGVSFW LVTAALLAAT
  medA19_r9_9  .....LLILG GVIALPSFAA SGGD....LD SSDLTGVSFW LVTAALLAAT
       PalB1   TMGKLLLILG SAIALPSFAA AGGD....LD ISDTVGVSFW LVTAGMLAAT
       PalB2   TMGKLLLILG SAIALPSFAA AGGD....LD ISDTVGVSFW LVTAGMLAAT
       PalB5   TMGKLLLILG SAIALPSFAA AGGD....LD ISDTVGVSFW LVTAGMLAAT
       PalB6   TMGKLLLILG SAIALPSFAA AGGD....LD ISDTVGVSFW LVTAGMLAAT
       PalB7   TMGKLLLILG SAIALPSFAA AGGD....LD ISDTVGVSFW LVTAGMLAAT
       PalB8   TMGKLLLILG SAIALPSFAA AGGD....LD ISDTVGVSFW LVTAGMLAAT
       PalE1   TMGKLLLILG SAIALPSFAA AGGD....LD ISDTVGVSFW LVTAGMLAAT
       PalE6   TMGKLLLILG SAIALPSFAA AGGD....LD ISDTVGVSFW LVTAGMLAAT
```

Figure 3-1

```
PalE7        TMGKLLLILG SAIALPSFAA AGGD....LD ISDTVGVSFW LVTAGMLAAT
RED19        .MGKLLLILG SVIALPTFAA GGGD....LD ASDYTGVSFW LVTAALLAST
RED2         .MGKLLLILG SVIALPTFAA GGGD....LD ASDYTGVSFW LVTAALLAST
RED23        .MGKLLLILG SVIALPTFAA GGGD....LD ASDYTGVSFW LVTAALLAST
RED27        .MGKLLLILG SVIALPTFAA GGGD....LD ASDYTGVSFW LVTAALLAST
RED30        .MGKLLLILG SVIALPTFAA GGGD....LD ASDYTGVSFW LVTAALLAST
RED4         .MGKLLLRLG SVIALPTFAA GGGD....LD ASDYTGVSFW LVTAALLAST
RED5         .MGKLLLILG SVIALPTFAA GGGD....LD ASDYTGVSFW LVTAALLAST
REDA9        .MGKLLLILG SVIALPTFAA GGGD....LD ASDYTGVSFW LVTAALLAST
REDB9        .MGKLLLILG SVIALPTFAA GGGD....LD ASDYTGVSFW LVTAALLAST
REDF9        .MGKLLLILG SVIALPTFAA GGGD....LD ASDYTGVSFW LVTAALLAST
REDr6a5a14   .MGKLLLILG SVIALPTFAA GGGD....PD ASDYTGVSFW LVTAALLAST
REDr6a5a6    .MGKLLLILG SVIALPTFAA GGGD....LD ASDYTGVSFW LVTAALLAST
REDr7_1_15   .MGKLLLILG SVIALPTFAA GGGD....LD ASGYTGVSFW LVTAALLAST
REDr7_1_16   .MGKRLVILG SVIALPTFAA GGGD....LD ASDYTGVSFW LVTAALLAST
REDr7_1_4    .MGKLLLILG SVIALPTFAA GGGD....LD ASDYTGVSFW LVTAALLAST
REDs3_15     .MGKLLLILG SVIALPTFAA GGGD....LD ASDYTGVSFW LVTAALLAST
REDs3_7      .MGKLLLILG SVIALPTFAA GGGD....LD ASDYTGVSFW LVTAALLAST
ANT32C12     ..MKLLLILG SAIALPSFAA AGGD....LD ISDTVGVSFW LVTAGMLAAT
HOT2C02      .......... ....MKVLML NPGD...... ...HVAISFW LISMAMVAAT

             51                              H         100
BAC31A8      VFFFVERDRV SAKWKTSLTV SGLVTGIAFW HYMYMRGVWI ETGDSP....
BAC40E8      VFFFVERDRV SAKWKTSLTV SGLVTGIAFW HYMYMRGVWI ETGDSP....
BAC64A5      VFFFVERDRV SAKWKTSLTV SGLVTGIAFW HYMYMRGVWI ETGDSP....
HOT0m1       VFFFVERDRV SAKWKTSLTV SGLVTGIAFW HYMYMRGVWI ETGDSP....
HOT75m1      VFFFVERDQV SAKWKTSLAV SGLITGIAFW HYLYMRGVWI DTGDTP....
HOT75m3      VFFFVERDQV SAKWKTSLTV SGLITGIAFW HYLYMRGVWI DTGDTP....
HOT75m4      VFFFVERDQV SAKWKTSLTV SGLITGIAFW HYLYMRGVWI DTGDTP....
HOT75m8      VFFFVERDQV SAKWKTSLTV SGLITGIAFW HYLYMRGVWI DTGDTP....
MB0m1        VFFFVERDRV SAKWKTSLTV SGLVTGIAFW HYMYMRGVWI ETGDSP....
MB0m2        VFFFVERDRV SAKWKTSLTV SGLVTGIAFW HYMYMRGVWI ETGDSP....
MB100m10     VFFFVERDRV SAKWKTSLTV SGLVTGIAFW HYMYMRGVWI ETGDSP....
MB100m5      VFFFVERDRV SAKWKTSLTV SGLVTGIAFW HYMYMRGVWI ETGDSP....
MB100m7      VFFFVERDRV SAKWKTSLTV SGLVTGIAFW HYMYMRGVWI ETGDSP....
MB100m9      VFFFVERDRV SAKWKTSLTV SGLVTGIAFW HYMYMRGVWI ETGDSP....
MB20m12      VFFFVERDRV SAKWKTSLTV SGLVTGIAFW HYMYMRGVWI ETGDSP....
MB20m2       VFFFVERDRV SAKWKTSLTV SGLVTGIAFW HYMYMRGVWI ETGDSP....
MB20m5       VFFFVERDRV SAKWKTSLTV SGLVTGIAFW HYMYMRGVWI ETGDSP....
MB40m1       VFFFVERDRV SAKWKTSLTV SGLVTGIAFW HYMYMRGVWI ETGDSP....
MB40m12      VFFFVERDRV SAKWKTSLTV SGLVTGIAFW HYMYMRGVWI ETGDSP....
MB40m5       VFFFVERDRV SAKWKTSLTV SGLVTGIAFW HYMYMRGVWI ETGDSP....
MED101       VFFFVERDRV SAKWKTSLTV SGLVTGIAFW HYMYMRGVWI ETGDSP....
MED102       VFFFVERDRV SAKWKTSLTV SGLVTGIAFW HYMYMRGVWI ETGDSP....
MED106       VFFFVERDRV SAKWKTSLTV SGLVTGIAFW HYMYMRGVWI ETGSSP....
MED202       VFFFVERDRV SAKWKTSLTV SGLVTGIAFW HYMYMRGVWI ETGDSP....
MED204       VFFFVERDRV SAKWKTSLTV SGLVTGIAFW HYMYMRGVWI ETGSSP....
MED208       VFFFVERDRV SAKWKTSLTV SGLVTGIAFW HYMYMRGVWI ETGDSP....
MED25        VFFFVERDRV SAKWKTSLTV SGLVTGIAFW HYMYMRGVWI ETGSSP....
MED26        VFFFVERDRV SAKWKTSLTV SGLVTGIAFW HYMYMRGVWI ETGDSP....
MED27        VFFFVERDRV SAKWKTSLTV SGLVTGIAFW HYMYMRGVWI ETGDSP....
MED36        VFFFVERDRV SAKWKTSLTV SGLVTGIAFW HYMYMRGVWI ETGSSP....
medA15_r8_1  VFFFVERDRV SAKWKTSLTV SGLVTGIAFW HYLYMRGVWV ETGETP....
medA15_R8_3  VFFFVERDQV SAKWKTSLTV SGLVTGIAFW HYLYMRGVWI ETGETP....
medA15_r8ex7 VFFFVERDQV SAKWKTSLTV SGLVTGIAFW HYLYMRGVWI ETGETP....
medA15_R8ex9 VFFFVERDQV SAKWKTSLTV SGLVTGIAFW HYLYMRGVWI ETGETP....
medA15_r9_3  VFFFVERDQV SAKWKTSLTV SGLVTGIAFW HYLYMRGVWI ETGETP....
medA15r10b5  VFFFVERDQV SAKWKTSLTV SGLVTGIAFW HYLYMRGVWI ETGETP....
medA15r11b3  VFFFIERDRV AAKWKTSLTV SGLVTGIAFW HYLYMRGVWV ETGESP....
medA15r11b9  VFFFVERDQV SAKWKTSLTV SGLVTGIAFW HYMYMRGVWI ETGDSP....
medA15r8b3   VFFFIERDRV AAKWKTSLTV SGLVTGIAFW HYMYMRGVWV ETGESP....
medA15r8b8   VFFIVERDRV SSKWKTSLTV SALVTLIAAV HYFYMRDVWV ATGESP....
medA15r8b9   VFFFIERDRV SAKWKTSLTV SGLVTGIAFW HYLYMRGVWV DSWTGP.GTG
```

Figure 3-2

H medA15r8ex4 VFFIVERDRV SSKWKTSLTV SALVTLIAAV HYFYMRDVWV ATGESP....
medA15r8ex6 VFFFVERDRV SAKWKTSLTV SGLVTGIAFW HYMYMRGVWI ETGDSP....
medA15r9b5 VFFFVERDRV AAKWKTSLTV SGLVTGIAFW HYMYMRGVWV ETGESP....
medA15r9b7 VFFFVERDQV SAKWKTSLTV SGLVTGIAFW HYLYMRGVWI ETGETP....
medA17_r8_11 VFFIVERDRV SAKWKTSLTV SALVTLIAAV HYFYMRDVWV ATGESP....
medA17_r8_15 VFFIVERDRV SAKWKTSLTV SALMTLIAAV HYFYMRDVWV ATGESP....
medA17_R8_6 VFFFVERDQV SAKWKTSLTV SGLITGIAFW HYLYMRGVWV ETGDSP....
medA17R9_1 VFFFIERDRV SAKWKTSLTV SGLVTGIAFW HYLYMRGVWV DSWNPETGMG
medA19_R8_16 VFFFVERDQV SAKWKTSLTV SGLITGIAFW HYLYMRGVWI DTGGSP....
medA19_R8_19 VFFFVERDQV SAKWKTSLTV SGLITGIAFW HYLYMRGVWI DTGGSP....
medA19_R8_20 VFFFVERDQV SAKWKTSLTV SGLVTGIAFW HYLYMRGVWI ETGETP....
medA19_r9_9 VFFFVERDQV SAKWKTSLTV SGLVTGIAFW HYLYMRGVWI ETGETP....
PalB1 VFFFVERDQV SAKWKTSLTV SGLITGIAFW HYLYMRGVWI DTGDTP....
PalB2 VFFFVERDQV SAEWKTSLTV SGLITGIAFW HYLYMRGVWI DTGDTP....
PalB5 VFFFVERDQV SAKWKTSLTV SGLITGIAFW HYLYMRGVWI DTGDTP....
PalB6 VFFFVERDQV SAKWKTSLTV SGLITGIAFW HYLYMRGVWI DTGDTP....
PalB7 VFFFVERDQV SAKWKTSLTV SGLITGIAFW HYLYMRGVWI DTGDTP....
PalB8 VFFFVERDQV SAKWKTSLTV SGLITGIAFW HYLYMRGVWI DTGDTP....
PalE1 VFFFVERDQV SAKWKTSLTV SGLITGIAFW HYLYMRGVWI DTGDTP....
PalE6 VFFFVERDQV SAKWKTSLTV SGLITGIAFW HYLYMRGVWI DTGDTP....
PalE7 VFFFVERDQV SAKWKTSLTV SGLITGIAFW HYLYMRGVWI DTGDTP....
RED19 VFFFVERDRV SAKWKTSLTV SGLVTGIAFW HYMYMRGVWI ETGDSP....
RED2 VFFFVERDRV SAKWKTSLTV SGLVTGIAFW HYMYMRGVWI ETGDSP....
RED23 VFFFVERDRV SAKWKTSLTV SGLVTGIAFW HYMYMRGVWI ETGDSP....
RED27 VFFFVERDRV SAKWKTSLTV SGLVTGIAFW HYMYMRGVWI ETGDSP....
RED30 VFFFVERDRV SAKWKTSLTV SGLVTGIAFW HYMYMRGVWI ETGSSP....
RED4 VFFFVERDRV SAKWKTSLTV SGLVTGIAFW HYMYMRGVWI ETGDSP....
RED5 VFFFVERDRV SAKWKTSLAV SGLITGIAFW HYMYMRGVWI ETGDSP....
REDA9 VFFFVERDRV SAKWKTSLAV SGLITGIAFW HCMYMRGVWI ETGDSP....
REDB9 VFSFVERDRV SAKWKTSLTV SGLITGIAFW HYMYMRGVWI ETGDSP....
REDF9 VFFFVERDRV SAKWKTSLTV SGLITGIAFW HYMYMRGVWI ETGDSP....
REDr6a5a14 VFFFVERDRV SAEWKTSLTV SGLVTGIAFW HYMYMRGVWI ETGDSP....
REDr6a5a6 VFFFVERDRV SAKWKTSLTV SGLVTGIAFW HYMYMRGVWI ETGDSP....
REDr7_1_15 VFFFVERDRV SAKWKTSLTV PGLITDIAFW HYMYMRGVWI ETGDSP....
REDr7_1_16 VFFFVERDRV SAKWKTSLTV SGLVTGIAFW HYMYMRGVWI ETGDSP....
REDr7_1_4 VFFFVERDRV SAKWKTSLTV PGLITDIAFW HYMYMRGVWI ETGDSP....
REDs3_15 VFFFVERDRV SAKWKTSLTV PGLVTGIAFW HYMYMRGVWI ETGDSP....
REDs3_7 VFFFVERDRV SAKWKTSLTV PGLITDIAFW HYMYMRGVWI ETGDSP....
ANT32C12 VFFFVERDQV SAKWKTSLTV SGLITGIAFW HYLYMRGVWI DTGDTP....
HOT2C02 AFFFLERDRV AAKWKTSLTV AGLVTGIAAW HYFYMRGVWV ATGDSP....

101 150
BAC31A8 ...TVFRYID WLLTVPLLIC EFYLILAAAT NVAGSLFKKL LVGSLVMLVF
BAC40E8 ...TVFRYID WLLTVPLLIC EFYLILAAAT NVAAGLFKKL LVGSLVMLVF
BAC64A5 ...TVFRYID WLLTVPLLIC EFYLILAAAT NVAGSLFKKL LVGSLVMLVF
HOT0m1 ...TVFRYID WLLTVPLLIC EFYLILAAAT NVAAGLFKKL LVGSLVMLVF
HOT75m1 ...TVFRYID WLLTVPLQMV EFYLILAACT SVAASLFKKL LAGSLVMLGA
HOT75m3 ...TVFRYID WLLTVPLQMV EFYLILAACT SVAASLFKKL LAGSLVMLGA
HOT75m4 ...TVFRYID WLLTVPLQVV EFYLILAACT SVAASLFKKL LAGSLVMLGA
HOT75m8 ...TVFRYID WLLTVPLQMV EFYLILAACT NVAASLFKKL LAGSLVMLGA
MB0m1 ...TVFRYID WLLTVPLLIC EFYLILAAAT NVAAGLFKKL LVGSLVMLVF
MB0m2 ...TVFRYID WLLTVPLLIC EFYLILAAAT NVAAGLFKKL LVGSLVMLVF
MB100m10 ...TVFRYID WLLTVPLLIC EFYLILAAAT NVAGSLFKKL LVGSLVMLVF
MB100m5 ...TVFRYID WLLTVPLLIC EFYLILAAAT NVAGSLFKKL LVGSLVMLVF
MB100m7 ...TVFRYID WLLTVPLLIC EFYLILAAAT NVAGSLFKKL LVGSLVMLVF
MB100m9 ...TVFRYID WLLTVPLLIC EFYLILAAAT NVAGSLFKKL LVGSLVMLVF
MB20m12 ...TVFRYID WLLTVPLLIC EFYLILAAAA NVAGSLFKKL LVGSLVMLVF
MB20m2 ...TVFRYID WLLTVPLLIC EFYLILAAAT NVAAGLFKKL LVGSLVMLVF
MB20m5 ...TVFRYID WLLTVPLLIC EFYLILAAAT NVAGSLFKKL LVGSLVMLVF
MB40m1 ...TVFRYID WLLTVPLLIC EFYLILAAAT NVAGSLFKKL LVGSLVMLVF
MB40m12 ...TVFRYID WLLTVPLLIC EFYLILAAAT NVAGSLFKKL LVGSLVMLVF
MB40m5 ...TVFRYID WLLTVPLLIC EFYLILAAAT NVAAGLFKKL LVGSLVMLVF
MED101 ...TVFRYID WLLTVPLLIC EFYLILAAAT NVAGSLFKKL LVGSLVMLVF

Figure 3-3

| | |
|---|---|
| MED102 | ...TVFRYID WLLTVPLLIC EFYLILAAAT NVAGSLFKKL LVGSLVMLVF |
| MED106 | ...TVFRYID WLLTVPLLIC EFYLILAAAT NVAGSLFKKL LVGSLVMLVF |
| MED202 | ...TVFRYID WLLTVPLLIC EFYLILAAAT NVAGSLFKKL LVGSLVMLVF |
| MED204 | ...TVFRYID WLLTVPLLIC EFYLILAAAT NVAGSLFKKL LVGSLVMLVF |
| MED208 | ...TVFRYID WLLTVPLLIC EFYLILAAAT NVAGSLFKKL LVGSLVMLVF |
| MED25 | ...TVFRYID WLLTVPLLIC EFYLILAAAT NVAGSLFKKL LVGSLVMLVF |
| MED26 | ...TVFRYID WLLTVPLLIC EFYLILAAAT NVAGSLFKKL LVGSLVMLVF |
| MED27 | ...TVFRYID WLLTVPLLIC EFYLILAAAT NVAGSLFKKL LVGSLVMLVF |
| MED36 | ...TVFRYID WLLTVPLLIC EFYLILAAAT NVAGSLFKKL LVGSLVMLVF |
| medA15_r8_1 | ...TVFRYID WLLTVPLLIC EFYLILAAAT NVAGSLFKKL LVGSLVMLVF |
| medA15_R8_3 | ...TVFRYID WLLTVPLLMV EFYLILAACT NVAGSLFKKL LGGSLVMLIA |
| medA15_r8ex7 | ...TVFRYID WLLTVPLLMV EFYLILAACT NVAGSLFKKL LIGSLVMLIA |
| medA15_R8ex9 | ...TVFRYID WLLTVPLLMV EFYLILAACT NVAGSLFKKL LIGSLVMLIA |
| medA15_r9_3 | ...TVFRYID WLLTVPLLMV EFYLILAACT NVAGSLFKKL LIGSLVMLIA |
| medA15r10b5 | ...TVFRYID WLLTVPLLMV EFYLILAACT NVAGSLFKKL LGGSLVMLIA |
| medA15r11b3 | ...TVFRYID WLLTVPLLIC EFYLILAAAT NVAGSLFKKL LIGSLVMLVF |
| medA15r11b9 | ...TVFRYID WLLTVPLLIC EFYLILAAAT NVAGSLFKKL LVGSLVMLVF |
| medA15r8b3 | ...TVFRYID WLLTVPLLIC EFYLILAAAT NVAGSLFKKL LVGSLVMLVF |
| medA15r8b8 | ...TVFRYID WLLTVPLLMI EFYFILAAVT TVSSGIFWRL LIGTVVMLVG |
| medA15r8b9 | ESPTEFRYID WLLTVPLLIC EFYLILAAAT NVAGSLFKKL LVGSLVMLIA |
| medA15r8ex4 | ...TVFRYID WLLTVPLLMI EFYFILAAVT TVSSGIFWRL LIGTVVMLVG |
| medA15r8ex6 | ...TVFRYID WLLTVPLLIC EFYLILAAAT NVAGSLFKKL LVGSLVMLVF |
| medA15r9b5 | ...TVFRYID WLLTVPLLIC EFYLILAAAT NVAGSLFKKL LIGSLVMLVF |
| medA15r9b7 | ...TVFRYID WLLTVPLLMV EFYLILAACT NVAGSLFKKL LGGSLVMLIA |
| medA17_r8_11 | ...TVFRYID WLLTVPLLMI EFYFILAAVT TVSSGIFWRL LVGTVIMLVG |
| medA17_r8_15 | ...TVFRYID WLLTVPLLMI EFYFILAAVT TVSSGIFWRL LVGTVIMLVG |
| medA17_R8_6 | ...TVFRYID WLLTVPLQMV EFYLILAACT NVAGSLFKKL LIGSLVMLIG |
| medA17R9_1 | ESPTEFRYID WLLTVPLLIC EFYLILAAAT NVAGSLFKKL LVGSLVMLIA |
| medA19_R8_16 | ...TVFRYID WLLTVPLQMV EFYLILAACT NVAGSLFKKL LVGSLVMLGA |
| medA19_R8_19 | ...TVFRYID WLLTVPLQMV EFYLILAACT NVAGSLFKKL LVGSLVMLGA |
| medA19_R8_20 | ...TVFRYID WLLTVPLLMV EFYLILAACT NVAGSLFKKL LIGSLVMLIA |
| medA19_r9_9 | ...TVFRYID WLLTVPLLMV EFYLILAACT NVAGSLFKKL LGGSLVMLIA |
| PalB1 | ...TVFRYID WLLTVPLQMV EFYLILAACT SVAASLFKKL LAGSLVMLGA |
| PalB2 | ...TVFRYID WLLTVPLQMV EFYLILAACT SVAASLFKKL LAGSLVMLGA |
| PalB5 | ...TVFRYID WLLTVPLQMV EFYLILAACT NVAASLFKKL LAGSLVMLGA |
| PalB6 | ...TVFRYID WLLTVPLQMV EFYLILAACT NVAASLFKKL LAGSLVMLGA |
| PalB7 | ...TVFRYID WLLTVPLQMV EFYLILAACT SVAASLFKKL LAGSLVMLGA |
| PalB8 | ...TVFRYID WLLTVPLQMV EFYLILAACT SVAASLFKKL LAGSLVMLGA |
| PalE1 | ...TVFRYID WLLTVPLQVV EFYLILAACT SVAASLFKKL LAGSLVMLGA |
| PalE6 | ...TVFRYID WLLTVPLQMV EFYLILAACT SVAASLFKKL LAGSLVMLGA |
| PalE7 | ...TVFRYID WLLTVPLQMV EFYLILAACT SVAASLFKKL LAGSLVMLGA |
| RED19 | ...TVFRYID WLLTVPLLIC EFYLILAAAT NVAGSLFKKL LVGSLVMLVF |
| RED2 | ...TVFRYID WLLTVPLLIC EFYLILAAAT NVAGSLFKKL LVGSLVMLVF |
| RED23 | ...TVFRYID WLLPVPLAIC EFYLILAAAT NVAGSLFKKL LVGSLVMLVF |
| RED27 | ...TVFRYID WLLTVPLLIC EFYLILAAAT NVAGSLFKKL LVGSLVMLVF |
| RED30 | ...TVFRYID WLLTVPLLIC EFYLILAAAT NVAGSLFKKL LVGSLVMLVF |
| RED4 | ...TVFRYID WLLTVPLLIC EFYLILAAAT NVAGSLFKKL LVGSLVMLVF |
| RED5 | ...TVFRYID WLLTVPLLIC EFYLILAAAT NVAGSLFKKL LVGSLVMLVF |
| REDA9 | ...TVFRYID WLLTVPLLIC EFYLILAAAT NVAGSLFKKL LVGSLVMLVF |
| REDB9 | ...TVFRYID WLLTVPLLIC EFYLILAAAT NVAGSLFKKL LVGSLVMLVF |
| REDF9 | ...TVFRYID WLLTVPLLIC EFYLILAAAT NVAGSLFKKL LVGSLVMLVF |
| REDr6a5a14 | ...TVFRYID WLLTVPLEIC EFYLILAAAT NVAGSLFKKL LVGSLVMLVF |
| REDr6a5a6 | ...TVFRYID WLLTVPLVIC EFYLILAAAT NVAGSLFKKL LVGSLVMLVF |
| REDr7_1_15 | ...TVFRYID WLLTVSLQIC EFYLILAAAT NVAGSLFKKL LVGSLVMLVF |
| REDr7_1_16 | ...TVFRYID WLLTVPLLIC EFYLILAAAT NVAGSLFKKL LVGSLVMLVF |
| REDr7_1_4 | ...TVFRYID WLLTVPLQIC EFYLILAAAT NVAGSLFKKL LVGSLVMLVF |
| REDs3_15 | ...AVFRYID WLLTVPLEIC EFYLILAAAT NVAGSLFKKL LVGSLVMLVF |
| REDs3_7 | ...TVFRYID WLLTVPLQIC EFYLILAAAT NVAGSLFKKL LVGSLVMLVF |
| ANT32C12 | ...TVFRYID WLLTVPLQMV EFYLILAACT SVAASLFKKL LAGSLVMLGA |
| HOT2C02 | ...TVLRYID WLITVPLQIV EFYVILAAMT AVASSLFWRL LIASIIMLVF |
| | 151 200 |
| BAC31A8 | GYMGEAGIMA AWPAFIIGCL AWVYMIYELW AGEG.KSACN TASPAVQSAY |

Figure 3-4

| | | | | | |
|---|---|---|---|---|---|
| BAC40E8 | GYMGEAGIMN | AWGAFVIGCL | AWVYMIYELW | AGEG.KAACN | TASPAVQSAY |
| BAC64A5 | GYMGEAGIMA | AWPAFIIGCL | AWVYMIYELY | AGEG.KSACN | TASPSVQSAY |
| HOT0m1 | GYMGEAGIMN | AWGAFVIGCL | AWVYMIYELW | AGEG.KAACN | TASPAVQSAY |
| HOT75m1 | GFAGEAGLAP | VLPAFIIGMA | GWLYMIYELY | MGEG.KAAVS | TASPAVNSAY |
| HOT75m3 | GFAGEAGLAP | VLPAFIIGMA | GWLYMIYELH | MGEG.KAAVS | TASPAVNSAY |
| HOT75m4 | GFAGEAGLAP | VLPAFIIGMA | GWLYMIYELY | MGEG.KAAVS | TASPAVNSAY |
| HOT75m8 | GFAGEAGLAP | VWPAFIIGMA | GWLYMIYELY | MGEG.KAAVS | TASPAVNSAY |
| MB0m1 | GYMGEAGIMN | AWPAFIIGCL | AWVYMIYELY | AGEG.KSACN | TASPSVQSAY |
| MB0m2 | GYMGEAGIMN | AWGAFVIGCL | AWVYMIYELW | LGEG.KAACN | TASPAVQSAY |
| MB100m10 | GYMGEAGIMA | AWPAFIVGCL | AWVYMIYELW | AGEG.KSACN | TASPAVQSAY |
| MB100m5 | GYMGEAGIMA | AWPAFIIGCL | AWVYMIYELY | AGEG.KSACN | TASPSVQSAY |
| MB100m7 | GYMGEAGIMA | AWPAFIIGCL | AWVYMIYELY | AGEG.KSACN | TASPSVQSAY |
| MB100m9 | GYMGEAGIMA | AWPAFIIGCL | AWVYMIYELW | AGEG.KSACN | TASPAVQSAY |
| MB20m12 | GYMGEAGIMA | AWPAFIIGCL | AWVYMIYELW | AGEG.KSACN | TASPAVQSAY |
| MB20m2 | GYMGEAGIMN | AWGAFVIGCL | AWVYMIYELW | AGEG.KAACN | TASPAVQSAY |
| MB20m5 | GYMGEAQIMA | AWPAFIIGCL | AWVYMIYELY | AGEG.KSACN | TASPSVQSAY |
| MB40m1 | GYMGEAGIMA | AWPAFIIGCL | AWVYMIYELY | AGEG.KSACN | TASPAVQSAY |
| MB40m12 | GYMGEAGIMA | AWPAFIIGCL | AWVYMIYELW | AGEG.KSACN | TASPAVQSAY |
| MB40m5 | GYMGEAGIMN | AWGAFVIGCL | AWVYMIYELW | AGEG.KAACN | TASPAVQSAY |
| MED101 | GYMGEAGIMA | AWPAFIIGCL | AWVYMIYELW | AGEG.KSACN | TASPAVQSAY |
| MED102 | GYMGEAGIMA | AWPAFIIGCL | AWVYMIYELW | AGEG.KSACN | TASPAVQSAY |
| MED106 | GYMGEAGIMA | AWPAFIIGCL | AWVYMIYELW | AGEG.KSACN | TASPAVQSAY |
| MED202 | GYMGEAGIMA | AWPAFIIGCL | AWVYMIYELW | AGEG.KSACN | TASPAVQSAY |
| MED204 | GYMGEAGIMA | AWPAFIIGCL | AWVYMIYELW | AGEG.KSACN | TASPAVQSAY |
| MED208 | GYMGEAGIMA | AWPAFIIGCL | AWVYMIYELW | AGEG.KSACN | TASPAVQSAY |
| MED25 | GYMGEAGIMA | AWPAFIIGCL | AWVYMIYELW | AGEG.KSACN | TASPAVQSAY |
| MED26 | GYMGEAGIMA | AWPAFIIGCL | AWVYMIYELW | AGEG.KSACN | TASPAVQSAY |
| MED27 | GYMGEAGIMA | AWPAFIIGCL | AWVYMIYELW | AGEG.KSACN | TASPAVQSAY |
| MED36 | GYMGEAGIMA | AWPAFIIGCL | AWVYMIYELW | AGEG.KSACN | TASPAVQSAY |
| medA15_r8_1 | GYMGEAGIMA | ALPAFIIGCL | AWIYMIYELW | AGEG.KSACN | TASPAVQSAY |
| medA15_R8_3 | GYMGESGSLP | VLPAFIVGCL | AWFYMIYELY | AGEG.KAAVT | TASPAVMSAY |
| medA15_r8ex7 | GYMGESGSLP | VLPAFLVGCA | AWLYMIYELY | AGEG.KAAVT | TASPAVMSAY |
| medA15_R8ex9 | GYMGESGSLP | VLPAFLVGCA | AWLYMIYELY | AGEG.KAAVT | TASPAVMSAY |
| medA15_r9_3 | GYMGESGNLP | VLPAFLIGCA | AWLYMIYELY | AGEG.KAAVT | TASPAVMSAY |
| medA15r10b5 | GYMGESGSLP | VLPAFIVGCL | AWFYMIYELY | AGEG.KAAVT | TASPAVMSAY |
| medA15r11b3 | GYMGEAGIMA | AWPAFIIGCL | AWVYMIYELW | AGEG.KSACN | TASPAVQSAY |
| medA15r11b9 | GYMGEAGIMA | AWPAFIIGCL | AWVYMIYELW | AGEG.KSACN | TASPAVQSAY |
| medA15r8b3 | GYMGEAGIMA | AWPAFIVGCL | AWFYMIYELW | AGEG.KSACN | TASPAVQSAY |
| medA15r8b8 | GYMGEAGMIS | VMTGFIIGMI | GWLYILYEIF | AGEASKANAS | SGSAACQTAF |
| medA15r8b9 | GYMGESGNAN | VMIAFVVGCL | AWLYMIYELW | AGEG.KAACN | TASPAVQSAY |
| medA15r8ex4 | GYMGEAGMIS | VMTGFIIGMI | GWLYILYEIF | AGEASKANAS | SGSAACQTAF |
| medA15r8ex6 | GYMGEAGIMA | AWPAFIIGCL | AWVYMIYELW | AGEG.KSACN | TASPAVQSAY |
| medA15r9b5 | GYMGEAGIMA | AWPAFIIGCL | AWFYMIYELW | AGEG.KSACN | TASPAVQSAY |
| medA15r9b7 | GYMGESGSLP | VLPAFIVGCL | AWFYMIYELY | AGEG.KAAVT | TASPAVMSAY |
| medA17_r8_11 | GYLGEAGMIS | VMTGFIIGMI | GWLYILYEIF | AGEASKANAS | SGSAACQTAF |
| medA17_r8_15 | GYLGEAGMIS | VMTGFIIGMI | GWLYILYEIF | AGEASKANAS | SGSAACQTAF |
| medA17_R8_6 | GFLGEAGMID | VTLAFVIGMA | GWLYMIYELY | MGEG.KAAVS | TASPAVNSAY |
| medA17R9_1 | GYMGESGNAN | VMIAFVVGCL | AWLYMIYELW | AGEG.KAACN | TASPAVQSAY |
| medA19_R8_16 | GFAGEAGLAP | ALPAFILGMA | GWVYMIYELY | MGEG.KAAVS | TASPAVNSAY |
| medA19_R8_19 | GFAGEAGLAP | ALPAFILGMA | GWVYMIYELY | MGEG.KAAVS | TASPAVNSAY |
| medA19_R8_20 | GYMGESGSLP | VLPAFLVGCA | AWLYMIYELY | AGEG.KAAVT | TASPAVMSAY |
| medA19_r9_9 | GYMGESGSLP | VLPAFIVGCL | AWFYMIYELY | AGEG.KAAVT | TASPAVMSAY |
| PalB1 | GFAGEAGLAP | VLPAFILGMA | GWLYMIYELH | MGEG.KAAVS | TASPAVNSAY |
| PalB2 | GFAGEAGLAP | VLPAFIIGMA | GWLYMIYELY | MGEG.KAAVS | TASPAVNSAY |
| PalB5 | GFAGEAGLAP | VWPAFIIGMA | GWLYMIYELY | MGEG.KAAVS | TASPAVNSAY |
| PalB6 | GFAGEAGLAP | VWPAFIIGMA | GWLYMIYELY | MGEG.KAAVS | TASPAVNSAY |
| PalB7 | GSAGEAGLAP | VLPAFIIGMA | GWLYMIYELY | MGEG.KAAVS | TASPAVNSAY |
| PalB8 | GFAGEAGLAP | VLPAFIIGMA | GWLYMIYELY | MGEG.KAAVS | TASPAVNSAY |
| PalE1 | GFAGEAGLAP | VLPAFIIGMA | GWLYMIYELY | MGEG.KAAVS | TASPAVNPAY |
| PalE6 | GFAGEAGLAP | VLPAFIIGMA | GWLYMIYELH | MGEG.KAAVS | TASPAVNSAY |
| PalE7 | GFAGEAGLAP | VLPAFIIGMA | GWLYMIYELY | MGEG.KAAVS | TASPAVNSAY |
| RED19 | GYMGEAGIMA | AWPAFIIGCL | AWVYMIYELW | AGEG.KSACN | TASPAVQSAY |
| RED2 | GYMGEAGIMA | AWPAFIIGCL | AWVYMIYELW | AGEG.KSACN | TASPAVQSAY |

Figure 3-5

| | | | | | |
|---|---|---|---|---|---|
| RED23 | GYMGEAGIMA | AWPAFIIGCL | AWVYMIYELW | AGEG.KSACN | TASPAVQSAY |
| RED27 | GYMGEAGIMA | AWPAFIIGCL | AWVYMIYELW | AGEG.KSACN | TASPAVQSAY |
| RED30 | GYMGEAGIMA | AWPAFIIGCL | AWVYMIYELW | AGEG.KSACN | TASPAVQSAY |
| RED4 | GYMGEAGIMA | AWPAFIIGCL | AWVYMIYELW | AGEG.KSACN | TASPAVQSAY |
| RED5 | GYMGEAGIMA | AWPAFIIGCL | AWVYMIYELW | AGEG.KSACN | TASPAVQSAY |
| REDA9 | GYMGEAGIMA | AWPAFIIGCL | AWVYMIYELW | AGEG.KSACN | TASPAVQSAY |
| REDB9 | GYMGEAGIMA | AWPAFIIGCL | AWVYMIYELW | AGEG.KSACN | TASPAVQSAY |
| REDF9 | GYMGEAGIMA | AWPAFIIGCL | AWVYMIYELW | AGEG.KSACN | TASPAVQSAY |
| REDr6a5a14 | GYMGEAGIMA | AWPAFIIGCL | AWVYMIYELW | AGEG.KSACN | TASPAVQSAY |
| REDr6a5a6 | GYMGEAGIMA | AWPAFIIGCL | AWVYMIYELW | AGEG.KSACN | TASPAVQSAY |
| REDr7_1_15 | GYMGEAGIMA | AWPAFIIGCL | AWVYMIYELW | AGEG.KSACN | TASPAVQSAY |
| REDr7_1_16 | GYMGEAGIMA | AWPAFIIGCL | AWVYMIYELW | AGEG.KSACN | TASPAVQSAY |
| REDr7_1_4 | GYMGEAGIMA | AWPAFIIGCL | AWVYMIYELW | AGEG.KSACN | TASPAVQSAY |
| REDs3_15 | GYMGEAGIMA | AWPAFIIGCL | AWVYMIYELW | AGEG.KSACN | TASPAVQSAY |
| REDs3_7 | GYMGEAGIMA | AWPAFIIGCL | AWVYMIYELW | AGEG.KSACN | TASPAVQSAY |
| ANT32C12 | GFAGEAGLAP | VLPAFIIGMA | GWLYMIYELY | MGEG.KAAVS | TASPAVNSAY |
| HOT2C02 | GYMGETGAMN | VTLAFVIGMA | GWLYIIYEVF | AGEASKASAG | SGNAAGQTAF |

| | | | | | |
|---|---|---|---|---|---|
| | 201 | | | | 250 |
| BAC31A8 | NTMMYIIIFG | WAIYPVGYFT | GYLMG..DGG | SALNLNLIYN | LADFVNKILF |
| BAC40E8 | NTMMYIIIFG | WAIYPVGYFT | GYLMG..DGG | SALNLNLIYD | LADFVNKILF |
| BAC64A5 | NTMMAIIVFG | WAIYPIGYFT | GYLMG..DGG | SALNLNLIYN | LADFVNKILF |
| HOT0m1 | NTMMYIIIFG | WAIYPVGYFT | GYLMG..DGG | SALNLNLIYN | LADFVNKILF |
| HOT75m1 | NAMMMIIVVG | WAIYPAGYAA | GYLMGG.EGV | YASNLNLIYN | LADLVNKILF |
| HOT75m3 | NAMMKIIVIG | WAIYPAGYAA | GYLMSG.DGV | YASNLNLIYN | LADFVNKILF |
| HOT75m4 | NAMMMIIVVG | WAIYPAGYAA | GYLMGG.EGV | YASNLNLIYN | LADFVNKILF |
| HOT75m8 | NAMMVIIVVG | WAIYPAGYAA | GYLMGG.EGV | YASNLNLIYN | LADLVNKILF |
| MB0m1 | NTMMAIIVFG | WAIYPVGYFT | GYLMG..DGG | SALNLNLIYN | LADFVNKILF |
| MB0m2 | NTMMMIIIFG | WAIYPVGYFT | GYLMG..DGG | SALNLNLIYN | LADFVNKILF |
| MB100m10 | NTMMYIIIVG | WAIYPVGYFT | GYLMG..DGG | SALNLNLIYN | LADFVNKILF |
| MB100m5 | NTMMAIIVFG | WAIYPVGYFT | GYLMG..DGG | SALNLNLIYN | LADFVNKILF |
| MB100m7 | NTMMAIIVFG | WAIYPVGYFT | GYLMG..DGG | SALNLNLIYN | LADFVNKILF |
| MB100m9 | NTMMYIIIFG | WAIYPVGYFT | GYLMG..DGG | SALNLNLIYN | LADFVNKILF |
| MB20m12 | NTMMYIIIFG | WAIYPVGYFT | GYLMG..DGG | SALNLNLIYN | LADFVNKILF |
| MB20m2 | NTMMYIIIFG | WAIYPVGYFT | GYLMG..DGG | SALNLNLIYN | LADFVNKILF |
| MB20m5 | NTMMAIIVFG | WAIYPVGYFT | GYLMG..DGG | SALNLNLIYN | LADFVNKILL |
| MB40m1 | NTMMYIIVFG | WAIYPVGYFT | GYLMG..DGG | SALNLNLIYN | LADFVNKILF |
| MB40m12 | NTMMYIIIVG | WAIYPVGYFT | GYLMG..DGG | SALNLNLIYN | LADFVNKILF |
| MB40m5 | NTMMYIIIFG | WAIYPVGYFT | GYLMG..DGG | SALNLNLIYN | LADFVNKNLF |
| MED101 | NTMMYIIIVG | WAIYPVGYFT | GYLMG..DGG | SALNLNLIYN | LADFVNKILF |
| MED102 | NTMMYIIIAG | WAIYPVGYFT | GYLMG..DGG | SALNLNLNYN | LADFVNKILF |
| MED106 | NTMMYIIIVG | WAIYPVGYFT | GYLMG..DGG | SALNLNLIYN | LADFVNKILF |
| MED202 | NTMMYIIIFG | WAIYLVGYFT | GYLMG..DGG | SALNLNLIYN | LADFVNKILF |
| MED204 | NTMMYIIIAG | WAIYPVGYFT | GYLMG..DGG | SALNLNLIYN | LADFVNKILF |
| MED208 | NTMMYIIIVG | WAIYPVGYFT | GYLMG..DGG | SALNLNLIYN | LADFVNKILF |
| MED25 | NTMMYIIIVG | WAIYPVGYFT | GYLMG..DGG | SALNLNLIYN | LADFVNKILF |
| MED26 | NTMMYIIIVG | WAIYPVGYFT | GYLMG..DGG | SALNLNLIYN | LADFVNKILF |
| MED27 | NTMMYIIIVG | WAIYPVGYFT | GYLMG..DGG | SALNLNLIYN | LADFVNKILF |
| MED36 | NTMMYIIIAG | WAIYPVGYFT | GYLMG..DGG | SALNLNLIYN | LADFVNKILF |
| medA15_r8_1 | NTMMYIIIFG | WLIYPVGYAS | GYLMG..DGG | SAMNLNLIYN | LADFVNKILF |
| medA15_R8_3 | NTMMLIIVVG | WAIYPAGYAA | GYLMGG.DGV | YAQNLNVIYN | LADFVNKILF |
| medA15_r8ex7 | NTMMLIIVVG | WAIYPAGYAA | GYLMGG.DGV | YAQNLNVIYN | LADFVNKILF |
| medA15_R8ex9 | NTMMLIIVVG | WAIYPAGYAA | GYLMGG.DGV | YAQNLNVIYN | LADFVNKILF |
| medA15_r9_3 | NTMMLIIVVG | WAIYPAGYAA | GYLMGG.DGV | YAQNLNVIYN | LADFVNKILF |
| medA15r10b5 | NTMMLIIVVG | WAIYPAGYAA | GYLMGG.DGV | YAQNLNVIYN | LADFVNKILF |
| medA15r11b3 | NTMMYIIIFG | WAIYPVGYFT | GYLMG..DGG | SALNLNLIYN | LADFVNKILF |
| medA15r11b9 | NTMMYIIIFG | WAIYLVGYFT | GYLMG..DGG | SALNLNLIYN | LADFVNKILF |
| medA15r8b3 | NTMMYIIIIG | WAIYPLGYFT | GYLMG..DGG | SALNLNLIYN | LADFVNKILF |
| medA15r8b8 | GALRLIVTVG | WAIYPIGYFV | GYLTGGG..A | DAATLNIVYN | LADFVNKIAF |
| medA15r8b9 | NTMMWIIIVG | WAIYPAGYAA | GYLMGG.ESV | YASNLNLIYN | LADFVNKILF |
| medA15r8ex4 | GALRLIVTVG | WAIYPIGYFV | GYLTGGG..A | DAATLNIVYN | LADFVNKIAF |
| medA15r8ex6 | NTMMYIIIFG | WAIYPVGYFT | GYLMG..DGG | SALNLNLIYN | LADFVNKILF |
| medA15r9b5 | NTMMYIIIIG | WAIYPVGYFT | GYLMG..DGG | SALNLNLIYN | LADFVNKILF |

Figure 3-6

| | | | | | |
|---|---|---|---|---|---|
| medA15r9b7 | NTMMLIIVVG | WAIYPAGYAA | GYLMGG.DGV | YAQNLNVIYN | LADFVNKILF |
| medA17_r8_11 | GALRLIVTIG | WAIYPLGYFL | GYLGGG...A | DPATLNIVYN | LADFVNKIAF |
| medA17_r8_15 | GALRLIVTIG | WAIYPLGYFL | GYLGGG...A | DPATLNIVYN | LADFVNKIAF |
| medA17_R8_6 | NAMMLIIVVG | WSIYPAGYVA | GYLMGG.EGV | YASNLNLIYN | LADFINKILF |
| medA17R9_1 | NTMMWIIIVG | WAIYPAGYAA | GYLMGG.ESV | YASNLNLIYN | LADFVNKILF |
| medA19_R8_16 | NAMMMIIVFG | WSIYPLGYVA | GYLMG...AV | DPSTLNLIYN | LADFINKILF |
| medA19_R8_19 | NAMMMIIVFG | WSIYPLGYVA | GYLMG...AV | DPSTLNLIYN | LADFINKILF |
| medA19_R8_20 | NTMMLIIVVG | WAIYPAGYAA | GYLMGG.DGV | YAQNLNVIYN | LADFVNKILF |
| medA19_r9_9 | NTMMLIIVVG | WAIYPAGYAA | GYLMGG.DGV | YAQNLNVIYN | LADFVNKILF |
| PalB1 | NAMMKIIVIG | WAIYPAGYAA | GYLMSG.DGV | YASNLNLIYN | LADFVNKILF |
| PalB2 | NAMMMIIVVG | WAIYPAGYAA | GYLMGG.EGV | YASNLNLIYN | LADFVNKILF |
| PalB5 | NAMMMIIVVG | WAIYPAGYAA | GYLMGG.EGV | YASNLNLIYN | LADFVNKILF |
| PalB6 | NAMMVIIVVG | WAIYPAGYAA | GYLMGG.EGV | YASNLNLIYN | LADFVNKILF |
| PalB7 | NAMMMIIVVG | WAIYPAGYAA | GYLMGG.EGV | YASNLNLIYN | LADFVNKILF |
| PalB8 | NAMMMIIVVG | WAIYPAGYAA | GYLMGG.EGV | YASNLNLIYN | LADLVNKILF |
| PalE1 | NAMMMIIVVG | WAIYPAGYAA | GYLMGG.EGV | YASNLNLIYN | LADFVNKILF |
| PalE6 | NAMMKIIVIG | WAIYPAGYAA | GYLMSG.DGV | YASNLNLIYN | LADFVNKILF |
| PalE7 | NAMMMIIVVG | WAIYPAGYAA | GYLMGG.EGV | YASNLNLIYN | LADFVNKILF |
| RED19 | NTMMYIIIVG | WAIYPVGYFT | GYLMG..DGG | SALNLNLIYN | LADFVNKILF |
| RED2 | NTMMYIIIVG | WAIYPVGYFT | GYLMG..DGG | SALNLNLIYN | LADFVNKILF |
| RED23 | NTMMYIIIFG | WAIYPVGYFT | GYLMG..DGG | SALNLNLIYN | LADFVNKILF |
| RED27 | NTMMYIIIFG | WAIYLVGYFT | GYLMG..DGG | SALNLNLIYN | LADFVNKILF |
| RED30 | NTMMYIIIFG | WAIYLVGYFT | GYLMG..DGG | SALNLNLIYN | LADFVNKILF |
| RED4 | NTMMYIIIVG | WAIYPVGYFT | GYLMG..DGG | SALNLNLIYN | LADFVNKILF |
| RED5 | NTMMYIIIVG | WAIYPVGYFT | GYLMG..DGG | SALNLNLIYN | LADFVNKILF |
| REDA9 | NTMMYIIVFG | WAIYPVGYFT | GYLMG..DGG | SALNLNLIYN | LADFVNKILF |
| REDB9 | NTMMYIIIFG | WAIYPVGYFT | GYLMG..DGG | SALNLNLIYN | LADFVNKILF |
| REDF9 | NTMMYIIIFG | WAIYPVGYFT | GYLMG..DGG | SALNLNLIYN | LADFVNKILF |
| REDr6a5a14 | NTMMYIIIFG | WAIYPVGYFT | GYLMG..DGG | SALNLNLIYN | LADFVNKILI |
| REDr6a5a6 | NTMMYIIIFG | WAIYPVGYFT | GYLMG..DGG | SALNLNLIYN | LADFVNKILF |
| REDr7_1_15 | NTMMYIIIFG | WAIYPVGYFT | GYLMG..DGG | SALNLNLIYN | LADFVNKILF |
| REDr7_1_16 | NTMMYIIIFG | WAIYLVGYFT | GYLMG..DGG | SALNLNLIYN | LADFVNKILF |
| REDr7_1_4 | NTMMYIIIFG | WAIYPVGYFT | GYLMG..DGG | SALNLNLIYN | LADFVNKILF |
| REDs3_15 | NTMMYIIIFG | WAIYPVGYFT | GYLMG..DGG | SALNLNLIYN | LADFVNKILF |
| REDs3_7 | NTMMYIIIFG | WAIYPVGYFT | GYLMG..DGG | SALNLNLIYN | LADFVNKILF |
| ANT32C12 | NAMMMIIVVG | WAIYPAGYAA | GYLMGG.EGV | YASNLNLIYN | LADFVNKILF |
| HOT2C02 | NALRLIVTVG | WAIYPIGYAV | GYFGG...GV | DAGSLNLIYN | LADFVNKIAF |

| | 251 | 266 |
|---|---|---|
| BAC31A8 | GLIIWNVAVK | ESSNA. |
| BAC40E8 | GLIIWNVAVK | ESSNAK |
| BAC64A5 | GLIIWNVAVK | ESSNAK |
| HOT0m1 | GLIIWNVAVK | ESSNA. |
| HOT75m1 | GLIIWNVAVK | ESSNA. |
| HOT75m3 | GLIIWNVAVK | ESSNA. |
| HOT75m4 | GLIIWNVAVK | ESSNA. |
| HOT75m8 | GLIIWNVAVK | ESSNA. |
| MB0m1 | GLIIWNVAVK | ESSNA. |
| MB0m2 | GLIIWNVAVK | ESSNA. |
| MB100m10 | GLIIWNVAVK | ESSNA. |
| MB100m5 | GLIIWNVAVK | ESSNA. |
| MB100m7 | GLIIWNAAVK | ESSNA. |
| MB100m9 | GLIIWNVAVK | ESSNA. |
| MB20m12 | GLIIWNVAVK | ESS... |
| MB20m2 | GLIIWNVAVK | ESSNA. |
| MB20m5 | GLIIWNVAVK | ESSNA. |
| MB40m1 | GLIIWNVAVK | ESSNA. |
| MB40m12 | GLIIWNVAVK | ESSNA. |
| MB40m5 | GLIIWNVAVK | ESS... |
| MED101 | GLIIWNVAVK | ESSNA. |
| MED102 | GLIIWNVAVK | ESSNA. |
| MED106 | GLIIWNVAVK | ESSNA. |
| MED202 | GLIIWNVAVK | ESSNA. |

Figure 3-7

| | | |
|---|---|---|
| MED204 | GLIIWNVAVK | ESSNA. |
| MED208 | GLIIWNVAVK | ESSNA. |
| MED25 | GLIIWNVAVK | ESSNA. |
| MED26 | GLIIWNVAVK | KSSNA. |
| MED27 | GLIIWNVAVK | ESSNA. |
| MED36 | GLIIWNVAVK | ESSNA. |
| medA15_r8_1 | GLIIWNVAVK | ESSNA. |
| medA15_R8_3 | GLVIWHVAVK | ESSNA. |
| medA15_r8ex7 | GLVIWHVAVK | ESSNA. |
| medA15_R8ex9 | GLVIWHVAVK | ESSNA. |
| medA15_r9_3 | GLVIWHVAVK | ESSNA. |
| medA15r10b5 | GLVIWHVAVK | ESSNA. |
| medA15r11b3 | GLIIWHVAVK | ESSNA. |
| medA15r11b9 | GLIIRNVAVK | ESSNA. |
| medA15r8b3 | GLIIWHVAVK | ESSNA. |
| medA15r8b8 | GLIIWAAAVK | ESSNA. |
| medA15r8b9 | GLIIWHVAVK | ESSNA. |
| medA15r8ex4 | GLIIWAAAVK | ESSNA. |
| medA15r8ex6 | GLIIWNVAVK | ESSNA. |
| medA15r9b5 | GLIIWHVAVK | ESSNA. |
| medA15r9b7 | GLVIWHVAVK | ESSNA. |
| medA17_r8_11 | GLIIWAAAVK | ESSNA. |
| medA17_r8_15 | GLIIWAAAVK | ESSNA. |
| medA17_R8_6 | GLIIWHVAVK | ESSNA. |
| medA17R9_1 | GLIIWHVAVK | ESSNA. |
| medA19_R8_16 | GLIIWHVAVK | ESSNA. |
| medA19_R8_19 | GLIIWHVAVK | ESSNA. |
| medA19_R8_20 | GLVIWHVAVK | ESSN.. |
| medA19_r9_9 | GLVIWHVAVK | ESSNA. |
| PalB1 | GLIIWNVAVK | ESSNA. |
| PalB2 | GLIIWNVAVK | ESSNA. |
| PalB5 | GLIIWNVAVK | ESSNA. |
| PalB6 | GLIIWNVAVK | ESSNA. |
| PalB7 | GLIIWNVAVK | ESSNA. |
| PalB8 | GLIIWNVAVK | ESSNA. |
| PalE1 | GLIIWNVAVK | ESSNA. |
| PalE6 | GLIIWNVAVK | ESSNA. |
| PalE7 | GLIIWNVAVK | ESSNA. |
| RED19 | GLIIWNVAVK | ESSNA. |
| RED2 | GLIIWNVAVK | ESSNA. |
| RED23 | GLIIWNVAVK | ESSNA. |
| RED27 | GLIIWNVAVK | ESSNA. |
| RED30 | GLIIWNVAVK | ESSNA. |
| RED4 | GLIIWNVAVK | ESSNA. |
| RED5 | GLIIWNVAVK | ESSNA. |
| REDA9 | GLIIWNVAVK | ESSNA. |
| REDB9 | GLIIWNVAVK | ESSNA. |
| REDF9 | GSIIWNVAVK | ESSNA. |
| REDr6a5a14 | GLIIWNVAVK | ESSNA. |
| REDr6a5a6 | GLIIWNVAVK | ESSNA. |
| REDr7_1_15 | GLIIWNVAVK | ESSNA. |
| REDr7_1_16 | GLIIWNVAVK | ESSNA. |
| REDr7_1_4 | GLIIWNVAVK | ESSNA. |
| REDs3_15 | GLIIWNVAVK | ESSNA. |
| REDs3_7 | GLIIWNVAVK | ESSN.. |
| ANT32C12 | GLIIWNVAVK | ESSNA. |
| HOT2C02 | GMAIYVAAVS | DSN... |

Figure 3-8

PROTEORHODOPSIN MUTANTS WITH IMPROVED OPTICAL CHARACTERISTICS

This application claims the benefit of Provisional Application 60/429,518, filed Nov. 26, 2002.

FIELD OF INVENTION

This present invention relates to the composition and use of proteorhodopsin mutants with improved optical characteristics. Particularly, the proteorhodopsin mutants have a mutation at a conserved amino acid residue of a naturally occurring proteorhodopsin variant or its equivalent sharing high identity.

BACKGROUND OF THE INVENTION

Proteorhodopsins are integral membrane proteins; they are isolated from uncultivated marine eubacteria and function as light-driven proton pumps. Upon absorption of light by the all-trans-retinal co-factor, proteorhodopsin goes through a photocycle with a number of intermediates. It is believed that upon excitation of the proteorhodopsin molecule by light stimulation, a proteorhodopsin/retinal complex is excited to an unstable intermediate energy state. Proteorhodopsin progresses through a series of unstable energy states that can vary in terms of energy plateaus or intermediates, e.g., an "M-like state" or "M-state", a "K-like state" or "K-state", an "N-like state" or "N-state", or an "O-like state" or "O-state". Subsequently, the complex reverts to a more stable basal state concomitant with transportation of a proton.

Proteorhodopsins are distantly related to bacteriorhodopsin from *Halobacterium salinarium* (22-24% sequence similarity). Hampp (*Appl. Microbiol. Biotechnol.* 53:633-9, 2000a) reviews the structure and function of bacteriorhodopsin, and its technical applications. Hampp (*Chem. Rev.* 100: 1755-76, 2000b) reviews the technical application of bacteriorhodopsin.

Proteorhodopsin and bacteriorhodopsin have some shared characteristics, but also have clearly different properties. Proteorhodopsins are more advantageous to use in some technical applications than bacteriorhodopsins because of the ease of expressing and producing proteorhodopsins. However, the conditions where the proteorhodopsins can be used in different applications are limited because wild-type proteorhodopsins exist in two distinct spectral forms depending on the extra-cellular pH. A basic form, which is a spectral form at a higher pH, is able to achieve an M-state of excitation and transport a proton upon exposure to an optical stimulation. An acidic form, which is a spectral form at a lower pH, is unable to exhibit the M-state of excitation and does not transport a proton upon exposure to an optical stimulation.

The properties of the two distinct pH-dependent spectral forms of the Bac31A8 proteorhodopsin have been characterized to some extent (Dioumaev, et al., *Biochem.* 41:5348-58, 2002; Krebs, et al., *BMC Physiol.* 2:1-8, 2002; Fredrich, et al., *J. Mol. Biol.* 321, 821-838, 2002). The D97 residue in the Bac31A8 proteorhodopsin was previously identified (Dioumaev, et al., 2002) as being part of the titratable group(s) involved in the pH dependent change in spectral and photochemical properties. However, the Bac31A8 D97N mutant protein appears only to exist as a single spectral form, the acidic form. An analysis of the photocycle intermediates of the Bac31A8 proteorhodopsin at different pH values showed that only the high pH ("basic") form exhibits the photocycle wherein protons are pumped across the membrane. Hence, this Bac31A8 D97N mutant is not very useful for most applications because the protein is unable to pump protons and form an M-state.

Béjà, et al. (*Science* 289:1902-6, 2000) disclose the cloning of a proteorhodopsin gene from an uncultivated member of the marine γ-proteobacteria (i.e., the "SAR86" group). The proteorhodopsin was functionally expressed in *E.coli* and bound all-trans-retinal to form an active light-driven proton pump.

Béjà, et al. (*Nature* 411:786-9, 2001) disclose the cloning of over twenty variant proteorhodopsin genes from various sources. The proteorhodopsin variants appear to belong to an extensive family of globally distributed proteorhodopsin variants that maximally absorb light at different wavelengths.

WO 01/83701 discloses specific proteorhodopsin gene and protein sequences retrieved from naturally occurring bacteria; the reference also discloses the use of these proteorhodopsin variants in a light-driven energy generation system.

Dioumaev, et al. (*Biochem.* 41:5348-58); Krebs, et al. (*BMC Physiol.* 2:1-8, 2002); and Friedrich, et al (*J. Mol. Biol.* 321, 821-38, 2002) disclose the properties of two distinct pH-dependent spectral forms of the Bac31A8 proteorhodopsin. Dioumaev, et al. also disclose that essentially only the acidic form is present in the Bac31A8 D97N mutant since the N residue is non-protonatable. Further, Dioumaev, et al. disclose that the D97E mutant causes minor changes in the absorbance maximum of the acidic and basic forms. An E108Q mutant causes the decay of the M-like state intermediate to be a hundred fold slower. Both the D97E and E108Q mutants have pH titration similar to that of the wild-type protein.

Varo, et al. (*Bioophysical J.*, 84:1202-1207 (2003)) describe the results of a thorough analysis of the photocyle of the wildtype Bac31A8 proteorhodopsin; the spectral properties and lifetimes of different intermediates in the photocycles are characterized.

WO 02/10207 discloses proton-translocating retinal protein, such as a *Halobacterium salinarim* bacteriorhodopsin, in which one or more positions of the amino acids that participate in proton-translocation, from the group of amino acid residues D38, R82, D85, D96, D102, D104, E194 and E204 are modified; such proton-translocating retinal proteins have a slower photocycle in comparison to with the wild-type proteins.

SUMMARY OF THE INVENTION

The present invention is directed to a proteorhodopsin mutant having improved optical characteristics; the mutant comprises a mutation in a conserved residue such as a histidine residue and/or an arginine residue of a proteorhodopsin variant. One improved optical characteristic of the mutant is having a lower pH ($pK_{rh}$), at which equal concentrations of the acidic and basic spectral form of the proteorhodopsin molecules are present. Another improved optical characteristic of the mutant is having a smaller difference in maximum absorption wavelength between the basic and the acidic form. The present invention also provides proteorhodopsin mutants comprising specific amino acid sequences.

A conserved histidine residue is at, for example, amino acid position 75 of Bac31A8, or position 77 of Hot75m1, or its equivalent position of a proteorhodopsin variant. A conserved arginine residue is at, for example, amino acid position 94 of Bac31A8, or position 96 of Hot75m1, or its equivalent position of a proteorhodopsin variant. Preferred mutations are substituting histidine with asparagine, glutamine, lysine, tryptophan, aspartic acid, or glutamnic acid; and substituting arginine to alanine, glutamic acid or glutamine.

The present invention also provides an isolated nucleic acid sequence encoding the proteorhodopsin mutant. The present invention further provides a method for preparing a proteorhodopsin mutant having improved optical characteristics.

DESCRIPTION OF THE FIGURES

FIG. 1-1 depicts the amino acid and nucleotide sequences of Hot75m1 (SEQ ID NOs: 1 and 2).

FIG. 1-2 depicts the amino acid and nucleotide sequences of Bac31A8 (SEQ ID NOs: 3 and 4).

FIG. 1-3 depicts the amino acid and nucleotide sequences of Bac40E8 (SEQ ID NOs: 5 and 6).

FIG. 1-4 depicts the amino acid and nucleotide sequences of Bac64A5 (SEQ ID NOs: 7 and 8).

FIG. 1-5 depicts the amino acid and nucleotide sequences of Hot0m1 (SEQ ID NOs: 9 and 10).

FIG. 1-6 depicts the amino acid and nucleotide sequences of Hot75m3 (SEQ ID NOs: 11 and 12).

FIG. 1-7 depicts the amino acid and nucleotide sequences of Hot75m4 (SEQ ID NOs: 13 and 14).

FIG. 1-8 depicts the amino acid and nucleotide sequences of Hot75m8 (SEQ ID NOs: 15 and 16).

FIG. 1-9 depicts the amino acid and nucleotide sequences of MB0m1 (SEQ ID NOs: 17 and 18).

FIG. 1-10 depicts the amino acid and nucleotide sequences of MB0m2 (SEQ ID NOs: 19 and 20).

FIG. 1-11 depicts the amino acid and nucleotide sequences of MB20m2 (SEQ ID NOs: 21 and 22).

FIG. 1-12 depicts the amino acid and nucleotide sequences of MB20m5 (SEQ ID NOs: 23 and 24).

FIG. 1-13 depicts the amino acid and nucleotide sequences of MB20m12 (SEQ ID NOs: 25 and 26).

FIG. 1-14 depicts the amino acid and nucleotide sequences of MB40m1 (SEQ ID NOs: 27 and 28).

FIG. 1-15 depicts the amino acid and nucleotide sequences of MB40m5 (SEQ ID NOs: 29 and 30).

FIG. 1-16 depicts the amino acid and nucleotide sequences of MB40m12 (SEQ ID NOs: 31 and 32).

FIG. 1-17 depicts the amino acid and nucleotide sequences of MB100m5 (SEQ ID NOs: 33 and 34).

FIG. 1-18 depicts the amino acid and nucleotide sequences of MB100m7 (SEQ ID NOs: 35 and 36).

FIG. 1-19 depicts the amino acid and nucleotide sequences of MB100m9 (SEQ ID NOs: 37 and 38).

FIG. 1-20 depicts the amino acid and nucleotide sequences of MB100m10 (SEQ ID NOs: 39 and 40).

FIG. 1-21 depicts the amino acid and nucleotide sequences of Pa1B1 (SEQ ID NOs: 41 and 42).

FIG. 1-22 depicts the amino acid and nucleotide sequences of Pa1B2 (SEQ ID NOs: 43 and 44).

FIG. 1-23 depicts the amino acid and nucleotide sequences of Pa1B5 (SEQ ID NOs: 45 and 46).

FIG. 1-24 depicts the amino acid and nucleotide sequences of Pa1B7 (SEQ ID NOs: 47 and 48).

FIG. 1-25 depicts the amino acid and nucleotide sequences of Pa1B6 (SEQ ID NOs: 49 and 50).

FIG. 1-26 depicts the amino acid and nucleotide sequences of Pa1B8 (SEQ ID NOs: 51 and 52).

FIG. 1-27 depicts the amino acid and nucleotide sequences of Pa1E1 (SEQ ID NOs: 53 and 54).

FIG. 1-28 depicts the amino acid and nucleotide sequences of Pa1E6 (SEQ ID NOs: 55 and 56).

FIG. 1-29 depicts the amino acid and nucleotide sequences of Pa1E7 (SEQ ID NOs: 57 and 58).

FIG. 1-30 depicts the amino acid and nucleotide sequences of MED26 (SEQ ID NOs: 59 and 60).

FIG. 1-31 depicts the amino acid and nucleotide sequences of MED27 (SEQ ID NOs: 61 and 62).

FIG. 1-32 depicts the amino acid and nucleotide sequences of MED36 (SEQ ID NOs: 63 and 64).

FIG. 1-33 depicts the amino acid and nucleotide sequences of MED101 (SEQ ID NOs: 65 and66).

FIG. 1-34 depicts the amino acid and nucleotide sequences of MED102 (SEQ ID NOs: 67 and 68).

FIG. 1-35 depicts the amino acid and nucleotide sequences of MED106 (SEQ ID NOs: 69 and 70).

FIG. 1-36 depicts the amino acid and nucleotide sequences of MED25 (SEQ ID NOs: 71 and 72).

FIG. 1-37 depicts the amino acid and nucleotide sequences of MED202 (SEQ ID NOs: 73 and 74).

FIG. 1-38 depicts the amino acid and nucleotide sequences of MED204 (SEQ ID NOs: 75 and 76).

FIG. 1-39 depicts the amino acid and nucleotide sequences of MED208 (SEQ ID NOs: 77 and 78).

FIG. 1-40 depicts the amino acid and nucleotide sequences of REDA9 (SEQ ID NOs: 79 and 80).

FIG. 1-41 depicts the amino acid and nucleotide sequences of REDB9 (SEQ ID NOs: 81 and 82).

FIG. 1-42 depicts the amino acid and nucleotide sequences of REDF9 (SEQ ID NOs: 83 and 84).

FIG. 1-43 depicts the amino acid and nucleotide sequences of RED19 (SEQ ID NOs: 85 and 86).

FIG. 1-44 depicts the amino acid and nucleotide sequences of RED2 (SEQ ID NOs: 87 and 88).

FIG. 1-45 depicts the amino acid and nucleotide sequences of RED23 (SEQ ID NOs: 89 and 90).

FIG. 1-46 depicts the amino acid and nucleotide sequences of RED27 (SEQ ID NOs: 91 and 92).

FIG. 1-47 depicts the amino acid and nucleotide sequences of RED30 (SEQ ID NOs: 93 and 94).

FIG. 1-48 depicts the amino acid and nucleotide sequences of RED4 (SEQ ID NOs: 95 and 96).

FIG. 1-49 depicts the amino acid and nucleotide sequences of RED5 (SEQ ID NOs: 97 and 98).

FIG. 1-50 depicts the amino acid and nucleotide sequences of REDr6a5a14 (SEQ ID NOs: 99 and 100).

FIG. 1-51 depicts the amino acid and nucleotide sequences of REDr6a5a6 (SEQ ID NOs: 101 and 102).

FIG. 1-52 depicts the amino acid and nucleotide sequences of REDr7__1__4 (SEQ ID NOs: 103 and 104).

FIG. 1-53 depicts the amino acid and nucleotide sequences of REDs3__7 (SEQ ID NOs: 105 and 106).

FIG. 1-54 depicts the amino acid and nucleotide sequences of REDr7__1__15 (SEQ ID NOs: 107 and 108).

FIG. 1-55 depicts the amino acid and nucleotide sequences of REDs3__15 (SEQ ID NOs: 109 and 110).

FIG. 1-56 depicts the amino acid and nucleotide sequences of medA15r8ex6 (SEQ ID NOs: 111 and 112).

FIG. 1-57 depicts the amino acid and nucleotide sequences of REDr7__1__16 (SEQ ID NOs: 113 and 114).

FIG. 1-58 depicts the amino acid and nucleotide sequences of medA15r11b9 (SEQ ID NOs: 115 and 116).

FIG. 1-59 depicts the amino acid and nucleotide sequences of medA15r9b5 (SEQ ID NOs: 117 and 118).

FIG. 1-60 depicts the amino acid and nucleotide sequences of medA15r8b3 (SEQ ID NOs: 119 and 120).

FIG. 1-61 depicts the amino acid and nucleotide sequences of medA15r11b3 (SEQ ID NOs: 121 and 122).

FIG. 1-62 depicts the amino acid and nucleotide sequences of medA15_r8__1 (SEQ ID NOs: 123 and 124).

FIG. 1-63 depicts the amino acid and nucleotide sequences of medA17R9__1 (SEQ ID NOs: 125 and 126).

FIG. 1-64 depicts the amino acid and nucleotide sequences of medA15r8b9 (SEQ ID NOs: 127 and 128).

FIG. 1-65 depicts the amino acid and nucleotide sequences of medA19_R8__16 (SEQ ID NOs: 129 and 130).

FIG. 1-66 depicts the amino acid and nucleotide sequences of medA19_R8__19 (SEQ ID NOs: 131 and 132).

FIG. 1-67 depicts the amino acid and nucleotide sequences of medA17_R8__6 (SEQ ID NOs: 133 and 134).

FIG. 1-68 depicts the amino acid and nucleotide sequences of medA15r9b7 (SEQ ID NOs: 135 and 136).

FIG. 1-69 depicts the amino acid and nucleotide sequences of medA15_R8__3 (SEQ ID NOs: 137 and 138).

FIG. 1-70 depicts the amino acid and nucleotide sequences of medA15r10b5 (SEQ ID NOs: 139 and 140).

FIG. 1-71 depicts the amino acid and nucleotide sequences of medA19_r9__9 (SEQ ID NOs: 141 and 142).

FIG. 1-72 depicts the amino acid and nucleotide sequences of medA15_r8ex7 (SEQ ID NOs: 143 and 144).

FIG. 1-73 depicts the amino acid and nucleotide sequences of medA19_R8__20 (SEQ ID NOs: 145 and 146).

FIG. 1-74 depicts the amino acid and nucleotide sequences of medA15_R8ex9 (SEQ ID NOs: 147 and 148).

FIG. 1-75 depicts the amino acid and nucleotide sequences of medA15_r9__3 (SEQ ID NOs: 149 and 150).

FIG. 1-76 depicts the amino acid and nucleotide sequences of medA17_r8__15 (SEQ ID NOs: 151 and 152).

FIG. 1-77 depicts the amino acid and nucleotide sequences of medA17_r8__11 (SEQ ID NOs: 153 and 154).

FIG. 1-78 depicts the amino acid and nucleotide sequences of medA15r8b8 (SEQ ID NOs: 155 and 156).

FIG. 1-79 depicts the amino acid and nucleotide sequences of medA15r8ex4 (SEQ ID NOs: 157 and 158).

FIG. 1-80 depicts the amino acid and nucleotide sequences of ANT32C12 PR (SEQ ID NOs: 159 and 160).

FIG. 1-81 depicts the amino acid and nucleotide sequences of HOT2C01 PR (SEQ ID NOs: 161 and 162).

FIGS. 2-1 to 2-11 show the amino acid and nucleotide sequences of proteorhodopsin mutants Bac31A8 H75K (SEQ ID NOs: 163 and 164), Bac31A8 H75N (SEQ ID NOs: 165 and 166), Bac31A8 H75Q (SEQ ID NOs: 167 and 168), Hot75m1 H77K (SEQ ID NOs: 169 and 170), Hot75m1 H77N (SEQ ID NOs: 171 and 172), Hot75m1 H77Q (SEQ ID NOs: 173 and 174), Hot75m1 H77E (SEQ ID NOs: 175 and 176), Hot75m1 H77W (SEQ ID NOs: 177 and 178), Hot75m1 R96A (SEQ ID NOs: 179 and 180), Hot75m1 R96E (SEQ ID NOs: 181 and 182), and Hot75m1 R96Q (SEQ ID NOs: 183 and 184).

FIGS. 3-1 to 3-8 depict an alignment of the amino acid sequences of 81 natural proteorhodopsin variants; Bac31A8 (SEQ ID NO: 3), Bac40E8 (SEQ ID No: 5), Bac64A5 (SEQ ID No: 7), Hot0m1 (SEQ ID No: 9), Hot75m1 (SEQ ID No: 1), Hot75m3 (SEQ ID No: 11), Hot75m4 (SEQ ID No: 13), Hot75m8 (SEQ ID No: 15), MB0m1 (SEQ ID No: 17), MB0m2 (SEQ ID No: 19), MB100m10 (SEQ ID No: 39), MB100m5 (SEQ ID No: 33), MB100m7 (SEQ ID No: 35), MB100m9 (SEQ ID No: 37), MB20m12 (SEQ ID No: 25), MB20m2 (SEQ ID No: 21), MB20m5 (SEQ ID No: 23), MB40m1 (SEQ ID No: 27), MB40m12 (SEQ ID No: 31), MB40m5 (SEQ ID No: 29), MED101 (SEQ ID No: 65), MED102 (SEQ ID No: 67), MED106 (SEQ ID No: 69), MED202 (SEQ ID No: 73), MED204 (SEQ ID No: 75), MED208 (SEQ ID No: 77), MED25 (SEQ ID No: 71), MED26 (SEQ ID No: 59), MED27 (SEQ ID No: 61), MED36 (SEQ ID No: 63), medA15_r8__1 (SEQ ID No: 123), medA15_R8__3 (SEQ ID No: 137), medA15__,8ex7 (SEQ ID No: 143), medA15_R8ex9 (SEQ ID No: 147), medA15_r9__3 (SEQ ID No: 149), medA15r10b5 (SEQ ID No: 139), medA15r11b3 (SEQ ID No: 121), medA15r11b9 (SEQ ID No: 115), medA15r8b3 (SEQ ID No: 119), medA15r8b8 (SEQ ID No: 155), medA15r8b9 (SEQ ID No: 127), medA15r8ex4 (SEQ ID No: 157), medA15r8ex6 (SEQ ID No: 111), medA15r9b5 (SEQ ID No: 117), medA15r9b7 (SEQ ID No: 135), medA17_r8__11 (SEQ ID No: 153), medA17_r8__15 (SEQ ID No: 151), medA17_R8__6 (SEQ ID No: 133),medA17R9__1 (SEQ ID No: 125), medA19_R8__16(SEQ ID No: 129), medA19_R8__19 (SEQ ID No: 131), medA19_R8__20 (SEQ ID No: 145), medA19_r9__9 (SEQ ID No: 141), Pa1B1 (SEQ ID No: 41), Pa1B2 (SEQ ID No: 43), Pa1B5 (SEQ ID No: 45), Pa1B6 (SEQ ID No: 49), Pa1B7 (SEQ ID No: 47), Pa1B8 (SEQ ID No: 51), Pa1E1 (SEQ ID No: 53), Pa1E6 (SEQ ID No: 55), Pa1E7 (SEQ ID No: 57), RED19 (SEQ ID No: 85), RED2 (SEQ ID No: 87), RED23 (SEQ ID No: 89), RED27 (SEQ ID No: 91), RED30 (SEQ ID No: 93), RED4 (SEQ ID No: 95), RED5 (SEQ ID No: 97), REDA9 (SEQ ID No: 79), REDB9 (SEQ ID No: 81), REDF9 (SEQ ID No: 83), REDr6a5a14 (SEQ ID No: 99), REDr6a5a6 (SEQ ID No: 101), REDr7__1__15 (SEQ ID No: 107), REDr7__1__16 (SEQ ID No: 113), REDr7__1__4 (SEQ ID No: 103),REDs3__15 (SEQ ID No: 109), REDs3__7 (SEQ ID No: 105), ANT32C12 PR (SEQ ID No: 159), HOT2C01 PR (SEQ ID No: 161). The bold "H" indicates the position of a conserved histidine, which corresponds to H75 of Bac31A8. The bold "R" indicates the position of a conserved arginine, which corresponds to R94 of Bac31A8.

FIG. 4 depicts the map of plasmid pTrcHis2-Hot75m1.

FIG. 5 shows the titration curves of absorption spectra of mutant Hot75m1 H77Q and wildtype (WT) Hot75m1 at pH 4.9, 6.0, 6.9, 8.1 and 9.1.

FIG. 6 shows the fraction of acidic form of Hot75m1 and Hot75m1 H77Q at various pH's.

FIG. 7-1 shows the extracellular pH changes with cells expressing Bac31A8 wild-type, with and without illumination.

FIG. 7-2 shows the extracellular pH changes with cells expressing a LacZ control protein, with and without illumination.

FIG. 7-3 shows the effect of extracellular pH on the proton-pumping rate for Bac31A8 wild-type and the H75N mutant.

DETAILED DESCRIPTION OF THE INVENTION

Definitions

As used in the specification and claims, the singular "a", "an" and "the" include the plural references unless the context clearly dictates otherwise. For example, the term polypeptide may include a plurality of polypeptides.

The term "derived" shall encompass derivation by information alone. For example, an amino acid sequence can be derived from a wild-type protein by using the information of the known amino acid sequence of the wild-type protein to chemically synthesize the amino acid sequence.

Figures 1, 7:
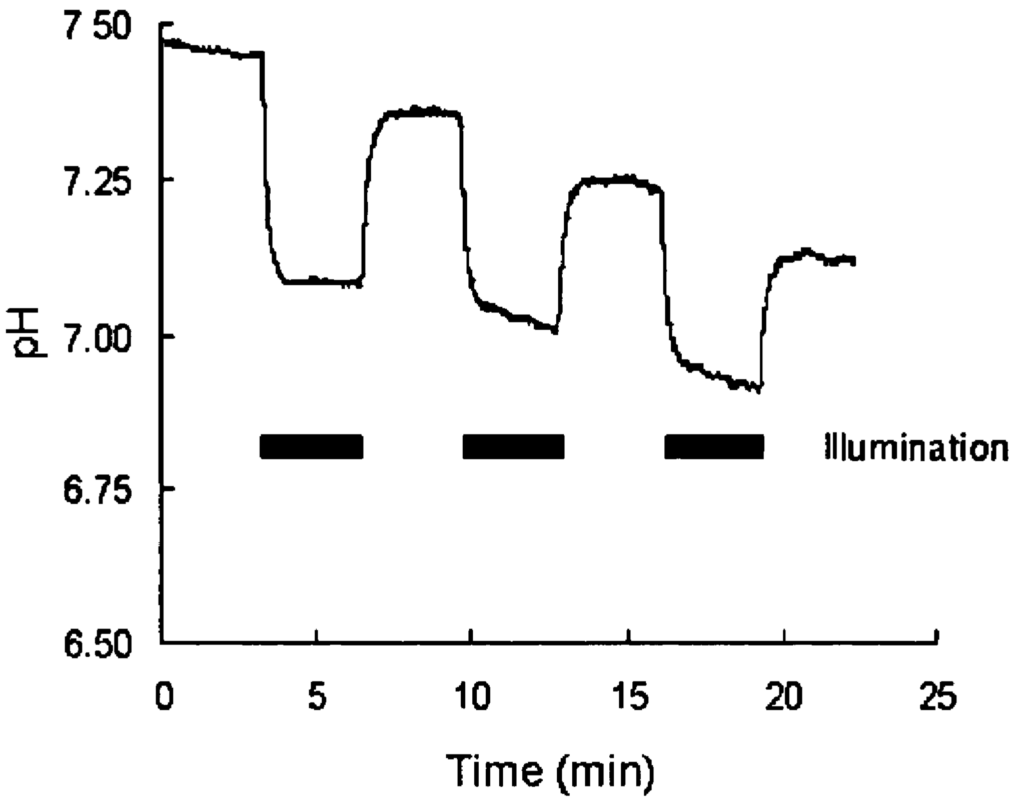

The term "proteorhodopsin variants" encompasses various naturally occurring proteorhodopsins and their homologues, either known or unknown, which are able to undergo a photocycle containing an "M-state" or "M-like state." FIGS. 1-1 to 1-81 provide the nucleotide and amino acid sequences of 81 proteorhodopsin variants; these proteorhodopsin variants show between 53 to 99.6% amino acid sequence identity to each other. The term "proteorhodopsin variant" includes proteins having an amino acid sequence that is at least 53%, preferably 90%, more preferably 95%, most preferably 97 or 98%, identical to that of any proteorhodopsin variant described in FIGS. 1-1 to 1-81. The term "proteorhodopsin variant" also encompasses fused proteorhodopsin constructed by fusing the amino acid sequences from two or more different naturally found proteorhodopsins, so that each amino acid sequence occupies an equivalent position in the resulting proteorhodopsin (even if these fused proteorhodopsin are not naturally occurring).

The term "proteorhodopsin mutant" for the purpose of this application refers to a proteorhodopsin variant comprising one or more mutations that substitutes one or more amino acid residues and/or nucleotides by different amino acids and/or nucleotide sequences.

The term "basal state" or "B-state" or B-like state" refers to the basal state of the photocycle of a proteorhodopsin molecule without light excitation; the basal absorption maxima of proteorhodopsin variants are in general between 480 nm and 530 nm, often between 488 and 526 nm.

The term "M-state" or "M-like state" refers to an excited spectral state in a photocycle as compared with the basal state; the absorption maxima of the M-state of proteorhodopsin variants in general are between 350 nm and 450 nm, often about 410 nm. The M-state is distinguished from other identified spectral states, the K-, N- and O-like states, which all have red-shifted absorbtion spectra (e.g. >530 nm) compared with the basal state.

The term "$pK_{rh}$" for the purpose of this application, refers to the pH at which equal concentrations of the acidic and basic spectral forms of the proteorhodopsin molecule are present. Applicants derive this term from $pK_a$, which is a term that identifies the pH at which equal concentrations of the acidic and basic forms of the molecule are present. If the $pK_{rh}$ of that particular proteorhodopsin is determined to be a specific value, that specific value is the pH where the basic and acidic form are present in equal concentrations. Shifting the pH of the environment relative to the $pK_{rh}$ will increase the concentration of the basic or acidic form present, depending upon the direction (more acidic or more basic) and the pH units shifted.

The term "wavelength maximum" for the purpose of this application, is the wavelength of maximum absorbance for proteorhodopsin at a specific pH.

Abbreviations

IPTG, Isopropyl β-D-thiogalactopyranoside.

MES, 2-(N-morpholino)ethanesulfonic acid.

MOPS, (3-N-morpholino)propanesulfonic acid.

TAPS, N-([tris(hydroxymethyl)methyl]amino)propanesulfonic acid.

CHES, 2-(N-cyclohexlamino)ethanesulfonic acid.

EDTA, Ethylenediaminetetraacetate.

Deposits

The *E. coli* containing the Bac31A8 clone (assigned ATCC No. PTA-3083), the *E. coli* containing the Bac40E8 clone (assigned ATCC No. PTA-3082), the *E. coli* containing the Bac41B4 clone (assigned ATCC No. PTA-3080), and the *E. coli* containing the Bac64A5 clone (assigned ATCC No. PTA-3081) were deposited with the ATCC Patent Depository (10801 University Blvd., Manassas, Va. 20110, U.S.A.) on Feb. 21, 2001.

The *E. coli* containing plasmid Pa1E6 (assigned ATCC No. PTA-3250), the *E. coli* containing the plasmid Hot0m1 (assigned ATCC No. PTA-3251), and the *E. coli* containing the plasmid Hot75m4 (assigned ATCC No. PTA-3252) were deposited with the ATCC Patent Depository (10801 University Blvd., Manassas, Va. 20110, U.S.A.) on Mar. 30, 2001.

Present Invention

The present invention is directed to a proteorhodopsin mutant having an improved optical characteristic. The mutant comprises a mutation in a conserved amino acid residue of a proteorhodopsin variant, which causes the spectral shifts. The improved optical characteristics include having a lower $pK_{rh}$ or a smaller difference in maximum absorption wavelength between the basic and the acidic form, in comparison with the proteorhodopsin variant from which the mutant is derived.

Proteorhodopsin and its Photochemical Properties

Proteorhodopsin is a trans-membrane protein with a structure of seven lipid membrane-spanning α-helices which form a generally cylinder shaped channel. When folded correctly and supplied with all-trans-retinal, the seven α-helices of proteorhodpsin are arranged as a cage surrounding the all-trans-retinal. A properly folded proteorhodopsin has the property of being able to bind all-trans-retinal and undergo a photocycle wherein a proton is transported. The source of all-trans-retinal includes chromophore retinal and chemical derivatives of all-trans-retinal. Chemical derivatives of retinal include, but are not limited to, 3-methyl-5-(1-pyryl)-2E,4E-pentadienal, 3,7-dimethyl-9-(1-pyryl)-2E,4E,6E,8E-nonatetraenal, all-trans-9-(4-azido-2,3,5,6-tetrafluorophenyl)-3,7-dimethyl-2,4,6,8-nonatetraenal, 2,3-dehydro-4-oxoretinal, and like compounds. Proteorhodopsin is a light-activated proton pump. Proteorhodopsin binds all-trans-retinal to form a pigment that absorbs in the visible wavelength range of light.

An all-trans-retinal covalently attached to a conserved lysine (K231 in Bac31A8 and K234 in Hot75M1) by a Schiff-base linkage contributes to the visible light chromophore of proteorhodopsin. The absorbance of light energy by this chromophore is converted through a photocycle into mechanical energy that pumps a proton from the interior to the exterior of the cellular host through the all-trans-retinal binding pocket. The resulting proton imbalance is then used by the cell as chemical energy.

Proteorhodopsin has two distinct pH-dependent spectral forms: a basic form and an acidic form. The basic form can undergo a photocycle that includes the excited M-state (or the M intermediate) and pump a proton, $H^+$, across the proteorhodopsin-containing membrane, from inside the cell to outside the cell. The basic form has a rapid photocycle and is able to transport protons out of a cell or cell vesicle. When the proteorhodopsin is present in a basic form and is stimulated by light, it first proceeds into an excited energy state, e.g. an M-state, then it proceeds back into the more basal energy or resting state, where upon it transports a proton. The charge or proton is transported thereby, pumping a proton through the membrane and out of the cell during this process. (See Dioumaev, et al. and Krebs, et al.)

The acidic form of proteorhodopsin is unable to undergo a photocycle that includes the M-state, and is unable to pump protons. Spectroscopic titration curves, plotting wavelength against absorbance in buffers of different pH, indicate that the concentration of the acidic form and the basic form of some wild-type proteorhodopsins are about equal at a pH range about 7-8 (i.e. $pK_{rh}$ is about 7-8). For example, Hot75m1 in intact cells has a $pK_{rh}$ value of about 8.2. Hot75m1 exhibits a shift in the absorption maxima of about 45 nm when the pH is changed from 4.9 to 9.1. Because only one form, the basic form, gives a productive photocycle, the formation of different spectral forms limits the conditions where the proteorhodopsins can be used for certain applications.

Different naturally occurring proteorhodopsin variants have different absoption maxima wavelengths. The absorption maxima wavelengths when the proteorhodopsin is in an acidic form range from about 534 to about 570 nm. The maximum wavelength when the proteorhodopsin is in a basic form falls within two groups: those that range from about 488 to about 494 nm, and those that range from about 516 to about 528 nm. Different naturally occurring proteorhodopsin variants also have different $pK_{rh}$ values, ranging from about 7.1 to about 8.6.

Without wishing to be bound by any theory, it is believed that the photochemical property of proteorhodopsin can be altered by, either one or a combination of, the pH, presence of an amphipathic molecule (such as a surfactant detergent), temperature of the environment, the presence of chemical additives in the environment (such as azide or glycerol or the like), and the water content of the medium containing the photeorhodopsin.

Improved Optical Property

As described above, a useful and productive form of proteorhodopsin is the basic form. To achieve a predominantly basic spectral form of a proteorhodopsin population with a $pK_{rh}$ of 8.0, a two or more pH unit shift to pH 10.0 or more is contemplated to exhibit an increased relative amount of the basic form versus the acidic form. However, such a basic environment is not an optimal pH for proteorhodopsins, since proteins in general tend to denature at such a high pH. Therefore, a proteorhodopsin mutant having a low $pK_{rh}$ value is desirable.

The proteorhodopsin mutant of the present invention preferably has an altered $pK_{rh}$ value that is lower (more acidic) than that of the naturally occurring proteorhodopsin. In one embodiment, the proteorhodopsin mutant has a $pK_{rh}$ value that is lower than neutral pH. This is because at near neutral pH, the polypeptide is more stable and has a longer shelf life. To allow the proteorhodopsin to undergo a photocycle wherein a proton is transported at near neutral pH, the $pK_{rh}$ value of the proteorhodopsin mutant should be reduced as much as possible so that the basic form can predominate at near a neutral pH range, for example, about 5.5-9.0, or about 6.0-9.0, or about 7.1-8.6.

The $pK_{rh}$ value of the proteorhodopsin mutant is reduced in comparison with that of the proteorhodopsin variant from which the mutant is derived. The $pK_{rh}$ value is reduced by at least 1.0, preferably, 2.0, and more preferably, 3.0 pH units.

In general, the value of the $pK_{rh}$ of proteorhodopsin mutant is reduced to lower than 7.0, preferably 6.0, more preferably 5.0, more preferably 4.0, and even more preferably 3.0.

A proteorhodopsin mutant in general has a broad range of pH in which the basic form predominates. The range of the pH values where the basic form of proteorhodopsin predominates is increased in the mutant by 1.0, preferably by 2.0, and more preferably by 3.0, when compared with the proteorhodopsin variant that the mutant is derived from. Preferably, the $pK_{rh}$ value of the proteorhodopsin mutant is low enough such that essentially only the basic form is present in the useful pH range.

In the proteorhodopsin mutant, the lower limit of the pH range where the basic form predominates is extended to at least pH 7.0, preferably 6.0, more preferably 5.0, more preferably 4.0, or 3.0. Alternatively, the proteorhodopsin mutant predominates in the basic form under all pH conditions.

In another embodiment of the invention, the proteorhodopsin mutant has a smaller difference in maximum absorption wavelength between the basic and the acidic form, in comparison with the proteorhodopsin variant from which the mutant is derived. Such mutants, of which the basic and acidic absorption maxima are closer to each other, are useful in applications where the environmental pH is close to the $pK_{rh}$ value. In such applications, both spectral forms will be present. A large difference in the absorption maxima of the acidic and basic forms will result in a broad composite absorption spectra (broader spectral width) because the acidic and basic absorption spectra are superimposed. When a mutant proteorhodopsin has a smaller difference in the absorption maxima of the acidic and basic forms, the composite absorption spectra will be narrower (smaller peak width).

The proteorhodopsin mutant has a difference in maximum absorption wavelength between the basic and the acidic form of less than 25 nm, preferably less than 20 nm, more preferably less than 15 nm, and most preferably, less than 10 nm.

Proteorhodopsin Variants

A proteorhodopsin variant that the mutant is derived from can be any naturally occurring proteorhodopsin. Proteorhodopsin variants, and nucleic acid sequences encoding thereof, have been obtained from naturally occurring members of the domain bacteria. Such members include marine bacteria, such as bacteria from the SAR86 group. Proteorhodopsin variants useful in the present invention include those derived from marine bacteria, as well as those derived or obtained from non-marine bacteria. There are many variant forms of proteorhodopsin; all of which can be used for the present invention.

The amino acid sequences of 29 proteorhodopsin variants from various sources are shown in FIGS. 1-1 to 1-29 (Baja, et al., *Nature* 411:786-9 (2001)). These include Hot75m1 (SEQ ID NO: 1), Bac31A8 (SEQ ID NO: 3), Bac40E8 (SEQ ID NO: 5), Bac41B4 (SEQ ID NO: 7), Bac64A5 (SEQ ID NO: 9), Hot0m1 (SEQ ID NO: 11), Hot75m3 (SEQ ID NO: 13), Hot75m4 (SEQ ID NO: 15), Hot75m8 (SEQ ID NO: 17), MB0m1 (SEQ ID NO: 19), MB0m2 (SEQ ID NO: 21), MB20m2 (SEQ ID NO: 23), MB20m5 (SEQ ID NO: 25), MB20m12 (SEQ ID NO: 27), MB40m1 (SEQ ID NO: 29), MB40m5 (SEQ ID NO: 31), MB100m5 (SEQ ID NO: 33), MB100m7 (SEQ ID NO: 35), MB100m9 (SEQ ID NO: 37), MB100m10 (SEQ ID NO: 39), Pa1B7 (SEQ ID NO: 41), Pa1B2 (SEQ ID NO: 43), Pa1B5 (SEQ ID NO: 45), Pa1B7 (SEQ ID NO: 47), Pa1B6 (SEQ ID NO: 49), Pa1B8 (SEQ ID NO: 51), Pa1E1 (SEQ ID NO: 53), Pa1E6 (SEQ ID NO: 55), and Pa1E7 (SEQ ID NO: 57).

The amino acid sequences of another 22 proteorhodopsin variants from the Mediterranean Sea and Red Sea are shown in FIGS. 1-30 to 1-51 (see Man, et al., *EMBO J.*, 22:1725-1731 (2003)). These include MED 26 (SEQ ID NO: 59), MED 27 (SEQ ID NO: 61)), MED36 (SEQ ID NO: 63), MED101 (SEQ ID NO: 65), MED102 (SEQ ID NO: 67), MED106 (SEQ ID NOs: 69). MED25 (SEQ ID NO: 71), MED202 (SEQ ID NOs: 73), MED204 (SEQ ID NO: 75). MED208 (SEQ ID NO: 77), REDA9 (SEQ ID NOs: 79), REDB9 (SEQ ID NO: 81), REDF9 (SEQ ID NO: 83), RED19 (SEQ ID NO: 85), RED2 (SEQ ID NO: 87), RED23 (SEQ ID NO: 89), RED27 (SEQ ID NO: 91), RED30 (SEQ ID NO: 93), RED4 (SEQ ID NO: 95), RED5 (SEQ ID NO: 97), REDr6a5a14 (SEQ ID NO: 99), and REDr6a5a6 (SEQ ID NO: 101).

The amino acid sequences of another 28 proteorhodopsin variants from the Mediterranean Sea and Red Sea are shown in FIGS. 1-52 to 1-79 (see Sabehi, et al., *Environ. Microbiol.*, 5: 842-9 (2003)). These include REDr7_1_4 (SEQ ID NO: 103), REDs3_7 (SEQ ID NO: 105), REDr7_1_15 (SEQ ID NO: 107), REDs3_15 (SEQ ID NO: 109), medA15r8ex6

(SEQ ID NO: 111), REDr7_1_16 (SEQ ID NO: 113), medA15r11b9 (SEQ ID NO: 115), medA15r9b5 (SEQ ID NO: 117), medA15r8b3 (SEQ ID NO: 119), medA15r11b3 (SEQ ID NO: 121), medA15_r8_1 (SEQ ID NO: 123), medA17R9_1 (SEQ ID NO: 125), medA15r8b9 (SEQ ID NO: 127), medA19_R8_16 (SEQ ID NO: 129), medA19_R8_19 (SEQ ID NO: 131), medA17_R8_6 (SEQ ID NO: 133), medA15r9b7 (SEQ ID NO: 135), medA15_R8_3 (SEQ ID NO: 137), medA15r10b5 (SEQ ID NO: 139), medA19_r9_9 (SEQ ID NO: 141), medA15_r8ex7 (SEQ ID NO: 143), medA19_R8_20 (SEQ ID NO: 145), medA15_R8ex9 (SEQ ID NO: 147), medA15_r9_3 (SEQ ID NO: 149), medA17_r8_15 (SEQ ID NO: 151), medA17_r8_11 (SEQ ID NO: 153), medA15r8b8 (SEQ ID NO: 155), and medA15r8ex4 (SEQ ID NO: 157).

The amino acid sequences of another 2 newly isolated proteorhodopsin variants from are shown in FIGS. 1-80 to 1-81 (see De La Torre, et al., *Proc. Natl. Acad. Sci. U.S.A.* 100: 12830-5 (2003)). These include ANT32C12 PR (SEQ ID NO: 159) and HOT2C01 PR (SEQ ID NO: 161).

The proteorhodopsin variant, from which the mutant is derived, can be a naturally occurring proteorhodopsin variant, including but not limited to those of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, and 161, orotherproteorhodopsin variants sharing at least 70%, or 80%, or 90%, or 95% amino acid identity with those listed sequences.

The nucleotide and amino acid sequences of the 81 proteorhodopsin variants (FIG. 1-1 to 1-81) can be used to prepare mutants for this invention. In addition, the nucleotide and amino acid sequences of the 81 proteorhodopsin variants can be altered by substitutions, additions or deletions to provide functionally equivalent molecules, which are suitable for preparing mutants for this invention. For example, due to the degeneracy of nucleotide coding sequences, other DNA sequences that encode substantially the same amino acid sequence as depicted in FIGS. 1-1 through 1-81 can be used in the practice of the present invention. The DNA sequence can be altered by a substitution of a different codon that encodes the same or a functionally equivalent amino acid residue within the sequence, thus producing a silent change. For example, an amino acid residue within the sequence can be substituted by another amino acid of a similar polarity, or a similar class. Non-polar (hydrophobic) amino acids include alanine, leucine, isoleucine, valine, proline, phenylalanine, tryptophan, glycine and methionine. Polar neutral amino acids include serine, threonine, cysteine, tyrosine, asparagine, and glutamine. Positively charged (basic) amino acids include arginine, lysine, and histidine. Negatively charged (acidic) amino acids include aspartic and glutamic acid.

In one embodiment of the invention, a proteorhodopsin mutant comprises the amino acid sequence of Bac31A8 H75K (SEQ ID NO: 163), Bac31A8 H75N (SEQ ID NO: 165), Bac31A8 H75Q (SEQ ID NO: 167), Hot75m1 H77K (SEQ ID NO: 169), Hot75m1 H77N (SEQ ID NO: 171), Hot75m1 H77Q (SEQ ID NO: 173), Hot 75m1 H77E (SEQ ID NO: 175), Hot75m1 H77W (SEQ ID NO: 177), Hot75m1 R96A (SEQ ID NO: 179), Hot75m1 R96E (SEQ ID NO: 181) and Hot75m1 R96Q (SEQ ID NO: 183).

Proteorhodopsin Mutation Sites

Naturally occurring proteorhodopsin variants have about 234 to 249 amino acids. Comparing the amino acid sequence of different forms of proteorhodopsins, while contrasting their physical, or chemical properties, can reveal specific target regions that are likely to produce useful mutant proteins, and direct the creation of new mutants with deliberately modified functions.

According to the invention, the sequences determined for proteorhodopsins Bac31A8 and/or Hot75m1 are compared with sequences of known proteorhodopsins (see FIGS. 1-1 through 1-81) or newly discovered proteorhodpsins in order to deduce sites for desirable mutations. To do this, the closeness of relation of the proteorhodopsins being compared is first determined.

Closeness of relation can be measured by comparing of amino-acid sequences. There are many methods of aligning protein sequences. Methods defining relatedness are described in Atlas of Protein Sequence and Structure, Margaret O. Dayhoff editor, vol. 5, supplement 2, 1976, National Biomedical Research Foundation, Georgetown University Medical Center, Washington, D.C., p. 3 ff., entitled SEARCH and ALIGN. As known in the art, related proteins can differ in the number of amino acids as well as the identity of each amino acid along the chain. That is, there can be deletions or insertions when two structures are aligned for maximum identity. For example, proteorhodopsin Bac31A8 has only 249 amino acids while proteorhodopsin Hot75m1 has 252 amino acids. Aligning the two sequences shows that Bac31A8 has no residue corresponding to 214 of Hot75M1. Thus, the amino acid sequence of Bac31A8 would appear very different from Hot75m1 unless a gap is recorded between locations 211 and 212 of Bac31A8 (see FIG. 2 for alignment). Based on the proper amino acid sequence alignment of Bac31A8 and Hot75m1, one can predict with a high degree of confidence that substituting Q, N or K for H at location 75 of proteorhodopsin Bac31A8 will incur the same altered photochemical and spectrophotometric characteristics as substituting Q, N or K for H at location 77 of proteorhodopsin Hot75M1.

The conserved amino acid D97 (Asp97) in the Bac31A8 proteorhodopsin is the amino acid residue that donates a proton to the retinal Schiff-base during the photocycle. The Bac31A8 D97N proteorhodopsin mutant is locked in the acidic form and is therefore incapable of pumping protons or undergoing a complete photocycle (Dioumaev, et al.). The Bac31A8 D97E proteorhodopsin mutant, which has a conserved amino acid replacement, has different wavelength spectra at acidic and basic pH compared with those of the wild-type Bac31A8 proteorhodopsin. However, the Bac31A8 D97E mutant has a similar pH dependent spectral change and a similar $pK_{rh}$ value compared with that of wild-type Bac31A8 proteorhodopsin (Dioumaev, et al.). Thus, a conservative replacement in the Asp97 position causes spectral changes, but not a change in the $pK_{rh}$ value. Since the nature and position of the proton-donating group is important for the proper functioning of the proteorhodopsin photocycle, it is unlikely that changes in D97 of Bac31A8 proteorhodopsin will allow for alteration of the $pK_{rh}$ value without disrupting the pumping of protons or the photocycle.

Conserved amino acid residues that are involved in the relay of protons through the all-trans-retinal binding site, but are not in direct contact with the all-trans-retinal cofactor, are likely to affect the pH dependent spectral shift and the $pK_{rh}$ value of proteorhodopsin, and allow for a continued pumping of protons and therefore a productive photocycle. Applicants have identified such conserved amino acid residues in proteorhodopsins.

The present invention provides a mutant proteorhodopsin wherein said proteorhodopsin has one or more mutations in conserved amino acid residues, wherein said one or more mutations cause said proteorhodopsin to have an altered photochemical property, wherein said mutant proteorhodopsin, when optically stimulated, undergoes a photocycle in which a proton is transported. The proteorhodopsin mutant of this invention has an improved optical characteristic in comparison with the proteorhodopsin variant. The improved optical characteristic is a lower $pK_{rh}$ value or a smaller difference in maximum absorption wavelength between a basic and an acidic form. The present invention has identified a number of conserved amino acid residues that may interact with the proton transported during the photocycle, thus altering the pH at which the basic form of the proteorhodopsin appears, and/or altering the spectrophotometic properties of the proteorhodopsin as compared with that of the wild-type.

Figures 2, 7:
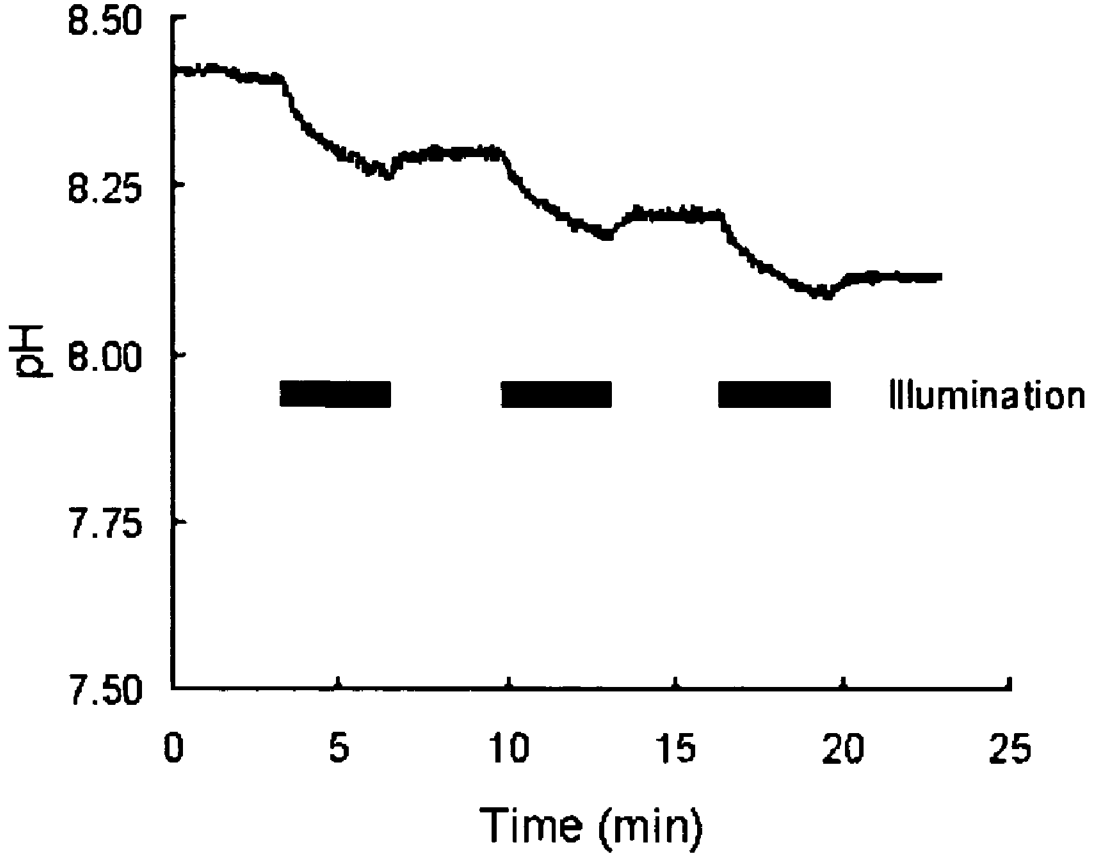
Figures 3, 7:
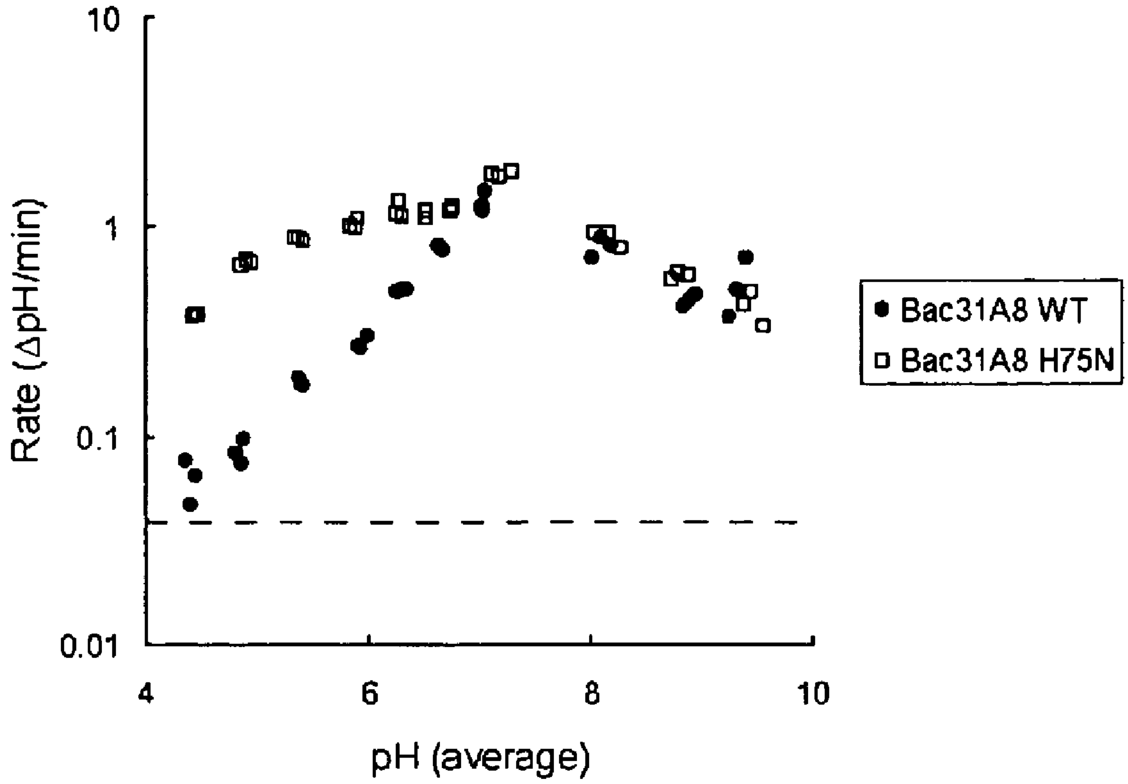

A conserved amino acid residue of proteorhodopsin is an amino acid that is found in the equivalent position of the 81 proteorhodopsins as depicted in FIG. 3. A conserved amino acid residue, which alters the photochemical property of the proteorhodopsin when substituted with a different amino acid, is important for this invention. FIG. 3 shows the alignment of amino acid sequences of 81 natural proteorhodopsin variants. Examples of conserved amino acid residues (H75, R94, D227 of BAC31A8) are shown in FIG. 3. Such conserved amino acid residues can affect the conformation of the protein and the positioning of the all-trans-retinal molecule in relation to the proteorhodopsin protein.

The present invention identifies that the conserved histidine and arginine residues of a proteorhodopsin variant are important for the proton transport during a photocycle. The conserved histidine residue (for example, H75 in Bac31A8 and H77 in Hot75m1) and the conserved arginine residue (for example, R94 in Bac31A8 and R96 in Hot75m1) are purportedly located near both the D97 residue and the all-trans-retinal molecule. These residues in proteorhodopsin interact with D97 or with another amino acid or a water molecule that interacts with D97, but do not interact directly with all trans-retinal. The conserved histidine and the conserved arginine are likely to be part of the hydrogen bondable groups responsible for the spectral change at different pH values.

Proteorhodopsin mutants, which have the conserved histidine substituted with an amino acid capable of forming a hydrogen bond, have an altered photochemical property that shifts the $pK_{rh}$ to a lower pH (more acidic) value than the wild-type proteorhodopsin. For example, mutations at H75 in Bac31A8 proteorhodopsin and at H77 in Hot75m1 proteorhodopsin lower the $pK_{rh}$ value of proteorhodopsin and expand the pH range of the basic form. In some H75 or H77 proteorhodopsin mutants, only the basic form exists in the pH range tested (such as pH 4.9-9.1). This is likely caused by the $pK_{rh}$ values being shifted so low that it is outside the pH value used in the experiment. It is possible that an acid form will appear at a lower pH. Such mutants in the basic form are able to undergo a photocycle that results in a proton transport and go into the M-state with photo stimulation.

Amino acids capable of forming a hydrogen bond and suitable for substituting histidine in this invention include asparagine, glutamine, lysine, arginine, serine, theonine, tyrosine, aspartic acid (in its protonated state at acid pH), glutamic acid (in its protonated state at acidic pH), tryptophan, and any synthetic amino acid that has a functional group that is able to contribute a hydrogen to form a hydrogen bond. Preferred proteorhopsin mutants have the conserved histidine residue substituted with glutamine (Q), asparagine (N), glutamic acid (E), lysine (K), aspartic acid (D), and tryptophan (W).

Proteorhodopsin mutants, which have the conserved arginine substituted with a different amino acid, have an altered photochemical property that results in less difference in maximum absorption wavelength between a basic and an acidic form than the wild-type proteorhodopsin. Preferred proteorhopsin mutants have the conserved arginine residue mutated to alanine, glutamic acid or glutamine.

The altered photochemical property of proteorhodopsin mutants can be identified by measuring the spectral shift of the proteorhodopsin in intact or whole cells, wherein the proteorhodopsin is present in the cytoplasmic membrane, or in a solubilized polypeptide form stabilized by an amphipathic molecule, or in a pure polypeptide form. In addition, the altered photochemical property can be identified by measuring the spectral shift of the proteorhodopsin in a membrane preparation, including but not limited to crude or partly purified membranes. Membrane preparations contain lipids and potentially membrane proteins other than proteorhodopsin.

The present invention provides a method for preparing a proteorhodopsin mutant having improved optical characteristics. The method comprises the steps of: (a) identifying a conserved amino acid residue of a wild-type proteorhodopsin variant, (b) mutagenizing the conserved amino acid residue and obtaining proteorhodopsin mutants, (c) determining the optical characteristics of the proteorhodopsin mutants, and (d) selecting the proteorhodopsin mutant having improved optical characteristics. The conserved amino acid residue, for example, is a histidine or an arginine residue. The wild-type proteorhodopsin variant can by mutagenized by any method, including but not limited to site-directed mutagenisis, known to a skilled person.

Nucleotide/Amino Acid Sequence of Proteorhodopsin Variants

The nucleotide and amino acid sequences of various proteorhodopsin variants (FIGS. 1-1 to 1-29) are deposited with Genbank under accession numbers AF349976-AF350003 and AF279106 (which contains the nucleotide sequence of a 105 kilobase genomic region that includes the gene encoding the Bac31A8 proteorhodopsin). The nucleotide and amino acid sequences of newly isolated proteorhodopsin variants (FIGS. 1-30 to 1-51) are deposited with Genbank under accession numbers AY210898-AY210919. The nucleotide and amino acid sequences of newly isolated proteorhodopsin variants (FIGS. 1-52 to 1-79) are deposited with Genbank under accession numbers AY250714-AY250741. The nucleotide and amino acid sequences of newly isolated proteorhodopsin variants (FIGS. 1-80 to 1-81) are deposited with Genbank under accession numbers AY372453 and AY372455. All these sequences are specifically incorporated herein by reference in this application. Any of these natural proteorhodopsin amino acid sequences can be used to make the proteorhodopsin mutants. For example, the natural proteorhodopsin variant include Hot75m1, Bac31A8, Bac40E8, Bac41B4, Bac64A5, Hot0m1, Hot75m3, Hot75m4, Hot75m8, MB0m1, MB0m2, MB20m2, MB20m5, MB20m12, MB40m1, MB40m5, MB100m5, MB100m7, MB100m9, MB100m10, PalB1, PalB2, PalB5, PalB7, PalB6, PalB8, PalE1, PalE6, PalE7, MED 26, MED27, MED36, MED101, MED102, MED106, MED25, MED202, MED204. MED208, REDA9, REDB9, REDF9, RED19, RED2, RED23, RED27, RED30, RED4, RED5, REDr6a5a14, REDr6a5a6, REDr7_1_4, REDs3_7, REDr7_1_15, REDs3_15, medA15r8ex6, REDr7_1_16, medA15r11b9, medA15r9b5, medA15r8b3, medA15r11b3, medA15_r8_1, medA17R9_1, medA15r8b9, medA19_R8_16, medA19_R8_19, medA17_R8_6, medA15r9b7, medA15_R8_3, medA15r10b5, medA19_r9_9, medA15_r8ex7, medA19_R8_20, medA15_R8ex9, medA15_r9_3, medA17_r8_15, medA17_r8_11, medA15r8b8, medA15r8ex4, ANT32C12 PR and HOT2C01 PR. Preferred natural proteorhodopsin variants are Hot75m1 and Bac31A8 proteorhodopsin.

The nucleotide sequence of any of the above proteorhodopsin genes can be obtained or derived using the method of Béjà, et al. (2000) or WO 01/83701. An example of a gene encoding a proteorhodopsin variant is the bacterioplankton Bacterial Artificial Chromosome (BAC) clone Bac31A8 (also known as EBAC31A08) (see WO 01/83701). One skilled in the art can obtain other genes encoding different proteorhodopsin variants using the identical techniques described above. One skilled in the art can also obtain or clone proteorhodopsin genes from organisms obtained from natural habitats by designing primers and using degenerate PCR, heterologous hybridization, or random sequencing of DNA.

Suitable Host

The proteorhodopsin is capable of proper folding and integrating into a membrane when expressed or synthesized in a suitable host. A suitable host is a cell that naturally expresses proteorhodopsin, such as the SAR 86 strain. A suitable host can also be a cell that naturally does not express proteorhodopsin. A suitable host includes a marine and a non-marine bacteria. Preferably, a suitable host is deficient in any outer-membrane protease, either naturally or constructed not to express such protease. An example of a suitable host is an eubacteria cell; preferably, a Gram-negative bacteria; for example, a proteobacteria such as a gamma-proteobacteria. The gamma-proteobacteria can belong to the Enterobacteriaceae family; such as *Escherichia, Edwardsiella, Citrobactor, Salmonella, Shigella, Klebsiella, Enterobacter, Serratia, Proteus*, and *Yersinia*. In the embodiment, the gamma-proteobacteria belonging to the *Salmonella* genus is *Salmonella typhimurium*. In another embodiment, the gamma-proteobacteria belonging to the *Escherichia* genus is *Escherichia coli.*

Optionally, the polypeptide is expressed or synthesized in a strain that is an outer membrane protease-deficient strain. Such suitable strains include the *E. coli* strains: UT5600 (as disclosed by Béjà, et al. (2000), and Dioumaev, et al.) and BL21-Codonplus-RIL. Alternatively, the gamma-proteobacteria is the SAR86 strain.

The present invention also provides for a host cell comprising a polynucleotide encoding the proteorhodopsin mutant. The suitable host cell is capable of expressing or synthesizing a functional proteorhodopsin from the polynucleotide. A functional proteorhodopsin is a polypeptide capable of undergoing a photocycle in a suitable environment.

The one or more mutations can be constructed by site-directed mutagenesis of a cloned proteorhodopsin gene. Specific designed mutations can be constructed or variability can be introduced to produce a variety of mutants. Such mutagenesis and other methods for manipulation of the nucleic acid and protein are well known to one skilled in the art and are described by Sambrook, et al. (*Molecular cloning: a laboratory manual*. 3d ed. Cold Spring Harbor Laboratory Press, Cold Spring harbor, N.Y.).

Suitable Vector

The present invention provides a polynucleotide encoding the proteorhodopsin mutant. One skilled in the art is able to construct a nucleotide sequence using the information of the amino acid sequence of the polypeptide, based on the universal genetic code. The polynucleotide optionally comprises a promoter operatively linked 5' to the open reading frame encoding the polynucleotide. The polynucleotide further comprises appropriate promoter control, translational control and stop and other necessary sequences in order to express that polypeptide in a suitable host.

The polynucleotide can be a chromosome, an episome, a plasmid, or any suitable expression vector. The polynucleotide is capable of amplification in a host cell. For an eubacterial host cell, a wide variety of expression vectors can be used for introduction by transformation, conjugation, transduction or transfection of the polynucleotide into the eubactaerial host cell. Vectors include plasmids, such as pBR322, pMB9, pBAD-TOPO® (from the pBAD TOPO® TA Expression Kit, Invitrogen, La Jolla, Calif.), pTrcHis2-TOPO® (from the pTrcHis2-TOPO® TA Expression Kit, Invitrogen, La Jolla, Calif.) and the like; cosmids, such as pVK100, and the like; and viruses such as P22, and the like.

Isolation of the Proteorhodopsin from a Host

The proteorhodopsin polypeptide can be purified from a host cell using a variety of methods, which follow a general scheme:

1. Lyse the host cells containing the polypeptide.
2. Dissolve the membrane with detergent.
3. Load impure polypeptide on His-tag affinity resin.
4. Wash resin to remove impurities.
5. Remove protein from column.
6. Exchange buffer and concentrate protein.

Methods of purification can differ for each intended use of the protein since requirements of yield and purity differ in each application.

Lysis can be carried out by sonication, osmotic shock, freeze thaw or French press or a combination of above methods. A preferred method of lysis is freeze-thaw followed by French press. Insoluble materials are removed by centrifugation (e.g. 1500×g, 30 min.) and the supernatant collected. The supernatant is further centrifuged (e.g. 150,000×g. 1 hour) and the pellet containing primarily membrane material is collected.

The membrane material can be solubilized with detergent. Useful detergents include, but are not limited to, dodecyl-β-maltoside, octyl-β-glucoside, or Triton® X-100. Dodecyl-β-maltoside (2%) is a preferred detergent.

The solubilized membrane material is incubated with His-tag affinity resin. For example, the solubilized membrane material is incubated with Talon™ resin from Clontech (Palo Alto, Calif.) overnight at 4° C. with gentle agitation.

The solubilized membrane material is purified from contaminating proteins by washing the resin, for example, with three column volumes of buffer containing 0.1% dodecyl-β-maltoside three times.

The purified polypeptide can be removed from His-tag purification resins by a variety of methods including, but not limited to, incubation with EDTA, incubation in acidic pH, or incubation at high temperature. A preferred method is to incubate the resin with a buffer containing 0.5 M EDTA.

The buffer can be exchanged by a variety of methods including, but not limited to, concentration and dilution using membrane based concentrators, dialysis, or desalting columns. In a preferred method, the protein is concentrated using a membrane based centrifugation concentrator device and then diluted into a desired buffer. The process is repeated to completely exchange the buffer. Then the protein is concentrated again using the same concentrator device.

Further methods for the isolation of the polypeptide in the crude or partly pure form are disclosed by Dioumaev, et al. and Krebs, et al., both of which are incorporated in this application by reference.

Specific Embodiments of the Invention

In one embodiment of the present invention, the proteorhodopsin mutant is derived from Hot75m1 proteorhodopsin variant with the conserved histidine substituted with a glutamine residue. The polypeptide is expressed from an *E. coli* host cell. When analyzed for its absorbance behavior in the membrane of intact cells, the mutant polypeptide exhibits a spectral shift with the $pK_{rh}$ value of less than about 5.8 (as compared with 7.2 of the wild-type proteorhodopsin). The shift of $pK_{rh}$ is about 1.4 units.

In another embodiment of the present invention, the proteorhodopsin mutant is derived from Hot75m1 proteorhodopsin variant with the conserved histidine substituted with an asparagine residue. The polypeptide is expressed from an *E. coli* host cell. When analyzed for its absorbance behavior in the membrane of intact cells, the polypeptide exhibits a spectral shift with the $pK_{rh}$ value of less than about 5.1. The shift in the $pK_{rh}$ is about 2.1 units.

In another embodiment of the present invention, the proteorhodopsin mutant is derived from Hot75m1 proteorhodopsin variant with the conserved histidine substituted with a lysine residue. The polypeptide is expressed from an *E. coli* host cell. When analyzed for its absorbance behavior in the membrane of intact cells, the polypeptide does not exhibit a spectral shift (or does not titrate) when analyzed at a pH range from 4.9 to 9.1. The shape of the curves obtained for this mutant proteorhodopsin, when absorbance of the polypeptide is plotted against the wavelength of the light source, is similar to the shape for the curve obtained from the basic form of the wild-type Hot75m1 proteorhodopsin. Also, the wavelength of the maxima absorbance of this mutant proteorhodopsin (about 495 nm) is much closer to the maxima of absorbance for the basic form of Hot75m1 (about 490 nm) than the acidic form of Hot75m1 (about 540 nm). Based on this reasoning, this mutant proteorhodopsin is likely in its basic form when the pH of its environment is from 4.9 to 9.1. It is likely that the $pK_{rh}$ of this mutant is shifted to a pH much lower than pH 4.9.

Technical Application of the Subject Polypeptide

The proteorhodopsin mutants taught herewith have many technical applications. For example, the proteohodopsin mutant can be incorporated into instruments or devices having photochromic applications, photoelectric applications, and/or phototransport applications.

Under photochromic applications, the polypeptide can be used for its light absorption properties for optical data storage, interferometry and/or photonics. Photochromic applications include, but are not limited to, holographic film. The proteorhodopsin mutant can be used as a photochromic all-trans-retinal protein for optical data storage devices. The proteorhodopsin mutant can be used in a device for information storage, such as 2-D storage, 3-D storage, holographic storage, associative storage, or the like. The proteorhodopsin mutant can be used in a device for information processing, such as optical bistability/light switching, optical filtering, signal conditioning, neural networks, spatial light modulators, phaseconjugation, pattern recognition, interferometry, or the like.

The present invention also provides a method of storing and retrieving optical data using the proteorhodopsin mutant of the invention. A method of storing and retrieving optical data, for example, comprises the steps of: (a) providing a film comprising the proteorhodopsin mutant immobilized in a matrix; (b) recording the optical data by exposing the film to light of a wavelength that is absorbed by the proteorhodopsin mutant in a predetermined pattern and selectively converting portions of the film to an excited state; (c) exposing the film of step (b) to light of a wavelength that is absorbed either by the basal or the excited state of the proteorhodopsin mutant; (d) detecting the optical data by an optical recording device. The detecting of step (d) can be conducted by any optical recording device. The optical recording device can be a video camera, which can be a charged coupled device (CCD). This method as applied to bacteriorhodopsin, and mutants thereof, is known in the art (see patents listed in Table 1) and can be readily modified by replacing the bacteriorhodopsin with the proteorhodopsin mutant of the invention.

Under photoelectric applications, the proteorhodopsin mutant can be used in devices for its light-induced changes in electric fields caused by proton transport, such as in ultrafast light detection, artifical retina, and/or light/motion detectors.

Under phototransport applications, the proteorhodopsin mutant can be used for its light-induced proton transport across a membrane, such as photovoltaic device. One such photovoltaic device is a light-driven energy generator comprising the polypeptide, whereby light energy can be converted to chemical energy. The manufacture and use of such a light-driven energy generator is disclosed in WO 01/83701. The proteorhodopsin mutant can also be used in devices for ATP generation in reactors, desalination of seawater, and/or conversion of sunlight into electricity.

The present invention provides for a light-driven energy generator comprising the use of the proteorhodopsin mutant. A light-driven energy generator comprises: (a) the proteorhodopsin mutant of the present invention, (b) a cell membrane, (c) a source of all-trans-retinal, and (d) a light source, wherein the proteorhodopsin mutant integrates within the cell membrane to produce an integrated proteorhodopsin mutant, and the integrated proteorhodopsin mutant binds covalently to all-trans-retinal to produce a light absorbing pigment. Light-driven energy generators as applied to natural proteorhodopsin variants are disclosed by WO 01/83701, and can be modified by replacing the proteorhodopsin with the proteorhodopsin mutants. The light-driven generator utilizes the proteorhodopsin mutant to convert light-energy into biochemical energy. The light-driven energy generator takes advantages of the functional properties of a proteorhodopsin mutant, which is expressed and correctly folded in a suitable host cell.

The proteorhodopsin mutant can also be used in devices for 2D harmonic generation, radiation detection, biosensor applications, or the like.

Hampp (*Chem. Rev.*,100: 1755-76 (2000)) discloses various uses and instruments and devices that utilize the photochemical properties of bacteriorhodopsin. Proteorhodopsin mutants of this invention can be used in the analogous manner as described by Hampp, which is specifically incorporated by reference.

Further, proteorhodopsin mutants can be used to replace bacteriorhodopsin (BR) for a variety of devices/processes that utilize bacteriorhodopsin, for example, in the following list of patents (Table 1), which are incorporated herein by reference.

TABLE 1

| Inventor(s) | Priority | Patent No(s). | Subject |
|---|---|---|---|
| Inatomi and Isoda | 26 Apr. 1983 | JP 59197849 | Photosensor |
| Isoda | 02 Mar. 1984 | JP 60185228 | Recording and reproducing method of information |
| Isoda and Daimon | 02 Mar. 1984 | JP 60184246 | Light recording medium |
| Inatomi | 19 Nov. 1984 | JP 61124384 | ATP reproduction bioreactor |
| Hikima, et al. | 09 Jul. 1985 | JP 62011158 | Biochemical element |
| Sora, et al. | 14 Sep. 1985 | JP 62063823 | Optical sensor |
| Arai, et al. | 08 Oct. 1986 | JP 63092946 U.S. Pat. No. 4965174 | Recording medium and process for forming color image with same |
| Arai, et al. | 08 Oct. 1986 | JP 63092947 | Protein-enzyme biochemical optical recording medium and imaging process |
| Inoue | 20 Mar. 1987 | JP 63231424 | Optical switch formed by using BR |
| Yamamoto, et al. | 20 Mar. 1987 | JP 63231337 | Recording medium and image forming method using same |
| Ogawa | 29 May 1987 | JP 63299374 U.S. Pat. No. 4896049 | Color image sensor obtained from visual photosensitive material; derived from biological substances |
| Inoue | 20 Jul. 1987 | JP 1023125 | Image pickup element |
| Oesterhelt, et al. | 10 Sep. 1987 | EP 306985 | BR modifications and methods for their preparation |
| Iwashita, et al. | 29 Oct. 1987 | JP 1116536 | Recording medium and color image forming device using same |
| Kawada, et al. | 21 Dec. 1987 | JP 1165186 | Switching device |
| Oyama, et al. | 28 Mar. 1988 | JP 1245810 | Ion permeating membrane and its control by light irradiation |
| Sakakibara and Fukuda | 12 Oct. 1988 | JP 2104600 | Photo-sensitive pigment, production thereof, optical recording material and colorant |
| Oyama, et al. | 18 Mar. 1989 | JP 2247233 | Ion transmission membrane and ion transfer method using the membrane |
| Ikematsu | 20 Mar. 1989 | JP 2247894 | Plastic optical memory element |
| Tokunaga and Nakasako | 27 Mar. 1989 | JP 2251949 | Photoreactive composition |
| Watanabe | 26 May 1989 | JP 2310538 | Optical switch using BR |
| Watanabe | 24 Jul. 1989 | JP 3054532 | Optical function element |
| Koyama | 25 Aug. 1989 | JP 3081756 | Optical recording material |
| Takeda, et al. | 28 Aug. 1989 | EP 417541 | Process for preparing a rhodopsin-coated membrane for use in transducers |
| Miyasaka and Shizukuishi | 13 Sep. 1989 | JP 3100524 U.S. Pat. No. 5279932 | Optical response element |
| Miyasaka | 18 Oct. 1989 | JP 3205520 U.S. Pat. No. 5107104 | Photoelectric transducer having photosensitive chromoprotein film, i.e. BR |
| Koyama and Yamaguchi | 29 Nov. 1989 | JP 3170500 | Orientation of photosensitive pigment protein |
| Miyasaka | 18 Dec. 1989 | JP 3188421 | Optical information-converting element |
| Koyama, et al | 02 Mar. 1990 | JP 3252530 | Color image photodetector |
| Hampp, et al. | 08 Mar. 1990 | EP 445758 U.S. Pat. No. 5223355 | Methods for improving the signal-to-noise ratio in holography when using br-based recording media |
| Oyama, et al. | 13 Apr. 1990 | JP 3295278 | Photoelectric conversion element |
| Miyasaka | 25 Apr. 1990 | JP 4006420 | Photoelectric conversion element |
| Miyasaka and Kitaguchi | 25 Apr. 1990 | JP 4009400 | Fixation of photosensitive chromoprotein |
| Saito, et al. | 08 Jun. 1990 | JP 4042585 | Photoresponsive excitable synthetic membrane and its manufacture |
| Saito, et al. | 31 Jul. 1990 | JP 4088995 | ATP synthesizing device |
| Miyasaki and Koyama | 28 Nov. 1990 | JP 3237769 | Color picture image sensor |
| Birge and | 23 Jan. 1991 | U.S. Pat. No. 5228001 | Optical random access |

TABLE 1-continued

| Inventor(s) | Priority | Patent No(s). | Subject |
|---|---|---|---|
| Lawrence | | | memory |
| Saito, et al. | 18 Feb. 1991 | JP 4262583 | Photoresponsive excitability artificial membrane and manufacture thereof |
| Miyasaka | 11 Apr. 1991 | JP 4312078<br>JP 4312079<br>JP 4312080<br>JP 4312081<br>U.S. Pat. No. 5260559 | Image information detecting method by photoelectric conversion element |
| Birge and Govender | 20 Apr. 1991 | U.S. Pat. No. 5253198 | Three-dimensional optical memory |
| Saito, et al. | 21 Aug. 1991 | JP 05048176 | Optical responsive exciting artificial film and method for manufacturing thereof |
| Saito, et al. | 12 Nov. 1991 | JP 5133795 | Bio-element |
| Fukuzawa and Kuwano | 12 Nov. 1991 | JP 5130880 | Hydrogen generator |
| Fukuzawa | 14 Nov. 1991 | JP 5227765 | Micro electrostatic actuator |
| Fuktuawa and Kuwano | 14 Nov. 1991 | JP 5136483 | Image detection method and image sensors |
| Fukuzawa and Kuwano | 14 Nov. 1991 | JP 5134187 | Close-view microscope |
| Fukuzawa and Kuwano | 14 Nov. 1991 | JP 5134188 | Close-view microscope |
| Haronian and Lewis | 07 Feb. 1992 | U.S. Pat. No. 5248899 | Neural network using photoelectric substance for storing or retrieving information |
| Miyasaka and Yamaguchi | 27 Jan. 1992 | JP 5204090 | Production of BR-oriented film |
| Miyasaka | 22 May 1992 | JP 5322645 | Light receiving element |
| Lewis, et al. | 30 Nov. 1992 | U.S. Pat. No. 5346789<br>WO 9311470 | Oriented biological material for optical information storage and processing |
| Miyasaka | 09 Dec. 1992 | JP 6174544 | Photodetector |
| Fukuzawa | 17 Dec. 1992 | JP 6235606 | Position detector |
| Miyasaka | 21 Dec. 1992 | JP 6186078 | Photoelectric conversion material |
| Takei and Shimzu | 24 Dec. 1992 | JP 6194612<br>U.S. Pat. No. 5618654 | Photo-controlled spatial light modulator |
| Tomita, et al. | 09 Feb. 1993 | JP 6234626 | Polymerizable proteoliposomes |
| Koyama | 12 Apr. 1993 | JP 6294682 | Photoelectric conversion element |
| Takei and Shimizu | 10 Jun. 1993 | JP 6347835 | Production of violet thin film |
| Fukuzawa, et al. | 04 Oct. 1993 | JP 7106616 | Optical energy conversion thin film and production thereof |
| Kato and Tanaka | 09 May 1994 | JP 7301591 | Moisture measuring method |
| Dyukova and vsevolodov | 26 May 1994 | U.S. Pat. No. 5518858 | Photochromic compositions and materials containing BR |
| Lewis, et al. | 09 Jun. 1994 | U.S. Pat. No. 5470690 | Optical information storage on a BR-containing film |
| Ikematsu and izeki | 16 Nov. 1994 | JP 8146469 | Optical information conversion element |
| Birge | 27 Dec. 1994 | U.S. Pat. No. 5559732<br>WO 9621228 | Branched photocycle optical memory device |
| Fitzpatrick | 23 Feb. 1995 | U.S. Pat. No. 5563704 | Camera and method for holographic interferometry using an erasable photosensitive photopolymer film |
| Otomo | 22 Mar. 1995 | JP 8261980 | Ion sensor |
| Kolodner and Rousseau | 05 Apr. 1996 | U.S. Pat. No. 5781330 | High efficiency optical switching and display devices |
| Rao, et al. | 05 Jun. 1996 | U.S. Pat. No. 5757525<br>WO 9746907 | All-optical devices |
| Rao, et al. | 09 Sep. 1996 | U.S. Pat. No. 5854710<br>WO 9810315 | Optical fourier processing |
| Fiedler, et al. | 25 Oct. 1996 | WO 9819217 | Method to prepare the production of structured metalcoatings using proteins |

TABLE 1-continued

| Inventor(s) | Priority | Patent No(s). | Subject |
|---|---|---|---|
| Rayfield and Hsu | 06 May 1997 | U.S. Pat. No. 5825725 | Method and apparatus for reversible optical data storage |

The following example further illustrate the present invention. These examples are intended merely to be illustrative of the present invention and are not to be construed as being limiting.

EXAMPLES

Example 1

Cloning of Proteorhodopsins into Expression Vector

Figure 4:
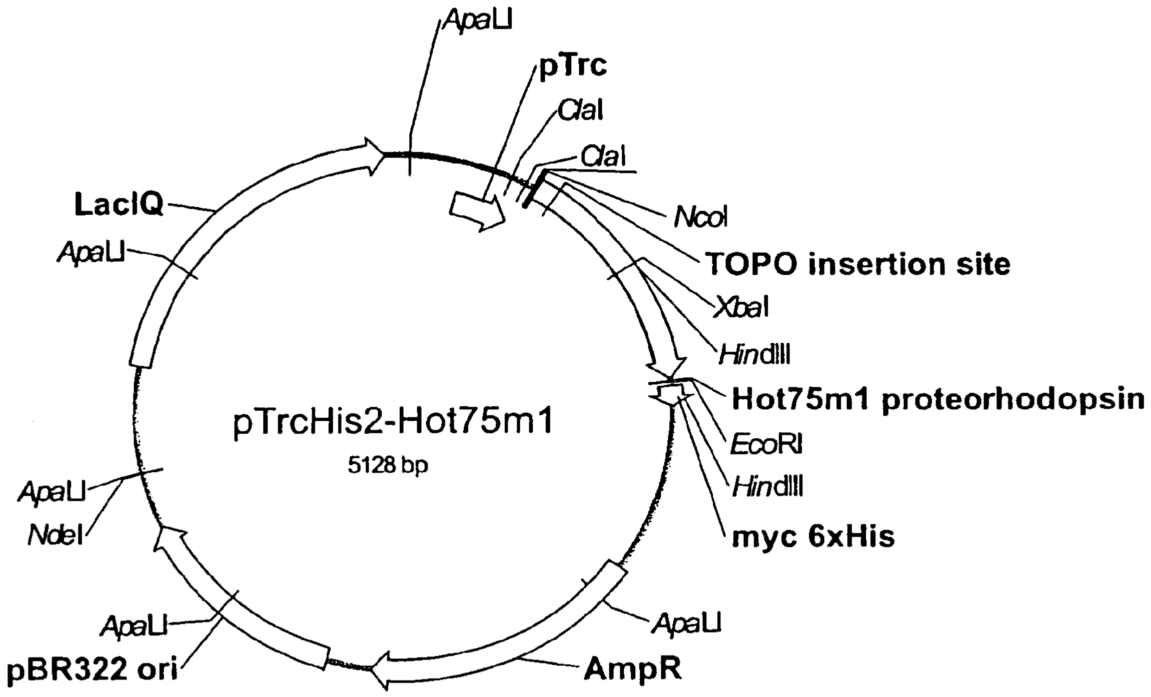

A total of 21 of the 81 known natural proteorhodopsin genes were cloned in the pTrcHis2 expression vector. Different natural proteorhodopsin genes were PCR amplified using Taq DNA Polymerase (Roche Applied Science) as described by the manufacturer. The primers used to amplify all proteorhodopsin variants were PR-u4 and PR-d2 (see Table 2) and the templates were pCR2.1 containing the relevant proteorhodopsin (Béjà, et al., 2000; Béjà, et al., 2001). The PCR products were cloned in the pTrcHis2 vector using the pTrcHis2 TOPO TA Expression Kit (Invitrogen, Carlsbad, Calif.), as described by the manufacturer. Restriction enzyme digestions of the plasmids were used to identify clones containing the insert in the correct orientation. The plasmids were sequenced using the primers pTrcHis Forward and pTrcHis Reverse to ensure that no sequence variations were introduced during the PCR and cloning procedure. The plasmids contain the pTrc promoter transcribing the proteorhodopsin gene with a C-terminal extension containing a myc epitope and six histidine 20 residues. A map of one of the expression plasmids is shown in FIG. 4.

TABLE 2

Sequences of Oligonucleotide Primers Used

| Primer name | Sequence (5' to 3') |
|---|---|
| PR-u4 (SEQ. ID NO: 185) | AAATTATTACTGATATTAGGTAGTG |
| PR-d2 (SEQ ID NO: 186) | AGCATTAGAAGATTCTTTAACAGC |
| pTrcHis Forward (SEQ ID NO: 187) | GAGGTATATATTAATGTATCG |
| pTrcHis Reverse (SEQ ID NO: 188) | GATTTAATCTGTATCAGG |
| 31A8-m6A (SEQ ID NO: 189) | TGTTACTGGTATTGCTTTCTGG**aAT**TACATGTACATGAGAGGGGT |
| 31A8-m6B (SEQ ID NO: 190) | ACCCCTGTCATGTACATGTA**ATt**CCAGAAAGCAATACCAGTAAGA |
| 31A8-m7A (SEQ ID NO: 191) | TGTTACTGGTATTGCTTTCTGG**cAg**TACATGTACATGAGAGGGGT |
| 31A8-m7B (SEQ ID NO: 192) | ACCCCTCTCATGTACATGTA**cTg**CCAGAAAGCAATACCAGTAACA |
| 31A8-m8A (SEQ ID NO: 193) | TGTTACTGGTATTGCTTTCTGG**aAa**TACATGTACATGAGAGGGGT |
| 31A8-m8B (SEQ ID NO: 194) | ACCCCTCTCATGTACATGTA**tTt**CCAGAAAGCAATACCAGTAAC |
| H75m1-m2A (SEQ ID NO: 195) | TTACTGGTATAGCTTTTTGG**aAT**TATCTCTATATGAGAGGTGTTT |
| H75m1-m2B (SEQ ID NO: 196) | AAACACCTCTCATATAGAGATA**ATt**CCAAAAAGCTATACCAGTAA |
| H75m1-m3A (SEQ ID NO: 197) | TTACTGGTATAGCTTTTTGG**CAg**TATCTCTATATGAGAGGTGTTT |
| H75m1-m3B (SEQ ID NO: 198) | AAACACCTCTCATATAGAGATA**cTG**CCAAAAAGCTATACCAGTAA |
| H75m1-m4A (SEQ ID NO: 199) | TTACTGGTATAGCTTTTTGG**aAa**TATCTCTATATGAGAGGTGTTT |

TABLE 2-continued

Sequences of Oligonucleotide Primers Used

| Primer name | Sequence (5' to 3') |
|---|---|
| H75m1-m4B (SEQ ID NO: 200) | AAACACCTCTCATATAGAGATA**tTt**CCAAAAAGCTATACCAGTAA |
| H75m1-m7A (SEQ ID NO: 201) | CTGGTGATACCCCAACAGTATTC**gcA**TATATTGATTGGTTATTAA |
| H75m1-m7B (SEQ ID NO: 202) | TTAATAACCAATCAATATA**Tgc**GAATACTGTTGGGGTATCACCAG |
| H75m1-m8A (SEQ ID NO: 203) | CTGGTGATACCCCAACAGTATTC**caA**TATATTGATTGGTTATTAA |
| H75m1-m8B (SEQ ID NO: 204) | TTAATAACCAATCAATATA**Ttg**GAATACTGTTGGGGTATCACCAG |
| H75m1-m9A (SEQ ID NO: 205) | CTGGTGATACCCCAACAGTATTC**gaA**TATATTGATTGGTTATTAA |
| H75m1-m9B (SEQ ID NO: 206) | TTAATAACCAATCAATATA**Ttc**GAATACTGTTGGGGTATCACCAG |
| H75m1-m12A (SEQ ID NO: 207) | TTACTGGTATAGCTTTTTGG**gAT**TATCTCTATATGAGAGGTGTTT |
| H75m1-m12B (SEQ ID NO: 208) | AAACACCTCTCATATAGAGATA**ATc**CCAAAAAGCTATACCAGTAA |
| H75m1-m13A (SEQ ID NO: 209) | TTACTGGTATAGCTTTTTGG**gaa**TATCTCTATATGAGAGGTGTTT |
| H75m1-m13B (SEQ ID NO: 210) | AAACACCTCTCATATAGAGATA**ttc**GCAAAAAGGTATACCAGTAA |
| H75m1-m15A (SEQ ID NO: 211) | TTACTGGTATAGCTTTTTGG**tgg**TATCTCTATATGAGAGGTGTTT |
| H75m1-m15B (SEQ ID NO: 212) | AAACACCTCTCATATAGAGATA**cca**CCAAAAAGCTATACCAGTAA |

The pTrcHis Forward and pTrcHis Reverse oligonucleotides were obtained from Invitrogen, the rest of the oligonucleotides were purchased from Operon, the primers used for site-directed mutagenesis were PAGE purified. Bold letters indicate the histidine or arginine codons that were mutated, lowercase letters indicate nucleotides that were changed compared to the wild-type sequence.

Measurement of Proteorhodopsin Spectra in Intact Cells

The proteorhodopsin expression plasmids and the control plasmid pTrcHis2-LacZ (Invitrogen) were transformed into competent cells of the strain BL21-Codonplus-RIL (Stratagene) as described by the manufacturer. The transformed cells were plated on LA+0.5% glucose+100 µg/ml carbenicillin+25 µg/ml chloramphenicol plates and incubated overnight at 37° C. Cells from these plates were grown in 6 ml LB+0.5% glucose+100 µg/ml carbenicillin+25 µg/ml chloramphenicol+10 µM all-trans-retinal medium in glass tubes at at 37° C. for 6 hours, where the cells reached early stationary phase. The cells constitutively express proteorhodopsins from the uninduced pTrc promoter. The cells were collected by centrifugation at 4,500×g for 6 minutes, the medium was discarded and the cells were resuspended in 5 ml sterile water. A 900 µl sample of cells were added to a 100 µl aliquot of concentrated buffer (1.0 M acetate (pH 4.9), 1.0 M MES (pH 5.8), 1.0 M MOPS (pH 6.7), 1.0 M TAPS (pH 8.1), or 1.0 M CHES (pH 9.1)). The spectra of the 21 natural proteorhodopsins were measured in intact cells at five different extracellular pH values using a spectrophotometer (On-Line Instrument Systems, Inc.) adapted for use with turbid samples by placing the photomultiplier detector adjacent to the sample cuvette. The absorption from a strain containing a control plasmid (pTrcHis2-LacZ) was subtracted from proteorhodopsin containing samples. To correct for differences in background light scattering caused by variations in cell densities between the sample and the reference, a linear baseline determined by least-squares fitting of the first ten and last ten wavelength and absorbance values in each spectrum was subtracted from each spectrum. The spectra were then adjusted to the same minimum value by subtracting the differences in minimum values.

Typical proteorhodopsin spectra, such as Bac31A8 and Hot75m1 inside intact cells at different pH values, can be constructed by plotting absorbance vs. wavelength. Two different spectral forms of the proteorhodopsin variants (Bac31A8 and Hot75m1) are observed under acidic conditions (pH 4.9) and basic conditions (pH 9.1). At intermediate pH values, spectra representing a mixture of the acidic and basic forms are observed.

To determine the $pK_{rh}$ value, the different adjusted absorbance intensities at each wavelength and pH were fitted to equation 1 by least-squares regression analysis using the Solver function of Microsoft Excel.

$$Abs=Abs_{Acidic}+Abs_{Basic\text{-}Acidic}*(10^{pH-pK_{rh}}) \quad (1)$$

A different value of $Abs_{Acidic}$ and $Abs_{Basic-Acidic}$ were fitted at each wavelength, but the same value of $pK_{rh}$ was fitted for data at all wavelengths. The values $Abs_{Acidic}$ and $Abs_{Basic-Acidic}$ were used to reconstruct wavelength spectra for Acidic and Basic forms of proteorhodopsin and from this data the wavelength maximum at acidic and basic pH were determined (Table 3). The wild-type Bac31 A8 proteorhodopsin in intact cells had absorbance maximum at 538 nm at acidic conditions and at 519 nm at basic conditions. The $pK_{rh}$ value of the titratable group(s) responsible for the spectral shift was determined to be 7.6. The wild-type Hot75m1 proteorhodopsin had absorbance maximum at 546 nm at acidic conditions and at 493 nm at basic conditions. The value of the $pK_{rh}$ of the titratable group(s) responsible for the spectral shift was determined to be 8.2.

Table 3 summarizes the results obtained with the 21 different proteorhodopsin genes expressed and characterized:

TABLE 3

Spectral Property of Proteorhodopsin Variants

| Protein | Name of expression plasmid | $pK_{rh}$ | Basic Max (nm) | Acidic Max (nm) |
|---|---|---|---|---|
| Bac31A8 | pTrcHis2-Bac31A8 | 7.6 | 521 | 538 |
| Bac40E8 | pTrcHis2-Bac40E8 | 7.7 | 519 | 538 |
| Bac64A5 | pTrcHis2-Bac64A5 | 7.6 | 519 | 538 |
| Hot0m1 | pTrcHis2-Hot0m1 | 8.0 | 518 | 538 |
| Hot75m1 | pTrcHis2-Hot75m1 | 8.2 | 493 | 546 |
| Hot75m3 | pTrcHis2-Hot75m3 | 7.2 | 488 | 538 |
| Hot75m4 | pTrcHis2-Hot75m4 | 7.6 | 490 | 538 |
| Hot75m8 | pTrcHis2-Hot75m8 | 8.0 | 493 | 538 |
| MB0m1 | pTrcHis2-MB0m1 | 7.9 | 518 | 540 |
| MB0m2 | pTrcHis2-MB0m2 | 7.9 | 523 | 540 |
| MB20m2 | pTrcHis2-MB20m2 | 7.9 | 523 | 538 |
| MB20m5 | pTrcHis2-MB20m5 | 8.2 | 526 | 569 |
| MB20m12 | pTrcHis2-MB20m12 | 7.6 | 524 | 540 |
| MB40m1 | pTrcHis2-MB40m1 | 7.7 | 519 | 538 |
| MB40m5 | pTrcHis2-MB40m5 | 8.5 | 525 | 558 |
| MB40m12 | pTrcHis2-MB40m12 | 7.5 | 523 | 536 |
| MB100m5 | pTrcHis2-MB100m5 | 7.8 | 523 | 538 |
| MB100m7 | pTrcHis2-MB100m7 | 8.1 | 524 | 550 |
| MB100m9 | pTrcHis2-MB100m9 | 7.3 | 524 | 538 |
| MB100m10 | pTrcHis2-MB100m10 | 7.7 | 524 | 538 |
| PalE6 | pTrcHis2-PalE6 | 7.1 | 490 | 542 |

We have expressed and measured the spectral properties at different pH values for 21 of the 81 known proteorhodopsins. All of them have different absorption spectra at acidic and basic conditions and the $pK_{rh}$ value is in the pH 7-8.5 range for all of the natural proteorhodopsin tested. Thus, the pH dependent shift in spectral properties is a property of the entire proteorhodopsin family.

Example 2

Mutagenesis of Proteorhodopsins

To test whether a conserved histidine residue (H75 in Bac31A8 and H77 in Hot75m1) and a conserved arginine residue (R96 in Hot75m1) are involved in forming the protonatable group responsible for the pH dependent change in the spectral properties of proteorhodopsin variants, these amino acid residues in Bac31A8 and Hot75m1 were mutagenized using the QuickChange Site-Directed Mutagenesis Kit (Stratagene) as described by the manufacturer Table 4 summarizes the templates and primers used to construct the different mutants.

TABLE 4

Templates and Primers Used to Construct Mutants

| Mutant | Name of expression plasmid | Template used | Primers used |
|---|---|---|---|
| Bac31A8 H75N | pTrcHis2-Bac31A8 H75N | pTrcHis2-Bac31A8 | 31A8-m6A and 31A8-m6B |
| Bac31A8 H75Q | pTrcHis2-Bac31A8 H75Q | pTrcHis2-Bac31A8 | 31A8-m7A and 31A8-m7B |
| Bac31A8 H75K | pTrcHis2-Bac31A8 H75K | pTrcHis2-Bac31A8 | 31A8-m8A and 31A8-m8B |
| Hot75M1 H77N | pTrcHis2-Hot75M1 H77N | pTrcHis2-Hot75M1 | H75m1-m2A and H75m1-m2B |
| Hot75M1 H77Q | pTrcHis2-Hot75M1 H77Q | pTrcHis2-Hot75M1 | H75m1-m3A and H75m1-m3B |
| Hot75M1 H77K | pTrcHis2-Hot75M1 H77K | pTrcHis2-Hot75M1 | H75m1-m4A and H75m1-m4B |
| Hot75M1 R96A | pTrcHis2-Hot75m1 R96A | pTrcHis2-Hot75M1 | H75m1-m7A and H75m1-m7B |
| Hot75M1 R96Q | pTrcHis2-Hot75m1 R96Q | pTrcHis2-Hot75M1 | H75m1-m8A and H75m1-m8B |
| Hot75M1 R96E | pTrcHis2-Hot75m1 R96E | pTrcHis2-Hot75M1 | H75m1-m9A and H75m1-m9B |
| Hot75M1 H77D | pTrcHis2-Hot75M1 H77D | pTrcHis2-Hot75M1 | H75m1-m12A and H75m1-m12B |
| Hot75M1 H77E | pTrcHis2-Hot75M1 H77E | pTrcHis2-Hot75M1 | H75m1-m13A and H75m1-m13B |
| Hot75M1 H77W | PTrcHis2-Hot75M1 H77W | pTrcHis2-Hot75M1 | H75m1-m15A and H75m1-m15B |

The plasmids were sequenced using the pTrcHis Forward primer (Invitrogen) to ensure that the desired mutations had been introduced into the plasmids.

These proteorhodopsin mutants were expressed; their spectra in intact cells at different pH values were measured and the $pK_{rh}$ values were calculated as described above.

(a) Histidine Residue

Table 5 summarizes the $pK_{rh}$ values and the absorption maxima of the acidic and basic spectra of the wild-type and mutants of Bac31 A8.

TABLE 5

$pK_{rh}$ and Absorption Maxima of BAC31A8 Mutants

| Protein | $pK_{rh}$ | Basic Max (nm) | Acidic Max (nm) |
|---|---|---|---|
| Bac31A8 | 7.6 | 519 | 538 |
| Bac31A8 H75Q | 6.0 | 518 | 540 |
| Bac31A8 H75N | NA | 521 | — |
| Bac31A8 H75K | NA | 522 | — |

Note:
"NA" means that no significant pH titration is observed, so a $pK_{rh}$ value cannot be determined.
"—" means that only a single absorption maximum can be reported because of the lack of titration in the pH range tested.

These results show that asparagine or glutamine mutations in the conserved histidine residue of Bac31 A8 resulted in a value of the $pK_{rh}$ that was shifted towards acidic pH. The Bac31A8 H75Q mutant has a $pK_{rh}$ value of 6.0 compared with 7.6 observed with the wild-type protein. Both the Bac31A8 H75N and Bac31A8 H75K mutants show no or very little pH dependent change in spectral properties, the mutant proteins appear to be only in the basic form in the pH range tested here. It is likely caused by the $pK_{rh}$ value being shifted so much to be outside the pH range of 4.9-9.1. The $pK_{rh}$ value of the Bac31A8 H75N mutant could not be determined accurately from these data, but is estimated to be 5.8 or lower.

Figure 5:
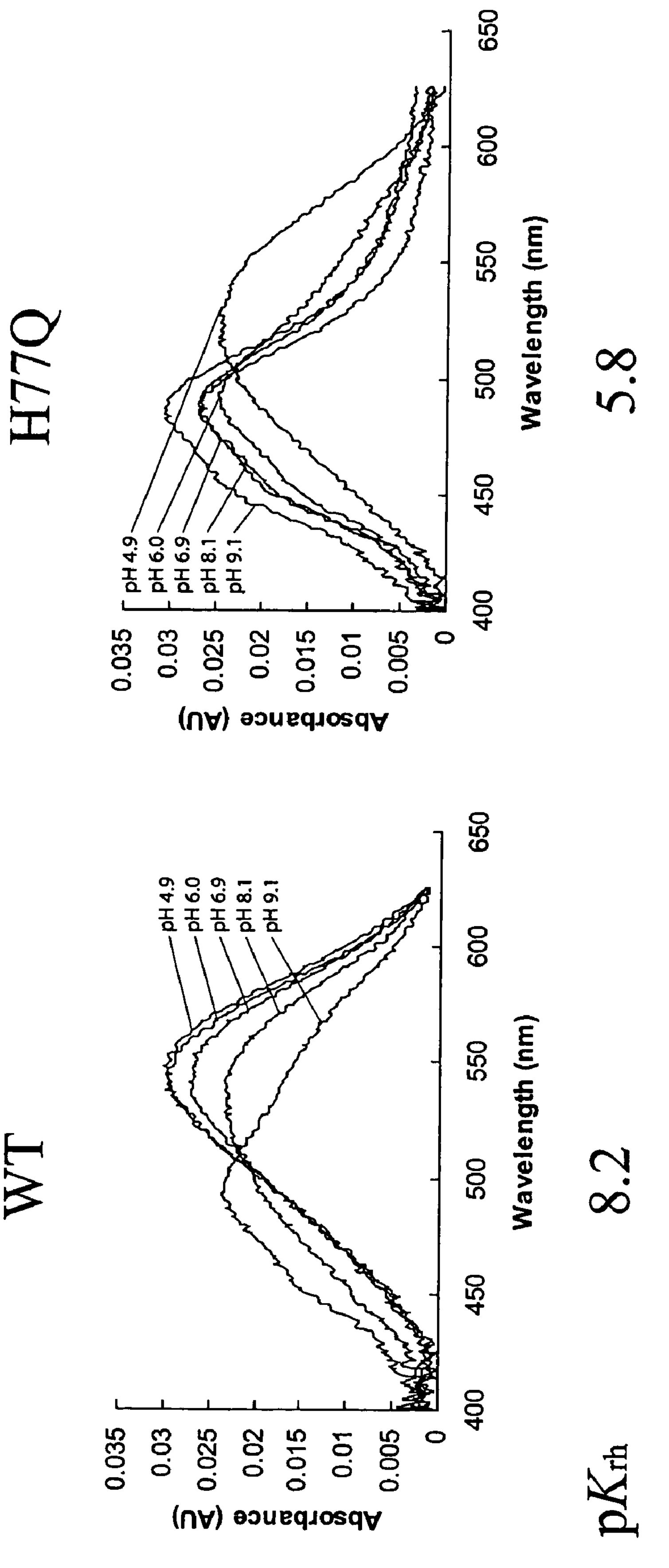
Figure 6:
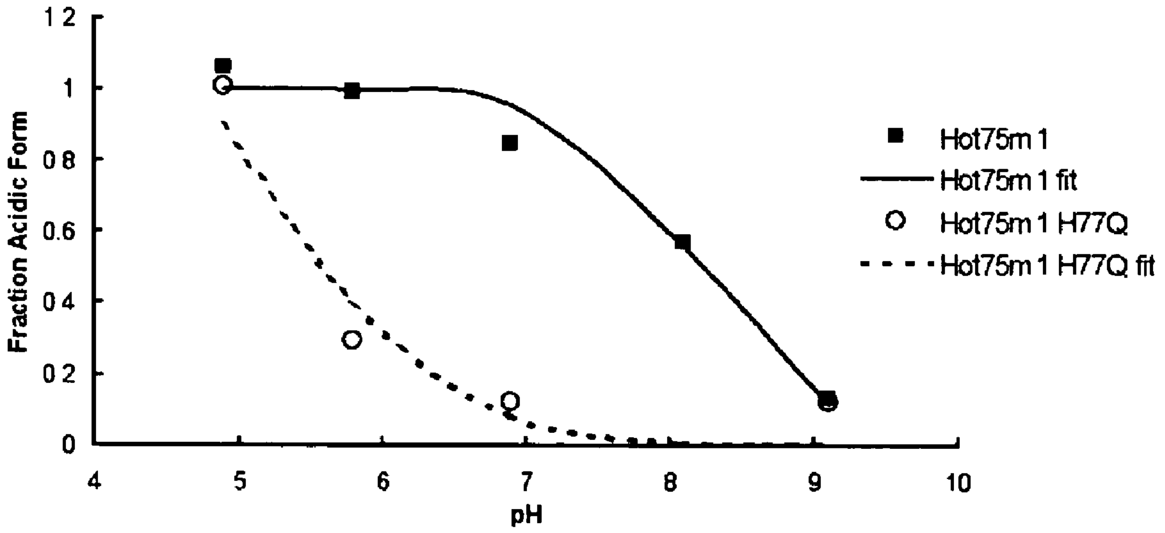

The spectra of Hot75m1 H77Q, Hot75m1 H77N, Hot75m1 H77K, Hot75m1 H77D, Hot75m1 H77E and Hot75m1 H77W at different pH values were determined. FIG. 5 shows the pH-dependent change in absorption spectra of the acid and the basic form of wild-type Hot75m1 and mutant Hot75m1 H77Q. The $pK_{rh}$ of the wild type is 8.2, which is lowered to 5.8 in the mutant. FIG. 6 shows the fraction of the acid form of Hot75m1 and Hot75m1 H77Q at different pH. The basic form clearly predominates at pH 9 and above for the wild-type Hot75m1 protein and at pH 7 and above for the Hot75m1 H77Q protein.

Table 6 summarizes the $pK_{rh}$ value and the maxima of the acidic and basic absorption spectra of the wild-type and six mutants.

TABLE 6

$pK_{rh}$ and Absorption Maxima of Hot75M1 Mutants

| Protein | $pK_{rh}$ | Basic Max (nm) | Acidic Max (nm) |
|---|---|---|---|
| Hot75M1 | 8.2 | 493 | 546 |
| Hot75M1 H77Q | 5.8 | 487 | 516 |
| Hot75M1 H77N | 5.5 | 487 | 497 |
| Hot75M1 H77K | NA | 500 | — |
| Hot75M1 H77D | NA | 515 | — |
| Hot75M1 H77E | 5.3 | 487 | 529 |
| Hot75M1 H77W | 5.8 | 486 | 529 |

Note:
"NA" means that no significant pH titration is observed, so a $pK_{rh}$ value cannot be determined.
"—" means that only a single absorption maximum can be reported because of the lack of titration in the pH range tested.

These results show that mutation in the conserved H77 histidine residue of Hot75m1 that changes it to asparagine, glutamine, glutamic acid or tryptophan resulted in a $pK_{rh}$ value that was significantly shifted towards acidic pH compared with that of the wildtype Hot75m1 protein. The Hot75m1 H77Q and the Hot75m1 H77W mutants have a $pK_{rh}$ value of 5.8 compared with 8.2 of the wild-type protein. The $pK_{rh}$ value of the Hot75m1 H77N and the Hot75m1 H77E mutants were even lower, with values of the $pK_{rh}$ of 5.5 and 5.3, respectively. The Hot75m1 H77K and Hot75m1 H77D mutants, where the histidine is changed to lysine or aspartic acid, respectively, show no or very little pH dependent change in spectral properties and appear to be only in the basic form in the pH range tested here. It is likely caused by the $pK_{rh}$ value being shifted so much to be outside the pH range of 4.9-9.1.

Thus, we have shown that mutations in the conserved histidine residue (H75 in Bac31A8 and H77 in Hot75m1) in two different proteorhodopsin variants give the same results. When the histidine is changed to an asparagine, glutamine, glutamic acid or a tryptophan, the value of the $pK_{rh}$ of the spectral shift was significantly lower. A proteorhodopsin with the histidine changed to lysine or aspartic acid shows no significant titration in the pH range tested, and appears to be in the basic form in the pH range of 4.9-9.1.

(b) Arginine Residue

A conserved arginine residue (R94 in Bac31A8 and R96 in Hot75m1) may affect the protonatable group or groups responsible for the pH dependent change in the spectral properties of proteorhodopsin. Therefore, the R96 amino acid residue in Hot75m1 was mutagenized to alanine, glutamic acid or glutamine, the proteorhodopsin variants were expressed, their spectra in intact cells at different pH values were measured and the values of the $pK_{rh}$'s of the spectral shift were calculated as described previously.

The spectra of Hot75m1 R96A, Hot75m1 R96E and Hot75m1 R96Q at different pH were determined.

Table 7 summarizes the $pK_{rh}$ values and the absorption maxima of the acidic and basic spectra of the different variants of Hot75m1.

TABLE 7

$pK_{rh}$ and Absorption Maxima of Hot75m1 Mutants

| Protein | $pK_{rh}$ | Basic Max (nm) | Acidic Max (nm) |
|---|---|---|---|
| Hot75m1 | 8.2 | 493 | 546 |
| Hot75m1 R96A | 8.0 | 492 | 512 |
| Hot75m1 R96E | 7.0 | 494 | 509 |
| Hot75m1 R96Q | 8.7 | 493 | 507 |

All three R96 mutants showed a significant change in wavelength maximum of the acidic form, with absorption maximum values in the 507-512 nm range compared with an acidic form wavelength maximum of 546 nm observed with the wild-type Hot75m1 protein. Thus, the Hot75m1 R96 mutants have a smaller difference in absorption maxima of the acidic and basic forms than the wild-type Hot75m1 proteorhodopsin. Such mutants are useful in some technical applications to provide a narrow bandwidth of the absorbance peak at a pH close to the $pK_{rh}$ in a device.

Mutations in the conserved R96 residue of Hot75m1 resulted in the $pK_{rh}$ values that were slightly different from that observed with the wildtype Hot75m1 protein. The Hot75m1 R96A and Hot75m1 R96E mutants have $pK_{rh}$ values of 8.0 and 7.0, respectively, slightly lower than the that of the wild-type Hot75m1 protein. The Hot75m1 R96Q protein where the arginine is changed to glutamine has a value of the $pK_{rh}$ of 8.7, slightly higher than that of the wildtype Hot75m1 protein. Thus, mutations in the R96 residue of Hot75m1 have some effects on the value of the $pK_{rh}$ of the spectral shift.

Example 3

Purification of Proteorhodopsins

The results described above were obtained with proteorhodopsins in intact cells, where the protein is present in the cytoplasmic membrane. To characterize the spectral properties of proteorhodopsin variants in the absence of other cell components, we purified wild-type and different mutant Bac31A8 and Hot75m1 proteorhodopsins as described below.

The proteorhodopsin (wild-type or mutant) expression plasmids were transformed into competent cells of the strain BL21-Codonplus-RIL (Stratagene) as described by the manufacturer. The transformed cells were plated on LA+0.5% glucose+100 μg/ml carbenicillin+25 μg/ml chloramphenicol plates and incubated overnight at 37° C.

Cells from these plates were grown in 200 ml LB+0.5% glucose+100 μg/ml carbenicillin+10 μM all-trans-retinal medium at 37° C. in baffled 500 ml shakeflasks. The cultures were inoculated directly from fresh transformation plates. Proteorhodopsin expression in the different cultures were induced when the $OD_{600}$ of the cultures were approximately 0.8 (after 4 hours growth) by adding 0.5 mM IPTG+10 μM all-trans-retinal and the cultures were incubated for additional 4 hours at 37° C. The cells were harvested by centrifugation at 3,500×g for 10 minutes and stored at −80° C. Cells were resuspended in lysis buffer containing 40 mM MOPS pH 7.0, 20 mM $MgCl_2$, 0.2 mg/ml lysozyme, 0.2 mg/ml DnaseI, 2% dodecyl-β-D-maltoside, and protease inhibitors (Complete, EDTA-free Protease Inhibitor Cocktail Tablets from Roche Applied Science; and lysed at 0° C. by sonication. The lysates were incubated 16 hours with the resin in Talon spin columns (Clontech) that had been equilibrated with 1 ml wash buffer containing 40 mM MOPS, pH 7.0 and 0.5% dodecyl-β-D-maltoside. The resin was washed three times with 1 ml wash buffer containing 40 mM MOPS, pH 7.0 and 0.5% dodecyl-β-D-maltoside. Proteorhodopsins were eluted from the resin two times with 0.5 ml elution buffer containing 40 mM MOPS pH 7.0, 0.5% dodecyl-β-D-maltoside and 250 mM EDTA. The two elutates were pooled and EDTA was removed by three successive ten-fold concentrations using a Microcon YM-10 centrifugal filter unit (Millipore) and dilutions with a buffer contained 40 mM MOPS, pH 7.0 as described by the manufacturer. The proteorhodopsin samples were then concentrated ten-fold and stored at 4° C.

Example 4

Measurement of Purified Proteorhodopsin Spectra

5 μl purified proteorhodopsin was diluted in 500 μl of buffer containing 100 mM either citrate (pH 3.54, 3.97, 4.50, or 5.03), acetate (pH 4.88), MES (pH 5.34, 5.80, or 6.35), MOPS (pH 6.75 or 7.32), TAPS (pH 7.91 or 8.43), CHES (pH 9.00 or 9.50), or CAPS (10.12 or 10.64). Wavelength spectra from 250 nm to 650 nm were obtained on a Cary3 spectrophotometer (Varian). The value of the $pK_{rh}$ of the spectral shift was calculated using equation 1 as described previously.

The spectra of detergent-solubilized and purified wild-type Bac31A8, Bac31A8 H75Q, Bac31A8 H75N and Bac31A8 H75K at different pH values were determined. Table 8 summarizes the $pK_{rh}$ value and the maxima of the acidic and basic absorption spectra of wild-type and different mutants.

TABLE 8

$pK_{rh}$ and Absorption Maxima of BAC31A8 Mutants

| Protein | $pK_{rh}$ | Basic Max (nm) | Acidic Max (nm) |
|---|---|---|---|
| Bac31A8 | 7.1 | 517 | 543 |
| Bac31A8 H75Q | 5.5 | 517 | 551 |
| Bac31A8 H75N | 5.2 | 517 | 534 |
| Bac31A8 H75K | NA | 516 | — |

Note:
"NA" means that no significant pH titration is observed, so a $pK_{rh}$ value cannot be determined.
"—" means that only a single absorption maximum can be reported because of the lack of titration in the pH range tested.

These results obtained with detergent-solubilized and purified Bac31A8 are similar to the results obtained with proteorhodopsins in intact cells. When the conserved H75 histidine residue of Bac31A8 is changed to asparagine or glutamine, the values of the $pK_{rh}$ of the spectral shift was significantly reduced. Purified Bac31 A8 H75Q mutant has a $pK_{rh}$ value of 5.5 and purified Bac31A8 H75N mutant has a $pK_{rh}$ value of 5.2. In comparison, the purified wild-type Bac31A8 protein has a $pK_{rh}$ value of 7.1. The purified Bac31A8 H75K mutant, where the histidine is changed to lysine, shows no or very little pH dependent change in spectral properties, the protein appears to be locked in the basic form in the pH (pH 4.9-9.1) range tested here.

The spectra of purified wild-type Hot75m1, Hot75m1 H77Q, Hot75m1 H77N and Hot75m1 H77K at different pH values were determined.

Table 9 summarizes the $pK_{rh}$ value and the maxima of the acidic and basic absorption spectra of different variants.

TABLE 9

$pK_{rh}$ and Absorption Maxima of Hot75M1 MUTANTS

| Protein | $pK_{rh}$ | Basic Max (nm) | Acidic Max (nm) |
|---|---|---|---|
| Hot75M1 | 8.4 | 504 | 538 |
| Hot75M1 H77Q | 6.3 | 508 | 531 |
| Hot75M1 H77N | 6.5 | 496 | 523 |
| Hot75M1 H77K | NA | 521 | — |

Note:
"NA" means that no significant pH titration is observed, so a $pK_{rh}$ value cannot be determined.
"—" means that only a single absorption maximum can be reported because of the lack of titration in the pH range tested.

These results with purified wild-type and mutant Hot75m1 proteorhodopsins show that when the conserved H77 histidine residue of Hot75m1 is changed to asparagine or glutamine, the $pK_{rh}$ value was significantly shifted towards the acidic pH. Purified Hot75m1 H77Q has a value of the $pK_{rh}$ of 6.3 and purified Hot75m1 H77N has a $pK_{rh}$ value of 6.5, compared with 8.4 of the wild-type protein. The purified Hot75m1 H77K mutant where the histidine is changed to lysine shows no or very little pH dependent change in spectral properties in the pH range (pH 4.9-9.1) tested here, and appears to have only one basic form.

In conclusion, mutations in a conserved histidine residue (H75 in Bac31A8 and H77 in Hot75m1) in two different proteorhodopsin variants give similar results. This was observed both when the protein is present in the cytoplasmic membrane in intact cells and with detergent-solubilized and purified protein. Changing the histidine to an asparagine or a glutamine, results in a significant lower $pK_{rh}$ value. Changing the histidine to a lysine results in a basic form only at pH 4.9-9.1, and likely to have a very low $pK_{rh}$ value.

Example 5

Determination of Proton Pumping

The basic form of proteorhodopsin can undergo a photocycle that includes the formation of the excited M-state (or M-like state) and pumping of a proton across the proteorhodopsin-containing membrane from inside the cell to outside the cell. To examine whether the proteorhodopsin variants do undergo a productive photocycle, we have determined the ability of these variants to pump protons. Proton pumping was measured as a change of the extracellular pH with illumination of cells expressing proteorhodopsin, caused by pumping of protons from inside the cells to the extracellular medium. We have also determined the pH dependence of proton pumping for Bac31A8 wild-type and the H75N mutant.

Production and Preparation of Cells. The proteorhodopsin (wild-type or mutant) expression plasmids were transformed into competent cells of the strain BL21-Codonplus-RIL (Stratagene) as described by the manufacturer. The transformed cells were plated on LA+0.5% glucose+100 μg/ml carbenicillin+25 μg/ml chloramphenicol plates and incubated overnight at 37° C. Cells from these plates were grown in 50 ml LB+0.5% glucose+100 μg/ml carbenicillin+10 μM all-trans-retinal medium at 37° C. in baffled 250 ml shake-flasks. The cultures were inoculated directly from fresh transformation plates. Proteorhodopsin expression in different cultures was induced when the $OD_{600}$ of the cultures was approximately 0.8 (after 4 hours growth) by adding 0.1 mM IPTG+10 μM all-trans-retinal, and the cultures were incubated for additional 4 hours at 37° C. The cells were harvested by centrifugation at 3,500×g for 10 minutes and stored at −80° C.

Cells were thawed and suspended in 150 mM NaCl without buffer (sparged with helium to remove carbon dioxide). Cells were washed an additional three times with 150 mM NaCl without buffer. The cells were suspended to an $OD_{600}$ of 2.0 in 150 mM NaCl. Cell samples were adjusted to between pH 7.5 and 8.5 with 0.5 M HCl or 0.5% NaOH.

Equipment and methods. The values of pH of 2.0 ml cell samples in 10 ml borosilicate glass tubes were measured using a Beckman (Fullerton, Calif.) Phi40pH meter with a voltage-out port connected to a National Instruments (Austin, Tex.) data acquisition board, which averaged the signal at one-second intervals and saved the data on a Pentium based personal computer. Cell samples were magnetically stirred and were illuminated from two sides by split fiber-optic cables attached to a 150-watt illuminator (Fiber-Lite A3200) from Dolan-Jenner Industries (Lawrence, Mass.) with an infrared filter (03FC569) from Melles Griot (Irvine, Calif.) and a 450 nm cut-on colored-glass filter (51284) from Oriel Instruments (Stratford, Conn.). The manual opening and closing of a shutter controlled light. The incident angle of light was held constant by the use of a custom-built cell holder. After the determination of pH for 3 minutes prior to illumination, the pH of the cell sample was determined during the 3 minutes of constant illumination. The pH of the cell sample was then measured for 3 minutes after illumination was stopped. This process was repeated two more times for each cell sample resulting in three repeated measurements of each cell sample.

FIG. 7-1 shows that the pH of the cells expressing Bac31A8 wild-type, which is an active proton pump, drifted slowly over time without illumination. However, a rapid (within a few seconds) change in pH occurred following illumination. After illumination was ended, the pH value of the cell samples returns to that before illumination. This pH change is a result of cellular mechanisms that control membrane potential.

FIG. 7-2 shows that the pH of cells expressing a LacZ control protein also drifted slowly over time without illumination. With illumination, the pH shifted slowly (over the entire 3 minutes) and minimally (at most 0.05 pH units), presumably from a temperature change at the pH probe. This temperature effect was reduced dramatically by the addition of the infrared filter, but it could not be completely eliminated.

Data Analysis. To remove the drift of the extracellular pH values with time mathematically, the data not affected by illumination was fitted to a model-independent polynomial approximation, equation 2, $$pH=A\times t^4+B\times t^3+C\times t^2+D\times t+E \quad (2)$$

where pH is the measured value of pH when illumination no longer affected pH (i.e. last ten seconds of data collected without illumination), A, B, C, D and E are empirically fit parameters and t is the time at which the values of pH were measured. The results of the above equation were subtracted from the entire data set to give the illumination dependent changes in pH. The illumination dependent changes were fitted to equation 3, an exponential decay model assuming that cells dynamically adjust proton flow to maintain membrane pH differential, $$\Delta pH=\Delta pH_{max}-\Delta pH_{max}\times e^{-kt} \quad (3)$$

where ΔpH is the change in pH due to illumination, $\Delta pH_{max}$ is a fit parameter indicating the maximal change in pH, k is a fit parameter indicating the rate at which that maximum is reached and t is the time after illumination is initiated. The value of the product of the two fit parameters, $\Delta pH_{max}\times k$, is the slope of a line tangent at t=0. This value represents the proton-pumping rate in units of ΔpH/min before a cellular response to proton pumping.

Ability to Pump Protons. To determine whether a proteorhodopsin variant is capable of pumping protons, the value of $\Delta pH_{max}\times k$ for cells expressing a proteorhodopsin variant is compared using the student-t test to the value of $\Delta pH_{max}\times k$ determined for cells expressing a LacZ control. The degrees of freedom, n, and the results of the student-t test at 60-99% confidence are given in Table 10. This test indicates whether a particular proteorhodopsin mutant is a proton pump at a given confidence. The negative result of this test does not indicate that a given proteorhodopsin mutant is not a proton pump; it only indicates that the assay is not sensitive enough to detect pumping by that mutant.

TABLE 10

Proton Pumping Results. (Result of t-test at given Confidence Interval)

| Proteorhodopsin | n | 60% | 75% | 90% | 95% | 97.5% | 99% |
|---|---|---|---|---|---|---|---|
| Bac31A8 Wild-type | 19 | Pump | Pump | Pump | Pump | Pump | Pump |
| Bac31A8 D97N | 19 | Not detected | Not detected | Not detected | Not detected | Not detected | Not detected |
| Bac31A8 E108Q | 19 | Not detected | Not detected | Not detected | Not detected | Not detected | Not detected |
| Bac31A8 H75K | 28 | Pump | Pump | Pump | Not detected | Not detected | Not detected |
| Bac31A8 H75K[a] | 40 | Pump | Pump | Pump | Pump | Pump | Not detected |
| Bac31A8 H75N | 19 | Pump | Pump | Pump | Pump | Pump | Pump |
| Bac31A8 H75Q | 16 | Pump | Pump | Pump | Pump | Pump | Pump |
| Hot75m1 Wild-type | 22 | Pump | Pump | Pump | Pump | Pump | Pump |
| Hot75m1 H77K | 19 | Pump | Not detected | Not detected | Not detected | Not detected | Not detected |
| Hot75m1 H77K[a] | 31 | Pump | Not detected | Not detected | Not detected | Not detected | Not detected |
| Hot75m1 H77N | 16 | Pump | Pump | Pump | Pump | Pump | Pump |
| Hot75m1 H77Q | 16 | Pump | Pump | Pump | Pump | Pump | Pump |
| Hot75m1 H77D | 22 | Not detected | Not detected | Not detected | Not detected | Not detected | Not detected |

TABLE 10-continued

| Proteorhodopsin | n | Proton Pumping Results. (Result of t-test at given Confidence Interval) 60% | 75% | 90% | 95% | 97.5% | 99% |
|---|---|---|---|---|---|---|---|
| Hot75m1 H77D[a] | 34 | Not detected | Not detected | Not detected | Not detected | Not detected | Not detected |
| Hot75m1 H77E | 19 | Pump | Pump | Pump | Pump | Pump | Pump |
| Hot75m1 H77W | 16 | Pump | Pump | Pump | Pump | Pump | Pump |
| Hot75m1 R96A | 16 | Pump | Pump | Pump | Pump | Pump | Pump |
| Hot75m1 R96E | 22 | Pump | Pump | Pump | Not detected | Not detected | Not detected |
| Hot75m1 R96E[a] | 34 | Pump | Pump | Pump | Pump | Not detected | Not detected |
| Hot75m1 R96Q | 19 | Pump | Pump | Pump | Pump | Pump | Pump |

Note:
"Pump" indicates that proton pumping is detected at the respective confidence level.
"Not detected" indicates that no strong evidence of proton pumping exists, but does not indicate that proton pumping is not occurring.
[a]The data for the two proteins with mutations at residues central to the proton pumping mechanism, Bac31A8 D97N and Bac31A8 E108Q, were included with the non proton pumping control data to allow for a greater value of n and a greater discrimination of proton pumping capability.

Using this assay, we observe proton pumping by the Bac31A8 and Hot75m1 wild-type proteorhodopsins as expected. No detectable proton pumping was observed with the Bac31A8 D97N mutant proteorhodopsin, which appears to exist in an acidic form only (Dioumaev, et al.). Since proteorhodopsin in the acidic form is unable to pump protons (Dioumaev, et al.), this confirms the feasibility to use this assay for determining whether proteorhodopsin mutants can undergo a photocycle that includes proton pumping. Proton pumping by the Bac31A8 E108Q, where the photocycle is more than a hundred fold slower than that of the wild-type protein mutant, was not detected. Proton pumping was detected for Bac31A8 wild-type, H75K, H75N, and H75Q; and Hot75m1 wild-type, R96A, H77K, H77N, H77Q, H77E, H77W, R96E and R96Q; which indicates that these proteins, when exposed to light, undergo a productive photocycle that includes proton pumping.

Dependence of Extracellular pH on Proton Pumping. The proteorhodopsins with mutations in the conserved histidine residue are expected to be better proton pumps at low pH than wildtype proteorhodopsin, since the lower $pK_{rh}$ value of the mutants results in a larger fraction of the protein in a productive basic form at low pH. To confirm this, we have compared the rate of proton pumping by Bac31A8 wildtype and the H75N mutant.

Cell samples produced in a manner similar to those used to detect proton-pumping activity were adjusted with 0.5 M HCl or 0.5% NaOH to various pH values and the rate of pumping was determined. The value of extracellular pH was determined from the average pH value over the course of the experiment. FIG. 7-3 displays the dependence of proton-pumping rate on the extracellular pH for the Bac31A8 wild-type and the H75N mutant. The results show that the Bac31A8 H75N mutant is a better proton pump than the Bac31A8 wild-type at acidic pH. The results confirm that a mutation lowering the $pK_{rh}$ value results in a proteorhodopsin mutant having an extended pH range where a productive photocycle is present.

Although the invention has been described with reference to the presently preferred embodiments, it should be understood that various modifications can be made without departing from the scope of the invention.

What is claimed is:

1. A proteorhodopsin mutant having improved optical characteristics, said mutant is a proteorhodopsin variant comprising a mutation in a conserved histidine residue, said proteorhodopsin variant having at least 90% identity with its corresponding naturally occurring proteorhodopsin, said conserved histidine is present at the position equivalent to position 75 of SEQ ID NO: 3 when the proteorhodopsin variant is aligned with SEQ ID NO: 3 for maximum identity, wherein said proteorhodopsin mutant has lower $pK_{rh}$ in comparison with the proteorhodopsin variant.

2. The proteorhodopsin mutant according to claim 1, wherein said naturally occurring proteorhodopsin comprises SEQ ID NO: 1, 3, 27, 103, 121, 125, 133, 139, 151, or 161.

3. The proteorhodopsin mutant according to claim 2, wherein said naturally occurring proteorhodopsin comprises SEQ ID NO: 1 or SEQ ID NO: 3.

4. The proteorhodopsin mutant according to claim 1, wherein said conserved histidine residue is mutated to an amino acid capable of forming a hydrogen bond.

5. The proteorhodopsin mutant according to claim 4, wherein said amino acid capable of forming a H-bond is asparagine, glutamine, lysine, arginine, tryptophan, serine, threonine, tyrosine, aspartic acid, or glutamic acid.

6. The proteorhodopsin mutant according to claim 5, wherein said amino acid capable of forming an H-bond is asparagine, glutamine, lysine, tryptophan, aspartic acid, or glutamic acid.

7. The proteorhodopsin mutant according to claim 1, comprising the amino acid sequence of SEQ ID NO: 165.

8. A method for preparing the proteorhodopsin mutant having improved optical characteristics according to claim 1, comprising the steps of:

(a) identifying the conserved histidine amino acid residue of the proteorhodopsin variant of claim 1, (b) mutagenizing the conserved histidine amino acid residue, and obtaining proteorhodopsin mutants, (c) determining the optical characteristics of the proteorhodopsin mutants, and (d) selecting the proteorhodopsin mutant having improved optical characteristics.

9. The method according to claim 8, wherein said conserved amino acid residue is mutagenized by site-directed mutagenesis.

10. The proteorhodopsin mutant according to claim 1, wherein the proteorhodopsin variant has at least 97% identity with the naturally occurring proteorhodopsin.

11. A proteorhodopsin mutant having improved optical characteristics, said mutant is a proteorhodopsin variant comprising a mutation in a conserved histidine residue, said proteorhodopsin variant is selected from the group consisting of SEQ ID NO: 1, 3, 27, 103, 121, 125, 133, 139, 151, and 161, or having at least 90% identity with the naturally occurring proteorhodopsin, said conserved histidine is present at the position equivalent to position 75 of SEQ ID NO: 3 when the proteorhodopsin variant is aligned with SEQ ID NO: 3 for maximum identity, wherein said proteorhodopsin mutant has lower $pK_{rh}$ in comparison with the proteorhodopsin variant.

12. The proteorhodopsin mutant according to claim 11, wherein the proteorhodopsin variant has at least 97% identity with the naturally occurring proteorhodopsin.

13. The proteorhodopsin mutant according to claim 11, wherein the naturally occurring proteorhodopsin comprises the amino acid sequence of SEQ ID NO: 3.

* * * * *

SEQUENCE LISTING

```
<160> NUMBER OF SEQ ID NOS: 212

<210> SEQ ID NO 1
<211> LENGTH: 252
<212> TYPE: PRT
<213> ORGANISM: Marine eubacteria

<400> SEQUENCE: 1

Thr Met Gly Lys Leu Leu Leu Ile Leu Gly Ser Ala Ile Ala Leu Pro
1               5                   10                  15

Ser Phe Ala Ala Ala Gly Gly Asp Leu Asp Ile Ser Asp Thr Val Gly
            20                  25                  30

Val Ser Phe Trp Leu Val Thr Ala Gly Met Leu Ala Ala Thr Val Phe
        35                  40                  45

Phe Phe Val Glu Arg Asp Gln Val Ser Ala Lys Trp Lys Thr Ser Leu
    50                  55                  60

Ala Val Ser Gly Leu Ile Thr Gly Ile Ala Phe Trp His Tyr Leu Tyr
65                  70                  75                  80

Met Arg Gly Val Trp Ile Asp Thr Gly Asp Thr Pro Thr Val Phe Arg
```

-continued

```
                85                  90                  95

Tyr Ile Asp Trp Leu Leu Thr Val Pro Leu Gln Met Val Glu Phe Tyr
            100                 105                 110

Leu Ile Leu Ala Ala Cys Thr Ser Val Ala Ala Ser Leu Phe Lys Lys
        115                 120                 125

Leu Leu Ala Gly Ser Leu Val Met Leu Gly Ala Gly Phe Ala Gly Glu
    130                 135                 140

Ala Gly Leu Ala Pro Val Leu Pro Ala Phe Ile Ile Gly Met Ala Gly
145                 150                 155                 160

Trp Leu Tyr Met Ile Tyr Glu Leu Tyr Met Gly Glu Gly Lys Ala Ala
                165                 170                 175

Val Ser Thr Ala Ser Pro Ala Val Asn Ser Ala Tyr Asn Ala Met Met
            180                 185                 190

Met Ile Ile Val Val Gly Trp Ala Ile Tyr Pro Ala Gly Tyr Ala Ala
        195                 200                 205

Gly Tyr Leu Met Gly Gly Glu Gly Val Tyr Ala Ser Asn Leu Asn Leu
    210                 215                 220

Ile Tyr Asn Leu Ala Asp Leu Val Asn Lys Ile Leu Phe Gly Leu Ile
225                 230                 235                 240

Ile Trp Asn Val Ala Val Lys Glu Ser Ser Asn Ala
                245                 250


<210> SEQ ID NO 2
<211> LENGTH: 756
<212> TYPE: DNA
<213> ORGANISM: Marine eubacteria

<400> SEQUENCE: 2

accatgggta aattattact gatattaggt agtgctattg cacttccatc atttgctgct      60

gctggtggcg atctagatat aagtgatact gttggtgttt cattctggct ggttacagct     120

ggtatgttag cggcaactgt gttctttttt gtagaaagag accaagtcag cgctaagtgg     180

aaaacttcac ttgctgtatc tggtttaatt actggtatag ctttttggca ttatctctat     240

atgagaggtg tttggataga cactggtgat accccaacag tattcagata tattgattgg     300

ttattaactg ttccattaca aatggttgag ttctatctaa ttcttgctgc ttgtacaagt     360

gttgctgctt cattatttaa gaagcttcta gctggttcat tagtaatgtt aggtgctgga     420

tttgcaggcg aagctggatt agctcctgta ttacctgctt tcattattgg tatggctgga     480

tggttataca tgatttatga gctatatatg ggtgaaggta aggctgctgt aagtactgca     540

agtcctgctg ttaactctgc atacaacgca atgatgatga ttattgttgt tggatgggca     600

atttatcctg ctggatatgc tgctggttac ctaatgggtg gcgaaggtgt atacgcttca     660

aacttaaacc ttatatataa ccttgccgac cttgttaaca agattctatt tggtttgatc     720

atttggaatg ttgctgttaa agaatcttct aatgct                               756


<210> SEQ ID NO 3
<211> LENGTH: 249
<212> TYPE: PRT
<213> ORGANISM: Marine eubacteria

<400> SEQUENCE: 3

Met Lys Leu Leu Leu Ile Leu Gly Ser Val Ile Ala Leu Pro Thr Phe
1               5                   10                  15

Ala Ala Gly Gly Gly Asp Leu Asp Ala Ser Asp Tyr Thr Gly Val Ser
            20                  25                  30
```

-continued

```
Phe Trp Leu Val Thr Ala Ala Leu Leu Ala Ser Thr Val Phe Phe Phe
        35                  40                  45

Val Glu Arg Asp Arg Val Ser Ala Lys Trp Lys Thr Ser Leu Thr Val
    50                  55                  60

Ser Gly Leu Val Thr Gly Ile Ala Phe Trp His Tyr Met Tyr Met Arg
65                  70                  75                  80

Gly Val Trp Ile Glu Thr Gly Asp Ser Pro Thr Val Phe Arg Tyr Ile
                85                  90                  95

Asp Trp Leu Leu Thr Val Pro Leu Leu Ile Cys Glu Phe Tyr Leu Ile
            100                 105                 110

Leu Ala Ala Ala Thr Asn Val Ala Gly Ser Leu Phe Lys Lys Leu Leu
        115                 120                 125

Val Gly Ser Leu Val Met Leu Val Phe Gly Tyr Met Gly Glu Ala Gly
    130                 135                 140

Ile Met Ala Ala Trp Pro Ala Phe Ile Ile Gly Cys Leu Ala Trp Val
145                 150                 155                 160

Tyr Met Ile Tyr Glu Leu Trp Ala Gly Glu Gly Lys Ser Ala Cys Asn
                165                 170                 175

Thr Ala Ser Pro Ala Val Gln Ser Ala Tyr Asn Thr Met Met Tyr Ile
            180                 185                 190

Ile Ile Phe Gly Trp Ala Ile Tyr Pro Val Gly Tyr Phe Thr Gly Tyr
        195                 200                 205

Leu Met Gly Asp Gly Gly Ser Ala Leu Asn Leu Asn Leu Ile Tyr Asn
    210                 215                 220

Leu Ala Asp Phe Val Asn Lys Ile Leu Phe Gly Leu Ile Ile Trp Asn
225                 230                 235                 240

Val Ala Val Lys Glu Ser Ser Asn Ala
                245
```

<210> SEQ ID NO 4
<211> LENGTH: 750
<212> TYPE: DNA
<213> ORGANISM: Marine eubacteria

<400> SEQUENCE: 4

```
atgaaattat tactgatatt aggtagtgtt attgcacttc ctacatttgc tgcaggtggt      60

ggtgaccttg atgctagtga ttacactggt gtttcttttt ggttagttac tgctgcttta     120

ttagcatcta ctgtattttt ctttgttgaa agagatagag tttctgcaaa atggaaaaca     180

tcattaactg tatctggtct tgttactggt attgctttct ggcattacat gtacatgaga     240

ggggtatgga ttgaaactgg tgattcgcca actgtattta gatacattga ttggttacta     300

acagttcctc tattaatatg tgaattctac ttaattcttg ctgctgcaac taatgttgct     360

ggatcattat ttaagaaatt actagttggt tctcttgtta tgcttgtgtt tggttacatg     420

ggtgaagcag gaatcatggc tgcatggcct gcattcatta ttgggtgttt agcttgggta     480

tacatgattt atgaattatg ggctggagaa ggaaaatctg catgtaatac tgcaagtcct     540

gctgtgcaat cagcttacaa cacaatgatg tatattatca tctttggttg ggcgatttat     600

cctgtaggtt atttcacagg ttacctgatg ggtgacggtg gatcagctct taacttaaac     660

cttatctata accttgctga ctttgttaac aagattctat ttggtttaat tatatggaat     720

gttgctgtta aagaatcttc taatgcttaa                                      750
```

<210> SEQ ID NO 5

-continued

<211> LENGTH: 252
<212> TYPE: PRT
<213> ORGANISM: Marine eubacteria

<400> SEQUENCE: 5

```
Thr Met Gly Lys Leu Leu Leu Ile Leu Gly Ser Val Ile Ala Leu Pro
1               5                   10                  15

Thr Phe Ala Ala Gly Gly Gly Asp Leu Asp Ala Ser Asp Tyr Thr Gly
            20                  25                  30

Val Ser Phe Trp Leu Val Thr Ala Ala Leu Leu Ala Ser Thr Val Phe
        35                  40                  45

Phe Phe Val Glu Arg Asp Arg Val Ser Ala Lys Trp Lys Thr Ser Leu
    50                  55                  60

Thr Val Ser Gly Leu Val Thr Gly Ile Ala Phe Trp His Tyr Met Tyr
65                  70                  75                  80

Met Arg Gly Val Trp Ile Glu Thr Gly Asp Ser Pro Thr Val Phe Arg
                85                  90                  95

Tyr Ile Asp Trp Leu Leu Thr Val Pro Leu Leu Ile Cys Glu Phe Tyr
            100                 105                 110

Leu Ile Leu Ala Ala Ala Thr Asn Val Ala Ala Gly Leu Phe Lys Lys
        115                 120                 125

Leu Leu Val Gly Ser Leu Val Met Leu Val Phe Gly Tyr Met Gly Glu
    130                 135                 140

Ala Gly Ile Met Asn Ala Trp Gly Ala Phe Val Ile Gly Cys Leu Ala
145                 150                 155                 160

Trp Val Tyr Met Ile Tyr Glu Leu Trp Ala Gly Glu Gly Lys Ala Ala
                165                 170                 175

Cys Asn Thr Ala Ser Pro Ala Val Gln Ser Ala Tyr Asn Thr Met Met
            180                 185                 190

Tyr Ile Ile Ile Phe Gly Trp Ala Ile Tyr Pro Val Gly Tyr Phe Thr
        195                 200                 205

Gly Tyr Leu Met Gly Asp Gly Gly Ser Ala Leu Asn Leu Asn Leu Ile
    210                 215                 220

Tyr Asp Leu Ala Asp Phe Val Asn Lys Ile Leu Phe Gly Leu Ile Ile
225                 230                 235                 240

Trp Asn Val Ala Val Lys Glu Ser Ser Asn Ala Lys
                245                 250
```

<210> SEQ ID NO 6
<211> LENGTH: 252
<212> TYPE: PRT
<213> ORGANISM: Marine eubacteria

<400> SEQUENCE: 6

```
Thr Met Gly Lys Leu Leu Leu Ile Leu Gly Ser Val Ile Ala Leu Pro
1               5                   10                  15

Thr Phe Ala Ala Gly Gly Gly Asp Leu Asp Ala Ser Asp Tyr Thr Gly
            20                  25                  30

Val Ser Phe Trp Leu Val Thr Ala Ala Leu Leu Ala Ser Thr Val Phe
        35                  40                  45

Phe Phe Val Glu Arg Asp Arg Val Ser Ala Lys Trp Lys Thr Ser Leu
    50                  55                  60

Thr Val Ser Gly Leu Val Thr Gly Ile Ala Phe Trp His Tyr Met Tyr
65                  70                  75                  80

Met Arg Gly Val Trp Ile Glu Thr Gly Asp Ser Pro Thr Val Phe Arg
                85                  90                  95
```

-continued

```
Tyr Ile Asp Trp Leu Leu Thr Val Pro Leu Leu Ile Cys Glu Phe Tyr
            100                 105                 110

Leu Ile Leu Ala Ala Ala Thr Asn Val Ala Ala Gly Leu Phe Lys Lys
        115                 120                 125

Leu Leu Val Gly Ser Leu Val Met Leu Val Phe Gly Tyr Met Gly Glu
    130                 135                 140

Ala Gly Ile Met Asn Ala Trp Gly Ala Phe Val Ile Gly Cys Leu Ala
145                 150                 155                 160

Trp Val Tyr Met Ile Tyr Glu Leu Trp Ala Gly Glu Gly Lys Ala Ala
                165                 170                 175

Cys Asn Thr Ala Ser Pro Ala Val Gln Ser Ala Tyr Asn Thr Met Met
            180                 185                 190

Tyr Ile Ile Ile Phe Gly Trp Ala Ile Tyr Pro Val Gly Tyr Phe Thr
        195                 200                 205

Gly Tyr Leu Met Gly Asp Gly Gly Ser Ala Leu Asn Leu Asn Leu Ile
    210                 215                 220

Tyr Asp Leu Ala Asp Phe Val Asn Lys Ile Leu Phe Gly Leu Ile Ile
225                 230                 235                 240

Trp Asn Val Ala Val Lys Glu Ser Ser Asn Ala Lys
                245                 250
```

<210> SEQ ID NO 7
<211> LENGTH: 252
<212> TYPE: PRT
<213> ORGANISM: Marine eubacteria

<400> SEQUENCE: 7

```
Thr Met Gly Lys Leu Leu Leu Ile Leu Gly Ser Val Ile Ala Leu Pro
1               5                   10                  15

Thr Phe Ala Ala Gly Gly Gly Asp Leu Asp Ala Ser Asp Tyr Thr Gly
            20                  25                  30

Val Ser Phe Trp Leu Val Thr Ala Ala Leu Leu Ala Ser Thr Val Phe
        35                  40                  45

Phe Phe Val Glu Arg Asp Arg Val Ser Ala Lys Trp Lys Thr Ser Leu
    50                  55                  60

Thr Val Ser Gly Leu Val Thr Gly Ile Ala Phe Trp His Tyr Met Tyr
65                  70                  75                  80

Met Arg Gly Val Trp Ile Glu Thr Gly Asp Ser Pro Thr Val Phe Arg
                85                  90                  95

Tyr Ile Asp Trp Leu Leu Thr Val Pro Leu Leu Ile Cys Glu Phe Tyr
            100                 105                 110

Leu Ile Leu Ala Ala Ala Thr Asn Val Ala Gly Ser Leu Phe Lys Lys
        115                 120                 125

Leu Leu Val Gly Ser Leu Val Met Leu Val Phe Gly Tyr Met Gly Glu
    130                 135                 140

Ala Gly Ile Met Ala Ala Trp Pro Ala Phe Ile Ile Gly Cys Leu Ala
145                 150                 155                 160

Trp Val Tyr Met Ile Tyr Glu Leu Tyr Ala Gly Glu Gly Lys Ser Ala
                165                 170                 175

Cys Asn Thr Ala Ser Pro Ser Val Gln Ser Ala Tyr Asn Thr Met Met
            180                 185                 190

Ala Ile Ile Val Phe Gly Trp Ala Ile Tyr Pro Ile Gly Tyr Phe Thr
        195                 200                 205

Gly Tyr Leu Met Gly Asp Gly Gly Ser Ala Leu Asn Leu Asn Leu Ile
```

-continued

```
    210                 215                 220

Tyr Asn Leu Ala Asp Phe Val Asn Lys Ile Leu Phe Gly Leu Ile Ile
225                 230                 235                 240

Trp Asn Val Ala Val Lys Glu Ser Ser Asn Ala Lys
                245                 250
```

<210> SEQ ID NO 8
<211> LENGTH: 757
<212> TYPE: DNA
<213> ORGANISM: Marine eubacteria

<400> SEQUENCE: 8

```
accatgggta aattattact gatattaggt agtgttattg cacttcctac atttgctgca     60

ggtggcggtg accttgatgc tagtgattac actggtgttt ctttttggtt agttacagct    120

gctctattag catctactgt atttttcttt gttgaaagag atagagtttc tgcaaaatgg    180

aaaacatcat taactgtatc tggtcttgtt actggtattg ctttctggca ttacatgtac    240

atgagaggag tatggattga aactggtgat tcgcctactg tatttagata cattgattgg    300

ttactaacag ttcctttatt aatatgtgaa ttctacttaa ttcttgctgc tgcaactaat    360

gttgccggct cattatttaa gaaacttcta gttggttctc ttgttatgct tgtgtttggt    420

tacatgggtg aagcaggaat tatggcagct tggcctgcat tcattattgg gtgtttagct    480

tgggtataca tgatttatga actatatgct ggagaaggaa aatctgcatg taatactgca    540

agtccttcgg ttcaatcagc ttacaacaca atgatggcta tcatagtctt cggttgggca    600

atttatccta taggttattt cacaggttac ctaatgggtg acggtggatc agctcttaac    660

ttaaacctta tttataacct tgctgacttt gttaacaaga ttctatttgg tttaattata    720

tggaatgttg ctgttaaaga atcttctaat gctaagg                             757
```

<210> SEQ ID NO 9
<211> LENGTH: 251
<212> TYPE: PRT
<213> ORGANISM: Marine eubacteria

<400> SEQUENCE: 9

```
Thr Met Gly Lys Leu Leu Leu Ile Leu Gly Ser Val Ile Ala Leu Pro
1               5                   10                  15

Thr Phe Ala Ala Gly Gly Gly Asp Leu Asp Ala Ser Asp Tyr Thr Gly
            20                  25                  30

Val Ser Phe Trp Leu Val Thr Ala Ala Leu Leu Ala Ser Thr Val Phe
        35                  40                  45

Phe Phe Val Glu Arg Asp Arg Val Ser Ala Lys Trp Lys Thr Ser Leu
    50                  55                  60

Thr Val Ser Gly Leu Val Thr Gly Ile Ala Phe Trp His Tyr Met Tyr
65                  70                  75                  80

Met Arg Gly Val Trp Ile Glu Thr Gly Asp Ser Pro Thr Val Phe Arg
                85                  90                  95

Tyr Ile Asp Trp Leu Leu Thr Val Pro Leu Leu Ile Cys Glu Phe Tyr
            100                 105                 110

Leu Ile Leu Ala Ala Ala Thr Asn Val Ala Ala Gly Leu Phe Lys Lys
        115                 120                 125

Leu Leu Val Gly Ser Leu Val Met Leu Val Phe Gly Tyr Met Gly Glu
    130                 135                 140

Ala Gly Ile Met Asn Ala Trp Gly Ala Phe Val Ile Gly Cys Leu Ala
145                 150                 155                 160
```

-continued

```
Trp Val Tyr Met Ile Tyr Glu Leu Trp Ala Gly Glu Gly Lys Ala Ala
                165                 170                 175

Cys Asn Thr Ala Ser Pro Ala Val Gln Ser Ala Tyr Asn Thr Met Met
            180                 185                 190

Tyr Ile Ile Ile Phe Gly Trp Ala Ile Tyr Pro Val Gly Tyr Phe Thr
        195                 200                 205

Gly Tyr Leu Met Gly Asp Gly Gly Ser Ala Leu Asn Leu Asn Leu Ile
    210                 215                 220

Tyr Asn Leu Ala Asp Phe Val Asn Lys Ile Leu Phe Gly Leu Ile Ile
225                 230                 235                 240

Trp Asn Val Ala Val Lys Glu Ser Ser Asn Ala
                245                 250


<210> SEQ ID NO 10
<211> LENGTH: 753
<212> TYPE: DNA
<213> ORGANISM: Marine eubacteria

<400> SEQUENCE: 10

accatgggta aattattact gatattaggt agtgttattg cacttcctac atttgctgca     60

ggtggtggtg accttgatgc tagtgattac actggtgttt ctttttggtt agttactgct    120

gctctattag catctactgt atttttcttt gttgaaagag atagagtttc tgcaaaatgg    180

aaaacatcat taactgtatc gggtcttgtt actggtattg ctttctggca ttacatgtac    240

atgagagggg tatggattga gaccggtgat tcgccaactg tatttagata cattgattgg    300

ttactaacag ttcctctatt gatatgtgaa ttctacttaa ttcttgctgc tgcaacaaat    360

gttgctgctg gcctgtttaa gaaattattg gttggttctc ttgttatgct tgtgtttggt    420

tacatgggtg aggcaggaat tatgaacgct tggggtgcat tcgttattgg gtgtttagct    480

tgggtataca tgatttatga actatgggct ggagaaggca aggctgcatg taatactgca    540

agtcctgctg tgcaatcagc ttacaacaca atgatgtata taatcatctt tggttgggca    600

atttatcctg taggttattt cacaggttac ctaatgggtg acggtggatc agctcttaac    660

ttaaacctta tctataacct tgctgacttt gttaacaaga ttctatttgg tttaattata    720

tggaatgttg ctgttaaaga atcttctaat gct                                 753


<210> SEQ ID NO 11
<211> LENGTH: 252
<212> TYPE: PRT
<213> ORGANISM: Marine eubacteria

<400> SEQUENCE: 11

Thr Met Gly Lys Leu Leu Leu Ile Leu Gly Ser Ala Ile Ala Leu Pro
1               5                   10                  15

Ser Phe Ala Ala Ala Gly Gly Asp Leu Asp Ile Ser Asp Thr Val Gly
            20                  25                  30

Val Ser Phe Trp Leu Val Thr Ala Gly Met Leu Ala Ala Thr Val Phe
        35                  40                  45

Phe Phe Val Glu Arg Asp Gln Val Ser Ala Lys Trp Lys Thr Ser Leu
    50                  55                  60

Thr Val Ser Gly Leu Ile Thr Gly Ile Ala Phe Trp His Tyr Leu Tyr
65                  70                  75                  80

Met Arg Gly Val Trp Ile Asp Thr Gly Asp Thr Pro Thr Val Phe Arg
                85                  90                  95
```

-continued

```
Tyr Ile Asp Trp Leu Leu Thr Val Pro Leu Gln Met Val Glu Phe Tyr
            100                 105                 110

Leu Ile Leu Ala Ala Cys Thr Ser Val Ala Ala Ser Leu Phe Lys Lys
        115                 120                 125

Leu Leu Ala Gly Ser Leu Val Met Leu Gly Ala Gly Phe Ala Gly Glu
    130                 135                 140

Ala Gly Leu Ala Pro Val Leu Pro Ala Phe Ile Ile Gly Met Ala Gly
145                 150                 155                 160

Trp Leu Tyr Met Ile Tyr Glu Leu His Met Gly Glu Gly Lys Ala Ala
                165                 170                 175

Val Ser Thr Ala Ser Pro Ala Val Asn Ser Ala Tyr Asn Ala Met Met
            180                 185                 190

Lys Ile Ile Val Ile Gly Trp Ala Ile Tyr Pro Ala Gly Tyr Ala Ala
        195                 200                 205

Gly Tyr Leu Met Ser Gly Asp Gly Val Tyr Ala Ser Asn Leu Asn Leu
    210                 215                 220

Ile Tyr Asn Leu Ala Asp Phe Val Asn Lys Ile Leu Phe Gly Leu Ile
225                 230                 235                 240

Ile Trp Asn Val Ala Val Lys Glu Ser Ser Asn Ala
                245                 250


<210> SEQ ID NO 12
<211> LENGTH: 757
<212> TYPE: DNA
<213> ORGANISM: Marine eubacteria

<400> SEQUENCE: 12

accatgggta aattattact gatattaggt agtgctattg cacttccatc atttgctgct      60

gctggtggcg atctagatat aagtgatact gttggtgttt cattctggct ggttacagct     120

ggtatgttag cggcaactgt attctttttt gtagaaagag accaagtcag cgctaagtgg     180

aaaacttcac ttactgtatc tggtttaatt actggtatag ctttttggca ttatctctac     240

atgagaggtg tttggataga tactggtgat acaccaacag tatttagata tattgattgg     300

ttattaactg ttccattaca aatggttgag ttctatctaa ttcttgctgc ttgtacaagt     360

gttgctgctt cattatttaa gaagcttcta gctggttcat tagtaatgtt aggtgctgga     420

tttgcaggcg aagctggttt agctcctgta ttacctgctt tcattattgg tatggctgga     480

tggttataca tgatttatga gctacatatg ggtgaaggta aggctgctgt aagtactgca     540

agtcctgctg ttaactctgc atacaacgca atgatgaaga ttattgttat tggatgggca     600

atttatcctg ctggatatgc tgctggttac ctaatgagtg gtgacggtgt atacgcttca     660

aacttaaacc ttatatataa ccttgctgac tttgttaaca agattctatt tggtttgatc     720

atttggaatg ttgctgttaa agaatcttct aatgcta                              757


<210> SEQ ID NO 13
<211> LENGTH: 252
<212> TYPE: PRT
<213> ORGANISM: Marine eubacteria

<400> SEQUENCE: 13

Thr Met Gly Lys Leu Leu Leu Ile Leu Gly Ser Ala Ile Ala Leu Pro
1               5                   10                  15

Ser Phe Ala Ala Ala Gly Gly Asp Leu Asp Ile Ser Asp Thr Val Gly
            20                  25                  30

Val Ser Phe Trp Leu Val Thr Ala Gly Met Leu Ala Ala Thr Val Phe
```

-continued

```
        35                  40                  45

Phe Phe Val Glu Arg Asp Gln Val Ser Ala Lys Trp Lys Thr Ser Leu
    50                  55                  60

Thr Val Ser Gly Leu Ile Thr Gly Ile Ala Phe Trp His Tyr Leu Tyr
65                  70                  75                  80

Met Arg Gly Val Trp Ile Asp Thr Gly Asp Thr Pro Thr Val Phe Arg
                85                  90                  95

Tyr Ile Asp Trp Leu Leu Thr Val Pro Leu Gln Val Val Glu Phe Tyr
            100                 105                 110

Leu Ile Leu Ala Ala Cys Thr Ser Val Ala Ala Ser Leu Phe Lys Lys
        115                 120                 125

Leu Leu Ala Gly Ser Leu Val Met Leu Gly Ala Gly Phe Ala Gly Glu
    130                 135                 140

Ala Gly Leu Ala Pro Val Leu Pro Ala Phe Ile Ile Gly Met Ala Gly
145                 150                 155                 160

Trp Leu Tyr Met Ile Tyr Glu Leu Tyr Met Gly Glu Gly Lys Ala Ala
                165                 170                 175

Val Ser Thr Ala Ser Pro Ala Val Asn Ser Ala Tyr Asn Ala Met Met
            180                 185                 190

Met Ile Ile Val Val Gly Trp Ala Ile Tyr Pro Ala Gly Tyr Ala Ala
        195                 200                 205

Gly Tyr Leu Met Gly Gly Glu Gly Val Tyr Ala Ser Asn Leu Asn Leu
    210                 215                 220

Ile Tyr Asn Leu Ala Asp Phe Val Asn Lys Ile Leu Phe Gly Leu Ile
225                 230                 235                 240

Ile Trp Asn Val Ala Val Lys Glu Ser Ser Asn Ala
                245                 250
```

<210> SEQ ID NO 14
<211> LENGTH: 756
<212> TYPE: DNA
<213> ORGANISM: Marine eubacteria

<400> SEQUENCE: 14

```
accatgggta aattattact gatattaggt agtgctattg cacttccatc atttgctgct      60

gctggtggcg atctagatat aagtgatact gttggtgttt cattctggct ggttacagct     120

ggtatgttag cggcaactgt gttctttttt gtagaaagag accaagtcag cgctaagtgg     180

aaaacttcac ttactgtatc tggtttaatt actggtatag ctttttggca ttatctctat     240

atgagaggtg tttggataga cactggtgat accccaacag tattcagata tattgattgg     300

ttattaactg ttccattaca agtggttgag ttctatctaa ttcttgctgc ttgtacaagt     360

gttgctgctt cattatttaa gaagcttcta gctggttcat tagtaatgtt aggtgctgga     420

tttgcaggcg aagctggatt agctcctgta ttacctgctt tcattattgg tatggctgga     480

tggttataca tgatttatga gctatatatg ggtgaaggta aggctgctgt aagtactgca     540

agtcctgctg ttaactctgc atacaacgca atgatgatga ttattgttgt tggatgggca     600

atttatcctg ctggatatgc tgctggttac ctaatgggtg gcgaaggtgt atacgcttca     660

aacttaaacc ttatatataa ccttgctgac tttgttaaca agattctatt tggtttgatc     720

atttggaatg ttgctgttaa agaatcttct aatgct                               756
```

<210> SEQ ID NO 15
<211> LENGTH: 252
<212> TYPE: PRT

<213> ORGANISM: Marine eubacteria

<400> SEQUENCE: 15

Thr Met Gly Lys Leu Leu Leu Ile Leu Gly Ser Ala Ile Ala Leu Pro
1               5                   10                  15

Ser Phe Ala Ala Ala Gly Gly Asp Leu Asp Ile Ser Asp Thr Val Gly
            20                  25                  30

Val Ser Phe Trp Leu Val Thr Ala Gly Met Leu Ala Ala Thr Val Phe
        35                  40                  45

Phe Phe Val Glu Arg Asp Gln Val Ser Ala Lys Trp Lys Thr Ser Leu
    50                  55                  60

Thr Val Ser Gly Leu Ile Thr Gly Ile Ala Phe Trp His Tyr Leu Tyr
65                  70                  75                  80

Met Arg Gly Val Trp Ile Asp Thr Gly Asp Thr Pro Thr Val Phe Arg
                85                  90                  95

Tyr Ile Asp Trp Leu Leu Thr Val Pro Leu Gln Met Val Glu Phe Tyr
            100                 105                 110

Leu Ile Leu Ala Ala Cys Thr Asn Val Ala Ala Ser Leu Phe Lys Lys
        115                 120                 125

Leu Leu Ala Gly Ser Leu Val Met Leu Gly Ala Gly Phe Ala Gly Glu
    130                 135                 140

Ala Gly Leu Ala Pro Val Trp Pro Ala Phe Ile Ile Gly Met Ala Gly
145                 150                 155                 160

Trp Leu Tyr Met Ile Tyr Glu Leu Tyr Met Gly Glu Gly Lys Ala Ala
                165                 170                 175

Val Ser Thr Ala Ser Pro Ala Val Asn Ser Ala Tyr Asn Ala Met Met
            180                 185                 190

Val Ile Ile Val Val Gly Trp Ala Ile Tyr Pro Ala Gly Tyr Ala Ala
        195                 200                 205

Gly Tyr Leu Met Gly Gly Glu Gly Val Tyr Ala Ser Asn Leu Asn Leu
    210                 215                 220

Ile Tyr Asn Leu Ala Asp Leu Val Asn Lys Ile Leu Phe Gly Leu Ile
225                 230                 235                 240

Ile Trp Asn Val Ala Val Lys Glu Ser Ser Asn Ala
                245                 250

<210> SEQ ID NO 16
<211> LENGTH: 756
<212> TYPE: DNA
<213> ORGANISM: Marine eubacteria

<400> SEQUENCE: 16
accatgggta aattattact gatattaggt agtgctattg cacttccatc atttgctgct 60
gctggtggcg atctagatat aagtgatact gttggtgttt cattctggct ggttacagct 120
ggtatgttag cggcaactgt gttctttttt gtagaaagag accaagtcag cgctaagtgg 180
aaaacttcac ttactgtatc tggtttaatt actggtatag ctttttggca ttatctctat 240
atgagaggtg tttggataga cactggtgat accccaacag tattcagata tattgattgg 300
ttattaactg ttccattaca aatggttgag ttctatctaa ttcttgctgc ttgtacaaat 360
gttgctgctt cattatttaa gaagcttcta gctggttcat tagtaatgtt aggtgctgga 420
tttgcaggcg aagctggatt ggctcctgta tggcctgctt tcattattgg tatggctgga 480
tggttataca tgatttatga gctatatatg ggtgaaggta aggctgctgt aagtactgca 540
agtcctgctg ttaactctgc atacaacgca atgatggtga ttattgttgt tggatgggca 600

-continued

```
atttatcctg ctggatatgc tgctggttac ctaatgggtg gcgaaggtgt atacgcttca    660

aacttaaacc ttatatataa ccttgccgac cttgttaaca agattctatt tggtttgatc    720

atttggaatg ttgctgttaa agaatcttct aatgct                              756


<210> SEQ ID NO 17
<211> LENGTH: 251
<212> TYPE: PRT
<213> ORGANISM: Marine eubacteria

<400> SEQUENCE: 17

Thr Met Gly Lys Leu Leu Leu Ile Leu Gly Ser Val Ile Ala Leu Pro
1               5                   10                  15

Thr Phe Ala Ala Gly Gly Gly Asp Leu Asp Ala Ser Asp Tyr Thr Gly
            20                  25                  30

Val Ser Phe Trp Leu Val Thr Ala Ala Leu Leu Ala Ser Thr Val Phe
        35                  40                  45

Phe Phe Val Glu Arg Asp Arg Val Ser Ala Lys Trp Lys Thr Ser Leu
    50                  55                  60

Thr Val Ser Gly Leu Val Thr Gly Ile Ala Phe Trp His Tyr Met Tyr
65                  70                  75                  80

Met Arg Gly Val Trp Ile Glu Thr Gly Asp Ser Pro Thr Val Phe Arg
                85                  90                  95

Tyr Ile Asp Trp Leu Leu Thr Val Pro Leu Leu Ile Cys Glu Phe Tyr
            100                 105                 110

Leu Ile Leu Ala Ala Ala Thr Asn Val Ala Ala Gly Leu Phe Lys Lys
        115                 120                 125

Leu Leu Val Gly Ser Leu Val Met Leu Val Phe Gly Tyr Met Gly Glu
    130                 135                 140

Ala Gly Ile Met Asn Ala Trp Pro Ala Phe Ile Ile Gly Cys Leu Ala
145                 150                 155                 160

Trp Val Tyr Met Ile Tyr Glu Leu Tyr Ala Gly Glu Gly Lys Ser Ala
                165                 170                 175

Cys Asn Thr Ala Ser Pro Ser Val Gln Ser Ala Tyr Asn Thr Met Met
            180                 185                 190

Ala Ile Ile Val Phe Gly Trp Ala Ile Tyr Pro Val Gly Tyr Phe Thr
        195                 200                 205

Gly Tyr Leu Met Gly Asp Gly Gly Ser Ala Leu Asn Leu Asn Leu Ile
    210                 215                 220

Tyr Asn Leu Ala Asp Phe Val Asn Lys Ile Leu Phe Gly Leu Ile Ile
225                 230                 235                 240

Trp Asn Val Ala Val Lys Glu Ser Ser Asn Ala
                245                 250


<210> SEQ ID NO 18
<211> LENGTH: 251
<212> TYPE: PRT
<213> ORGANISM: Marine eubacteria

<400> SEQUENCE: 18

Thr Met Gly Lys Leu Leu Leu Ile Leu Gly Ser Val Ile Ala Leu Pro
1               5                   10                  15

Thr Phe Ala Ala Gly Gly Gly Asp Leu Asp Ala Ser Asp Tyr Thr Gly
            20                  25                  30

Val Ser Phe Trp Leu Val Thr Ala Ala Leu Leu Ala Ser Thr Val Phe
        35                  40                  45
```

-continued

```
Phe Phe Val Glu Arg Asp Arg Val Ser Ala Lys Trp Lys Thr Ser Leu
    50                  55                  60

Thr Val Ser Gly Leu Val Thr Gly Ile Ala Phe Trp His Tyr Met Tyr
65                  70                  75                  80

Met Arg Gly Val Trp Ile Glu Thr Gly Asp Ser Pro Thr Val Phe Arg
                85                  90                  95

Tyr Ile Asp Trp Leu Leu Thr Val Pro Leu Leu Ile Cys Glu Phe Tyr
            100                 105                 110

Leu Ile Leu Ala Ala Ala Thr Asn Val Ala Ala Gly Leu Phe Lys Lys
        115                 120                 125

Leu Leu Val Gly Ser Leu Val Met Leu Val Phe Gly Tyr Met Gly Glu
    130                 135                 140

Ala Gly Ile Met Asn Ala Trp Pro Ala Phe Ile Ile Gly Cys Leu Ala
145                 150                 155                 160

Trp Val Tyr Met Ile Tyr Glu Leu Tyr Ala Gly Glu Gly Lys Ser Ala
                165                 170                 175

Cys Asn Thr Ala Ser Pro Ser Val Gln Ser Ala Tyr Asn Thr Met Met
            180                 185                 190

Ala Ile Ile Val Phe Gly Trp Ala Ile Tyr Pro Val Gly Tyr Phe Thr
        195                 200                 205

Gly Tyr Leu Met Gly Asp Gly Gly Ser Ala Leu Asn Leu Asn Leu Ile
    210                 215                 220

Tyr Asn Leu Ala Asp Phe Val Asn Lys Ile Leu Phe Gly Leu Ile Ile
225                 230                 235                 240

Trp Asn Val Ala Val Lys Glu Ser Ser Asn Ala
                245                 250
```

<210> SEQ ID NO 19
<211> LENGTH: 753
<212> TYPE: DNA
<213> ORGANISM: Marine eubacteria

<400> SEQUENCE: 19

```
accatgggta aattattact gatattaggt agtgttattg cacttcctac atttgctgca      60

ggtggtggtg accttgatgc tagtgattac actggtgttt ctttttggtt agttactgct     120

gctttattag catctactgt atttttcttt gttgaaagag atagagtttc tgcaaaatgg     180

aaaacatcat taactgtatc tggtcttgtt actggtattg ctttctggca ttacatgtac     240

atgagagggg tatggattga aactggtgat tcgccaactg tatttagata cattgattgg     300

ttactaacag ttcctctatt aatatgtgaa ttctacttaa ttcttgctgc tgctactaat     360

gttgctgctg gcctgtttaa gaaattattg gttggttctc ttgttatgct tgtgtttggt     420

tacatgggtg aagcaggaat tatgaacgct tggggtgcat tcgttattgg gtgtttagct     480

tgggtataca tgatttatga gctttggctt ggagaaggaa aagctgcgtg taatacagca     540

agtcctgctg ttcagtcagc ttacaacaca atgatgatga tcatcatctt tggttgggca     600

atttatcctg taggttattt cacaggttac ctaatgggtg acggtggatc agcacttaac     660

ttaaacctta tctataacct tgctgacttt gttaacaaga ttctatttgg tttaattata     720

tggaatgttg ctgttaaaga atcttctaat gct                                  753
```

<210> SEQ ID NO 20
<211> LENGTH: 753
<212> TYPE: DNA
<213> ORGANISM: Marine eubacteria -continued

<400> SEQUENCE: 20

```
accatgggta aattattact gatattaggt agtgttattg cacttcctac atttgctgca      60
ggtggtggtg accttgatgc tagtgattac actggtgttt ctttttggtt agttactgct     120
gctttattag catctactgt atttttcttt gttgaaagag atagagtttc tgcaaaatgg     180
aaaacatcat taactgtatc tggtcttgtt actggtattg ctttctggca ttacatgtac     240
atgagagggg tatggattga aactggtgat tcgccaactg tatttagata cattgattgg     300
ttactaacag ttcctctatt aatatgtgaa ttctacttaa ttcttgctgc tgctactaat     360
gttgctgctg gcctgtttaa gaaattattg gttggttctc ttgttatgct tgtgtttggt     420
tacatgggtg aagcaggaat tatgaacgct tggggtgcat tcgttattgg gtgtttagct     480
tgggtataca tgatttatga gctttggctt ggagaaggaa aagctgcgtg taatacagca     540
agtcctgctg ttcagtcagc ttacaacaca atgatgatga tcatcatctt tggttgggca     600
atttatcctg taggttattt cacaggttac ctaatgggtg acggtggatc agcacttaac     660
ttaaacctta tctataacct tgctgacttt gttaacaaga ttctatttgg tttaattata     720
tggaatgttg ctgttaaaga atcttctaat gct                                 753
```

<210> SEQ ID NO 21
<211> LENGTH: 251
<212> TYPE: PRT
<213> ORGANISM: Marine eubacteria

<400> SEQUENCE: 21

```
Thr Met Gly Lys Leu Leu Leu Ile Leu Gly Ser Val Ile Ala Leu Pro
1               5                   10                  15

Thr Phe Ala Ala Gly Gly Gly Asp Leu Asp Ala Ser Asp Tyr Thr Gly
            20                  25                  30

Val Ser Phe Trp Leu Val Thr Ala Ala Leu Leu Ala Ser Thr Val Phe
        35                  40                  45

Phe Phe Val Glu Arg Asp Arg Val Ser Ala Lys Trp Lys Thr Ser Leu
    50                  55                  60

Thr Val Ser Gly Leu Val Thr Gly Ile Ala Phe Trp His Tyr Met Tyr
65                  70                  75                  80

Met Arg Gly Val Trp Ile Glu Thr Gly Asp Ser Pro Thr Val Phe Arg
                85                  90                  95

Tyr Ile Asp Trp Leu Leu Thr Val Pro Leu Leu Ile Cys Glu Phe Tyr
            100                 105                 110

Leu Ile Leu Ala Ala Ala Thr Asn Val Ala Ala Gly Leu Phe Lys Lys
        115                 120                 125

Leu Leu Val Gly Ser Leu Val Met Leu Val Phe Gly Tyr Met Gly Glu
    130                 135                 140

Ala Gly Ile Met Asn Ala Trp Gly Ala Phe Val Ile Gly Cys Leu Ala
145                 150                 155                 160

Trp Val Tyr Met Ile Tyr Glu Leu Trp Ala Gly Glu Gly Lys Ala Ala
                165                 170                 175

Cys Asn Thr Ala Ser Pro Ala Val Gln Ser Ala Tyr Asn Thr Met Met
            180                 185                 190

Tyr Ile Ile Ile Phe Gly Trp Ala Ile Tyr Pro Val Gly Tyr Phe Thr
        195                 200                 205

Gly Tyr Leu Met Gly Asp Gly Gly Ser Ala Leu Asn Leu Asn Leu Ile
    210                 215                 220
```

-continued

```
Tyr Asn Leu Ala Asp Phe Val Asn Lys Ile Leu Phe Gly Leu Ile Ile
225                 230                 235                 240

Trp Asn Val Ala Val Lys Glu Ser Ser Asn Ala
                245                 250


<210> SEQ ID NO 22
<211> LENGTH: 753
<212> TYPE: DNA
<213> ORGANISM: Marine eubacteria

<400> SEQUENCE: 22

accatgggta aattattact gatattaggt agtgttattg cacttcctac atttgctgca      60

ggtggtggtg accttgatgc tagtgattac actggtgttt ctttttggtt agttactgct     120

gctttattag catctactgt atttttcttt gttgaaagag atagagtttc tgcaaaatgg     180

aaaacatcat taactgtatc tggtcttgtt actggtattg ctttctggca ttacatgtac     240

atgagagggg tatggattga aactggtgat tcgccaactg tatttagata cattgattgg     300

ttactaacag ttcctctatt aatatgtgaa ttctacttaa ttcttgctgc tgcaactaat     360

gttgctgctg gcctgtttaa gaaattattg gttggttctc ttgttatgct tgtgtttggt     420

tacatgggtg aggcaggaat tatgaacgct tggggtgcat tcgttattgg gtgtttagct     480

tgggtataca tgatttatga actatgggct ggagaaggca aggctgcatg taatactgca     540

agtcctgctg tgcaatcagc ttacaacaca atgatgtata taatcatctt tggttgggca     600

atttatcctg taggttattt cacaggttac ctaatgggtg acggtggatc agctcttaac     660

ttaaacctta tctataacct tgctgacttt gttaacaaga ttctatttgg tttaattata     720

tggaatgttg ctgttaaaga atcttctaat gct                                  753


<210> SEQ ID NO 23
<211> LENGTH: 251
<212> TYPE: PRT
<213> ORGANISM: Marine eubacteria

<400> SEQUENCE: 23

Thr Met Gly Lys Leu Leu Leu Ile Leu Gly Ser Val Ile Ala Leu Pro
1               5                   10                  15

Thr Phe Ala Ala Gly Gly Gly Asp Leu Asp Ala Ser Asp Tyr Thr Gly
            20                  25                  30

Val Ser Phe Trp Leu Val Thr Ala Ala Leu Leu Ala Ser Thr Val Phe
        35                  40                  45

Phe Phe Val Glu Arg Asp Arg Val Ser Ala Lys Trp Lys Thr Ser Leu
    50                  55                  60

Thr Val Ser Gly Leu Val Thr Gly Ile Ala Phe Trp His Tyr Met Tyr
65                  70                  75                  80

Met Arg Gly Val Trp Ile Glu Thr Gly Asp Ser Pro Thr Val Phe Arg
                85                  90                  95

Tyr Ile Asp Trp Leu Leu Thr Val Pro Leu Leu Ile Cys Glu Phe Tyr
            100                 105                 110

Leu Ile Leu Ala Ala Ala Thr Asn Val Ala Gly Ser Leu Phe Lys Lys
        115                 120                 125

Leu Leu Val Gly Ser Leu Val Met Leu Val Phe Gly Tyr Met Gly Glu
    130                 135                 140

Ala Gln Ile Met Ala Ala Trp Pro Ala Phe Ile Ile Gly Cys Leu Ala
145                 150                 155                 160

Trp Val Tyr Met Ile Tyr Glu Leu Tyr Ala Gly Glu Gly Lys Ser Ala
```

-continued

```
                165                 170                 175

Cys Asn Thr Ala Ser Pro Ser Val Gln Ser Ala Tyr Asn Thr Met Met
            180                 185                 190

Ala Ile Ile Val Phe Gly Trp Ala Ile Tyr Pro Val Gly Tyr Phe Thr
        195                 200                 205

Gly Tyr Leu Met Gly Asp Gly Gly Ser Ala Leu Asn Leu Asn Leu Ile
    210                 215                 220

Tyr Asn Leu Ala Asp Phe Val Asn Lys Ile Leu Leu Gly Leu Ile Ile
225                 230                 235                 240

Trp Asn Val Ala Val Lys Glu Ser Ser Asn Ala
                245                 250
```

<210> SEQ ID NO 24
<211> LENGTH: 753
<212> TYPE: DNA
<213> ORGANISM: Marine eubacteria

<400> SEQUENCE: 24

```
accatgggta aattattact gatattaggt agtgttattg cacttcctac atttgctgca      60

ggtggcggtg accttgatgc tagtgattac actggtgttt ctttttggtt agttacagct     120

gctctattag catctactgt atttttcttt gttgaaagag atagagtttc tgcaaaatgg     180

aaaacatcat taactgtatc tggtcttgtt actggtattg ctttctggca ttacatgtac     240

atgagagggg tatggattga aactggtgat tcgccaactg tatttagata cattgattgg     300

ttactaacag ttcctctatt aatatgtgaa ttctacttaa ttcttgctgc tgctactaat     360

gttgctggat cattatttaa gaaattacta gttggttctc ttgttatgct tgtgtttggt     420

tacatgggtg aagcacaaat tatggctgca tggcctgcat tcattattgg gtgtttagct     480

tgggtataca tgatttatga actatatgct ggagaaggaa aatctgcatg taatactgca     540

agtccttcgg ttcaatcagc ttacaacaca atgatggcta tcatagtctt cggttgggca     600

atttatcctg taggttattt cacaggttac ctaatgggtg acggtgggtc agctcttaac     660

ttaaacctta tttataacct tgctgacttt gttaacaaga ttctacttgg tttaattata     720

tggaatgttg ctgttaaaga atcttctaat gct                                  753
```

<210> SEQ ID NO 25
<211> LENGTH: 249
<212> TYPE: PRT
<213> ORGANISM: Marine eubacteria

<400> SEQUENCE: 25

```
Thr Met Gly Lys Leu Leu Leu Ile Leu Gly Ser Val Ile Ala Leu Pro
1               5                   10                  15

Thr Phe Ala Ala Gly Gly Gly Asp Leu Asp Ala Ser Asp Tyr Thr Gly
            20                  25                  30

Val Ser Phe Trp Leu Val Thr Ala Ala Leu Leu Ala Ser Thr Val Phe
        35                  40                  45

Phe Phe Val Glu Arg Asp Arg Val Ser Ala Lys Trp Lys Thr Ser Leu
    50                  55                  60

Thr Val Ser Gly Leu Val Thr Gly Ile Ala Phe Trp His Tyr Met Tyr
65                  70                  75                  80

Met Arg Gly Val Trp Ile Glu Thr Gly Asp Ser Pro Thr Val Phe Arg
                85                  90                  95

Tyr Ile Asp Trp Leu Leu Thr Val Pro Leu Leu Ile Cys Glu Phe Tyr
            100                 105                 110
```

-continued

```
Leu Ile Leu Ala Ala Ala Ala Asn Val Ala Gly Ser Leu Phe Lys Lys
        115                 120                 125

Leu Leu Val Gly Ser Leu Val Met Leu Val Phe Gly Tyr Met Gly Glu
    130                 135                 140

Ala Gly Ile Met Ala Ala Trp Pro Ala Phe Ile Ile Gly Cys Leu Ala
145                 150                 155                 160

Trp Val Tyr Met Ile Tyr Glu Leu Trp Ala Gly Glu Gly Lys Ser Ala
                165                 170                 175

Cys Asn Thr Ala Ser Pro Ala Val Gln Ser Ala Tyr Asn Thr Met Met
            180                 185                 190

Tyr Ile Ile Ile Phe Gly Trp Ala Ile Tyr Pro Val Gly Tyr Phe Thr
        195                 200                 205

Gly Tyr Leu Met Gly Asp Gly Gly Ser Ala Leu Asn Leu Asn Leu Ile
    210                 215                 220

Tyr Asn Leu Ala Asp Phe Val Asn Lys Ile Leu Phe Gly Leu Ile Ile
225                 230                 235                 240

Trp Asn Val Ala Val Lys Glu Ser Ser
                245
```

<210> SEQ ID NO 26
<211> LENGTH: 748
<212> TYPE: DNA
<213> ORGANISM: Marine eubacteria

<400> SEQUENCE: 26

```
accatgggta aattattact gatattaggt agtgttattg cacttcctac atttgctgca      60

ggtggtggtg accttgatgc tagtgattac actggtgttt ctttttggtt agttactgct     120

gctttattag catctactgt atttttcttt gttgaaagag atagagtttc tgcaaaatgg     180

aaaacatcat taactgtatc tggtcttgtt actggtattg ctttctggca ttacatgtac     240

atgagagggg tatggattga aactggtgat tcgccaactg tatttagata cattgattgg     300

ttactaacag ttcctctatt aatatgtgaa ttctacttaa ttcttgctgc tgcagctaat     360

gttgctggat cattatttaa gaaattacta gttggttctc ttgttatgct tgtgtttggt     420

tacatgggtg aagcaggaat catggctgca tggcctgcat tcattattgg gtgtttagct     480

tgggtataca tgatttatga attatgggct ggagaaggaa aatctgcatg taatactgca     540

agtcctgctg tgcaatcagc ctacaacaca atgatgtata ttatcatctt tggttgggcg     600

atttatcctg taggttattt cacaggttac ttgatgggtg acggtggatc agctcttaac     660

ttaaacctta tctataacct tgctgacttt gttaacaaga ttctatttgg tttaattata     720

tggaatgttg ctgttaaaga atcttcta                                        748
```

<210> SEQ ID NO 27
<211> LENGTH: 251
<212> TYPE: PRT
<213> ORGANISM: Marine eubacteria

<400> SEQUENCE: 27

```
Thr Met Gly Lys Leu Leu Leu Ile Ile Gly Ser Val Ile Ala Leu Pro
1               5                   10                  15

Thr Phe Ala Ala Gly Gly Gly Asp Leu Asp Ala Ser Asp Tyr Thr Gly
            20                  25                  30

Val Ser Phe Trp Leu Val Thr Ala Ala Leu Leu Ala Ser Thr Val Phe
        35                  40                  45
```

-continued

```
Phe Phe Val Glu Arg Asp Arg Val Ser Ala Lys Trp Lys Thr Ser Leu
    50                  55                  60

Thr Val Ser Gly Leu Val Thr Gly Ile Ala Phe Trp His Tyr Met Tyr
65                  70                  75                  80

Met Arg Gly Val Trp Ile Glu Thr Gly Asp Ser Pro Thr Val Phe Arg
                85                  90                  95

Tyr Ile Asp Trp Leu Leu Thr Val Pro Leu Leu Ile Cys Glu Phe Tyr
            100                 105                 110

Leu Ile Leu Ala Ala Ala Thr Asn Val Ala Gly Ser Leu Phe Lys Lys
        115                 120                 125

Leu Leu Val Gly Ser Leu Val Met Leu Val Phe Gly Tyr Met Gly Glu
    130                 135                 140

Ala Gly Ile Met Ala Ala Trp Pro Ala Phe Ile Ile Gly Cys Leu Ala
145                 150                 155                 160

Trp Val Tyr Met Ile Tyr Glu Leu Tyr Ala Gly Glu Gly Lys Ser Ala
                165                 170                 175

Cys Asn Thr Ala Ser Pro Ala Val Gln Ser Ala Tyr Asn Thr Met Met
            180                 185                 190

Tyr Ile Ile Val Phe Gly Trp Ala Ile Tyr Pro Val Gly Tyr Phe Thr
        195                 200                 205

Gly Tyr Leu Met Gly Asp Gly Gly Ser Ala Leu Asn Leu Asn Leu Ile
    210                 215                 220

Tyr Asn Leu Ala Asp Phe Val Asn Lys Ile Leu Phe Gly Leu Ile Ile
225                 230                 235                 240

Trp Asn Val Ala Val Lys Glu Ser Ser Asn Ala
                245                 250
```

<210> SEQ ID NO 28
<211> LENGTH: 753
<212> TYPE: DNA
<213> ORGANISM: Marine eubacteria

<400> SEQUENCE: 28

```
accatgggta aattattact gataataggt agtgttattg cacttcctac atttgctgca     60

ggtggcggtg accttgatgc tagtgattac actggtgttt ctttttggtt agttacagct    120

gctctattag catctactgt atttttcttt gttgaaagag atagagtttc tgcaaaatgg    180

aaaacatcat taactgtatc tggtcttgtt actggtattg ctttctggca ttacatgtac    240

atgagaggag tatggattga aactggtgat tcgccaactg tatttagata cattgattgg    300

ttactaacag ttcctttatt aatatgtgaa ttctacttaa ttcttgctgc tgcaactaat    360

gttgccggct cattatttaa gaaacttcta gttggttctc ttgttatgct tgtgtttggt    420

tacatgggtg aagcaggaat tatggcagct tggcctgcat tcattattgg gtgtttagct    480

tgggtatata tgatttatga actatatgct ggagaaggaa aatctgcatg taatacagca    540

agtcctgctg tgcaatcagc ttacaacaca atgatgtata ttatcgtctt tggttgggcg    600

atttatcctg taggttattt cacaggttac ctgatgggtg acggtggatc agctcttaac    660

ttaaacctta tctataacct tgctgacttt gttaacaaga ttctatttgg tttaattata    720

tggaatgttg ctgttaaaga atcttctaat gct                                 753
```

<210> SEQ ID NO 29
<211> LENGTH: 249
<212> TYPE: PRT
<213> ORGANISM: Marine eubacteria -continued

<400> SEQUENCE: 29

```
Thr Met Gly Lys Leu Leu Leu Ile Leu Gly Ser Val Ile Ala Leu Pro
1               5                   10                  15

Thr Phe Ala Ala Gly Gly Gly Asp Leu Asp Ala Ser Asp Tyr Thr Gly
            20                  25                  30

Val Ser Phe Trp Leu Val Thr Ala Ala Leu Leu Ala Ser Thr Val Phe
        35                  40                  45

Phe Phe Val Glu Arg Asp Arg Val Ser Ala Lys Trp Lys Thr Ser Leu
    50                  55                  60

Thr Val Ser Gly Leu Val Thr Gly Ile Ala Phe Trp His Tyr Met Tyr
65                  70                  75                  80

Met Arg Gly Val Trp Ile Glu Thr Gly Asp Ser Pro Thr Val Phe Arg
                85                  90                  95

Tyr Ile Asp Trp Leu Leu Thr Val Pro Leu Leu Ile Cys Glu Phe Tyr
            100                 105                 110

Leu Ile Leu Ala Ala Ala Thr Asn Val Ala Ala Gly Leu Phe Lys Lys
        115                 120                 125

Leu Leu Val Gly Ser Leu Val Met Leu Val Phe Gly Tyr Met Gly Glu
    130                 135                 140

Ala Gly Ile Met Asn Ala Trp Gly Ala Phe Val Ile Gly Cys Leu Ala
145                 150                 155                 160

Trp Val Tyr Met Ile Tyr Glu Leu Trp Ala Gly Glu Gly Lys Ala Ala
                165                 170                 175

Cys Asn Thr Ala Ser Pro Ala Val Gln Ser Ala Tyr Asn Thr Met Met
            180                 185                 190

Tyr Ile Ile Ile Phe Gly Trp Ala Ile Tyr Pro Val Gly Tyr Phe Thr
        195                 200                 205

Gly Tyr Leu Met Gly Asp Gly Gly Ser Ala Leu Asn Leu Asn Leu Ile
    210                 215                 220

Tyr Asn Leu Ala Asp Phe Val Asn Lys Asn Leu Phe Gly Leu Ile Ile
225                 230                 235                 240

Trp Asn Val Ala Val Lys Glu Ser Ser
                245
```

<210> SEQ ID NO 30
<211> LENGTH: 748
<212> TYPE: DNA
<213> ORGANISM: Marine eubacteria

<400> SEQUENCE: 30

```
accatgggta aattattact gatattaggt agtgttattg cacttcctac atttgctgca     60

ggtggtggtg accttgatgc tagtgattac actggtgttt ctttttggtt agttactgct    120

gctctattag catctactgt atttttcttt gttgaaagag atagagtttc tgcaaaatgg    180

aaaacatcat taactgtatc gggtcttgtt actggtattg ctttctggca ttacatgtac    240

atgagagggg tatggattga gactggtgat tcgccaactg tatttagata cattgattgg    300

ttactaacag ttcctctatt gatatgtgaa ttctacttaa ttcttgctgc tgcaacaaat    360

gttgctgctg gcctgtttaa gaaattattg gttggttctc ttgttatgct tgtgtttggt    420

tacatgggtg aggcaggaat tatgaacgct tggggtgcat tcgttattgg gtgtttagct    480

tgggtataca tgatttatga actatgggct ggagaaggca aggctgcatg taatactgca    540

agtcctgctg tgcaatcagc ttacaacaca atgatgtata taatcatctt tggttgggca    600

atttatcctg taggttattt cacaggttac ctaatgggtg acggtggatc agctcttaac    660
```

ttaaacctta tctataacct tgctgacttt gttaacaaga atctatttgg tttaattata 720
tggaatgttg ctgttaaaga atcttcta 748

<210> SEQ ID NO 31
<211> LENGTH: 251
<212> TYPE: PRT
<213> ORGANISM: Marine eubacteria

<400> SEQUENCE: 31

```
Thr Met Gly Lys Leu Leu Arg Ile Leu Gly Ser Val Ile Ala Leu Pro
1               5                   10                  15

Thr Phe Ala Ala Gly Gly Gly Asp Leu Asp Ala Ser Asp Tyr Thr Gly
            20                  25                  30

Val Ser Phe Trp Leu Val Thr Ala Ala Leu Leu Ala Ser Thr Val Phe
        35                  40                  45

Phe Phe Val Glu Arg Asp Arg Val Ser Ala Lys Trp Lys Thr Ser Leu
    50                  55                  60

Thr Val Ser Gly Leu Val Thr Gly Ile Ala Phe Trp His Tyr Met Tyr
65                  70                  75                  80

Met Arg Gly Val Trp Ile Glu Thr Gly Asp Ser Pro Thr Val Phe Arg
                85                  90                  95

Tyr Ile Asp Trp Leu Leu Thr Val Pro Leu Leu Ile Cys Glu Phe Tyr
            100                 105                 110

Leu Ile Leu Ala Ala Ala Thr Asn Val Ala Gly Ser Leu Phe Lys Lys
        115                 120                 125

Leu Leu Val Gly Ser Leu Val Met Leu Val Phe Gly Tyr Met Gly Glu
    130                 135                 140

Ala Gly Ile Met Ala Ala Trp Pro Ala Phe Ile Ile Gly Cys Leu Ala
145                 150                 155                 160

Trp Val Tyr Met Ile Tyr Glu Leu Trp Ala Gly Glu Gly Lys Ser Ala
                165                 170                 175

Cys Asn Thr Ala Ser Pro Ala Val Gln Ser Ala Tyr Asn Thr Met Met
            180                 185                 190

Tyr Ile Ile Ile Val Gly Trp Ala Ile Tyr Pro Val Gly Tyr Phe Thr
        195                 200                 205

Gly Tyr Leu Met Gly Asp Gly Gly Ser Ala Leu Asn Leu Asn Leu Ile
    210                 215                 220

Tyr Asn Leu Ala Asp Phe Val Asn Lys Ile Leu Phe Gly Leu Ile Ile
225                 230                 235                 240

Trp Asn Val Ala Val Lys Glu Ser Ser Asn Ala
                245                 250
```

<210> SEQ ID NO 32
<211> LENGTH: 753
<212> TYPE: DNA
<213> ORGANISM: Marine eubacteria

<400> SEQUENCE: 32
accatgggta aattattacg gatattaggt agtgttattg cacttcctac atttgctgca 60
ggtggcggtg accttgatgc tagtgattac actggtgttt ctttttggtt agttacagct 120
gctctattag catctactgt atttttcttt gttgaaagag atagagtttc tgcaaaatgg 180
aaaacatcat taactgtatc tggtcttgtt actggtattg ctttctggca ttacatgtat 240
atgagaggag tatggattga aactggtgat tcgccaactg tatttagata cattgattgg 300

-continued

```
ttactaacag ttcctttatt aatatgtgaa ttctacttaa ttcttgctgc tgcaactaat    360

gttgctggat cattatttaa gaaattacta gttggttctc ttgttatgct tgtgtttggt    420

tacatgggtg aagcaggaat catggctgca tggcctgcat tcattattgg gtgtttagct    480

tgggtataca tgatttatga actatgggct ggagaaggaa aatctgcatg taatactgca    540

agtcctgctg tgcaatcagc ttacaacaca atgatgtata tcatcatcgt tggttgggcg    600

atttatcctg taggttattt cacaggttac ctgatgggtg acggtggatc agctcttaac    660

ttaaacctta tctataacct tgctgacttt gttaacaaga ttctatttgg tttaattata    720

tggaatgttg ctgttaaaga atcttctaat gct                                 753
```

<210> SEQ ID NO 33
<211> LENGTH: 251
<212> TYPE: PRT
<213> ORGANISM: Marine eubacteria

<400> SEQUENCE: 33

```
Thr Met Gly Lys Leu Leu Leu Ile Leu Gly Ser Val Ile Ala Leu Pro
1               5                   10                  15

Thr Phe Ala Ala Gly Gly Gly Asp Leu Asp Ala Ser Asp Tyr Thr Gly
            20                  25                  30

Val Ser Phe Trp Leu Val Thr Ala Ala Leu Leu Ala Ser Thr Val Phe
        35                  40                  45

Phe Phe Val Glu Arg Asp Arg Val Ser Ala Lys Trp Lys Thr Ser Leu
    50                  55                  60

Thr Val Ser Gly Leu Val Thr Gly Ile Ala Phe Trp His Tyr Met Tyr
65                  70                  75                  80

Met Arg Gly Val Trp Ile Glu Thr Gly Asp Ser Pro Thr Val Phe Arg
                85                  90                  95

Tyr Ile Asp Trp Leu Leu Thr Val Pro Leu Leu Ile Cys Glu Phe Tyr
            100                 105                 110

Leu Ile Leu Ala Ala Ala Thr Asn Val Ala Gly Ser Leu Phe Lys Lys
        115                 120                 125

Leu Leu Val Gly Ser Leu Val Met Leu Val Phe Gly Tyr Met Gly Glu
    130                 135                 140

Ala Gly Ile Met Ala Ala Trp Pro Ala Phe Ile Ile Gly Cys Leu Ala
145                 150                 155                 160

Trp Val Tyr Met Ile Tyr Glu Leu Tyr Ala Gly Glu Gly Lys Ser Ala
                165                 170                 175

Cys Asn Thr Ala Ser Pro Ser Val Gln Ser Ala Tyr Asn Thr Met Met
            180                 185                 190

Ala Ile Ile Val Phe Gly Trp Ala Ile Tyr Pro Val Gly Tyr Phe Thr
        195                 200                 205

Gly Tyr Leu Met Gly Asp Gly Gly Ser Ala Leu Asn Leu Asn Leu Ile
    210                 215                 220

Tyr Asn Leu Ala Asp Phe Val Asn Lys Ile Leu Phe Gly Leu Ile Ile
225                 230                 235                 240

Trp Asn Val Ala Val Lys Glu Ser Ser Asn Ala
                245                 250
```

<210> SEQ ID NO 34
<211> LENGTH: 753
<212> TYPE: DNA
<213> ORGANISM: Marine eubacteria

<400> SEQUENCE: 34

-continued

```
accatgggta aattattact gatattaggt agtgttattg cacttcctac atttgctgca     60

ggtggcggtg accttgatgc tagtgattac actggtgttt ctttttggtt agttacagct    120

gctctattag catctactgt atttttcttt gttgaaagag atagagtttc tgcaaaatgg    180

aaaacatcat taactgtatc tggtcttgtt actggtattg ctttctggca ttacatgtac    240

atgagaggag tatggattga aactggtgat tcgccaactg tatttagata cattgattgg    300

ttactaacag ttcctttatt aatatgtgaa ttctacttaa ttcttgctgc tgcaactaat    360

gttgccggct cattatttaa gaaacttcta gttggttctc ttgttatgct tgtgtttggt    420

tacatgggtg aagcaggaat tatggcagct tggcctgcat tcattattgg gtgtttagct    480

tgggtataca tgatttatga actatatgct ggagaaggaa aatctgcatg taatactgca    540

agtccttcgg ttcaatcagc ttacaacaca atgatggcta tcatagtctt cggttgggca    600

atttatcctg taggttattt cacaggttac ctaatgggtg acggtggatc agctcttaac    660

ttaaacctta tttataacct tgctgacttt gttaacaaga ttctatttgg tttaattata    720

tggaatgttg ctgttaaaga atcttctaat gct                                 753
```

<210> SEQ ID NO 35
<211> LENGTH: 251
<212> TYPE: PRT
<213> ORGANISM: Marine eubacteria

<400> SEQUENCE: 35

```
Thr Met Gly Lys Leu Leu Leu Ile Leu Gly Ser Val Ile Ala Leu Pro
1               5                   10                  15

Thr Phe Ala Ala Gly Gly Gly Asp Leu Asp Ala Ser Asp Tyr Thr Gly
            20                  25                  30

Val Ser Phe Trp Leu Val Thr Ala Ala Leu Leu Ala Ser Thr Val Phe
        35                  40                  45

Phe Phe Val Glu Arg Asp Arg Val Ser Ala Lys Trp Lys Thr Ser Leu
    50                  55                  60

Thr Val Ser Gly Leu Val Thr Gly Ile Ala Phe Trp His Tyr Met Tyr
65                  70                  75                  80

Met Arg Gly Val Trp Ile Glu Thr Gly Asp Ser Pro Thr Val Phe Arg
                85                  90                  95

Tyr Ile Asp Trp Leu Leu Thr Val Pro Leu Leu Ile Cys Glu Phe Tyr
            100                 105                 110

Leu Ile Leu Ala Ala Ala Thr Asn Val Ala Gly Ser Leu Phe Lys Lys
        115                 120                 125

Leu Leu Val Gly Ser Leu Val Met Leu Val Phe Gly Tyr Met Gly Glu
    130                 135                 140

Ala Gly Ile Met Ala Ala Trp Pro Ala Phe Ile Ile Gly Cys Leu Ala
145                 150                 155                 160

Trp Val Tyr Met Ile Tyr Glu Leu Tyr Ala Gly Glu Gly Lys Ser Ala
                165                 170                 175

Cys Asn Thr Ala Ser Pro Ser Val Gln Ser Ala Tyr Asn Thr Met Met
            180                 185                 190

Ala Ile Ile Val Phe Gly Trp Ala Ile Tyr Pro Val Gly Tyr Phe Thr
        195                 200                 205

Gly Tyr Leu Met Gly Asp Gly Gly Ser Ala Leu Asn Leu Asn Leu Ile
    210                 215                 220

Tyr Asn Leu Ala Asp Phe Val Asn Lys Ile Leu Phe Gly Leu Ile Ile
225                 230                 235                 240
```

-continued

Trp Asn Ala Ala Val Lys Glu Ser Ser Asn Ala
245 250

<210> SEQ ID NO 36
<211> LENGTH: 753
<212> TYPE: DNA
<213> ORGANISM: Marine eubacteria

<400> SEQUENCE: 36
accatgggta aattattact gatattaggt agtgttattg cacttcctac atttgctgca 60
ggtggtggtg accttgatgc tagtgattac actggtgttt ctttttggtt agttactgct 120
gctttattag catctactgt atttttcttt gttgaaagag atagagtttc tgcaaaatgg 180
aaaacatcat taactgtatc tggtcttgtt actggtattg ctttctggca ttacatgtac 240
atgagagggg tatggattga aactggtgat tcgccaactg tatttagata cattgattgg 300
ttactaacag ttcctctatt aatatgtgaa ttctacttaa ttcttgctgc tgctactaat 360
gttgccggct cattatttaa gaaacttcta gttggttctc ttgttatgct tgtgtttggt 420
tacatgggtg aagcaggaat tatggcagct tggcctgcat tcattattgg gtgtttagct 480
tgggtataca tgatttatga actatatgct ggagaaggaa aatctgcatg taatactgca 540
agtccttcgg ttcaatcagc ttacaacaca atgatggcta tcatagtctt cggttgggca 600
atttatcctg taggttattt cacaggttac ctaatgggtg acggtggatc agctcttaac 660
ttaaacctta tttataacct tgctgacttt gttaacaaga ttctatttgg tttaattata 720
tggaatgctg ctgttaaaga atcttctaat gct 753

<210> SEQ ID NO 37
<211> LENGTH: 251
<212> TYPE: PRT
<213> ORGANISM: Marine eubacteria

<400> SEQUENCE: 37

Thr Met Gly Lys Leu Leu Leu Ile Leu Gly Ser Val Ile Ala Leu Pro
1 5 10 15

Thr Phe Ala Ala Gly Gly Gly Asp Leu Asp Ala Ser Asp Tyr Thr Gly
20 25 30

Val Ser Phe Trp Leu Val Thr Ala Ala Leu Leu Ala Ser Thr Val Phe
35 40 45

Phe Phe Val Glu Arg Asp Arg Val Ser Ala Lys Trp Lys Thr Ser Leu
50 55 60

Thr Val Ser Gly Leu Val Thr Gly Ile Ala Phe Trp His Tyr Met Tyr
65 70 75 80

Met Arg Gly Val Trp Ile Glu Thr Gly Asp Ser Pro Thr Val Phe Arg
85 90 95

Tyr Ile Asp Trp Leu Leu Thr Val Pro Leu Leu Ile Cys Glu Phe Tyr
100 105 110

Leu Ile Leu Ala Ala Ala Thr Asn Val Ala Gly Ser Leu Phe Lys Lys
115 120 125

Leu Leu Val Gly Ser Leu Val Met Leu Val Phe Gly Tyr Met Gly Glu
130 135 140

Ala Gly Ile Met Ala Ala Trp Pro Ala Phe Ile Ile Gly Cys Leu Ala
145 150 155 160

Trp Val Tyr Met Ile Tyr Glu Leu Trp Ala Gly Glu Gly Lys Ser Ala
165 170 175

-continued

```
Cys Asn Thr Ala Ser Pro Ala Val Gln Ser Ala Tyr Asn Thr Met Met
            180                 185                 190

Tyr Ile Ile Ile Phe Gly Trp Ala Ile Tyr Pro Val Gly Tyr Phe Thr
        195                 200                 205

Gly Tyr Leu Met Gly Asp Gly Gly Ser Ala Leu Asn Leu Asn Leu Ile
    210                 215                 220

Tyr Asn Leu Ala Asp Phe Val Asn Lys Ile Leu Phe Gly Leu Ile Ile
225                 230                 235                 240

Trp Asn Val Ala Val Lys Glu Ser Ser Asn Ala
                245                 250
```

```
<210> SEQ ID NO 38
<211> LENGTH: 753
<212> TYPE: DNA
<213> ORGANISM: Marine eubacteria

<400> SEQUENCE: 38

accatgggta aattattact gatattaggt agtgttattg cacttcctac atttgctgca      60

ggtggtggtg accttgatgc tagtgattac actggtgttt ctttttggtt agttactgct     120

gctttattag catctactgt atttttcttt gttgaaagag atagagtttc tgcaaaatgg     180

aaaacatcat taactgtatc tggtcttgtt actggtattg ctttctggca ttacatgtat     240

atgagagggg tatggattga aactggtgat tcgccaactg tatttagata catagattgg     300

ttactaacag ttcctttatt aatatgtgaa ttctacttaa ttcttgccgc tgcaactaat     360

gttgctggat cattatttaa gaaattactt gttggttctc ttgttatgct tgtgtttggt     420

tacatgggtg aagcaggaat catggctgca tggcctgcat tcattattgg gtgtttagct     480

tgggtataca tgatttatga actatgggct ggagaaggaa aatctgcatg taatactgca     540

agtcctgctg tgcaatcagc ttacaacaca atgatgtata tcatcatctt tggttgggcg     600

atttatcctg taggttattt cacaggttac cttatgggtg acggtggatc agcacttaac     660

ttaaacctta tttataacct tgctgacttt gttaacaaga ttctatttgg tttaattata     720

tggaatgttg ctgttaaaga atcttctaat gct                                   753
```

```
<210> SEQ ID NO 39
<211> LENGTH: 251
<212> TYPE: PRT
<213> ORGANISM: Marine eubacteria

<400> SEQUENCE: 39

Thr Met Gly Lys Leu Leu Leu Ile Leu Gly Ser Val Ile Ala Leu Pro
1               5                   10                  15

Thr Phe Ala Ala Gly Gly Gly Asp Leu Asp Ala Ser Asp Tyr Thr Gly
            20                  25                  30

Val Ser Phe Trp Leu Val Thr Ala Ala Leu Leu Ala Ser Thr Val Phe
        35                  40                  45

Phe Phe Val Glu Arg Asp Arg Val Ser Ala Lys Trp Lys Thr Ser Leu
    50                  55                  60

Thr Val Ser Gly Leu Val Thr Gly Ile Ala Phe Trp His Tyr Met Tyr
65                  70                  75                  80

Met Arg Gly Val Trp Ile Glu Thr Gly Asp Ser Pro Thr Val Phe Arg
                85                  90                  95

Tyr Ile Asp Trp Leu Leu Thr Val Pro Leu Leu Ile Cys Glu Phe Tyr
            100                 105                 110

Leu Ile Leu Ala Ala Ala Thr Asn Val Ala Gly Ser Leu Phe Lys Lys
```

-continued

```
        115                 120                 125

Leu Leu Val Gly Ser Leu Val Met Leu Val Phe Gly Tyr Met Gly Glu
    130                 135                 140

Ala Gly Ile Met Ala Ala Trp Pro Ala Phe Ile Val Gly Cys Leu Ala
145                 150                 155                 160

Trp Val Tyr Met Ile Tyr Glu Leu Trp Ala Gly Glu Gly Lys Ser Ala
                165                 170                 175

Cys Asn Thr Ala Ser Pro Ala Val Gln Ser Ala Tyr Asn Thr Met Met
            180                 185                 190

Tyr Ile Ile Ile Val Gly Trp Ala Ile Tyr Pro Val Gly Tyr Phe Thr
        195                 200                 205

Gly Tyr Leu Met Gly Asp Gly Gly Ser Ala Leu Asn Leu Asn Leu Ile
    210                 215                 220

Tyr Asn Leu Ala Asp Phe Val Asn Lys Ile Leu Phe Gly Leu Ile Ile
225                 230                 235                 240

Trp Asn Val Ala Val Lys Glu Ser Ser Asn Ala
                245                 250


<210> SEQ ID NO 40
<211> LENGTH: 753
<212> TYPE: DNA
<213> ORGANISM: Marine eubacteria

<400> SEQUENCE: 40

accatgggta aattattact gatattaggt agtgttattg cacttcctac atttgctgca      60

ggtggcggtg accttgatgc tagtgattac actggtgttt ctttttggtt agttacagct     120

gctctattag cgtctactgt atttttcttt gttgaaagag atagagtttc tgcaaaatgg     180

aaaacatcat taactgtatc tggtcttgtt actggtattg ctttctggca ttacatgtat     240

atgagaggag tatggattga aactggtgat tcgccaactg tatttagata cattgattgg     300

ttactaacag ttcctttatt aatatgtgaa ttctacttaa ttcttgctgc tgcaactaat     360

gttgccggct cattatttaa gaaacttcta gttggttctc ttgttatgct tgtgtttggt     420

tacatgggtg aagcaggaat aatggcggct tggcctgcat tcatcgttgg atgtttagca     480

tgggtatata tgatttatga actatgggct ggtgaaggaa aatctgcatg taatactgca     540

agtcctgctg tacagtcagc ttacaacaca atgatgtata tcatcatcgt tggttgggca     600

atttatcctg taggttattt cacaggttac ctaatgggtg acggtggatc agctcttaat     660

ctaaacctta tttataacct tgctgacttt gttaacaaga ttctatttgg tttaattata     720

tggaatgttg ctgttaaaga atcttctaat gct                                  753


<210> SEQ ID NO 41
<211> LENGTH: 252
<212> TYPE: PRT
<213> ORGANISM: Marine eubacteria

<400> SEQUENCE: 41

Thr Met Gly Lys Leu Leu Leu Ile Leu Gly Ser Ala Ile Ala Leu Pro
1               5                   10                  15

Ser Phe Ala Ala Ala Gly Gly Asp Leu Asp Ile Ser Asp Thr Val Gly
            20                  25                  30

Val Ser Phe Trp Leu Val Thr Ala Gly Met Leu Ala Ala Thr Val Phe
        35                  40                  45

Phe Phe Val Glu Arg Asp Gln Val Ser Ala Lys Trp Lys Thr Ser Leu
    50                  55                  60
```

-continued

Thr Val Ser Gly Leu Ile Thr Gly Ile Ala Phe Trp His Tyr Leu Tyr
65 70 75 80

Met Arg Gly Val Trp Ile Asp Thr Gly Asp Thr Pro Thr Val Phe Arg
85 90 95

Tyr Ile Asp Trp Leu Leu Thr Val Pro Leu Gln Met Val Glu Phe Tyr
100 105 110

Leu Ile Leu Ala Ala Cys Thr Ser Val Ala Ala Ser Leu Phe Lys Lys
115 120 125

Leu Leu Ala Gly Ser Leu Val Met Leu Gly Ala Gly Phe Ala Gly Glu
130 135 140

Ala Gly Leu Ala Pro Val Leu Pro Ala Phe Ile Leu Gly Met Ala Gly
145 150 155 160

Trp Leu Tyr Met Ile Tyr Glu Leu His Met Gly Glu Gly Lys Ala Ala
165 170 175

Val Ser Thr Ala Ser Pro Ala Val Asn Ser Ala Tyr Asn Ala Met Met
180 185 190

Lys Ile Ile Val Ile Gly Trp Ala Ile Tyr Pro Ala Gly Tyr Ala Ala
195 200 205

Gly Tyr Leu Met Ser Gly Asp Gly Val Tyr Ala Ser Asn Leu Asn Leu
210 215 220

Ile Tyr Asn Leu Ala Asp Phe Val Asn Lys Ile Leu Phe Gly Leu Ile
225 230 235 240

Ile Trp Asn Val Ala Val Lys Glu Ser Ser Asn Ala
245 250

<210> SEQ ID NO 42
<211> LENGTH: 756
<212> TYPE: DNA
<213> ORGANISM: Marine eubacteria

<400> SEQUENCE: 42
accatgggta aattattact gatattaggt agtgctattg cacttccatc atttgctgct 60
gctggtggcg atctagatat aagtgatact gttggtgttt cattctggct ggttacagct 120
ggtatgttag cggcaactgt attctttttt gtagaaagag accaagtcag cgctaagtgg 180
aaaacttcac ttactgtatc tggtttaatt actggtatag ctttttggca ttatctctac 240
atgagaggtg tttggataga tactggtgat acaccaacag tatttagata tattgattgg 300
ctattaactg ttccattaca aatggttgag ttctatctaa ttcttgctgc ttgtacaagt 360
gttgctgctt cattatttaa gaagcttcta gctggttcat tagtaatgtt aggtgctgga 420
tttgcaggcg aagctggttt agctcctgta ttacctgctt tcattcttgg tatggctggt 480
tggttataca tgatttatga gctacatatg ggtgaaggta aggctgctgt aagtactgca 540
agtcctgctg ttaactctgc ttacaatgca atgatgaaga ttattgttat tggatgggca 600
atttatcctg ctggatatgc tgctggttac ctaatgagtg gtgacggtgt atacgcttca 660
aacttaaacc ttatatataa ccttgctgac tttgttaaca agattctatt tggtttgatc 720
atttggaatg ttgctgttaa agaatcttct aatgct 756

<210> SEQ ID NO 43
<211> LENGTH: 252
<212> TYPE: PRT
<213> ORGANISM: Marine eubacteria

<400> SEQUENCE: 43

-continued

```
Thr Met Gly Lys Leu Leu Leu Ile Leu Gly Ser Ala Ile Ala Leu Pro
1               5                   10                  15

Ser Phe Ala Ala Ala Gly Gly Asp Leu Asp Ile Ser Asp Thr Val Gly
            20                  25                  30

Val Ser Phe Trp Leu Val Thr Ala Gly Met Leu Ala Ala Thr Val Phe
        35                  40                  45

Phe Phe Val Glu Arg Asp Gln Val Ser Ala Glu Trp Lys Thr Ser Leu
    50                  55                  60

Thr Val Ser Gly Leu Ile Thr Gly Ile Ala Phe Trp His Tyr Leu Tyr
65                  70                  75                  80

Met Arg Gly Val Trp Ile Asp Thr Gly Asp Thr Pro Thr Val Phe Arg
                85                  90                  95

Tyr Ile Asp Trp Leu Leu Thr Val Pro Leu Gln Met Val Glu Phe Tyr
            100                 105                 110

Leu Ile Leu Ala Ala Cys Thr Ser Val Ala Ala Ser Leu Phe Lys Lys
        115                 120                 125

Leu Leu Ala Gly Ser Leu Val Met Leu Gly Ala Gly Phe Ala Gly Glu
    130                 135                 140

Ala Gly Leu Ala Pro Val Leu Pro Ala Phe Ile Ile Gly Met Ala Gly
145                 150                 155                 160

Trp Leu Tyr Met Ile Tyr Glu Leu Tyr Met Gly Glu Gly Lys Ala Ala
                165                 170                 175

Val Ser Thr Ala Ser Pro Ala Val Asn Ser Ala Tyr Asn Ala Met Met
            180                 185                 190

Met Ile Ile Val Val Gly Trp Ala Ile Tyr Pro Ala Gly Tyr Ala Ala
        195                 200                 205

Gly Tyr Leu Met Gly Gly Glu Gly Val Tyr Ala Ser Asn Leu Asn Leu
    210                 215                 220

Ile Tyr Asn Leu Ala Asp Phe Val Asn Lys Ile Leu Phe Gly Leu Ile
225                 230                 235                 240

Ile Trp Asn Val Ala Val Lys Glu Ser Ser Asn Ala
                245                 250
```

<210> SEQ ID NO 44
<211> LENGTH: 756
<212> TYPE: DNA
<213> ORGANISM: Marine eubacteria

<400> SEQUENCE: 44

```
accatgggta aattattact gatattaggt agtgctattg cacttccatc atttgctgct     60

gctggtggcg atctagatat aagtgatact gttggtgttt cattctggct ggttacagct    120

ggtatgttag cggcaactgt gttctttttt gtagaaagag accaagtcag cgctgagtgg    180

aaaacttcac ttactgtatc tggtttaatt actggtatag ctttttggca ttatctctat    240

atgagaggtg tttggataga tactggtgat accccaacag tattcagata tattgattgg    300

ttattaactg ttccattaca aatggttgag ttctatctaa ttcttgctgc ttgtacaagt    360

gttgctgctt cattatttaa gaagcttcta gctggttcat tagtaatgtt aggtgctgga    420

tttgcaggcg aagctggatt agctcctgta ttacctgctt tcattattgg tatggctgga    480

tggttataca tgatttatga gctatatatg ggtgaaggta aggctgctgt aagtactgca    540

agtcctgctg ttaactctgc atacaacgca atgatgatga ttattgttgt tggatgggca    600

atttatcctg ctggatatgc tgctggttac ctaatgggtg gcgaaggtgt atacgcttca    660

aacttaaacc ttatatataa ccttgctgac tttgttaaca agattctatt tggtttgatc    720
```

-continued

```
atttggaatg ttgctgttaa agaatcttct aatgct                           756


<210> SEQ ID NO 45
<211> LENGTH: 252
<212> TYPE: PRT
<213> ORGANISM: Marine eubacteria

<400> SEQUENCE: 45

Thr Met Gly Lys Leu Leu Leu Ile Leu Gly Ser Ala Ile Ala Leu Pro
1               5                   10                  15

Ser Phe Ala Ala Ala Gly Gly Asp Leu Asp Ile Ser Asp Thr Val Gly
            20                  25                  30

Val Ser Phe Trp Leu Val Thr Ala Gly Met Leu Ala Ala Thr Val Phe
        35                  40                  45

Phe Phe Val Glu Arg Asp Gln Val Ser Ala Lys Trp Lys Thr Ser Leu
    50                  55                  60

Thr Val Ser Gly Leu Ile Thr Gly Ile Ala Phe Trp His Tyr Leu Tyr
65                  70                  75                  80

Met Arg Gly Val Trp Ile Asp Thr Gly Asp Thr Pro Thr Val Phe Arg
                85                  90                  95

Tyr Ile Asp Trp Leu Leu Thr Val Pro Leu Gln Met Val Glu Phe Tyr
            100                 105                 110

Leu Ile Leu Ala Ala Cys Thr Asn Val Ala Ala Ser Leu Phe Lys Lys
        115                 120                 125

Leu Leu Ala Gly Ser Leu Val Met Leu Gly Ala Gly Phe Ala Gly Glu
    130                 135                 140

Ala Gly Leu Ala Pro Val Trp Pro Ala Phe Ile Ile Gly Met Ala Gly
145                 150                 155                 160

Trp Leu Tyr Met Ile Tyr Glu Leu Tyr Met Gly Glu Gly Lys Ala Ala
                165                 170                 175

Val Ser Thr Ala Ser Pro Ala Val Asn Ser Ala Tyr Asn Ala Met Met
            180                 185                 190

Met Ile Ile Val Val Gly Trp Ala Ile Tyr Pro Ala Gly Tyr Ala Ala
        195                 200                 205

Gly Tyr Leu Met Gly Gly Glu Gly Val Tyr Ala Ser Asn Leu Asn Leu
    210                 215                 220

Ile Tyr Asn Leu Ala Asp Phe Val Asn Lys Ile Leu Phe Gly Leu Ile
225                 230                 235                 240

Ile Trp Asn Val Ala Val Lys Glu Ser Ser Asn Ala
                245                 250


<210> SEQ ID NO 46
<211> LENGTH: 756
<212> TYPE: DNA
<213> ORGANISM: Marine eubacteria

<400> SEQUENCE: 46

accatgggta aattattact gatattaggt agtgctattg cacttccatc atttgctgct      60

gctggtggcg atctagatat aagtgatact gttggtgttt cattctggct ggttacagct     120

ggtatgttag cggcaactgt gttctttttt gtagaaagag accaagtcag cgctaagtgg     180

aaaacttcac ttactgtatc tggtttaatt actggtatag ccttttggca ttatctctat     240

atgagaggtg tttggataga cactggtgat accccaacag tattcagata tattgattgg     300

ttattaactg ttccattaca aatggttgag ttctatctaa ttcttgctgc ttgtacaaat     360
```

-continued

```
gttgctgctt cattatttaa gaagcttcta gctggttcat tagtaatgtt aggtgctgga    420

tttgcaggcg aagctggatt agctcctgta tggcctgctt tcattattgg tatggctgga    480

tggttataca tgatttatga gctatatatg ggtgaaggta aggctgctgt aagtactgca    540

agtcctgctg ttaactctgc atacaacgca atgatgatga ttattgttgt tggatgggca    600

atttatcctg ctggatatgc tgctggttac ctaatgggtg gcgaaggtgt atacgcttca    660

aacctaaacc ttatatataa ccttgctgac tttgttaaca agattctatt tggtttgatc    720

atttggaatg ttgctgttaa agaatcttct aatgct                              756
```

<210> SEQ ID NO 47
<211> LENGTH: 252
<212> TYPE: PRT
<213> ORGANISM: Marine eubacteria

<400> SEQUENCE: 47

```
Thr Met Gly Lys Leu Leu Leu Ile Leu Gly Ser Ala Ile Ala Leu Pro
1               5                   10                  15

Ser Phe Ala Ala Ala Gly Gly Asp Leu Asp Ile Ser Asp Thr Val Gly
            20                  25                  30

Val Ser Phe Trp Leu Val Thr Ala Gly Met Leu Ala Ala Thr Val Phe
        35                  40                  45

Phe Phe Val Glu Arg Asp Gln Val Ser Ala Lys Trp Lys Thr Ser Leu
    50                  55                  60

Thr Val Ser Gly Leu Ile Thr Gly Ile Ala Phe Trp His Tyr Leu Tyr
65                  70                  75                  80

Met Arg Gly Val Trp Ile Asp Thr Gly Asp Thr Pro Thr Val Phe Arg
                85                  90                  95

Tyr Ile Asp Trp Leu Leu Thr Val Pro Leu Gln Met Val Glu Phe Tyr
            100                 105                 110

Leu Ile Leu Ala Ala Cys Thr Ser Val Ala Ala Ser Leu Phe Lys Lys
        115                 120                 125

Leu Leu Ala Gly Ser Leu Val Met Leu Gly Ala Gly Ser Ala Gly Glu
    130                 135                 140

Ala Gly Leu Ala Pro Val Leu Pro Ala Phe Ile Ile Gly Met Ala Gly
145                 150                 155                 160

Trp Leu Tyr Met Ile Tyr Glu Leu Tyr Met Gly Glu Gly Lys Ala Ala
                165                 170                 175

Val Ser Thr Ala Ser Pro Ala Val Asn Ser Ala Tyr Asn Ala Met Met
            180                 185                 190

Met Ile Ile Val Val Gly Trp Ala Ile Tyr Pro Ala Gly Tyr Ala Ala
        195                 200                 205

Gly Tyr Leu Met Gly Gly Glu Gly Val Tyr Ala Ser Asn Leu Asn Leu
    210                 215                 220

Ile Tyr Asn Leu Ala Asp Phe Val Asn Lys Ile Leu Phe Gly Leu Ile
225                 230                 235                 240

Ile Trp Asn Val Ala Val Lys Glu Ser Ser Asn Ala
                245                 250
```

<210> SEQ ID NO 48
<211> LENGTH: 756
<212> TYPE: DNA
<213> ORGANISM: Marine eubacteria

<400> SEQUENCE: 48

```
accatgggta aattattact gatattaggt agtgctattg cgcttccatc atttgctgct     60
```

-continued

```
gctggtggcg atctagatat aagtgatact gttggtgttt cattctggct ggttacggct    120

ggtatgttag cggcaactgt attctttttt gtagaaagag accaagtcag cgctaagtgg    180

aaaacttcac ttactgtatc tggtttaatt actggtatag ctttttggca ttatctctac    240

atgagaggtg tttggataga tactggtgat acaccaacag tatttagata tattgattgg    300

ttattaactg ttccattaca aatggttgag ttctatctaa ttcttgccgc ttgtacaagt    360

gttgctgctt cattatttaa gaagcttcta gctggttcat tggtaatgtt aggtgctgga    420

tctgcaggcg aagctggatt agctcctgta ttacctgctt tcattattgg tatggctgga    480

tggttataca tgatttatga gctatatatg ggtgaaggta aggctgctgt aagtactgca    540

agtcctgctg ttaactctgc atacaacgca atgatgatga ttattgttgt tggatgggca    600

atttatcctg ctggatatgc tgctggttac ctaatgggtg gcgaaggtgt atacgcttca    660

aacttaaacc tcatatataa ccttgctgac tttgttaaca agattctatt tggtttgatc    720

atttggaatg ttgctgttaa agaatcttct aatgct                              756


<210> SEQ ID NO 49
<211> LENGTH: 252
<212> TYPE: PRT
<213> ORGANISM: Marine eubacteria

<400> SEQUENCE: 49

Thr Met Gly Lys Leu Leu Leu Ile Leu Gly Ser Ala Ile Ala Leu Pro
1               5                   10                  15

Ser Phe Ala Ala Ala Gly Gly Asp Leu Asp Ile Ser Asp Thr Val Gly
            20                  25                  30

Val Ser Phe Trp Leu Val Thr Ala Gly Met Leu Ala Ala Thr Val Phe
        35                  40                  45

Phe Phe Val Glu Arg Asp Gln Val Ser Ala Lys Trp Lys Thr Ser Leu
    50                  55                  60

Thr Val Ser Gly Leu Ile Thr Gly Ile Ala Phe Trp His Tyr Leu Tyr
65                  70                  75                  80

Met Arg Gly Val Trp Ile Asp Thr Gly Asp Thr Pro Thr Val Phe Arg
                85                  90                  95

Tyr Ile Asp Trp Leu Leu Thr Val Pro Leu Gln Met Val Glu Phe Tyr
            100                 105                 110

Leu Ile Leu Ala Ala Cys Thr Asn Val Ala Ala Ser Leu Phe Lys Lys
        115                 120                 125

Leu Leu Ala Gly Ser Leu Val Met Leu Gly Ala Gly Phe Ala Gly Glu
    130                 135                 140

Ala Gly Leu Ala Pro Val Trp Pro Ala Phe Ile Ile Gly Met Ala Gly
145                 150                 155                 160

Trp Leu Tyr Met Ile Tyr Glu Leu Tyr Met Gly Glu Gly Lys Ala Ala
                165                 170                 175

Val Ser Thr Ala Ser Pro Ala Val Asn Ser Ala Tyr Asn Ala Met Met
            180                 185                 190

Val Ile Ile Val Val Gly Trp Ala Ile Tyr Pro Ala Gly Tyr Ala Ala
        195                 200                 205

Gly Tyr Leu Met Gly Gly Glu Gly Val Tyr Ala Ser Asn Leu Asn Leu
    210                 215                 220

Ile Tyr Asn Leu Ala Asp Phe Val Asn Lys Ile Leu Phe Gly Leu Ile
225                 230                 235                 240

Ile Trp Asn Val Ala Val Lys Glu Ser Ser Asn Ala
```

-continued 245 250

<210> SEQ ID NO 50
<211> LENGTH: 756
<212> TYPE: DNA
<213> ORGANISM: Marine eubacteria

<400> SEQUENCE: 50
accatgggta aattattact gatattaggt agtgctattg cacttccatc atttgctgct 60
gctggtggcg atctagatat aagtgatact gttggtgttt cattctggct ggttacagct 120
ggtatgttag cggcaactgt gttctttttt gtagaaagag accaagtcag cgctaagtgg 180
aaaacttcac ttactgtatc tggtttaatt actggtatag ctttttggca ttatctctat 240
atgagaggtg tttggataga cactggtgat accccaacag tattcagata tattgattgg 300
ttattaactg ttccattaca aatggttgag ttctatctaa ttcttgctgc ttgtacaaat 360
gttgctgctt cattatttaa gaagcttcta gctggttcat tagtaatgtt aggtgctgga 420
tttgcaggcg aagctggatt agctcctgta tggcctgctt tcattattgg tatggctgga 480
tggttataca tgatttatga gctatatatg ggtgaaggta aggctgctgt aagtactgca 540
agtcctgctg ttaactctgc atacaacgca atgatggtga ttattgttgt tggatgggca 600
atttatcctg ctggatatgc tgctggttac ctaatgggtg gcgaaggtgt atacgcttca 660
aacctaaacc ttatatataa ccttgctgac tttgttaaca agattctatt tggtttgatc 720
atttggaatg ttgctgttaa agaatcttct aatgct 756

<210> SEQ ID NO 51
<211> LENGTH: 252
<212> TYPE: PRT
<213> ORGANISM: Marine eubacteria

<400> SEQUENCE: 51

Thr Met Gly Lys Leu Leu Leu Ile Leu Gly Ser Ala Ile Ala Leu Pro
1 5 10 15

Ser Phe Ala Ala Ala Gly Gly Asp Leu Asp Ile Ser Asp Thr Val Gly
20 25 30

Val Ser Phe Trp Leu Val Thr Ala Gly Met Leu Ala Ala Thr Val Phe
35 40 45

Phe Phe Val Glu Arg Asp Gln Val Ser Ala Lys Trp Lys Thr Ser Leu
50 55 60

Thr Val Ser Gly Leu Ile Thr Gly Ile Ala Phe Trp His Tyr Leu Tyr
65 70 75 80

Met Arg Gly Val Trp Ile Asp Thr Gly Asp Thr Pro Thr Val Phe Arg
85 90 95

Tyr Ile Asp Trp Leu Leu Thr Val Pro Leu Gln Met Val Glu Phe Tyr
100 105 110

Leu Ile Leu Ala Ala Cys Thr Ser Val Ala Ala Ser Leu Phe Lys Lys
115 120 125

Leu Leu Ala Gly Ser Leu Val Met Leu Gly Ala Gly Phe Ala Gly Glu
130 135 140

Ala Gly Leu Ala Pro Val Leu Pro Ala Phe Ile Ile Gly Met Ala Gly
145 150 155 160

Trp Leu Tyr Met Ile Tyr Glu Leu Tyr Met Gly Glu Gly Lys Ala Ala
165 170 175

Val Ser Thr Ala Ser Pro Ala Val Asn Ser Ala Tyr Asn Ala Met Met
180 185 190

-continued

```
Met Ile Ile Val Val Gly Trp Ala Ile Tyr Pro Ala Gly Tyr Ala Ala
        195                 200                 205

Gly Tyr Leu Met Gly Gly Glu Gly Val Tyr Ala Ser Asn Leu Asn Leu
    210                 215                 220

Ile Tyr Asn Leu Ala Asp Leu Val Asn Lys Ile Leu Phe Gly Leu Ile
225                 230                 235                 240

Ile Trp Asn Val Ala Val Lys Glu Ser Ser Asn Ala
                245                 250


<210> SEQ ID NO 52
<211> LENGTH: 756
<212> TYPE: DNA
<213> ORGANISM: Marine eubacteria

<400> SEQUENCE: 52

accatgggta aattattact gatattaggt agtgctattg cacttccatc atttgctgct      60

gctggtggcg atctagatat aagtgatact gttggtgttt cattctggct ggttacagct     120

ggtatgttag cggcaactgt gttctttttt gtagaaagag accaagtcag cgctaagtgg     180

aaaacttcac ttactgtatc tggtttaatt actggtatag ctttttggca ttatctctat     240

atgagaggtg tttggataga cactggtgat accccaacag tattcagata tattgattgg     300

ttattaactg ttccattaca aatggttgag ttctatctaa ttcttgctgc ttgtacaagt     360

gttgctgctt cattatttaa gaagcttcta gctggttcat tagtaatgtt aggtgctgga     420

tttgcaggcg aagctggatt agctcctgta ttacctgctt tcattattgg tatggctgga     480

tggttataca tgatttatga gctatatatg ggtgaaggta aggctgctgt aagtactgca     540

agtcctgctg ttaactctgc atacaacgca atgatgatga ttattgttgt tggatgggca     600

atttatcctg ctggatatgc tgctggttac ctaatgggtg gcgaaggtgt atacgcttca     660

aacttaaacc ttatatataa ccttgctgac cttgttaaca agattctatt tggtttgatc     720

atttggaatg ttgctgttaa agaatcttct aatgct                               756


<210> SEQ ID NO 53
<211> LENGTH: 252
<212> TYPE: PRT
<213> ORGANISM: Marine eubacteria

<400> SEQUENCE: 53

Thr Met Gly Lys Leu Leu Leu Ile Leu Gly Ser Ala Ile Ala Leu Pro
1               5                   10                  15

Ser Phe Ala Ala Ala Gly Gly Asp Leu Asp Ile Ser Asp Thr Val Gly
            20                  25                  30

Val Ser Phe Trp Leu Val Thr Ala Gly Met Leu Ala Ala Thr Val Phe
        35                  40                  45

Phe Phe Val Glu Arg Asp Gln Val Ser Ala Lys Trp Lys Thr Ser Leu
    50                  55                  60

Thr Val Ser Gly Leu Ile Thr Gly Ile Ala Phe Trp His Tyr Leu Tyr
65                  70                  75                  80

Met Arg Gly Val Trp Ile Asp Thr Gly Asp Thr Pro Thr Val Phe Arg
                85                  90                  95

Tyr Ile Asp Trp Leu Leu Thr Val Pro Leu Gln Val Val Glu Phe Tyr
            100                 105                 110

Leu Ile Leu Ala Ala Cys Thr Ser Val Ala Ala Ser Leu Phe Lys Lys
        115                 120                 125
```

-continued

```
Leu Leu Ala Gly Ser Leu Val Met Leu Gly Ala Gly Phe Ala Gly Glu
    130                 135                 140

Ala Gly Leu Ala Pro Val Leu Pro Ala Phe Ile Ile Gly Met Ala Gly
145                 150                 155                 160

Trp Leu Tyr Met Ile Tyr Glu Leu Tyr Met Gly Glu Gly Lys Ala Ala
                165                 170                 175

Val Ser Thr Ala Ser Pro Ala Val Asn Pro Ala Tyr Asn Ala Met Met
            180                 185                 190

Met Ile Ile Val Val Gly Trp Ala Ile Tyr Pro Ala Gly Tyr Ala Ala
        195                 200                 205

Gly Tyr Leu Met Gly Gly Glu Gly Val Tyr Ala Ser Asn Leu Asn Leu
    210                 215                 220

Ile Tyr Asn Leu Ala Asp Phe Val Asn Lys Ile Leu Phe Gly Leu Ile
225                 230                 235                 240

Ile Trp Asn Val Ala Val Lys Glu Ser Ser Asn Ala
                245                 250


<210> SEQ ID NO 54
<211> LENGTH: 756
<212> TYPE: DNA
<213> ORGANISM: Marine eubacteria

<400> SEQUENCE: 54

accatgggta aattattact gatattaggt agtgctattg cacttccatc atttgctgct      60

gctggtggcg atctagatat aagtgatact gttggtgttt cattctggct ggttacagct     120

ggtatgttag cggcaactgt gttctttttt gtagaaagag accaagtcag cgctaagtgg     180

aaaacttcac ttactgtatc tggtttaatt actggtatag ctttttggca ttatctctat     240

atgagaggtg tttggataga cactggtgat accccaacag tattcagata tattgattgg     300

ttattaactg ttccattaca agtggttgag ttctatctaa ttcttgctgc ttgtacaagt     360

gttgctgctt cattatttaa gaagcttcta gctggttcat tagtaatgtt aggtgctgga     420

tttgcaggcg aagctggatt agctcctgta ttacctgctt tcattattgg tatggctgga     480

tggttataca tgatttatga gctatatatg ggtgaaggca aggctgctgt aagtactgca     540

agtcctgctg ttaaccctgc atacaacgca atgatgatga ttattgttgt tggatgggca     600

atttatcctg ctggatatgc tgctggttac ctaatgggtg gcgaaggtgt atacgcttca     660

aacttaaacc ttatatataa ccttgctgac tttgttaaca agattctatt tggtttgatc     720

atttggaatg ttgctgttaa agaatcttct aatgct                               756


<210> SEQ ID NO 55
<211> LENGTH: 252
<212> TYPE: PRT
<213> ORGANISM: Marine eubacteria

<400> SEQUENCE: 55

Thr Met Gly Lys Leu Leu Leu Ile Leu Gly Ser Ala Ile Ala Leu Pro
1               5                   10                  15

Ser Phe Ala Ala Ala Gly Gly Asp Leu Asp Ile Ser Asp Thr Val Gly
            20                  25                  30

Val Ser Phe Trp Leu Val Thr Ala Gly Met Leu Ala Ala Thr Val Phe
        35                  40                  45

Phe Phe Val Glu Arg Asp Gln Val Ser Ala Lys Trp Lys Thr Ser Leu
    50                  55                  60

Thr Val Ser Gly Leu Ile Thr Gly Ile Ala Phe Trp His Tyr Leu Tyr
```

-continued

```
65                  70                  75                  80

Met Arg Gly Val Trp Ile Asp Thr Gly Asp Thr Pro Thr Val Phe Arg
                85                  90                  95

Tyr Ile Asp Trp Leu Leu Thr Val Pro Leu Gln Met Val Glu Phe Tyr
            100                 105                 110

Leu Ile Leu Ala Ala Cys Thr Ser Val Ala Ala Ser Leu Phe Lys Lys
        115                 120                 125

Leu Leu Ala Gly Ser Leu Val Met Leu Gly Ala Gly Phe Ala Gly Glu
    130                 135                 140

Ala Gly Leu Ala Pro Val Leu Pro Ala Phe Ile Ile Gly Met Ala Gly
145                 150                 155                 160

Trp Leu Tyr Met Ile Tyr Glu Leu His Met Gly Glu Gly Lys Ala Ala
                165                 170                 175

Val Ser Thr Ala Ser Pro Ala Val Asn Ser Ala Tyr Asn Ala Met Met
            180                 185                 190

Lys Ile Ile Val Ile Gly Trp Ala Ile Tyr Pro Ala Gly Tyr Ala Ala
        195                 200                 205

Gly Tyr Leu Met Ser Gly Asp Gly Val Tyr Ala Ser Asn Leu Asn Leu
    210                 215                 220

Ile Tyr Asn Leu Ala Asp Phe Val Asn Lys Ile Leu Phe Gly Leu Ile
225                 230                 235                 240

Ile Trp Asn Val Ala Val Lys Glu Ser Ser Asn Ala
                245                 250


<210> SEQ ID NO 56
<211> LENGTH: 756
<212> TYPE: DNA
<213> ORGANISM: Marine eubacteria

<400> SEQUENCE: 56

accatgggta aattattact gatattaggt agtgctattg cacttccatc atttgctgct     60

gctggtggcg atctagatat aagtgatact gttggtgttt cattctggct ggttacagct    120

ggtatgttag cggcaactgt attctttttt gtagaaagag accaagtcag cgctaagtgg    180

aaaacttcac ttactgtatc tggtttaatt actggtatag ctttttggca ttatctctac    240

atgagaggtg tttggataga tactggtgat acaccaacag tatttagata tattgattgg    300

ttattaactg ttccattaca aatggttgag ttctatctaa ttcttgctgc ttgtacaagt    360

gttgctgctt cattatttaa gaagcttcta gctggttcat tagtaatgtt aggtgctgga    420

tttgcaggcg aagctggttt agctcctgta ttacctgctt tcattattgg tatggctgga    480

tggttataca tgatttatga gctacatatg ggtgaaggta aggctgctgt aagtactgca    540

agtcctgctg ttaactctgc atacaacgca atgatgaaga ttattgttat tggatgggca    600

atttatcctg ctggatatgc tgctggttac ctaatgagtg gtgacggtgt atacgcttca    660

aacttaaacc ttatatataa ccttgctgac tttgttaaca agattctatt tggtttgatc    720

atttggaatg ttgctgttaa agaatcttct aatgct                              756


<210> SEQ ID NO 57
<211> LENGTH: 252
<212> TYPE: PRT
<213> ORGANISM: Marine eubacteria

<400> SEQUENCE: 57

Thr Met Gly Lys Leu Leu Leu Ile Leu Gly Ser Ala Ile Ala Leu Pro
1               5                   10                  15
```

-continued

```
Ser Phe Ala Ala Ala Gly Gly Asp Leu Asp Ile Ser Asp Thr Val Gly
            20                  25                  30

Val Ser Phe Trp Leu Val Thr Ala Gly Met Leu Ala Ala Thr Val Phe
        35                  40                  45

Phe Phe Val Glu Arg Asp Gln Val Ser Ala Lys Trp Lys Thr Ser Leu
    50                  55                  60

Thr Val Ser Gly Leu Ile Thr Gly Ile Ala Phe Trp His Tyr Leu Tyr
65                  70                  75                  80

Met Arg Gly Val Trp Ile Asp Thr Gly Asp Thr Pro Thr Val Phe Arg
                85                  90                  95

Tyr Ile Asp Trp Leu Leu Thr Val Pro Leu Gln Met Val Glu Phe Tyr
            100                 105                 110

Leu Ile Leu Ala Ala Cys Thr Ser Val Ala Ala Ser Leu Phe Lys Lys
        115                 120                 125

Leu Leu Ala Gly Ser Leu Val Met Leu Gly Ala Gly Phe Ala Gly Glu
    130                 135                 140

Ala Gly Leu Ala Pro Val Leu Pro Ala Phe Ile Ile Gly Met Ala Gly
145                 150                 155                 160

Trp Leu Tyr Met Ile Tyr Glu Leu Tyr Met Gly Glu Gly Lys Ala Ala
                165                 170                 175

Val Ser Thr Ala Ser Pro Ala Val Asn Ser Ala Tyr Asn Ala Met Met
            180                 185                 190

Met Ile Ile Val Val Gly Trp Ala Ile Tyr Pro Ala Gly Tyr Ala Ala
        195                 200                 205

Gly Tyr Leu Met Gly Gly Glu Gly Val Tyr Ala Ser Asn Leu Asn Leu
    210                 215                 220

Ile Tyr Asn Leu Ala Asp Phe Val Asn Lys Ile Leu Phe Gly Leu Ile
225                 230                 235                 240

Ile Trp Asn Val Ala Val Lys Glu Ser Ser Asn Ala
                245                 250
```

<210> SEQ ID NO 58
<211> LENGTH: 756
<212> TYPE: DNA
<213> ORGANISM: Marine eubacteria

<400> SEQUENCE: 58

```
accatgggta aattattact gatattaggt agtgctattg cacttccatc atttgctgct      60

gctggtggcg atctagatat aagtgatact gttggtgttt cattctggct ggttacagct     120

ggtatgttag cggcaactgt gttctttttt gtagaaagag accaagtcag cgctaagtgg     180

aaaacttcac ttactgtatc tggtttaatt actggtatag ctttttggca ttatctctat     240

atgagaggtg tttggataga tactggtgat accccaacag tattcagata tattgattgg     300

ttattaactg ttccattaca aatggttgag ttctatctaa ttcttgctgc ttgtacaagt     360

gttgctgctt cattatttaa gaagcttcta gctggttcat tagtaatgtt aggtgctgga     420

tttgcaggcg aagctggatt agctcctgta ttacctgctt tcattattgg tatggctgga     480

tggctataca tgatttatga gctatatatg ggtgaaggta aggctgctgt aagtactgca     540

agtcctgctg ttaactctgc atacaacgca atgatgatga ttattgttgt tggatgggca     600

atttatcctg ctggatatgc tgctggttac ctaatgggtg gcgaaggcgt atacgcttca     660

aacttaaacc ttatatataa ccttgctgac tttgttaaca agattctatt tggtttgatc     720

atttggaatg ttgctgttaa agaatcttct aatgct                               756
```

<210> SEQ ID NO 59
<211> LENGTH: 250
<212> TYPE: PRT
<213> ORGANISM: Marine eubacteria

<400> SEQUENCE: 59

Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Val Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Lys Ser Ser Asn Ala
                245                 250

<210> SEQ ID NO 60
<211> LENGTH: 751
<212> TYPE: DNA
<213> ORGANISM: Marine eubacteria

<400> SEQUENCE: 60
atgggtaaat tattactgat attaggtagt gttatcgcgc ttccaacatt tgctgctggc 60
ggtggcgatc ttgatgctag tgactacact ggtgtttcat tctggttagt tactgctgct 120
ctattagcgt ctactgtatt cttctttgtt gaaagagata gagtgtctgc aaaatggaaa 180
acttcattaa cagtatctgg tttagttact ggtattgctt tttggcatta tatgtacatg 240
agaggtgtat ggatagaaac tggtgattcg cctactgtct ttagatacat cgactggtta 300
ttaactgtgc ctttactaat atgtgagttc tatctgatac ttgctgcagc tactaatgtt 360
gctggttcat tatttaagaa attgctagtt ggttctcttg tgatgcttgt gtttggttac 420

-continued atgggtgaag caggaataat ggcagcttgg cctgcattca tcattggatg tttagcatgg 480
gtatatatga tttatgaact atgggctggt gaaggaaaat ctgcatgcaa tactgcaagt 540
cctgctgtac agtcagctta caacacaatg atgtatatca tcatcgttgg ttgggcaatt 600
tatcctgtag gttatttcac aggttaccta atgggtgacg gtggatcagc tcttaatcta 660
aaccttattt ataaccttgc tgactttgtt aacaagattc tatttggttt aattatatgg 720
aatgttgctg ttaaaaaatc ttctaatgct a 751

<210> SEQ ID NO 61
<211> LENGTH: 250
<212> TYPE: PRT
<213> ORGANISM: Marine eubacteria

<400> SEQUENCE: 61

Met Gly Lys Leu Leu Leu Ile Leu Gly Asn Val Ile Ala Leu Pro Thr
1 5 10 15

Phe Ala Ala Gly Gly Gly Asp Leu Asp Ala Ser Asp Tyr Thr Gly Val
20 25 30

Ser Phe Trp Leu Val Thr Ala Ala Leu Leu Ala Ser Thr Val Phe Phe
35 40 45

Phe Val Glu Arg Asp Arg Val Ser Ala Lys Trp Lys Thr Ser Leu Thr
50 55 60

Val Ser Gly Leu Val Thr Gly Ile Ala Phe Trp His Tyr Met Tyr Met
65 70 75 80

Arg Gly Val Trp Ile Glu Thr Gly Asp Ser Pro Thr Val Phe Arg Tyr
85 90 95

Ile Asp Trp Leu Leu Thr Val Pro Leu Leu Ile Cys Glu Phe Tyr Leu
100 105 110

Ile Leu Ala Ala Ala Thr Asn Val Ala Gly Ser Leu Phe Lys Lys Leu
115 120 125

Leu Val Gly Ser Leu Val Met Leu Val Phe Gly Tyr Met Gly Glu Ala
130 135 140

Gly Ile Met Ala Ala Trp Pro Ala Phe Ile Ile Gly Cys Leu Ala Trp
145 150 155 160

Val Tyr Met Ile Tyr Glu Leu Trp Ala Gly Glu Gly Lys Ser Ala Cys
165 170 175

Asn Thr Ala Ser Pro Ala Val Gln Ser Ala Tyr Asn Thr Met Met Tyr
180 185 190

Ile Ile Ile Val Gly Trp Ala Ile Tyr Pro Val Gly Tyr Phe Thr Gly
195 200 205

Tyr Leu Met Gly Asp Gly Gly Ser Ala Leu Asn Leu Asn Leu Ile Tyr
210 215 220

Asn Leu Ala Asp Phe Val Asn Lys Ile Leu Phe Gly Leu Ile Ile Trp
225 230 235 240

Asn Val Ala Val Lys Glu Ser Ser Asn Ala
245 250

<210> SEQ ID NO 62
<211> LENGTH: 751
<212> TYPE: DNA
<213> ORGANISM: Marine eubacteria

<400> SEQUENCE: 62
atgggtaaat tattactgat attaggtaat gttatcgcgc ttccaacatt tgctgctggc 60
ggtggcgatc ttgatgctag tgactacact ggtgtttcat tctggttagt tactgctgct 120

-continued

```
ctattagcgt ctactgtatt cttctttgtt gaaagagata gagtgtctgc aaaatggaaa    180

acttcattaa cagtatctgg tttagttact ggtattgctt tttggcatta tatgtacatg    240

agaggtgtat ggatagaaac tggtgattcg cctactgtct ttagatacat cgactggtta    300

ttaactgtgc ctttactaat atgtgagttc tatctgatac ttgctgcagc tactaatgtt    360

gctggttcat tatttaagaa attgctagtt ggttctcttg tgatgcttgt gttcggttac    420

atgggtgaag caggaataat ggcagcttgg cctgcattca tcattgggtg tttagcatgg    480

gtatatatga tttatgagct atgggctggt gaaggaaaat ctgcatgtaa tactgcaagt    540

cctgctgtac agtcagctta caacactatg atgtatatta tcattgttgg ttgggcgatt    600

tatcctgtag gctatttcac tggttacctc atgggtgacg gtggatcagc tcttaattta    660

aaccttattt ataaccttgc tgactttgtt aacaagattc tatttggttt aattatatgg    720

aatgttgctg ttaaagaatc ttctaatgct a                                   751
```

```
<210> SEQ ID NO 63
<211> LENGTH: 250
<212> TYPE: PRT
<213> ORGANISM: Marine eubacteria

<400> SEQUENCE: 63

Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Ser Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Ala Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250
```

-continued

<210> SEQ ID NO 64
<211> LENGTH: 751
<212> TYPE: DNA
<213> ORGANISM: Marine eubacteria

<400> SEQUENCE: 64

```
atgggtaaat tattactgat attaggtagt gttattgcgc ttccaacatt tgccgctggc      60

ggtggcgatc ttgatgctag tgactacact ggtgtttctt tctggttagt tactgctgct     120

ctattagcat ctactgtatt cttctttgtt gaaagggata gagtatctgc aaaatggaaa     180

acttcattaa cagtatctgg tttagttact ggtattgctt tttggcatta tatgtacatg     240

agaggtgtat ggatagaaac tggtagttca cctactgtct ttagatacat tgactggcta     300

ttaacagtgc ctttactaat atgtgagttc tatttaatac ttgccgcagc tactaatgtt     360

gctggttcat tatttaagaa attgctagtt ggttctcttg tgatgcttgt gtttggttac     420

atgggtgaag caggaataat ggcagcttgg cctgcattca tcattggatg tttagcatgg     480

gtatatatga tttatgagct atgggctggt gaaggaaaat ctgcatgtaa tactgcaagt     540

cctgctgtac agtcagctta caacacaatg atgtatatca tcatcgctgg ttgggcaatt     600

tatcctgtag gttatttcac aggttaccta atgggtgacg gtggatcagc tcttaatcta     660

aaccttattt ataaccttgc tgactttgtt aacaagattc tatttggttt aattatatgg     720

aatgttgctg ttaaagaatc ttctaatgct a                                    751
```

<210> SEQ ID NO 65
<211> LENGTH: 250
<212> TYPE: PRT
<213> ORGANISM: Marine eubacteria

<400> SEQUENCE: 65

```
Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Val Gly Trp Ala Ile Tyr Pro Val Gly Tyr Phe Thr Gly
```

-continued

```
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250


<210> SEQ ID NO 66
<211> LENGTH: 751
<212> TYPE: DNA
<213> ORGANISM: Marine eubacteria

<400> SEQUENCE: 66

atgggtaaat tattactgat attaggtagt gttatcgcgc ttccaacatt tgctgctggc     60

ggtggcgatc ttgatgctag tgactacact ggtgtttcat tctggttagt tactgctgct    120

ctattagcgt ctactgtatt cttctttgtt gaaagagata gagtgtctgc aaaatggaaa    180

acttcattaa cagtatctgg tttagttact ggtattgctt tttggcatta tatgtacatg    240

agaggtgtat ggatagaaac tggtgattcg cctactgtct ttagatacat cgactggtta    300

ttaactgtgc ctttactaat atgtgagttc tatctgatac ttgctgcagc tactaatgtt    360

gctggttcat tatttaagaa attgctagtt ggttctcttg tgatgcttgt gtttggttac    420

atgggtgaag caggaataat ggcagcttgg cctgcattca tcattggatg tttagcatgg    480

gtatatatga tttatgaact atgggctggt gaaggaaaat ctgcatgcaa tactgcaagt    540

cctgctgtac agtcagctta caacacaatg atgtatatca tcatcgttgg ttgggcaatt    600

tatcctgtag gttatttcac aggttaccta atgggtgacg gtggatcagc tcttaatcta    660

aaccttattt ataaccttgc tgactttgtt aacaagattc tatttggttt aattatatgg    720

aatgttgctg ttaaagaatc ttctaatgct a                                   751


<210> SEQ ID NO 67
<211> LENGTH: 250
<212> TYPE: PRT
<213> ORGANISM: Marine eubacteria

<400> SEQUENCE: 67

Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Ser Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140
```

-continued

```
Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Ala Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Asn Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250
```

<210> SEQ ID NO 68
<211> LENGTH: 751
<212> TYPE: DNA
<213> ORGANISM: Marine eubacteria

<400> SEQUENCE: 68

```
atgggtaaat tattactgat attaggtagt gttatcgcgc ttccaacatt tgctgctggc      60

ggtggcgatc ttgatgctag tgactacact ggtgtttcat tctggttagt tactgctgct     120

ctattagcgt ctactgtatt cttctttgtt gaaagagata gagtgtctgc aaaatggaaa     180

acttcattaa cagtatctgg tttagttact ggtattgctt tttggcatta tatgtacatg     240

agaggtgtat ggatagaaac tggtagttca cctactgtct ttagatacat tgactggcta     300

ttaacagtgc ctttactaat atgtgagttc tatttaatac ttgccgcagc tactaatgtt     360

gctggttcat tatttaagaa attgctagtt ggttctcttg ttatgcttgt gttcggttac     420

atgggtgaag caggaataat ggcagcttgg cctgcattca tcattgggtg tttagcatgg     480

gtatatatga tttatgagct atgggctggt gaaggaaaat ctgcatgtaa tactgcaagt     540

cctgctgtac agtcagctta caacacaatg atgtatatca tcatcgctgg ttgggcaatt     600

tatcctgtag gttatttcac aggttaccta atgggtgacg gtggatcagc tcttaatcta     660

aaccttaatt ataaccttgc tgactttgtt aacaagattc tatttggttt aattatatgg     720

aatgttgctg ttaaagaatc ttctaatgct a                                    751
```

<210> SEQ ID NO 69
<211> LENGTH: 250
<212> TYPE: PRT
<213> ORGANISM: Marine eubacteria

<400> SEQUENCE: 69

```
Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80
```

-continued

```
Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Val Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250


<210> SEQ ID NO 70
<211> LENGTH: 751
<212> TYPE: DNA
<213> ORGANISM: Marine eubacteria

<400> SEQUENCE: 70

atgggtaaat tattactgat attaggtagt gttatcgcgc ttccaacatt tgctgctggc      60

ggtggcgatc ttgatgctag tgactatact ggtgtttcat tctggttagt tactgctgct     120

ctattagcgt ctactgtatt cttctttgtt gaaagagata gagtgtctgc aaaatggaaa     180

acttcattaa cagtatctgg tttagttact ggtattgctt tttggcatta tatgtacatg     240

agaggtgtat ggatagaaac tggtgattcg cctactgtct ttagatacat agactggtta     300

ttaactgtgc ctttactaat atgtgagttc tatctgatac ttgctgcagc tactaatgtt     360

gctggttcat tatttaagaa attgctagtt ggttctcttg tgatgcttgt gtttggttac     420

atgggtgaag caggaataat ggcagcttgg cctgcattca tcattggatg tttagcatgg     480

gtatatatga tttatgaact atgggctggt gaaggaaaat ctgcatgcaa tactgcaagt     540

cctgctgtac aatcagctta caacacaatg atgtatatca tcatcgttgg ttgggcaatt     600

tatcctgtag gttatttcac aggttaccta atgggtgacg gtggatcagc tcttaatcta     660

aaccttattt ataaccttgc tgactttgtt aacaagattc tatttggttt aattatatgg     720

aatgttgctg ttaaagaatc ttctaatgct a                                    751


<210> SEQ ID NO 71
<211> LENGTH: 250
<212> TYPE: PRT
<213> ORGANISM: Marine eubacteria

<400> SEQUENCE: 71

Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
```

-continued

```
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Ser Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Val Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250
```

<210> SEQ ID NO 72
<211> LENGTH: 751
<212> TYPE: DNA
<213> ORGANISM: Marine eubacteria

<400> SEQUENCE: 72

```
atgggtaaat tattactgat attaggtagt gttattgcgc ttccaacatt tgccgctggc      60

ggtggcgatc ttgatgctag tgactacact ggtgtttctt tctggttagt tactgctgct     120

ctattagcat ctactgtatt cttctttgtt gaaagggata gagtatctgc aaaatggaaa     180

acttcattaa cagtatctgg tttagttact ggtattgctt tttggcatta tatgtacatg     240

agaggtgtat ggatagaaac tggtagttca cctactgtct ttagatacat tgactggcta     300

ttaacagtgc ctttactaat atgtgagttc tatttaatac ttgccgcagc tactaatgtt     360

gctggttcat tatttaagaa attgctagtt ggttctcttg ttatgcttgt gttcggttac     420

atgggtgaag caggaataat ggcagcttgg cctgcattca tcattggatg tttagcatgg     480

gtatatatga tttatgaact atgggctggt gaaggaaaat ctgcatgcaa tactgcaagt     540

cctgctgtac agtcagctta caacacaatg atgtatatca tcatcgttgg ttgggcaatt     600

tatcctgtag gttatttcac aggttaccta atgggtgacg gtggatcagc tcttaatcta     660

aaccttattt ataaccttgc tgactttgtt aacaagattc tatttggttt aattatatgg     720

aatgttgctg ttaaagaatc ttctaatgct a                                    751
```

-continued

<210> SEQ ID NO 73
<211> LENGTH: 250
<212> TYPE: PRT
<213> ORGANISM: Marine eubacteria

<400> SEQUENCE: 73

```
Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Phe Gly Trp Ala Ile Tyr Leu Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250
```

<210> SEQ ID NO 74
<211> LENGTH: 751
<212> TYPE: DNA
<213> ORGANISM: Marine eubacteria

<400> SEQUENCE: 74

```
atgggtaaat tattactgat attaggtagt gttattgcgc ttccaacatt tgccgctggt      60

ggtggtgacc tggatgctag tgactacact ggtgtatctt tctggttagt tactgctgct     120

ctattagcat ctactgtatt tttctttgtt gaaagagaca gagtttctgc taaatggaaa     180

acatcattaa cagtatctgg tttagttact ggtattgctt tttggcatta catgtacatg     240

agaggtgtat ggattgaaac tggtgattca ccaactgttt ttagatacat cgactggttg     300

ctaactgtgc ctttactaat ttgtgagttc tacttaatac tagcagcagc tactaacgtt     360

gctggttctt tattcaagaa attactagtt ggttctcttg ttatgcttgt gtttggttac     420

atgggtgaag caggaattat ggcagcctgg cctgcattca ttataggatg tttagcatgg     480
```

-continued

```
gtatacatga tttatgaatt atgggctgga gaaggaaagt ctgcatgtaa cactgcaagt    540

cctgcagttc agtcagctta caacacaatg atgtatatca tcatctttgg ttgggctatt    600

taccttgtag gttatttcac tggttaccta atgggtgacg gtggatcagc tcttaactta    660

aaccttatct ataaccttgc tgactttgtt aacaagattc tatttggttt aattatatgg    720

aatgttgctg ttaaagaatc ttctaatgct a                                   751


<210> SEQ ID NO 75
<211> LENGTH: 250
<212> TYPE: PRT
<213> ORGANISM: Marine eubacteria

<400> SEQUENCE: 75

Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Ser Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Ala Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250


<210> SEQ ID NO 76
<211> LENGTH: 751
<212> TYPE: DNA
<213> ORGANISM: Marine eubacteria

<400> SEQUENCE: 76

atgggtaaat tattactgat attaggtagt gttattgcgc ttccaacatt tgccgctggc     60

ggtggcgatc ttgatgctag tgactacact ggtgtttctt tctggttagt tactgctgct    120

ctattagcat ctactgtatt cttctttgtt gaaagggata gagtatctgc aaaatggaaa    180
```

-continued

```
acttcattaa cagtatctgg tttagttact ggtattgctt tttggcatta tatgtacatg    240

agaggtgtat ggatagaaac tggtagttca cctactgtct ttagatacat tgactggcta    300

ttaacagtgc ctttactaat atgtgagttc tatttaatac ttgccgcagc tactaatgtt    360

gctggttcat tatttaagaa attgctagtt ggttctcttg ttatgcttgt gttcggttac    420

atgggtgaag caggaataat ggcagcttgg cctgcattca tcattgggtg tttagcatgg    480

gtatatatga tttatgagct atgggctggt gaaggaaaat ctgcatgtaa tactgcaagt    540

cctgctgtac agtcagctta caacacaatg atgtatatca tcatcgctgg ttgggcaatt    600

tatcctgtag gttatttcac aggttaccta atgggtgacg gtggatcagc tcttaatcta    660

aaccttattt ataaccttgc tgactttgtt aacaagattc tatttggttt aattatatgg    720

aatgttgctg ttaaagaatc ttctaatgct a                                   751
```

```
<210> SEQ ID NO 77
<211> LENGTH: 250
<212> TYPE: PRT
<213> ORGANISM: Marine eubacteria

<400> SEQUENCE: 77

Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Val Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250


<210> SEQ ID NO 78
```

<211> LENGTH: 751
<212> TYPE: DNA
<213> ORGANISM: Marine eubacteria

<400> SEQUENCE: 78
atgggtaaat tattactgat attaggtagt gttatcgcgc ttccaacatt tgctgctggc 60
ggtggcgatc ttgatgctag tgactacact ggtgtttcat tctggttagt tactgctgct 120
ctattagcgt ctactgtatt cttctttgtt gaaagagata gagtgtctgc aaaatggaaa 180
acttcattaa cagtatctgg tttagttact ggtattgctt tttggcatta tatgtacatg 240
agaggtgtat ggatagaaac tggtgattcg cctactgtct ttagatacat cgactggtta 300
ttaactgtgc ctttactaat atgtgagttc tatctgatac ttgctgcagc tactaatgtt 360
gctggttcat tatttaagaa attgctagtt ggttctcttg tgatgcttgt gtttggttac 420
atgggtgaag caggaataat ggcagcttgg cctgcattca tcattggatg tttagcatgg 480
gtatatatga tttatgaact atgggctggt gaaggaaaat ctgcatgcaa tactgcaagt 540
cctgctgtac agtcagctta caacacaatg atgtatatca tcatcgttgg ttgggcaatt 600
tatcctgtag gttatttcac aggttaccta atgggtgacg gtggatcagc tcttaatcta 660
aaccttattt ataaccttgc tgactttgtt aacaagattc tatttggttt aattatatgg 720
aatgttgctg ttaaagaatc ttctaatgct a 751

<210> SEQ ID NO 79
<211> LENGTH: 250
<212> TYPE: PRT
<213> ORGANISM: Marine eubacteria

<400> SEQUENCE: 79

Met Gly Lys Leu Leu Leu Ile Leu Gly Ser Val Ile Ala Leu Pro Thr
1 5 10 15

Phe Ala Ala Gly Gly Gly Asp Leu Asp Ala Ser Asp Tyr Thr Gly Val
20 25 30

Ser Phe Trp Leu Val Thr Ala Ala Leu Leu Ala Ser Thr Val Phe Phe
35 40 45

Phe Val Glu Arg Asp Arg Val Ser Ala Lys Trp Lys Thr Ser Leu Ala
50 55 60

Val Ser Gly Leu Ile Thr Gly Ile Ala Phe Trp His Cys Met Tyr Met
65 70 75 80

Arg Gly Val Trp Ile Glu Thr Gly Asp Ser Pro Thr Val Phe Arg Tyr
85 90 95

Ile Asp Trp Leu Leu Thr Val Pro Leu Leu Ile Cys Glu Phe Tyr Leu
100 105 110

Ile Leu Ala Ala Ala Thr Asn Val Ala Gly Ser Leu Phe Lys Lys Leu
115 120 125

Leu Val Gly Ser Leu Val Met Leu Val Phe Gly Tyr Met Gly Glu Ala
130 135 140

Gly Ile Met Ala Ala Trp Pro Ala Phe Ile Ile Gly Cys Leu Ala Trp
145 150 155 160

Val Tyr Met Ile Tyr Glu Leu Trp Ala Gly Glu Gly Lys Ser Ala Cys
165 170 175

Asn Thr Ala Ser Pro Ala Val Gln Ser Ala Tyr Asn Thr Met Met Tyr
180 185 190

Ile Ile Val Phe Gly Trp Ala Ile Tyr Pro Val Gly Tyr Phe Thr Gly
195 200 205

-continued

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250

<210> SEQ ID NO 80
<211> LENGTH: 750
<212> TYPE: DNA
<213> ORGANISM: Marine eubacteria

<400> SEQUENCE: 80
atgggtaaat tattactgat attaggtagt gttattgcac ttcctacatt tgctgcaggt 60
ggtggtgacc ttgatgctag tgattacact ggtgtttctt tttggttagt tactgctgct 120
ttattagcat ctactgtatt tttctttgtt gaaagagata gagtttctgc aaaatggaaa 180
acatcattag ctgtatctgg tcttattact ggtattgcgt tctggcattg catgtacatg 240
agaggggtat ggattgaaac tggtgattcg ccaactgtat ttagatacat tgattggtta 300
ctaacagttc ctctattaat atgtgaattc tacttaattc ttgctgctgc aactaatgtt 360
gctggatcat tatttaagaa attactagtt ggttctcttg ttatgcttgt gtttggttac 420
atgggtgaag caggaatcat ggctgcatgg cctgcattca ttattgggtg tttagcttgg 480
gtatacatga tttatgaatt atgggctgga gaaggaaaat ctgcatgtaa tactgcaagt 540
cctgctgtgc aatcagctta caacacaatg atgtatatta tcgtctttgg ttgggcgatt 600
tatcctgtag gttatttcac aggttacctg atgggtgacg gtggatcagc tcttaactta 660
aaccttatct ataaccttgc tgactttgtt aacaagattc tatttggttt aattatatgg 720
aatgttgctg ttaaagaatc ttctaatgct 750

<210> SEQ ID NO 81
<211> LENGTH: 250
<212> TYPE: PRT
<213> ORGANISM: Marine eubacteria

<400> SEQUENCE: 81

Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Ser
        35                  40                  45

Phe Val Glu Arg Asp Arg Val Ser Ala Lys Trp Lys Thr Ser Leu Thr
    50                  55                  60

Val Ser Gly Leu Ile Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp

-continued 145 150 155 160

Val Tyr Met Ile Tyr Glu Leu Trp Ala Gly Glu Gly Lys Ser Ala Cys
165 170 175

Asn Thr Ala Ser Pro Ala Val Gln Ser Ala Tyr Asn Thr Met Met Tyr
180 185 190

Ile Ile Ile Phe Gly Trp Ala Ile Tyr Pro Val Gly Tyr Phe Thr Gly
195 200 205

Tyr Leu Met Gly Asp Gly Gly Ser Ala Leu Asn Leu Asn Leu Ile Tyr
210 215 220

Asn Leu Ala Asp Phe Val Asn Lys Ile Leu Phe Gly Leu Ile Ile Trp
225 230 235 240

Asn Val Ala Val Lys Glu Ser Ser Asn Ala
245 250

<210> SEQ ID NO 82
<211> LENGTH: 750
<212> TYPE: DNA
<213> ORGANISM: Marine eubacteria

<400> SEQUENCE: 82
atgggtaaat tattactgat attaggtagt gttattgcac ttcctacatt tgctgcaggt 60
ggtggtgacc ttgatgctag tgattacact ggtgtttctt tttggttagt tactgctgct 120
ttattagcat ctactgtatt ttcctttgtt gaaagagata gagtttctgc aaaatggaaa 180
acatcattaa ctgtatctgg tcttattact ggtattgctt tctggcatta catgtacatg 240
agaggggtat ggattgaaac tggtgattcg ccaactgtat ttagatacat tgattggtta 300
ctaacagttc ctctattaat atgtgaattc tacttaattc ttgctgctgc aactaatgtt 360
gctggatcat tatttaagaa attactagtt ggttctcttg ttatgcttgt gtttggttac 420
atgggtgaag caggaatcat ggctgcatgg cctgcattca ttattgggtg tttagcttgg 480
gtatacatga tttatgaatt atgggctgga gaaggaaaat ctgcatgtaa tactgcaagt 540
cctgctgtgc aatcagctta caacacaatg atgtatatta tcatctttgg ttgggcgatt 600
tatcctgtag gttatttcac aggttacctg atgggtgacg gtggatcagc tcttaactta 660
aaccttatct ataaccttgc tgactttgtt aacaagattc tatttggttt aattatatgg 720
aatgttgctg ttaaagaatc ttctaatgct 750

<210> SEQ ID NO 83
<211> LENGTH: 250
<212> TYPE: PRT
<213> ORGANISM: Marine eubacteria

<400> SEQUENCE: 83

Met Gly Lys Leu Leu Leu Ile Leu Gly Ser Val Ile Ala Leu Pro Thr
1 5 10 15

Phe Ala Ala Gly Gly Gly Asp Leu Asp Ala Ser Asp Tyr Thr Gly Val
20 25 30

Ser Phe Trp Leu Val Thr Ala Ala Leu Leu Ala Ser Thr Val Phe Phe
35 40 45

Phe Val Glu Arg Asp Arg Val Ser Ala Lys Trp Lys Thr Ser Leu Thr
50 55 60

Val Ser Gly Leu Ile Thr Gly Ile Ala Phe Trp His Tyr Met Tyr Met
65 70 75 80

Arg Gly Val Trp Ile Glu Thr Gly Asp Ser Pro Thr Val Phe Arg Tyr
85 90 95

-continued

```
Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Phe Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Ser Ile Ile Trp
225                 230                 235                 240

Asn Val Ala Val Lys Glu Ser Ser Asn Ala
                245                 250


<210> SEQ ID NO 84
<211> LENGTH: 750
<212> TYPE: DNA
<213> ORGANISM: Marine eubacteria

<400> SEQUENCE: 84

atgggtaaat tattactgat attaggtagt gttattgcac ttcctacatt tgctgcaggt      60

ggtggtgacc ttgatgctag tgattacact ggtgtttctt tttggttagt tactgctgct     120

ttattagcat ctactgtatt tttctttgtt gaaagagata gagtttctgc aaaatggaaa     180

acatcattaa ctgtatctgg tcttattact ggtattgctt tctggcatta catgtacatg     240

agaggggtat ggattgaaac tggtgattcg ccaaccgtat ttagatacat tgattggtta     300

ctaacagttc ctctattaat atgtgaattc tacttaattc ttgctgctgc aactaatgtt     360

gctggatcat tatttaagaa attactagtt ggttctcttg ttatgcttgt gtttggttac     420

atgggtgaag caggaatcat ggctgcatgg cctgcattca ttattgggtg tttagcttgg     480

gtatacatga tttatgaatt atgggctgga gaaggaaaat ctgcatgtaa tactgcaagt     540

cctgctgtgc aatcagctta caacacaatg atgtatatta tcatctttgg ttgggcgatt     600

tatcctgtag gttatttcac aggttacctg atgggtgacg gtggatcagc acttaactta     660

aaccttatct ataaccttgc tgactttgtt aacaagattc tatttggttc aattatatgg     720

aatgttgctg ttaaagaatc ttctaatgct                                      750


<210> SEQ ID NO 85
<211> LENGTH: 250
<212> TYPE: PRT
<213> ORGANISM: Marine eubacteria

<400> SEQUENCE: 85

Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30
```

-continued

```
Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Val Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250
```

<210> SEQ ID NO 86
<211> LENGTH: 751
<212> TYPE: DNA
<213> ORGANISM: Marine eubacteria

<400> SEQUENCE: 86

```
atgggtaaat tattactgat attaggtagt gttattgcac ttcctacatt tgctgcaggt      60

ggtggtgacc ttgatgctag tgattacact ggtgtttctt tttggttagt tactgctgct     120

ttattagcgt ctactgtatt cttctttgtt gaaagagata gagtgtctgc aaaatggaaa     180

acttcattaa cagtatctgg tttagttact ggtattgctt tttggcatta tatgtacatg     240

agaggtgtat ggatagaaac tggtgattcg cctactgtct ttagatacat cgactggtta     300

ttaactgtgc ctttactaat atgtgagttc tatctgatac ttgctgcagc tactaatgtt     360

gctggttcat tatttaagaa attgctagtt ggttctcttg tgatgcttgt gtttggttac     420

atgggtgaag caggaataat ggcagcttgg cctgcattca tcattgggtg tttagcatgg     480

gtatatatga tttatgaact atgggctggt gaaggaaaat ctgcatgcaa tactgcaagt     540

cctgctgtac agtcagctta caacacaatg atgtatatca tcatcgttgg ttgggcaata     600

tatcctgtag gttatttcac aggttaccta atgggtgacg gtggatcagc tcttaatcta     660

aaccttatct ataaccttgc tgactttgtt aacaagattc tatttggttt aattatatgg     720

aatgttgctg ttaaagaatc ttctaatgct a                                    751
```

<210> SEQ ID NO 87
<211> LENGTH: 250

-continued

<212> TYPE: PRT
<213> ORGANISM: Marine eubacteria

<400> SEQUENCE: 87

```
Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Val Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250
```

<210> SEQ ID NO 88
<211> LENGTH: 751
<212> TYPE: DNA
<213> ORGANISM: Marine eubacteria

<400> SEQUENCE: 88

```
atgggtaaat tattactgat attaggtagt gttatcgcgc ttccaacatt tgctgctggc      60

ggtggcgatc ttgatgctag tgactatact ggtgtttcat tctggttagt tactgctgct     120

ctattagcgt ctactgtatt cttctttgtt gaaagagata gagtgtctgc aaaatggaaa     180

acttcattaa cagtatctgg tttagttact ggtattgctt tttggcatta tatgtacatg     240

agaggtgtat ggatagaaac tggtgattcg cctactgtct ttagatacat cgactggtta     300

ttaactgtgc ctttactaat atgtgagttc tatctgatac ttgctgcagc tactaatgtt     360

gctggttcat tatttaagaa attgctagtt ggttctcttg tgatgcttgt gtttggttac     420

atgggtgaag caggaataat ggcagcttgg cctgcattca tcattggatg tttagcatgg     480

gtatatatga tttatgaact atgggctggt gaaggaaaat ctgcatgcaa tactgcaagt     540
```

-continued

```
cctgctgtac agtcagctta caacacaatg atgtatatca tcatcgttgg ttgggcaatt    600

tatcctgtag gctatttcac aggttaccta atgggtgacg gtggatcagc tcttaatcta    660

aaccttattt ataaccttgc tgactttgtt aacaagattc tatttggttt aattatatgg    720

aatgttgctg ttaaagaatc ttctaatgct a                                   751
```

```
<210> SEQ ID NO 89
<211> LENGTH: 250
<212> TYPE: PRT
<213> ORGANISM: Marine eubacteria

<400> SEQUENCE: 89

Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Pro Val Pro Leu Ala Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Phe Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250
```

```
<210> SEQ ID NO 90
<211> LENGTH: 751
<212> TYPE: DNA
<213> ORGANISM: Marine eubacteria

<400> SEQUENCE: 90

atgggtaaat tattactgat attaggtagt gttattgcac ttcctacatt tgctgcaggt     60

ggtggtgacc ttgatgctag tgattacact ggtgtttctt tttggttagt tactgctgct    120

ttattagcat ctactgtatt tttctttgtt gaaagagata gagtttctgc aaaatggaaa    180

acatcattaa ctgtatctgg tcttgttact ggtattgctt tctggcatta catgtacatg    240
```

-continued

```
agaggggtat ggattgaaac tggtgattcg ccaactgtat ttagatacat tgattggtta    300

ctaccagttc ctctagcaat atgtgaattc tacttaattc ttgctgctgc aactaatgtt    360

gctggatcat tatttaagaa attactagtt ggttctcttg ttatgcttgt gtttggttac    420

atgggtgaag caggaatcat ggctgcatgg cctgcattca ttattgggtg tttagcttgg    480

gtatacatga tttatgaatt atgggctgga gaaggaaaat ctgcatgtaa tactgcaagt    540

cctgctgtgc aatcagctta caacacaatg atgtatatta tcatctttgg ttgggcgatt    600

tatcctgtag gttatttcac aggttacctg atgggtgacg gtggatcagc tcttaactta    660

aaccttatct ataaccttgc tgactttgtt aacaagattc tatttggttt aattatatgg    720

aatgttgctg ttaaagaatc ttctaatgct a                                    751
```

<210> SEQ ID NO 91
<211> LENGTH: 250
<212> TYPE: PRT
<213> ORGANISM: Marine eubacteria

<400> SEQUENCE: 91

```
Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Phe Gly Trp Ala Ile Tyr Leu Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250
```

<210> SEQ ID NO 92
<211> LENGTH: 751
<212> TYPE: DNA

-continued

<213> ORGANISM: Marine eubacteria

<400> SEQUENCE: 92
atgggtaaat tattactgat attaggtagt gttattgcgc ttccaacatt tgccgctggt 60
ggtggtgacc tggatgctag tgactacact ggtgtatctt tctggttagt tactgctgct 120
ctattagcat ctactgtatt tttctttgtt gaaagagaca gagtttctgc taaatggaaa 180
acatcattaa cagtatctgg tttagttact ggtattgctt tttggcatta catgtacatg 240
agaggtgtat ggattgaaac tggtgattca ccaactgttt ttagatacat cgactggttg 300
ctaactgtgc ctttactaat ttgtgagttc tacttaatac tagcagcagc tactaacgtt 360
gctggttctt tattcaagaa attactagtt ggttctcttg ttatgcttgt gtttggttac 420
atgggtgaag caggaattat ggcagcctgg cctgcattca ttataggatg tttagcatgg 480
gtatacatga tttatgaatt atgggctgga gaaggaaagt ctgcatgtaa cactgcaagt 540
cctgcagttc agtcagctta caacacaatg atgtatatca tcatctttgg ttgggctatt 600
taccttgtag gttatttcac tggttaccta atgggtgacg gtggatcagc tcttaactta 660
aaccttatct ataaccttgc tgactttgtt aacaagattc tatttggttt aattatatgg 720
aatgttgctg ttaaagaatc ttctaatgct a 751

<210> SEQ ID NO 93
<211> LENGTH: 250
<212> TYPE: PRT
<213> ORGANISM: Marine eubacteria

<400> SEQUENCE: 93

Met Gly Lys Leu Leu Leu Ile Leu Gly Ser Val Ile Ala Leu Pro Thr
1 5 10 15

Phe Ala Ala Gly Gly Gly Asp Leu Asp Ala Ser Asp Tyr Thr Gly Val
20 25 30

Ser Phe Trp Leu Val Thr Ala Ala Leu Leu Ala Ser Thr Val Phe Phe
35 40 45

Phe Val Glu Arg Asp Arg Val Ser Ala Lys Trp Lys Thr Ser Leu Thr
50 55 60

Val Ser Gly Leu Val Thr Gly Ile Ala Phe Trp His Tyr Met Tyr Met
65 70 75 80

Arg Gly Val Trp Ile Glu Thr Gly Ser Ser Pro Thr Val Phe Arg Tyr
85 90 95

Ile Asp Trp Leu Leu Thr Val Pro Leu Leu Ile Cys Glu Phe Tyr Leu
100 105 110

Ile Leu Ala Ala Ala Thr Asn Val Ala Gly Ser Leu Phe Lys Lys Leu
115 120 125

Leu Val Gly Ser Leu Val Met Leu Val Phe Gly Tyr Met Gly Glu Ala
130 135 140

Gly Ile Met Ala Ala Trp Pro Ala Phe Ile Ile Gly Cys Leu Ala Trp
145 150 155 160

Val Tyr Met Ile Tyr Glu Leu Trp Ala Gly Glu Gly Lys Ser Ala Cys
165 170 175

Asn Thr Ala Ser Pro Ala Val Gln Ser Ala Tyr Asn Thr Met Met Tyr
180 185 190

Ile Ile Ile Phe Gly Trp Ala Ile Tyr Leu Val Gly Tyr Phe Thr Gly
195 200 205

Tyr Leu Met Gly Asp Gly Gly Ser Ala Leu Asn Leu Asn Leu Ile Tyr
210 215 220

-continued

```
Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250
```

<210> SEQ ID NO 94
<211> LENGTH: 751
<212> TYPE: DNA
<213> ORGANISM: Marine eubacteria

<400> SEQUENCE: 94

```
atgggtaaat tattactgat attaggtagt gttattgcgc ttccaacatt tgccgctggc     60

ggtggcgatc ttgatgctag tgactacact ggtgtttctt tctggttagt tactgctgct    120

ctattagcat ctactgtatt cttctttgtt gaaagggata gagtatctgc aaaatggaaa    180

acttcattaa cagtatctgg tttagttact ggtattgctt tttggcatta tatgtacatg    240

agaggtgtat ggatagaaac tggtagttca cctactgtct ttagatacat tgactggcta    300

ttaacagtgc ctttactaat atgtgagttc tatttaatac ttgccgcagc tactaatgtt    360

gctggttcat tatttaagaa attgctagtt ggttctcttg ttatgcttgt gtttggttac    420

atgggtgaag caggaattat ggcagcctgg cctgcattca ttataggatg tttagcatgg    480

gtatacatga tttatgaatt atgggctgga gaaggaaagt ctgcatgtaa cactgcaagt    540

cctgcagttc agtcagctta caacacaatg atgtatatca tcatctttgg ttgggctatt    600

taccttgtag gttatttcac tggttaccta atgggtgacg gtggatcagc tcttaactta    660

aaccttatct ataaccttgc tgactttgtt aacaagattc tatttggttt aattatatgg    720

aatgttgctg ttaaagaatc ttctaatgct a                                   751
```

<210> SEQ ID NO 95
<211> LENGTH: 250
<212> TYPE: PRT
<213> ORGANISM: Marine eubacteria

<400> SEQUENCE: 95

```
Met Gly Lys Leu Leu Leu Arg Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160
```

-continued

```
Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Val Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250


<210> SEQ ID NO 96
<211> LENGTH: 751
<212> TYPE: DNA
<213> ORGANISM: Marine eubacteria

<400> SEQUENCE: 96

atgggtaaat tattactgag attaggtagt gttatcgcgc ttccaacatt tgctgctggc      60

ggtggcgatc ttgatgctag tgactatact ggtgtttcat tctggttagt tactgctgct     120

ctattagcgt ctactgtatt cttctttgtt gaaagagata gagtgtctgc aaaatggaaa     180

acttcattaa cagtatctgg tttagttact ggtattgctt tttggcatta tatgtacatg     240

agaggtgtat ggatagaaac tggtgattcg cctactgtct ttagatacat cgactggtta     300

ttaactgtgc ctttactaat atgtgagttc tatctgatac ttgctgcagc tactaatgtt     360

gctggttcat tatttaagaa attgctagtt ggttctcttg tgatgcttgt gtttggttac     420

atgggtgaag caggaataat ggcagcttgg cctgcattca tcattggatg tttagcatgg     480

gtatatatga tttatgaact atgggctggt gaaggaaaat ctgcatgcaa tactgcaagt     540

cctgctgtac agtcagctta caacacaatg atgtatatca tcatcgttgg ttgggcaatt     600

tatcctgtag gttatttcac aggttaccta atgggtgacg gtggatcagc tcttaatcta     660

aaccttattt ataaccttgc tgactttgtt aacaagattc tatttggttt aattatatgg     720

aatgttgctg ttaaagaatc ttctaatgct a                                    751


<210> SEQ ID NO 97
<211> LENGTH: 250
<212> TYPE: PRT
<213> ORGANISM: Marine eubacteria

<400> SEQUENCE: 97

Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Ala
    50                  55                  60

Val Ser Gly Leu Ile Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
```

-continued

```
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Val Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250


<210> SEQ ID NO 98
<211> LENGTH: 751
<212> TYPE: DNA
<213> ORGANISM: Marine eubacteria

<400> SEQUENCE: 98

atgggtaaat tattactgat attaggtagt gttattgcac ttcctacatt tgctgcaggt      60

ggtggtgacc ttgatgctag tgattacact ggtgtttctt tttggttagt tactgctgct     120

ttattagcat ctactgtatt tttctttgtt gaaagagata gagtttctgc aaaatggaaa     180

acatcattag ctgtatctgg tcttattact ggtattgcgt tctggcatta catgtacatg     240

agaggggtat ggattgaaac tggtgattcg ccaactgtat ttagatacat tgattggtta     300

ctaacagttc ctctattaat atgtgaattc tacttaattc ttgctgctgc aactaatgtt     360

gctggatcat tatttaagaa attactagtt ggttctcttg ttatgcttgt gtttggttac     420

atgggtgaag caggaatcat ggctgcatgg cctgcattca ttattgggtg tttagcttgg     480

gtatacatga tttatgaatt atgggctgga gaaggaaaat ctgcatgtaa tactgcaagt     540

cctgctgtgc agtcagctta caacacaatg atgtatatca tcatcgttgg ttgggcaata     600

tatcctgtag gttatttcac aggttaccta atgggtgacg gtggatcagc tcttaatcta     660

aaccttattt ataaccttgc tgactttgtt aacaagattc tatttggttt aattatatgg     720

aatgttgctg ttaaagaatc ttctaatgct a                                    751


<210> SEQ ID NO 99
<211> LENGTH: 250
<212> TYPE: PRT
<213> ORGANISM: Marine eubacteria

<400> SEQUENCE: 99

Met Gly Lys Leu Leu Leu Ile Leu Gly Ser Val Ile Ala Leu Pro Thr
1               5                   10                  15

Phe Ala Ala Gly Gly Gly Asp Pro Asp Ala Ser Asp Tyr Thr Gly Val
            20                  25                  30

Ser Phe Trp Leu Val Thr Ala Ala Leu Leu Ala Ser Thr Val Phe Phe
        35                  40                  45
```

-continued

```
Phe Val Glu Arg Asp Arg Val Ser Ala Glu Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Glu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Phe Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Ile Gly Leu Ile Ile Trp
225                 230                 235                 240

Asn Val Ala Val Lys Glu Ser Ser Asn Ala
                245                 250
```

<210> SEQ ID NO 100
<211> LENGTH: 751
<212> TYPE: DNA
<213> ORGANISM: Marine eubacteria

<400> SEQUENCE: 100

```
atgggtaaat tattactgat cttaggtagt gttattgcac ttcctacatt tgctgcaggt      60

ggtggtgacc ctgatgctag tgattacact ggtgtttctt tttggttagt tactgctgct     120

ttattagcat ctactgtatt tttctttgtt gaaagagata gagtttctgc agaatggaaa     180

acatcattaa ctgtatctgg tcttgttact ggtattgctt tctggcatta catgtacatg     240

agaggggtat ggattgaaac tggtgattcg ccaactgtat ttagatacat tgattggtta     300

ctaacagttc ctctagaaat atgtgaattc tacttaattc ttgctgctgc aactaatgtt     360

gctggatcat tatttaagaa attactagtt ggttctcttg ttatgcttgt gtttggttac     420

atgggtgaag caggaatcat ggctgcatgg cctgcattca ttattgggtg tttagcttgg     480

gtatacatga tttatgaatt atgggctgga gaaggaaaat ctgcatgtaa tactgcaagt     540

cctgctgtgc aatcagctta caacacaatg atgtatatta tcatctttgg ttgggcgatt     600

tatcctgtag gttatttcac aggttacctg atgggtgacg gtggatcagc tcttaactta     660

aaccttatct ataaccttgc tgactttgtt aacaagattc taattggttt aattatatgg     720

aatgttgctg ttaaagaatc ttctaatgct a                                    751
```

<210> SEQ ID NO 101
<211> LENGTH: 250
<212> TYPE: PRT
<213> ORGANISM: Marine eubacteria

<400> SEQUENCE: 101

Met Gly Lys Leu Leu Leu Ile Leu Gly Ser Val Ile Ala Leu Pro Thr
1 5 10 15

Phe Ala Ala Gly Gly Gly Asp Leu Asp Ala Ser Asp Tyr Thr Gly Val
20 25 30

Ser Phe Trp Leu Val Thr Ala Ala Leu Leu Ala Ser Thr Val Phe Phe
35 40 45

Phe Val Glu Arg Asp Arg Val Ser Ala Lys Trp Lys Thr Ser Leu Thr
50 55 60

Val Ser Gly Leu Val Thr Gly Ile Ala Phe Trp His Tyr Met Tyr Met
65 70 75 80

Arg Gly Val Trp Ile Glu Thr Gly Asp Ser Pro Thr Val Phe Arg Tyr
85 90 95

Ile Asp Trp Leu Leu Thr Val Pro Leu Val Ile Cys Glu Phe Tyr Leu
100 105 110

Ile Leu Ala Ala Ala Thr Asn Val Ala Gly Ser Leu Phe Lys Lys Leu
115 120 125

Leu Val Gly Ser Leu Val Met Leu Val Phe Gly Tyr Met Gly Glu Ala
130 135 140

Gly Ile Met Ala Ala Trp Pro Ala Phe Ile Ile Gly Cys Leu Ala Trp
145 150 155 160

Val Tyr Met Ile Tyr Glu Leu Trp Ala Gly Glu Gly Lys Ser Ala Cys
165 170 175

Asn Thr Ala Ser Pro Ala Val Gln Ser Ala Tyr Asn Thr Met Met Tyr
180 185 190

Ile Ile Ile Phe Gly Trp Ala Ile Tyr Pro Val Gly Tyr Phe Thr Gly
195 200 205

Tyr Leu Met Gly Asp Gly Gly Ser Ala Leu Asn Leu Asn Leu Ile Tyr
210 215 220

Asn Leu Ala Asp Phe Val Asn Lys Ile Leu Phe Gly Leu Ile Ile Trp
225 230 235 240

Asn Val Ala Val Lys Glu Ser Ser Asn Ala
245 250

<210> SEQ ID NO 102
<211> LENGTH: 751
<212> TYPE: DNA
<213> ORGANISM: Marine eubacteria

<400> SEQUENCE: 102
atgggtaaat tattactgat cttaggtagt gttattgcac ttcctacatt tgctgcaggt 60
ggtggtgacc ttgatgctag tgattacact ggtgtttctt tttggttagt tactgctgct 120
ttattagcat ctactgtatt tttctttgtt gaaagagata gagtttctgc aaaatggaaa 180
acatcattaa ctgtatctgg tcttgttact ggtattgctt tctggcatta catgtacatg 240
agaggggtat ggattgaaac tggtgattcg ccaactgtat ttagatacat tgattggtta 300
ctaacagttc ctctagtaat atgtgaattc tacttaattc ttgctgctgc aactaatgtt 360
gctggatcat tatttaagaa attactagtt ggttctcttg ttatgcttgt gtttggttac 420
atgggtgaag caggaatcat ggctgcatgg cctgcattca ttattgggtg tttagcttgg 480
gtatacatga tttatgaatt atgggctgga gaaggaaaat ctgcatgtaa tactgcaagt 540
cctgctgtgc aatcagctta caacacgatg atgtatatta tcatctttgg ttgggcgatt 600

-continued tatcctgtag gttatttcac aggttacctg atgggtgacg gtggatcagc tcttaactta 660
aaccttatct ataaccttgc tgactttgtt aacaagattc tatttggttt aattatatgg 720
aatgttgctg ttaaagaatc ttctaatgct a 751

<210> SEQ ID NO 103
<211> LENGTH: 250
<212> TYPE: PRT
<213> ORGANISM: Marine eubacteria

<400> SEQUENCE: 103

Met Gly Lys Leu Leu Leu Ile Leu Gly Ser Val Ile Ala Leu Pro Thr
1 5 10 15

Phe Ala Ala Gly Gly Gly Asp Leu Asp Ala Ser Asp Tyr Thr Gly Val
20 25 30

Ser Phe Trp Leu Val Thr Ala Ala Leu Leu Ala Ser Thr Val Phe Phe
35 40 45

Phe Val Glu Arg Asp Arg Val Ser Ala Lys Trp Lys Thr Ser Leu Thr
50 55 60

Val Pro Gly Leu Ile Thr Asp Ile Ala Phe Trp His Tyr Met Tyr Met
65 70 75 80

Arg Gly Val Trp Ile Glu Thr Gly Asp Ser Pro Thr Val Phe Arg Tyr
85 90 95

Ile Asp Trp Leu Leu Thr Val Pro Leu Gln Ile Cys Glu Phe Tyr Leu
100 105 110

Ile Leu Ala Ala Ala Thr Asn Val Ala Gly Ser Leu Phe Lys Lys Leu
115 120 125

Leu Val Gly Ser Leu Val Met Leu Val Phe Gly Tyr Met Gly Glu Ala
130 135 140

Gly Ile Met Ala Ala Trp Pro Ala Phe Ile Ile Gly Cys Leu Ala Trp
145 150 155 160

Val Tyr Met Ile Tyr Glu Leu Trp Ala Gly Glu Gly Lys Ser Ala Cys
165 170 175

Asn Thr Ala Ser Pro Ala Val Gln Ser Ala Tyr Asn Thr Met Met Tyr
180 185 190

Ile Ile Ile Phe Gly Trp Ala Ile Tyr Pro Val Gly Tyr Phe Thr Gly
195 200 205

Tyr Leu Met Gly Asp Gly Gly Ser Ala Leu Asn Leu Asn Leu Ile Tyr
210 215 220

Asn Leu Ala Asp Phe Val Asn Lys Ile Leu Phe Gly Leu Ile Ile Trp
225 230 235 240

Asn Val Ala Val Lys Glu Ser Ser Asn Ala
245 250

<210> SEQ ID NO 104
<211> LENGTH: 751
<212> TYPE: DNA
<213> ORGANISM: Marine eubacteria

<400> SEQUENCE: 104
atgggtaaat tattactgat attaggtagt gttattgcac ttcctacatt tgctgcaggt 60
ggtggtgacc ttgatgctag tgattacact ggtgtttctt tttggttagt tactgctgct 120
ttattagcat ctactgtatt tttctttgtt gaaagagata gagtttctgc aaaatggaaa 180
acatcattaa ctgtacctgg tcttattact gatattgctt tctggcatta catgtacatg 240
agaggggtat ggattgaaac tggtgattcg ccaactgtat ttagatacat tgattggtta 300

-continued

```
ctaacagttc ctctacaaat atgtgaattc tacttaattc ttgctgctgc aactaatgtt    360

gctggatcat tatttaagaa attactagtt ggttctcttg ttatgcttgt gtttggttac    420

atgggtgaag caggaatcat ggctgcatgg cctgcattca ttattgggtg tttagcttgg    480

gtatacatga tttatgaatt atgggctgga gaaggaaaat ctgcatgtaa tactgcgagt    540

cctgctgtgc aatcagctta caacacaatg atgtatatta tcatctttgg ttgggcgatt    600

tatcctgtag gttatttcac aggttacctg atgggtgacg gtggatcagc tcttaactta    660

aaccttatct ataaccttgc tgactttgtt aacaagattc tatttggttt aattatatgg    720

aatgttgctg ttaaagaatc ttctaatgct a                                   751
```

```
<210> SEQ ID NO 105
<211> LENGTH: 249
<212> TYPE: PRT
<213> ORGANISM: Marine eubacteria

<400> SEQUENCE: 105

Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Pro Gly Leu Ile Thr Asp Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Gln Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Phe Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn
                245

<210> SEQ ID NO 106
<211> LENGTH: 748
<212> TYPE: DNA
<213> ORGANISM: Marine eubacteria
```

-continued

<400> SEQUENCE: 106

```
atgggtaaat tattactgat attaggtagt gttattgcac ttcctacatt tgctgcaggt      60

ggtggtgacc ttgatgctag tgattacact ggtgtttctt tttggttagt tactgctgct     120

ttattagcat ctactgtatt tttctttgtt gaaagagata gagtttctgc aaaatggaaa     180

acatcattaa ctgtacctgg tcttattact gatattgctt tctggcatta catgtacatg     240

agaggggtat ggattgaaac tggtgattcg ccaactgtat ttagatacat tgattggtta     300

ctaacagttc ctctacaaat atgtgaattc tacttaattc ttgctgctgc aactaatgtt     360

gctggatcat tatttaagaa attactagtt ggttctcttg ttatgcttgt gtttggttac     420

atgggtgaag caggaatcat ggctgcatgg cctgcattca ttattgggtg tttagcttgg     480

gtatacatga tttatgaatt atgggctgga gaaggaaaat ctgcatgtaa tactgcgagt     540

cctgctgtgc aatcagctta caacacaatg atgtatatta tcatctttgg ttgggcgatt     600

tatcctgtag gttatttcac aggttacctg atgggtgacg gtggatcagc tcttaactta     660

aaccttatct ataaccttgc tgactttgtt aacaagattc tatttggttt aattatatgg     720

aatgttgctg ttaaagaatc ttctaatt                                        748
```

<210> SEQ ID NO 107
<211> LENGTH: 250
<212> TYPE: PRT
<213> ORGANISM: Marine eubacteria

<400> SEQUENCE: 107

```
Met Gly Lys Leu Leu Leu Ile Leu Gly Ser Val Ile Ala Leu Pro Thr
1               5                   10                  15

Phe Ala Ala Gly Gly Gly Asp Leu Asp Ala Ser Gly Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Pro Gly Leu Ile Thr Asp Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Ser Leu Gln Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Phe Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
```

-continued 225 230 235 240

Asn Val Ala Val Lys Glu Ser Ser Asn Ala
245 250

<210> SEQ ID NO 108
<211> LENGTH: 751
<212> TYPE: DNA
<213> ORGANISM: Marine eubacteria

<400> SEQUENCE: 108
atgggtaaat tattactgat attaggtagt gttattgcac ttcctacatt tgctgcaggt 60
ggtggtgacc ttgatgctag tggttacact ggtgtttctt tttggttagt tactgctgct 120
ttattagcat ctactgtatt tttctttgtt gaaagagata gagtttctgc aaaatggaaa 180
acatcattaa ctgtacctgg tcttattact gatattgctt tctggcatta catgtacatg 240
agaggggtat ggattgaaac tggtgattcg ccaactgtat ttagatacat tgattggtta 300
ctaacagttt ctctacaaat atgtgaattc tacttaattc ttgctgctgc aactaatgtt 360
gctggatcat tatttaagaa attactagtt ggttctcttg ttatgcttgt gtttggttac 420
atgggtgaag caggaatcat ggctgcatgg cctgcattca ttattgggtg tttagcttgg 480
gtatacatga tttatgaatt atgggctgga gaaggaaaat ctgcatgtaa tactgcgagt 540
cctgctgtgc aatcagctta caacacaatg atgtatatta tcatctttgg ttgggcgatt 600
tatcctgtag gttatttcac aggttacctg atgggtgacg gtggatcagc tcttaactta 660
aaccttatct ataaccttgc tgactttgtt aacaagattc tatttggttt aattatatgg 720
aatgttgctg ttaaagaatc ttctaatgct a 751

<210> SEQ ID NO 109
<211> LENGTH: 250
<212> TYPE: PRT
<213> ORGANISM: Marine eubacteria

<400> SEQUENCE: 109

Met Gly Lys Leu Leu Leu Ile Leu Gly Ser Val Ile Ala Leu Pro Thr
1 5 10 15

Phe Ala Ala Gly Gly Gly Asp Leu Asp Ala Ser Asp Tyr Thr Gly Val
20 25 30

Ser Phe Trp Leu Val Thr Ala Ala Leu Leu Ala Ser Thr Val Phe Phe
35 40 45

Phe Val Glu Arg Asp Arg Val Ser Ala Lys Trp Lys Thr Ser Leu Thr
50 55 60

Val Pro Gly Leu Val Thr Gly Ile Ala Phe Trp His Tyr Met Tyr Met
65 70 75 80

Arg Gly Val Trp Ile Glu Thr Gly Asp Ser Pro Ala Val Phe Arg Tyr
85 90 95

Ile Asp Trp Leu Leu Thr Val Pro Leu Glu Ile Cys Glu Phe Tyr Leu
100 105 110

Ile Leu Ala Ala Ala Thr Asn Val Ala Gly Ser Leu Phe Lys Lys Leu
115 120 125

Leu Val Gly Ser Leu Val Met Leu Val Phe Gly Tyr Met Gly Glu Ala
130 135 140

Gly Ile Met Ala Ala Trp Pro Ala Phe Ile Ile Gly Cys Leu Ala Trp
145 150 155 160

Val Tyr Met Ile Tyr Glu Leu Trp Ala Gly Glu Gly Lys Ser Ala Cys
165 170 175

```
Asn Thr Ala Ser Pro Ala Val Gln Ser Ala Tyr Asn Thr Met Met Tyr
            180                 185                 190

Ile Ile Ile Phe Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250
```

<210> SEQ ID NO 110
<211> LENGTH: 751
<212> TYPE: DNA
<213> ORGANISM: Marine eubacteria

<400> SEQUENCE: 110

```
atgggtaaat tattactgat attaggtagt gttattgcac ttcctacatt tgctgcaggt     60

ggtggtgacc ttgatgctag tgattacact ggtgtttctt tttggttagt tactgctgct    120

ttattagcat ctactgtatt tttctttgtt gaaagagata gagtttctgc aaaatggaaa    180

acatcattaa ctgtacctgg tcttgttact ggtattgctt tctggcatta catgtacatg    240

agaggggtat ggattgaaac tggtgattcg ccagctgtat ttagatacat tgattggtta    300

ctaacagttc ctctagagat atgtgaattc tacttgattc ttgctgctgc aactaatgtt    360

gctggatcat tatttaagaa attactagtt ggttctcttg ttatgcttgt gtttggttac    420

atgggtgaag caggaatcat ggctgcatgg cctgcattca ttattgggtg tttagcttgg    480

gtatacatga tttatgaatt atgggctgga gaaggaaaat ctgcatgtaa tactgcaagt    540

cctgctgtgc aatcagctta caacacaatg atgtatatta tcatctttgg ttgggcgatt    600

tatcctgtag gttatttcac aggttacctg atgggtgacg gtggatcagc tcttaactta    660

aaccttatct ataaccttgc tgactttgtt aacaagattc tatttggttt aattatatgg    720

aatgttgctg ttaaagaatc ttctaatgct a                                   751
```

<210> SEQ ID NO 111
<211> LENGTH: 250
<212> TYPE: PRT
<213> ORGANISM: Marine eubacteria

<400> SEQUENCE: 111

```
Met Gly Lys Leu Leu Val Met Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110
```

-continued

```
Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Phe Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250
```

<210> SEQ ID NO 112
<211> LENGTH: 751
<212> TYPE: DNA
<213> ORGANISM: Marine eubacteria

<400> SEQUENCE: 112

```
atgggtaaat tattagtgat gttaggtagt gttattgcgc ttccaacatt tgccgctggt      60

ggtggtgacc tggatgctag tgactacact ggtgtatctt tctggttagt tactgctgct     120

ctattagcat ctactgtatt tttctttgtt gaaagagaca gagtttctgc taaatggaaa     180

acatcattaa cagtatctgg tttagttact ggtattgctt tttggcatta catgtacatg     240

agaggtgtat ggattgaaac tggtgattca ccaactgttt ttagatacat cgactggttg     300

ctaactgtgc ctttactaat ttgtgagttc tacttaatac tagcagcagc tactaacgtt     360

gctggttctt tattcaagaa attactagtt ggttctcttg ttatgcttgt gtttggttac     420

atgggtgaag caggaattat ggcagcctgg cctgcattca ttataggatg tttagcatgg     480

gtatacatga tttatgaatt atgggctgga gaaggaaagt ctgcatgtaa cactgcaagt     540

cctgcagttc agtcagctta caacacaatg atgtatatca tcatctttgg ttgggctatt     600

taccctgtag gttatttcac tggttaccta atgggtgacg gtggatcagc tcttaactta     660

aaccttatct ataaccttgc tgactttgtt aacaagattc tatttggttt aattatatgg     720

aatgttgctg ttaaagaatc ttctaatgct a                                    751
```

<210> SEQ ID NO 113
<211> LENGTH: 250
<212> TYPE: PRT
<213> ORGANISM: Marine eubacteria

<400> SEQUENCE: 113

```
Met Gly Lys Arg Leu Val Ile Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
```

-continued

```
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Phe Gly Trp Ala Ile Tyr Leu Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250
```

<210> SEQ ID NO 114
<211> LENGTH: 751
<212> TYPE: DNA
<213> ORGANISM: Marine eubacteria

<400> SEQUENCE: 114

```
atgggtaaaa gattagtgat attaggtagt gttattgcgc ttccaacatt tgccgctggt     60

ggtggtgacc tggatgctag tgactacact ggtgtatctt tctggttagt tactgctgct    120

ctattagcat ctactgtatt tttctttgtt gaaagagaca gagtttctgc taaatggaaa    180

acatcattaa cagtatctgg tttagttact ggtattgctt tttggcatta catgtacatg    240

agaggtgtat ggattgaaac tggtgattca ccaactgttt ttagatacat cgactggttg    300

ctaactgtgc ctttactaat ttgtgagttc tacttaatac tagcagcagc tactaacgtt    360

gctggttctt tattcaagaa attactagtt ggttctcttg ttatgcttgt gtttggttac    420

atgggtgaag caggaattat ggcagcctgg cctgcattca ttataggatg tttagcatgg    480

gtatacatga tttatgaatt atgggctgga gaaggaaagt ctgcatgtaa cactgcaagt    540

cctgcagttc agtcagctta caacacaatg atgtatatca tcatctttgg ttgggctatt    600

taccttgtag gttatttcac tggttaccta atgggtgacg gtggatcagc tcttaactta    660

aaccttatct ataaccttgc tgactttgtt aacaagattc tatttggttt aattatatgg    720

aatgttgctg ttaaagaatc ttctaatgct a                                    751
```

<210> SEQ ID NO 115
<211> LENGTH: 250
<212> TYPE: PRT
<213> ORGANISM: Marine eubacteria

<400> SEQUENCE: 115

-continued

Met Gly Lys Ala Leu Leu Met Leu Gly Ser Val Ile Ala Leu Pro Thr
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Pro Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Ile Glu Thr Gly Asp Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Phe Gly Trp Ala Ile Tyr Leu Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Arg
225                 230                 235                 240

Asn Val Ala Val Lys Glu Ser Ser Asn Ala
                245                 250

<210> SEQ ID NO 116
<211> LENGTH: 751
<212> TYPE: DNA
<213> ORGANISM: Marine eubacteria

<400> SEQUENCE: 116
atgggtaaag cattactgat gttaggtagt gttattgcgc ttccaacatt tgccgctggt 60
ggtggtgacc tggatgctag tgactacact ggtgtatctt tctggttagt tactgctgct 120
ccattagcat ctactgtatt tttctttgtt gaaagagaca gagtttctgc taaatggaaa 180
acatcattaa cagtatctgg tttagttact ggtattgctt tttggcatta catgtacatg 240
agaggtgtat ggattgaaac tggtgattca ccaactgttt ttagatacat cgactggttg 300
ctaactgtgc ctttactaat ttgtgagttc tacttaatac tagcagcagc tactaacgtt 360
gctggttctt tattcaagaa attactagtt ggttctcttg ttatgcttgt gtttggttac 420
atgggtgaag caggaattat ggcagcctgg cctgcattca ttataggatg tttagcatgg 480
gtatacatga tttatgaatt atgggctgga gaaggaaagt ctgcatgtaa cactgcaagt 540
cctgcagttc agtcagctta caacacaatg atgtatatca tcatctttgg ttgggctatt 600
taccttgtag gttatttcac tggttaccta atgggtgacg gtggatcagc tcttaactta 660

-continued

```
aaccttatct ataaccttgc tgactttgtt aacaagattc tatttggttt aattataagg    720

aatgttgctg ttaaagaatc ttctaatgct a                                   751


<210> SEQ ID NO 117
<211> LENGTH: 250
<212> TYPE: PRT
<213> ORGANISM: Marine eubacteria

<400> SEQUENCE: 117

Met Gly Lys Gly Leu Leu Met Leu Gly Ser Val Ile Ala Leu Pro Ser
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Val Glu Arg Asp Arg Val Ala Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Val Glu Thr Gly Glu Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Ile Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Phe Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Ile Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

His Val Ala Val Lys Glu Ser Ser Asn Ala
                245                 250


<210> SEQ ID NO 118
<211> LENGTH: 751
<212> TYPE: DNA
<213> ORGANISM: Marine eubacteria

<400> SEQUENCE: 118

atgggtaaag gattactgat gttaggtagt gttattgcgc ttccatcttt tgctgctggc     60

ggtggcgatc ttgatgctag tgactataca ggtgtttcat tctggttggt tactgctgca    120

ttattagcct caactgtttt cttctttgtt gaaagagaca gagttgctgc aaaatggaaa    180

acatcgttaa cagtatctgg tcttgttact ggtattgctt tttggcatta catgtacatg    240

agaggggttt gggtagagac tggtgaatca ccaactgtat tcagatatat tgactggcta    300

ctaacagtac cattattaat atgtgagttc tacttaatac ttgcagctgc aactaatgtt    360
```

-continued

```
gctggttctt tatttaaaaa gctattaatt ggttctcttg ttatgcttgt gtttggttac    420

atgggtgaag caggaatcat ggcagcttgg cctgcattca ttattgggtg cttagcttgg    480

ttctacatga tttatgaact atgggctggt gaaggaaagt ctgcttgtaa tactgcaagt    540

ccagctgttc aatcagcata caacacgatg atgtatatta ttatcattgg ttgggctatt    600

taccctgtag gttactttac tggttaccta atgggtgacg gcggatctgc cttaaactta    660

aacctaattt ataaccttgc tgacttcgtt aacaagattc tatttggttt aattatctgg    720

catgttgctg ttaaagaatc ttctaatgct a                                   751
```

<210> SEQ ID NO 119
<211> LENGTH: 250
<212> TYPE: PRT
<213> ORGANISM: Marine eubacteria

<400> SEQUENCE: 119

```
Met Gly Lys Leu Leu Leu Ile Leu Gly Ser Val Ile Ala Leu Pro Ser
1               5                   10                  15

Phe Ala Ala Gly Gly Gly Asp Leu Asp Ala Gly Asp Tyr Thr Gly Val
            20                  25                  30

Ser Phe Trp Leu Val Thr Ala Ala Leu Leu Ala Ser Thr Val Phe Phe
        35                  40                  45

Phe Ile Glu Arg Asp Arg Val Ala Ala Lys Trp Lys Thr Ser Leu Thr
    50                  55                  60

Val Ser Gly Leu Val Thr Gly Ile Ala Phe Trp His Tyr Met Tyr Met
65                  70                  75                  80

Arg Gly Val Trp Val Glu Thr Gly Glu Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Trp Pro Ala Phe Ile Val Gly Cys Leu Ala Trp
145                 150                 155                 160

Phe Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Ile Gly Trp Ala Ile Tyr Pro Leu Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240

His Val Ala Val Lys Glu Ser Ser Asn Ala
                245                 250
```

<210> SEQ ID NO 120
<211> LENGTH: 751
<212> TYPE: DNA
<213> ORGANISM: Marine eubacteria

<400> SEQUENCE: 120

-continued

```
atgggtaaat tattattgat cttaggtagt gttattgcgc ttccttcatt tgcagctggt     60

ggcggcgacc ttgatgctgg tgattacact ggtgttagtt tttggttagt gactgcagct    120

cttttggctt caactgtatt tttctttatt gaaagagata gagttgctgc taaatggaag    180

acatctttaa cagtatctgg tctagttact ggtattgctt tctggcatta catgtacatg    240

agaggtgttt gggtcgaaac tggtgaatca ccaactgtat tcagatatat tgactggcta    300

cttacagtgc ctttattaat atgtgagttt tatctgattc ttgcagctgc aactaatgtt    360

gctggttctt tatttaagaa gcttttagtt ggttctcttg taatgcttgt atttggttat    420

atgggcgaag caggaattat ggcagcttgg cctgcattca ttgttggatg tttagcttgg    480

ttctatatga tttatgagct atgggctgga gaaggaaaat ctgcatgcaa tactgcaagt    540

ccagctgttc aatcagcata caacacaatg atgtatatta ttatcattgg ttgggctatt    600

tatcctcttg ggtactttac tggttaccta atgggtgacg gcggatcagc cttaaactta    660

aacctaattt ataaccttgc tgactttgtt aacaagattc tatttggttt aatcatatgg    720

catgtcgctg ttaaagaatc ttctaatgct a                                   751
```

<210> SEQ ID NO 121
<211> LENGTH: 250
<212> TYPE: PRT
<213> ORGANISM: Marine eubacteria

<400> SEQUENCE: 121

```
Met Gly Lys Gln Leu Leu Ile Leu Gly Ser Val Ile Ala Leu Pro Ser
1               5                   10                  15

Phe Ala Ala Gly Gly Gly Asp Leu Asp Ala Ser Asp Tyr Thr Gly Val
            20                  25                  30

Ser Phe Trp Leu Val Thr Ala Ala Leu Leu Ala Ser Thr Val Phe Phe
        35                  40                  45

Phe Ile Glu Arg Asp Arg Val Ala Ala Lys Trp Lys Thr Ser Leu Thr
    50                  55                  60

Val Ser Gly Leu Val Thr Gly Ile Ala Phe Trp His Tyr Leu Tyr Met
65                  70                  75                  80

Arg Gly Val Trp Val Glu Thr Gly Glu Ser Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Ile Gly Ser Leu Val Met Leu Val Phe Gly Tyr Met Gly Glu Ala
    130                 135                 140

Gly Ile Met Ala Ala Trp Pro Ala Phe Ile Ile Gly Cys Leu Ala Trp
145                 150                 155                 160

Val Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
            180                 185                 190

Ile Ile Ile Phe Gly Trp Ala Ile Tyr Pro Val Gly Tyr Phe Thr Gly
        195                 200                 205

Tyr Leu Met Gly Asp Gly Gly Ser Ala Leu Asn Leu Asn Leu Ile Tyr
    210                 215                 220

Asn Leu Ala Asp Phe Val Asn Lys Ile Leu Phe Gly Leu Ile Ile Trp
225                 230                 235                 240
```

-continued

```
His Val Ala Val Lys Glu Ser Ser Asn Ala
                245                 250


<210> SEQ ID NO 122
<211> LENGTH: 751
<212> TYPE: DNA
<213> ORGANISM: Marine eubacteria

<400> SEQUENCE: 122

atgggtaaac aattactgat cttaggtagt gttattgcgc ttccatcttt tgctgctggc      60

ggtggcgatc ttgatgctag tgactataca ggtgtttcat tctggttagt tactgctgca     120

ttattagcct caactgtttt ctttttttatt gaaagagaca gagttgctgc aaaatggaaa     180

acgtcgttaa cagtatctgg ccttgttact ggtattgctt tttggcacta cttgtatatg     240

agaggagttt gggtagagac tggtgaatca ccaactgtat tcagatatat tgactggtta     300

ctaacagtac cattattaat atgtgagttt tacttaatac ttgcagctgc aactaatgtt     360

gctggttctt tatttaaaaa gctattaatt ggttctcttg tgatgcttgt gtttggttac     420

atgggtgaag caggaatcat ggcggcttgg cctgcattca ttattgggtg cttagcttgg     480

gtctatatga tatatgagct atgggctggt gaaggaaaat ctgcatgtaa tactgcaagt     540

ccagctgttc aatcagcata caacacaatg atgtatatta ttatctttgg ttgggctatt     600

taccctgtag gttactttac tggttaccta atgggtgacg gcggatctgc cttaaactta     660

aaccttatct ataaccttgc tgacttcgtt aacaagattc tatttggttt aattatctgg     720

catgttgctg ttaaagaatc ttctaatgct a                                    751


<210> SEQ ID NO 123
<211> LENGTH: 250
<212> TYPE: PRT
<213> ORGANISM: Marine eubacteria

<400> SEQUENCE: 123

Met Gly Lys Leu Leu Met Met Leu Gly Ser Val Ile Ala Leu Pro Ser
1               5                   10                  15

Phe Ala Ala Ser Gly Gly Asp Leu Asp Ala Ser Asp Tyr Thr Gly Val
            20                  25                  30

Ser Phe Gly Leu Val Thr Ala Ala Leu Leu Ala Ser Thr Val Phe Phe
        35                  40                  45

Phe Val Glu Arg Asp Arg Val Ser Ala Lys Trp Lys Thr Ser Leu Thr
    50                  55                  60

Val Ser Gly Leu Val Thr Gly Ile Ala Phe Trp His Tyr Leu Tyr Met
65                  70                  75                  80

Arg Gly Val Trp Val Glu Thr Gly Glu Thr Pro Thr Val Phe Arg Tyr
                85                  90                  95

Ile Asp Trp Leu Leu Thr Val Pro Leu Leu Ile Cys Glu Phe Tyr Leu
            100                 105                 110

Ile Leu Ala Ala Ala Thr Asn Val Ala Gly Ser Leu Phe Lys Lys Leu
        115                 120                 125

Leu Val Gly Ser Leu Val Met Leu Val Phe Gly Tyr Met Gly Glu Ala
    130                 135                 140

Gly Ile Met Ala Ala Leu Pro Ala Phe Ile Ile Gly Cys Leu Ala Trp
145                 150                 155                 160

Ile Tyr Met Ile Tyr Glu Leu Trp Ala Gly Glu Gly Lys Ser Ala Cys
                165                 170                 175

Asn Thr Ala Ser Pro Ala Val Gln Ser Ala Tyr Asn Thr Met Met Tyr
```

-continued

```
            180                 185                 190

Ile Ile Ile Phe Gly Trp Leu Ile Tyr Pro Val Gly Tyr Ala Ser Gly
        195                 200                 205

Tyr Leu Met Gly Asp Gly Gly Ser Ala Met Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250
```

<210> SEQ ID NO 124
<211> LENGTH: 751
<212> TYPE: DNA
<213> ORGANISM: Marine eubacteria

<400> SEQUENCE: 124

```
atgggtaaat tattaatgat gttaggtagt gttattgcgc ttccttcatt tgcggcaagt      60

ggtggcgatt tggatgctag tgattacact ggtgtttcat ttgggttggt gactgcagct     120

ttattagctt caactgtatt tttctttgtt gaaagagata gagtttctgc taaatggaag     180

acatctttga cagtatcagg tttagttact ggtattgctt tttggcatta cttatatatg     240

agaggtgtat gggttgaaac tggtgaaact ccaacagtat ttagatatat tgattggtta     300

ttaactgttc cattactaat ctgcgagttt tatttaattc tagctgctgc aactaacgta     360

gctggttcat tatttaagaa actacttgtt ggttcacttg taatgcttgt gtttggatac     420

atgggtgaag caggaatcat ggcagctttg cctgcattca ttattgggtg tttggcatgg     480

atatatatga tttatgagct ttgggctgga gaagggaaat ctgcatgcaa tactgcaagt     540

cctgccgttc aatcagctta caacaccatg atgtacatca tcatttttgg ttggttaatc     600

tatccagttg gttatgcatc aggctatcta atgggcgatg gcggatcagc tatgaactta     660

aacttaatat ataaccttgc tgactttgtt aacaagattc tatttggttt aattatctgg     720

aatgttgctg ttaaagaatc ttctaatgct a                                    751
```

<210> SEQ ID NO 125
<211> LENGTH: 258
<212> TYPE: PRT
<213> ORGANISM: Marine eubacteria

<400> SEQUENCE: 125

```
Met Gly Lys Gly Leu Leu Met Leu Gly Ser Val Ile Ala Leu Pro Ser
1               5                   10                  15

Phe Ala Ala Gly Gly Gly Asn Leu Asn Ala Ala Asp Val Thr Gly Val
            20                  25                  30

Ser Phe Trp Leu Val Thr Ala Ala Leu Leu Ala Ser Thr Val Phe Phe
        35                  40                  45

Phe Ile Glu Arg Asp Arg Val Ser Ala Lys Trp Lys Thr Ser Leu Thr
    50                  55                  60

Val Ser Gly Leu Val Thr Gly Ile Ala Phe Trp His Tyr Leu Tyr Met
65                  70                  75                  80

Arg Gly Val Trp Val Asp Ser Trp Asn Pro Glu Thr Gly Met Gly Glu
                85                  90                  95

Ser Pro Thr Glu Phe Arg Tyr Ile Asp Trp Leu Leu Thr Val Pro Leu
            100                 105                 110

Leu Ile Cys Glu Phe Tyr Leu Ile Leu Ala Ala Ala Thr Asn Val Ala
        115                 120                 125
```

-continued

```
Gly Ser Leu Phe Lys Lys Leu Leu Val Gly Ser Leu Val Met Leu Ile
    130                 135                 140

Ala Gly Tyr Met Gly Glu Ser Gly Asn Ala Asn Val Met Ile Ala Phe
145                 150                 155                 160

Val Val Gly Cys Leu Ala Trp Leu Tyr Met Ile Tyr Glu Leu Trp Ala
                165                 170                 175

Gly Glu Gly Lys Ala Ala Cys Asn Thr Ala Ser Pro Ala Val Gln Ser
            180                 185                 190

Ala Tyr Asn Thr Met Met Trp Ile Ile Ile Val Gly Trp Ala Ile Tyr
        195                 200                 205

Pro Ala Gly Tyr Ala Ala Gly Tyr Leu Met Gly Gly Glu Ser Val Tyr
    210                 215                 220

Ala Ser Asn Leu Asn Leu Ile Tyr Asn Leu Ala Asp Phe Val Asn Lys
225                 230                 235                 240

Ile Leu Phe Gly Leu Ile Ile Trp His Val Ala Val Lys Glu Ser Ser
                245                 250                 255

Asn Ala
```

<210> SEQ ID NO 126
<211> LENGTH: 775
<212> TYPE: DNA
<213> ORGANISM: Marine eubacteria

<400> SEQUENCE: 126

```
atgggtaaag gattactgat gttaggtagt gttattgcac ttccatcctt tgcagctggt      60

ggaggcaact taaatgcagc tgatgtaact ggtgtatctt tttggctagt tactgccgct     120

ttacttgctt caacagtatt ctttttttatt gaaagagata gagtttctgc aaaatggaag     180

acatcactaa cagtatctgg tttagttact ggtattgctt tttggcatta cctttacatg     240

agaggtgttt gggttgattc ttggaatcct gaaacaggaa tgggagaatc tccaactgaa     300

tttagatata ttgattggtt actaacagta cctttattaa tttgtgagtt ttatctaata     360

ttagctgctg caacaaatgt tgctggttca ttattcaaaa aattattagt tggttcattg     420

gtcatgctta ttgcaggata catgggtgaa tctggtaatg ccaatgtgat gattgcattc     480

gtagttggat gcttagcatg gttgtatatg atatatgaat tgtgggctgg tgaaggtaaa     540

gcagcttgca atacagcaag ccctgctgtt caatcagcat acaatacaat gatgtggatc     600

attattgtag gttgggctat atatcctgct ggatatgctg ctggctattt gatgggtgga     660

gaaagcgttt atgcttctaa ccttaacctg atatataacc ttgctgactt tgttaacaag     720

attttatttg gtttaatcat ttggcatgtt gctgttaaag aatcttctaa tgcta          775
```

<210> SEQ ID NO 127
<211> LENGTH: 257
<212> TYPE: PRT
<213> ORGANISM: Marine eubacteria

<400> SEQUENCE: 127

```
Met Gly Lys Leu Leu Val Met Leu Gly Ser Val Ile Ala Leu Pro Ser
1               5                   10                  15

Phe Ala Ala Gly Gly Gly Asn Leu Asp Ala Ala Asp Val Thr Gly Val
            20                  25                  30

Ser Phe Trp Leu Val Thr Ala Ala Leu Leu Ala Ser Thr Val Phe Phe
        35                  40                  45

Phe Ile Glu Arg Asp Arg Val Ser Ala Lys Trp Lys Thr Ser Leu Thr
```

-continued

```
    50                  55                  60

Val Ser Gly Leu Val Thr Gly Ile Ala Phe Trp His Tyr Leu Tyr Met
65                  70                  75                  80

Arg Gly Val Trp Val Asp Ser Trp Thr Gly Pro Gly Thr Gly Glu Ser
                85                  90                  95

Pro Thr Glu Phe Arg Tyr Ile Asp Trp Leu Leu Thr Val Pro Leu Leu
            100                 105                 110

Ile Cys Glu Phe Tyr Leu Ile Leu Ala Ala Ala Thr Asn Val Ala Gly
        115                 120                 125

Ser Leu Phe Lys Lys Leu Leu Val Gly Ser Leu Val Met Leu Ile Ala
    130                 135                 140

Gly Tyr Met Gly Glu Ser Gly Asn Ala Asn Val Met Ile Ala Phe Val
145                 150                 155                 160

Val Gly Cys Leu Ala Trp Leu Tyr Met Ile Tyr Glu Leu Trp Ala Gly
                165                 170                 175

Glu Gly Lys Ala Ala Cys Asn Thr Ala Ser Pro Ala Val Gln Ser Ala
            180                 185                 190

Tyr Asn Thr Met Met Trp Ile Ile Ile Val Gly Trp Ala Ile Tyr Pro
        195                 200                 205

Ala Gly Tyr Ala Ala Gly Tyr Leu Met Gly Gly Glu Ser Val Tyr Ala
    210                 215                 220

Ser Asn Leu Asn Leu Ile Tyr Asn Leu Ala Asp Phe Val Asn Lys Ile
225                 230                 235                 240

Leu Phe Gly Leu Ile Ile Trp His Val Ala Val Lys Glu Ser Ser Asn
                245                 250                 255

Ala
```

<210> SEQ ID NO 128
<211> LENGTH: 772
<212> TYPE: DNA
<213> ORGANISM: Marine eubacteria

<400> SEQUENCE: 128

```
atgggtaaat tattagtgat gttaggtagt gttattgcac ttccatcctt tgcagctggt     60

ggaggtaact tagatgcagc tgatgtaact ggtgtatctt tttggctagt tactgcggct    120

ttacttgctt caacagtatt ctttttttatt gaaagagata gagtttctgc aaaatggaag    180

acatcactaa cagtatctgg tttagttact ggtattgcat tttggcatta cctttatatg    240

agaggcgttt gggttgattc ttggactggt ccaggaaccg gagaatctcc aactgaattt    300

agatatattg attggttact aacagtacct ttattaattt gtgagtttta tctaatatta    360

gctgctgcaa caaatgttgc tggttcatta ttcaaaaaat tattagttgg ttcattggtc    420

atgcttattg caggatacat gggtgaatct ggtaatgcca atgtgatgat tgcattcgta    480

gttggatgct tagcatggtt gtatatgata tatgaattgt gggctggtga aggtaaagca    540

gcttgcaata cagcaagccc tgctgttcaa tcagcataca atacaatgat gtggatcatt    600

attgtaggtt gggctatata tcctgctgga tatgctgctg gctatttgat gggtggagaa    660

agcgtttatg cttctaacct taacctgata tataaccttg ctgactttgt taacaagatt    720

ttatttggtt taatcatttg gcatgttgct gttaaagaat cttctaatgc ta            772
```

<210> SEQ ID NO 129
<211> LENGTH: 249
<212> TYPE: PRT
<213> ORGANISM: Marine eubacteria

<400> SEQUENCE: 129

Met Gly Lys Leu Leu Val Met Leu Gly Gly Val Ile Ala Leu Pro Ser
1               5                   10                  15

Phe Ala Ala Gly Gly Gly Asp Leu Asp Ile Gly Asp Ser Val Gly Val
            20                  25                  30

Ser Phe Trp Leu Val Thr Ala Ala Met Leu Ala Ala Thr Val Phe Phe
        35                  40                  45

Phe Val Glu Arg Asp Gln Val Ser Ala Lys Trp Lys Thr Ser Leu Thr
    50                  55                  60

Val Ser Gly Leu Ile Thr Gly Ile Ala Phe Trp His Tyr Leu Tyr Met
65                  70                  75                  80

Arg Gly Val Trp Ile Asp Thr Gly Gly Ser Pro Thr Val Phe Arg Tyr
                85                  90                  95

Ile Asp Trp Leu Leu Thr Val Pro Leu Gln Met Val Glu Phe Tyr Leu
            100                 105                 110

Ile Leu Ala Ala Cys Thr Asn Val Ala Gly Ser Leu Phe Lys Lys Leu
        115                 120                 125

Leu Val Gly Ser Leu Val Met Leu Gly Ala Gly Phe Ala Gly Glu Ala
    130                 135                 140

Gly Leu Ala Pro Ala Leu Pro Ala Phe Ile Leu Gly Met Ala Gly Trp
145                 150                 155                 160

Val Tyr Met Ile Tyr Glu Leu Tyr Met Gly Glu Gly Lys Ala Ala Val
                165                 170                 175

Ser Thr Ala Ser Pro Ala Val Asn Ser Ala Tyr Asn Ala Met Met Met
            180                 185                 190

Ile Ile Val Phe Gly Trp Ser Ile Tyr Pro Leu Gly Tyr Val Ala Gly
        195                 200                 205

Tyr Leu Met Gly Ala Val Asp Pro Ser Thr Leu Asn Leu Ile Tyr Asn
    210                 215                 220

Leu Ala Asp Phe Ile Asn Lys Ile Leu Phe Gly Leu Ile Ile Trp His
225                 230                 235                 240

Val Ala Val Lys Glu Ser Ser Asn Ala
                245

<210> SEQ ID NO 130
<211> LENGTH: 748
<212> TYPE: DNA
<213> ORGANISM: Marine eubacteria

<400> SEQUENCE: 130
atgggtaaat tattagtgat gttaggtggt gttattgcac ttccttcttt tgctgctggt 60
ggtggtgatc tagatatagg agactccgtt ggagtttcat tctggcttgt tactgctgct 120
atgttagctg ctactgtttt cttttttgtt gaaagagacc aagtaagcgc aaagtggaaa 180
acatcattaa cagtatcagg tttaattact ggtattgctt tttggcatta tctttacatg 240
agaggtgtat ggatagatac aggtggaagc ccaacagtat ttagatatat tgattggttg 300
ctaactgttc cattacaaat ggttgagttt tatttaattc ttgcagcttg tactaatgta 360
gctggttcat tatttaagaa actgcttgtt ggttcattag taatgttagg tgctggattt 420
gctggtgaag ctggactagc tcctgcattg cctgctttca tacttggtat ggctggatgg 480
gtatacatga tatatgagct gtatatgggt gaaggtaaag ctgcggtgag tactgctagt 540
cctgccgtaa attctgctta caatgcaatg atgatgatta tagtttttgg ttggtctatt 600

```
tatccactgg gatatgttgc tggctattta atgggtgcag tagatccaag tacattaaat    660

ctaatataca accttgctga ttttattaat aagattttat tcggtttaat aatctggcat    720

gttgctgtta aagaatcttc taatgcta                                       748
```

<210> SEQ ID NO 131
<211> LENGTH: 249
<212> TYPE: PRT
<213> ORGANISM: Marine eubacteria

<400> SEQUENCE: 131

```
Met Gly Lys Leu Leu Met Ile Leu Gly Gly Val Ile Ala Leu Pro Ser
1               5                   10                  15

Phe Ala Ala Gly Gly Gly Asp Leu Asp Ile Gly Asp Ser Val Gly Val
                20                  25                  30

Ser Phe Trp Leu Val Thr Ala Ala Met Leu Ala Ala Thr Val Phe Phe
            35                  40                  45

Phe Val Glu Arg Asp Gln Val Ser Ala Lys Trp Lys Thr Ser Leu Thr
        50                  55                  60

Val Ser Gly Leu Ile Thr Gly Ile Ala Phe Trp His Tyr Leu Tyr Met
65                  70                  75                  80

Arg Gly Val Trp Ile Asp Thr Gly Gly Ser Pro Thr Val Phe Arg Tyr
                85                  90                  95

Ile Asp Trp Leu Leu Thr Val Pro Leu Gln Met Val Glu Phe Tyr Leu
            100                 105                 110

Ile Leu Ala Ala Cys Thr Asn Val Ala Gly Ser Leu Phe Lys Lys Leu
        115                 120                 125

Leu Val Gly Ser Leu Val Met Leu Gly Ala Gly Phe Ala Gly Glu Ala
130                 135                 140

Gly Leu Ala Pro Ala Leu Pro Ala Phe Ile Leu Gly Met Ala Gly Trp
145                 150                 155                 160

Val Tyr Met Ile Tyr Glu Leu Tyr Met Gly Glu Gly Lys Ala Ala Val
                165                 170                 175

Ser Thr Ala Ser Pro Ala Val Asn Ser Ala Tyr Asn Ala Met Met Met
            180                 185                 190

Ile Ile Val Phe Gly Trp Ser Ile Tyr Pro Leu Gly Tyr Val Ala Gly
        195                 200                 205

Tyr Leu Met Gly Ala Val Asp Pro Ser Thr Leu Asn Leu Ile Tyr Asn
210                 215                 220

Leu Ala Asp Phe Ile Asn Lys Ile Leu Phe Gly Leu Ile Ile Trp His
225                 230                 235                 240

Val Ala Val Lys Glu Ser Ser Asn Ala
                245
```

<210> SEQ ID NO 132
<211> LENGTH: 748
<212> TYPE: DNA
<213> ORGANISM: Marine eubacteria

<400> SEQUENCE: 132

```
atgggtaaat tattaatgat cttaggtggt gttattgcac ttccttcttt tgctgctggt     60

ggtggtgatc tagatatagg agactctgtt ggagtttcat tctggcttgt tactgctgct    120

atgttagctg ctactgtttt cttttttgtt gaaagagacc aagtaagcgc aaagtggaaa    180

acatcattaa cagtatcagg tttaattact ggtattgctt tttggcatta tctttacatg    240

agaggtgtat ggatagatac aggtggaagc ccaacagtat ttagatatat tgattggttg    300
```

-continued

```
ctaactgttc cattacaaat ggttgagttt tatttaattc ttgcagcttg tactaatgta    360

gctggttcat tatttaagaa actgcttgtt ggttcattag taatgttagg tgctggattt    420

gctggtgaag ctggattagc tcctgcattg cctgctttca tacttggtat ggctggatgg    480

gtatacatga tatatgagct gtatatgggt gaaggtaaag ctgcggtgag tactgctagt    540

cctgccgtaa attctgctta caatgcaatg atgatgatta tagtttttgg ttggtctatt    600

tatccactgg gatatgttgc tggctattta atgggtgcag tagatccaag tacattaaat    660

ctaatataca accttgctga ttttattaat aagattttat tcggtttaat aatctggcat    720

gttgctgtta aagaatcttc taatgcta                                        748
```

<210> SEQ ID NO 133
<211> LENGTH: 251
<212> TYPE: PRT
<213> ORGANISM: Marine eubacteria

<400> SEQUENCE: 133

```
Met Gly Lys Leu Leu Met Ile Leu Gly Gly Val Ile Ala Leu Pro Ser
1               5                   10                  15

Phe Ala Ala Gly Gly Gly Asp Leu Asp Ile Gly Asp Ser Val Gly Val
            20                  25                  30

Ser Phe Trp Leu Val Thr Ala Ala Met Leu Ala Ala Thr Val Phe Phe
        35                  40                  45

Phe Val Glu Arg Asp Gln Val Ser Ala Lys Trp Lys Thr Ser Leu Thr
    50                  55                  60

Val Ser Gly Leu Ile Thr Gly Ile Ala Phe Trp His Tyr Leu Tyr Met
65                  70                  75                  80

Arg Gly Val Trp Val Glu Thr Gly Asp Ser Pro Thr Val Phe Arg Tyr
                85                  90                  95

Ile Asp Trp Leu Leu Thr Val Pro Leu Gln Met Val Glu Phe Tyr Leu
            100                 105                 110

Ile Leu Ala Ala Cys Thr Asn Val Ala Gly Ser Leu Phe Lys Lys Leu
        115                 120                 125

Leu Ile Gly Ser Leu Val Met Leu Ile Gly Gly Phe Leu Gly Glu Ala
    130                 135                 140

Gly Met Ile Asp Val Thr Leu Ala Phe Val Ile Gly Met Ala Gly Trp
145                 150                 155                 160

Leu Tyr Met Ile Tyr Glu Leu Tyr Met Gly Glu Gly Lys Ala Ala Val
                165                 170                 175

Ser Thr Ala Ser Pro Ala Val Asn Ser Ala Tyr Asn Ala Met Met Leu
            180                 185                 190

Ile Ile Val Val Gly Trp Ser Ile Tyr Pro Ala Gly Tyr Val Ala Gly
        195                 200                 205

Tyr Leu Met Gly Gly Glu Gly Val Tyr Ala Ser Asn Leu Asn Leu Ile
    210                 215                 220

Tyr Asn Leu Ala Asp Phe Ile Asn Lys Ile Leu Phe Gly Leu Ile Ile
225                 230                 235                 240

Trp His Val Ala Val Lys Glu Ser Ser Asn Ala
                245                 250
```

<210> SEQ ID NO 134
<211> LENGTH: 754
<212> TYPE: DNA
<213> ORGANISM: Marine eubacteria -continued

<400> SEQUENCE: 134

```
atgggtaaat tattaatgat attaggtggt gttattgcac ttccttcttt tgctgctggt     60
ggtggtgatc tagatatagg agactctgtt ggagtttcat tctggcttgt tactgctgct    120
atgttagctg ctactgtttt ctttttgtt gaaagagacc aagtaagcgc aaaatggaaa    180
acatcattaa cagtatcagg tttaataaca ggtattgctt tctggcacta cttgtatatg    240
agaggggttt gggtagaaac aggcgattca ccaactgtat ttagatatat agattggctt    300
ttaactgtac cactacaaat ggtagagttt tatctgatat tagctgcatg taccaatgtt    360
gctggatctt tatttaaaaa gctactaatc ggttcattgg tgatgttgat aggaggtttc    420
ctaggtgaag ctggtatgat agatgtaaca ctagcttttg taattggaat ggctggatgg    480
ctatatatga tctatgagct atacatgggt gaaggtaaag ctgcggtgag tactgctagt    540
cctgccgtaa attctgctta caatgcaatg atgcttatta ttgttgttgg ttggtcaatc    600
tatcctgctg gatatgttgc tggctatctt atgggcggtg aaggagtata tgcctcaaat    660
ctaaacttaa tatataacct tgctgatttt atcaacaaga ttctatttgg tttaattata    720
tggcatgttg ctgttaaaga atcttctaat gcta                                 754
```

<210> SEQ ID NO 135
<211> LENGTH: 251
<212> TYPE: PRT
<213> ORGANISM: Marine eubacteria

<400> SEQUENCE: 135

```
Met Gly Lys Gln Leu Leu Ile Leu Gly Gly Val Ile Ala Leu Pro Ser
1               5                   10                  15

Phe Ala Ala Ser Gly Gly Asp Leu Asp Ser Ser Asp Leu Thr Gly Val
            20                  25                  30

Ser Phe Trp Leu Val Thr Ala Ala Leu Leu Ala Ala Thr Val Phe Phe
        35                  40                  45

Phe Val Glu Arg Asp Gln Val Ser Ala Lys Trp Lys Thr Ser Leu Thr
    50                  55                  60

Val Ser Gly Leu Val Thr Gly Ile Ala Phe Trp His Tyr Leu Tyr Met
65                  70                  75                  80

Arg Gly Val Trp Ile Glu Thr Gly Glu Thr Pro Thr Val Phe Arg Tyr
                85                  90                  95

Ile Asp Trp Leu Leu Thr Val Pro Leu Leu Met Val Glu Phe Tyr Leu
            100                 105                 110

Ile Leu Ala Ala Cys Thr Asn Val Ala Gly Ser Leu Phe Lys Lys Leu
        115                 120                 125

Leu Gly Gly Ser Leu Val Met Leu Ile Ala Gly Tyr Met Gly Glu Ser
    130                 135                 140

Gly Ser Leu Pro Val Leu Pro Ala Phe Ile Val Gly Cys Leu Ala Trp
145                 150                 155                 160

Phe Tyr Met Ile Tyr Glu Leu Tyr Ala Gly Glu Gly Lys Ala Ala Val
                165                 170                 175

Thr Thr Ala Ser Pro Ala Val Met Ser Ala Tyr Asn Thr Met Met Leu
            180                 185                 190

Ile Ile Val Val Gly Trp Ala Ile Tyr Pro Ala Gly Tyr Ala Ala Gly
        195                 200                 205

Tyr Leu Met Gly Gly Asp Gly Val Tyr Ala Gln Asn Leu Asn Val Ile
    210                 215                 220

Tyr Asn Leu Ala Asp Phe Val Asn Lys Ile Leu Phe Gly Leu Val Ile
```

-continued

```
225                 230                 235                 240

Trp His Val Ala Val Lys Glu Ser Ser Asn Ala
                245                 250
```

<210> SEQ ID NO 136
<211> LENGTH: 754
<212> TYPE: DNA
<213> ORGANISM: Marine eubacteria

<400> SEQUENCE: 136

```
atgggtaaac aattactgat tttaggtggt gttattgcac ttccttcgtt tgctgcaagt     60

gggggcgatc ttgattctag tgatcttact ggagtttctt tttggcttgt tactgctgct    120

ctcttagctg ctactgtttt ctttttttgtt gaaagagatc aagtaagtgc taaatggaaa    180

acatcactta cagtttctgg tttagttact ggtattgcat tctggcatta tctttatatg    240

agaggtgtgt ggatcgaaac tggtgaaacg ccaacagtat ttagatatat tgattggttg    300

ctaactgttc ctttgctaat ggttgagttc tacttaatcc ttgcagcgtg cacaaatgtt    360

gcgggttcat tatttaagaa actacttggt ggttcgcttg taatgcttat tgcaggatat    420

atgggtgagt ctggaagtct tccagtattg cctgcattca ttgttgggtg cttagcatgg    480

ttctacatga tttatgaact atatgctggt gaaggtaagg ctgcagttac tactgctagt    540

cctgctgtta tgtctgcata caatactatg atgttgatta tcgtagtagg ttgggcaatt    600

tacccagctg gatatgctgc tggttaccta atgggtggtg atggcgtata tgctcagaat    660

ttaaacgtta tatataacct tgctgacttt gttaacaaga ttttatttgg tttagttatc    720

tggcatgttg ctgttaaaga atcttctaat gcta                                754
```

<210> SEQ ID NO 137
<211> LENGTH: 251
<212> TYPE: PRT
<213> ORGANISM: Marine eubacteria

<400> SEQUENCE: 137

```
Met Gly Lys Leu Leu Met Ile Leu Gly Gly Val Ile Ala Leu Pro Ser
1               5                   10                  15

Phe Ala Ala Ser Gly Gly Asp Leu Asp Ser Ser Asp Leu Thr Gly Val
            20                  25                  30

Ser Phe Trp Leu Val Thr Ala Ala Leu Leu Ala Ala Thr Val Phe Phe
        35                  40                  45

Phe Val Glu Arg Asp Gln Val Ser Ala Lys Trp Lys Thr Ser Leu Thr
    50                  55                  60

Val Ser Gly Leu Val Thr Gly Ile Ala Phe Trp His Tyr Leu Tyr Met
65                  70                  75                  80

Arg Gly Val Trp Ile Glu Thr Gly Glu Thr Pro Thr Val Phe Arg Tyr
                85                  90                  95

Ile Asp Trp Leu Leu Thr Val Pro Leu Leu Met Val Glu Phe Tyr Leu
            100                 105                 110

Ile Leu Ala Ala Cys Thr Asn Val Ala Gly Ser Leu Phe Lys Lys Leu
        115                 120                 125

Leu Gly Gly Ser Leu Val Met Leu Ile Ala Gly Tyr Met Gly Glu Ser
    130                 135                 140

Gly Ser Leu Pro Val Leu Pro Ala Phe Ile Val Gly Cys Leu Ala Trp
145                 150                 155                 160

Phe Tyr Met Ile Tyr Glu Leu Tyr Ala Gly Glu Gly Lys Ala Ala Val
                165                 170                 175
```

-continued

```
Thr Thr Ala Ser Pro Ala Val Met Ser Ala Tyr Asn Thr Met Met Leu
            180                 185                 190

Ile Ile Val Val Gly Trp Ala Ile Tyr Pro Ala Gly Tyr Ala Ala Gly
        195                 200                 205

Tyr Leu Met Gly Gly Asp Gly Val Tyr Ala Gln Asn Leu Asn Val Ile
    210                 215                 220

Tyr Asn Leu Ala Asp Phe Val Asn Lys Ile Leu Phe Gly Leu Val Ile
225                 230                 235                 240

Trp His Val Ala Val Lys Glu Ser Ser Asn Ala
                245                 250
```

<210> SEQ ID NO 138
<211> LENGTH: 754
<212> TYPE: DNA
<213> ORGANISM: Marine eubacteria

<400> SEQUENCE: 138

```
atgggtaaat tattaatgat cttaggtggt gtcattgcgc ttccttcgtt tgctgcaagt     60

ggtggcgatc ttgattctag tgatcttact ggagtatctt tttggcttgt tactgctgct    120

ctcttagctg ctactgtttt cttttttgtt gaaagagatc aagtaagtgc taaatggaaa    180

acatcactta cagtttctgg tttagttact ggtattgcat tctggcatta tctctatatg    240

agaggtgtgt ggatcgaaac tggtgaaacg ccaacagtat ttagatatat tgattggttg    300

ctaactgttc cgttactaat ggttgagttc tacttaattc ttgcggcttg cacaaatgtt    360

gcgggctcat tatttaagaa actactaggt ggttcgcttg taatgcttat tgcaggatat    420

atgggtgagt ctggaagtct tccagtattg cctgcattca ttgttggatg cctagcatgg    480

ttctacatga tttatgaact atatgctggt gaaggtaagg ctgcagttac tactgctagt    540

cctgctgtta tgtctgcata caatactatg atgttgatta tcgtagtagg ttgggcaatt    600

tacccggctg gatatgctgc tggataccta atgggtggtg atggcgtata tgctcagaat    660

ttaaacgtta tatataatct tgctgacttt gttaacaaga ttttatttgg tttagttatc    720

tggcatgtcg ctgttaaaga atcttctaat gcta                                754
```

<210> SEQ ID NO 139
<211> LENGTH: 251
<212> TYPE: PRT
<213> ORGANISM: Marine eubacteria

<400> SEQUENCE: 139

```
Met Gly Lys Leu Leu Val Ile Leu Gly Gly Val Ile Ala Leu Pro Pro
1               5                   10                  15

Phe Ala Ala Ser Gly Gly Asp Leu Asp Ser Ser Asp Leu Thr Gly Val
            20                  25                  30

Ser Phe Trp Leu Val Thr Ala Ala Leu Leu Ala Ala Thr Val Phe Phe
        35                  40                  45

Phe Val Glu Arg Asp Gln Val Ser Ala Lys Trp Lys Thr Ser Leu Thr
    50                  55                  60

Val Ser Gly Leu Val Thr Gly Ile Ala Phe Trp His Tyr Leu Tyr Met
65                  70                  75                  80

Arg Gly Val Trp Ile Glu Thr Gly Glu Thr Pro Thr Val Phe Arg Tyr
                85                  90                  95

Ile Asp Trp Leu Leu Thr Val Pro Leu Leu Met Val Glu Phe Tyr Leu
            100                 105                 110
```

-continued

```
Ile Leu Ala Ala Cys Thr Asn Val Ala Gly Ser Leu Phe Lys Lys Leu
        115                 120                 125

Leu Gly Gly Ser Leu Val Met Leu Ile Ala Gly Tyr Met Gly Glu Ser
    130                 135                 140

Gly Ser Leu Pro Val Leu Pro Ala Phe Ile Val Gly Cys Leu Ala Trp
145                 150                 155                 160

Phe Tyr Met Ile Tyr Glu Leu Tyr Ala Gly Glu Gly Lys Ala Ala Val
                165                 170                 175

Thr Thr Ala Ser Pro Ala Val Met Ser Ala Tyr Asn Thr Met Met Leu
            180                 185                 190

Ile Ile Val Val Gly Trp Ala Ile Tyr Pro Ala Gly Tyr Ala Ala Gly
        195                 200                 205

Tyr Leu Met Gly Gly Asp Gly Val Tyr Ala Gln Asn Leu Asn Val Ile
    210                 215                 220

Tyr Asn Leu Ala Asp Phe Val Asn Lys Ile Leu Phe Gly Leu Val Ile
225                 230                 235                 240

Trp His Val Ala Val Lys Glu Ser Ser Asn Ala
                245                 250


<210> SEQ ID NO 140
<211> LENGTH: 754
<212> TYPE: DNA
<213> ORGANISM: Marine eubacteria

<400> SEQUENCE: 140

atgggtaaac tattagtgat attaggtggt gtcattgcgc ttcctccgtt tgctgcaagt      60

ggtggcgatc ttgattctag tgatcttact ggagtatctt tttggcttgt tactgctgct     120

ctcttagctg ctactgtttt cttttttgtt gaaagagatc aagtaagtgc taaatggaaa     180

acatcactta cagtttctgg tttagttact ggtattgcat tctggcatta tctctatatg     240

agaggtgtgt ggatcgaaac tggtgaaacg ccaacagtat ttagatatat tgattggttg     300

ctaactgttc cgttactaat ggttgagttc tacttaattc ttgcagcttg cacaaatgtt     360

gcgggctcat tatttaagaa actactaggt ggttcgcttg taatgcttat tgcaggatat     420

atgggtgagt ctggaagtct tccagtattg cctgcattca ttgttggatg cctagcatgg     480

ttctacatga tttatgaact atatgctggt gaaggtaagg ctgcagttac tactgctagt     540

cctgctgtta tgtctgcata caatactatg atgttgatta tcgtagtagg ttgggcaatt     600

tacccggctg gatatgctgc tggataccta atgggtggtg atggcgtata tgctcagaat     660

ttaaacgtta tatataatct tgctgacttt gttaacaaga ttttatttgg tttagttatc     720

tggcatgtcg ctgttaaaga atcttctaat gcta                                  754


<210> SEQ ID NO 141
<211> LENGTH: 247
<212> TYPE: PRT
<213> ORGANISM: Marine eubacteria

<400> SEQUENCE: 141

Leu Leu Ile Leu Gly Gly Val Ile Ala Leu Pro Ser Phe Ala Ala Ser
1               5                   10                  15

Gly Gly Asp Leu Asp Ser Ser Asp Leu Thr Gly Val Ser Phe Trp Leu
            20                  25                  30

Val Thr Ala Ala Leu Leu Ala Ala Thr Val Phe Phe Phe Val Glu Arg
        35                  40                  45

Asp Gln Val Ser Ala Lys Trp Lys Thr Ser Leu Thr Val Ser Gly Leu
```

-continued

```
    50                  55                  60

Val Thr Gly Ile Ala Phe Trp His Tyr Leu Tyr Met Arg Gly Val Trp
65                  70                  75                  80

Ile Glu Thr Gly Glu Thr Pro Thr Val Phe Arg Tyr Ile Asp Trp Leu
                85                  90                  95

Leu Thr Val Pro Leu Leu Met Val Glu Phe Tyr Leu Ile Leu Ala Ala
            100                 105                 110

Cys Thr Asn Val Ala Gly Ser Leu Phe Lys Lys Leu Leu Gly Gly Ser
        115                 120                 125

Leu Val Met Leu Ile Ala Gly Tyr Met Gly Glu Ser Gly Ser Leu Pro
    130                 135                 140

Val Leu Pro Ala Phe Ile Val Gly Cys Leu Ala Trp Phe Tyr Met Ile
145                 150                 155                 160

Tyr Glu Leu Tyr Ala Gly Glu Gly Lys Ala Ala Val Thr Thr Ala Ser
                165                 170                 175

Pro Ala Val Met Ser Ala Tyr Asn Thr Met Met Leu Ile Ile Val Val
            180                 185                 190

Gly Trp Ala Ile Tyr Pro Ala Gly Tyr Ala Ala Gly Tyr Leu Met Gly
        195                 200                 205

Gly Asp Gly Val Tyr Ala Gln Asn Leu Asn Val Ile Tyr Asn Leu Ala
    210                 215                 220

Asp Phe Val Asn Lys Ile Leu Phe Gly Leu Val Ile Trp His Val Ala
225                 230                 235                 240

Val Lys Glu Ser Ser Asn Ala
                245
```

<210> SEQ ID NO 142
<211> LENGTH: 742
<212> TYPE: DNA
<213> ORGANISM: Marine eubacteria

<400> SEQUENCE: 142

```
ttattgatat taggtggtgt tattgcactt ccttcgtttg ctgcaagtgg gggcgatctt      60

gattctagtg atcttactgg agtttctttt tggcttgtta ctgctgctct cttagctgct     120

actgttttct tttttgttga aagagatcaa gtaagtgcta aatggaaaac atcacttaca     180

gtttctggtt tagttactgg tattgcattc tggcattatc tttatatgag aggtgtgtgg     240

atcgaaactg gtgaaacgcc aacagtattt agatatattg attggttgct aactgttcct     300

ttgctaatgg ttgagttcta cttaatcctt gcagcgtgca caaatgttgc gggttcatta     360

tttaagaaac tacttggtgg ttcgcttgta atgcttattg caggatatat gggtgagtct     420

ggaagtcttc cagtattgcc tgcattcatt gttgggtgct tagcatggtt ctacatgatt     480

tatgaactat atgctggtga aggtaaggct gcagttacta ctgctagtcc tgctgttatg     540

tctgcataca atactatgat gttgattatc gtagtaggtt gggcaattta cccagctgga     600

tatgctgctg gttacctaat gggtggtgat ggcgtatatg ctcagaattt aaacgttata     660

tataaccttg ctgactttgt taacaagatt ttatttggtt tagttatctg gcatgttgct     720

gttaaagaat cttctaatgc ta                                              742
```

<210> SEQ ID NO 143
<211> LENGTH: 251
<212> TYPE: PRT
<213> ORGANISM: Marine eubacteria

<400> SEQUENCE: 143

-continued

Met Gly Lys Leu Leu Leu Ile Leu Gly Gly Val Ile Ala Leu Pro Ser
1 5 10 15

Phe Ala Ala Ser Gly Gly Asp Leu Asp Ser Ser Asp Leu Thr Gly Val
20 25 30

Ser Phe Trp Leu Val Thr Ala Ala Leu Leu Ala Ala Thr Val Phe Phe
35 40 45

Phe Val Glu Arg Asp Gln Val Ser Ala Lys Trp Lys Thr Ser Leu Thr
50 55 60

Val Ser Gly Leu Val Thr Gly Ile Ala Phe Trp His Tyr Leu Tyr Met
65 70 75 80

Arg Gly Val Trp Ile Glu Thr Gly Glu Thr Pro Thr Val Phe Arg Tyr
85 90 95

Ile Asp Trp Leu Leu Thr Val Pro Leu Leu Met Val Glu Phe Tyr Leu
100 105 110

Ile Leu Ala Ala Cys Thr Asn Val Ala Gly Ser Leu Phe Lys Lys Leu
115 120 125

Leu Ile Gly Ser Leu Val Met Leu Ile Ala Gly Tyr Met Gly Glu Ser
130 135 140

Gly Ser Leu Pro Val Leu Pro Ala Phe Leu Val Gly Cys Ala Ala Trp
145 150 155 160

Leu Tyr Met Ile Tyr Glu Leu Tyr Ala Gly Glu Gly Lys Ala Ala Val
165 170 175

Thr Thr Ala Ser Pro Ala Val Met Ser Ala Tyr Asn Thr Met Met Leu
180 185 190

Ile Ile Val Val Gly Trp Ala Ile Tyr Pro Ala Gly Tyr Ala Ala Gly
195 200 205

Tyr Leu Met Gly Gly Asp Gly Val Tyr Ala Gln Asn Leu Asn Val Ile
210 215 220

Tyr Asn Leu Ala Asp Phe Val Asn Lys Ile Leu Phe Gly Leu Val Ile
225 230 235 240

Trp His Val Ala Val Lys Glu Ser Ser Asn Ala
245 250

<210> SEQ ID NO 144
<211> LENGTH: 754
<212> TYPE: DNA
<213> ORGANISM: Marine eubacteria

<400> SEQUENCE: 144
atgggtaaat tattactgat tttaggcggt gttattgcgc ttccttcgtt tgctgcaagt 60
ggaggcgatc ttgattctag tgatcttact ggagtatctt tttggcttgt tactgctgct 120
ctcttagctg ctactgtttt ctttttttgtt gaaagagatc aagtaagcgc taaatggaaa 180
acatcactta cagtttctgg tttagttact ggtattgcat tctggcatta tctctatatg 240
agaggtgtgt ggatcgaaac cggtgaaaca ccaacagtat ttagatatat tgattggttg 300
ctaactgttc cgttactaat ggttgagttc tacttaatcc tcgcagcttg cactaatgtt 360
gcaggttcat tatttaagaa actactaatt ggttcgcttg taatgcttat tgcaggatat 420
atgggtgagt ctggaagtct tccagtattg cctgcattcc ttgttgggtg cgcagcatgg 480
ttatacatga tttatgaact atatgctggt gaaggtaagg ctgcagttac tactgctagt 540
cctgctgtta tgtctgcata caatactatg atgttgatta tcgtagtagg ttgggcaata 600
tacccagctg gatatgctgc tggttactta atgggtggag atggcgtata tgctcagaat 660

-continued

```
ttaaacgtta tatataacct tgctgacttt gttaacaaga ttttatttgg tttagttatc    720

tggcatgttg ctgttaaaga atcttctaat gcta                                754


<210> SEQ ID NO 145
<211> LENGTH: 250
<212> TYPE: PRT
<213> ORGANISM: Marine eubacteria

<400> SEQUENCE: 145

Met Gly Lys Leu Leu Leu Ile Leu Gly Gly Val Ile Ala Leu Pro Ser
1               5                   10                  15

Phe Ala Ala Ser Gly Gly Asp Leu Asp Ser Ser Asp Leu Thr Gly Val
            20                  25                  30

Ser Phe Trp Leu Val Thr Ala Ala Leu Leu Ala Ala Thr Val Phe Phe
        35                  40                  45

Phe Val Glu Arg Asp Gln Val Ser Ala Lys Trp Lys Thr Ser Leu Thr
    50                  55                  60

Val Ser Gly Leu Val Thr Gly Ile Ala Phe Trp His Tyr Leu Tyr Met
65                  70                  75                  80

Arg Gly Val Trp Ile Glu Thr Gly Glu Thr Pro Thr Val Phe Arg Tyr
                85                  90                  95

Ile Asp Trp Leu Leu Thr Val Pro Leu Leu Met Val Glu Phe Tyr Leu
            100                 105                 110

Ile Leu Ala Ala Cys Thr Asn Val Ala Gly Ser Leu Phe Lys Lys Leu
        115                 120                 125

Leu Ile Gly Ser Leu Val Met Leu Ile Ala Gly Tyr Met Gly Glu Ser
    130                 135                 140

Gly Ser Leu Pro Val Leu Pro Ala Phe Leu Val Gly Cys Ala Ala Trp
145                 150                 155                 160

Leu Tyr Met Ile Tyr Glu Leu Tyr Ala Gly Glu Gly Lys Ala Ala Val
                165                 170                 175

Thr Thr Ala Ser Pro Ala Val Met Ser Ala Tyr Asn Thr Met Met Leu
            180                 185                 190

Ile Ile Val Val Gly Trp Ala Ile Tyr Pro Ala Gly Tyr Ala Ala Gly
        195                 200                 205

Tyr Leu Met Gly Gly Asp Gly Val Tyr Ala Gln Asn Leu Asn Val Ile
    210                 215                 220

Tyr Asn Leu Ala Asp Phe Val Asn Lys Ile Leu Phe Gly Leu Val Ile
225                 230                 235                 240

Trp His Val Ala Val Lys Glu Ser Ser Asn
                245                 250


<210> SEQ ID NO 146
<211> LENGTH: 751
<212> TYPE: DNA
<213> ORGANISM: Marine eubacteria

<400> SEQUENCE: 146

atgggtaaat tattattgat cttaggcggt gttattgcgc ttccttcgtt tgctgcaagt     60

ggaggcgatc ttgattctag tgatcttact ggagtatctt tttggcttgt tactgctgct    120

ctcttagctg ctactgtttt ctttttttgtt gaaagagatc aagtaagcgc taaatggaaa    180

acatcactta cagtttctgg tttagttact ggtattgcat tctggcatta tctctatatg    240

agaggtgtgt ggatcgaaac cggtgaaaca ccaacagtat ttaggtatat tgattggttg    300

ctaactgttc cgttactaat ggttgagttc tacttaatcc tcgcagcttg cactaatgtt    360
```

-continued

```
gcaggttcat tatttaagaa actactaatt ggttcgcttg taatgcttat tgcaggatat    420

atgggtgagt ctggaagtct tccagtattg cctgcattcc ttgttgggtg cgcagcatgg    480

ttatacatga tttatgaact atatgctggt gaaggtaagg ctgcagttac tactgctagt    540

cctgctgtta tgtctgcata caatactatg atgttgatta tcgtagtagg ttgggcaata    600

tacccagctg gatatgctgc tggttactta atgggtggag atggcgtata tgctcagaat    660

ttaaacgtta tatataacct tgctgacttt gttaacaaga ttttatttgg tttagttatc    720

tggcatgttg ctgttaaaga atcttctaat c                                   751
```

```
<210> SEQ ID NO 147
<211> LENGTH: 251
<212> TYPE: PRT
<213> ORGANISM: Marine eubacteria

<400> SEQUENCE: 147

Met Gly Lys Leu Leu Leu Ile Leu Gly Gly Val Ile Ala Leu Pro Ser
1               5                   10                  15

Phe Ala Ala Ser Gly Gly Asp Leu Asp Ser Ser Asp Leu Thr Gly Val
            20                  25                  30

Ser Phe Trp Leu Val Thr Ala Ala Leu Leu Ala Ala Thr Val Phe Phe
        35                  40                  45

Phe Val Glu Arg Asp Gln Val Ser Ala Lys Trp Lys Thr Ser Leu Thr
    50                  55                  60

Val Ser Gly Leu Val Thr Gly Ile Ala Phe Trp His Tyr Leu Tyr Met
65                  70                  75                  80

Arg Gly Val Trp Ile Glu Thr Gly Glu Thr Pro Thr Val Phe Arg Tyr
                85                  90                  95

Ile Asp Trp Leu Leu Thr Val Pro Leu Leu Met Val Glu Phe Tyr Leu
            100                 105                 110

Ile Leu Ala Ala Cys Thr Asn Val Ala Gly Ser Leu Phe Lys Lys Leu
        115                 120                 125

Leu Ile Gly Ser Leu Val Met Leu Ile Ala Gly Tyr Met Gly Glu Ser
    130                 135                 140

Gly Ser Leu Pro Val Leu Pro Ala Phe Leu Val Gly Cys Ala Ala Trp
145                 150                 155                 160

Leu Tyr Met Ile Tyr Glu Leu Tyr Ala Gly Glu Gly Lys Ala Ala Val
                165                 170                 175

Thr Thr Ala Ser Pro Ala Val Met Ser Ala Tyr Asn Thr Met Met Leu
            180                 185                 190

Ile Ile Val Val Gly Trp Ala Ile Tyr Pro Ala Gly Tyr Ala Ala Gly
        195                 200                 205

Tyr Leu Met Gly Gly Asp Gly Val Tyr Ala Gln Asn Leu Asn Val Ile
    210                 215                 220

Tyr Asn Leu Ala Asp Phe Val Asn Lys Ile Leu Phe Gly Leu Val Ile
225                 230                 235                 240

Trp His Val Ala Val Lys Glu Ser Ser Asn Ala
                245                 250


<210> SEQ ID NO 148
<211> LENGTH: 754
<212> TYPE: DNA
<213> ORGANISM: Marine eubacteria

<400> SEQUENCE: 148
```

-continued

```
atgggtaaat tattactgat cttaggcggt gttattgcgc ttccttcgtt tgctgcaagt     60

ggaggcgatc ttgattctag tgatcttact ggagtatctt tttggcttgt tactgctgct    120

ctcttagctg ctactgtttt cttttttgtt gaaagagatc aagtaagcgc taaatggaaa    180

acatcactta cagtttctgg tttagttact ggtattgcat tctggcatta tctctatatg    240

agaggtgtgt ggatcgaaac cggtgaaaca ccaacagtat ttagatatat tgattggttg    300

ctaactgttc cgttactaat ggttgagttc tacttaatcc tcgcagcttg cactaatgtt    360

gcaggttcat tatttaagaa actactaatt ggttcgcttg taatgcttat tgcaggatat    420

atgggtgagt ctggaagtct tccagtattg cctgcattcc ttgttgggtg cgcagcatgg    480

ttatacatga tttatgaact atatgctggt gaaggtaagg ctgcagttac tactgctagt    540

cctgctgtta tgtctgcata caatactatg atgttgatta tcgtagtagg ttgggcaata    600

tacccagctg gatatgctgc tggttactta atgggtggag atggcgtata tgctcagaat    660

ttaaacgtta tatataacct tgctgacttc gttaacaaga ttttatttgg tttagttatc    720

tggcatgttg ctgttaaaga atcttctaat gcta                                754
```

<210> SEQ ID NO 149
<211> LENGTH: 251
<212> TYPE: PRT
<213> ORGANISM: Marine eubacteria

<400> SEQUENCE: 149

```
Met Gly Lys Arg Leu Val Ile Leu Gly Gly Val Ile Ala Leu Pro Ser
1               5                   10                  15

Phe Ala Ala Ser Gly Gly Asp Leu Asp Ser Ser Asp Leu Thr Gly Val
            20                  25                  30

Ser Phe Trp Leu Val Thr Ala Ala Leu Leu Ala Ala Thr Val Phe Phe
        35                  40                  45

Phe Val Glu Arg Asp Gln Val Ser Ala Lys Trp Lys Thr Ser Leu Thr
    50                  55                  60

Val Ser Gly Leu Val Thr Gly Ile Ala Phe Trp His Tyr Leu Tyr Met
65                  70                  75                  80

Arg Gly Val Trp Ile Glu Thr Gly Glu Thr Pro Thr Val Phe Arg Tyr
                85                  90                  95

Ile Asp Trp Leu Leu Thr Val Pro Leu Leu Met Val Glu Phe Tyr Leu
            100                 105                 110

Ile Leu Ala Ala Cys Thr Asn Val Ala Gly Ser Leu Phe Lys Lys Leu
        115                 120                 125

Leu Ile Gly Ser Leu Val Met Leu Ile Ala Gly Tyr Met Gly Glu Ser
    130                 135                 140

Gly Asn Leu Pro Val Leu Pro Ala Phe Leu Ile Gly Cys Ala Ala Trp
145                 150                 155                 160

Leu Tyr Met Ile Tyr Glu Leu Tyr Ala Gly Glu Gly Lys Ala Ala Val
                165                 170                 175

Thr Thr Ala Ser Pro Ala Val Met Ser Ala Tyr Asn Thr Met Met Leu
            180                 185                 190

Ile Ile Val Val Gly Trp Ala Ile Tyr Pro Ala Gly Tyr Ala Ala Gly
        195                 200                 205

Tyr Leu Met Gly Gly Asp Gly Val Tyr Ala Gln Asn Leu Asn Val Ile
    210                 215                 220

Tyr Asn Leu Ala Asp Phe Val Asn Lys Ile Leu Phe Gly Leu Val Ile
225                 230                 235                 240
```

-continued

```
Trp His Val Ala Val Lys Glu Ser Ser Asn Ala
                245                 250


<210> SEQ ID NO 150
<211> LENGTH: 754
<212> TYPE: DNA
<213> ORGANISM: Marine eubacteria

<400> SEQUENCE: 150

atgggtaaaa gattagtgat cttaggcggt gttattgcgc ttccttcgtt tgctgcaagt      60

ggaggcgatc ttgattctag tgatcttact ggagtatctt tttggcttgt tactgctgct     120

ctcttagctg ctactgtttt ctttttgtt gaaagagatc aagtaagcgc taaatggaaa     180

acatcactta cagtttctgg tttagttact ggtattgcat tctggcatta tctctatatg     240

agaggtgtgt ggatcgaaac cggtgaaaca ccaacagtat ttagatatat tgattggttg     300

ctaactgttc cgttactaat ggttgagttc tacttaatcc tcgcagcttg cactaatgtt     360

gcaggttcat tatttaagaa actactaatt ggttcgcttg taatgcttat tgcaggatat     420

atgggtgagt ctggaaatct tccagtattg cctgcattcc ttattgggtg cgcagcatgg     480

ttatacatga tttatgaact atatgctggt gaaggtaagg ctgcagttac tactgctagt     540

cctgctgtta tgtctgcata caatactatg atgttgatta tcgtagtagg ttgggcaata     600

tacccagctg gatatgctgc tggttactta atgggtggag atggcgtata tgctcagaat     660

ttaaacgtta tatataacct tgctgacttt gttaacaaga ttttatttgg tttagttatc     720

tggcatgttg ctgttaaaga atcttctaat gcta                                754


<210> SEQ ID NO 151
<211> LENGTH: 254
<212> TYPE: PRT
<213> ORGANISM: Marine eubacteria

<400> SEQUENCE: 151

Ser Lys Lys Leu Leu Ala Thr Phe Leu Val Val Thr Ser Ile Pro Ala
1               5                   10                  15

Ile Ala Leu Ala Gly Gly His Ser Ser Gly Gly Leu Ala Gly Asp Asp
            20                  25                  30

Cys Val Gly Val Thr Phe Trp Ile Ile Ser Met Ala Met Val Ala Ser
        35                  40                  45

Thr Val Phe Phe Ile Val Glu Arg Asp Arg Val Ser Ala Lys Trp Lys
    50                  55                  60

Thr Ser Leu Thr Val Ser Ala Leu Met Thr Leu Ile Ala Ala Val His
65                  70                  75                  80

Tyr Phe Tyr Met Arg Asp Val Trp Val Ala Thr Gly Glu Ser Pro Thr
                85                  90                  95

Val Phe Arg Tyr Ile Asp Trp Leu Leu Thr Val Pro Leu Leu Met Ile
            100                 105                 110

Glu Phe Tyr Phe Ile Leu Ala Ala Val Thr Thr Val Ser Ser Gly Ile
        115                 120                 125

Phe Trp Arg Leu Leu Val Gly Thr Val Ile Met Leu Val Gly Gly Tyr
    130                 135                 140

Leu Gly Glu Ala Gly Met Ile Ser Val Met Thr Gly Phe Ile Ile Gly
145                 150                 155                 160

Met Ile Gly Trp Leu Tyr Ile Leu Tyr Glu Ile Phe Ala Gly Glu Ala
                165                 170                 175

Ser Lys Ala Asn Ala Ser Ser Gly Ser Ala Ala Cys Gln Thr Ala Phe
```

-continued

```
            180                 185                 190

Gly Ala Leu Arg Leu Ile Val Thr Ile Gly Trp Ala Ile Tyr Pro Leu
        195                 200                 205

Gly Tyr Phe Leu Gly Tyr Leu Gly Gly Gly Ala Asp Pro Ala Thr Leu
    210                 215                 220

Asn Ile Val Tyr Asn Leu Ala Asp Phe Val Asn Lys Ile Ala Phe Gly
225                 230                 235                 240

Leu Ile Ile Trp Ala Ala Ala Val Lys Glu Ser Ser Asn Ala
                245                 250
```

<210> SEQ ID NO 152
<211> LENGTH: 763
<212> TYPE: DNA
<213> ORGANISM: Marine eubacteria

<400> SEQUENCE: 152

```
agcaagaaac ttcttgcgac atttctagta gtaacatcaa taccagcaat agcattagct      60

ggtgggcatt catctggtgg tttagcagga gatgactgcg taggtgttac tttctggatt     120

atttctatgg ctatggttgc ttcaacagta ttctttattg ttgagcgtga cagagttagt     180

gcgaaatgga aaacatcatt aacagtatca gcgcttatga ctttaatcgc agctgttcac     240

tatttctaca tgagagatgt ttgggtagca actggcgaat caccaacagt ctttagatat     300

atagattggt tgttaacagt tccacttcta atgattgagt tctactttat cttagcagcg     360

gttacaactg tatcttcagg aattttctgg agattactag taggtactgt aataatgcta     420

gtaggtggat acttaggtga agctggaatg atttcggtaa tgacaggttt cattataggg     480

atgataggtt ggctatacat tctttatgaa atctttgcag gtgaagctag caaagcaaat     540

gcttctagtg gaagtgcagc ttgtcaaaca gcctttggag ctttacgttt aatcgtaacc     600

attggttggg caatttatcc gctaggatat ttcttaggtt atctaggcgg tggggcagac     660

ccagctacat taaacattgt ttacaactta gctgactttg taaacaaaat tgcttttggt     720

ttaattatat gggcagcagc tgttaaagaa tcttctaatg cta                      763
```

<210> SEQ ID NO 153
<211> LENGTH: 254
<212> TYPE: PRT
<213> ORGANISM: Marine eubacteria

<400> SEQUENCE: 153

```
Ser Lys Lys Leu Leu Ala Thr Phe Leu Val Val Thr Ser Ile Pro Ala
1               5                   10                  15

Ile Ala Leu Ala Gly Gly His Ser Ser Gly Gly Leu Ala Gly Asp Asp
            20                  25                  30

Tyr Val Gly Val Thr Phe Trp Ile Ile Ser Met Ala Met Val Ala Ser
        35                  40                  45

Thr Val Phe Phe Ile Val Glu Arg Asp Arg Val Ser Ala Lys Trp Lys
    50                  55                  60

Thr Ser Leu Thr Val Ser Ala Leu Val Thr Leu Ile Ala Ala Val His
65                  70                  75                  80

Tyr Phe Tyr Met Arg Asp Val Trp Val Ala Thr Gly Glu Ser Pro Thr
                85                  90                  95

Val Phe Arg Tyr Ile Asp Trp Leu Leu Thr Val Pro Leu Leu Met Ile
            100                 105                 110

Glu Phe Tyr Phe Ile Leu Ala Ala Val Thr Thr Val Ser Ser Gly Ile
        115                 120                 125
```

-continued

```
Phe Trp Arg Leu Leu Val Gly Thr Val Ile Met Leu Val Gly Gly Tyr
    130                 135                 140

Leu Gly Glu Ala Gly Met Ile Ser Val Met Thr Gly Phe Ile Ile Gly
145                 150                 155                 160

Met Ile Gly Trp Leu Tyr Ile Leu Tyr Glu Ile Phe Ala Gly Glu Ala
                165                 170                 175

Ser Lys Ala Asn Ala Ser Ser Gly Ser Ala Ala Cys Gln Thr Ala Phe
            180                 185                 190

Gly Ala Leu Arg Leu Ile Val Thr Ile Gly Trp Ala Ile Tyr Pro Leu
        195                 200                 205

Gly Tyr Phe Leu Gly Tyr Leu Gly Gly Gly Ala Asp Pro Ala Thr Leu
    210                 215                 220

Asn Ile Val Tyr Asn Leu Ala Asp Phe Val Asn Lys Ile Ala Phe Gly
225                 230                 235                 240

Leu Ile Ile Trp Ala Ala Ala Val Lys Glu Ser Ser Asn Ala
                245                 250
```

```
<210> SEQ ID NO 154
<211> LENGTH: 763
<212> TYPE: DNA
<213> ORGANISM: Marine eubacteria

<400> SEQUENCE: 154

agcaagaaac ttcttgcgac atttctagta gtaacatcaa taccagcaat agcattagct     60

ggtgggcatt catctggtgg tttagcagga gatgactacg taggtgttac tttctggatt    120

atttctatgg ctatggttgc ttcaacagta ttctttattg ttgagcgtga cagagttagt    180

gcgaaatgga aaacatcatt aacagtatca gcgcttgtga ctttaatcgc agctgttcac    240

tatttctaca tgagagatgt ttgggtagca actggcgaat caccaacagt ctttagatat    300

atagattggt tgttaacagt tccacttcta atgattgagt tctactttat cttagcagcg    360

gttacaactg tatcttcagg aattttctgg agattactag taggtactgt aataatgcta    420

gtaggtggat acttaggtga agctggaatg atttcggtaa tgacaggttt cattataggg    480

atgataggtt ggctatacat tctttatgaa atctttgcag gtgaagctag caaagcaaat    540

gcttctagtg gaagtgcagc ttgtcaaaca gcctttggag ctttacgttt aatcgtaacc    600

attggttggg caatttatcc gctaggatat ttcttaggtt atctaggcgg tggggcagac    660

ccagctacat taaacattgt ttacaactta gctgactttg taaacaaaat tgcttttggt    720

ttaattatat gggcagcagc tgttaaagaa tcttctaatg cta                      763
```

```
<210> SEQ ID NO 155
<211> LENGTH: 254
<212> TYPE: PRT
<213> ORGANISM: Marine eubacteria

<400> SEQUENCE: 155

Ser Lys Lys Phe Phe Ser Thr Leu Leu Leu Val Thr Ser Leu Pro Thr
1               5                   10                  15

Leu Ala Leu Ala Gly Gly His Ser Ser Gly Leu Ala Gly Asp Asp Tyr
            20                  25                  30

Val Gly Val Thr Phe Trp Ile Ile Ser Met Ala Met Val Ala Ser Thr
        35                  40                  45

Val Phe Phe Ile Val Glu Arg Asp Arg Val Ser Ser Lys Trp Lys Thr
    50                  55                  60
```

-continued

```
Ser Leu Thr Val Ser Ala Leu Val Thr Leu Ile Ala Ala Val His Tyr
65                  70                  75                  80

Phe Tyr Met Arg Asp Val Trp Val Ala Thr Gly Glu Ser Pro Thr Val
                85                  90                  95

Phe Arg Tyr Ile Asp Trp Leu Leu Thr Val Pro Leu Leu Met Ile Glu
            100                 105                 110

Phe Tyr Phe Ile Leu Ala Ala Val Thr Thr Val Ser Ser Gly Ile Phe
        115                 120                 125

Trp Arg Leu Leu Ile Gly Thr Val Val Met Leu Val Gly Gly Tyr Met
    130                 135                 140

Gly Glu Ala Gly Met Ile Ser Val Met Thr Gly Phe Ile Ile Gly Met
145                 150                 155                 160

Ile Gly Trp Leu Tyr Ile Leu Tyr Glu Ile Phe Ala Gly Glu Ala Ser
                165                 170                 175

Lys Ala Asn Ala Ser Ser Gly Ser Ala Ala Cys Gln Thr Ala Phe Gly
            180                 185                 190

Ala Leu Arg Leu Ile Val Thr Val Gly Trp Ala Ile Tyr Pro Ile Gly
        195                 200                 205

Tyr Phe Val Gly Tyr Leu Thr Gly Gly Gly Ala Asp Ala Ala Thr Leu
    210                 215                 220

Asn Ile Val Tyr Asn Leu Ala Asp Phe Val Asn Lys Ile Ala Phe Gly
225                 230                 235                 240

Leu Ile Ile Trp Ala Ala Ala Val Lys Glu Ser Ser Asn Ala
                245                 250
```

<210> SEQ ID NO 156
<211> LENGTH: 763
<212> TYPE: DNA
<213> ORGANISM: Marine eubacteria

<400> SEQUENCE: 156

```
agcaaaaagt tttttcgac gcttctatta gtaacatcct tgccaacttt agctttagca      60

ggtgggcatt catctggtct tgctggagat gactatgtag gtgttacttt ctggattatt    120

tccatggcta tggttgcgtc aacagtattt ttcattgtgg agcgtgacag agttagctca    180

aaatggaaaa catcattaac agtatcagct ttggttacat taattgctgc agtgcattat    240

ttttatatga gagatgtatg ggtagcaact ggtgaatcac caacagtatt tagatatata    300

gattggttat taacagtgcc actattaatg attgagttct actttatttt agcagcggta    360

actacagttt cttcaggaat attctggaga ctattaattg gtacagttgt aatgctagta    420

ggtgggtata tgggtgaagc tggaatgatc tcagtgatga caggtttcat tatcgggatg    480

atcggttggc tatatattct ttacgaaatc tttgctggtg aagctagtaa agcaaacgct    540

tctagtggaa gcgcagcatg ccaaacagca tttggtgcgt tacgtttaat cgttacagtt    600

ggttgggcga tctatccaat aggatacttc gtaggctatc taactggtgg tggtgcagac    660

gcagctacac taaacatagt ttacaactta gctgattttg taaacaaaat tgcctttggt    720

ttaatcatat gggcagcagc tgttaaagaa tcttctaatg cta                      763
```

<210> SEQ ID NO 157
<211> LENGTH: 254
<212> TYPE: PRT
<213> ORGANISM: Marine eubacteria

<400> SEQUENCE: 157

```
Ser Lys Lys Phe Phe Ser Thr Leu Leu Leu Val Thr Ser Leu Pro Thr
```

-continued

```
1               5                   10                  15

Leu Ala Leu Ala Gly Gly His Ser Ser Gly Leu Ala Gly Asp Asp Tyr
            20                  25                  30

Val Gly Val Thr Phe Trp Ile Ile Ser Met Ala Met Val Ala Ser Thr
        35                  40                  45

Val Phe Phe Ile Val Glu Arg Asp Arg Val Ser Ser Lys Trp Lys Thr
    50                  55                  60

Ser Leu Thr Val Ser Ala Leu Val Thr Leu Ile Ala Ala Val His Tyr
65                  70                  75                  80

Phe Tyr Met Arg Asp Val Trp Val Ala Thr Gly Glu Ser Pro Thr Val
                85                  90                  95

Phe Arg Tyr Ile Asp Trp Leu Leu Thr Val Pro Leu Leu Met Ile Glu
            100                 105                 110

Phe Tyr Phe Ile Leu Ala Ala Val Thr Thr Val Ser Ser Gly Ile Phe
        115                 120                 125

Trp Arg Leu Leu Ile Gly Thr Val Val Met Leu Val Gly Gly Tyr Met
    130                 135                 140

Gly Glu Ala Gly Met Ile Ser Val Met Thr Gly Phe Ile Ile Gly Met
145                 150                 155                 160

Ile Gly Trp Leu Tyr Ile Leu Tyr Glu Ile Phe Ala Gly Glu Ala Ser
                165                 170                 175

Lys Ala Asn Ala Ser Ser Gly Ser Ala Ala Cys Gln Thr Ala Phe Gly
            180                 185                 190

Ala Leu Arg Leu Ile Val Thr Val Gly Trp Ala Ile Tyr Pro Ile Gly
        195                 200                 205

Tyr Phe Val Gly Tyr Leu Thr Gly Gly Gly Ala Asp Ala Ala Thr Leu
    210                 215                 220

Asn Ile Val Tyr Asn Leu Ala Asp Phe Val Asn Lys Ile Ala Phe Gly
225                 230                 235                 240

Leu Ile Ile Trp Ala Ala Ala Val Lys Glu Ser Ser Asn Ala
                245                 250
```

<210> SEQ ID NO 158
<211> LENGTH: 763
<212> TYPE: DNA
<213> ORGANISM: Marine eubacteria

<400> SEQUENCE: 158

```
agcaaaaagt ttttttcgac gcttctatta gtaacatcct tgccaacttt agctttagca     60

ggtgggcatt catctggtct tgctggagat gactatgtag gtgttacttt ctggattatt    120

tccatggcta tggttgcgtc aacagtattt ttcattgtgg agcgtgacag agttagctca    180

aaatggaaaa catcattaac agtatcagct ttggttacat taattgctgc agtgcattat    240

ttttatatga gagatgtatg ggtagcaact ggtgaatcac caacagtatt tagatatata    300

gattggttat taacagtgcc actattaatg attgagttct actttatttt agcagcggta    360

actacagttt cttcaggaat attctggaga ctattaattg gtacagttgt aatgctagta    420

ggtgggtata tgggtgaagc tggaatgatc tcagtgatga caggtttcat tatcgggatg    480

atcggttggc tatatattct ttacgaaatc tttgctggtg aagctagtaa agcaaacgct    540

tctagtggaa gcgcagcatg ccaaacagca tttggtgcgt tacgtttaat cgttacagtt    600

ggttgggcga tctatccaat aggatacttc gtaggctatc taactggtgg tggtgcagac    660

gcagctacac taaacatagt ttacaactta gctgattttg taaacaaaat tgcctttggt    720
```

-continued ttaatcatat gggcagcagc tgttaaagaa tcttctaatg cta 763

<210> SEQ ID NO 159
<211> LENGTH: 250
<212> TYPE: PRT
<213> ORGANISM: Marine eubacteria

<400> SEQUENCE: 159

Met Lys Leu Leu Leu Ile Leu Gly Ser Ala Ile Ala Leu Pro Ser Phe
1               5                   10                  15

Ala Ala Ala Gly Gly Asp Leu Asp Ile Ser Asp Thr Val Gly Val Ser
            20                  25                  30

Phe Trp Leu Val Thr Ala Gly Met Leu Ala Ala Thr Val Phe Phe Phe
        35                  40                  45

Val Glu Arg Asp Gln Val Ser Ala Lys Trp Lys Thr Ser Leu Thr Val
    50                  55                  60

Ser Gly Leu Ile Thr Gly Ile Ala Phe Trp His Tyr Leu Tyr Met Arg
65                  70                  75                  80

Gly Val Trp Ile Asp Thr Gly Asp Thr Pro Thr Val Phe Arg Tyr Ile
                85                  90                  95

Asp Trp Leu Leu Thr Val Pro Leu Gln Met Val Glu Phe Tyr Leu Ile
            100                 105                 110

Leu Ala Ala Cys Thr Ser Val Ala Ala Ser Leu Phe Lys Lys Leu Leu
        115                 120                 125

Ala Gly Ser Leu Val Met Leu Gly Ala Gly Phe Ala Gly Glu Ala Gly
    130                 135                 140

Leu Ala Pro Val Leu Pro Ala Phe Ile Ile Gly Met Ala Gly Trp Leu
145                 150                 155                 160

Tyr Met Ile Tyr Glu Leu Tyr Met Gly Glu Gly Lys Ala Ala Val Ser
                165                 170                 175

Thr Ala Ser Pro Ala Val Asn Ser Ala Tyr Asn Ala Met Met Met Ile
            180                 185                 190

Ile Val Val Gly Trp Ala Ile Tyr Pro Ala Gly Tyr Ala Ala Gly Tyr
        195                 200                 205

Leu Met Gly Gly Glu Gly Val Tyr Ala Ser Asn Leu Asn Leu Ile Tyr
    210                 215                 220

Asn Leu Ala Asp Phe Val Asn Lys Ile Leu Phe Gly Leu Ile Ile Trp
225                 230                 235                 240

Asn Val Ala Val Lys Glu Ser Ser Asn Ala
                245                 250

<210> SEQ ID NO 160
<211> LENGTH: 750
<212> TYPE: DNA
<213> ORGANISM: Marine eubacteria

<400> SEQUENCE: 160
atgaaattat tattgatctt aggtagtgct attgcacttc catcatttgc tgctgctggt 60
ggcgatctag atataagtga tactgttggt gtttcattct ggctggttac agctggtatg 120
ttagcggcaa ctgtgttctt ttttgtagaa agagaccaag tcagcgctaa gtggaaaact 180
tcacttactg tatctggttt aattactggt atagcttttt ggcattatct ctatatgaga 240
ggtgtttgga tagacactgg tgatacccca acagtattca gatatattga ttggttatta 300
actgttccat tacaaatggt tgagttctat ctaattcttg ctgcttgtac aagtgttgct 360
gcttcattat ttaagaagct tctagctggt tcattagtaa tgttaggtgc tggatttgca 420

-continued

```
ggcgaagctg gattagctcc tgtattacct gctttcatta ttggtatggc tggatggtta    480

tacatgattt atgagctata tatgggtgaa ggtaaggctg ctgtaagtac tgcaagtcct    540

gctgttaact ctgcatacaa cgcaatgatg atgattattg ttgttggatg ggcaatttat    600

cctgctggat atgctgctgg ttacctaatg ggtggcgaag gtgtatacgc ttcaaactta    660

aaccttatat ataaccttgc tgactttgtt aacaagattc tatttggttt gatcatttgg    720

aatgttgcag ttaaagaatc tagtaatgct                                     750
```

```
<210> SEQ ID NO 161
<211> LENGTH: 230
<212> TYPE: PRT
<213> ORGANISM: Marine eubacteria

<400> SEQUENCE: 161

Met Lys Val Leu Met Leu Asn Pro Gly Asp His Val Ala Ile Ser Phe
1               5                   10                  15

Trp Leu Ile Ser Met Ala Met Val Ala Ala Thr Ala Phe Phe Phe Leu
            20                  25                  30

Glu Arg Asp Arg Val Ala Ala Lys Trp Lys Thr Ser Leu Thr Val Ala
        35                  40                  45

Gly Leu Val Thr Gly Ile Ala Ala Trp His Tyr Phe Tyr Met Arg Gly
    50                  55                  60

Val Trp Val Ala Thr Gly Asp Ser Pro Thr Val Leu Arg Tyr Ile Asp
65                  70                  75                  80

Trp Leu Ile Thr Val Pro Leu Gln Ile Val Glu Phe Tyr Val Ile Leu
                85                  90                  95

Ala Ala Met Thr Ala Val Ala Ser Ser Leu Phe Trp Arg Leu Leu Ile
            100                 105                 110

Ala Ser Ile Ile Met Leu Val Phe Gly Tyr Met Gly Glu Thr Gly Ala
        115                 120                 125

Met Asn Val Thr Leu Ala Phe Val Ile Gly Met Ala Gly Trp Leu Tyr
    130                 135                 140

Ile Ile Tyr Glu Val Phe Ala Gly Glu Ala Ser Lys Ala Ser Ala Gly
145                 150                 155                 160

Ser Gly Asn Ala Ala Gly Gln Thr Ala Phe Asn Ala Leu Arg Leu Ile
                165                 170                 175

Val Thr Val Gly Trp Ala Ile Tyr Pro Ile Gly Tyr Ala Val Gly Tyr
            180                 185                 190

Phe Gly Gly Gly Val Asp Ala Gly Ser Leu Asn Leu Ile Tyr Asn Leu
        195                 200                 205

Ala Asp Phe Val Asn Lys Ile Ala Phe Gly Met Ala Ile Tyr Val Ala
    210                 215                 220

Ala Val Ser Asp Ser Asn
225                 230
```

```
<210> SEQ ID NO 162
<211> LENGTH: 690
<212> TYPE: DNA
<213> ORGANISM: Marine eubacteria

<400> SEQUENCE: 162

atgaaagtat taatgctaaa tcccggagat cacgttgcga tttcgttttg gttgatctct     60

atggccatgg ttgccgctac tgctttcttc tttcttgaaa gagatcgtgt agcagctaaa    120

tggaaaacgt cccttacagt agctggttta gttactggta ttgcggcgtg gcactacttc    180
```

-continued

```
tacatgagag gcgtatgggt tgctactggt gactcaccaa ctgtccttcg ttacattgac    240

tggttgatta ctgtgcctct acaaatcgta gaattctacg taattcttgc agcgatgact    300

gctgttgctt caagcctttt ctggagacta ttaattgcat caattattat gcttgtcttt    360

ggttacatgg gtgaaactgg agcgatgaat gtaactctag ccttcgtaat aggtatggct    420

ggatggttat acatcatcta cgaggttttt gcaggtgaag caagcaaggc aagtgctggt    480

agtggaaacg ctgctggtca gactgcattt aacgcattga gattaattgt tacagtagga    540

tgggcaattt atccaattgg ttatgctgta ggttacttcg gtggtggcgt agacgccggt    600

tcattgaact taatctataa ccttgcagac tttgttaata aaattgcatt tggtatggct    660

atttatgtag ctgcagtatc agacagcaac                                     690
```

<210> SEQ ID NO 163
<211> LENGTH: 249
<212> TYPE: PRT
<213> ORGANISM: Marine eubacteria

<400> SEQUENCE: 163

```
Met Lys Leu Leu Leu Ile Leu Gly Ser Val Ile Ala Leu Pro Thr Phe
1               5                   10                  15

Ala Ala Gly Gly Gly Asp Leu Asp Ala Ser Asp Tyr Thr Gly Val Ser
            20                  25                  30

Phe Trp Leu Val Thr Ala Ala Leu Leu Ala Ser Thr Val Phe Phe Phe
        35                  40                  45

Val Glu Arg Asp Arg Val Ser Ala Lys Trp Lys Thr Ser Leu Thr Val
    50                  55                  60

Ser Gly Leu Val Thr Gly Ile Ala Phe Trp Lys Tyr Met Tyr Met Arg
65                  70                  75                  80

Gly Val Trp Ile Glu Thr Gly Asp Ser Pro Thr Val Phe Arg Tyr Ile
                85                  90                  95

Asp Trp Leu Leu Thr Val Pro Leu Leu Ile Cys Glu Phe Tyr Leu Ile
            100                 105                 110

Leu Ala Ala Ala Thr Asn Val Ala Gly Ser Leu Phe Lys Lys Leu Leu
        115                 120                 125

Val Gly Ser Leu Val Met Leu Val Phe Gly Tyr Met Gly Glu Ala Gly
    130                 135                 140

Ile Met Ala Ala Trp Pro Ala Phe Ile Ile Gly Cys Leu Ala Trp Val
145                 150                 155                 160

Tyr Met Ile Tyr Glu Leu Trp Ala Gly Glu Gly Lys Ser Ala Cys Asn
                165                 170                 175

Thr Ala Ser Pro Ala Val Gln Ser Ala Tyr Asn Thr Met Met Tyr Ile
            180                 185                 190

Ile Ile Phe Gly Trp Ala Ile Tyr Pro Val Gly Tyr Phe Thr Gly Tyr
        195                 200                 205

Leu Met Gly Asp Gly Gly Ser Ala Leu Asn Leu Asn Leu Ile Tyr Asn
    210                 215                 220

Leu Ala Asp Phe Val Asn Lys Ile Leu Phe Gly Leu Ile Ile Trp Asn
225                 230                 235                 240

Val Ala Val Lys Glu Ser Ser Asn Ala
                245
```

<210> SEQ ID NO 164
<211> LENGTH: 750
<212> TYPE: DNA

-continued

<213> ORGANISM: Marine eubacteria

<400> SEQUENCE: 164
atgaaattat tactgatatt aggtagtgtt attgcacttc ctacatttgc tgcaggtggt 60
ggtgaccttg atgctagtga ttacactggt gtttcttttt ggttagttac tgctgcttta 120
ttagcatcta ctgtattttt ctttgttgaa agagatagag tttctgcaaa atggaaaaca 180
tcattaactg tatctggtct tgttactggt attgctttct ggaaatacat gtacatgaga 240
ggggtatgga ttgaaactgg tgattcgcca actgtattta gatacattga ttggttacta 300
acagttcctc tattaatatg tgaattctac ttaattcttg ctgctgcaac taatgttgct 360
ggatcattat ttaagaaatt actagttggt tctcttgtta tgcttgtgtt tggttacatg 420
ggtgaagcag gaatcatggc tgcatggcct gcattcatta ttgggtgttt agcttgggta 480
tacatgattt atgaattatg ggctggagaa ggaaaatctg catgtaatac tgcaagtcct 540
gctgtgcaat cagcttacaa cacaatgatg tatattatca tctttggttg ggcgatttat 600
cctgtaggtt atttcacagg ttacctgatg ggtgacggtg gatcagctct taacttaaac 660
cttatctata accttgctga ctttgttaac aagattctat ttggtttaat tatatggaat 720
gttgctgtta aagaatcttc taatgcttaa 750

<210> SEQ ID NO 165
<211> LENGTH: 249
<212> TYPE: PRT
<213> ORGANISM: Marine eubacteria

<400> SEQUENCE: 165

Met Lys Leu Leu Leu Ile Leu Gly Ser Val Ile Ala Leu Pro Thr Phe
1 5 10 15

Ala Ala Gly Gly Gly Asp Leu Asp Ala Ser Asp Tyr Thr Gly Val Ser
20 25 30

Phe Trp Leu Val Thr Ala Ala Leu Leu Ala Ser Thr Val Phe Phe Phe
35 40 45

Val Glu Arg Asp Arg Val Ser Ala Lys Trp Lys Thr Ser Leu Thr Val
50 55 60

Ser Gly Leu Val Thr Gly Ile Ala Phe Trp Asn Tyr Met Tyr Met Arg
65 70 75 80

Gly Val Trp Ile Glu Thr Gly Asp Ser Pro Thr Val Phe Arg Tyr Ile
85 90 95

Asp Trp Leu Leu Thr Val Pro Leu Leu Ile Cys Glu Phe Tyr Leu Ile
100 105 110

Leu Ala Ala Ala Thr Asn Val Ala Gly Ser Leu Phe Lys Lys Leu Leu
115 120 125

Val Gly Ser Leu Val Met Leu Val Phe Gly Tyr Met Gly Glu Ala Gly
130 135 140

Ile Met Ala Ala Trp Pro Ala Phe Ile Ile Gly Cys Leu Ala Trp Val
145 150 155 160

Tyr Met Ile Tyr Glu Leu Trp Ala Gly Glu Gly Lys Ser Ala Cys Asn
165 170 175

Thr Ala Ser Pro Ala Val Gln Ser Ala Tyr Asn Thr Met Met Tyr Ile
180 185 190

Ile Ile Phe Gly Trp Ala Ile Tyr Pro Val Gly Tyr Phe Thr Gly Tyr
195 200 205

Leu Met Gly Asp Gly Gly Ser Ala Leu Asn Leu Asn Leu Ile Tyr Asn
210 215 220

-continued

Leu Ala Asp Phe Val Asn Lys Ile Leu Phe Gly Leu Ile Ile Trp Asn
225 230 235 240

Val Ala Val Lys Glu Ser Ser Asn Ala
245

<210> SEQ ID NO 166
<211> LENGTH: 750
<212> TYPE: DNA
<213> ORGANISM: Marine eubacteria

<400> SEQUENCE: 166
atgaaattat tactgatatt aggtagtgtt attgcacttc ctacatttgc tgcaggtggt 60
ggtgaccttg atgctagtga ttacactggt gtttcttttt ggttagttac tgctgcttta 120
ttagcatcta ctgtattttt ctttgttgaa agagatagag tttctgcaaa atggaaaaca 180
tcattaactg tatctggtct tgttactggt attgctttct ggaattacat gtacatgaga 240
ggggtatgga ttgaaactgg tgattcgcca actgtattta gatacattga ttggttacta 300
acagttcctc tattaatatg tgaattctac ttaattcttg ctgctgcaac taatgttgct 360
ggatcattat ttaagaaatt actagttggt tctcttgtta tgcttgtgtt tggttacatg 420
ggtgaagcag gaatcatggc tgcatggcct gcattcatta ttgggtgttt agcttgggta 480
tacatgattt atgaattatg ggctggagaa ggaaaatctg catgtaatac tgcaagtcct 540
gctgtgcaat cagcttacaa cacaatgatg tatattatca tctttggttg ggcgatttat 600
cctgtaggtt atttcacagg ttacctgatg ggtgacggtg gatcagctct taacttaaac 660
cttatctata accttgctga ctttgttaac aagattctat ttggtttaat tatatggaat 720
gttgctgtta aagaatcttc taatgcttaa 750

<210> SEQ ID NO 167
<211> LENGTH: 249
<212> TYPE: PRT
<213> ORGANISM: Marine eubacteria

<400> SEQUENCE: 167

Met Lys Leu Leu Leu Ile Leu Gly Ser Val Ile Ala Leu Pro Thr Phe
1 5 10 15

Ala Ala Gly Gly Gly Asp Leu Asp Ala Ser Asp Tyr Thr Gly Val Ser
20 25 30

Phe Trp Leu Val Thr Ala Ala Leu Leu Ala Ser Thr Val Phe Phe Phe
35 40 45

Val Glu Arg Asp Arg Val Ser Ala Lys Trp Lys Thr Ser Leu Thr Val
50 55 60

Ser Gly Leu Val Thr Gly Ile Ala Phe Trp Gln Tyr Met Tyr Met Arg
65 70 75 80

Gly Val Trp Ile Glu Thr Gly Asp Ser Pro Thr Val Phe Arg Tyr Ile
85 90 95

Asp Trp Leu Leu Thr Val Pro Leu Leu Ile Cys Glu Phe Tyr Leu Ile
100 105 110

Leu Ala Ala Ala Thr Asn Val Ala Gly Ser Leu Phe Lys Lys Leu Leu
115 120 125

Val Gly Ser Leu Val Met Leu Val Phe Gly Tyr Met Gly Glu Ala Gly
130 135 140

Ile Met Ala Ala Trp Pro Ala Phe Ile Ile Gly Cys Leu Ala Trp Val
145 150 155 160

-continued

```
Tyr Met Ile Tyr Glu Leu Trp Ala Gly Glu Gly Lys Ser Ala Cys Asn
                165                 170                 175

Thr Ala Ser Pro Ala Val Gln Ser Ala Tyr Asn Thr Met Met Tyr Ile
            180                 185                 190

Ile Ile Phe Gly Trp Ala Ile Tyr Pro Val Gly Tyr Phe Thr Gly Tyr
        195                 200                 205

Leu Met Gly Asp Gly Gly Ser Ala Leu Asn Leu Asn Leu Ile Tyr Asn
    210                 215                 220

Leu Ala Asp Phe Val Asn Lys Ile Leu Phe Gly Leu Ile Ile Trp Asn
225                 230                 235                 240

Val Ala Val Lys Glu Ser Ser Asn Ala
                245
```

<210> SEQ ID NO 168
<211> LENGTH: 750
<212> TYPE: DNA
<213> ORGANISM: Marine eubacteria

<400> SEQUENCE: 168

```
atgaaattat tactgatatt aggtagtgtt attgcacttc ctacatttgc tgcaggtggt      60

ggtgaccttg atgctagtga ttacactggt gtttcttttt ggttagttac tgctgcttta     120

ttagcatcta ctgtattttt ctttgttgaa agagatagag tttctgcaaa atggaaaaca     180

tcattaactg tatctggtct tgttactggt attgctttct ggcagtacat gtacatgaga     240

ggggtatgga ttgaaactgg tgattcgcca actgtattta gatacattga ttggttacta     300

acagttcctc tattaatatg tgaattctac ttaattcttg ctgctgcaac taatgttgct     360

ggatcattat ttaagaaatt actagttggt tctcttgtta tgcttgtgtt tggttacatg     420

ggtgaagcag gaatcatggc tgcatggcct gcattcatta ttgggtgttt agcttgggta     480

tacatgattt atgaattatg ggctggagaa ggaaaatctg catgtaatac tgcaagtcct     540

gctgtgcaat cagcttacaa cacaatgatg tatattatca tctttggttg ggcgatttat     600

cctgtaggtt atttcacagg ttacctgatg ggtgacggtg gatcagctct taacttaaac     660

cttatctata accttgctga ctttgttaac aagattctat ttggtttaat tatatggaat     720

gttgctgtta aagaatcttc taatgcttaa                                      750
```

<210> SEQ ID NO 169
<211> LENGTH: 252
<212> TYPE: PRT
<213> ORGANISM: Marine eubacteria

<400> SEQUENCE: 169

```
Thr Met Gly Lys Leu Leu Leu Ile Leu Gly Ser Ala Ile Ala Leu Pro
1               5                   10                  15

Ser Phe Ala Ala Ala Gly Gly Asp Leu Asp Ile Ser Asp Thr Val Gly
            20                  25                  30

Val Ser Phe Trp Leu Val Thr Ala Gly Met Leu Ala Ala Thr Val Phe
        35                  40                  45

Phe Phe Val Glu Arg Asp Gln Val Ser Ala Lys Trp Lys Thr Ser Leu
    50                  55                  60

Ala Val Ser Gly Leu Ile Thr Gly Ile Ala Phe Trp Lys Tyr Leu Tyr
65                  70                  75                  80

Met Arg Gly Val Trp Ile Asp Thr Gly Asp Thr Pro Thr Val Phe Arg
                85                  90                  95

Tyr Ile Asp Trp Leu Leu Thr Val Pro Leu Gln Met Val Glu Phe Tyr
```

-continued

```
            100                 105                 110

Leu Ile Leu Ala Ala Cys Thr Ser Val Ala Ala Ser Leu Phe Lys Lys
        115                 120                 125

Leu Leu Ala Gly Ser Leu Val Met Leu Gly Ala Gly Phe Ala Gly Glu
    130                 135                 140

Ala Gly Leu Ala Pro Val Leu Pro Ala Phe Ile Ile Gly Met Ala Gly
145                 150                 155                 160

Trp Leu Tyr Met Ile Tyr Glu Leu Tyr Met Gly Glu Gly Lys Ala Ala
                165                 170                 175

Val Ser Thr Ala Ser Pro Ala Val Asn Ser Ala Tyr Asn Ala Met Met
            180                 185                 190

Met Ile Ile Val Val Gly Trp Ala Ile Tyr Pro Ala Gly Tyr Ala Ala
        195                 200                 205

Gly Tyr Leu Met Gly Gly Glu Gly Val Tyr Ala Ser Asn Leu Asn Leu
    210                 215                 220

Ile Tyr Asn Leu Ala Asp Leu Val Asn Lys Ile Leu Phe Gly Leu Ile
225                 230                 235                 240

Ile Trp Asn Val Ala Val Lys Glu Ser Ser Asn Ala
                245                 250


<210> SEQ ID NO 170
<211> LENGTH: 756
<212> TYPE: DNA
<213> ORGANISM: Marine eubacteria

<400> SEQUENCE: 170

accatgggta aattattact gatattaggt agtgctattg cacttccatc atttgctgct     60

gctggtggcg atctagatat aagtgatact gttggtgttt cattctggct ggttacagct    120

ggtatgttag cggcaactgt gttctttttt gtagaaagag accaagtcag cgctaagtgg    180

aaaacttcac ttgctgtatc tggtttaatt actggtatag ctttttggaa atatctctat    240

atgagaggtg tttggataga cactggtgat accccaacag tattcagata tattgattgg    300

ttattaactg ttccattaca aatggttgag ttctatctaa ttcttgctgc ttgtacaagt    360

gttgctgctt cattatttaa gaagcttcta gctggttcat tagtaatgtt aggtgctgga    420

tttgcaggcg aagctggatt agctcctgta ttacctgctt tcattattgg tatggctgga    480

tggttataca tgatttatga gctatatatg ggtgaaggta aggctgctgt aagtactgca    540

agtcctgctg ttaactctgc atacaacgca atgatgatga ttattgttgt tggatgggca    600

atttatcctg ctggatatgc tgctggttac ctaatgggtg gcgaaggtgt atacgcttca    660

aacttaaacc ttatatataa ccttgccgac cttgttaaca agattctatt tggtttgatc    720

atttggaatg ttgctgttaa agaatcttct aatgct                              756


<210> SEQ ID NO 171
<211> LENGTH: 252
<212> TYPE: PRT
<213> ORGANISM: Marine eubacteria

<400> SEQUENCE: 171

Thr Met Gly Lys Leu Leu Leu Ile Leu Gly Ser Ala Ile Ala Leu Pro
1               5                   10                  15

Ser Phe Ala Ala Ala Gly Gly Asp Leu Asp Ile Ser Asp Thr Val Gly
            20                  25                  30

Val Ser Phe Trp Leu Val Thr Ala Gly Met Leu Ala Ala Thr Val Phe
        35                  40                  45
```

-continued

Phe Phe Val Glu Arg Asp Gln Val Ser Ala Lys Trp Lys Thr Ser Leu
    50                  55                  60

Ala Val Ser Gly Leu Ile Thr Gly Ile Ala Phe Trp Asn Tyr Leu Tyr
65                  70                  75                  80

Met Arg Gly Val Trp Ile Asp Thr Gly Asp Thr Pro Thr Val Phe Arg
                85                  90                  95

Tyr Ile Asp Trp Leu Leu Thr Val Pro Leu Gln Met Val Glu Phe Tyr
            100                 105                 110

Leu Ile Leu Ala Ala Cys Thr Ser Val Ala Ala Ser Leu Phe Lys Lys
        115                 120                 125

Leu Leu Ala Gly Ser Leu Val Met Leu Gly Ala Gly Phe Ala Gly Glu
    130                 135                 140

Ala Gly Leu Ala Pro Val Leu Pro Ala Phe Ile Ile Gly Met Ala Gly
145                 150                 155                 160

Trp Leu Tyr Met Ile Tyr Glu Leu Tyr Met Gly Glu Gly Lys Ala Ala
                165                 170                 175

Val Ser Thr Ala Ser Pro Ala Val Asn Ser Ala Tyr Asn Ala Met Met
            180                 185                 190

Met Ile Ile Val Val Gly Trp Ala Ile Tyr Pro Ala Gly Tyr Ala Ala
        195                 200                 205

Gly Tyr Leu Met Gly Gly Glu Gly Val Tyr Ala Ser Asn Leu Asn Leu
    210                 215                 220

Ile Tyr Asn Leu Ala Asp Leu Val Asn Lys Ile Leu Phe Gly Leu Ile
225                 230                 235                 240

Ile Trp Asn Val Ala Val Lys Glu Ser Ser Asn Ala
                245                 250

<210> SEQ ID NO 172
<211> LENGTH: 756
<212> TYPE: DNA
<213> ORGANISM: Marine eubacteria

<400> SEQUENCE: 172
accatgggta aattattact gatattaggt agtgctattg cacttccatc atttgctgct 60
gctggtggcg atctagatat aagtgatact gttggtgttt cattctggct ggttacagct 120
ggtatgttag cggcaactgt gttctttttt gtagaaagag accaagtcag cgctaagtgg 180
aaaacttcac ttgctgtatc tggtttaatt actggtatag ctttttggaa ttatctctat 240
atgagaggtg tttggataga cactggtgat accccaacag tattcagata tattgattgg 300
ttattaactg ttccattaca aatggttgag ttctatctaa ttcttgctgc ttgtacaagt 360
gttgctgctt cattatttaa gaagcttcta gctggttcat tagtaatgtt aggtgctgga 420
tttgcaggcg aagctggatt agctcctgta ttacctgctt tcattattgg tatggctgga 480
tggttataca tgatttatga gctatatatg ggtgaaggta aggctgctgt aagtactgca 540
agtcctgctg ttaactctgc atacaacgca atgatgatga ttattgttgt tggatgggca 600
atttatcctg ctggatatgc tgctggttac ctaatgggtg gcgaaggtgt atacgcttca 660
aacttaaacc ttatatataa ccttgccgac cttgttaaca agattctatt tggtttgatc 720
atttggaatg ttgctgttaa agaatcttct aatgct 756

<210> SEQ ID NO 173
<211> LENGTH: 252
<212> TYPE: PRT
<213> ORGANISM: Marine eubacteria -continued

<400> SEQUENCE: 173

```
Thr Met Gly Lys Leu Leu Leu Ile Leu Gly Ser Ala Ile Ala Leu Pro
1               5                   10                  15

Ser Phe Ala Ala Ala Gly Gly Asp Leu Asp Ile Ser Asp Thr Val Gly
            20                  25                  30

Val Ser Phe Trp Leu Val Thr Ala Gly Met Leu Ala Ala Thr Val Phe
        35                  40                  45

Phe Phe Val Glu Arg Asp Gln Val Ser Ala Lys Trp Lys Thr Ser Leu
    50                  55                  60

Ala Val Ser Gly Leu Ile Thr Gly Ile Ala Phe Trp Gln Tyr Leu Tyr
65                  70                  75                  80

Met Arg Gly Val Trp Ile Asp Thr Gly Asp Thr Pro Thr Val Phe Arg
                85                  90                  95

Tyr Ile Asp Trp Leu Leu Thr Val Pro Leu Gln Met Val Glu Phe Tyr
            100                 105                 110

Leu Ile Leu Ala Ala Cys Thr Ser Val Ala Ala Ser Leu Phe Lys Lys
        115                 120                 125

Leu Leu Ala Gly Ser Leu Val Met Leu Gly Ala Gly Phe Ala Gly Glu
    130                 135                 140

Ala Gly Leu Ala Pro Val Leu Pro Ala Phe Ile Ile Gly Met Ala Gly
145                 150                 155                 160

Trp Leu Tyr Met Ile Tyr Glu Leu Tyr Met Gly Glu Gly Lys Ala Ala
                165                 170                 175

Val Ser Thr Ala Ser Pro Ala Val Asn Ser Ala Tyr Asn Ala Met Met
            180                 185                 190

Met Ile Ile Val Val Gly Trp Ala Ile Tyr Pro Ala Gly Tyr Ala Ala
        195                 200                 205

Gly Tyr Leu Met Gly Gly Glu Gly Val Tyr Ala Ser Asn Leu Asn Leu
    210                 215                 220

Ile Tyr Asn Leu Ala Asp Leu Val Asn Lys Ile Leu Phe Gly Leu Ile
225                 230                 235                 240

Ile Trp Asn Val Ala Val Lys Glu Ser Ser Asn Ala
                245                 250
```

<210> SEQ ID NO 174
<211> LENGTH: 756
<212> TYPE: DNA
<213> ORGANISM: Marine eubacteria

<400> SEQUENCE: 174

```
accatgggta aattattact gatattaggt agtgctattg cacttccatc atttgctgct      60

gctggtggcg atctagatat aagtgatact gttggtgttt cattctggct ggttacagct     120

ggtatgttag cggcaactgt gttctttttt gtagaaagag accaagtcag cgctaagtgg     180

aaaacttcac ttgctgtatc tggtttaatt actggtatag ctttttggca gtatctctat     240

atgagaggtg tttggataga cactggtgat accccaacag tattcagata tattgattgg     300

ttattaactg ttccattaca aatggttgag ttctatctaa ttcttgctgc ttgtacaagt     360

gttgctgctt cattatttaa gaagcttcta gctggttcat tagtaatgtt aggtgctgga     420

tttgcaggcg aagctggatt agctcctgta ttacctgctt tcattattgg tatggctgga     480

tggttataca tgatttatga gctatatatg ggtgaaggta aggctgctgt aagtactgca     540

agtcctgctg ttaactctgc atacaacgca atgatgatga ttattgttgt tggatgggca     600
```

-continued

```
atttatcctg ctggatatgc tgctggttac ctaatgggtg gcgaaggtgt atacgcttca    660

aacttaaacc ttatatataa ccttgccgac cttgttaaca agattctatt tggtttgatc    720

atttggaatg ttgctgttaa agaatcttct aatgct                              756
```

<210> SEQ ID NO 175
<211> LENGTH: 252
<212> TYPE: PRT
<213> ORGANISM: Marine eubacteria

<400> SEQUENCE: 175

```
Thr Met Gly Lys Leu Leu Leu Ile Leu Gly Ser Ala Ile Ala Leu Pro
1               5                   10                  15

Ser Phe Ala Ala Ala Gly Gly Asp Leu Asp Ile Ser Asp Thr Val Gly
            20                  25                  30

Val Ser Phe Trp Leu Val Thr Ala Gly Met Leu Ala Ala Thr Val Phe
        35                  40                  45

Phe Phe Val Glu Arg Asp Gln Val Ser Ala Lys Trp Lys Thr Ser Leu
    50                  55                  60

Ala Val Ser Gly Leu Ile Thr Gly Ile Ala Phe Trp Glu Tyr Leu Tyr
65                  70                  75                  80

Met Arg Gly Val Trp Ile Asp Thr Gly Asp Thr Pro Thr Val Phe Arg
                85                  90                  95

Tyr Ile Asp Trp Leu Leu Thr Val Pro Leu Gln Met Val Glu Phe Tyr
            100                 105                 110

Leu Ile Leu Ala Ala Cys Thr Ser Val Ala Ala Ser Leu Phe Lys Lys
        115                 120                 125

Leu Leu Ala Gly Ser Leu Val Met Leu Gly Ala Gly Phe Ala Gly Glu
    130                 135                 140

Ala Gly Leu Ala Pro Val Leu Pro Ala Phe Ile Ile Gly Met Ala Gly
145                 150                 155                 160

Trp Leu Tyr Met Ile Tyr Glu Leu Tyr Met Gly Glu Gly Lys Ala Ala
                165                 170                 175

Val Ser Thr Ala Ser Pro Ala Val Asn Ser Ala Tyr Asn Ala Met Met
            180                 185                 190

Met Ile Ile Val Val Gly Trp Ala Ile Tyr Pro Ala Gly Tyr Ala Ala
        195                 200                 205

Gly Tyr Leu Met Gly Gly Glu Gly Val Tyr Ala Ser Asn Leu Asn Leu
    210                 215                 220

Ile Tyr Asn Leu Ala Asp Leu Val Asn Lys Ile Leu Phe Gly Leu Ile
225                 230                 235                 240

Ile Trp Asn Val Ala Val Lys Glu Ser Ser Asn Ala
                245                 250
```

<210> SEQ ID NO 176
<211> LENGTH: 756
<212> TYPE: DNA
<213> ORGANISM: Marine eubacteria

<400> SEQUENCE: 176

```
accatgggta aattattact gatattaggt agtgctattg cacttccatc atttgctgct     60

gctggtggcg atctagatat aagtgatact gttggtgttt cattctggct ggttacagct    120

ggtatgttag cggcaactgt gttctttttt gtagaaagag accaagtcag cgctaagtgg    180

aaaacttcac ttgctgtatc tggtttaatt actggtatag ctttttggga atatctctat    240

atgagaggtg tttggataga cactggtgat accccaacag tattcagata tattgattgg    300
```

-continued

```
ttattaactg ttccattaca aatggttgag ttctatctaa ttcttgctgc ttgtacaagt    360

gttgctgctt cattatttaa gaagcttcta gctggttcat tagtaatgtt aggtgctgga    420

tttgcaggcg aagctggatt agctcctgta ttacctgctt tcattattgg tatggctgga    480

tggttataca tgatttatga gctatatatg ggtgaaggta aggctgctgt aagtactgca    540

agtcctgctg ttaactctgc atacaacgca atgatgatga ttattgttgt tggatgggca    600

atttatcctg ctggatatgc tgctggttac ctaatgggtg gcgaaggtgt atacgcttca    660

aacttaaacc ttatatataa ccttgccgac cttgttaaca agattctatt tggtttgatc    720

atttggaatg ttgctgttaa agaatcttct aatgct                              756
```

```
<210> SEQ ID NO 177
<211> LENGTH: 252
<212> TYPE: PRT
<213> ORGANISM: Marine eubacteria

<400> SEQUENCE: 177

Thr Met Gly Lys Leu Leu Leu Ile Leu Gly Ser Ala Ile Ala Leu Pro
1               5                   10                  15

Ser Phe Ala Ala Ala Gly Gly Asp Leu Asp Ile Ser Asp Thr Val Gly
            20                  25                  30

Val Ser Phe Trp Leu Val Thr Ala Gly Met Leu Ala Ala Thr Val Phe
        35                  40                  45

Phe Phe Val Glu Arg Asp Gln Val Ser Ala Lys Trp Lys Thr Ser Leu
    50                  55                  60

Ala Val Ser Gly Leu Ile Thr Gly Ile Ala Phe Trp Trp Tyr Leu Tyr
65                  70                  75                  80

Met Arg Gly Val Trp Ile Asp Thr Gly Asp Thr Pro Thr Val Phe Arg
                85                  90                  95

Tyr Ile Asp Trp Leu Leu Thr Val Pro Leu Gln Met Val Glu Phe Tyr
            100                 105                 110

Leu Ile Leu Ala Ala Cys Thr Ser Val Ala Ala Ser Leu Phe Lys Lys
        115                 120                 125

Leu Leu Ala Gly Ser Leu Val Met Leu Gly Ala Gly Phe Ala Gly Glu
    130                 135                 140

Ala Gly Leu Ala Pro Val Leu Pro Ala Phe Ile Ile Gly Met Ala Gly
145                 150                 155                 160

Trp Leu Tyr Met Ile Tyr Glu Leu Tyr Met Gly Glu Gly Lys Ala Ala
                165                 170                 175

Val Ser Thr Ala Ser Pro Ala Val Asn Ser Ala Tyr Asn Ala Met Met
            180                 185                 190

Met Ile Ile Val Val Gly Trp Ala Ile Tyr Pro Ala Gly Tyr Ala Ala
        195                 200                 205

Gly Tyr Leu Met Gly Gly Glu Gly Val Tyr Ala Ser Asn Leu Asn Leu
    210                 215                 220

Ile Tyr Asn Leu Ala Asp Leu Val Asn Lys Ile Leu Phe Gly Leu Ile
225                 230                 235                 240

Ile Trp Asn Val Ala Val Lys Glu Ser Ser Asn Ala
                245                 250

<210> SEQ ID NO 178
<211> LENGTH: 756
<212> TYPE: DNA
<213> ORGANISM: Marine eubacteria
```

-continued

<400> SEQUENCE: 178

```
accatgggta aattattact gatattaggt agtgctattg cacttccatc atttgctgct     60
gctggtggcg atctagatat aagtgatact gttggtgttt cattctggct ggttacagct    120
ggtatgttag cggcaactgt gttctttttt gtagaaagag accaagtcag cgctaagtgg    180
aaaacttcac ttgctgtatc tggtttaatt actggtatag ctttttggtg gtatctctat    240
atgagaggtg tttggataga cactggtgat accccaacag tattcagata tattgattgg    300
ttattaactg ttccattaca aatggttgag ttctatctaa ttcttgctgc ttgtacaagt    360
gttgctgctt cattatttaa gaagcttcta gctggttcat tagtaatgtt aggtgctgga    420
tttgcaggcg aagctggatt agctcctgta ttacctgctt tcattattgg tatggctgga    480
tggttataca tgatttatga gctatatatg ggtgaaggta aggctgctgt aagtactgca    540
agtcctgctg ttaactctgc atacaacgca atgatgatga ttattgttgt tggatgggca    600
atttatcctg ctggatatgc tgctggttac ctaatgggtg gcgaaggtgt atacgcttca    660
aacttaaacc ttatatataa ccttgccgac cttgttaaca agattctatt tggtttgatc    720
atttggaatg ttgctgttaa agaatcttct aatgct                              756
```

<210> SEQ ID NO 179
<211> LENGTH: 252
<212> TYPE: PRT
<213> ORGANISM: Marine eubacteria

<400> SEQUENCE: 179

```
Thr Met Gly Lys Leu Leu Leu Ile Leu Gly Ser Ala Ile Ala Leu Pro
1               5                   10                  15

Ser Phe Ala Ala Ala Gly Gly Asp Leu Asp Ile Ser Asp Thr Val Gly
            20                  25                  30

Val Ser Phe Trp Leu Val Thr Ala Gly Met Leu Ala Ala Thr Val Phe
        35                  40                  45

Phe Phe Val Glu Arg Asp Gln Val Ser Ala Lys Trp Lys Thr Ser Leu
    50                  55                  60

Ala Val Ser Gly Leu Ile Thr Gly Ile Ala Phe Trp His Tyr Leu Tyr
65                  70                  75                  80

Met Arg Gly Val Trp Ile Asp Thr Gly Asp Thr Pro Thr Val Phe Ala
                85                  90                  95

Tyr Ile Asp Trp Leu Leu Thr Val Pro Leu Gln Met Val Glu Phe Tyr
            100                 105                 110

Leu Ile Leu Ala Ala Cys Thr Ser Val Ala Ala Ser Leu Phe Lys Lys
        115                 120                 125

Leu Leu Ala Gly Ser Leu Val Met Leu Gly Ala Gly Phe Ala Gly Glu
    130                 135                 140

Ala Gly Leu Ala Pro Val Leu Pro Ala Phe Ile Ile Gly Met Ala Gly
145                 150                 155                 160

Trp Leu Tyr Met Ile Tyr Glu Leu Tyr Met Gly Glu Gly Lys Ala Ala
                165                 170                 175

Val Ser Thr Ala Ser Pro Ala Val Asn Ser Ala Tyr Asn Ala Met Met
            180                 185                 190

Met Ile Ile Val Val Gly Trp Ala Ile Tyr Pro Ala Gly Tyr Ala Ala
        195                 200                 205

Gly Tyr Leu Met Gly Gly Glu Gly Val Tyr Ala Ser Asn Leu Asn Leu
    210                 215                 220

Ile Tyr Asn Leu Ala Asp Leu Val Asn Lys Ile Leu Phe Gly Leu Ile
```

-continued

```
225                 230                 235                 240

Ile Trp Asn Val Ala Val Lys Glu Ser Ser Asn Ala
                245                 250


<210> SEQ ID NO 180
<211> LENGTH: 756
<212> TYPE: DNA
<213> ORGANISM: Marine eubacteria

<400> SEQUENCE: 180

accatgggta aattattact gatattaggt agtgctattg cacttccatc atttgctgct      60

gctggtggcg atctagatat aagtgatact gttggtgttt cattctggct ggttacagct     120

ggtatgttag cggcaactgt gttctttttt gtagaaagag accaagtcag cgctaagtgg     180

aaaacttcac ttgctgtatc tggtttaatt actggtatag ctttttggca ttatctctat     240

atgagaggtg tttggataga cactggtgat accccaacag tattcgcata tattgattgg     300

ttattaactg ttccattaca aatggttgag ttctatctaa ttcttgctgc ttgtacaagt     360

gttgctgctt cattatttaa gaagcttcta gctggttcat tagtaatgtt aggtgctgga     420

tttgcaggcg aagctggatt agctcctgta ttacctgctt tcattattgg tatggctgga     480

tggttataca tgatttatga gctatatatg ggtgaaggta aggctgctgt aagtactgca     540

agtcctgctg ttaactctgc atacaacgca atgatgatga ttattgttgt tggatgggca     600

atttatcctg ctggatatgc tgctggttac ctaatgggtg gcgaaggtgt atacgcttca     660

aacttaaacc ttatatataa ccttgccgac cttgttaaca agattctatt tggtttgatc     720

atttggaatg ttgctgttaa agaatcttct aatgct                               756


<210> SEQ ID NO 181
<211> LENGTH: 252
<212> TYPE: PRT
<213> ORGANISM: Marine eubacteria

<400> SEQUENCE: 181

Thr Met Gly Lys Leu Leu Leu Ile Leu Gly Ser Ala Ile Ala Leu Pro
1               5                   10                  15

Ser Phe Ala Ala Ala Gly Gly Asp Leu Asp Ile Ser Asp Thr Val Gly
            20                  25                  30

Val Ser Phe Trp Leu Val Thr Ala Gly Met Leu Ala Ala Thr Val Phe
        35                  40                  45

Phe Phe Val Glu Arg Asp Gln Val Ser Ala Lys Trp Lys Thr Ser Leu
    50                  55                  60

Ala Val Ser Gly Leu Ile Thr Gly Ile Ala Phe Trp His Tyr Leu Tyr
65                  70                  75                  80

Met Arg Gly Val Trp Ile Asp Thr Gly Asp Thr Pro Thr Val Phe Glu
                85                  90                  95

Tyr Ile Asp Trp Leu Leu Thr Val Pro Leu Gln Met Val Glu Phe Tyr
            100                 105                 110

Leu Ile Leu Ala Ala Cys Thr Ser Val Ala Ala Ser Leu Phe Lys Lys
        115                 120                 125

Leu Leu Ala Gly Ser Leu Val Met Leu Gly Ala Gly Phe Ala Gly Glu
    130                 135                 140

Ala Gly Leu Ala Pro Val Leu Pro Ala Phe Ile Ile Gly Met Ala Gly
145                 150                 155                 160

Trp Leu Tyr Met Ile Tyr Glu Leu Tyr Met Gly Glu Gly Lys Ala Ala
                165                 170                 175
```

-continued

```
Val Ser Thr Ala Ser Pro Ala Val Asn Ser Ala Tyr Asn Ala Met Met
            180                 185                 190

Met Ile Ile Val Val Gly Trp Ala Ile Tyr Pro Ala Gly Tyr Ala Ala
        195                 200                 205

Gly Tyr Leu Met Gly Gly Glu Gly Val Tyr Ala Ser Asn Leu Asn Leu
    210                 215                 220

Ile Tyr Asn Leu Ala Asp Leu Val Asn Lys Ile Leu Phe Gly Leu Ile
225                 230                 235                 240

Ile Trp Asn Val Ala Val Lys Glu Ser Ser Asn Ala
                245                 250
```

<210> SEQ ID NO 182
<211> LENGTH: 756
<212> TYPE: DNA
<213> ORGANISM: Marine eubacteria

<400> SEQUENCE: 182

```
accatgggta aattattact gatattaggt agtgctattg cacttccatc atttgctgct     60

gctggtggcg atctagatat aagtgatact gttggtgttt cattctggct ggttacagct    120

ggtatgttag cggcaactgt gttctttttt gtagaaagag accaagtcag cgctaagtgg    180

aaaacttcac ttgctgtatc tggtttaatt actggtatag ctttttggca ttatctctat    240

atgagaggtg tttggataga cactggtgat accccaacag tattcgaata tattgattgg    300

ttattaactg ttccattaca aatggttgag ttctatctaa ttcttgctgc ttgtacaagt    360

gttgctgctt cattatttaa gaagcttcta gctggttcat tagtaatgtt aggtgctgga    420

tttgcaggcg aagctggatt agctcctgta ttacctgctt tcattattgg tatggctgga    480

tggttataca tgatttatga gctatatatg ggtgaaggta aggctgctgt aagtactgca    540

agtcctgctg ttaactctgc atacaacgca atgatgatga ttattgttgt tggatgggca    600

atttatcctg ctggatatgc tgctggttac ctaatgggtg gcgaaggtgt atacgcttca    660

aacttaaacc ttatatataa ccttgccgac cttgttaaca agattctatt tggtttgatc    720

atttggaatg ttgctgttaa agaatcttct aatgct                              756
```

<210> SEQ ID NO 183
<211> LENGTH: 252
<212> TYPE: PRT
<213> ORGANISM: Marine eubacteria

<400> SEQUENCE: 183

```
Thr Met Gly Lys Leu Leu Leu Ile Leu Gly Ser Ala Ile Ala Leu Pro
1               5                   10                  15

Ser Phe Ala Ala Ala Gly Gly Asp Leu Asp Ile Ser Asp Thr Val Gly
            20                  25                  30

Val Ser Phe Trp Leu Val Thr Ala Gly Met Leu Ala Ala Thr Val Phe
        35                  40                  45

Phe Phe Val Glu Arg Asp Gln Val Ser Ala Lys Trp Lys Thr Ser Leu
    50                  55                  60

Ala Val Ser Gly Leu Ile Thr Gly Ile Ala Phe Trp His Tyr Leu Tyr
65                  70                  75                  80

Met Arg Gly Val Trp Ile Asp Thr Gly Asp Thr Pro Thr Val Phe Gln
                85                  90                  95

Tyr Ile Asp Trp Leu Leu Thr Val Pro Leu Gln Met Val Glu Phe Tyr
            100                 105                 110
```

-continued

```
Leu Ile Leu Ala Ala Cys Thr Ser Val Ala Ala Ser Leu Phe Lys Lys
        115                 120                 125

Leu Leu Ala Gly Ser Leu Val Met Leu Gly Ala Gly Phe Ala Gly Glu
    130                 135                 140

Ala Gly Leu Ala Pro Val Leu Pro Ala Phe Ile Ile Gly Met Ala Gly
145                 150                 155                 160

Trp Leu Tyr Met Ile Tyr Glu Leu Tyr Met Gly Glu Gly Lys Ala Ala
                165                 170                 175

Val Ser Thr Ala Ser Pro Ala Val Asn Ser Ala Tyr Asn Ala Met Met
            180                 185                 190

Met Ile Ile Val Val Gly Trp Ala Ile Tyr Pro Ala Gly Tyr Ala Ala
        195                 200                 205

Gly Tyr Leu Met Gly Gly Glu Gly Val Tyr Ala Ser Asn Leu Asn Leu
    210                 215                 220

Ile Tyr Asn Leu Ala Asp Leu Val Asn Lys Ile Leu Phe Gly Leu Ile
225                 230                 235                 240

Ile Trp Asn Val Ala Val Lys Glu Ser Ser Asn Ala
                245                 250
```

<210> SEQ ID NO 184
<211> LENGTH: 756
<212> TYPE: DNA
<213> ORGANISM: Marine eubacteria

<400> SEQUENCE: 184

```
accatgggta aattattact gatattaggt agtgctattg cacttccatc atttgctgct      60

gctggtggcg atctagatat aagtgatact gttggtgttt cattctggct ggttacagct     120

ggtatgttag cggcaactgt gttctttttt gtagaaagag accaagtcag cgctaagtgg     180

aaaacttcac ttgctgtatc tggtttaatt actggtatag ctttttggca ttatctctat     240

atgagaggtg tttggataga cactggtgat accccaacag tattccaata tattgattgg     300

ttattaactg ttccattaca aatggttgag ttctatctaa ttcttgctgc ttgtacaagt     360

gttgctgctt cattatttaa gaagcttcta gctggttcat tagtaatgtt aggtgctgga     420

tttgcaggcg aagctggatt agctcctgta ttacctgctt tcattattgg tatggctgga     480

tggttataca tgatttatga gctatatatg ggtgaaggta aggctgctgt aagtactgca     540

agtcctgctg ttaactctgc atacaacgca atgatgatga ttattgttgt tggatgggca     600

atttatcctg ctggatatgc tgctggttac ctaatgggtg gcgaaggtgt atacgcttca     660

aacttaaacc ttatatataa ccttgccgac cttgttaaca agattctatt tggtttgatc     720

atttggaatg ttgctgttaa agaatcttct aatgct                               756
```

<210> SEQ ID NO 185
<211> LENGTH: 25
<212> TYPE: DNA
<213> ORGANISM: artificial sequence
<220> FEATURE:
<223> OTHER INFORMATION: Synthetic

<400> SEQUENCE: 185

```
aaattattac tgatattagg tagtg                                            25
```

<210> SEQ ID NO 186
<211> LENGTH: 24
<212> TYPE: DNA
<213> ORGANISM: artificial sequence
<220> FEATURE:

-continued

<223> OTHER INFORMATION: Synthetic

<400> SEQUENCE: 186
agcattagaa gattctttaa cagc 24

<210> SEQ ID NO 187
<211> LENGTH: 21
<212> TYPE: DNA
<213> ORGANISM: artificial sequence
<220> FEATURE:
<223> OTHER INFORMATION: Synthetic

<400> SEQUENCE: 187
gaggtatata ttaatgtatc g 21

<210> SEQ ID NO 188
<211> LENGTH: 18
<212> TYPE: DNA
<213> ORGANISM: artificial sequence
<220> FEATURE:
<223> OTHER INFORMATION: Synthetic

<400> SEQUENCE: 188
gatttaatct gtatcagg 18

<210> SEQ ID NO 189
<211> LENGTH: 45
<212> TYPE: DNA
<213> ORGANISM: artificial sequence
<220> FEATURE:
<223> OTHER INFORMATION: Synthetic

<400> SEQUENCE: 189
tgttactggt attgctttct ggaattacat gtacatgaga ggggt 45

<210> SEQ ID NO 190
<211> LENGTH: 45
<212> TYPE: DNA
<213> ORGANISM: artificial sequence
<220> FEATURE:
<223> OTHER INFORMATION: Synthetic

<400> SEQUENCE: 190
acccctctca tgtacatgta attccagaaa gcaataccag taaca 45

<210> SEQ ID NO 191
<211> LENGTH: 45
<212> TYPE: DNA
<213> ORGANISM: artificial sequence
<220> FEATURE:
<223> OTHER INFORMATION: Synthetic

<400> SEQUENCE: 191
tgttactggt attgctttct ggcagtacat gtacatgaga ggggt 45

<210> SEQ ID NO 192
<211> LENGTH: 45
<212> TYPE: DNA
<213> ORGANISM: artificial sequence
<220> FEATURE:
<223> OTHER INFORMATION: Synthetic

<400> SEQUENCE: 192
acccctctca tgtacatgta ctgccagaaa gcaataccag taaca 45

-continued

<210> SEQ ID NO 193
<211> LENGTH: 45
<212> TYPE: DNA
<213> ORGANISM: artificial sequence
<220> FEATURE:
<223> OTHER INFORMATION: Synthetic

<400> SEQUENCE: 193
tgttactggt attgctttct ggaaatacat gtacatgaga ggggt 45

<210> SEQ ID NO 194
<211> LENGTH: 44
<212> TYPE: DNA
<213> ORGANISM: artificial sequence
<220> FEATURE:
<223> OTHER INFORMATION: Synthetic

<400> SEQUENCE: 194
acccctctca tgtacatgta tttccagaaa gcaataccag taac 44

<210> SEQ ID NO 195
<211> LENGTH: 45
<212> TYPE: DNA
<213> ORGANISM: artificial sequence
<220> FEATURE:
<223> OTHER INFORMATION: Synthetic

<400> SEQUENCE: 195
ttactggtat agctttttgg aattatctct atatgagagg tgttt 45

<210> SEQ ID NO 196
<211> LENGTH: 45
<212> TYPE: DNA
<213> ORGANISM: artificial sequence
<220> FEATURE:
<223> OTHER INFORMATION: Synthetic

<400> SEQUENCE: 196
aaacacctct catatagaga taattccaaa aagctatacc agtaa 45

<210> SEQ ID NO 197
<211> LENGTH: 45
<212> TYPE: DNA
<213> ORGANISM: artificial sequence
<220> FEATURE:
<223> OTHER INFORMATION: Synthetic

<400> SEQUENCE: 197
ttactggtat agctttttgg cagtatctct atatgagagg tgttt 45

<210> SEQ ID NO 198
<211> LENGTH: 45
<212> TYPE: DNA
<213> ORGANISM: artificial sequence
<220> FEATURE:
<223> OTHER INFORMATION: Synthetic

<400> SEQUENCE: 198
aaacacctct catatagaga tactgccaaa aagctatacc agtaa 45

<210> SEQ ID NO 199
<211> LENGTH: 45
<212> TYPE: DNA
<213> ORGANISM: artificial sequence
<220> FEATURE:
<223> OTHER INFORMATION: Synthetic -continued

<400> SEQUENCE: 199
ttactggtat agctttttgg aaatatctct atatgagagg tgttt 45

<210> SEQ ID NO 200
<211> LENGTH: 45
<212> TYPE: DNA
<213> ORGANISM: artificial sequence
<220> FEATURE:
<223> OTHER INFORMATION: Synthetic

<400> SEQUENCE: 200
aaacacctct catatagaga tatttccaaa aagctatacc agtaa 45

<210> SEQ ID NO 201
<211> LENGTH: 45
<212> TYPE: DNA
<213> ORGANISM: artificial sequence
<220> FEATURE:
<223> OTHER INFORMATION: Synthetic

<400> SEQUENCE: 201
ctggtgatac cccaacagta ttcgcatata ttgattggtt attaa 45

<210> SEQ ID NO 202
<211> LENGTH: 45
<212> TYPE: DNA
<213> ORGANISM: artificial sequence
<220> FEATURE:
<223> OTHER INFORMATION: Synthetic

<400> SEQUENCE: 202
ttaataacca atcaatatat gcgaatactg ttggggtatc accag 45

<210> SEQ ID NO 203
<211> LENGTH: 45
<212> TYPE: DNA
<213> ORGANISM: artificial sequence
<220> FEATURE:
<223> OTHER INFORMATION: Synthetic

<400> SEQUENCE: 203
ctggtgatac cccaacagta ttccaatata ttgattggtt attaa 45

<210> SEQ ID NO 204
<211> LENGTH: 45
<212> TYPE: DNA
<213> ORGANISM: artificial sequence
<220> FEATURE:
<223> OTHER INFORMATION: Synthetic

<400> SEQUENCE: 204
ttaataacca atcaatatat tggaatactg ttggggtatc accag 45

<210> SEQ ID NO 205
<211> LENGTH: 45
<212> TYPE: DNA
<213> ORGANISM: artificial sequence
<220> FEATURE:
<223> OTHER INFORMATION: Synthetic

<400> SEQUENCE: 205
ctggtgatac cccaacagta ttcgaatata ttgattggtt attaa 45

<210> SEQ ID NO 206
<211> LENGTH: 45

-continued

<212> TYPE: DNA
<213> ORGANISM: artificial sequence
<220> FEATURE:
<223> OTHER INFORMATION: Synthetic

<400> SEQUENCE: 206
ttaataacca atcaatatat tcgaatactg ttggggtatc accag 45

<210> SEQ ID NO 207
<211> LENGTH: 45
<212> TYPE: DNA
<213> ORGANISM: artificial sequence
<220> FEATURE:
<223> OTHER INFORMATION: Synthetic

<400> SEQUENCE: 207
ttactggtat agctttttgg gattatctct atatgagagg tgttt 45

<210> SEQ ID NO 208
<211> LENGTH: 45
<212> TYPE: DNA
<213> ORGANISM: artificial sequence
<220> FEATURE:
<223> OTHER INFORMATION: Synthetic

<400> SEQUENCE: 208
aaacacctct catatagaga taatcccaaa aagctatacc agtaa 45

<210> SEQ ID NO 209
<211> LENGTH: 45
<212> TYPE: DNA
<213> ORGANISM: artificial sequence
<220> FEATURE:
<223> OTHER INFORMATION: Synthetic

<400> SEQUENCE: 209
ttactggtat agctttttgg gaatatctct atatgagagg tgttt 45

<210> SEQ ID NO 210
<211> LENGTH: 45
<212> TYPE: DNA
<213> ORGANISM: artificial sequence
<220> FEATURE:
<223> OTHER INFORMATION: Synthetic

<400> SEQUENCE: 210
aaacacctct catatagaga tattcccaaa aagctatacc agtaa 45

<210> SEQ ID NO 211
<211> LENGTH: 45
<212> TYPE: DNA
<213> ORGANISM: artificial sequence
<220> FEATURE:
<223> OTHER INFORMATION: Synthetic

<400> SEQUENCE: 211
ttactggtat agctttttgg tggtatctct atatgagagg tgttt 45

<210> SEQ ID NO 212
<211> LENGTH: 45
<212> TYPE: DNA
<213> ORGANISM: artificial sequence -continued

```
<220> FEATURE:
<223> OTHER INFORMATION: Synthetic

<400> SEQUENCE: 212

aaacacctct catatagaga taccaccaaa aagctatacc agtaa                 45
```